US012668613B2

(12) United States Patent
Baum et al.

(10) Patent No.: US 12,668,613 B2
(45) Date of Patent: Jun. 30, 2026

(54) CHIMERIC INSECTICIDAL PROTEINS TOXIC OR INHIBITORY TO LEPIDOPTERAN PESTS

(71) Applicant: Monsanto Technology LLC, St. Louis, MO (US)

(72) Inventors: James A. Baum, Webster Groves, MO (US); Thomas A. Cerruti, Newton, MA (US); Crystal L. Dart, Norton, MA (US); Leigh H. English, Chesterfield, MO (US); Stanislaw Flasinski, Ballwin, MO (US); Xiaoran Fu, Belmont, MA (US); Victor M. Guzov, Cambridge, MA (US); Arlene R. Howe, Clarkson Valley, MO (US); Jay P. Morgenstern, Cambridge, MA (US); James K. Roberts, Chesterfield, MO (US); Sara A. Salvador, Wildwood, MO (US); Jinling Wang, Belmont, MA (US)

(73) Assignee: Monsanto Technology LLC, St. Louis, MO (US)

( * ) Notice: Subject to any disclaimer, the term of this patent is extended or adjusted under 35 U.S.C. 154(b) by 271 days.

(21) Appl. No.: 18/633,982

(22) Filed: Apr. 12, 2024

(65) Prior Publication Data

US 2024/0309057 A1     Sep. 19, 2024

Related U.S. Application Data

(60) Division of application No. 17/698,936, filed on Mar. 18, 2022, now Pat. No. 11,987,603, which is a division of application No. 16/658,938, filed on Oct. 21, 2019, now Pat. No. 11,286,284, which is a continuation of application No. 15/656,616, filed on Jul. 21, 2017, now Pat. No. 10,487,123, which is a continuation-in-part of application No. 14/884,469, filed on Oct. 15, 2015, now Pat. No. 10,233,217.

(60) Provisional application No. 62/064,989, filed on Oct. 16, 2014.

(51) Int. Cl.
*C07K 14/325* (2006.01)
*C12N 15/82* (2006.01)
*C12N 15/62* (2006.01)

(52) U.S. Cl.
CPC ........ *C07K 14/325* (2013.01); *C12N 15/8286* (2013.01); *C07K 2319/00* (2013.01); *C12N 15/62* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 5,188,642 A | 2/1993 | Shah et al. | |
| 5,273,746 A | 12/1993 | Payne et al. | |
| 5,312,910 A | 5/1994 | Kishore et al. | |
| 5,322,687 A | 6/1994 | Donovan et al. | |
| 5,500,365 A | 3/1996 | Fischhoff et al. | |
| 5,508,264 A | 4/1996 | Bradfisch et al. | |
| 5,510,471 A | 4/1996 | Lebrun et al. | |
| 5,627,061 A | 5/1997 | Barry et al. | |
| 5,633,435 A | 5/1997 | Barry et al. | |
| 5,633,448 A | 5/1997 | Lebrun et al. | |
| 5,723,756 A | 3/1998 | Peferoen et al. | |
| 5,723,758 A | 3/1998 | Payne et al. | |
| 5,728,925 A | 3/1998 | Herrera-Estrella et al. | |
| 5,880,275 A | 3/1999 | Fischhoff et al. | |
| 5,942,664 A | 8/1999 | Baum et al. | |
| 6,017,534 A | 1/2000 | Marlvar et al. | |
| 6,033,874 A | 3/2000 | Baum et al. | |
| 6,204,246 B1 | 3/2001 | Bosch et al. | |
| 6,218,188 B1* | 4/2001 | Cardineau .......... | C12N 15/8286 435/468 |
| 6,501,009 B1 | 12/2002 | Romano | |
| 6,593,293 B1* | 7/2003 | Baum .................. | C07K 14/325 514/4.5 |
| 6,713,063 B1 | 3/2004 | Malvar et al. | |
| 6,962,705 B2 | 11/2005 | Malvar et al. | |
| 7,064,249 B2 | 6/2006 | Corbin et al. | |
| 7,070,982 B2 | 7/2006 | Malvar et al. | |
| 7,193,133 B2 | 3/2007 | Lassner et al. | |
| 7,510,878 B2 | 3/2009 | Abad et al. | |
| 7,772,465 B2 | 8/2010 | Abad et al. | |
| 7,812,129 B1 | 10/2010 | Abad et al. | |
| 8,344,207 B2 | 1/2013 | Bogdanova et al. | |

(Continued)

FOREIGN PATENT DOCUMENTS

| | | |
|---|---|---|
| AU | 2012200658 | 3/2012 |
| CN | 103763916 | 4/2014 |

(Continued)

OTHER PUBLICATIONS

Pardo Lopez et al, Peptides (2009) 30:589-595, pp. 591-592. (Year: 2009).*
Aronson et al, FEMS Microbiol. Lett. (2001) 195:1-8. (Year: 2001).*
Herrero et al, Biochem. J. (2004) 384:507-513. (Year: 2004).*
Abdul-Rauf et al, Curr. Microbiol. (1999) 39, 94-98. (Year: 1999).*
USPTO: Response to Final Office Action regarding U.S. Appl. No. 17/671,011, filed Oct. 30, 2024.
USPTO: Advisory Action regarding U.S. Appl. No. 17/671,011, mailed Oct. 15, 2024.

(Continued)

*Primary Examiner* — Mykola V. Kovalenko
(74) *Attorney, Agent, or Firm* — Dentons US LLP; David Lanzotti

(57) ABSTRACT

Nucleotide sequences are disclosed that encode novel chimeric insecticidal proteins exhibiting Lepidopteran inhibitory activity. Particular embodiments provide compositions and transformed plants, plant parts, and seeds containing the recombinant nucleic acid molecules encoding one or more of the chimeric insecticidal proteins.

19 Claims, No Drawings

Specification includes a Sequence Listing.

(56) References Cited

U.S. PATENT DOCUMENTS

| | | | |
|---|---|---|---|
| 8,609,936 B2 | 12/2013 | Baum et al. | |
| 10,233,217 B2 | 3/2019 | Baum et al. | |
| 10,487,123 B2 | 11/2019 | Baum et al. | |
| 10,494,408 B2 | 12/2019 | Baum et al. | |
| 10,494,409 B2 | 12/2019 | Baum et al. | |
| 10,611,806 B2 | 4/2020 | Baum et al. | |
| 11,286,284 B2 | 3/2022 | Baum et al. | |
| 11,987,603 B2 | 5/2024 | Baum et al. | |
| 12,264,182 B2 | 4/2025 | Baum et al. | |
| 2001/0026940 A1 | 10/2001 | Cardineau et al. | |
| 2002/0064865 A1 | 5/2002 | Malvar et al. | |
| 2003/0046726 A1* | 3/2003 | Koziel | C07K 14/325 |
| | | | 800/278 |
| 2003/0119158 A1* | 6/2003 | Malvar | A61P 43/00 |
| | | | 536/23.7 |
| 2006/0021087 A1 | 1/2006 | Baum et al. | |
| 2006/0112447 A1 | 5/2006 | Bogdanova et al. | |
| 2008/0172762 A1 | 7/2008 | Cerf et al. | |
| 2008/0256667 A1 | 10/2008 | Dersch et al. | |
| 2008/0280361 A1 | 11/2008 | Calabotta et al. | |
| 2008/0282432 A1 | 11/2008 | Duncan et al. | |
| 2009/0138985 A1 | 5/2009 | Martinell et al. | |
| 2009/0142837 A1 | 6/2009 | Adams, Jr. et al. | |
| 2009/0313721 A1 | 12/2009 | Abad et al. | |
| 2009/0313722 A1 | 12/2009 | Abad et al. | |
| 2010/0004176 A1 | 1/2010 | Sampson et al. | |
| 2010/0017914 A1 | 1/2010 | Hart et al. | |
| 2010/0077507 A1 | 3/2010 | Abad et al. | |
| 2010/0077508 A1 | 3/2010 | Abad et al. | |
| 2010/0137216 A1 | 6/2010 | Carozzi et al. | |
| 2010/0160231 A1 | 6/2010 | Sampson et al. | |
| 2010/0192256 A1 | 7/2010 | Abad et al. | |
| 2010/0197592 A1 | 8/2010 | Heinrichs | |
| 2010/0269221 A1 | 10/2010 | Abad et al. | |
| 2010/0317569 A1 | 12/2010 | Lira et al. | |
| 2010/0319092 A1 | 12/2010 | Lira et al. | |
| 2010/0319093 A1 | 12/2010 | Lira et al. | |
| 2011/0030096 A1 | 2/2011 | Lira et al. | |
| 2011/0055968 A1 | 3/2011 | Cerf et al. | |
| 2011/0112013 A1 | 5/2011 | Abad et al. | |
| 2011/0154536 A1 | 6/2011 | Abad et al. | |
| 2012/0047606 A1 | 2/2012 | Abad et al. | |
| 2012/0117690 A1 | 5/2012 | Cerf et al. | |
| 2012/0167259 A1 | 6/2012 | Liu et al. | |
| 2012/0192310 A1 | 7/2012 | Abad et al. | |
| 2012/0210462 A1 | 8/2012 | Bermudez et al. | |
| 2012/0233726 A1 | 9/2012 | Abad et al. | |
| 2012/0317681 A1 | 12/2012 | Meade et al. | |
| 2013/0055469 A1 | 2/2013 | Sampson et al. | |
| 2013/0097735 A1 | 4/2013 | Bowen et al. | |
| 2013/0104259 A1 | 4/2013 | Sampson et al. | |
| 2013/0117884 A1 | 5/2013 | Hargiss et al. | |
| 2013/0167264 A1 | 6/2013 | Sampson et al. | |
| 2013/0219570 A1 | 8/2013 | Lira et al. | |
| 2013/0269060 A1 | 10/2013 | Baum et al. | |
| 2013/0303440 A1 | 11/2013 | Sampson et al. | |
| 2013/0310543 A1 | 11/2013 | Sampson et al. | |
| 2014/0007292 A1 | 1/2014 | Cert et al. | |
| 2014/0033361 A1 | 1/2014 | Altier et al. | |
| 2014/0033363 A1 | 1/2014 | Sampson | |
| 2014/0196175 A1 | 7/2014 | Sampson et al. | |
| 2014/0223598 A1 | 8/2014 | Sampson et al. | |
| 2014/0223599 A1 | 8/2014 | Sampson et al. | |
| 2014/0245491 A1 | 8/2014 | Sampson et al. | |
| 2014/0298538 A1 | 10/2014 | Heinrichs et al. | |
| 2014/0366227 A1 | 12/2014 | Gatehouse et al. | |
| 2014/0373195 A1 | 12/2014 | Sampson et al. | |
| 2020/0040044 A1 | 2/2020 | Baum et al. | |
| 2020/0277340 A1 | 9/2020 | Baum et al. | |
| 2022/0306703 A1 | 9/2022 | Baum et al. | |
| 2025/0154210 A1 | 5/2025 | Baum et al. | |

FOREIGN PATENT DOCUMENTS

| | | |
|---|---|---|
| EP | 0189707 | 8/1986 |
| EP | 0218571 | 4/1987 |
| EP | 0508909 | 10/1992 |
| EP | 0924299 | 6/1999 |
| ES | 2203310 | 4/2004 |
| JP | 2009505679 | 2/2009 |
| JP | 2013514769 | 5/2013 |
| WO | 1990010076 | 9/1990 |
| WO | 1993008693 | 5/1993 |
| WO | 1999024581 | 5/1999 |
| WO | 2001014562 | 3/2001 |
| WO | 2001019859 | 3/2001 |
| WO | 2002014517 | 2/2002 |
| WO | 2002015701 | 2/2002 |
| WO | 2004020636 | 3/2004 |
| WO | 2007027777 | 3/2007 |
| WO | 2011075588 | 6/2011 |
| WO | 2012109430 | 8/2012 |
| WO | 2013134734 | 9/2013 |
| WO | 2014008054 | 1/2014 |
| WO | 201405881 | 4/2014 |

OTHER PUBLICATIONS

USPTO: Response to Non-Final Office Action regarding U.S. Appl. No. 17/671,011, filed May 29, 2024.

USPTO: Final Office Action regarding U.S. Appl. No. 17/671,011, mailed Aug. 21, 2024.

USPTO: Response to Final Office Action regarding U.S. Appl. No. 17/671,011, filed Sep. 17, 2024.

Baig et al., "cry Genes Profiling and the Toxicity of Isolates of Bacillus Thuringiensis from Soil Samples Against American Bollworm, Helicoverpa armigera," Journal of Applied Microbiology, 109:1967-1978 (2010).

Bravo et al., "Mode of Action of Bacillus Thuringiensis Cry and Cyt Toxins and their Potential fo rinsect Control," Toxins, 49:423-435 (2007).

Database UniProt, Database Accession No. D9US3MO (2010).

De Maagd et al., "Bacillus thuringiensis delta-endotoxin Cry1C domain ill can Function as a Specificity Determinant for Spodoptera exigua in Different, but Not All, Cry1=Cry1C Hybrids," Applied and Environmental Microbiology, 66 (4):1559-1563 (2000).

Della-Cioppa et al., "Translocation of the Precursor of 5-enolpyruvylshikimate-3-Phosphate Synthase into Chloroplasts of Higher Plants in vitro," Proceedings of the National Academy of Sciences USA, 83:6873-6877 (1986).

International Search Repot mailed on Jun. 6, 2016, in international Patent Application No. PCTUS2015/055800.

IUPAC-IUB Joint Commission on Biochemical Nomenclature, "Nomenclature and Symbolism fo Amino Acids and Peptides," European Journal of Biochemistry, 138:9-37 (1984).

James, "Global Status of Commercialized Biotech/GM Crops: 2012," iSAAA Brief No. 44 (2012).

Klee et al., 'Cloning of an Arabidopsis thaliana Gene Encoding 5-Enolpyruvylshikimate-3-Phosphate Synthase: Sequence Analysis and Manipulation to Obtain Glyphosate-Tolerant Plants, molecular & General Genetics, 210:437-442 (1987).

Knight et al., "A Strategy fo rShuffling Numerous Bacillus thuringiensis Crystal Protein Domains," Journal of Economic Entomology, 97:1805-1813 (2004).

Lucena et al., "Molecular Approaches to Improve the Insecticidal Activity of Bacillus Thuringiensis Cry toxins," Toxins, 6(8):2393-2423 (2014).

Pardo-Lopez et al., "Bacillsu thuringiensis Insecticidal Three-Domain Cry Toxins: Mode of Action, Insect Resistance and Consequences for Crop Protection," FEMS Microbiology Reviews, 37:3-22 (2013).

Thompson et al., "CLUSTAL W: Improving the Sensitivity of Progressive Multiple Sequence Alignment Through Sequence Weighting, Position-Specific Gap Penalties and Weight Matrix Choice," Nucleic Acids Research, 22:4673-4680 (1994).

Extended European Search Report and Opinion regarding European Application No. 20171022.5, dated Aug. 10, 2020.

(56) References Cited

OTHER PUBLICATIONS

Extended European Search Report and Opinion regarding European Application No. 20171024.1, dated Aug. 7, 2020.
Extended European Search Report and Opinion regarding European Application No. 20171026.6, dated Aug. 10, 2020.
Extended European Search Report and Opinion regarding European Application No. 20171028.2, dated Aug. 10, 2020.
Perlak, et al., "Insect Resistant Cotton Plants," Nature Biotechnology 8:9390943, 1990.
USPTO: Restriction Requirement regarding U.S. Appl. No. 16/874,186, dated Mar. 16, 2021.
USPTO: Response to Restriction Requirement regarding U.S. Appl. No. 16/874,186, filed Jun. 8, 2020.
USPTO: Non-Final Office Action regarding U.S. Appl. No. 16/874,186, dated Jun. 30, 2021.
UniProt Accession No. CR1FA, dated May 30, 2000.
Office Action regarding Peru App. No. 000604-2017/DIN, dated Jul. 8, 2021.
USPTO: Response to non-final Office Action regarding U.S. Appl. No. 16/874,186, filed Sep. 29, 2021.
USPTO: Notice of Allowance regarding U.S. Appl. No. 16/874,186, dated Nov. 3, 2021.
Fourgoux-Nicol et al., Plant Mol. Biol. (1999) 40:857-872.
Herrero et al., Biochem J. (2004) 384-507-513.
Abdul-Rauf et al., Curr. Microbiol. (1999) 39,94-98.
Pardo Lopez et al., Peptides (2009) 30:589-595.
GenBank Accession No. AF362020, dated Apr. 2, 2002.
GenBank Accession No. KC204726, dated Aug. 25, 2013.
Aronson et al., "Why Bacillus thuringiensis insecticidal toxins are so effective: unique features of their mode of action," FEMS Microbiology Letters, 195:1-8 (2001).

Bravo et al., "Evolution of Bacillus thuringiencis Cry toxins insecticidal activity," Microbial Biotechnology, 6:17-26 (2012).
Gen Bank Database, Apr. 25, 1994, Accession No. AAA 22344.1.
Gen Bank Database, Apr. 26, 1993, Accession No. AAA 22331.1.
GenBank Database, Apr. 18, 2005, Accession No. CAA 31951.1.
GenBank Database, Apr. 26, 1993, Accession No. AAA 22561.1.
GenBank Database, Aug. 24, 1998, Accession No. AAC 32850.1.
GenBank Database, Dec. 31, 2013, Accession No. AEH 31431.1.
GenBank Database, Nov. 18, 2005, Accession No. ABB 76664.1.
Hernandez-Rodriguez et al., "Shared Midgut Binding Sites for Cry1A. 105, CrylAa, Cry IAb, Cry IAc and CrylFa Proteins from Bacillus thuringiensis in Two Important Corn Pests, Ostrinia nubilalis and Spodoptera frugiperda," PLOS One, 8(7): e68164:1-9 (2013).
Office Action in corresponding Application No. JP 2017-0520352, mailed Feb. 5, 2019.
USPTO: Restriction Requirement regarding U.S. Appl. No. 16/658,938, dated Mar. 16, 2021.
USPTO: Response to Restriction Requirement regarding U.S. Appl. No. 16/658,938, filed Jun. 8, 2021.
USPTO: Non-Final Office Action regarding U.S. Appl. No. 16/658,938, dated Jun. 23, 2021.
USPTO: Response to Non-Final Office Action regarding U.S. Appl. No. 16/658,938, filed Sep. 22, 2021.
USPTO: Notice of Allowance regarding U.S. Appl. No. 16/658,938, dated Nov. 24, 2021.
USPTO: Requirement for Restriction/Election regarding U.S. Appl. No. 17/671,011, mailed Dec. 20, 2023.
USPTO: Response to Restriction Requirement regarding U.S. Appl. No. 17/671,011, filed Jan. 17, 2024.
USPTO: Non-Final Office Action regarding U.S. Appl. No. 17/671,011, mailed Apr. 4, 2024.
U.S. Appl. No. 19/030,863, filed Jan. 17, 2025, Baum, et al..
USPTO: Notice of Allowance regarding U.S. Appl. No. 17/671,011, mailed Dec. 26, 2024.

* cited by examiner

SEQUENCE LISTING

```
Sequence total quantity: 130
SEQ ID NO: 1              moltype = DNA   length = 3570
FEATURE                   Location/Qualifiers
misc_feature              1..3570
                          note = Recombinant nucleotide sequence used for expression
                           in a bacterial cell encoding TIC1100.
source                    1..3570
                          mol_type = other DNA
                          organism = synthetic construct
SEQUENCE: 1
atggagatag tgaataatca gaatcaatgc gtgccttata attgtttgaa taatcccgaa    60
atcgaaatat tagaaggcgg aagaatatca gttggtaata ccccaattga tatttctctt   120
tcgcttactc agtttctttt gagtgaattt gtcccaggtg cggggtttgt attaggatta   180
attgatttaa tatgggggatt tgtaggtcct tcccaatggg acgcatttct tgctcaagtg   240
gaacagttaa ttaaccaaag aatagcagaa gctgtaagaa atacagcaat tcaggaatta   300
gagggaatgg cacgggttta tagaacctat gctactgctt ttgctgagtg ggaaaaagct   360
cctgatgacc cagagctaag agaagcacta cgtacacaat ttacagcaac tgagacttat   420
ataagtggaa gaatatccgt tttaaaaatt caaacttttg aagtacagct gttatcagtg   480
tttgcccaag ctgcaaattt acatttatct ttattaagag acgttgtgtt ttttgggcaa   540
agatgggggtt tttcaacgac aaccgtaaat aattactaca atgatttaac agaagggatt   600
agtacctata cagattatgc tgtacgctgg tacaatacgg gattagaacg tgtatgggga   660
ccggattcta gagattgggt aaggtataat caatttagaa gagaattaac actaactgta   720
ttagatatcg ttgctctgtt cccgaattat gatagtagaa gatatccaat tcgaacagtt   780
tcccaattaa caagagaaat ttatacaaac ccagtattag aaaattttga tggtagtttt   840
cgaggctcgg ctcagggcat agaaagaagt attaggagtc cacatttgat ggatatactt   900
aacagtataa ccatctatac ggatgctcat aggggttatt attattggtc agggcatcaa   960
ataatggctt ctcctgtcgg tttttcgggg ccagaattca cgtttccgct atatggaacc  1020
atgggaaatg cagctccaca acaacgtatt gttgctcaac taggtcaggg cgtgtataga  1080
acattatcgt ccactttata tagaagacct tttaatatag ggataaataa tcaacaacta  1140
tctgttcttg acgggacaga atttgcttat ggaacctcct caaatttgcc atccgctgta  1200
tacagaaaaa gcggaacggt agattcgctg gatgaaatac cgccacagaa taacaacgtg  1260
ccacctaggc aaggatttag tcatcgatta agccatgttt caatgtttcg ttcaggcttt  1320
agtaatagta gtgtaagtat aataagagct cctatgttct cttggataca tcgtagtgct  1380
gaatttaata atataattgc atcggatagt attaatcaaa tacctttagt gaaaggattt  1440
agagtttggg ggggcaccctc tgtcattaca ggaccaggat ttacaggagg ggatatcctt  1500
cgaagaaata cctttggtga ttttgtatct ctacaagtca atattaattc accaattacc  1560
caaagatacc gtttaagatt tcgttacgct tccagtaggg atgcacgagt tatagtatta  1620
acaggagcgg catccacagg agtgggaggc caagttagtg taaatatgcc tcttcagaaa  1680
actatggaaa taggggagaa cttaacatct agaacattta gatataccga tttttagtaat  1740
ccttttcat ttagagctaa tccagatata attgggataa gtgaacaacc tctatttggt  1800
gcaggttcta ttagtagcgg tgaactttat atagataaaa ttgaaattat tctagcagat  1860
gcaacatttg aagcagaatc tgatttagaa gagcgcgcaa aggcggtgaa tgcgctgttt  1920
acgtctacaa accaactagg gctaaaaaca aatgtaacgg attatcatat tgatcaagtg  1980
tccaatttag ttacgtattt atcggatgaa ttttgtctgg atgaaaagcg agaattgtcc  2040
gagaaagtca aacatgcgaa gcgactcagt gatgaacgca atttactcca agattcaaat  2100
ttcaaagaca ttaataggca accagaacgt gggtggggcg gaagtacagg gattaccatc  2160
caaggagggg atgacgtatt taaagaaaat tacgtcacac tatcaggtac ctttgatgag  2220
```

```
tgctatccaa catatttgta tcaaaaaatc gatgaatcaa aattaaaagc ctttacccgt  2280
tatcaattaa gagggtatat cgaagatagt caagacttag aaatctattt aattcgctac  2340
aatgcaaaac atgaaacagt aaatgtgcca ggtacgggtt ccttatggcc gctttcagcc  2400
caaagtccaa tcggaaagtg tggagagccg aatcgatgcg cgccacacct tgaatggaat  2460
cctgacttag attgttcgtg tagggatgga gaaaagtgtg cccatcattc gcatcatttc  2520
tccttagaca ttgatgtagg atgtacagac ttaaatgagg acctaggtgt atgggtgatc  2580
tttaagatta agacgcaaga tgggcacgca agactaggga atctagagtt tctcgaagag  2640
aaaccattag taggagaagc gctagctcgt gtgaaaagag cggagaaaaa atggagagac  2700
aaacgtgaaa aattggaatg ggaaacaaat atcgtttata aagaggcaaa agaatctgta  2760
gatgctttat ttgtaaactc tcaatatgat caattacaag cggatacgaa tattgccatg  2820
attcatgcgg cagataaacg tgttcatagc attcgagaag cttatctgcc tgagctgtct  2880
gtgattccgg gtgtcaatgc ggctattttt gaagaattag aagggcgtat tttcactgca  2940
ttctccctat atgatgcgag aaatgtcatt aaaaatggtg attttaataa tggcttatcc  3000
tgctggaacg tgaaagggca tgtagatgta gaagaacaaa acaaccaacg ttcggtcctt  3060
gttgttccgg aatgggaagc agaagtgtca caagaagttc gtgtctgtcc gggtcgtggc  3120
tatatccttc gtgtcacagc gtacaaggag ggatatggag aaggttgcgt aaccattcat  3180
gagatcgaga acaatacaga cgaactgaag tttagcaact gcgtagaaga ggaaatctat  3240
ccaaataaca cggtaaactg taatgattat actgtaaatc aagaagaata cggaggtgcg  3300
tacacttctc gtaatcgagg atataacgaa gctccttccg taccagctga ttatgcgtca  3360
gtctatgaag aaaaatcgta tacagatgga cgaagagaga atccttgtga atttaacaga  3420
gggtataggg attacacgcc actaccagtt ggttatgtga caaaagaatt agaatacttc  3480
ccagaaaccg ataaggtatg gattgagatt ggagaaacgg aaggaacatt tatcgtggac  3540
agcgtggaat tactccttat ggaggaatga                                    3570
```

```
SEQ ID NO: 2               moltype = DNA   length = 3570
FEATURE                    Location/Qualifiers
misc_feature              1..3570
                          note = Synthetic nucleotide sequence designed for
                          expression in a plant cell encoding TIC1100.
source                    1..3570
                          mol_type = other DNA
                          organism = synthetic construct
SEQUENCE: 2
atggagattg tgaacaacca gaaccagtgc gttccttaca actgcttgaa caacccctgag  60
attgagattc ttgaggggtgg tagaatttct gttggcaaca ctcctattga catctctttg  120
agtttgactc aattcttgtt gagtgagttc gttcctggtg ctggtttcgt cttgggtttg  180
attgatttga tttggggttt cgttggtcct agtcaatggg atgctttctt ggctcaagtt  240
gagcaattga ttaaccagag gatcgctgag gctgtgagga cactgctat tcaagagttg  300
gagggtatgg ctagagttta cagaacttac gctactgctt tcgctgagtg ggagaaggct  360
cctgatgacc ctgagttgag ggaggctttg agaactcaat tcactgctac tgagacttac  420
atcagtggta gaatcagtgt cttgaagatt caaacttttcg aggttcaatt gctttctgtg  480
ttcgctcaag ctgcaaactt gcacttgtct ttgcttagat atgttgtgtt ctttggtcaa  540
agatggggtt tctccactac taccgtgaac aattactaca acgatttgac tgagggtatt  600
tctacttaca ctgattacgc tgttagatgg tacaacactg gtttggagag agtttggggt  660
ccagattcca gagattgggt cagatacaac cagttcagaa gggagttgac tttgactgtc  720
ttggacattg ttgctctctt ccctaactac gatagtcgtc gttaccctat tagaactgtt  780
tctcaactta ctagggaaat ctacactaac cctgttcttg agaacttcga tggtagtttc  840
cgtggtagtg ctcaagggat tgagcgttcc attcgttctc ctcatcttat ggacattctt  900
aactctatta ctatctacac tgatgctcat cgtggttact attactggtc tggtcatcaa  960
attatggcta gtcctgttgg tttcagtggt cctgagttca ctttccctct ttacggtact  1020
atgggcaacg ctgcacctca acagaggatc gttgctcaac ttggtcaagg tgtttacagg  1080
actctttctt caacccttta caggcgtcct ttcaacattg ggatcaacaa ccagcagctt  1140
tctgttcttg atggaaccga gttcgcttac ggaacctctt caaaccttcc tagtgctgtt  1200
tacaggaagt ctggaaccgt tgacagtctt gatgagattc caccgcagaa caataacgtt  1260
ccacccaggc aaggcttcag tcataggctt tctcatgttt ctatgttccg ctctggattc  1320
agcaactctt cagtttctat tatcagggct ccaatgttct cgtggattca taggtctgcc  1380
gagttcaaca acattatcgc ttccgatagc attaaccaga ttccacttgt taagggattc  1440
cgtgtttggg gaggcacctc tgttattacc ggaccaggct tcaccggagg cgacattctt  1500
cgtcgtaaca ccttcggaga tttcgtttca cttcaagtga acattaactc accaatcacc  1560
cagcgctaca ggcttcgctt ccgctacgca tcatccaggg atgcaaggggt gatcgtgctt  1620
accggagcag cctcaaccgg agtgggaggc caagtgagcg tgaacatgcc acttcagaag  1680
acgatggaga tcggcgagaa ccttacctca agaacctttc gttacaccga tttcagcaac  1740
ccattcagct ttcgtgcaaa cccagacatc ataggggatct cagagcagcc actgtttgga  1800
gctggatcaa tctcatccgg agagctttac atcgacaaga tcgagatcat actcgcagat  1860
gcaaccttcg aggctgagag cgatctggag cgtgcacaga aggcagtgaa cgcactcttt  1920
acctctacca accagctcgg actcaagacc aacgtgaccg attaccacat cgaccaagtg  1980
agcaacctcg tgacctacct ctcagatgag ttctgcttgg atgagaaacg cgaactcagc  2040
gagaaggtga agcacgcaaa gcgtctctca gatgagcgta acctcctcca ggatagcaat  2100
ttcaaggaca tcaatcgtca gccagagcgt ggatggggag gctcaaccgg aatcaccatc  2160
caggagggcg atgatgtgtt taaggagaat tacgtgacac tctccggaac attcgatgag  2220
tgctacccaa catcctcta tcagaagatc gacgagtcca agctcaaggc gttcacccgt  2280
tatcagctcc gtggctacat cgaggatagt caagacctgg aaatctacct catccgctac  2340
aatgcaaagc acgagacagt gaatgtgcca ggaacaggct ccctctggcc actctccgca  2400
cagtctccaa tcggcaagtg cggcgagcca aatcgctgcg cacatcatt cgagggtaat  2460
cccgacctgg actgctcctg ccgcgacggc gagagtgcg cccaccactc ccaccacttt  2520
agcctggaca tcgacgtggg ctgtacgac ctgaatgagg atctgggcgt gtgggtgatc  2580
tttaagatca agacacagga cggccacgcc gccctgggca atctggagtt tctggaggag  2640
aagcctctgg tgggcgaagc cctggcccgc gtgaagcgcg ccgagaagaa atggcgcgac  2700
aaacgcgaga aactggaatg ggaaacaaac atcgtgtaca agaagccaa agaatccgtg  2760
```

-continued

```
gacgccctat ttgtgaactc ccagtatgac cagctacagg ccgacacaaa catcgcgatg   2820
atccacgctg cggacaagcg cgtgcactcc atacgcgaag cctatctacc cgaactatcc   2880
gtgatacccg gcgtcaatgc cgcgatcttt gaagaattgg aaggccgcat cttcacagcc   2940
tttagcctct atgacgcccg aaatgtcatc aagaatggcg actttaacaa tgggctatcc   3000
tgttggaatg tcaaagggca cgtggacgtc gaagagcaga acaatcagcg atccgtctta   3060
gtcgtacccg aatgggaagc cgaagtctcc caggaagtcc gagtctgtcc tggtagaggt   3120
tacatcttga gagtgactgc ttacaaggag ggttacggtg agggatgcgt gactattcac   3180
gagattgaga acaacactga tgagttgaag ttcagtaact gcgtggagga ggaaatctac   3240
cccaacaaca ctgtgacttg taacgattac accgtgaacc aggaggaata cggaggcgct   3300
tacacctcca gaaaccgtgg atacaatgag gctccctcgg tccccgctga ttatgctcc   3360
gtctatgagg agaagtccta caccgatgga aggcgcgaga atccctgcga gttcaatcgc   3420
ggctatcgag actacactcc gctacccgtt ggctatgtca caaaggaact ggaatacttc   3480
ccggaaacag acaaagtctg gatcgaaatc ggcgaaacag aagggacgtt catagtcgat   3540
agcgtagaac ttctccttat ggaagaatga                                    3570

SEQ ID NO: 3                moltype = DNA   length = 3570
FEATURE                     Location/Qualifiers
misc_feature                1..3570
                            note = Synthetic nucleotide sequence designed for
                             expression in a plant cell encoding TIC1100.
source                      1..3570
                            mol_type = other DNA
                            organism = synthetic construct
SEQUENCE: 3
atggagattg tgaacaacca gaaccagtgc gttccttaca actgcttgaa caaccctgag   60
attgagattc ttgagggtgg tagaattttct gttggcaaca ctcctattga catctctttg   120
agtttgactc aattcttgtt gagtgagttc gttcctggtg ctggtttcgt cttgggtttg   180
attgatttga tttgggggttt cgttggtcct agtcaatggg atgctttctt ggctcaagtt   240
gagcaattga ttaaccagag gatcgctgag gctgtgagga cactgctat tcaagagttg   300
gagggtatgg ctagagttta cagaaacttac gctactgctt tctgagtg ggagaaggct   360
cctgatgacc ctgagttgag ggaggctttg agaactcaat tcactgctac tgagacttac   420
atcagtggta gaatcagtgt cttgaagatt caaacttcg aggttcaatt gctttctgtg   480
ttcgctcaag ctgcaaactt gcacttgtct ttgcttagag atgttgtgtt ctttggtcaa   540
agatggggtt tctccactac taccgtgaac aattactaca acgatttgac tgagggtatt   600
tctacttaca ctgattacgc tgttagatgg tacaacactg gtttggagag agtttggggt   660
ccagattcca gagattgggt cagatacaac cagttcagaa gggagttgac tttgactgtc   720
ttggacattg ttgctctctt ccctaactac gatagtcgtc gttacccat tagaactgtt   780
tctcaactta ctagggaaat ctacactaac cctgttcttg agaacttcga tggtagtttc   840
cgtggtagtg ctcaagggat tgagcgttct attcgttctc ctcatcttat ggacattctt   900
aactctatta ctatctacac tgatgctcat cgtggttact attactggtc tggtcatcaa   960
attatggcta gtcctgttgg tttcagtggt cctgagttca ctttccctct ttacggtact   1020
atgggcaacg ctgcacctca acagaggatc gttgctcaac ttggtcaagg tgtttacagg   1080
actctttctt caacccttta caggcgtcct ttcaacattg ggatcaacaa ccagcagctt   1140
tctgttcttg atggaaccga gttcgcttac ggaacctctt caaaccttcc tagtgctgtt   1200
tacaggaagt ctggaaccgt tgacagtctt gatgagattc caccgcagaa caataacgtt   1260
ccacccaggc aaggcttcag tcataggctt tctcatgttt ctatgttccg ctctggattc   1320
agcaactctt cagtttctat tatcagggct ccaatgtctt cgtggattca taggtctgcc   1380
gagttcaaca acattatcgc ttccgatagc attaaccaga ttccacttgt taagggattc   1440
cgtgtttggg gaggcacctc tgttattacc ggaccaggct tcaccggagg cgacattctt   1500
cgtcgtaaca ccttcggaga tttcgtttca cttcaagtga acattaactc accaatcacc   1560
cagcgctaca ggcttcgctt ccgctacgca tcatccgaag atgcaaggt gatcgtgctt   1620
accggagcag cctcaaccgg agtgggaggc caagtgagcg tgaacatgcc acttcagaag   1680
acgatggaga tcggcgagaa ccttacctca agaacctttc gttacaccga tttcagcaac   1740
ccattcagct ttcgtgcaaa cccagacatc ataggatct cagagcagcc actgtttgga   1800
gctggatcaa tctcatccgg agagcttac atcgacaaga tcgagatcat actcgcagat   1860
gcaaccttcg aggctgagag cgatctggag cgtgcacaga aggcagtgaa cgcactcttt   1920
acctctacca accagctcgg actcaagacc aacgtgaccg attaccacat cgaccaagtg   1980
agcaacctcg tgacctacct ctcagatgag ttctgcttgg atgagaaacg cgaactcagc   2040
gagaaggtga agcacgcaaa gcgtctctca gatgagcgta acctcctcca ggatagcaat   2100
ttcaaggaca tcaatcgtca gccagagcgt ggatgggggag gctcaaccgg aatcaccatc   2160
cagggaggcg atgatgtgtt taaggagaat tacgtggacac tctccggaac attcgatgag   2220
tgctacccaa catacctcta tcagaagatc gacgagtcca agctcaaggc gttcacccgt   2280
tatcagctcc gtggctacat cgaggatagt caagacctgg aaatctacct catccgctac   2340
aatgcaaagc acgagacagt gaatgtacca ggaacagcct ccctctggcc actctccgca   2400
cagtctccaa tcggcaagtg cggcgagcca aatcgctgcg cgccacacct gggagtggaat   2460
cccgacctgg actgctcctg ccgcgacggc gagaagtgcg cccaccactc ccaccacttt   2520
agcctggaca tcgacgtggg ctgtacagac ctgaatgagg atctgggcgt gtgggtgatc   2580
tttaagatca agacacagga cggccacgcc cgcctgggca atctggagt tctggaggag   2640
aagcctctgg tgggcgaagc cctggcccgc gtgaagcgcg ccgagaagaa atggcgcgac   2700
aaacgcgaga aactggaatg ggaaacaaac atcgtgtaca agaagccaa agaatccgtg   2760
gacgccctat ttgtgaactc ccagtatgac cagctacagg ccgacacaaa catcgcgatg   2820
atccacgctg cggacaagcg cgtgcactcc atacgcgaag cctatctacc cgaactatcc   2880
gtgatacccg gcgtcaatgc cgcgatcttt gaagaattgg aaggccgcat cttcacagcc   2940
tttagcctct atgacgcccg aaatgtcatc aagaatggcg actttaacaa tgggctatcc   3000
tgttggaatg tcaaagggca cgtggacgtc gaagagcaga acaatcagcg atccgtctta   3060
gtcgtacccg aatgggaagc cgaagtctcc caggaagtcc gagtctgtcc tggtagaggt   3120
tacatcttga gagtgactgc ttacaaggag ggttacggtg agggatgcgt gactattcac   3180
gagattgaga acaacactga tgagttgaag ttcagtaact gcgtggagga ggaaatctac   3240
cccaacaaca ctgtgacttg taacgattac accgtgaacc aggaggaata cggaggcgct   3300
```

```
tacacctcca gaaaccgtgg atacaatgag gctccctcgg tccccgctga ttatgcctcc  3360
gtctatgagg agaagtccta caccgatgga aggcgcgaga atccctgcga gttcaatcgc  3420
ggctatcgag actacactcc gctaccgtt  ggctatgtca caaaggaact ggaatacttc  3480
ccggaaacag acaaagtctg gatcgaaatc ggcgaaacag aagggacgtt catagtcgat  3540
agcgtagaac ttctccttat ggaagaatga                                    3570

SEQ ID NO: 4              moltype = AA   length = 1189
FEATURE                   Location/Qualifiers
REGION                    1..1189
                          note = Amino acid sequence of the chimeric protein TIC1100.
source                    1..1189
                          mol_type = protein
                          organism = synthetic construct
SEQUENCE: 4
MEIVNNQNQC VPYNCLNNPE IEILEGGRIS VGNTPIDISL SLTQFLLSEF VPGAGFVLGL  60
IDLIWGFVGP SQWDAFLAQV EQLINQRIAE AVRNTAIQEL EGMARVYRTY ATAFAEWEKA  120
PDDPELREAL RTQFTATETY ISGRISVLKI QTFEVQLLSV FAQAANLHLS LLRDVVFFGQ  180
RWGFSTTTVN NYYNDLTEGI STYTDYAVRW YNTGLERVWG PDSRDWVRYN QFRRELTLTV  240
LDIVALFPNY DSRRYPIRTV SQLTREIYTN PVLENFDGSF RGSAQGIERS IRSPHLMDIL  300
NSITIYTDAH RGYYYWSGHQ IMASPVGFSG PEFTFPLYGT MGNAAPQQRI VAQLGQGVYR  360
TLSSTLYRRP FNIGINNQQL SVLDGTEFAY GTSSNLPSAV YRKSGTVDSL DEIPPQNNNV  420
PPRQGFSHRL SHVSMFRSGF SNSSVSIIRA PMFSWIHRSA EFNNIIASDS INQIPLVKGF  480
RVWGGTSVIT GPGFTGGDIL RRNTFGDFVS LQVNINSPIT QRYRLRFRYA SSRDARVIVL  540
TGAASTGVGG QVSVNMPLQK TMEIGENLTS RTFRYTDFSN PFSFRANPDI IGISEQPLFG  600
AGSISSGELY IDKIEIILAD ATFEAESDLE RAQKAVNALF TSTNQLGLKT NVTDYHIDQV  660
SNLVTYLSDE FCLDEKRELS EKVKHAKRLS DERNLLQDSN FKDINRQPER GWGGSTGITI  720
QGGDDVFKEN YVTLSGTFDE CYPTYLYQKI DESKLKAFTR YQLRGYIEDS QDLEIYLIRY  780
NAKHETVNVP GTGSLWPLSA QSPIGKCGEP NRCAPHLEWN PDLDCSCRDG EKCAHHSHHF  840
SLDIDVGCTD LNEDLGVWVI FKIKTQDGHA RLGNLEFLEE KPLVGEALAR VKRAEKKWRD  900
KREKLEWETN IVYKEAKESV DALFVNSQYD QLQADTNIAM IHAADKRVHS IREAYLPELS  960
VIPGVNAAIF EELEGRIFTA FSLYDARNVI KNGDFNNGLS CWNVKGHVDV EEQNNQRSVL  1020
VVPEWEAEVS QEVRVCPGRG YILRVTAYKE GYGEGCVTIH EIENNTDELK FSNCVEEEIY  1080
PNNTVTCNDY TVNQEEYGGA YTSRNRGYNE APSVPADYAS VYEEKSYTDG RRENPCEFNR  1140
GYRDYTPLPV GYVTKELEYF PETDKVWIEI GETEGTFIVD SVELLLMEE            1189

SEQ ID NO: 5              moltype = DNA   length = 3672
FEATURE                   Location/Qualifiers
misc_feature              1..3672
                          note = Recombinant nucleotide sequence used for expression
                           in a bacterial cell encoding TIC860.
source                    1..3672
                          mol_type = other DNA
                          organism = synthetic construct
SEQUENCE: 5
atgacttcaa ataggaaaaa tgagaatgaa attatataatg ctttatcgat tccaacggta  60
tcgaatcctt ccacgcaaat gaatctatca ccagatgctc gtattgaaga tagcttgtgt  120
gtagccgagg tgaacaatat tgatccattt gttagcgcat caacagtcca aacgggtata  180
aacatagctg gtagaatatt gggcgtatta ggtgtgccgt ttgctggaca actagctagt  240
ttttatagtt ttcttgttgg ggaattatgg cctagtggca gagatccatg ggaaattttc  300
ctggaacatg tagaacaact tataagacaa caagtaacag aaaatactag gaatacggct  360
attgctcgat tagaaggtct aggaagaggc tatagatctt accagcaggc tcttgaaact  420
tggttagata accgaaatga tgcaagatca agaagcatta ttcttgagcg ctatgttgct  480
ttagaacttg acattactac tgctataccg cttttcagaa tacgaaatga agaagttcca  540
ttattaatga tatatgctca agctgcaaat ttacacctat tattattgag agacgcatcc  600
cttttggta  gtgaatgggg gatggcatct tccgatgtta accaatatta ccaagaacaa  660
atcagatata cagaggaata ttctaaccat tgcgtacaat ggtataatac agggctaaat  720
aacttaagag ggacaaatgc tgaaagttgg ttgcggtata tcaattccg  tagagaccta  780
acgttagggg tattagattt agtagcccta ttcccaagct atgatactcg cacttatcca  840
atcaatacga gtgctcagtt aacaagagaa atttatacag atccaattgg gagaacaaat  900
gcaccttcag gatttgcaag tacgaattgg tttaataata atgcaccatc gtttttctgcc  960
atagaggctg ccattttcag gcctccgcat ctacttgatt ttccagaaca acttacaatt  1020
tacagtgcat caagccgttg gagtagcact caacatatga attattgggt gggacatagg  1080
cttaacttcc gcccaatagg agggacatta aatacctcaa cacaaggact tactaataat  1140
acttcaatta atcctgtaac attacagtttt acgtctcgag acgtttatag aacagaatca  1200
aatgcaggga caaatatact atttactact cctgtgaatg gagtaccttg ggctagattt  1260
aattttataa accctcagaa tatttatgaa agaggcgcca ctacctacag tcaaccgtat  1320
cagggagttg ggattcaatt atttgattca gaaactgaat taccaccaga aacaacagaa  1380
cgaccaaatt atgaatcata gagtcataga ttatctcata taggactaat cataggaaac  1440
actttgagag caccagtcta ttcttggacg catcgtagtg cagatcgtac gaatacgatt  1500
ggaccaaata gaattaatca aatacctttta gtgaaaggat ttagagtttg gggggggcacc  1560
tctgtcatta caggaccagg atttacagga ggggatatcc ttcgaagaaa tacctttggt  1620
gattttgtat ctctacaagt caatattaat tcaccaatta cccaaagata ccgtttaaga  1680
tttcgttacg cttccagtag ggatgcacga gttatagtat taacaggagc ggcatccaca  1740
ggagtgggag gccaagttag tgtaaatatg cctcttcaga aactatgga aatagggggag  1800
aacttaaacat ctagaacatt tagatatacc gattttagta atcctttttc atttagagct  1860
aatccagata taattgggat aagtgaacaa cctctatttg gtgcaggttc tattagtagc  1920
ggtgaacttt atatagataa aattgaaatt attctagcag atgcaacatt tgaagcagaa  1980
tctgatttag aaagagcgca gaaggcggtg aatgcgctgt ttacgtctac aaaccaacta  2040
gggctaaaaa caaatgtaac ggattatcat attgatcaag tgtccaattt agttacgtat  2100
```

-continued

```
ttatcggatg aattttgtct ggatgaaaag cgagaattgt ccgagaaagt caaacatgcg   2160
aagcgactca gtgatgaacg caatttactc caagattcaa atttcaaaga cattaatagg   2220
caaccagaac gtgggtgggg cggaagtaca gggattacca tccaaggagg ggatgacgta   2280
tttaaagaaa attacgtcac actatcaggt acctttgatg agtgctatcc aacatatttg   2340
tatcaaaaaa tcgatgaatc aaaattaaaa gcctttaccc gttatcaatt aagagggtat   2400
atcgaagata gtcaagactt agaaatctat ttaattcgct acaatgcaaa acatgaaaca   2460
gtaaatgtgc caggtacggg ttccttatgg ccgctttcag cccaaagtcc aatcggaaag   2520
tgtggagagc cgaatcgatg cgcgccacac cttgaatgga atcctgactt agattgttcg   2580
tgtagggatg gagaaaagtg tgcccatcat tcgcatcatt tctccttaga cattgatgta   2640
ggatgtacag acttaaatga ggacctaggt gtatgggtga tctttaagat taagacgcaa   2700
gatgggcacg caagactagg gaatctagag tttctcgaag agaaaccatt agtaggagaa   2760
gcgctagctc gtgtgaaaag agcggagaaa aaatggagag acaaacgtga aaaattggaa   2820
tgggaaacaa atatcgttta taaagaggca aaagaatctg tagatgcttt atttgtaaac   2880
tctcaatatg atcaattaca agcggatacg aatattgcca tgattcatgc ggcagataaa   2940
cgtgttcata gcattcgaga agcttatctg cctgagctgt ctgtgattcc gggtgtcaat   3000
gcggctattt ttgaagaatt agaagggcgt attttcactg cattctccct atatgatgcg   3060
agaaatgtca ttaaaaatgg tgattttaat aatggcttat cctgctggaa cgtgaaaggg   3120
catgtagatg tagaagaaca aaacaaccaa cgttcggtcc ttgttgttcc ggaatgggaa   3180
gcagaagtgt cacaagaagt tcgtgtctgt ccgggtcgtg gctatatcct tcgtgtcaca   3240
gcgtacaagg agggatatgg agaaggttgc gtaaccattc atgagatcga gaacaataca   3300
gacgaactga agtttagcaa ctgcgtagaa gaggaaatct atccaaataa cacggtaacg   3360
tgtaatgatt atactgtaaa tcaagaagaa tacggaggtg cgtacacttc tcgtaatcga   3420
ggatataacg aagctccttc cgtaccagct gattatgcgc cagtctatga agaaaaatcg   3480
tatacagatg gacgaagaga gaatccttgt gaatttaaca gagggtatag ggattacacg   3540
ccactaccag ttggttatgt gacaaaagaa ttagaatact tcccagaaac cgataaggta   3600
tggattgaga ttggagaaac ggaaggaaca tttatcgtgg acagcgtgga attactcctt   3660
atggaggaat ag                                                       3672
```

```
SEQ ID NO: 6              moltype = DNA  length = 3672
FEATURE                  Location/Qualifiers
misc_feature             1..3672
                         note = Synthetic nucleotide sequence designed for
                         expression in a plant cell encoding TIC860.
source                   1..3672
                         mol_type = other DNA
                         organism = synthetic construct
SEQUENCE: 6
atgaccagca accggaagaa cgagaacgag atcatcaacg ccctgagcat ccgaccgtg    60
agcaaccta gcacccagat gaacctgagc cctgacgctc gcatcgagga ctccctctgc   120
gtggctgagg tgaacaacat cgaccgttc gtgtccgcct ccaccgtgca gaccggcatc    180
aacatcgcgg gccgcatcct cggcgtgctc ggcgtgcccc ttgcgggcca gctcgcctcc   240
ttctactcct tcctcgtggg agagctgtgg ccctccggcc gcgaccgtg ggagatcttc    300
ctggacacg tggagcagct catccgccag caagtcaccg agaacacccg caacaccgcc   360
atcgcccgcc tggagggcct gggccgtggc taccgctcct accagcaagc cctggagacc   420
tggctcgaca accgcaacga cgcccgctcc cgctccatca tcctggagcg ctacgtcgcc   480
ctggaactgg acatcaccac tgccatccca ctcttccgca tcaggaacga ggaggtgcct   540
ctgctgatgg tgtacgccca ggctgcgaac ctgcacctgc tgctgctgcg cgacgcaagc   600
ctgtttggct ccgagtgggg tatggcaagc tccgacgtca accagtacta ccaggagcag   660
atccgctaca ccgaggagta cagcaaccac tgcgtccagt ggtacaacac cggtctgaac   720
aatctcagag ggaccaacgc tgagagctgg ctgcgctaca ccagttccg gcgggatctg    780
accctaggtg tcctggatct ggtcgctctg ttcccgagct acgataccag gacgtaccct   840
atcaacacct ctgctcagct taccaggag atctacactg atcctatcgg taggactaac   900
gctcctagtg gtttcgccag cactaactgg ttcaacaaca acgcgcctag tttctctgcc   960
atcgaggcgg cgatcttccg gcctcctcac ctcctcgact tcccggagca gcttactatc   1020
tactctgcgt cttcgcggtg gtcttcgact cagcacatga actactgggt tggtcaccgg   1080
cttaacttcc gcccgattgg aggaactctt aacaccagta cgcaaggtct tacgaacaac   1140
acttccatca acccggttac gttgcagttc acgtctcggg acgtttaccg gacggagtcg   1200
aatgctggga cgaacatcct gttcacgaca ccggtgaatg gtgttccgtg ggcacgtttc   1260
aacttcatca acccgcagaa catctacgag cgtggagcaa cgacatactc gcaacctac   1320
caaggcgttg gcatccaact gtttgactcg gagacggaac tgccaccaga gacgacagaa   1380
cgtccgaatt acgagtcata ctcacacaga ctatcacaca ttggactcat tatcggaaac   1440
acactgagag caccagtgta ctcatggaca catcggtcag cagatcgtac gaacaccatc   1500
ggacccaatc ggatcaacca gatcccgctc gtgaagggct ccgcgtgtgt gggcggcacc   1560
tccgtcatca ccggtccggg cttcaccggc ggcacatcc tccgccgcaa caccttcggc   1620
gacttcgtgt cactccaagt gaacatcaac agcccgatca cccagcgcta tcgcctccgc   1680
ttccgctacg cctcctcccg cgacgctaga gtgatcgtgc tcaccggagc ggcgtccaca   1740
ggcgtaggcg gccaagtgtc tgtgaacatg ccgctccaga agactatgga gattggtgag   1800
aacctcacct ctcgcacctt ccgctacacc gacttctcca atccgttctc cttcagagcc   1860
aacccagaca tcatcggcat ctccgagcag cctctctttg gcgctggctc catctcctcc   1920
ggcgagctgt acatcgacaa gattgagatc atccttgccg acgccacctt cgaagctgag   1980
tccgatctcg agcgcgccca gaaggccgtg aacgccctct tcactagcac taaccagctc   2040
ggcctcaaga ctaacgtgac cgactaccac attgaccaag tgagcaacct agtgacctac   2100
cttagcgacg agttctgcct tgacgagaag cgtgagctga gcgagaaggt gaagcacgcc   2160
aagcgcctct ccgacgacgc gcaacctcctc caggactcca acttcaagga catcaaccgc   2220
cagcccgagc gcggctgggg cggtagcacc ggcatcacca tccaggggcgg tgacgatgtg   2280
ttcaaggaga actacgtgac cctctccggc accttcgacg agtgctaccc gacctacctc   2340
taccagaaga tcgacgagtc caagctcaag gcgttcaccc gctaccagct tcgcggctac   2400
atcgaggact cccaggatct ggagatctac ctcatccgct acaacgccaa gcacgagacc   2460
gtgaacgtgc ccggcaccgg ctccctctgg ccgctctccg cccagagccc tatcggcaag   2520
```

-continued

```
tgcggcgagc ccaaccgctg cgcgcctcac ctggagtgga accctgacct cgactgctcc   2580
tgccgcgacg gcgagaagtg cgcccaccat agccaccact tctctctcga catcgacgtg   2640
ggctgcaccg acctcaacga ggatctgggc gtgtgggtga tcttcaagat caagacccag   2700
gacggccacg ccaggctggg caacctggag ttcctggagg agaagcctct ggtgggtgag   2760
gccctggcca gggtcaagag ggctgagaag aaatggaggg acaagaggga gaagctggag   2820
tgggagacca acatcgtgta caaggaggct aaggagtccg tggacgctct gttcgtcaac   2880
tctcagtacg atcagctcca ggctgacacc aacatcgcta tgatccacgc tgcggataag   2940
agggtccact ctatcaggga ggcttacctg cctgagcttt ctgtcatccc tggtgtcaac   3000
gcggcaatct tcgaggaact tgagggccgc atcttcactg cgttctcgct ttacgatgcg   3060
cggaacgtca ttaagaacgg tgacttcaac aatggtcttt cgtcgtgaca cgtcaagggt   3120
catgtcgatg tcgaggaaca gaacaaccag cggtcggtcc ttgtcgttcc cgagtgggag   3180
gccgaggtct cgcaagaggt ccgggtctgc cctgggcgcg ggtacattct tcgtgtcact   3240
gcgtacaagg agggctacgg cgagggctgc gttactattc atgagattga gaacaatacg   3300
gatgagctta agtttagtaa ctgtgttgag gaggagatct acccgaacaa tacggttacg   3360
tgcaatgatt acacggtgaa ccaggaggaa tacggcggag catacacctc acgtaataga   3420
gggtacaatg aggcaccgtc agttccggca gattatgcct cagtttatga ggagaagtcc   3480
tacacggatg gaagacgcga gaatccatgt gagtttaata gaggataccg agactacaca   3540
ccactcccag ttggatacgt tacaaaggag ttggaatact cccagaaac agataaagtt    3600
tggatagaga tcggagaaac agaaggaacc ttcatcgtgg acagtgtaga actgctgctg   3660
atggaagaat ga                                                      3672
```

```
SEQ ID NO: 7              moltype = AA   length = 1223
FEATURE                  Location/Qualifiers
REGION                   1..1223
                         note = Amino acid sequence of the chimeric protein TIC860.
source                   1..1223
                         mol_type = protein
                         organism = synthetic construct
SEQUENCE: 7
MTSNRKNENE IINALSIPTV SNPSTQMNLS PDARIEDSLC VAEVNNIDPF VSASTVQTGI   60
NIAGRILGVL GVPFAGQLAS FYSFLVGELW PSGRDPWEIF LEHVEQLIRQ QVTENTRNTA   120
IARLEGLGRG YRSYQQALET WLDNRNDARS RSIILERYVA LELDITTAIP LPRIRNEEVP   180
LLMVYAQAAN LHLLLLRDAS LFGSEWGMAS SDVNQYYQEQ IRYTEEYSNH CVQWYNTGLN   240
NLRGTNAESW LRYNQFRRDL TLGVLDLVAL FPSYDTRTYP INTSAQLTRE IYTDPIGRTN   300
APSGFASTNW FNNNAPSFSA IEAAIFRPPH LLDFPEQLTI YSASSRWSST QHMNYWVGHR   360
LNFRPIGGTL NTSTQGLTNN TSINPVTLQF TSRDVYRTES NAGTNILFTT PVNGVPWARF   420
NFINPQNIYE RGATTYSQPY QGVGIQLFDS ETELPPETTE RPNYESYSHR LSHIGLIIGN   480
TLRAPVYSWT HRSADRTNTI GPNRINQIPL VKGFRVWGGT SVITGPGFTG GDILRRNTFG   540
DFVSLQVNIN SPITQRYRLR FRYASSRDAR VIVLTGAAST GVGGQVSVNM PLQKTMEIGE   600
NLTSRTFRYT DFSNPFSFRA NPDIIGISEQ PLFGAGSISS GELYIDKIEI ILADATFEAE   660
SDLERAQKAV NALFTSTNQL GLKTNVTDYH IDQVSNLVTY LSDEFCLDEK RELSEKVKHA   720
KRLSDERNLL QDSNFKDINR QPERGWGGST GITIQGGDDV FKENYVTLSG TFDECYPTYL   780
YQKIDESKLK AFTRYQLRGY IEDSQDLEIY LIRYNAKHET VNVPGTGSLW PLSAQSPIGK   840
CGEPNRCAPH LEWNPDLDCS CRDGEKCAHH SHHFSLDIDV GCTDLNEDLG VWVIFKIKTQ   900
DGHARLGNLE FLEEKPLVGE ALARVKRAEK KWRDKREKLE WETNIVYKEA KESVDALFVN   960
SQYDQLQADT NIAMIHAADK RVHSIREAYL PELSVIPGVN AAIFEELEGR IFTAFSLYDA   1020
RNVIKNGDFN NGLSCWNVKG HVDVEEQNNQ RSVLVVPEWE AEVSQEVRVC PGRGYILRVT   1080
AYKEGYGEGC VTIHEIENNT DELKFSNCVE EEIYPNNTVT CNDYTVNQEE YGGAYTSRNR   1140
GYNEAPSVPA DYASVYEEKS YTDGRRENPC EFNRGYRDYT PLPVGYVTKE LEYFPETDKV   1200
WIEIGETEGT FIVDSVELLL MEE                                           1223
```

```
SEQ ID NO: 8              moltype = DNA   length = 3564
FEATURE                  Location/Qualifiers
misc_feature             1..3564
                         note = Recombinant nucleotide sequence used for expression
                          in a bacterial cell encoding TIC867.
source                   1..3564
                         mol_type = other DNA
                         organism = synthetic construct
SEQUENCE: 8
atgacttcaa ataggaaaaa tgagaatgaa attataaatg ctttatcgat tccagctgta   60
tcgaatcatt ccgcacaaat gaatctatca accgatgctc gtattgagga tagcttgtgt   120
atagccgagg ggaacaatat cgatccattt gttagcgcat caacagtcca aacgggtatt   180
aacatagctg gtagaatact aggtgtatta ggcgtaccgt tcgctggaca aatagctagt   240
ttttatagtt ttcttgttgg tgaattatgg ccccgcggca gagatccttg ggaaattttc   300
ctagaacatg tcgaacaact tataagacaa caagtaacag aaaatactag ggatacggct   360
cttgctcgat tacaaggttt aggaaattcc tttagagcct atcaacagtc acttgaagat   420
tggctagaaa accgtgatga tgcaagaacg agaagtgttc tttataccca atatatagct   480
ttagaacttg attttcttaa tgcgatgccg cttttcgcaa ttagaaacca agaagttcca   540
ttattaatgg tatatgctca agctgcaaat ttacacctat tattattgag agatgcctct   600
ctttttggta gtgaatttgg gcttacatcc caagaaattc aacgttatta tgagcgccaa   660
gtggaaaaaa cgagagaata ttctgattat tgcgcaagat ggtataatac gggtttaaat   720
aatttgagag ggacaaatgc tgaaagttgg ttgcgatata tcaattccg tagagactta   780
acgctaggag tattagatct agtggcacta ttcccaagct agtgacacgt tgtttatcca   840
atgaatacca gtgctcaatt aacaagagaa atttatacag atccaattgg agaacaaat   900
gcaccttcag gatttgcaag tacgaattgg tttaataata atgcaccatc gttttctgcc   960
atagaggctg ccgttattag gcctccgcat ctacttgatt ttccagaaca gcttacaatt   1020
ttcagcgtat taagtcgatg gagtaatact caatatatga attactgggt gggacataga   1080
cttgaatcgc gaacaataag ggggtcatta agtacctcga cacacggaaa taccaatact   1140
```

-continued

```
tctattaatc ctgtaacatt acagttcaca tctcgagacg tttatagaac agaatcattt    1200
gcagggataa atatacttct aactactcct gtgaatggag taccttgggc tagatttaat    1260
tggagaaatc ccctgaattc tcttagaggt agccttctct atactatagg gtatactgga    1320
gtgggggacac aactatttga ttcagaaact gaattaccac cagaaacaac agaacgacca    1380
aattatgaat cttacagtca tagattatct aatataagac taatatcagg aaacactttg    1440
agagcaccag tatattcttg gacgcaccgt agtgcagatc gtacaaatac cattagttca    1500
gatagcatta cacaaatacc attggtaaag gcgcataccc tccaatcggg taccactgta    1560
gtaaaagggc cagggtttac aggaggggat atcctccgtc gaacaagtgg aggaccattt    1620
gcttttagta atgttaatct agattttaac ttgtcacaaa ggtatcgtgc tagaattcgt    1680
tatgcctcta ctactaacct aagaaatttac gtaacggttg caggtgaacg aattttttgct   1740
ggtcaatttg acaaaactat ggatgctggt gccccattaa cattccaatc ttttagttac    1800
gcaactatta atacagcttt tacattccca gaaagatcga gcagcttgac tgtaggtgcc    1860
gatacgttta gttcaggtaa tgaagtttat gtagatagat ttgaattaat cccagttact    1920
gcaaccttcg aggcagaatc tgatttagaa agagcacaaa aggcggtgaa tgagctgttt    1980
acttcttcca atcaaatcgg gttaaaaaca gatgtgacgg attatcatat tgatcaagta    2040
tccaatttag ttgagtgttt atctgatgaa ttttgtctgg atgaaaaaaa agaattgtcc    2100
gagaaagtca aacatgcgaa gcgacttagt gatgagcgga atttacttca agatccaaac    2160
tttagaggga tcaatagaca actagaccgt ggctggagag gaagtacgga tattaccatc    2220
caaggaggcg atgacgtatt caaagagaat tacgttacgc tattgggtac ctttgatgag    2280
tgctatccaa cgtatttata tcaaaaaata gatgagtcga aattaaaagc ctataccgt     2340
taccaattaa gagggtatat cgaagatagt caagacttag aaatctattt aattcgctac    2400
aatgccaaac acgaaacagt aaatgtgcca ggtacgggtt ccttatggcc gctttcagcc    2460
ccaagtccaa tcggaaaatg tgcccatcat tcccatcatt tctccttgga cattgatgtt    2520
ggatgtacag acttaaatga ggacttaggt gtatgggtga tattcaagat taagacgcaa    2580
gatggccatg caagactagg aaatctagaa tttctcgaag agaaaccatt agtaggagaa    2640
gcactagctc gtgtgaaaag agcggagaaa aaatggagag acaaacgtga aaaattggaa    2700
tgggaaacaa atattgttta taaagaggca aaagaatctg tagatgcttt atttgtaaac    2760
tctcaatatg atagattaca agcggatacc aacatcgcga tgattcatgc ggcagataaa    2820
cgcgttcata gcattcgaga agcttatctg cctgagctgt ctgtgattcc gggtgtcaat    2880
gcggctattt ttgaagaatt agaagggcgt attttcactg cattctccct atatgatgcg    2940
agaaatgtca ttaaaaatgg tgattttaat aatggcttat cctgctggaa cgtgaaaggg    3000
catgtagatg tagaagaaca aaacaaccac cgttcggtcc ttgttgttcc ggaatgggaa    3060
gcagaagtgt cacaagaagt tcgtgtctgt ccgggtcgtg gctatatcct tcgtgtcaca    3120
gcgtacaagg agggatatgg agaaggttgc gtaaccattc atatcaatcga gaacaataca    3180
gacgaactga agtttagcaa ctgtgtagaa gaggaagtat atccaaacaa cacggtaacg    3240
tgtaatgatt atactgcgac tcaagaagaa tatgagggta cgtacacttc tcgtaatcga    3300
ggatatgacg gagcctatga aagcaattct tctgtaccag ctgattatgc atcagcctat    3360
gaagaaaaag catatacaga tggacgaaga dacaatcctt gtgaatctaa cagaggatat    3420
ggggattaca caccactacc agctggctat gtgacaaaag aattagagta cttcccagaa    3480
accgataagg tatggattga gatcggagaa acggaaggaa cattcatcgt ggacagcgtg    3540
gaattacttc ttatggagga atag                                           3564

SEQ ID NO: 9          moltype = DNA   length = 3564
FEATURE               Location/Qualifiers
misc_feature         1..3564
                     note = Synthetic nucleotide sequence designed for
                      expression in a plant cell encoding TIC867.
source               1..3564
                     mol_type = other DNA
                     organism = synthetic construct
SEQUENCE: 9
atgaccagca accgaaagaa cgagaacgag atcatcaacg ccctgtccat accggccgtg    60
tcaaaccact ccgcccagat gaacctctcc accgacgcga ggatcgagga ctccctctgc    120
atcgccgagg gcaacaacat cgaccgttc gtgtctgcaa gcacggtcca gaccggcatc     180
aacatcgcgg gccgcatcct gggcgtgctc ggcgtgccgt tcgcgggtca aatcgcctct    240
ttctactcat tcctcgtggg cgagctgtgg ccgcgcggac gtgaccgtg ggaaatcttc      300
ctggagcacg ttgagcagct catccggcag caagtgaccg agaacaccag ggacaccgca    360
ctggcacggc tccagggcct tggcaacagc ttccgcgcct accagcagtc gctggaggac    420
tggctggaga accgagacga cgccagaacc cgctcagttc tgtacacaca gtacatcgca    480
ctagagctgg acttcctcaa cgctatgccg ctcttcgcca tccgtaacca ggaagtaccg    540
cttctgatgt tgtacgcaca agcagcgaac ctccatctgc tcctgctgcg agacgcatct    600
ctgttcggca gtgagttcgg gctgacgagc caggagatcc agcgctacta cgagcgccaa    660
gtggagaaga ctcgtgagta cagcgactac tgcgcgcgct ggtacaacac gggcttgaac    720
aaccttcgcg ggacaaacgc cgaatcctgg cttcgctaca acagttccg ccgcgacctc    780
acgctgggtg tgctggacct ggtcgcgctc ttcccgtcct acgacacacg ggtgtaccca    840
atgaacacga cgcacagct cacccgtgag atctacacag atcccatcgg ccgcaccaac    900
gctcccagtg gcttcgcaag cacgaattgg ttcaacaata acgctcctc tttctctgcc     960
atcgaggccg ctgtcatcag accgccgcac ttactcgatt tcccggagca gctcactatc    1020
ttctctgtgt tgtcccggtg gtcgaacacg cagtacatga actactgggt gggccacagg    1080
ctagagagcc ggaccatccg tggcagtctc tcaacctcga cccacggcaa cacgaacacg    1140
agcatcaacc ctgtcactct ccagtttaca tctagggacg tttacaggac agagtcgttc    1200
gctggcatta acattctgtt gaccactccg gtgaacggcg tcccttgggc ccgcttcaac   1260
tggaggaatc ctctgaactc actgcgcggc agccttctct cactatcgg ctacaccggc     1320
gttgggacaa aactcttcga ctcggagacc gagctgccga ccgagaccaa ccgagcggcct   1380
aactacgaga gttattcaca caggctctcc aacatccgct tgatttctgg gaacaccttg    1440
cgggctccgg tgtactcctg gacgcaccgc agcgccgaca gaactaatac catcagctcc    1500
gactcgatca cccagatccc gctggtgaag gctcacacgc ttcagtcggg caccacagtc    1560
gtcaaggggc ctggcttcac cggcggcgac atcctgcgtc gcacatctgg cggacccttc     1620
gccttcagca acgtgaactt ggacttcaat ttgtcacagc ggtatcgtgc cagaatccgg    1680
```

-continued

```
tacgccagca ctacgaacct gcgaatctat gttactgtgg cgggcgagcg gatcttcgcc    1740
gggcaattcg acaagacgat ggacgcggga gcacctctga cattccagtc attctcttac    1800
gccacgatca acacggcatt cacgtttccg gagcgttcca gtagcctgac cgtgggcgct    1860
gataccttca gtagcgggaa cgaggtgtac gttgaccgtt tcgagctgat cccggtcacc    1920
gccaccttcg aagctgagtc ggacctggag cgtgcacaga aggcagtcaa cgagctgttc    1980
acctctagca accagatcgg cctcaagacc gacgtcacag actaccacat cgaccaagtg    2040
tccaacctgg tcgagtgcct tagcgacgag ttctgcctag acgagaagaa ggagctgtcg    2100
gagaaggtca aacacgccaa gcgtctgagc gatgagcgca acctgctcca agaccctaac    2160
ttccgtggca tcaacaggca gcttgaccgt ggctggcgcg gctcgacgga catcacgatc    2220
cagggtggcg acgacgtatt caaggagaat tacgtgacct tgcttgggac gtttgacgag    2280
tgctatccca cctacctcta ccagaagatt gatgaatcga aattgaaggc gtacacgaga    2340
taccagctcc gtggctacat cgaggacagc caggacttgg agatctacct catacgctac    2400
aacgctaaac atgagaccgt gaacgtccct gggacgggca gtctgtggcc actctctgct    2460
cctagcccta tcggcaagtg cgctcaccac tcgcaccact tcagccttga catcgacgtg    2520
ggatgtactg acctcaacga agacctgggc gtctgggtta tcttcaagat caagacccag    2580
gacggccacg cccgactcgg caacctggag ttcctggagg agaaaccact ggtgggcgag    2640
gcgctcgccc gcgtgaagcg tgccgagaag aagtggcggg acaagaggga gaagctagaa    2700
tgggagacga acatcgtgta caaggaggcc aaggaaagcg tcgatgccct gttcgtgaac    2760
tcacagtacg accgtctcca ggcggacacg aacatcgcca tgatccacgc ggctgacaag    2820
cgcgtccact ccatccgcga ggcgtactta ccggagctgt cggtgatccc aggcgtaaac    2880
gcggcgatct tcgaggagct agagggacgc atcttcacag cgttcagcct gtacgacgca    2940
cgcaacgtca tcaagaacgg cgatttcaac aacggactgt cctgctggaa cgtgaagggc    3000
cacgtcgatg tcgaggaaca gaacaaccac cgctctgtcc tggtggtccc agagtgggag    3060
gccgaggtct cccaggaggt ccgcgtgtgc cctgggcgtg gctacatcct ccgtgtgaca    3120
gcctacaagg agggctacgg tgagggctgc gtcaccattc acgagatcga gaacaacact    3180
gacgaactca agttctcgaa ttgcgtggag gaggaggtgt acccgaacaa tacggtgacg    3240
tgcaacgact acacggcaac ccaagaggag tacgagggca cctacaccag taggaaccgt    3300
ggctacgacg gtgcctacga gtcgaactcc agcgtccctg cggactacgc cagcgcgtac    3360
gaggagaagg cttacaccga cggacgccgg gacaacccat gcgagagcaa ccgtggctac    3420
ggcgactaca ctcctctccc ggccggatac gtcacaaagg agctggagta tttcccagag    3480
acggacaagg tgtggatcga aatcggagag acagagggaa ccttcatcgt ggacagcgtg    3540
gagctgctcc tcatggagga gtga                                          3564
```

SEQ ID NO: 10          moltype = AA   length = 1187
FEATURE                Location/Qualifiers
REGION                 1..1187
                       note = Amino acid sequence of the chimeric protein TIC867.
source                 1..1187
                       mol_type = protein
                       organism = synthetic construct SEQUENCE: 10
```
MTSNRKNENE IINALSIPAV SNHSAQMNLS TDARIEDSLC IAEGNNIDPF VSASTVQTGI    60
NIAGRILGVL GVPFAGQIAS FYSFLVGELW PRGRDPWEIF LEHVEQLIRQ QVTENTRDTA    120
LARLQGLGNS FRAYQQSLED WLENRDDART RSVLYTQYIA LELDFLNAMP LFAIRNQEVP    180
LLMVYAQAAN LHLLLLRDAS LFGSEFGLTS QEIQRYYERQ VEKTREYSDY CARWYNTGLN    240
NLRGTNAESW LRYNQFRRDL TLGVLDLVAL FPSYDTRVYP MNTSAQLTRE IYTDPIGRTN    300
APSGFASTNW FNNNAPSFSA IEAAVIRPPH LLDFPEQLTI FSVLSRWSNT QYMNYWVGHR    360
LESRTIRGSL STSTHGNTNT SINPVTLQFT SRDVYRTESF AGINILLTTP VNGVPWARFN    420
WRNPLNSLRG SLLYTIGYTG VGTQLFDSET ELPPETTERP NYESYSHRLS NIRLISGNTL    480
RAPVYSWTHR SADRTNTISS DSITQIPLVK AHTLQSGTTV VKGPGFTGGD ILRRTSGGPF    540
AFSNVNLDFN LSQRYRARIR YASTTNLRIY VTVAGERIFA GQFDKTMDAG APLTFQSFSY    600
ATINTAFTFP ERSSSLTVGA DTFSSGNEVY VDRFELIPVT ATFEAESDLE RAQKAVNELF    660
TSSNQIGLKT DVTDYHIDQV SNLVECLSDE FCLDEKKELS EKVKHAKRLS DERNLLQDPN    720
FRGINRQLDR GWRGSTDITI QGGDDVFKEN YVTLLGTFDE CYPTYLYQKI DESKLKAYTR    780
YQLRGYIEDS QDLEIYLIRY NAKHETVNVP GTGSLWPLSA PSPIGKCAHH SHHFSLDIDV    840
GCTDLNEDLG VWVIFKIKTQ DGHARLGNLE FLEEKPLVGE ALARVKRAEK KWRDKREKLE    900
WETNIVYKEA KESVDALFVN SQYDRLQADT NIAMIHAADK RVHSIREAYL PELSVIPGVN    960
AAIFEELEGR IFTAFSLYDA RNVIKNGDFN NGLSCWNVKG HVDVEEQNNH RSVLVVPEWE    1020
AEVSQEVRVC PGRGYILRVT AYKEGYGEGC VTIHEIENNT DELKFSNCVE EEVYPNNTVT    1080
CNDYTATQEE YEGTYTSRNR GYDGAYESNS SVPADYASAY EEKAYTDGRR DNPCESNRGY    1140
GDYTPLPAGY VTKELEYFPE TDKVWIEIGE TEGTFIVDSV ELLLMEE                 1187
```

SEQ ID NO: 11          moltype = DNA   length = 3642
FEATURE                Location/Qualifiers
misc_feature           1..3642
                       note = Recombinant nucleotide sequence used for expression
                        in a bacterial cell encoding TIC867_20.
source                 1..3642
                       mol_type = other DNA
                       organism = synthetic construct SEQUENCE: 11
```
atgacttcaa ataggaaaaa tgagaatgaa attataaatg ctttatcgat tccagctgta    60
tcgaatcatt ccgcacaaat gaatctatca accgatgctc gtattgagga tagcttgtgt    120
atagccgagg ggaacaatat cgatccattt gttagcgcat caagtgtcca aacgggtatt    180
aacatagctg gtagaatact aggtgtatta ggcgtaccgt ttgctggaca aatagctagt    240
ttttatagtt ttcttgttgg tgaattatgg ccccgcggca gagatccttg ggaaattttc    300
ctagaacatg tcgaacaact tataagacaa caagtaacag aaaatactag ggatacggct    360
cttgctcgat tacaaggttt aggaaattcc tttagagcct atcaacagtc acttgaagat    420
tggctagaaa accgtgatga tgcaagaacg agaagtgttc tttatcccca atatatagcc    480
```

```
ttagaacttg attttcttaa tgcgatgccg cttttcgcaa ttagaaacca agaagttcca   540
ttattaatgg tatatgctca agctgcaaat ttacacctat tattattgag agatgcctct   600
cttttttggta gtgaatttgg gcttacatcc caagaaattc aacgttatta tgagcgccaa   660
gtggaaaaaa cgagagaata ttctgattat tgcgcaagat ggtataatac gggtttaaat   720
aatttgagag ggacaaatgc tgaaagttgg ttgcgatata atcaattccg tagagactta   780
acgctaggag tattagatct agtggcacta ttcccaagct atgacacgcg tgtttatcca   840
atgaatacca gtgctcaatt aacaagagaa atttatacag atccaattgg gagaacaaat   900
gcaccttcag gatttgcaag tacgaattgg tttaataata atgcaccatc gttttctgcc   960
atagaggctg ccgttattag gcctccgcat ctacttgatt ttccagaaca gcttacaatt  1020
ttcagcgtat taagtcgatg gagtaatact caatatatga attactgggt gggacataga  1080
cttgaatcgc gaacaataag ggggtcatta agtacctcga cacacggaaa taccaatact  1140
tctattaatc ctgtaacatt acagttcaca tctcgagacg tttatagaac agaatcattt  1200
gcagggataa atatacttct aactactcct gtgaatggag taccttgggc tagatttaat  1260
tggagaaatc ccctgaattc tcttagaggt agccttctct atactatagg gtatactgga  1320
gtggggacac aactatttga ttcagaaact gaattaccac cagaaacaac agaacgacca  1380
aattatgaat cttacagtca tagattatct aatataagac taatatcagg aaacactttg  1440
agagcaccag tatattcttg gacgcaccgt agtgcgatc gtacaaatac cattagttca  1500
gatagcatta cacaaatacc attggtaaag gcgcataccc tccaatcggt taccactgta  1560
gtaaaagggc cagggtttac aggagggggat atcctccgtc gaacaagtgg aggaccattt  1620
gcttttagta atgttaatct agattttaac ttgtcacaaa ggtatcgtgc tagaattcgt  1680
tatgcctcta ctactaacct aagaatttac gtaacggttg caggtgaacg aatttttgct  1740
ggtcaatttg acaaaactat ggatgctggt gcccatcca cattccaatc ttttagttac  1800
gcaactatta atacagcttt tacattccca gaaagatcga gcagcttgac tgtaggtgcc  1860
gatacgttta gttcaggtaa tgaagtttat gtagatagat ttgaattaat cccagttact  1920
gcaacctttg aggcagaata tgatttagaa agagcgcaaa aggtggtgaa tgccctgttt  1980
acgtctacaa accaactagg gctaaaaaca gatgtgaccg attatcatat tgatcaggta  2040
tccaatctag ttgcgtgttt atcggatgaa ttttgtctgg atgaaaagag agaattgtcc  2100
gagaaagtta aacatgcaaa gcgactcagt gatgagcgga atttacttca agatccaaac  2160
ttcagaggga tcaataggca accagaccgt ggctggagag gaagtacgga tattactatc  2220
caaggaggag atgacgtatt caaagagaat tacgttacgc taccgggtac ctttgatgag  2280
tgctatccaa cgtatttata tcaaaaaata gatgagtcga aattaaaagc ctataccgt   2340
tatcaattaa gagggtatat cgaagatagt caagacttag aaatctattt aattcgttac  2400
aatgcaaaac acgaaatagt aaatgtacca ggtacaggaa gtttatggcc tctttctgta  2460
gaaaatcaaa ttggaccttg tggagaaccg aatcgatgcg cgccacacct tgaatggaat  2520
cctgatttac actgttcctg cagagacggg gaaaaatgtg cacatcattc tcatcatttc  2580
tctttggaca ttgatgttgg atgtacagac ttaaatgagg acttaggtgt atgggtgata  2640
ttcaagatta agacgcaaga tggccacgca cgactaggga atctagagtt tctcgaagag  2700
aaaccattat taggagaagc actagctcgt gtgaaaagag cggagaaaaa atggagagac  2760
aaacgcgaaa cattacaatt ggaaacaact atcgtttata aagaggcaaa agaatctgta  2820
gatgctttat ttgtaaactc tcaatatgat agattacaag cggatacgaa catcgcgatg  2880
attcatgcgg cagataaacg cgttcataga attcgagaag cgtatctgcc ggagctgtct  2940
gtgattccgg gtgtcaatgc ggctattttt gaagaattag aagagcgtat tttcactgca  3000
ttttccctat atgatgcgag aaatatattt aaaaatgcag atttcaataa tggcttatta  3060
tgctggaacg tgaaagggca tgtagaggta gaagaacaaa acaatcaccg ttcagtcctg  3120
gttatcccag aatgggaggc agaagtgtca caagaggttc gtgtctgtcc aggtcgtggc  3180
tatatcctc gtgttacagc gtacaaagag ggatatggag aaggttgcgt aacgatccat  3240
gagatcgaga acaatacaga cgaactgaaa ttcaacaact gtgtagaaga ggaagtatat  3300
ccaaacaaca cggtaacgtg tattaattat actgcgactc aagaagaata tgagggtacg  3360
tacacttctc gtaatcgagg atatgacgaa gcctatggta ataacccttc cgtaccagct  3420
gattatgcgt cagtctatga agaaaaatcg tatacagata gacgaagaga gaatccttgt  3480
gaatctaaca gaggatatg agattacaca ccactaccag ctggttatgt aacaaaggaa  3540
ttagagtact cccagagac cgataaggta tggattgaga ttggagaaac agaaggaaca  3600
ttcatcgtgg acagcgtgga attactcctt atggaggaat ag                      3642
```

```
SEQ ID NO: 12              moltype = DNA   length = 3642
FEATURE                    Location/Qualifiers
misc_feature              1..3642
                           note = Synthetic nucleotide sequence designed for
                            expression in a plant cell encoding TIC867_20.
source                     1..3642
                           mol_type = other DNA
                           organism = synthetic construct
SEQUENCE: 12
atgaccagca accgaaagaa cgagaacgag atcatcaacg ccctgtccat accggccgtg   60
tcaaaccact ccgcccagat gaacctctcc accgacgcga ggatcgagga ctccctctgc  120
atcgccgagg gcaacaacat cgaccgttc gtgtctgcaa gcacggtcca gaccggcatc  180
aacatcgcgg gccgcatcct gggcgtgctc ggcgtgccct cgcgggtca aatcgcctct   240
ttctactcat tcctcgtggg cgagctgtgg ccgcgcggac gtgaccgtg ggaaatcttc  300
ctggacgaca ttgagcagct catccggcag caagtgaccg agaacaccag ggacaccgca  360
ctggcacggc tccagggcct tggcaacagc ttccgcgcct accagcagtc gctggaggac  420
tggctcggaga accgagacga cgccagaacc cgctcagttc tgtacacaca gtacatcgcc  480
ctagagctga acttcctcaa cgctatgccg ctcttcgcca tccgtaacca ggaagtaccg   540
cttctgatgg tgtacgcaca agcagcgaac ctccatctgc tcctgctgcg agacgcatct  600
ctgttcggca gtgagttcgg gctgacgagc caggagatcc agctacta cgagcgccaa   660
gtggagaaga ctcgtgagta cagcgactac tgcgcgcgct ggtacaacac gggcttgaac  720
aaccttcgcg ggacaaacgc cgaatcctgg cttcgctaca accagttccg ccgcgacctc  780
acgctgggtg tgctggacct ggtcgcgctc ttccgtcct cgacacacg ggtgtaccca  840
atgaacacga gcgcacagct cacccgtgag atctacacag atcccatcgg ccgcaccaac  900
gctcccagtg gcttcgcaag cacgaattgg ttcaacaata acgctccttc tttctctgcc  960
```

-continued

```
atcgaggccg ctgtcatcag accgccgcac ttactcgatt tcccggagca gctcactatc  1020
ttctctgtgt tgtcccggtg gtcgaacacg cagtacatga actactgggt gggccacagg  1080
ctagagagcc ggaccatccg tggcagtctc tcaacctcga cccacggcaa cacgaacacg  1140
agcatcaacc ctgtcactct ccagtttaca tctaggacg tttacaggac agagtcgttc  1200
gctggcatta acattctgtt gaccactccg gtgaacggcg tcccttgggc ccgcttcaac  1260
tggaggaatc ctctgaactc actgcgcggc agccttctct acactatcgg ctacaccggc  1320
gttgggacgc aactcttcga ctcggagacc gagctgccgc ccgagaccac cgagcggcct  1380
aactacgaga gttattcaca caggctctcc aacatccgct tgatttctgg gaacaccttg  1440
cgggctccgg tgtactcctg gacgcaccgc agcgccgaca gaactaatac catcagctcc  1500
gactcgatca cccagatccc gctggtgaag gctcacacgc ttcagtcggg caccacagtc  1560
gtcaagggcc ctggcttcac cggcggcgac atcctgcgtc gcacatctgg cggacccttc  1620
gccttcagca acgtgaactt ggacttcaat ttgtcacagc ggtatcgtgc cagaatccgg  1680
tacgccagca ctacgaacct gcgaatctat gttactgtgg cgggcgagcg gatcttcgcc  1740
gggcaattcg acaagacgat ggacgcggga gcacctctga cattccagtc attctcttac  1800
gccacgatca acacggcatt cacgtttccg gagcgttcca gtagcctgac cgtgggcgct  1860
gataccttca gtagcgggaa cgaggtgtac gttgaccgtt tcgagctgat cccggtcacc  1920
gccaccttcg aggccgagta cgaccttgag cgcgcccaga aggtggtgaa cgccctcttc  1980
actagcacta accagctagg cctgaagact gacgtgaccg actaccacat cgaccaagtg  2040
agcaacctag tggcctgcct ctccgacgag ttctgcctcg acgagaagcg cgagctgtcc  2100
gagaaggtga agcacgccaa gcgcctctcc gacgagcgca acctgctcca ggaccccaac  2160
ttcagggca tcaacaggca gcccgaccgc ggctggcgcg gctccaccga catcaccatc  2220
cagggcggtg acgacgtatt caaggagaac tacgttaccc tcccggcac cttcgacgag  2280
tgttacccca cctacctcta ccagaagatc gacgagtcca agctgaaggc ctacaccgc  2340
taccagctcc gcggctacat cgaggactcc caggacctgg aaatctacct catccgctac  2400
aacgccaagc acgagatcgt gaacgtgcct ggcaccggca gcctctggcc tctcagcgtg  2460
gagaaccaga tcggcccttg cggcgagcct aaccgctgcg cccctcacct cgagtggaac  2520
cctgacctcc actgctcgtg cagggacggc gagaagtgcg cccaccatag ccaccacttc  2580
tctctggaca tcgacgtggg ctgcaccgac ctgaacgagg acctgggcgt gtgggttatc  2640
ttcaagatca agacccagga cggtcacgcc aggctgggta acctggagtt ccttgaggaa  2700
aagcctctgc tggggaggc cctggccagg gtcaagaggc ctgagaagaa atggagggat  2760
aagagggaga ccctgcagct ggagaccact atcgtctaca aggaggctaa ggagtctgtc  2820
gatgctctgt tcgtcaactc tcagtacgat agactgcaag ctgataccaa catcgctatg  2880
atccacgctg cggataagcg ggtccaccgg atccgggagg cttaccttcc ggagctttct  2940
gtcatcccgg gtgtcaacgc tgcgatcttc gaggaacttg aggaacggat cttcactgcg  3000
tttagtcttt acgatgcgcg gaacatcatc aagaacgggg acttcaacaa tggtctgctg  3060
tgctggaacg tcaagggtca tgtcgaggtc gaggaacaaa acaatcatcg tagtgtcctt  3120
gtcattcctg agtgggaggc ggaggtctct caagaggtcc gtgtttgccc ggggcgtggg  3180
tacattcttc gtgttactgc gtacaaggag gggtacgggg aggggtgcgt tactattcat  3240
gagattgaga acaatcatga tgagcttaag ttcaacaatt gtgttgagga ggaggtttac  3300
ccgaacaata ctgttacgtg catcaactac acggcaacgc aagaggaata cgagggacg  3360
tacacctcgc gtaatagagg gtatgatgag gcgtacggaa acaacccgtc ggttccagca  3420
gattatgcct cggtttatga ggagaagtcg tacacggata gacgacgcga gaatccatgt  3480
gagtcaaatc gaggatacgg agattacaca ccattaccag tacacggta tacaaaggag  3540
ttggaatact tcccggaaac agataaagtt tggattgaaa tcggagaaac agaaggaaca  3600
ttcatcgtcg actcagtaga attgttgttg atggaagaat ga                     3642
```

SEQ ID NO: 13        moltype = AA   length = 1213
FEATURE              Location/Qualifiers
REGION               1..1213
                     note = Amino acid sequence of the chimeric protein variant
                     TIC867_20.
source               1..1213
                     mol_type = protein
                     organism = synthetic construct
SEQUENCE: 13
```
MTSNRKNENE IINALSIPAV SNHSAQMNLS TDARIEDSLC IAEGNNIDPF VSASTVQTGI   60
NIAGRILGVL GVPFAGQIAS FYSFLVGELW PRGRDPWEIF LEHVEQLIRQ QVTENTRDTA  120
LARLQGLGNS FRAYQQSLED WLENRDDART RSVLYTQYIA LELDFLNAMP LFAIRNQEVP  180
LLMVYAQAAN LHLLLLRDAS LFGSEFGLTS QEIQRYYERQ VEKTREYSDY CARWYNTGLN  240
NLRGTNAESW LRYNQFRRDL TLGVLDLVAL FPSYDTRVYP MNTSAQLTRE IYTDPIGRTN  300
APSGFASTNW FNNNAPSFSA IEAAVIRPPH LLDFPEQLTI FSVLSRWSNT QYMNYWVGHR  360
LESRTIRGSL STSTHGNTNT SINPVTLQFT SRDVYRTESF AGINILLTTP VNGVPWARFN  420
WRNPLNSLRG SLLYTIGYTG VGTQLFDSET ELPPETTERP NYESYSHRLS NIRLISGNTL  480
RAPVYSWTHR SADRTNTISS DSITQIPLVK AHTLQSGTTV VKGPGFTGGD ILRRTSGGPF  540
AFSNVNLDFN LSQRYRARIR YASTTNLRIY VTVAGERIFA GQFDKTMDAG APLTFQSFSY  600
ATINTAFTFP ERSSSLTVGA DTFSSGNEVY VDRFELIPVT ATFEAEYDLE RAQKVVNALF  660
TSTNQLGLKT DVTDYHIDQV SNLVACLSDE FCLDEKRELS EKVKHAKRLS DERNLLQDPN  720
FRGINRQPDR GWRGSTDITI QGGDDVFKEN YVTLPGTFDE CYPTYLYQKI DESKLKAYTR  780
YQLRGYIEDS QDLEIYLIRY NAKHEIVNVP GTGSLWPLSV ENQIGPCGEP NRCAPHLEWN  840
PDLHCSCRDG EKCAHHSHHF SLDIDVGCTD LNEDLGVWVI FKIKTQDGHA RLGNLEFLEE  900
KPLLGEALAR VKRAEKKWRD KRETLQLETT IVYKEAKESV DALFVNSQYD RLQADTNIAM  960
IHAADKRVHR IREAYLPELS VIPGVNAAIF EELEERIFTA FSLYDARNII KNGDFNNGLL  1020
CWNVKGHVEV EEQNNHRSVL VIPEWEAEVS QEVRVCPGRG YILRVTAYKE GYGEGCVTIH  1080
EIENNTDELK FNNCVEEEVY PNNTVTCINY TATQEEYEGT YTSRNRGYDE AYGNNPSVPA  1140
DYASVYEEKS YTDRRRENPC ESNRGYGDYT PLPAGYVTKE LEYFPETDKV WIEIGETEGT  1200
FIVDSVELLL MEE                                                    1213
```

SEQ ID NO: 14        moltype = DNA   length = 3690
FEATURE              Location/Qualifiers -continued

```
misc_feature        1..3690
                    note = Recombinant nucleotide sequence used for expression
                    in a bacterial cell encoding TIC867_21.
source              1..3690
                    mol_type = other DNA
                    organism = synthetic construct
SEQUENCE: 14
atgacttcaa ataggaaaaa tgagaatgaa attataaatg ctttatcgat tccagctgta   60
tcgaatcatt ccgcacaaat gaatctatca accgatgctc gtattgagga tagcttgtgt   120
atagccgagg ggaacaatat cgatccattt gttagcgcat caacagtcca aacgggtatt   180
aacatagctg gtagaatact aggtgtatta ggcgtaccgt ttgctggaca aatagctagt   240
ttttatagtt ttcttgttgg tgaattatgg ccccgcggca gagatccttg ggaaattttc   300
ctagaacatg tcgaacaact tataagacaa caagtagca aaaatactag ggatacggct   360
cttgctcgat tacaaggttt aggaaattcc tttagagcct atcaacagtc acttgaagat   420
tggctagaaa accgtgatga tgcaagaacg agaagtgttc tttataccca atatatagcc   480
ttagaacttg attttcttaa tgcgatgccg cttttcgcaa ttagaaacca agaagttcca   540
ttattaatgg tatatgctca agctgcaaat ttacacctat tattattgag agatgcctct   600
ctttttggta gtgaatttgg gcttacatcc caagaaattc aacgttatta tgagcgcaa   660
gtggaaaaaa cgagagaata ttctgattat tgcgcaagat ggtataatac gggtttaaat   720
aatttgagag ggacaaatgc tgaaagttgg ttgcgatata atcaattccg tagagactta   780
acgctaggag tattagatct agtggcacta ttcccaagct atgacacgcg tgtttatcca   840
atgaatacca gtgctcaatt aacaagagaa atttatacag atccaattgg gagaacaaat   900
gcaccttcag gatttgcaag tacgaattgg tttaataata atgcaccatc gtttctgcc   960
atagaggctg ccgttattag gcctccgcat ctacttgatt ttccagaaca gcttacaatt   1020
ttcagcgtat taagtcgatg gagtaatact caatatatga attactgggt gggacataga   1080
cttgaatcgc gaacaataag ggggtcatta agtacctcga cacacgaata taccaatact   1140
tctattaatc ctgtaacatt acagttcaca tctcgagacg tttatagaac agaatcattt   1200
gcagggataa atatacttct aactactcct gtgaatggag taccttgggc tagatttaat   1260
tggagaaatc ccctgaattc tcttagaggt agccttctct atactatagg gtatactgga   1320
gtgggacac aactatttga ttcagaaact gaattaccac cagaaacaac agaacgacca   1380
aattatgaat cttacagtca tagattatct aatataagac taatatcagg aaacactttg   1440
agagcaccag tatattcttg gacgcaccgt agtgcagatc gtacaaatac cattagttca   1500
gatagcatta cacaaatacc attggtaaag gcgcataccc tccaatcggg taccactgta   1560
gtaaaagggc cagggtttac aggaggggat atcctccgtc gaacaagtgg aggaccattt   1620
gcttttagta atgttaatct agatttaac ttgtcacaaa ggtatcgtgc tagaattcgt   1680
tatgcctcta ctactaacct aagaaattac gtaacggttg caggtgaacg aattttttgct   1740
ggtcaatttg acaaaactat ggatgctggt gccccattaa cattccaatc ttttagttac   1800
gcaactatta atacagcttt tacattccca gaaagatcga gcagcttgac tgtaggtgcc   1860
gatacgttta gttcaggtaa tgaagtttat gtagatagat ttgaattaat cccagttact   1920
gcaaccggaa cgacaaccta tgagtatgaa gagaagcaga atctagaaaa agcgcagaaa   1980
gcgttgaacg ctttgtttac ggatggcacg aatggctatc tacaaatgga tgccactgat   2040
tatgatatca atcaaactgc aaacttaata gaatgtgtat cagatgaatt gtatgcaaaa   2100
gaaaagatag ttttattaga tgaagtcaaa tatgcgaagc ggcttagcat atcacgtaac   2160
ctacttttga acgatgattt agaatttca gatggatttg gagaaaacgg atggacgaca   2220
agtgataata tttcaatcca ggcggataat ccccttttta aggggaatta tttaaaaatg   2280
tttgggcaa gagatattga tggaacccta tttccaactt atctctatca aaaaatagat   2340
gagtccaggt taaaaccata tacacgttat cgagtaaggg ggtttgtggg aagtagtaaa   2400
aatctaaaat tagtggtaac acgctatgag aaagaaattg atgccattat gaatgttcca   2460
aatgatttgg cacatatgca gcttaaccct tcatgtggag attatcgctg tgaatcatcg   2520
tcccagtttt tggtgaacca agtgcatcct acaccaacag ctggatatgc tcttgatatg   2580
tatgcatgcc cgtcaagttc agataaaaaa catattatgt gtcacgatcg tcatccattt   2640
gattttcata ttgacaccgg agaattaaat ccaaacacaa acctgggtat tgatgtcttg   2700
tttaaaattt ctaatccaaa tggatacgct acattaggga atctagaagt cattgaagaa   2760
ggaccactaa cagatgaagc attggtacat gtaaaacaaa aggaaaagaa atggcgtcag   2820
cacatggaga aaaaacgaat ggaaacacaa caagcctatg atccagcaaa acaagctgta   2880
gatgcattat ttacaaatga acaagagtta gactatcata ctactttaga tcatattcag   2940
aacgccgatc agctggtaca ggcgattccc tatgtacacc atgcttggtt accggatgct   3000
ccaggtatga actatgatgt atatcaaggg ttaaacgcac gtatcatgca ggcgtacaat   3060
ttatatgata cacgaaatgt cataataaat ggtgacttta cacaaggact acaaggatgg   3120
cacgcaacag gaaaagcagc ggtacaacaa atagatggag cttcagtatt agttctatca   3180
aactggagtg ccgaggtatc tcagaatctg catgcccaag atcatcatgg atatatgtta   3240
cgtgtgattg ccaaaaaaga aggtcctgga aaagggtatg taatgatgat ggattttaat   3300
ggaaagcagg aaacacttac gttcacttct tgtgaagaag atatataac aaaaacaata   3360
gaggtattcc cggaaagtga tcgaatacga attgaaatgg agaaaacaga gggtacgttt   3420
tatgtagata gcatcgagtt gctttgtatg caaggatatg ctagcgataa taacccgcac   3480
acgggtaata tgtatgagca aagttataat ggaaattata tcaaaatac tagcgatgtg   3540
tatcaccaag atatataaa caactataac caaaattcta gtagtatgta taatcaaaat   3600
tatattaaca atgatgacct gcattccggt tgcacatgta accaagggca taactctggc   3660
tgtacatgta atcaaggata taaccgttag                                    3690

SEQ ID NO: 15       moltype = DNA   length = 3690
FEATURE             Location/Qualifiers
misc_feature        1..3690
                    note = Synthetic nucleotide sequence designed for
                    expression in a plant cell encoding TIC867_21.
source              1..3690
                    mol_type = other DNA
                    organism = synthetic construct
SEQUENCE: 15
```

```
atgaccagca accgaaagaa cgagaacgag atcatcaacg ccctgtccat accggccgtg   60
tcaaaccact ccgcccagat gaacctctcc accgacgcga ggatcgagga ctccctctgc  120
atcgccgagg gcaacaacat cgacccgttc gtgtctgcaa gcacggtcca gaccggcatc  180
aacatcgcgg gccgcatcct gggcgtgctc ggcgtgccct cgcggggtca aatcgcctct  240
ttctactcat tcctcgtggg cgagctgtgg ccgcgcgaac gtgacccgtg ggaaatcttc  300
ctggagcacg ttgagcagct catccggcag caagtgaccg agaacaccag ggacaccgca  360
ctggcacggc tccagggcct tggcaacagc ttccgcgcct accagcagtc gctggaggac  420
tggctggaga accgagacga cgccagaacc cgctcagttc tgtacacaca gtacatcgcc  480
ctagagctgg acttcctcaa cgctatgccg ctcttcgcca tccgtaacca ggaagtaccg  540
cttctgatgg tgtacgcaca agcagcgaac ctccatctgc tcctgctgcg agacgcatct  600
ctgttcggca gtgagttcgg gctgacgagc caggagatcc agcgctacta cgagcgccaa  660
gtggagaaga ctcgtgagta cagcgactac tgcgcgcgct ggtacaacac gggcttgaac  720
aaccttcgcg ggacaaacgc cgaatcctgg cttcgctaca accagttccg ccgcgacctc  780
acgctgggtg tgctggacct ggtcgcgctc ttcccgtcct acgacaccgg ggtgtaccca  840
atgaacacga gcgcacagct cacccgtgag atctacacag atcccatcgg ccgcaccaac  900
gctcccagtg gcttcgcaag cacgaattgg ttcaacaata acgctccttc tttctctgcc  960
atcgaggccg ctgtcatcag accgccgcac ttactcgatt tcccggagca gctcactatc 1020
ttctctgtgt tgtcccggtg gtcgaacacg cagtacatga actactgggt gggccacagg 1080
ctagagagcc ggaccatccg tggcagtctc tcaacctcga cccacggcaa cacgaacacg 1140
agcatcaacc ctgtcactct ccagtttaca tctagggacg tttacaggac agagtcgttc 1200
gctggcatta acattctgtt gaccactccg gtgaacggcg tcccttgggc ccgcttcaac 1260
tggagtaatc ctctgaactc actgcgcggc agccttctct acaatatcgg ctacaccggc 1320
gttgggacgc aactcttcga ctcggagacc gagctgccgc ccgagaccac cgagcggcct 1380
aactacgaga gttattcaca caggctctcc aacatccgct tgatttctgg gaacaccttg 1440
cgggctccgg tgtactcctg gacgcaccgc agcgccgaca gaactaatac catcagctcc 1500
gactcgatca cccagatccc gctggtgaag gctcacacgt ttcagtcggg caccacagtc 1560
gtcaagggcc ctggcttcac cggcggcgac atcctgcgtc gcacatctgg cggacccttc 1620
gccttcagca acgtgaactt ggacttcaat ttgtcacagc ggtatcgtgc cagaatccgg 1680
tacgccagca ctacgaacct gcgaatctat gttactgtgg cgggcgagcg gatcttcgcc 1740
gggcaattcg acaagacgat ggacgcggga gcacctctga cattccagtc attctcttac 1800
gccacgatca cacggcatt cacgtttccg gagcgttcca gtagcctgac cgtgggcgct 1860
gataccttca gtagcgggaa cgaggtgtac gttgaccgtt tcgagctgat cccggtcacc 1920
gccaccggga ctaccaccta cgagtacgag gagaagcaga atctcgagaa ggctcagaag 1980
gctctgaacg ctctgttcac tgacgggacc aacggctacc tccagatgga cgccactgac 2040
tacgacatca accagacagc taacctgatt gagtgtgtga gtgacgaact gtacgctaag 2100
gagaagatcg tactcctgga cgaggtgaag tacgctaagc gcctgagcat tagccgtaac 2160
ctgctgctga acgacgatct ggagttcagc gacggctttg gcgagaacgg ctggaccacc 2220
agcgacaaca tctccatcca ggccgacaat ccactcttca aaggcaacta cctcaagatg 2280
ttcggagcca gggacatcga cggcaccctc tttccgacct acctctacca gaagatcgac 2340
gagtcccgcc tcaaaccta caccccgctac agggtgcgcg gcttcgtggg cagcagcaag 2400
aacctcaagc tcgtggtcac acggtatgag aaggagatcg acgccatcat gaacgtgccc 2460
aacgatctcc cccacatgca gctcaatcca tcctgcggcg actaccggtg cgagtccagc 2520
tcccagttcc tcgtgaacca ggtgcaccct actccgaccg ctggctatgc cctggacatg 2580
tacgcctgcc ctagttcctc cgacaagaag cacatcatgt gccacgaccg tcatccgttc 2640
gacttccaca tcgacaccgg cgaactgaac ccgaacacca acctgggcat cgacgtactg 2700
ttcaagattt ccaacccgaa cgggtacgcc accttgggca acctggaggt catcgaagaa 2760
ggcccgctga ccgacgaggc cctggtccac gtcaaacaga aggagaagaa gtggcggcag 2820
cacatggaga agaacgcggat ggagactcaa caagcctacg acccggccaa gcaagctgtg 2880
gacgctctgt tcaccaacga gcaagagctt gactaccaca ctactcttga ccacatccag 2940
aatgctgacc agcttgtcca ggctattccg tacgtccacc acgcttggct accggacgct 3000
ccagggatga actacgatgt gtaccagggt ctgaacgcgc ggatcatgca agcgtacaac 3060
ctgtacgacg cgcgtaacgt catcatcaac ggtgacttca ctcagggtct tcaaggttga 3120
cacgcgactg gcaaagcggc agtccagcag attgatggtg cgtctgttct tgtgttgagc 3180
aactggtctg cggaggtttc tcagaacctg cacgcacagg atcaccacgg ctacatgctg 3240
agggtgattg ctaagaagga gggccctggc aaaggctacg tcatgatgat ggacttcaac 3300
ggaaagcaag aaaccctgac cttcactagc tgtgaggagg gctacatcac taagaccatt 3360
gaggtctttc cggagtctga ccgcatccgg atcgagatgg cgagaccga aggcacgttc 3420
tacgtggact ccatcgaact cctctgcatg caaggctacg cctccgacaa caacccacac 3480
acgggcaaca tgtacgagca gtcctacaac gggaactaca accagaacac ctccgatgtg 3540
taccatcagg gctacatcaa caactacaac cagaacagca gcagcatgta caaccagaac 3600
tacatcaaca acgatgactt gcactcgggt tgcacctgca accagggtca acagtgggg 3660
tgcacgtgca accagggata caaccgttga                                  3690
```

```
SEQ ID NO: 16          moltype = AA  length = 1229
FEATURE                Location/Qualifiers
REGION                 1..1229
                       note = Amino acid sequence of the chimeric protein variant
                       TIC867_21.
source                 1..1229
                       mol_type = protein
                       organism = synthetic construct SEQUENCE: 16
MTSNRKNENE IINALSIPAV SNHSAQMNLS TDARIEDSLC IAEGNNIDPF VSASTVQTGI   60
NIAGRILGVL GVPFAGQIAS FYSFLVGELW PRGRDPWEIF LEHVEQLIRQ QVTENTRDTA  120
LARLQGLGNS FRAYQQSLED WLENRDDART RSVLYTQYIA LELDFLNAMP LFAIRNQEVP  180
LLMVYAQAAN LHLLLLRDAS LFGSEFGLTS QEIQRYYERQ VEKTREYSDY CARWYNTGLN  240
NLRGTNAESW LRYNQFRRDL TLGVLDLVAL FPSYDTRVYP MNTSAQLTRE IYTDPIGRTN  300
APSGFASTNW FNNNAPSFSA IEAAVIRPPH LLDFPEQLTI FSVLSRWSNT QYMNYWVGHR  360
LESRTIRGSL STSTHGNTNT SINPVTLQFT SRDVYRTESF AGINILLTTP VNGVPWARFN  420
```

```
WRNPLNSLRG SLLYTIGYTG VGTQLFDSET ELPPETTERP NYESYSHRLS NIRLISGNTL  480
RAPVYSWTHR SADRTNTISS DSITQIPLVK AHTLQSGTTV VKGPGFTGGD ILRRTSGGPF  540
AFSNVNLDFN LSQRYRARIR YASTTNLRIY VTVAGERIFA GQFDKTMDAG APLTFQSFSY  600
ATINTAFTFP ERSSSLTVGA DTFSSGNEVY VDRFELIPVT ATGTTTYEYE EKQNLEKAQK  660
ALNALFTDGT NGYLQMDATD YDINQTANLI ECVSDELYAK EKIVLLDEVK YAKRLSISRN  720
LLLNDDLEFS DGFGENGWTT SDNISIQADN PLFKGNYLKM FGARDIDGTL FPTYLYQKID  780
ESRLKPYTRY RVRGFVGSSK NLKLVVTRYE KEIDAIMNVP NDLAHMQLNP SCGDYRCESS  840
SQFLVNQVHP TPTAGYALDM YACPSSSDKK HIMCHDRHPF DFHIDTGELN PNTNLGIDVL  900
FKISNPNGYA TLGNLEVIEE GPLTDEALVH VKQKEKKWRQ HMEKKRMETQ QAYDPAKQAV  960
DALFTNEQEL DYHTTLDHIQ NADQLVQAIP YVHHAWLPDA PGMNYDVYQG LNARIMQAYN 1020
LYDARNVIIN GDFTQGLQGW HATGKAAVQQ IDGASVLVLS NWSAEVSQNL HAQDHHGYML 1080
RVIAKKEGPG KGYVMMMDFN GKQETLTFTS CEEGYITKTI EVFPESDRIR IEMGETEGTF 1140
YVDSIELLCM QGYASDNNPH TGNMYEQSYN GNYNQNTSDV YHQGYINNYN QNSSSMYNQN 1200
YINNDDLHSG CTCNQGHNSG CTCNQGYNR                                  1229

SEQ ID NO: 17          moltype = DNA  length = 3432
FEATURE                Location/Qualifiers
misc_feature           1..3432
                       note = Recombinant nucleotide sequence used for expression
                       in a bacterial cell encoding TIC867_22.
source                 1..3432
                       mol_type = other DNA
                       organism = synthetic construct
SEQUENCE: 17
atgacttcaa ataggaaaaa tgagaatgaa attataaatg ctttatcgat tccagctgta  60
tcgaatcatt ccgcacaaat gaatctatca accgatgctc gttgagga tagcttgtgt  120
atagccgagg ggaacaatat cgatccattt gttagcgcat caacagtcca aacgggtatt  180
aacatagctg gtagaatact aggtgtatta ggcgtaccgt ttgctggaca aatagctagt  240
ttttatagtt ttcttgttgg tgaattatgg ccccgcggca gagatccttg ggaaattttc  300
ctagaacatg tcgaacaact tataagacaa caagtaacag aaaatactag ggatacggct  360
cttgctcgat tacaaggttt aggaaattcc tttagagcct atcaacagtc acttgaagat  420
tggctagaaa accgtgatga tgcaagaacg agaagtgttc tttatcccca atatatagcc  480
ttagaacttg attttcttaa tgcgatgccg cttttcgcaa ttagaaacca agaagttcca  540
ttattaatgg tatatgctca agctgcaaat ttacacctat tattattgag agatgcctct  600
cttttggta gtgaatttgg gcttacatcc caagaaattc aacgttatta tgagcgccaa  660
gtggaaaaaa cgagagaata ttctgattat tgcgcaagat ggtataatac gggtttaaat  720
aatttgagag ggacaaatgc tgaaagttgg ttgcgatata atcaattccg tagagactta  780
acgctaggag tattagatct agtggcacta ttcccaagct atgacacgcg tgtttatcca  840
atgaatacca gtgctcaatt aacaagagaa atttatacag atccaattgg gagaacaaat  900
gcaccttcag gatttgcaag tacgaattgg tttaataata atgcaccatc gtttctgcc  960
atagaggctg ccgttattag gcctccgcat ctacttgatt ttccagaaca gcttacaatt 1020
ttcagcgtat taagtcgatg gagtaatact caatatatga attctgggt gggacataga 1080
cttgaatcgc gaacaataag ggggtcatta agtacctcga cacacggaaa taccaatact 1140
tctattaatc ctgtaacatt acagttcaca tctcgagacg tttatagaac agaatcattt 1200
gcagggataa atatacttct aactactcct gtgaatggag taccttgggc tagatttaat 1260
tggagaaatc ccctgaattc tcttagaggt agccttctct atactatagg gtatactgga 1320
gtggggacac aactatttga ttcagaaact gaattaccac cagaaacaac agaacgacca 1380
aattatgaat cttacagtca tagattatct aatataagac taatatcagg aaacactttg 1440
agagcaccag tatattcttg gacgcaccgt agtgcagatc gtacaaatac cattagttca 1500
gatagcatta cacaaatacc attggtaaag gcgcataccc tccaatcggg taccactgta 1560
gtaaaagggc cagggtttac aggaggggat atcctccgtc gaacaagtgg aggaccattt 1620
gcttttagta atgttaatct agattttaac ttgtcacaaa ggtatcgtgc tagaattcgt 1680
tatgcctcta ctactaacct aagaaattac gtaacggttg caggtgaacg aatttttgct 1740
ggtcaatttg acaaaactat ggatgctggt gccccattaa cattccaatc ttttagttac 1800
gcaactatta atacagcttt tacattccca gaaaagatca gcagcttgac tgtaggtgcc 1860
gatacgttta gttcaggtaa tgaagtttat gtagatagat ttgaattaat cccagttact 1920
gcaaccaatc cgacgcgaga ggcggaagag gatctagaag cagcgaagaa agcggtggcg 1980
agcttgttta cacgtacaag ggacggatta caagtaaatg tgacagatta tcaagtcgat 2040
caagcggcaa atttagtgtc atgcttatca gatgaacaat atgggcatga caaaaagatg 2100
ttattggaag cggtaagagc ggcaaaacgc ctcagccgag aacgcaactt acttcaggat 2160
ccagatttta atacaatcaa tagtacagaa gaaaatggat ggaaagcaag taacggcgtt 2220
actattagcg agggcggtcc attctataaa ggccgtgcgc ttcagctagc aagcgcaaga 2280
gaaaattacc aacatacat ttatcaaaaa gtaaatgcat cagagttaaa gccgtataca 2340
cgttatagac tggatgggtt cgtgaagagt agtcaagatt tagaaattga tctcattcac 2400
catcataaag tccatctcgt gaaaaatgta ccagataatt tagtatccga tacttactcg 2460
gatggttctt gcagtggaat gaatcgatgt gaggaacaac agatggtaaa tgcgcaactg 2520
gaaacagaac atcatcatcc gatggattgc tgtgaagcgg ctcaaacaca tgagtttttct 2580
tcctatatta atacaggcga tctaaattca agtgtagate aaggcatttg ggttgtattg 2640
aaagttcgaa caaccgatgg ttatgcgacg ctaggaaatc ttgaattggt agaggtcgga 2700
ccgttatcgg gtgaatctct agaacgtgaa caaagggata atgcgaaatg gagtgcagag 2760
ctaggaagaa agcgtgcaga aacagatcgc gtgtatcaag atgccaaaca atccatcaat 2820
catttatttg tggattatca agatcaacaa ttaaatccag aaataggat ggcagatatt 2880
attgacgctc aaaatcttgt cgcatcaatt tcagatgtgt atagcgatgc agtactgcaa 2940
atccctgaa ttaactatga gatttacaca gagctatcac atcgcttaca acaagcatg 3000
tatctgtata cgtctcgaaa tgcggtgcaa aatgggggact ttaacagcgg tctagatagt 3060
tggaatgcaa caggggggggc tacggtacaa caggatggca atacgcattt cttagttctt 3120
tctcattggg atgcacaagt ttctcaacaa tttagagtgc agccgaattg taaatatgta 3180
ttacgtgtaa cagcagagaa agtaggcggc ggagacggat acgtgacaat ccgggatggt 3240
gctcatcata cagaaaagct tacatttaat gcatgtgatt atgatataaa tggcacgtac 3300
```

```
gtgactgata atacgtatct aacaaaagaa gtggtattct attcacatac agaacacatg   3360
tgggtagagg taagtgaaac agaaggtgca tttcatatag atagtattga attcgttgaa   3420
acagaaaagt ag                                                        3432

SEQ ID NO: 18          moltype = DNA  length = 3432
FEATURE                Location/Qualifiers
misc_feature           1..3432
                       note = Synthetic nucleotide sequence designed for
                        expression in a plant cell encoding TIC867_22.
source                 1..3432
                       mol_type = other DNA
                       organism = synthetic construct SEQUENCE: 18
atgaccagca accgaaagaa cgagaacgag atcatcaacg ccctgtccat accggccgtg   60
tcaaaccact ccgcccagat gaacctctcc accgacgcga ggatcgagga ctccctctgc   120
atcgccgagg gcaacaacat cgacccgttc gtgtctgcaa gcacggtcca gaccggcatc   180
aacatcgcgg gccgcatcct gggcgtgctc ggcgtgccct cgcggggtca aatcgcctct   240
ttctactcat tcctcgtggg cgagctgtgg ccgcgcggac gtgacccgtg ggaaatcttc   300
ctggagcacg ttgagcagct catccggcag caagtgaccg agaacaccag ggacaccgca   360
ctggcacggc tccagggcct tggcaacagc ttccgcgcct accagcagtc gctggaggac   420
tggctggaga accgagacga cgccagaacc cgctcagttc tgtacacaca gtacatcgcc   480
ctagagctgg acttcctcaa cgctatgccg ctcttcgcca tccgtaacca ggaagtaccg   540
cttctgatgg tgtacgcaca agcagcgaac ctccatctgc tcctgctgcg agacgcatct   600
ctgttcggca gtgagttcgg gctgacgagc caggagatcc agcgctacta cgagcgccaa   660
gtggagaaga ctcgtgagta cagcgactac tgcgcgcgct ggtacaacac gggcttgaac   720
aaccttcgcg ggacaaacgc cgaatcctgg cttcgctaca ccagttccg ccgcgacctc   780
acgctgggtg tgctggacct ggtcgcgctc ttcccgtcct acgacacacg ggtgtaccca   840
atgaacacga gcgcacagct cacccgtgag atctacacag atcccatcgg ccgcaccaac   900
gctcccagtg gcttcgcaag cacgaattgg ttcaacaata acgctccttc tttctctgcc   960
atcgaggccg ctgtcatcag accgccgcac ttactcgatt cccggagca gctcactatc   1020
ttctctgtgt tgtcccggtg gtcgaacacg cagtacatga actactgggt gggccacagg   1080
ctagagagcc ggaccatccg tggcagtctc tcaacctcga cccacggcaa cacgaacacg   1140
agcatcaacc ctgtcactct ccagtttaca tctaggacg tttacaggac agagtcgttc   1200
gctggcatta acattctgtt gaccactccg gtgaacggcg tcccttgggc ccgcttcaac   1260
tggaggaatc ctctgaactc actgcgcggc agccttctct acactatcgg ctacaccggt   1320
gttgggacgc aactcttcga ctcggagacc gagctgccgc ccgagaccac cgagcggcct   1380
aactacgaga gttattcaca caggctctcc aacatccgct tgatttctgg gaacaccttg   1440
cgggctccgg tgtactcctg gacgcaccgc agcgccgaca gaactaatac catcagctcc   1500
gactcgatca cccagatccc gctggtgaag gctcacacgc ttcagtcggg caccacagtc   1560
gtcaagggcc ctggcttcac cggcggcgac atcctgcgtc gcacatctgg cggacccttc   1620
gccttcagca acgtgaactt ggacttcaat ttgtcacagc ggtatcgtgc cagaatccgg   1680
tacgccagca ctacgaacct gcgaatctat gttactgtgg cgggcgagcg gatcttcgcc   1740
gggcaattcg acaagacgat ggacgcggga gcacctctga cattccagtc attctcttac   1800
gccacgatca acacgcatt cacgtttccg gagcgttcca gtagcctgac cgtgggcgct   1860
gataccttca gtagcgggaa cgaggtgtac gttgaccgtt tcgagctgat cccggtcacc   1920
gccaccaacc cgacgcggga agctgaggaa gacttggaag ccgccaagaa agcggtcgcc   1980
agcctgttta ctcggacgcg ggacgggctc caagtgaatg tgaccgacta tcaagtggat   2040
caggccgcta acctcgtgtc atgcctgagc gacgagcagt acggtcacga caagaaaatg   2100
ctgctggagg ccgtccgggc cgccaagcgg ctgtccaggg agcgtaacct gctacaagat   2160
cccgactta acacgatcaa cagcacagag gagaatggct ggaaggccag caacggagtt   2220
acgataaggc agggcggtcc gttctacaag ggtcgtgccc tccagctcgc ctctgcaagg   2280
gagaactatc caacctacat ctatcagaag gtgaacgcat ccgagcttaa gccctcacaca  2340
cgctaccgcc tggacgggt cgttaagtcc agtcaagacc tagagataga cctcatccac   2400
caccacaaag tgcatctggt caagaacgtt cccgataatc tcgtgagcga tacctactca   2460
gacggctcat gctctggcat gaacagatgt gaggagcaac agatggttaa tgctcaactc   2520
gaaaccgagc atcatcatcc tatggattgc tgcgaggccg cgcagaccca tgagttcagc   2580
tcttacatca acaccggaga cctcaacagt agcgtggatc agggaatttg ggtggtgctt   2640
aaagtgcgta caaccgacgg ctacgccacc ctcggcaacc ttgagcttgt cgaggtcgga   2700
ccacttagcg gcgagtccct ggaacgtgag cagcgggaca acgccaaatg gagcgcagag   2760
ctagggcgca aacgcgcgga gacggaccgg gtttatcagg acgcgaagca gtccatcaat   2820
cacctcttcg tggattatca ggaccagcag cttaatccag agatcggcat ggccgacatc   2880
atcgacgccc agaacctagt agcgtcgatt tccgatgtct attccgacgc cgtgcttcaa   2940
atacctggca tcaactacga gatctacaca gagttgtcca caggctcca gcaagcgtca   3000
tacctctaca ccagccgcaa cgccgtccag aatggcgact tcaattccgg actagactcc   3060
tggaacgcca cgggcggagc tacggtgcaa caagacggca acacccactt cctcgtactt   3120
agccactggg acgctcaagt gagtcagcaa ttccgggttc agccgaactg caagtacgtc   3180
ctgcgcgtaa cggccgagaa ggttggaggc ggagacggc acgttaccat ccgcgacggc   3240
gctcaccaca ccgagaaact gacgttcaac gcttgtgact acgacatcaa cggcacttac   3300
gtgacggaca acacctacct gacgaaggag gtgggtgttct attctcacac cgagcacatg   3360
tgggttgagg tcagcgagac cgagggagcc ttccacattg acagcatcga gttcgtggag   3420
actgagaagt ga                                                        3432

SEQ ID NO: 19          moltype = AA  length = 1143
FEATURE                Location/Qualifiers
REGION                 1..1143
                       note = Amino acid sequence of the chimeric protein variant
                        TIC867_22.
source                 1..1143
                       mol_type = protein
```

-continued

```
                              organism = synthetic construct
SEQUENCE: 19
MTSNRKNENE IINALSIPAV SNHSAQMNLS TDARIEDSLC IAEGNNIDPF VSASTVQTGI  60
NIAGRILGVL GVPFAGQIAS FYSFLVGELW PRGRDPWEIF LEHVEQLIRQ QVTENTRDTA  120
LARLQGLGNS FRAYQQSLED WLENRDDART RSVLYTQYIA LELDFLNAMP LFAIRNQEVP  180
LLMVYAQAAN LHLLLLRDAS LFGSEFGLTS QEIQRYYERQ VEKTREYSDY CARWYNTGLN  240
NLRGTNAESW LRYNQFRRDL TLGVLDLVAL FPSYDTRVYP MNTSAQLTRE IYTDPIGRTN  300
APSGFASTNW FNNNAPSFSA IEAAVIRPPH LLDFPEQLTI FSVLSRWSNT QYMNYWVGHR  360
LESRTIRGSL STSTHGNTNT SINPVTLQFT SRDVYRTESF AGINILLTTP VNGVPWARFN  420
WRNPLNSLRG SLLYTIGYTG VGTQLFDSET ELPPETTERP NYESYSHRLS NIRLISGNTL  480
RAPVYSWTHR SADRTNTISS DSITQIPLVK AHTLQSGTTV VKGPGFTGGD ILRRTSGGPF  540
AFSNVNLDFN LSQRYRARIR YASTTNLRIY VTVAGERIFA GQFDKTMDAG APLTFQSFSY  600
ATINTAFTFP ERSSSLTVGA DTFSSGNEVY VDRFELIPVT ATNPTREAEE DLEAAKKAVA  660
SLFTRTRDGL QVNVTDYQVD QAANLVSCLS DEQYGHDKKM LLEAVRAAKR LSRERNLLQD  720
PDFNTINSTE ENGWKASNGV TISEGGPFYK GRALQLASAR ENYPTYIYQK VNASELKPYT  780
RYRLDGFVKS SQDLEIDLIH HHKVHLVKNV PDNLVSDTYS DGSCSGMNRC EEQQMVNAQL  840
ETEHHHPMDC CEAAQTHEFS SYINTGDLNS SVDQGIWVVL KVRTTDGYAT LGNLELVEVG  900
PLSGESLERE QRDNAKWSAE LGRKRAETDR VYQDAKQSIN HLFVDYQDQQ LNPEIGMADI  960
IDAQNLVASI SDVYSDAVLQ IPGINYEIYT ELSNRLQQAS YLYTSRNAVQ NGDFNSGLDS  1020
WNATGGATVQ QDGNTHFLVL SHWDAQVSQQ FRVQPNCKYV LRVTAEKVGG GDGYVTIRDG  1080
AHHTEKLTFN ACDYDINGTY VTDNTYLTKE VVFYSHTEHM WVEVSETEGA FHIDSIEFVE  1140
TEK                                                              1143

SEQ ID NO: 20            moltype = DNA   length = 3696
FEATURE                  Location/Qualifiers
misc_feature             1..3696
                         note = Synthetic nucleotide sequence designed for
                          expression in a plant cell encoding TIC867_23.
source                   1..3696
                         mol_type = other DNA
                         organism = synthetic construct
SEQUENCE: 20
atgaccagca accgaaagaa cgagaacgag atcatcaacg ccctgtccat accggccgtg  60
tcaaaccact ccgcccagat gaacctctcc accgacgcga ggatcgagga ctccctctgc  120
atcgccgagg gcaacaacat cgacccgttc gtgtctgcaa gcacggtcca gaccggcatc  180
aacatcgcgg gccgcatcct gggcgtgctc ggcgtgccct cgcgggtca aatcgcctct  240
ttctactcat tcctcgtggg cgagctgtgg ccgcgcggac gtgacccgtg ggaaatcttc  300
ctggagcacg ttgagcagct catccggcag caagtgaccg agaacaccag ggacaccgca  360
ctggcacggc tccagggcct tggcaacagc ttccgcgcct accagcagtc gctggaggac  420
tggctggaga accgagacga cgccagaacc cgctcagttc tgtacacaca gtacatcgcc  480
ctagagctgg acttcctcaa cgctatgccg ctcttcgcca tccgtaacca ggaagtaccg  540
cttctgatgg tgtacgcaca agcagcgaac ctccatctgc tcctgctgcg agacgcatct  600
ctgttcggca gtgagttcgg gctgacgagc caggagatcc agcgctacta cgagcgccaa  660
gtggagaaga ctcgtgagta cagcgactac tgcgcgcgct ggtacaacac gggcttgaac  720
aaccttcgcg ggacaaacgc cgaatcctgg cttcgctaca accagttccg ccgcgacctc  780
acgctggtgt gctggaccct ggtcgcgctc ttcccgtcct acgacacacg ggtgtaccca  840
atgaacacga gcgcacagct cacccgtgag atctacacag atcccatcgg ccgcaccaac  900
gctcccagtg gcttcgcaag cacgaattgg ttcaacaata acgctccttc tttctctgcc  960
atcgaggccg ctgtcatcag accgccgcac ttactcgatt tcccggagca gctcactatc  1020
ttctctgtgt tgtcccggtg gtcgaacacg cagtacatga actactgggt gggccacagg  1080
ctagagaccg ggaccatccg tggcagtctc tcaacctcga cccacggcaa cacgaacacg  1140
agcatcaacc ctgtcactct ccagtttaca tctaggacg tttacaggac agagtcgttc  1200
gctggcatta acattctgtt gaccactccg gtgaacggcg tcccttgggc ccgcttcaac  1260
tggaggaatc ctctgaactc actgcgcggc agccttctct cactatcgg ctacaccggc  1320
gttggcgacgc aactcttcga ctcggagacc gagctgccgc ccgagaccac cgagcggcct  1380
aactacgaga gttattcaca caggctctcc aacatccgct tgatttctgg gaacaccttg  1440
cgggctccgg tgtactcctg gacgcaccgc agcgccgaca gaactaatac catcagctcc  1500
gactcgatca cccagatccc gctggtgaag gctcacacgc ttcagtcggg caccacagtc  1560
gtcaagggcc ctggcttcac cggcggcgac atcctgcgtc gcacatctgg cggacccttc  1620
gccttcagca acgtgaactt ggacttcaat ttgtcacagc ggtatcgtgc cagaatccgg  1680
tacgccagca ctacgaacct gcgaatctat gttactgtgg cgggcgagcg gatcttcgcc  1740
gggcaattcg acaagacgat ggacgcggga gcacctctga cattccagtc attctcttac  1800
gccacgatca acacggcatt cacgtttccg gagcgttcca gtagcctgac cgtgggcgct  1860
gataccttca gtagcgggaa cgaggtgtac gttgaccgtt cgagctgat cccggtcaac  1920
gccaccacgg cgaccttcga ggcggagtat gacttggagc gggctcagga ggccgtcaac  1980
gcgctgttca caaacaccaa tcctcgccgc ctcaagacgg gtgtgactga ttaccacatt  2040
gacgaggtct ccaacttggt cgcgtgtctg tccgatgagt tctgcctgga cgagaagcgg  2100
gaactgctgg agaaggtcaa gtacgccaag cgcctctccg acgaaaggaa cctcctccaa  2160
gatcccaact ttacttccat taacaagcag ccggacttca tctccaccaa cgagcagtcc  2220
aacttcacct caatccacga gcagtcggag cacgggtggt ggggcagcga gaacatcacc  2280
atccaagagg gcaacgacgt cttcaaggag aactacgtga tcctgcccgg caccttcaac  2340
gagtgttacc gacctatct ctaccagaag attggcgaag cggaactcaa ggcttacacc  2400
cgttaccaac tgagtggcta cattgaggac tcacaagacc tggaaatcta cctgatccgc  2460
tacaacgcca agcacgagac cctcgacgtg cctggcacgga gccgtctg cgccttgagc  2520
gtggagtctc ctatcggtcg ttgcggcgag cccaatcgct gcgctccgca ctttgagtgg  2580
aatcctgatt tggattgctc ctgccgagac ggtgagaaat gcgcccacca ctcgcaccac  2640
ttcagcctag acatcgacgt gggctgcatc gacctgcacg agaacttggg cgtctgggtc  2700
gtgttcaaga tcaagacaca ggaggggcat gctcggcttg gaacctgga gttcatcgag  2760
gagaagccac tgctgggtga agccttgtca cgggtgaaac gcgccgagaa gaagtggcgg  2820
```

```
gacaaacggg agaagctcca gttggagaca aagcgtgtgt acacagaggc caaggaggcc 2880
gtggatgcct tgttcgtgga cagtcagtac gacaggctgc aagcggacac caacatcggg 2940
atgatccacg cggctgataa gcttgttcac agaatccgcg aggcgtacct gtcagagctt 3000
agcgtgatcc caggcgtcaa cgccgaaatc ttcgaggaac tggagggccg cattatcacg 3060
gcaatctcac tttatgacgc gaggaatgtg gtcaagaacg gtgacttcaa caacggcttg 3120
gcgtgttgga acgttaaagg gcacgtggat gtacaacagt cacaccacag aagtgtcttg 3180
gtcatcccgg agtgggaggc ggaagtgagc caggccgtcc gggtctgccc tgggcgcggt 3240
tacatcctcc gcgtgacagc gtacaaggag ggctacggtg agggctgcgt gacgatccac 3300
gagattgaga caacacggga cgagcttaag ttcaagaact gcgaggagga ggaagtgtac 3360
ccgacagaca ccggcacctg caacgactac accgcccacc aagggaccgc cgcctgcaac 3420
agccgcaacg cgggctatga agatgcgtac gaggttgata ccaccgcctc agtgaactac 3480
aaaccgactt atgaggagga gacatacacg gacgtcaggc gcgacaacca ttgtgagtac 3540
gaccgtggct acgtgaacta tccgccggtg ccagcgggcc acatgacgaa ggagctagaa 3600
tacttccctg agacggacaa ggtgtggatt gaaatcggcg agaccgaggg caagtttatc 3660
gtggattctg tcgagctgct gctaatggag gagtag       3696
```

```
SEQ ID NO: 21              moltype = AA   length = 1231
FEATURE                    Location/Qualifiers
REGION                     1..1231
                           note = Amino acid sequence of the chimeric protein variant
                           TIC867_23.
source                     1..1231
                           mol_type = protein
                           organism = synthetic construct
SEQUENCE: 21
MTSNRKNENE IINALSIPAV SNHSAQMNLS TDARIEDSLC IAEGNNIDPF VSASTVQTGI  60
NIAGRILGVL GVPFAGQIAS FYSFLVGELW PRGRDPWEIF LEHVEQLIRQ QVTENTRDTA 120
LARLQGLGNS FRAYQQSLED WLENRDDART RSVLYTQYIA LELDFLNAMP LFAIRNQEVP 180
LLMVYAQAAN LHLLLLRDAS LFGSEFGLTS QEIQRYYERQ VEKTREYSDY CARWYNTGLN 240
NLRGTNAESW LRYNQFRRDL TLGVLDLVAL FPSYDTRVYP MNTSAQLTRE IYTDPIGRTN 300
APSGFASTNW FNNNAPSFSA IEAAVIRPPH LLDFPEQLTI FSVLSRWSNT QYMNYWVGHR 360
LESRTIRGSL STSTHGNTNT SINPVTLQFT SRDVYRTESF AGINILLTTP VNGVPWARFN 420
WRNPLNSLRG SLLYTIGYTG VGTQLFDSET ELPPETTERP NYESYSHRLS NIRLISGNTL 480
RAPVYSWTHR SADRTNTISS DSITQIPLVK AHTLQSGTTV VKGPGFTGGD ILRRTSGGPF 540
AFSNVNLDFN LSQRYRARIR YASTTNLRIY VTVAGERIFA GQFDKTMDAG APLTFQSFSY 600
ATINTAFTFP ERSSSLTVGA DTFSSGNEVY VDRFELIPVT ATTATFEAEY DLERAQEAVN 660
ALFTNTNPRR LKTGVTDYHI DEVSNLVACL SDEFCLDEKR ELLEKVKYAK RLSDERNLLQ 720
DPNFTSINKQ PDFISTNEQS NFTSIHEQSE HGWWGSENIT IQEGNDVFKE NYVILPGTFN 780
ECYPTYLYQK IGEAELKAYT RYQLSGYIED SQDLEIYLIR YNAKHETLDV PGTESVWPLS 840
VESPIGRCGE PNRCAPHFEW NPDLDCSCRD GEKCAHHSHH FSLDIDVGCI DLHENLGVWV 900
VFKIKTQEGH ARLGNLEFIE EKPLLGEALS RVKRAEKKWR DKREKLQLET KRVYTEAKEA 960
VDALFVDSQY DRLQADTNIG MIHAADKLVH RIREAYLSEL SVIPGVNAEI FEELEGRIIT 1020
AISLYDARNV VKNGDFNNGL ACWNVKGHVD VQQSHHRSVL VIPEWEAEVS QAVRVCPGRG 1080
YILRVTAYKE GYGEGCVTIH EIENNTDELK FKNCEEEEVY PTDTGTCNDY TAHQGTAACN 1140
SRNAGYEDAY EVDTTASVNY KPTYEEETYT DVRRDNHCEY DRGYVNYPPV PAGYMTKELE 1200
YFPETDKVWI EIGETEGKFI VDSVELLLME E        1231
```

```
SEQ ID NO: 22              moltype = DNA   length = 3666
FEATURE                    Location/Qualifiers
misc_feature               1..3666
                           note = Synthetic nucleotide sequence designed for
                           expression in a plant cell encoding TIC867_24.
source                     1..3666
                           mol_type = other DNA
                           organism = synthetic construct
SEQUENCE: 22
atgaccagca accgaaagaa cgagaacgag atcatcaacg ccctgtccat accggccgtg  60
tcaaaccact ccgcccagat gaacctctcc accgacgcga ggatcgagga ctccctctgc 120
atcgccgagg gcaacaacat cgacccgttc gtgtctgcaa caccggtcca gaccggcatc 180
aacatcgcgg gccgcatcct gggcgtgctc ggcgtgcctt cgcgggtca aatcgcctct 240
ttctactcat tcctcgtggg cgagctgtgg ccgcgcggac gtgacccgtg ggaaatcttc 300
ctggagcacg ttgagcagct catccggcag caagtgaccg agaacaccag ggacaccgca 360
ctggcacggc tccagggcct tggcaacagc ttccgcgcct accagcagtc gctggaggac 420
tggctggaga accgagacga cgccagaacc cgctcagttc tgtacacaca gtacatcgct 480
ctagagctgg acttcctcaa cgctatgccg ctcttcgcca tccgtaacca ggaagtaccg 540
cttctgatgg tgtacgcaca agcagcgaac ctccatctgc tcctgctgcg agacgcatct 600
ctgttcggca gtgagttcgg gctgacgagc caggagatcc agcgctacta cgagcgccaa 660
gtggagaaga ctcgtgagta cagcgactac tgcgcgcgct ggtacaacac gggcttgaac 720
aaccttcgcg gcacaaacgc cgaatcctgg cttcgctaca accagttccg ccgcgacctc 780
acgctgggtg tgctggacct ggtcgcgctc ttcccgtcct acgacacacg ggtgtaccca 840
atgaacacga gcgcacagct cacccgtgag atctacacag atcccatcgg ccgcaccaac 900
gctcccagtg gcttcgcaag cacgaattgg ttcaacaata acgctccttc tttctctgcc 960
atcgaggccg ctgtcatcag accgccgcac ttactcgatt tcccggagca gctcactatc 1020
ttctctgtgt tgtcccggtg gtcgaacacg cagtacatga actactgggt gggccacagg 1080
ctagagagcc ggaccatccg tggcagtctc tcaacctcga cccacggcaa cacgaacacg 1140
agcatcaacc ctgtcactct ccagtttaca tctaggacg tttacaggac agagtcgttc 1200
gctggcatta acattctgtt gaccactccg gtgaacggcg tcccttgggc ccgcttcaac 1260
tggaggaatc ctctgaactc actgcgcggc agccttctct cactatcgg ctacaccggc 1320
gttgggacgc aactcttcga ctcggagacc gagctgccgc ccgagaccac cgagcggcct 1380
```

```
aactacgaga gttattcaca caggctctcc aacatccgct tgatttctgg gaacaccttg  1440
cgggctccgg tgtactcctg gacgcaccgc agcgccgaca gaactaatac catcagctcc  1500
gactcgatca cccagatccc gctggtgaag gctcacacgc ttcagtcggg caccacagtc  1560
gtcaagggcc ctggcttcac cggcggcgac atcctgcgtc gcacatctgg cggacccttc  1620
gccttcagca acgtgaactt ggacttcaat ttgtcacagc ggtatcgtgc cagaatccgg  1680
tacgccagca ctacgaacct gcgaatctat gttactgtgg cgggcgagcg gatcttcgcc  1740
gggcaattcg acaagacgat ggacgcggga gcacctctga cattccagtc attctcttac  1800
gccacgatca cacggcatt cacgtttccg gagcgttcca gtagcctgac cgtgggcgct  1860
gataccttca gtagcgggaa cgaggtgtac gttgaccgtt tcgagctgat cccggtcacc  1920
gccaccaccg cgacgtttga agctgaatcc gacctcgagc gtgcgcgcaa ggcggtgaac  1980
gctctgttca cgagcaccaa ccctcgtggc ttgaagacgg atgtgacgga ctaccacatc  2040
gaccaagtct cgaacctcgt ggagtgcctg agcgacgagt tctgtcttga caagaagcgc  2100
gagctgctgg aggaggtgaa gtacgccaag cgcctctccg atgagcgcaa cctgctccaa  2160
gatcctacct tcacgtcgat ttccggccaa accgaccgtg gatggatcgg ctcgactggc  2220
atctccatcc agggcggcga cgacatcttc aaggagaact atgttcggct gccgggcacg  2280
gtggacgagt gttacccgac gtacctctac cagaagatag acgagagtca actcaagtcc  2340
tacacgcggt atcagttacg tggctacatt gaagactccc aggacttgga aatctatctc  2400
atacggtaca acgccaagca cgagacctta agcgtgccgg gaacggagtc gccctggcca  2460
agctctggcg tgtacccttc cggtaggtgc ggcgagccca accgctgtgc acctcgaatc  2520
gaatggaacc cggaccttga ctgctcttgc cggtacggcg agaagtgcgt ccatcattct  2580
caccacttca gcttggacat tgacgtcggc tgcaccgacc tcaatgaaga cctcggagtg  2640
tgggtcatct tcaagatcaa gacacaggac gggcacgcga aactaggaaa cctggagttc  2700
atcgaggaga agccactcct cggcaaggca ctttccaggg tcaagcgggc cgagaagaaa  2760
tggagggaca agtacgagaa actccagctc gaaacaaagc gggtgtacac ggaggcaaag  2820
gaatccgtgg acgccctgtt cgtggactct cagtacgaca agctccaggc gaacacaaac  2880
attggcatca tccacggtgc ggacaagcaa gtgcacagga tacgggagcc ttacctctcg  2940
gagctgccgg tgattccctc gatcaacgcg gcgatcttcg aggaactgga gggccacatc  3000
ttcaaggcgt attctctgta cgacgcgcgt aacgtcatca agaacggcga cttcaacaat  3060
gggctgtcct gctggaacgt taaaggccac gtcgatgtcc agcagaacca ccataggtca  3120
gtcctggtgc tgagcgaggt ggaggcggag gtgtcccaga aggtgcgctg tgtgcccggat  3180
cgcggctaca tcttgagggt gacagcctac aaggagggct acggcgaggg ctgtgtcacg  3240
atccatgagt tcgaggacaa cacggatgtc ctgaaattcc gtaacttcgt cgaggaggag  3300
gtctatccca acaacaccgt gacctgcaac gactacacga ccaatcagtc ggctgagggc  3360
agtaccgatg cctgcaacag ctacaaccgt ggttacgaag atggatacga gaaccgctac  3420
gagcccaatc cttcggctcc cgtgaattac actcccacgt acgaggaggg catgtacact  3480
gacactcagg gctacaacca ttgcgtcagc gaccgtggct accgcaacca cacgccgctc  3540
ccagcgggct acgtgacgct ggagctggaa tactttcccg agacagaaca agtgtggata  3600
gagatcggcg agaccgaggg cacattcatc gtgggctctg tggaattgct cctcatggag  3660
gagtaa                                                             3666
```

```
SEQ ID NO: 23          moltype = AA  length = 1221
FEATURE                Location/Qualifiers
REGION                 1..1221
                       note = Amino acid sequence of the chimeric protein variant
                       TIC867_24.
source                 1..1221
                       mol_type = protein
                       organism = synthetic construct
SEQUENCE: 23
MTSNRKNENE IINALSIPAV SNHSAQMNLS TDARIEDSLC IAEGNNIDPF VSASTVQTGI   60
NIAGRILGVL GVPFAGQIAS FYSFLVGELW PRGRDPWEIF LEHVEQLIRQ QVTENTRDTA  120
LARLQGLGNS FRAYQQSLED WLENRDDART RSVLYTQYIA LELDFLNAMP LFAIRNQEVP  180
LLMVYAQAAN LHLLLLRDAS LFGSEFGLTS QEIQRYYERQ VEKTREYSDY CARWYNTGLN  240
NLRGTNAESW LRYNQFRRDL TLGVLDLVAL FPSYDTRVYP MNTSAQLTRE IYTDPIGRTN  300
APSGFASTNW FNNNAPSFSA IEAAVIRPPH LLDFPEQLTI FSVLSRWSNT QYMNYWVGHR  360
LESRTIRGSL STSTHGNTNT SINPVTLQFT SRDVYRTESF AGINILLTTP VNGVPWARFN  420
WRNPLNSLRG SLLYTIGYTG VGTQLFDSET ELPPETTERP NYESYSHRLS NIRLISGNTL  480
RAPVYSWTHR SADRTNTISS DSITQIPLVK AHTLQSGTTV VKGPGFTGGD ILRRTSGGPF  540
AFSNVNLDFN LSQRYRARIR YASTTNLRIY VTVAGERIFA GQPDKTMDAG APLTFQSFSY  600
ATINTAFTFP ERSSSLTVGA DTFSSGNEVY VDRFELIPVT ATTATFEAES DLERARKAVN  660
ALFTSTNPRG LKTDVTDYHI DQVSNLVECL SDEFCLDKKR ELLEEVKYAK RLSDERNLLQ  720
DPTFTSISGQ TDRGWIGSTG ISIQGGDDIF KENYVRLPGT VDECYPTYLY QKIDESQLKS  780
YTRYQLRGYI EDSQDLEIYL IRYNAKHETL SVPGTESPWP SSGVYPSGRC GEPNRCAPRI  840
EWNPDLDCSC RYGEKCVHHS HHFSLDIDVG CTDLNEDLGV WVIFKIKTQD GHAKLGNLEF  900
IEEKPLLGKA LSRVKRAEKK WRDKYEKLQL ETKRVYTEAK ESVDALFVDS QYDKLQANTN  960
IGIIHGADKQ VHRIREPYLS ELPVIPSINA AIFEELEGHI FKAYSLYDAR NVIKNGDFNN  1020
GLSCWNVKGH VDVQQNHHRS VLVLSEWEAE VSQKVRVCPD RGYILRVTAY KEGYGEGCVT  1080
IHEFEDNTDV LKFRNFVEEE VYPNNTVTCN DYTTNQSAEG STDACNSYNR GYEDGYENRY  1140
EPNPSAPVNY TPTYEEGMYT DTQGYNHCVS DRGYRNHTPL PAGYVTLELE YFPETEQVWI  1200
EIGETEGTFI VGSVELLLME E                                            1221
```

```
SEQ ID NO: 24          moltype = DNA  length = 3651
FEATURE                Location/Qualifiers
misc_feature           1..3651
                       note = Synthetic nucleotide sequence designed for
                        expression in a plant cell encoding TIC867_25.
source                 1..3651
                       mol_type = other DNA
                       organism = synthetic construct
```

```
SEQUENCE: 24
atgaccagca accgaaagaa cgagaacgag atcatcaacg ccctgtccat accggccgtg  60
tcaaaccact ccgcccagat gaacctctcc accgacgcga ggatcgagga ctccctctgc  120
atcgccgagg gcaacaacat cgaccgttc gtgtctgcaa gcacggtcca gaccggcatc  180
aacatcgcgg gccgcatcct gggcgtgctc ggcgtgcctt tcgcgggtca aatcgcctct  240
ttctactcat tcctcgtggg cgagctgtgg ccgcgcggac gtgacccgtg ggaaatcttc  300
ctggagcacg ttgagcagct catccggcag caagtgaccg agaacaccag ggacaccgca  360
ctggcacggc tccagggcct tggcaacagc ttccgcgcct accagcagtc gctggaggac  420
tggctggaaa accgagacga cgccagaacc cgctcagttc tgtacacaca gtacatcgct  480
ctagagctgg acttcctcaa cgctatgccg ctcttcgcca tccgtaacca ggaagtaccg  540
cttctgatgg tgtacgcaca agcagcgaac ctccatctgc tcctgctgcg agacgcatct  600
ctgttcggca gtgagttcgg gctgacgagc caggagatcc agcgctacta cgagcgccaa  660
gtggagaaga ctcgtgagta cagcgactac tgcgcgcgct ggtacaacac gggcttgaac  720
aaccttcgcg ggacaaacgc cgaatcctgg cttcgctaca accagttccg ccgcgacctc  780
acgctgggtg tgctggacct ggtcgcgctc ttcccgtcct acgacacacg ggtgtaccca  840
atgaacacga gcgcacagct cacccgtgag atctacacag atcccatcgg ccgcaccaac  900
gctcccagtg gcttcgcaag cacgaattgg ttcaacaata acgctccttc tttctctgcc  960
atcgaggccg ctgtcatcag accgccgcac ttactcgatt tcccggagca gctcactatc  1020
ttctctgtgt tgtcccggtg gtcgaacacg cagtacatga actactgggt gggccacagg  1080
ctagagagcc ggaccatccg tggcagtctc tcaacctcga cccacggcaa cacgaacacg  1140
agcatcaacc ctgtcactct ccagtttaca tctagggacg tttacaggac agagtcgttc  1200
gctggcatta acattctgtt gaccactccg gtgaacggcg tcccttgggc ccgcttcaac  1260
tggaggaatc ctctgaactc actgcgcggc agccttctct acactatcgg ctacaccggc  1320
gttgggacgc aactcttcga ctcggagacc gagctgccgc ccgagaccac cgagcggcct  1380
aactacgaga gttattcaca caggctctcc aacatccgt tgatttctgg gaacaccttg  1440
cgggctccgg tgtactcctg gacgcaccgc agcgccgaca gaactaatac catcagctcc  1500
gactcgatca cccagatccc gctggtgaag gctcacacgc ttcagtcggg caccacagtc  1560
gtcaagggcc ctggcttcac cggcggcgac atcctgcgtc gcacatctgg cggacccttc  1620
gccttcagca acgtgaactt ggacttcaat ttgtcacagc ggtatcgtgc cagaatccgg  1680
tacgccagca ctacgaacct gcgaatctat gttactgtgg cgggcgagcg gatcttcgcc  1740
gggcaattcg acaagacgat ggacgcggga gcacctctga cattccagtc attctcttac  1800
gccacgatca cacggcatt cacgtttccg gagcgttcca gtagcctgac cgtgggcgct  1860
gataccttca gtagcgggaa cgaggtgtac gttgaccgtt tcgagctgat cccggtcacc  1920
gccaccgatg ctacctttga agcagagtcc gacttggaac gtgcacagaa ggcagtgaac  1980
gcactcttca cctcaagcaa ccagatcgga ttgaagacag atgtgacaga ttaccacatc  2040
gaccaagtga gcaacttggt ggattgcttg tcagatgagt tctgcttgga tgagaagcgt  2100
gaactctccg agaaggtgaa gcacgcaaag cgtctctcag atgaacgtaa tctccttcaa  2160
gaccctaact ttcgtggtat caatcgtcag ccagatcgtg gatggcgtgg atcaacagac  2220
atcaccatcc agggaggcga tgatgtgttc aaggagaact acgtgaccct cccaggaacc  2280
gtggatgaat gctacccaac ctacctctac cagaagatcg acgagtcaaa gctcaaggct  2340
tacacccgtt atgaactccg tggctacatc gaagatagcc aggatctcga aatctatctc  2400
atccgttaca atgctaagca cgaaatcgtg aatgtgccag gaaccggctc actctggcca  2460
ctctcagcac agtcaccaat cggcaagtgc ggcgaaccca gatctgtcc tcctcatctc  2520
gaatggaatc ccgatctcga ctgctcctgc cgagacggcg agaagtgtgc acatcactca  2580
caccacttca ccctcgacat cgacgtgggc tgcaccgacc tcaatgaaga cctgggcgtg  2640
tgggtgatct tcaagatcaa gacccaggac ggccacgcac gactgggcaa tctggagttt  2700
ctggaggaga agccactgct tggcgaggca ctggcacgag tgaaacgaac gcgagaagaaa  2760
tggcgagaca aacgtgagaa gctgcaactg gagaccaaca tcgtgtacaa agaggccaaa  2820
gagtcagttg acgccctgtt tgtcaatagc cagtatgacc gactgcaagt tgacaccaac  2880
atcgccatga tccacgctgc ggacaagcgc gtccaccgca tccgcgaggc ttatctgccc  2940
gagctgagcg tcattcccgg cgtcaatgcc gcgatcttcg aggagttaga gggccgcatc  3000
ttcaccgcct acagcctcta tgacgcccgc aatgtcatta agaatggcga cttcaacaat  3060
ggcttactat gctggaatgt caaagggcac gttgacgtcg aggagcagaa caatcaccgc  3120
agcgtcttag tcatacccga gtgggaggcc gaagtcagcc aggaagtccg cgtctgtcca  3180
gggcgcgggt acatcctgcg ggtcaccgcc tacaaagagg gatacggcga gggttgtgtc  3240
accatacacg agatagagga caataccgac gaactcaagt tcagcaattg tgtcgaggag  3300
gaagtctatc ccaacaatac cgtaacctgc aacaactaca ccggaacccca ggaggagtat  3360
gaagggacgt acacctcgcg gaaccaggc tatgacgaag cctatgggaa caacccgtcg  3420
gtgcctgctg actatgcgtc ggtctatgag gagaaatcgt acacggacgg gcggcgggag  3480
aatccgtgtg agtcgaatcg cgggtatggt gactacacgc cgctaccgg gctgcatgta  3540
acgaaagacc tggaatactt cccggacacg acaaagtat ggatagagat aggcgagacg  3600
gagggaacgt tcatcgtgga ctcggtagag ctgctgctca tggaggagtg a  3651
```

```
SEQ ID NO: 25          moltype = AA  length = 1216
FEATURE                Location/Qualifiers
REGION                 1..1216
                       note = Amino acid sequence of the chimeric protein variant
                        TIC867_25.
source                 1..1216
                       mol_type = protein
                       organism = synthetic construct
SEQUENCE: 25
MTSNRKNENE IINALSIPAV SNHSAQMNLS TDARIEDSLC IAEGNNIDPF VSASTVQTGI  60
NIAGRILGVL GVPFAGQIAS FYSFLVGELW PRGRDPWEIF LEHVEQLIRQ QVTENTRDTA  120
LARLQGLGNS FRAYQQSLED WLENRDDART RSVLYTQYIA LELDFLNAMP LFAIRNQEVP  180
LLMVYAQAAN LHLLLLRDAS LFGSEFGLTS QEIQRYYERQ VEKTREYSDY CARWYNTGLN  240
NLRGTNAESW LRYNQFRRDL TLGVLDLVAL FPSYDTRVYP MNTSAQLTRE IYTDPIGRTN  300
APSGFASTNW FNNNAPSFSA IEAAVIRPPH LLDFPEQLTI FSVLSRWSNT QYMNYWVGHR  360
LESRTIRGSL STSTHGNTNT SINPVTLQFT SRDVYRTESF AGINILLTTP VNGVPWARFN  420
```

-continued

```
WRNPLNSLRG SLLYTIGYTG VGTQLFDSET ELPPETTERP NYESYSHRLS NIRLISGNTL   480
RAPVYSWTHR SADRTNTISS DSITQIPLVK AHTLQSGTTV VKGPGFTGGD ILRRTSGGPF   540
AFSNVNLDFN LSQRYRARIR YASTTNLRIY VTVAGERIFA GQFDKTMDAG APLTFQSFSY   600
ATINTAFTFP ERSSSLTVGA DTFSSGNEVY VDRFELIPVT ATDATFEAES DLERAQKAVN   660
ALFTSSNQIG LKTDVTDYHI DQVSNLVDCL SDEFCLDEKR ELSEKVKHAK RLSDERNLLQ   720
DPNFRGINRQ PDRGWRGSTD ITIQGGDDVF KENYVTLPGT VDECYPTYLY QKIDESKLKA   780
YTRYELRGYI EDSQDLEIYL IRYNAKHEIV NVPGTGSLWP LSAQSPIGKC GEPNRCAPHL   840
EWNPDLDCSC RDGEKCAHHS HHFTLDIDVG CTDLNEDLGV WVIFKIKTQD GHARLGNLEF   900
LEEKPLLGEA LARVKRAEKK WRDKREKLQL ETNIVYKEAK ESVDALFVNS QYDRLQVDTN   960
IAMIHAADKR VHRIREAYLP ELSVIPGVNA AIFEELEGRI FTAYSLYDAR NVIKNGDFNN  1020
GLLCWNVKGH VDVEEQNNHR SVLVIPEWEA EVSQEVRVCP GRGYILRVTA YKEGYGEGCV  1080
TIHEIEDNTD ELKFSNCVEE EVYPNNTVTC NNYTGTQEEY EGTYTSRNQG YDEAYGNNPS  1140
VPADYASVYE EKSYTDGRRE NPCESNRGYG DYTPLPAGYV TKDLEYFPET DKVWIEIGET  1200
EGTFIVDSVE LLLLMEE                                               1216

SEQ ID NO: 26            moltype = DNA   length = 3600
FEATURE                  Location/Qualifiers
misc_feature             1..3600
                         note = Recombinant nucleotide sequence used for expression
                         in a bacterial cell encoding TIC868.
source                   1..3600
                         mol_type = other DNA
                         organism = synthetic construct
SEQUENCE: 26
atgacttcaa ataggaaaaa tgagaatgaa attataaatg ctttatcgat tccagctgta   60
tcgaatcatt ccgcacaaat gaatctatca accgatgctc gtatttgagga tagcttgtgt  120
atagccgagg ggaacaatat cgatccattt gttagcgcat caacagtcca aacgggtatt  180
aacatagctg gtagaatact aggtgtatta ggcgtaccgt ttgctggaca aatagctagt  240
ttttatagtt ttcttgttgg tgaattatgg ccccgcggca gagatccttg ggaaattttc  300
ctagaacatg tcgaacaact tataagacaa caagtaacag aaaatactag ggatacggct  360
cttgctcgat tacaaggttt aggaaattcc tttagagcct atcaacagtc acttgaagat  420
tggctagaaa accgtgatga tgcaagaacg agaagtgttc tttataccca atatatagcc  480
ttagaacttg attttcttaa tgcgatgccg cttttcgcaa ttagaaacca agaagttcca  540
ttattaatgg tatatgctca agctgcaaat ttacacctat tattattgag agatgcctct  600
cttttggta gtgaatttgg gcttacatcc caagaaattc aacgttatta tgagcgccaa  660
gtggaaaaaa cgagagaata ttctgattat tgcgcaagat ggtataatac gggtttaaat  720
aatttgagag ggacaaatgc tgaaagttgg ttgcgatata atcaattccg tagagactta  780
acgctaggag tattagatct agtggcacta ttcccaagct atgacacgcg tgtttatcca  840
atgaatacca gtgctcaatt aacaagagaa atttatacag atccaattgg gagaacaaat  900
gcaccttcag gatttgcaag tacgaattgg tttaataata atgcaccatc gttttctgcc  960
atagaggctg ccgttattag gcctccgcat ctacttgatt ttccagaaca gcttacaatt  1020
ttcagcgtat taagtcgatg gagtaatact caatatatga attactgggt gggacataga  1080
cttgaatcgc gaacaataag ggggtcatta agtacctcga cacacggaaa taccaatact  1140
tctattaatc ctgtaacatt acagttcaca tctcgagacg tttatagaac agaatcattt  1200
gcagggataa atatacttct aactactcct gtgaatggag taccttgggc tagatttaat  1260
tggagaaatc ccctgaattc tcttagaggt agccttctct atactatagg gtatactgga  1320
gtggggacac aactatttga ttcagaaact gaattaccac cagaaacaac gaaacgacca  1380
aattatgaat cttacagtca tagattatct aatataagac taatatcagg aaacactttg  1440
agagcaccag tatattcttg gacgcaccgt agtgcagatc gtacaaatac cattagttca  1500
gatagcatta atcaaatacc tttagtgaaa ggatttagag tttgggggggg cacctctgtc  1560
attacaggac caggatttac aggaggggat atccttcgaa gaaatacctt tggtgatttt  1620
gtatctctac aagtcaatat taattcacca attacccaaa gataccgttt aagatttcgt  1680
tacgcttcca gtagggatgc acgagttata gtattaacag gagcggcatc cacaggagtg  1740
ggaggccaag ttagtgtaaa tatgcctctt cagaaaacta tggaaatagg ggagaactta  1800
acatctagaa catttagata taccgatttt agtaatcctt tttcatttag agctaatcca  1860
gatataattg ggataagtga acaacctcta tttggtgcag gttctattag tagcggtgaa  1920
ctttatatag ataaaattga aattattcta gcagatgcaa catttgaagc agaatctgat  1980
ttagaaaagg cacaaaaggc ggtgaatgag ctgtttactt cttccaatca aatcgggtta  2040
aaaacagatg tgacggatta tcatattgat caagtatcca atttagttga gtgtttatct  2100
gatgaatttt gtctggatga aaaaaaagaa ttgtccgaga aagtcaaaca tgcgaagcga  2160
cttagtgatg agcggaattt acttcaagat ccaaacttta gagggatcaa tagacaacta  2220
gaccgtggct ggagaggaag tacggatatt accatccaag gaggcgatga cgtattcaaa  2280
gagaattacg ttacgctatt gggtaccttt gatgagtgct atccaacgta tttatatcaa  2340
aaaatagatg agtcgaaatt aaaagcctat acccgttacg aattaagagg gtatatcgaa  2400
gatagtcaag acttagaaat ctatttaatt cgctacaatg ccaaacacga aacagtaaat  2460
gtgccaggta cgggttcctt atggccgctt tcagccccaa gtccaatcgg aaaatgtgcc  2520
catcattccc atcatttctc cttggacatt gatgttggat gtacagactt aaatgaggac  2580
ttaggtgtat gggtgatatt caagattaag acgcaagatg gccatgcaag actaggaaat  2640
ctagaatttc tcgaagagaa accattagta ggagagcac tagctcgtgt gaaaaagacg  2700
gagaaaaaat ggagagacaa acgtgaaaaa ttggaatggg aaacaaatat tgtttataaa  2760
gaggcaaaag aatctgtaga tgctttattt gtaaactctc aatatgatag attacaagcg  2820
gataccaaca tcgcgatgat tcatgcggca gataaacgcg ttcatagcat tcgagaagct  2880
tatctgcctg agctgtctgt gattccgggt gtcaatgcgg ctatttttga agaattagaa  2940
gggcgtattt tcactgcatt ctccctatat gatgcgagaa atgtcattaa aaatggtgat  3000
tttaataatg gcttatcctg ctggaacgtg aaagggcatg tagatgtaga agaacaaaac  3060
aaccaccgtt cggtccttgt tgttccggaa tgggaagcag aagtgtcaca gaagttcgt  3120
gtctgtccgg gtcgtggcta tatccttcgt gtcacagcgt acaaggaggg atatggggaa  3180
ggttgcgtaa ccattcatga gatcgagaac aatacagacg aactgaagtt tagcaactgt  3240
gtagaagagg aagtatatcc aaacaacacg gtaacgtgta atgattatac tgcgactcaa  3300
```

```
gaagaatatg agggtacgta cacttctcgt aatcgaggat atgacggagc ctatgaaagc  3360
aattcttctg taccagctga ttatgcatca gcctatgaag aaaaagcata tacagatgga  3420
cgaagagaca atccttgtga atctaacaga ggatatgggg attacacacc actaccagct  3480
ggctatgtga caaaagaatt agagtacttc ccagaaaccg ataaggtatg gattgagatc  3540
ggagaaacgg aaggaacatt catcgtggac agcgtggaat tacttcttat ggaggaatag  3600
```

SEQ ID NO: 27          moltype = DNA   length = 3600
FEATURE                Location/Qualifiers
misc_feature           1..3600
                       note = Synthetic nucleotide sequence designed for
                        expression in a plant cell encoding TIC868.
source                 1..3600
                       mol_type = other DNA
                       organism = synthetic construct
SEQUENCE: 27

```
atgacgagca accggaagaa cgagaacgag atcatcaacg ccctctcgat ccctgctgtt  60
tcaaaccact ccgcgcagat gaacctgtcc accgacgcgc gcatcgagga ctccctctgc  120
atagccgagg gcaacaacat cgacccattc gtgtcggcca gcacggttca gaccggcatc  180
aacatcgcgg gccgtatcct cggcgtcctc ggtgtcccat tcgccggtca gatcgcgtcc  240
ttctactcgt tccttgtggg cgagctgtgg cctcgcggtc gtgacccgtg ggagatcttc  300
ctggagcatg tggagcagtt gatccggcag caagtcacgg agaacacccg cgatactgct  360
ctggccaggc tacagggcct gggaaactcc tttcgggcat accagcagtc actgaggac  420
tggttggaga acaggatga cgcgcgaaca cgctcggtac tctacaccca gtacatcgct  480
ctcgaactcg acttcctgaa cgctatgccg ctgttcgcca tcaggaacca ggaagttcca  540
ctccttatgt tgtacgccca ggccgccaac ttacatctgc tcctgctgcg ggacgccagc  600
ctgttcggct ccgagttcgg actcacatct caagaaatcc agcgttacta cgagcgccaa  660
gtggagaaga cccgtgagta cagtgactac tgcgctcgat ggtacaacac agggctcaac  720
aacctgcgcg gcaccaacgc tgagtcatgg ctccgttaca accagttccg ccgcgacttg  780
actttgggtg tcctagacct ggtggcgcta ttcccgtctt acgacacacg ggtgtaccca  840
atgaacacta gcgcgcaact cacgcgggag atctacacag acccaatcgg ccggacgaac  900
gcaccctccg gtttcgcatc cacgaattgg ttcaacaaca acgcaccctc cttctcggca  960
atcgaggccg ccgtcatccg ccctcctcac ctgctcgact ttcccgagca gctcacgatc  1020
ttctccgtgc tctcacgctg gtccaacaca cagtacatga actactgggt cgggcaccga  1080
ttggagagta ggacgatccg tggcagcttg agcaccagta cccacggcaa caccaacacc  1140
tccatcaacc cagttacgct acagttcacg agcgccgacg tttaccggac tgagtcgttc  1200
gcgggcatta acatccttct gacaacgccc gtcaacggcg tcccgtgggc ccggttcaac  1260
tggcgtaacc cgttgaactc cctgcgcggg tcattgctct acaccatcgg gtacacgggc  1320
gtcggcaccc agctcttcga cagtgaaact gagctgccgc ccgagaccac ggaacgcccg  1380
aactacgagt cctacagcca ccgcctgtcc aacatccggc tcatctctgg caacacgctg  1440
cgtgcgccgg tgtactcctg gacacaccgc agcgccgacc ggaccaacac gatctcttcc  1500
gactccatta accagatccc gctcgtgaag ggcttccgtg tgtggggtgg cacgagcgtc  1560
atcaccggtc cgggcttcac cggtggagac atactgcggc gcaacacttt cggcgacttc  1620
gtttcgttgc aagtgaacat caactcgccg atcacccagc gttaccgtct gaggttccgc  1680
tacgcttcaa gccgcgacgc gagggtcatt gtcctgaccg gagccgcgtc cacaggcgtg  1740
ggaggccaag tctcagtcaa catgcctctc cagaagacga tggagatagg cgagaacttg  1800
actagccgaa ccttccggta cactgatttc tcgaacccct tctcattcag agcgaaccct  1860
gacatcattg ggatctccga gcaaccgctg ttcggtgctg gctccatcag ctctggcgaa  1920
ctgtacatcg acaagattga gatcatcctg gcggatgcga cgttcgaggc cgagtctgac  1980
ctggagcggg ctcagaaggc tgtcaacgaa ctgttcacca gcagcaacca gattgggctc  2040
aagaccgacg tcacggacta tcacattgac caagtgtcca accttgtgga gtgcctgtcc  2100
gacgagttct gcctcgacga gaagaaggag ctgtccgaga aggtcaaaca gcgaaagcgt  2160
ctgagtgacg agcggaattt gctccaggac ccgaacttcc gtggcatcaa ccgccagctc  2220
gaccgtggtt ggcgcgggag tacagacatc accatccagg gaggcgacga tgtgttcaag  2280
gagaactatg tgacgctgct cgggactttc gacgaatgct acccgacgta tctctaccag  2340
aagatagacg agagtaaatt gaaggcgtac acccgctacc agcttcgcgg gtacatcgag  2400
gatagtcagg acctggaaat ctacctgatc cgatacaacg ccaagcacga gacagtgaac  2460
gtgccaggca cgggctcact ttggccattg agcgctccct ctccaatcgg aaagtgcgct  2520
caccactcgc accacttctc tctggacatc gacgtgggct gcaccgacct caacgaggac  2580
ctgggtgtct gggttatctt caagattaag acccaggacg gacatgcccg cctcggcaac  2640
ctggagttcc ttgaggagaa gcctctcgtg ggcgaggccc tcgctcgtgt gaagcgcgcc  2700
gagaagaaat ggcgagacaa gcgggagaag ctggagtggg agaccaacat cgtgtacaag  2760
gaggccaagg agtcagtgga cgcactcttc gtcaacagcc agtacgaccg cctccaggct  2820
gacaccaaca tcgccatgat ccacgcggct gacaagcggg tccacagcat ccgtgaggcg  2880
tacctgcccg agctgtcagt gatccctggt gtgaaccggg cgatcttcga ggaactggag  2940
ggccgcatct tcacagcatt cagcctgtac gatgccagga atgttattaa gaacggtgac  3000
ttcaacaacg ggctgagttg ctggaacgtc aagggccatg tggacgtcga ggagcagaac  3060
aaccaccggt ccgtgctggt cgtgccggag tgggaggcag aggtgagcca ggaggtccgc  3120
gtctgccctg gtcgcggcta catcctccgt gtgactgcgt acaaggaagg ctacggtgaa  3180
ggctgcgtga ctatccacga gatcgagaac aacaccgacg agctcaagtt ctcgaactgt  3240
gtggaggagg aggtgtaccc gaacaacacc gttacttgca acgactacac tgccacgcaa  3300
gaggagtacg agggcactta cacttccgg aatcgcggct atgatggcgc gtacgagtcc  3360
aacagcagcg tgcctgcgga ttatgcgtcc gcttacgagg agaaggcgta caccgacgga  3420
cggagggaca acccttgcga gtccaaccgt ggctacggtg actacactcc gctgcccgcc  3480
gggtacgtca ccaaggagct ggagtacttc ccggagaccg acaaagtctg gatcgagatc  3540
ggcgagacgg agggcactta catcgtggac tcggtcgagc tgctactgat ggaggagtga  3600
```

SEQ ID NO: 28          moltype = AA   length = 1199
FEATURE                Location/Qualifiers
REGION                 1..1199

```
                         note = Amino acid sequence of the chimeric protein TIC868.
source                   1..1199
                         mol_type = protein
                         organism = synthetic construct
SEQUENCE: 28
MTSNRKNENE IINALSIPAV SNHSAQMNLS TDARIEDSLC IAEGNNIDPF VSASTVQTGI  60
NIAGRILGVL GVPFAGQIAS FYSFLVGELW PRGRDPWEIF LEHVEQLIRQ QVTENTRDTA  120
LARLQGLGNS FRAYQQSLED WLENRDDART RSVLYTQYIA LELDFLNAMP LFAIRNQEVP  180
LLMVYAQAAN LHLLLLRDAS LFGSEFGLTS QEIQRYYERQ VEKTREYSDY CARWYNTGLN  240
NLRGTNAESW LRYNQFRRDL TLGVLDLVAL FPSYDTRVYP MNTSAQLTRE IYTDPIGRTN  300
APSGFASTNW FNNNAPSFSA IEAAVIRPPH LLDFPEQLTI FSVLSRWSNT QYMNYWVGHR  360
LESRTIRGSL STSTHGNTNT SINPVTLQFT SRDVYRTESF AGINILLTTP VNGVPWARFN  420
WRNPLNSLRG SLLYTIGYTG VGTQLFDSET ELPPETTERP NYESYSHRLS NIRLISGNTL  480
RAPVYSWTHR SADRTNTISS DSINQIPLVK GFRVWGGTSV ITGPGFTGGD ILRRNTFGDF  540
VSLQVNINSP ITQRYRLRFR YASSRDARVI VLTGAASTGV GGQVSVNMPL QKTMEIGENL  600
TSRTFRYTDF SNPFSFRANP DIIGISEQPL FGAGSISSGE LYIDKIEIIL ADATFEAESD  660
LERAQKAVNE LFTSSNQIGL KTDVTDYHID QVSNLVECLS DEFCLDEKKE LSEKVKHAKR  720
LSDERNLLQD PNFRGINRQL DRGWRGSTDI TIQGGDDVFK ENYVTLLGTF DECYPTLYQ  780
KIDESKLKAY TRYQLRGYIE DSQDLEIYLI RYNAKHETVN VPGTGSLWPL SAPSPIGKCA  840
HHSHHFSLDI DVGCTDLNED LGVWVIFKIK TQDGHARLGN LEFLEEKPLV GEALARVKRA  900
EKKWRDKREK LEWETNIVYK EAKESVDALF VNSQYDRLQA DTNIAMIHAA DKRVHSIREA  960
YLPELSVIPG VNAAIFEELE GRIFTAFSLY DARNVIKNGD FNNGLSCWNV KGHVDVEEQN  1020
NHRSVLVVPE WEAEVSQEVR VCPGRGYILR VTAYKEGYGE GCVTIHEIEN NTDELKFSNC  1080
VEEEVYPNNT VTCNDYTATQ EEYEGTYTSR NRGYDGAYES NSSVPADYAS AYEEKAYTDG  1140
RRDNPCESNR GYGDYTPLPA GYVTKELEYF PETDKVWIEI GETEGTFIVD SVELLLMEE  1199

SEQ ID NO: 29            moltype = DNA  length = 3600
FEATURE                  Location/Qualifiers
misc_feature             1..3600
                         note = Synthetic nucleotide sequence designed for
                          expression in a plant cell encoding TIC868_9.
source                   1..3600
                         mol_type = other DNA
                         organism = synthetic construct
SEQUENCE: 29
atgacgagca accggaagaa cgagaacgag atcatcaacg ccctctcgat ccctgctgtt  60
tcaaaccact ccgcgcagat gaacctgtcc accgacgcgc gcatcgagga ctccctctgc  120
atagccgagg gcaacaacat cgacccattc gtgtcggcca gcacggttca gaccggcatc  180
aacatcgcgg gccgtatcct cggtcgcctc ggtgtcctca tcgccggtca gatcgcgtcc  240
ttctactcgt tccttgtggg cgagctgtgg cctcgcggtc gtgacccgtg ggagatcttc  300
ctggagcatg tggagcagtt gatccggcag caagtcacgg agaacacccg cgatactgct  360
ctggccaggc tacagggcct gggaaactcc tttcgggcat accagcagtc actggaggac  420
tggttggaga acagggatga cgcgcgaaca cgctcggtac tctacaccca gtacatcgct  480
ctcgaactcg acttcctgaa cgctatgccg ctgttcgcca tcaggaacca ggaagttcca  540
ctccttatgg tgtacgccca ggcgccaac ttacatctgc tcctgctgcg ggacgccagc  600
ctgttcggct ccgagttcgg actcacatct caagaaatcc agcgttacta cgagcgccaa  660
gtggagaaga cccgtgagta cagtgactac tgcgctcgat ggtacaacac agggctcaac  720
agcctgcgcg gcaccaacgc tgagtcatgg ctccgttaca accagttccg ccgcgacttg  780
actttgggtg tcctagacct ggtggcgcta ttcccgtctt acgacacacg ggtgtaccca  840
atgaacacta gcgcgcaact cacgcgggag atctacacag acccaatcgg ccggacgaac  900
gcaccctccg gtttcgcatc cacgaattgg ttcaacaaca acgcaccctc cttctcggca  960
atcgaggccg ccgtcatccg ccctcctcac ctgctcgact tccccgagca gctcacgatc  1020
ttctccgtgc tctcacgctg gtccaacaca cagtacatga actactggt cgggcaccga  1080
ttggagagta ggacgatccg tggcagcttg agcaccagta cccacggcaa caccaacacc  1140
tccatcaacc cagttacgct acagttcacg agccgcgacg tttaccggac tgagtcgcag  1200
gcgggcatta acatccttat gacaacgccc gtcaacggcg tcccgtgggc ccggttcaac  1260
tggcgtaacc cgaagaactc cctgcgcggg tcattgctct acaccatcgg gtacacgggc  1320
gtcggcaccc agctcttcga cagtgaaact gagctgccgc ccgagaccac ggaacgcccg  1380
aactacgagt cctacagcca ccgcctgtcc aacatccggc tcatctctgg caacacgctg  1440
cgtgcgccgg tgtactcctg gacacaccgc agcgccgacc ggaccaacac gatctcttcc  1500
gactccatta accagatccc gctcgtgaag ggcttccgtg tgtggggtgg cacgagcgtc  1560
atcaccggtc cgggcttcac cggtggagac atactgcggc gcaacacttt cggcgacttc  1620
gtttcgttgc aagtgaacat caactcgccg atcacccagc gttaccgtct gaggttccgc  1680
tacgcttcaa gccgcgacgc gagggtcatt gtcctgaccg gcgccagcac cggtgtgggc  1740
ggaggccaag tctcagtcaa catgcctctc cagaagacga tggagatagg cgagaacttg  1800
actagccgaa ccttccggta cactgatttc tcgaacccct tctcattcag agcgaaccct  1860
gacatcattg gatctccga gcaaccgctg ttcggtgctg gctccatcag ctctggcgaa  1920
ctgtacatcg acaagattga gatcatcctg gcggatgcga cgttcgaggc cgatctgac  1980
ctggagcggg ctcagaaggc tgtcaacgaa ctgttcacca gcagcaacca gattgggctc  2040
aagaccgacg tcacggacta tcacattgac caagtgtcca accttgtgga gtgcctgtcc  2100
gacgagttct gcctcgacga gaagaaggag ctgtccgaga aggtcaaaca cgcgaagcgt  2160
ctgagtgacg agcggaattt gctccaggac ccgaacttcc gtggcatcaa ccgccagctc  2220
gaccgtggtt ggcgcgggag tacagacatc accatccagg gaggcgacga tgtgttcaag  2280
gagaactatg tgacgctgct cgggacttc gacgaatgct acccgacatc tctctaccag  2340
aagatagagc agagtaaatt gaaggcgtac acccgctacc agcttcgcg gtacatcgag  2400
gatagtcagg acctgaaat ctacctgatc cgatacaacg ccaagcacga gacagtgaac  2460
gtgccaggca cgggctcact ttggccattg agcgctccct ctccaatcgg aaagtgcgct  2520
caccactcgc accacttctc tctggacatc gacgtgggct gcaccgacct caacgaggac  2580
ctgggtgtct gggttatctt caagattaag acccaggacg gacatgcccg cctcggcaac  2640
```

```
ctggagttcc ttgaggagaa gcctctcgtg ggcgaggccc tcgctcgtgt gaagcgcgcc   2700
gagaagaaat ggcgagacaa gcgggagaag ctggagtggg agaccaacat cgtgtacaag   2760
gaggccaagg agtcagtgga cgcactcttc gtcaacagcc agtacgaccg cctccaggct   2820
gacaccaaca tcgccatgat ccacgcggct gacaagcggg tccacagcat ccgtgaggcg   2880
tacctgcccg agctgtcagt gatccctggt gtgaaccgcg cgatcttcga ggaactggag   2940
ggccgcatct tcacagcatt cagcctgtac gatgccagga atgttattaa gaacggtgac   3000
ttcaacaacg ggctgagttg ctggaacgtc aagggccatg tggacgtcga ggagcagaac   3060
aaccaccggt ccgtgctggt cgtgccggag tgggaggcag aggtgagcca ggaggtccgc   3120
gtctgccctg gtcgcggcta catcctccgt gtgactgcgt acaaggaagg ctacggtgaa   3180
ggctgcgtga ctatccacga gatcgagaac aacaccgacg agctcaagtt ctcgaactgt   3240
gtggaggagg aggtgtaccc gaacaacacc gttacttgca acgactacac tgccacgcaa   3300
gaggagtacg agggcactta cacttccggg aatcgcggct atgatggcgc gtacgagtcc   3360
aacagcagcg tgcctgcgga ttatgcgtcc gcttacgagg agaaggcgta caccgacgga   3420
cggagggaca acccttgcga gtccaaccgt ggctacggtg actacactcc gctgcccgcc   3480
gggtacgtca ccaaggagct ggagtacttc ccggagaccg acaaagtctg gatcgagatc   3540
ggcgagacgg agggcacttt catcgtggac tcggtcgagc tgctactgat ggaggagtga   3600
```

SEQ ID NO: 30            moltype = AA   length = 1199
FEATURE                  Location/Qualifiers
REGION                   1..1199
                         note = Amino acid sequence of the chimeric protein variant
                          TIC868_9.
source                   1..1199
                         mol_type = protein
                         organism = synthetic construct
SEQUENCE: 30
```
MTSNRKNENE IINALSIPAV SNHSAQMNLS TDARIEDSLC IAEGNNIDPF VSASTVQTGI   60
NIAGRILGVL GVPFAGQIAS FYSFLVGELW PRGRDPWEIF LEHVEQLIRQ QVTENTRDTA   120
LARLQGLGNS FRAYQQSLED WLENRDDART RSVLYTQYIA LELDFLNAMP LFAIRNQEVP   180
LLMVYAQAAN LHLLLLRDAS LFGSEFGLTS QEIQRYYERQ VEKTREYSDY CARWYNTGLN   240
SLRGTNAESW LRYNQFRRDL TLGVLDLVAL FPSYDTRVYP MNTSAQLTRE IYTDPIGRTN   300
APSGFASTNW FNNNAPSFSA IEAAVIRPPH LLDFPEQLTI FSVLSRWSNT QYMNYWVGHR   360
LESRTIRGSL STSTHGNTNT SINPVTLQFT SRDVYRTESQ AGINILMTTP VNGVPWARFN   420
WRNPKNSLRG SLLYTIGYTG VGTQLFDSET ELPPETTERP NYESYSHRLS NIRLISGNTL   480
RAPVYSWTHR SADRTNTISS DSINQIPLVK GFRVWGGTSV ITGPGFTGGD ILRRNTFGDF   540
VSLQVNINSP ITQRYRLRFR YASSRDARVI VLTGAASTGV GGQVSVNMPL QKTMEIGENL   600
TSRTFRYTDF SNPFSFRANP DIIGISEQPL FGAGSISSGE LYIDKIEIIL ADATFEAESD   660
LERAQKAVNE LFTSSNQIGL KTDVTDYHID QVSNLVECLS DEFCLDEKKE LSEKVKHAKR   720
LSDERNLLQD PNFRGINRQL DRGWRGSTDI TIQGGDDVFK ENYVTLLGTF DECYPTLYQ   780
KIDESKLKAY TRYQLRGYIE DSQDLEIYLI RYNAKHETVN VPGTGSLWPL SAPSPIGKCA   840
HHSHHFSLDI DVGCTDLNED LGVWVIFKIK TQDGHARLGN LEFLEEKPLV GEALARVKRA   900
EKKWRDKREK LEWETNIVYK EAKESVDALF VNSQYDRLQA DTNIAMIHAA DKRVHSIREA   960
YLPELSVIPG VNAAIFEELE GRIFTAFSLY DARNVIKNGD FNNGLSCWNV KGHVDVEEQN   1020
NHRSVLVVPE WEAEVSQEVR VCPGRGYILR VTAYKEGYGE GCVTIHEIEN NTDELKFSNC   1080
VEEEVYPNNT VTCNDYTATQ EEYEGTYTSR NRGYDGAYES NSSVPADYAS AYEEKAYTDG   1140
RRDNPCESNR GYGDYTPLPA GYVTKELEYF PETDKVWIEI GETEGTFIVD SVELLLMEE   1199
```

SEQ ID NO: 31            moltype = DNA   length = 3678
FEATURE                  Location/Qualifiers
misc_feature             1..3678
                         note = Recombinant nucleotide sequence used for expression
                          in a bacterial cell encoding TIC868_10.
source                   1..3678
                         mol_type = other DNA
                         organism = synthetic construct
SEQUENCE: 31
```
atgacttcaa ataggaaaaa tgagaatgaa attataaatg ctttatcgat tccagctgta   60
tcgaatcatt ccgcacaaat gaatctatca accgatgctc gtattgagga tagcttgtgt   120
atagccgagg ggaacaatat cgatccattt gttagcgcat caacagtcca aacgggtatt   180
aacatagctg gtagaatact aggtgtatta ggcgtaccgt ttgctggaca aatagctagt   240
ttttatagtt ttcttgttgg tgaattatgg ccccgcggca gagatccttg ggaaattttc   300
ctagaacatg tcgaacaact tataagacaa caagtaacag aaaatactag ggatacggct   360
cttgctcgat tacaaggttt aggaaattcc tttagagcct atcaacagtc acttgaagat   420
tggctagaaa accgtgtga tgcaagaacg agaagtgttc tttatacca atatatagcc   480
ttagaacttg attttcttaa tgcgatgccg ctttttcgcaa ttagaaacca agaagttcca   540
ttattaatgg tatatgctca agctgcaaat ttacacctat tattattgag agatgcctct   600
cttttttggta gtgaatttgg gcttacatcc caagaaattc aacgttatta tgagcgccaa   660
gtggaaaaaa cgagagaata ttctgattat tgcgcaagat ggtataatac gggtttaaat   720
aatttgagag ggacaaatgc tgaaagttgg ttgcgatata tcaattccg tagagactta   780
acgctaggag tattagatct agtggcacta ttcccaagct atgacacgcg tgtttatcca   840
atgaatacca gtgctcaatt aacaagagaa atttatacag atccaattgg gagaacaaat   900
gcaccttcag gatttgcaag tacgaattgg tttaataata atgcaccatc gttttctgcc   960
atagaggctg ccgttattag gcctccgcat ctacttgatt ttccagaaca gcttacaatt   1020
ttcagcgtat taagtcgatg gagtaatact caatatatga attactgggt gggacataga   1080
cttgaatcgc gaacaataag ggggtcatta agtacctcga cacacggaaa taccaatact   1140
tctattaatc ctgtaacatt acagttcaca tctcgagacg tttatagaac agaatcattt   1200
gcagggataa atatacttct aactactcct gtgaatggag taccttgggc tagatttaat   1260
tggagaaatc ccctgaattc tcttagaggt agccttctct atactatagg gtatactgga   1320
gtggggcac aactatttga ttcagaaact gaattaccac cagaaacaac agaacgacca   1380
```

-continued

```
aattatgaat cttacagtca tagattatct aatataagac taatatcagg aaacactttg   1440
agagcaccag tatattcttg gacgcaccgt agtgcagatc gtacaaatac cattagttca   1500
gatagcatta atcaaatacc tttagtgaaa ggatttagag tttgggggg cacctctgtc    1560
attacaggac caggatttac aggaggggat atccttcgaa gaaatacctt tggtgatttt   1620
gtatctctac aagtcaatat taattcacca attacccaaa gataccgttt aagatttcgt   1680
tacgcttcca gtagggatgc acgagttata gtattaacag gagcggcatc cacaggagtg   1740
ggaggccaag ttagtgtaaa tatgcctctt cagaaaacta tggaaatagg ggagaactta   1800
acatctagaa catttagata taccgatttt agtaatcctt tttcatttag agctaatcca   1860
gatataattg ggataagtga acaacctcta tttggtgcag gttctattag tagcggtgaa   1920
ctttatatag ataaaattga aattattcta gcagatgcaa catttgaggc agaatatgat   1980
ttagaaaagag cgcaaaaggt ggtgaatgcc ctgtttacgt ctacaaacca actagggcta   2040
aaaacagatg tgacggatta tcatattgat caggtatcca atctagttgc gtgtttatcg   2100
gatgaatttt gtctggatga aaagagagaa ttgtccgaga aagttaaaca tgcaaagcga   2160
ctcagtgatg agcggaattt acttcaagat ccaaacttca gagggatcaa taggcaacca   2220
gaccgtggct ggagaggaag tacggatatt actatccaag gagggagatga cgtattcaaa  2280
gagaattacg ttacgctacc gggtaccttt gatgagtgct atccaacgta tttatatcaa   2340
aaaatagatg agtcgaaatt aaaagcctat acccgttatc aattaagagg gtatatcgaa   2400
gatagtcaag acttagaaat ctatttaatt cgttacaatg caaaacacga aatagtaaat   2460
gtaccaggta caggaagttt atggcctctt tctgtagaaa atcaaattgg accttgtgga   2520
gaaccgaatc gatgcgcgcc acaccttgaa tggaatcctg atttacactg ttcctgcaga   2580
gacgggaaa aatgtgcaca tcattctcat catttctctt tggacattga tgttggatgt    2640
acagacttaa atgaggactt aggtgtatgg gtgatattca agattaagac gcaagatggc   2700
cacgcacgac tagggaatct agagtttctc gaagagaaac cattattagg agaagcacta   2760
gctcgtgtga aaagagcgga gaaaaaatgg agagacaaac gcgaaacatt acaattggaa   2820
acaactatcg tttataaaga ggcaaaagaa tctgtagatg ctttatttgt aaactctcaa   2880
tatgatagat tacaagcgga tacgaacatc gcgatgattc atgcggcgaa taaacgcgtt   2940
catagaattc gagaagcgta tctgccggag ctgtctgtga ttccgggtgt caatgcggct   3000
attttgaag aattagaaga gcgtattttc actgcatttt ccctatatga tgcgagaaat    3060
attattaaaa atgcgatttt caataatggc ttattatgct ggaacgtgaa agggcatgta   3120
gaggtagaag aacaaaacaa tcaccgttca gtcctggtca gtcctggtc gggaggcagaa   3180
gtgtcacaag aggttcgtgt ctgtccaggt cgtggctata tccttcgtgt tacagcgtac   3240
aaagagggat atggagaagg ttgcgtaacg atccatgaga tcgagaacaa tacagacgaa   3300
ctgaaattca acaactgtgt agaagaggaa gtatatccaa acaacacggt aacgtgtatt   3360
aattatactg cgactcaaga agaatatgag ggtacgtaca cttctcgtaa tcgaggatat   3420
gacgaagcct atggtaataa cccttccgta ccagctgatt atgcgtcagt ctatgaagaa   3480
aaatcgtata cagatagacg aagagagaat ccttgtgaat ctaacagagg atatggagat   3540
tacacaccac taccagctgg ttatgtaaca aaggaattag agtacttccc agagaccgat   3600
aaggtatgga ttgagattgg agaaacagaa ggaacattca tcgtggacag cgtggaatta   3660
ctccttatgg aggaatag                                                 3678
```

SEQ ID NO: 32          moltype = DNA  length = 3678
FEATURE                Location/Qualifiers
misc_feature           1..3678
                       note = Synthetic nucleotide sequence designed for
                        expression in a plant cell encoding TIC868_10.
source                 1..3678
                       mol_type = other DNA
                       organism = synthetic construct
SEQUENCE: 32

```
atgacgagca accggaagaa cgagaacgag atcatcaacg ccctctcgat ccctgctgtt   60
tcaaaccact ccgcgcagat gaacctgtcc accgacgcgc gcatcgagga ctccctctgc   120
atagccgagg gcaacaacat cgacccattc gtgtcggcca gcacggttca gaccggcatc   180
aacatcgcgg gccgtatcct cggcgtcctc ggtgtcccat tcgccggtca gatcgcgtcc   240
ttctactcgt tccttgtggg cgagctgtgg cctcgcggtc gtgacccgtg ggagatcttc   300
ctggacatg tggagcagtt gatccggcag caagtcacgg agaacacccg cgatactgct   360
ctggccaggc tacagggcct gggaaactcc tttcgggcat accagcagtc actggaggac   420
tggttggaga acaggdatga cgcgcgaaca cgctcggtac tctacaccca gtacatcgct   480
ctcgaactcg acttcctgaa cgctatgccg ctgttcgcca tcaggaacca ggaagttcca   540
ctccttatgg tgtacgccca ggccgccaac ttacatctgc tcctgctgcg ggacgccagc   600
ctgttcggct ccgagttcgg actcacatct caagaaatcc agcgttacta cgagcgcgaa   660
gtggagaaga cccgtgagta cagtgactac tgcgctcgat ggtacaacac agggctcaac   720
aacctgcgcg gcaccaacgc tgagtcatgg ctccgttaca accagttccg ccgcgacttg   780
actttgggtg tcctagacct ggtggcgcta ttccccgtctt acgacacacg ggtgtaccca   840
atgaacacta gcgcgcaact cacgcgggag atctcacacg accaatcgg ccggacgaac    900
gcacctccg gtttcgcatc cacgaattgg ttcaacaaca acgcaccctc cttctcggca   960
atcgaggccg ccgtcatccg ccctcctcac ctgctcgact ttcccgagca gctcacgatc   1020
ttctccgtgc tctcacgctg gtccaacaca cagtacatga actactgggt cgggcaccga   1080
ttggagagta ggacgatccg tggcagcttg agcaccagta cccacggcaa caccaacacc   1140
tccatcaacc cagttacgct acagttcacg agccgcgacg tttaccggac tgagtcgttc   1200
gcgggcatta acatccttct gacaacgccc gtcaacggcg tcccgtgggc ccggttcaac   1260
tggcgtaacc cgttgaactc cctgcgcggg tcattgctct cacaccatcgg gtacacgggc   1320
gtcggcaccc agctcttcga cagtgaaact gagctgccgc ccgagaccac ggaacgcccg   1380
aactacgagt cctacagcca ccgcctgtcc aacatccggc tcatctctgg caacacgctg   1440
cgtgcgccgg tgtactcctg gacacaccgc agcgccgacc ggacccaacac gatctcttcc   1500
gactccatta accagatccc gctcgtgaag ggcttccgtg tgtggggtgg cacgagcgtc   1560
atcaccggtc cgggcttcac cggtggagac atactgcggg gcaacacttt cggcgacttc   1620
gtttcgttgc aagtgaacat caactcgccg atcacccagc gttaccgtct gaggttccgc   1680
tacgcttcaa gccgcgacgc gagggtcatt gtcctgaccg gagccgcgtc cacaggcgtg   1740
ggaggccaag tctcagtcaa catgcctctc cagaagacga tggagatagg cgagaacttg   1800
```

-continued

```
actagccgaa ccttccggta cactgatttc tcgaaccctt tctcattcag agcgaaccct   1860
gacatcattg ggatctccga gcaaccgctg ttcggtgctg gctccatcag ctctggcgaa   1920
ctgtacatcg acaagattga gatcatcctg gcggatgcga cgttcgaggc cgagtacgac   1980
cttgagcgcg cccagaaggt ggtgaacgcc ctcttcacta gcactaacca gctaggcctg   2040
aagactgacg tgaccgacta ccacatcgac caagtgagca acctagtggc ctgcctctcg   2100
gacgagttct gcctcgacga gaagcgcgag ctgtccgaga aggtgaagca cgccaagcgc   2160
ctctccgacg agcgcaacct gctccaggac cccaacttca ggggcatcaa caggcagccc   2220
gaccgcggct ggcgcggctc caccgacatc accatccagg gcggtgacga cgtattcaag   2280
gagaactacg ttaccctccc cggcaccttc gacgagtgtt accccaccta cctctaccag   2340
aagatcgacg agtccaagtc gaaggcctac acccgctacc agctccgcgg ctacatcgag   2400
gactcccagg acctgaaat ctacctcatc cgctacaacg ccaagcacga gatcgtgaac    2460
gtgcctggca ccggcagcct ctggcctctc agcgtggaga accagatcgg cccttgcggc   2520
gagcctaacc gctgcgcccc tcacctcgag tggaaccctg acctccactg ctcgtgcagg   2580
gacggcgaga agtgcgccca ccatagccac cacttctctc tggacatcga cgtgggctgc   2640
accgacctga acgaggacct gggcgtgtgg gttatcttca agatcaagac ccaggacggt   2700
cacgccaggc tgggtaacct ggagttcctt gaggaaaagc ctctgctggg tgaggccctg   2760
gccagggtca agagggctga gaagaaatgg agggataaga gggagaccct gcagctggag   2820
accactatcg tctacaagga ggctaaggag tctgtcgatg ctctgttcgt caactctcag   2880
tacgatagac tgcaagctga taccaacatc gctatgatcc acgctgcgga taagcgggtc   2940
caccggatcc gggaggctta ccttccggag ctttctgtca tcccgggtgt caacgctgcg   3000
atcttcgagg aacttgagga acggatcttc actgcgttta gtctttacga tgcgcggaac   3060
atcatcaaga acgggggactt caacaatggt ctgctgtgct ggaacgtcaa gggtcatgtc   3120
gaggtcgagg aacaaaacaa tcatcgtagt gtccttgtca ttcctgagtg gggaggcgga   3180
gtctctcaag aggtccgtgt ttgcccgggg cgtgggtaca ttcttcgtgt tactgcgtac   3240
aaggaggggt acggggaggg gtgcgttact attcatgaga ttgagaacaa tactgatgag   3300
cttaagttca caattgtgt tgaggaggag gtttacccga acaatactgt tacgtgcatc    3360
aactacacgg caacgcaaga ggaatacgag gggacgtaca cctcgcgtaa tagagggtat   3420
gatgaggcgt acggaaacaa cccgtcggtt ccagcagatt atgcctcggt ttatgaggag   3480
aagtcgtaca cggatagacg acgcgagaat ccatgtgagt caaatcgagg atacggagat   3540
tacacaccat taccagcagg atacgttaca aaggagttgg aatacttccc ggaaacagat   3600
aaagtttgga ttgaaatcgg agaaacagaa ggaacattca tcgtcgactc agtagaattg   3660
ttgttgatgg aagaatga                                                 3678
```

```
SEQ ID NO: 33          moltype = AA   length = 1225
FEATURE                Location/Qualifiers
REGION                 1..1225
                       note = Amino acid sequence of the chimeric protein variant
                        TIC868_10.
source                 1..1225
                       mol_type = protein
                       organism = synthetic construct
SEQUENCE: 33
MTSNRKNENE IINALSIPAV SNHSAQMNLS TDARIEDSLC IAEGNNIDPF VSASTVQTGI   60
NIAGRILGVL GVPFAGQIAS FYSFLVGELW PRGRDPWEIF LEHVEQLIRQ QVTENTRDTA   120
LARLQGLGNS FRAYQQSLED WLENRDDART RSVLYTQYIA LELDFLNAMP LFAIRNQEVP   180
LLMVYAQAAN LHLLLLRDAS LFGSEFGLTS QEIQRYYERQ VEKTREYSDY CARWYNTGLN   240
NLRGTNAESW LRYNQFRRDL TLGVLDLVAL FPSYDTRVGP MNTSAQLTRE IYTDPIGRTN   300
APSGFASTNW FNNNAPSFSA IEAAVIRPPH LLDFPEQLTI FSVLSRWSNT QYMNYWVGHR   360
LESRTIRGSL STSTHGNTNT SINPVTLQFT SRDVYRTESF AGINILLTTP VNGVPWARFN   420
WRNPLNSLRG SLLYTIGYTG VGTQLFDSET ELPPETTERP NYESYSHRLS NIRLISGNTL   480
RAPVYSWTHR SADRTNTISS DSINQIPLVK GFRVWGGTSV ITGPGFTGGD ILRRNTFGDF   540
VSLQVNINSP ITQRYRLRFR YASSRDARVI VLTGAASTGV GGQVSVNMPL QKTMEIGENL   600
TSRTFRYTDF SNPFSRANP DIIGISEQPL FGAGSISSGE LYIDKIEIIL ADATFEAEYD    660
LERAQKVVNA LFTSTNQLGL KTDVTDYHID QVSNLVACLS DEFCLDEKRE LSEKVKHAKR   720
LSDERNLLQD PNFRGINRQP DRGWRGSTDI TIQGGDDVFK ENYVTLPGTF DECYPTYLYQ   780
KIDESKLKAY TRYQLRGYIE DSQDLEIYLI RYNAKHEIVN VPGTGSLWPL SVENQIGPCG   840
EPNRCAPHLE WNPDLHCSCR DGEKCAHHSH HFSLDIDVGC TDLNEDLGVW VIFKIKTQDG   900
HARLGNLEFL EEKPLLGEAL ARVKRAEKKW RDKRETLQLE TTIVYKEAKE SVDALFVNSQ   960
YDRLQADTNI AMIHAADKRV HRIREAYLPE LSVIPGVNAA IFEELEERIF TAFSLYDARN   1020
IIKNGDFNNG LLCWNVKGHV EVEEQNNHRS VLVIPEWEAE VSQEVRVCPG RGYILRVTAY   1080
KEGYGEGCVT IHEIENNTDE LKFNNCVEEE VYPNNTVTCI NYTATQEEYE GTYTSRNRGY   1140
DEAYGNNPSV PADYASVYEE KSYTDRRREN PCESNRGYGD YTPLPAGYVT KELEYFPETD   1200
KVWIEIGETE GTFIVDSVEL LLMEE                                         1225
```

```
SEQ ID NO: 34          moltype = DNA   length = 3726
FEATURE                Location/Qualifiers
misc_feature           1..3726
                       note = Recombinant nucleotide sequence used for expression
                        in a bacterial cell encoding TIC868_11.
source                 1..3726
                       mol_type = other DNA
                       organism = synthetic construct
SEQUENCE: 34
atgacttcaa ataggaaaaa tgagaatgaa attataaatg ctttatcgat tccagctgta   60
tcgaatcatt ccgcacaaat gaatctatca accgatgctc gtattgagga tagcttgtgt   120
atagccgagg gaacaatat cgatccattt gttagcgcat caacagtcca aacgggtatt    180
aacatagctg gtagaatact aggtgtatta ggcgtaccgt ttgctggaca aatagctagt   240
ttttatagtt ttcttgttgg tgaattatgg ccccgcggca gagatccttg ggaaattttc   300
ctagaacatg tcgaacaact tataagacaa caagtaacag aaaatactag ggatacggct   360
```

-continued

```
cttgctcgat tacaaggttt aggaaattcc tttagagcct atcaacagtc acttgaagat   420
tggctagaaa accgtgatga tgcaagaacg agaagtgttc tttataccca atatatagcc   480
ttagaacttg attttcttaa tgcgatgccg cttttcgcaa ttagaaacca agaagttcca   540
ttattaatga tatatgctca agctgcaaat ttacacctat tattattgag agatgcctct   600
cttttttggta gtgaatttgg gcttacatcc caagaaattc aacgttatta tgagcgccaa   660
gtggaaaaaa cgagagaata ttctgattat tgcgcaagat ggtataaatac gggttttaaat   720
aatttgagag ggacaaatgc tgaaagttgg ttgcgatata atcaattccg tagagactta   780
acgctaggag tattagatct agtggcacta ttcccaagct atgacacgcg tgtttatcca   840
atgaataccaa gtgctcaatt aacaagagaa atttatacag atccaattgg gagaacaaat   900
gcaccttcag gatttgcaag tacgaattgg tttaataata atgcaccatc gttttctgcc   960
atagaggctg ccgttattag gcctccgcat ctacttgatt ttccagaaca gcttacaatt   1020
ttcagcgtat taagtcgatg gagtaatact caatatatga attactgggt gggacataga   1080
cttgaatcgc gaacaataag ggggtcatta agtacctcga cacacggaaa taccaatact   1140
tctattaatc ctgtaacatt acagttcaca tctcgagacg tttatagaac agaatcattt   1200
gcagggataa atatacttct aactactcct gtgaatggag taccttgggc tagatttaat   1260
tggagaaatc ccctgaattc tcttagaggt agccttctct atactatagg gtatactgga   1320
gtggggacac aactatttga ttcagaaact gaattaccac cagaaacaac agaacgacca   1380
aattatgaat cttacagtca tagattatct aatataagac taatatcgag aaacactttg   1440
agagcaccag tatattcttg gacgcaccgt agtgcagatc gtacaaatac cattagttca   1500
gatagcatta atcaaatacc tttagtgaaa ggatttagag tttgggggggg cacctctgtc   1560
attacaggac caggatttac aggaggggat atccttcgaa gaaatacctt tggtgatttt   1620
gtatctctac aagtcaatat taattcacca attacccaaa gataccgttt aagatttcgt   1680
tacgcttcca gtagggatgc acgagttata gtattaacag gagcggcatc cacaggagtg   1740
ggaggccaag ttagtgtaaa tatgcctctt cagaaaacta tggaaatagg ggagaactta   1800
acatctagaa catttagata taccgatttt agtaatcctt tttcatttag agctaatcca   1860
gatataattg ggataagtga acaacctcta tttggtgcag gttctattag tagcggtgaa   1920
ctttatatag ataaaaattga aattattcta gcagatgcac caggaacgac aacctatgag   1980
tatgaagaga agcagaatct agaaaaagcg cagaaagcgt tgaacgcttt gtttacggat   2040
ggcacgaatg gctatctaca aatggatgcc actgattatg atatcaatca aactgcaaac   2100
ttaatagaat gtgtatcaga tgaattgtat gcaaaagaaa agatagtttt attagatgaa   2160
gtcaaatatg cgaagcggct tagcatatca cgtaacctac ttttgaacga tgatttagaa   2220
ttttcagatg gatttggaga aaacggatgg acgacaagtg ataatatttc aatccaggcg   2280
gataatcccc tttttaaggg gaattattta aaaatgtttg gggcaagaga tattgatgga   2340
accctatttc caacttatct ctatcaaaaa atagatgagt ccaggttaaa accatataca   2400
cgttatcgag taagagggtt tgtgggaagt agtaaaaatc taaaattagt ggtaacacgc   2460
tatgagaaag aaattgatgc cattatgaat gttccaaatg atttggcaca tatgcagctt   2520
aacccttcat gtggagatta tcgctgtgaa tcatcgtccc agttttttggt gaaccaagtg   2580
catcctacac caacagctgg atatgctctt gatatgtatg catgcccgtc aagttcagat   2640
aaaaaacata ttatgtgtca cgatcgtcat ccatttgatt ttcatattga caccggagaa   2700
ttaaatccaa acacaaacct gggtattgat gtcttgttta aaatttctaa tccaaatgga   2760
tacgctacat tagggaatct agaagtcatt gaagaaggac cactaacaga tgaagcattg   2820
gtacatgtaa aacaaaagga aaagaaatgg cgtcagcaca tggagaaaaa acgaatggaa   2880
acacaacaag cctatgatcc agcaaaacaa gctgtagatg cattatttac aaatgaacaa   2940
gagttagact atcatactac tttagatcat attcagaacc ccgatcagct ggtacaggcg   3000
attccctatg tacaccatgc ttggttaccg gatgctccag gtatgaacta tgatgtatat   3060
caagggttaa acgcacgtat catgcaggcg tacaatttat atgatgcacg aaatgtcata   3120
ataaatggtg actttacaca aggactacaa ggatggcacg caacaggaaa agcagcggta   3180
caacaaatag atggagcttc agtattagtt ctatcaaact ggagtgccga ggtatctcag   3240
aatctgcatg cccaagatca tcatggatat atgttacgtg tgattgccaa aaaagaaggt   3300
cctggaaaag ggtatgtaat gatgatggat tttaatggaa agcaggaaac acttacgttc   3360
acttcttgtg aagaaggata tataacaaaa acaatagagg tattcccgga aagtgatcga   3420
atacgaattg aaatgggaga aacagagggt acgttttatg tagatagcat cgagttgctt   3480
tgtatgcaag gatatgctag cgataataac ccgcacacgg gtaatatgta tgagcaaagt   3540
tataatggaa attataatca aaatactagc gatgtgtatc accaaggata tataaacaac   3600
tataaccaaa attctagtag tatgtataat caaaattata ttaacaatga tgacctgcat   3660
tccggttgca catgtaacca agggcataac tctggctgta catgtaatca aggatataac   3720
cgttag                                                                 3726
                                                                       3726
```

```
SEQ ID NO: 35          moltype = DNA   length = 3726
FEATURE                Location/Qualifiers
misc_feature           1..3726
                       note = Synthetic nucleotide sequence designed for
                        expression in a plant cell encoding TIC868_11.
source                 1..3726
                       mol_type = other DNA
                       organism = synthetic construct
SEQUENCE: 35
atgacgagca accggaagaa cgagaacgag atcatcaacg ccctctcgat ccctgctgtt    60
tcaaaccact ccgcgcagat gaacctgtcc accgacgcgc gcatcgagga ctccctctgc   120
atagccgagg gcaacaacat cgacccattc gtgtcggcca gcacggttca gaccggcatc   180
aacatcgcgg gccgtatcct cggcgtcctc ggtgtcccat tcgccggtca gatcgcgtcc   240
ttctactcgt tccttgtggg cgagctgtgg cctcgcggtc gtgacccgtg ggagatcttc   300
ctggagcatg tggagcagtt gatccggcag caagtcacgg agaacacccg cgatactgct   360
ctggccaggc tacaggcct gggaaactcc tttcggccat accagcagtc actgaggac    420
tggttggaga acaggatgtg cgcgcgaaca cgctcggtac tctacaccca gtacatcgct   480
ctcgaactcg acttcctgaa cgctatgccg ctgttcgcca tcaggaacca ggaagttcca   540
ctccttatgt gtgtacgccca ggccgccaac ttacatctgc tcctgctgcg ggacgccagc   600
ctgttcggct ccgagttcgg actcacatct caagaaatcc agcgttacta cgagcgccaa   660
gtggagaaga cccgtgagta cagtgactac tgcgctcgat ggtacaacac agggctcaac   720
```

```
aacctgcgcg gcaccaacgc tgagtcatgg ctccgttaca accagttccg ccgcgacttg   780
actttgggtg tcctagacct ggtggcgcta ttcccgtctt acgacacacg ggtgtaccca   840
atgaacacta gcgcgcaact cacgcgggag atctacacag acccaatcgg ccggacgaac   900
gcaccctccg gtttcgcatc cacgaattgg ttcaacaaca acgcaccctc cttctcggca   960
atcgaggccg ccgtcatccg ccctcctcac ctgctcgact ttcccgagca gctcacgatc  1020
ttctccgtgc tctcacgctg gtccaacaca cagtacatga actactgggt cgggcaccga  1080
ttggagagta ggacgatccg tggcagcttg agcaccagta cccacggcaa caccaacacc  1140
tccatcaacc cagttacgct acagttcacg agccgcgacg tttaccggac tgagtcgttc  1200
gcgggcatta acatccttct gacaacgccc gtcaacggcg tcccgtgggc ccggttcaac  1260
tggcgtaacc cgttgaactc cctgcgcggg tcattgctct acaccatcgg gtacacgggt  1320
gtcggcaccc agctcttcga cagtgaaact gagctgccgc ccgagaccac ggaacgcccg  1380
aactacgagt cctacagcca ccgcctgtcc aacatccggc tcatctctgg caacacgctg  1440
cgtgcgccgg tgtactcctg gacacaccgc agcgccgacc ggaccaacac gatctcttcc  1500
gactccatta accagatccc gctcgtgaag ggcttcgtgg tgtggggtgg cacgagcgtc  1560
atcaccggtc cgggcttcac cggtggagac atactgcggc gcaacacttt cggcgacttc  1620
gtttcgttgc aagtgaacat caactcgccg atcacccagc gttaccgtct gaggttccgc  1680
tacgcttcaa gccgcgacgc gagggtcatt gtcctgaccg gagccgcgtc cacaggcgtg  1740
ggaggccaag tctcagtcaa catgcctctc cagaagacga tggagatagg cgagaacttg  1800
actagccgaa ccttccggta cactgatttc tcgaaccctt tctcattcag agcgaaccct  1860
gacatcattg ggatctccga gcaaccgctg ttcggtgctg gctccatcag ctctggcgaa  1920
ctgtacatcg acaagattga gatcatcctg gcggatgcga cggggactac cacctacgag  1980
tacgaaaagg agcagaatct cgagaaggct cagaaggctc tgaacgctct gttcactgac  2040
gggaccaacg gctacctcca gatggacgcc actgactacg acatcaacca gacagctaac  2100
ctgattgagt gtgtgagtga cgaactgtac gctaaggaga agatcgtact cctggacgag  2160
gtgaagtacg ctaagcgcct gagcattagc cgtaacctgc tgctgaacga cgatctggag  2220
ttcagcgacg gctttggcga gaacgggtgg accaccagcg acaacatctc catccaggcc  2280
gacaatccac tcttcaaagg caactacctc aagatgttcg gagccaggga catcgacggc  2340
accctctttc cgacctacct ctaccagaag atcgacgagt cccgcctcaa accctacacc  2400
cgctacaggg tgcgcggctt cgtgggcagc agcaagaacc tcaagctcgt ggtcacacgg  2460
tatgagaagg agatcgacgc catcatgaac gtgcccaacg atctcgccca catgcagctc  2520
aatccatcct gcggcgacta ccggtgcgag tccagctccc agttcctcgt gaaccaggtg  2580
caccctactc cgaccgctgg ctatgccctg gacatgtacg cctgccctag ttcctccgac  2640
aagaagcaca tcatgtgcca cgaccgtcat ccgttcgact ccacatcga caccggcgaa  2700
ctgaacccga acaccaacct gggcatcgac gtactgttca agatttccaa cccgaacggg  2760
tacgccacct tgggcaacct ggaggtcatc gaagaaggcc cgctgaccga cgaggccctg  2820
gtccacgtca aacagaagga gaagaagtgg cggcagcaca tggagaagaa gcggatggag  2880
actcaacaag cctacgaccc ggccaagcaa gctgtggacg ctctgttcac caacgagcaa  2940
gagcttgact accacactac tcttgaccac atccagaatg ctgaccagct tgtccaggct  3000
attccgtacg tccaccacgc ttggctaccg gacgctccag gcatgaacta cgatgtgtac  3060
cagggtctga cgcgcgcgat catgcaagcg tacaacctgt acgacgcgcg taacgtcatc  3120
atcaacggtg acttcactca gggtcttcaa ggttggcacg cgactggcaa agcggcagtc  3180
cagcagattg atggtgcgtc tgttcttgtg ttgagcaact ggtctgcgga ggtttctcag  3240
aacctgcacg cacaggatca ccacggctac atgctgaaggt tgattgctaa gaaggagggc  3300
cctggcaaag gctacgtcat gatgatggac ttcaacggaa agcaagaaac cctgaccttc  3360
actagctgtg aggagggcta catcactaag accattgagg tctttccgga gtctgaccgc  3420
atccggatcg agatgggcga gaccgaaggc acgttctacg tggactccat cgaactcctc  3480
tgcatgcaag gctacgcctc cgacaacaac ccacacacgg gcaacatgta cgagcagtcc  3540
tacaacgggg actacaacca gaacacctcc gatgtgtacc atcagggcta catcaacaac  3600
tacaaccaga acagcagcag catgtacaac cagaactaca tcaacaacga tgacttgcac  3660
tcgggttgca cctgcaacca gggtcacaac agtgggtgca cgtgcaacca gggatacaac  3720
cgttga                                                                   3726
```

```
SEQ ID NO: 36            moltype = AA  length = 1241
FEATURE                  Location/Qualifiers
REGION                   1..1241
                         note = Amino acid sequence of the chimeric protein variant
                         TIC868_11.
source                   1..1241
                         mol_type = protein
                         organism = synthetic construct
SEQUENCE: 36
MTSNRKNENE IINALSIPAV SNHSAQMNLS TDARIEDSLC IAEGNNIDPF VSASTVQTGI    60
NIAGRILGVL GVPFAGQIAS FYSFLVGELW PRGRDPWEIF LEHVEQLIRQ QVTENTRDTA   120
LARLQGLGNS FRAYQQSLED WLENRDDART RSVLYTQYIA LELDFLNAMP LFAIRNQEVP   180
LLMVYAQAAN LHLLLLRDAS LFGSEFGLTS QEIQRYYERQ VEKTREYSDY CARWYNTGLN   240
NLRGTNAESW LRYNQFRRDL TLGVLDLVAL FPSYDTRVYP MNTSAQLTRE IYTDPIGRTN   300
APSGFASTNW FNNNAPSFSA IEAAVIRPPH LLDFPEQLTI FSVLSRWSNT QYMNYWVGHR   360
LESRTIRGSL STSTHGNTNT SINPVTLQFT SRDVYRTESF AGINILLTTP VNGVPWARFN   420
WRNPLNSLRG SLLYTIGYTG VGTQLFDSET ELPPETTERP NYESYSHRLS NIRLISGNTL   480
RAPVYSWTHR SADRTNTISS DSINQIPLVK GFRVWGGTSV ITGPGFTGGD ILRRNTFGDF   540
VSLQVNINSP ITQRYRLRFR YASSRDARVI VLTGAASTGV GGQVSVNMPL QKTMEIGENL   600
TSRTFRYTDF SNPFSFRANP DIIGISEQPL FGAGSISSGE LYIDKIEIIL ADATGTTTYE   660
YEEKQNLEKA QKALNALFTD GTNGYLQMDA TDYDINQTAN LIECVSDELY AKEKIVLLDE   720
VKYAKRLSIS RNLLLNDDLE FSDGFGENGW TTSDNISIQA DNPLFKGNYL KMFGARDIDG   780
TLFPTYLYQK IDESRLKPYT RYRVRGFVGS SKNLKLVVTR YEKEIDAIMN VPNDLAHMQL   840
NPSCGDYRCE SSSQFLVNQV HPTPTAGYAL DMYACPSSSD KKHIMCHDRH PPFDFHIDTGE   900
LNPNTNLGID VLFKISNPNG YATLGNLEVI EEGPLTDEAL VHVKQKEKKW RQHMEKKRME   960
TQQAYDPAKQ AVDALFTNEQ ELDYHTTLDH IQNADQLVQA IPYVHHAWLP DAPGMNYDVY  1020
QGLNARIMQA YNLYDARNVI INGDFTQGLQ GWHATGKAAV QQIDGASLVV LSNWSAEVSQ  1080
```

```
NLHAQDHHGY MLRVIAKKEG PGKGYVMMMD FNGKQETLTF TSCEEGYITK TIEVFPESDR   1140
IRIEMGETEG TFYVDSIELL CMQGYASDNN PHTGNMYEQS YNGNYNQNTS DVYHQGYINN   1200
YNQNSSSMYN QNYINNDDLH SGCTCNQGHN SGCTCNQGYN R                       1241

SEQ ID NO: 37          moltype = DNA   length = 3468
FEATURE                Location/Qualifiers
misc_feature           1..3468
                       note = Recombinant nucleotide sequence used for expression
                       in a bacterial cell encoding TIC868_12.
source                 1..3468
                       mol_type = other DNA
                       organism = synthetic construct SEQUENCE: 37
atgacttcaa ataggaaaaa tgagaatgaa attataaatg ctttatcgat tccagctgta   60
tcgaatcatt ccgcacaaat gaatctatca accgatgctc gtattgagga tagcttgtgt   120
atagccgagg ggaacaatat cgatccattt gttagcgcat caacagtcca aacgggtatt   180
aacatagctg gtagaatact aggtgtatta ggcgtaccgt ttgctggaca aatagctagt   240
ttttatagtt ttcttgttgg tgaattatgg ccccgcggca gagatccttg ggaaattttc   300
ctagaacatg tcgaacaact tataagacaa caagtaacag aaaatactag ggatacggct   360
cttgctcgat tacaaggttt aggaaattcc tttagagcct atcaacagtc acttgaagat   420
tggctagaaa accgtgatga tgcaagaacg agaagtgttc tttataccca atatatagcc   480
ttagaacttg attttcttaa tgcgatgccg cttttcgcaa ttagaaacca agaagttcca   540
ttattaatgg tatatgctca agctgcaaat ttacacctat tattattgag agatgcctct   600
ctttttggta gtgaatttgg gcttacatcc caagaaattc aacgttatta tgagcgccaa   660
gtggaaaaaa cgagagaata ttctgattat tgcgcaagat ggtataatac gggtttaaat   720
aatttgagag ggacaaatgc tgaaagttgg ttgcgatata atcaattccg tagagactta   780
acgctaggag tattagatct agtggcacta ttcccaagct atgacacgcg tgtttatcca   840
atgaatacca gtgctcaatt aacaagagaa atttatacag atccaattgg gagaacaaat   900
gcaccttcag gatttgcaag tacgaattgg tttaataata atgcaccatc gttttctgcc   960
atagagcctg ccgttattag gcctccgcat ctacttgatt ttccagaaca gcttacaatt   1020
ttcagcgtat taagtcgatg gagtaatact caatatatga attactgggt gggacataga   1080
cttgaatcgc gaacaataag ggggtcatta agtacctcga cacacggaaa taccaatact   1140
tctattaatc ctgtaacatt acagttcaca tctcgagacg tttatagaac agaatcattt   1200
gcagggataa atatacttct aactactcct gtgaatggag taccttgggc tagatttaat   1260
tggagaaatc ccctgaattc tcttagaggt agccttctct atactatagg gtatactgga   1320
gtggggacac aactatttga ttcagaaact gaattaccac cagaaacaac agaacgacca   1380
aattatgaat cttacagtca tagattatct aatataagac taatatcagg aaacactttg   1440
agagcaccag tatattcttg gacgcaccgt agtgcagatc gtacaaatac cattagttca   1500
gatagcatta atcaaatacc tttagtgaaa ggatttagag tttgggggg cacctctgtc   1560
attacaggac caggatttac aggaggggat atccttcgaa gaaatacctt tggtgatttt   1620
gtatctctac aagtcaatat taattcacca attacccaaa gataccgttt aagatttcgt   1680
tacgcttcca gtagggatgc acgagttata gtattaacag gagcggcatc cacaggagtg   1740
ggaggccaag ttagtgtaaa tatgcctctt cagaaaacta tggaaatagg ggagaactta   1800
acatctagaa catttagata taccgatttt agtaatcctt tttcatttag agctaatcca   1860
gatataattg ggataagtga acaacctcta tttggtgcag gttctattag tagcggtgaa   1920
ctttatatag ataaaattga aattattcta gcagatgcaa caaatccgac gcgagaggcg   1980
gaagaggatc tagaagcagc gaagaaagcg gtggcagact tgtttacacg tacaaggggac  2040
ggattacaag taaatgtgac agattatcaa gtcgatcaag cggcaaattt agtgtcatgc   2100
ttatcagatg aacaatatgg gcatgacaaa aagatgttat tggaagcggt aagagcggca   2160
aaacgcctca gccgagaacg caacttactt caggatccag atttttaatac aatcaatagt   2220
acagaagaaa atggatggaa agcaagtaac ggcgttacta ttagcgaggg cggtccattc   2280
tataaaggcc gtgcgcttca gctagcaagc gcaagagaaa attacccaac atacatttat   2340
caaaaagtaa atgcatcaga gttaaagccg tatacacgtt atagactgga tgggttcgtg   2400
aagagtagtc aagatttaga aattgatctc attcaccatc ataaagtcca tctcgtgaaa   2460
aatgtaccag ataatttagt atccgatact tactcggatg gttcttgcag tggaatgaat   2520
cgatgtgagg aacaacagat ggtaaatgcg caactggaaa cagaacatca tcatccgatg   2580
gattgctgtg aagcggctca aacacatgag ttttcttcct atattaatac aggcgatcta   2640
aattcaagtg tagatcaagg catttgggtt gtattgaaag ttcgaacaac cgatggttat   2700
gcgacgctag gaaatcttga attggtagag gtcggaccgt tatcgggtga atctctagaa   2760
cgtgaacaaa gggataatgc gaaatggagt gcagagctag gaagaaagcg tgcagaaaca   2820
gatcgcgtgt atcaagatgc caaacaatcc atcaatcatt tatttgtgga ttatcaagat   2880
caacaattaa atccagaaat agggatggca gatattattg acgctcaaaa tcttgtcgca   2940
tcaatttcag atgtgtatag cgatgcagta ctgcaaatcc ctggaattaa ctatgagatt   3000
tacacagatg tatccaatcg cttacaacaa gcatcgtatc tgtatacgtc tcgaaatgcg   3060
gtgcaaaatg gggactttaa cagcggtcta gatagttgga atgcaacagg gggggctacg   3120
gtacaacagg atggcaatac gcatttctta gttctttctc attgggatgc acaagtttct   3180
caacaattta gagtgcagcc gaattgtaaa tatgtattac gtgtaacagc agagaaagta   3240
ggcggcggag acggatacgt gacaatccgg gatggtgctc atcatacaga aaagcttaca   3300
tttaatgcat gtgattatga tataaatggc acgtacgtga tcgataatac gtatctaaca   3360
aaagaagtgg tattctattc acatacgaaa cacatgtggg tagaggtaag tgaaacagaa   3420
ggtgcatttc atatagatag tattgaattc gttgaaacag aaaagtag              3468

SEQ ID NO: 38          moltype = DNA   length = 3468
FEATURE                Location/Qualifiers
misc_feature           1..3468
                       note = Synthetic nucleotide sequence designed for
                       expression in a plant cell encoding TIC868_12.
source                 1..3468
                       mol_type = other DNA
```

-continued

```
                         organism = synthetic construct
SEQUENCE: 38
atgacgagca accggaagaa cgagaacgag atcatcaacg ccctctcgat ccctgctgtt    60
tcaaaccact ccgcgcagat gaacctgtcc accgacgcgc gcatcgagga ctccctctgc   120
atagccgagg gcaacaacat cgacccattc gtgtcggcca gcacggttca gaccggcatc   180
aacatcgcgg gccgtatcct cggcgtcctc ggtgtcccat cgccggtca gatcgcgtcc    240
ttctactcgt tccttgtggg cgagctgtgg cctcgcggtc gtgacccgtg ggagatcttc   300
ctggagcatg tggagcagtt gatccggcag caagtcacgg agaacacccg cgatactgct   360
ctggccaggc tacagggcct gggaaactcc tttcgggcat accagcagtc actggaggac   420
tggttggaga acagggatga cgcgcgaaca cgctcggtac tctacaccca gtacatcgct   480
ctcgaactcg acttcctgaa cgctatgccg ctgttcgcca tcaggaacca ggaagttcca   540
ctccttatgg tgtacgccca ggccgccaac ttacatctgc tcctgctgcg ggacgccagc   600
ctgttcggct ccgagttcgg actcacatct caagaaatcc agcgttacta cgagcgcaa    660
gtggagaaga cccgtgagta cagtgactac tgcgctcaat ggtacaacac agggctcaac   720
aacctgcgcg gcaccaacgc tgagtcatgg ctccgttaca accagttccg ccgcgacttg   780
actttgggtg tcctagacct ggtggcgcta ttcccgtctt acgacacacg ggtgtaccca   840
atgaacacta gcgcgcaact cacgcgggag atctacacag acccaatcgg ccggacgaac   900
gcaccctccg gtttcgcatc cacgaattgg ttcaacaaca acgcaccctc cttctcgaca   960
atcgaggccg ccgtcatccg ccctcctcac ctgctcgact ttcccgagca gctcacgatc  1020
ttctccgtgc tctcacgctg gtccaacaca cagtacatga actactgggt cgggcaccga  1080
ttggagagta ggacgatccg tggcagcttg agcaccagta cccacggcaa caccaacacc  1140
tccatcaacc cagttacgct acagttcacg agccgcgacg tttaccggac tgagtcgttc  1200
gcgggcatta acatccttct gacaacgccc gtcaacggcg tcccgtgggc ccggttcaac  1260
tggcgtaacc cgttgaactc cctgcgcggg tcattgctct acaccatcgg gtacacgggc  1320
gtcggcaccc agctcttcga cagtgaaact gagctgccgc ccgagaccac ggaacgcccg  1380
aactacgagt cctacagcca ccgcctgtcc aacatccggc tcatctctgg caacacgctg  1440
cgtgcgccgg tgtactcctg gacacaccgc agcgccgacc ggaccaacac gatctcttcc  1500
gactccatta accagatccc gctcgtgaag ggcttccgtg tgtggggtgg cacgagcgtc  1560
atcaccggtc cgggcttcac cggtggagac atactgcggc gcaacacttt cggcgacttc  1620
gtttcgttgc aagtgaacat caactcgccg atcacccagc gttaccgtct gaggttccgc  1680
tacgcttcaa gccgcgacgc gagggtcatt gtcctgaccg gagccgcgtc cacaggcgtg  1740
ggaggccaag tctcagtcaa catgcctctc cagaagacga tggagatagg cgagaacttg  1800
actagccgaa ccttccggta cactgatttc tcgaacccct tctcattcag agcgaaccct  1860
gacatcattg ggatctccga gcaaccgctg ttcggtgctg gctccatcga ctctggcgaa  1920
ctgtacatcg acaagattga gatcatcctg gcggatgcga cgaacccgac gcgggaagct  1980
gaggaagact tggaagccgc caagaaagcg gtcgccagcc tgtttactcg gacgcgggac  2040
gggctccaag tgaatgtgac ggactatcaa gtggatcagg ccgctaacct cgtgtcatgc  2100
ctgagcgacg agcagtacgg tcacgacaag aaaatgctgc tggaggccgt ccgggccgcc  2160
aagcggctgt ccagggagcg taacctgcta caagatcccg actttaacac gatcaacagc  2220
acagaggaga atggctggaa ggccagcaac ggagttacga taagcgaggg cggtccgttc  2280
tacaagggtc gtgccctcca gctcgcctct gcaagggaga actatccaac ctacatctat  2340
cagaaggtga acgcatccga gcttaagccc tacacacgct accgcctgga cgggttcgtt  2400
aagtccagtc aagacctaga gatagacctc atccaccacc acaaagtgca tctggtcaag  2460
aacgttcccg ataatctcgt gagcgatacc tactcagacg gctcatgctc tggcatgaac  2520
agatgtgagg agcaacagat ggttaatgct caactcgaaa ccgagcatca tcatcctatg  2580
gattgctgcg aggccgcgca gacccatgag ttcagctctt acatcaacac cggagacctc  2640
aacagtagcg tggatcaggg aatttggtg gtgcttaaag tgcgtacaac cgacggctac  2700
gccaccctcg gcaaccttga gcttgtcgag gtcggaccac ttagcggcga gtccctggaa  2760
cgtgagcagc gggacaacgc caaatggagc gcagagctag ggcgcaaacg cgcggagacg  2820
gaccgggttt atcaggacgc gaagcagtcc atcaatacc tcttcgtgga ttatcaggac  2880
cagcagctta atccagagat cggcatggcc gacatcatcg acgcccagaa cctagtagcg  2940
tcgatttccg atgtctattc cgacgccgtg cttcaaatac ctggcatcaa ctacgagatc  3000
tacacagagt tgtccaacag gctccagcaa gcgtcatacc tctacaccag ccgcaacgcc  3060
gtccagaatg gcgacttcaa ttccggacta gactcctgga acgccacggg cggagctacg  3120
gtgcaacaag acggcaacac ccacttcctc gtacttagcc actgggacgc tcaagtgagt  3180
cagcaattcc gggttcagcc gaactgcaag tacgtcctgc gcgtaacggc cgagaaggtt  3240
ggaggcggag acggctacgt taccatccgc gacggcgctc accacccga gaaactgacg  3300
ttcaacgctt gtgactacga catcaacggc acttacgtga cggacaacac ctacctgacg  3360
aaggaggtgg tgttctattc tcacaccgag cacatgtggg ttgaggtcag cgagaccgag  3420
ggagccttcc acattgacag catcgagttc gtggagactg agaagtga             3468

SEQ ID NO: 39          moltype = AA  length = 1155
FEATURE                Location/Qualifiers
REGION                 1..1155
                       note = Amino acid sequence of the chimeric protein variant
                       TIC868_12.
source                 1..1155
                       mol_type = protein
                       organism = synthetic construct
SEQUENCE: 39
MTSNRKNENE IINALSIPAV SNHSAQMNLS TDARIEDSLC IAEGNNIDPF VSASTVQTGI    60
NIAGRILGVL GVPFAGQIAS FYSFLVGELW PRGRDPWEIF LEHVEQLIRQ QVTENTRDTA   120
LARLQGLGNS FRAYQQSLED WLENRDDART RSVLYTQYIA LELDFLNAMP LFAIRNQEVP   180
LLMVYAQAAN LHLLLLRDAS LFGSEFGLTS QEIQRYYERQ VEKTREYSDY CARWYNTGLN   240
NLRGTNAESW LRYNQFRRDL TLGVLDLVAL FPSYDTRVYP MNTSAQLTRE IYTDPIGRTN   300
APSGFASTNW FNNNAPSFSA IEAAVIRPPH LLDFPEQLTI FSVLSRWSNT QYMNYWVGHR   360
LESRTIRGSL STSTHGNTNT SINPVTLQFT SRDVYRTESF AGINILLTTP VNGVPWARFN   420
WRNPLNSLRG SLLYTIGYTG VGTQLFDSET ELPPETTERP NYESYSHRLS NIRLISGNTL   480
RAPVYSWTHR SADRTNTISS DSINQIPLVK GFRVWGGTSV ITGPGFTGGD ILRRNTFGDF   540
```

```
VSLQVNINSP ITQRYRLRFR YASSRDARVI VLTGAASTGV GGQVSVNMPL QKTMEIGENL  600
TSRTFRYTDF SNPFSFRANP DIIGISEQPL FGAGSISSGE LYIDKIEIIL ADATNPTREA  660
EEDLEAAKKA VASLFTRTRD GLQVNVTDYQ VDQAANLVSC LSDEQYGHDK KMLLEAVRAA  720
KRLSRERNLL QDPDFNTINS TEENGWKASN GVTISEGGPF YKGRALQLAS ARENYPTYIY  780
QKVNASELKP YTRYRLDGFV KSSQDLEIDL IHHHKVHLVK NVPDNLVSDT YSDGSCSGMN  840
RCEEQQMVNA QLETEHHHPM DCCEAAQTHE FSSYINTGDL NSSVDQGIWV VLKVRTTDGY  900
ATLGNLELVE VGPLSGESLE REQRDNAKWS AELGRKRAET DRVYQDAKQS INHLFVDYQD  960
QQLNPEIGMA DIIDAQNLVA SISDVYSDAV LQIPGINYEI YTELSNRLQQ ASYLYTSRNA 1020
VQNGDFNSGL DSWNATGGAT VQQDGNTHFL VLSHWDAQVS QQFRVQPNCK YVLRVTAEKV 1080
GGGDGYVTIR DGAHHTEKLT FNACDYDING TYVTDNTYLT KEVVFYSHTE HMWVEVSETE 1140
GAFHIDSIEF VETEK                                                 1155

SEQ ID NO: 40          moltype = DNA  length = 3732
FEATURE                Location/Qualifiers
misc_feature           1..3732
                       note = Synthetic nucleotide sequence designed for
                        expression in a plant cell encoding TIC868_13.
source                 1..3732
                       mol_type = other DNA
                       organism = synthetic construct
SEQUENCE: 40
atgacgagca accggaagaa cgagaacgag atcatcaacg ccctctcgat ccctgctgtt   60
tcaaaccact ccgcgcagat gaacctgtcc accgacgcgc gcatcgagga ctccctctgc  120
atagccgagg gcaacaacat cgacccattc gtgtcggcca gcacggttca gaccggcatc  180
aacatcgcgg gccgtatcct cggcgtcctc ggtgtcccat tcgccggtca gatcgcgtcc  240
ttctactcgt tccttgtggg cgagctgtgg cctcgccgtc gtgacccgtg ggagatcttc  300
ctggagcatg tggagcagtt gatccggcag caagtcacgg agaacacccg cgatactgct  360
ctggccaggc tacagggcct gggaaactcc tttcgggcat accagcagtc actggaggac  420
tggttggaga cagggatga cgcgcgaaca cgctcggtac tctacaccca gtacatcgct  480
ctcgaactcg acttcctgaa cgctatgccg ctgttcgcca tcaggaacca ggaagttcca  540
ctccttatgg tgtacgccca ggccgccaac ttacatctgc tcctgctgcg ggacgccagc  600
ctgttcggct ccgagttcgg actcacatct caagaaatcc agcgttacta cgagcgccaa  660
gtggagaaga cccgtgagta cagtgactac tgcgctcgat ggtacaacac agggctcaac  720
aacctgcgcg gcaccaacgc tgagtcatcg ctccgttaca accagttccg ccgcgacttg  780
actttgggtg tcctagacct ggtggcgcta ttcccgtctt acgacacacg ggtgtaccca  840
atgaacacta cgcgcgaact cacgcgggag atctacacag acccaatcgg ccggacgaac  900
gcaccctccg gtttcgcatc cacgaattgg ttcaacaaca acgcacctc cttctcggca  960
atcgaggccg ccgtcatccg ccctcctcac ctgctcgact ttcccgagca gctcacgatc 1020
ttctccgtgc tctcacgctg gtccaacaca cagtacatga actatgggt cgggcaccga 1080
ttggagagta ggacgatccg tggcagcttg agcaccagta cccacggcaa caccaacacc 1140
tccatcaacc cagttacgct acagttcacg agccgcgacg tttaccggac tgagtcgttc 1200
gcgggcatta acatccttct gacaacgccc gtcaacggcg tcccgtgggc ccggttcaac 1260
tggcgtaacc cgttgaactc cctgcgcggg tcattgctct acaccatggg gtacacgggc 1320
gtcggcaccc agctcttcga cagtgaaact gagctgccgc ccgagaccac ggaacgcccg 1380
aactacgagt cctacagcca ccgcctgtcc aacatccggc tcatctctgg caacacgctg 1440
cgtgcgccgg tgtactcctg gacacaccgc agcgccgacc ggaccaacac gatctcttcc 1500
gactccatta accagatccc gctcgtgaag ggcttccgtg tgtggggtgg cacgagcgtc 1560
atcaccggtc cgggcttcac cggtggagac atactgcggc gcaacacttt cggcgacttc 1620
gtttcgttgc aagtgaacat caactcgccg atcacccagc gttaccgtct gaggttccgc 1680
tacgcttcaa gccgcgacgc gagggtcatt gtcctgaccg gagccgcgtc cacaggcgtg 1740
ggaggccaag tctcagtcaa catgcctctc cagaagacga tggagatagg cgagaacttg 1800
actagccgaa ccttccggta cactgatttc tcgaacccat tctcattcag agcgaaccct 1860
gacatcattg ggatctccga gcaaccgctg ttcggtgctg gctccatcag ctctggcgaa 1920
ctgtacatcg acaagattga gatcatcctg gcggatgcga cgacggcgac cttcgaggcg 1980
gagtatgact tggagcgggc tcaggaggcc gtcaacgcgc tgttcacaaa caccaatcct 2040
cgccgcctca agacgggtgt gactgattac cacattgacg aggtctccaa cttggtcgcg 2100
tgtctgtccg atgagttctg cctggacgag aagcgggaac tgctggagaa ggtcaagtac 2160
gccaagcgcc tctccgacga aaggaacctc ctccaagatc ccaactttac ttccattaac 2220
aagcagccgg acttcatctc caccaacgag cagtccaact tcacctcaat ccacgagcag 2280
tcggagcacg ggtggtgggg cagcgagaac atcaccatcc aagagggcaa cgacgtcttc 2340
aaggagaact acgtgatcct gcccggcacc ttcaacgagt gttacccgac ctatctctac 2400
cagaagattg gcgaagcgga actcaaggct tacacccgtt accaactgag tggctacatt 2460
gaggactcac aagacctgga aatctacctg atccgctaca acgccaagca cgagaccctc 2520
gacgtgcgtg gcacggagtc cgtctggccc ttgagcgtgg agtctcctat cggtcgttgc 2580
ggcgagccca tcgctcgcgc tccgcacttt gagtggaatc ctgatttgga ttgctcctgc 2640
cgagacggtg agaaatgcgc ccaccactcg caccacttca gcctagacat cgacgtgggc 2700
tgcatcgacc tgcacgagaa cttgggcgtc tgggtcgtgt tcaagatcaa gacacaggag 2760
ggccatgctc ggcttgggaa cctggagttc atcgaggaga agccactgct gggtgaagcc 2820
ttgtcacggg tgaaacgcgc cgagaagaag tggcggaaca aacggagaca gctccagttg 2880
gagacaaagc gtgtgtacac agaggccaag gaggccgtgg atgccttgtt cgtggacagt 2940
cagtacgaca ggctgcaagc ggacaccaac atcgggatga tccacgcggc tgataagctt 3000
gttcacgaga tccgcgaggc gtacctgtca gagcttagcg tgatcccagg cgtcaacgcc 3060
gaaatcttcg aggaactgga gggccgcatt atcacggcaa tctcacttta tgacgcgagg 3120
aatgtggtca gaacggtga cttcaacaac ggcttgacgt taaagggcaa tatcaacggt 3180
gtggatgtac aacagtcaca ccacagaagt gtcttggtca tcccggagtg gggaggcgaa 3240
gtggagccagg ccgtccgggt ctgccctggg cgcggttaca tcctccgcgt gacagcgtac 3300
aaggaggggct acggtgaggg ctgcgtgacg atccacgaga ttgagaacaa cacggacgag 3360
cttaagttca agaactgcga ggaggaggaa gtgtacccga cagacaccgg cacctgcaac 3420
gactacaccg cccaccaagg gaccgccgcc tgcaacagcc gcaacgcggg ctatgaagat 3480
```

```
gcgtacgagg ttgataccac cgcctcagtg aactacaaac cgacttatga ggaggagaca  3540
tacacggacg tcaggcgcga caaccattgt gagtacgacc gtggctacgt gaactatccg  3600
ccggtgccag cgggctacat gacgaaggag ctagaatact tccctgagac ggacaaggtg  3660
tggattgaaa tcggcgagac cgagggcaag tttatcgtgg attctgtcga gctgctgcta  3720
atggaggagt ag                                                      3732

SEQ ID NO: 41           moltype = AA  length = 1243
FEATURE                 Location/Qualifiers
REGION                  1..1243
                        note = Amino acid sequence of the chimeric protein variant
                        TIC868_13.
source                  1..1243
                        mol_type = protein
                        organism = synthetic construct
SEQUENCE: 41
MTSNRKNENE IINALSIPAV SNHSAQMNLS TDARIEDSLC IAEGNNIDPF VSASTVQTGI  60
NIAGRILGVL GVPFAGQIAS FYSFLVGELW PRGRDPWEIF LEHVEQLIRQ QVTENTRDTA  120
LARLQGLGNS FRAYQQSLED WLENRDDART RSVLYTQYIA LELDFLNAMP LFAIRNQEVP  180
LLMVYAQAAN LHLLLLRDAS LFGSEFGLTS QEIQRYYERQ VEKTREYSDY CARWYNTGLN  240
NLRGTNAESW LRYNQFRRDL TLGVLDLVAL FPSYDTRVYP MNTSAQLTRE IYTDPIGRTN  300
APSGFASTNW FNNNAPSFSA IEAAVIRPPH LLDFPEQLTI FSVLSRWSNT QYMNYWVGHR  360
LESRTIRGSL STSTHGNTNT SINPVTLQFT SRDVYRTESF AGINILLTTP VNGVPWARFN  420
WRNPLNSLRG SLLYTIGYTG VGTQLFDSET ELPPETTERP NYESYSHRLS NIRLISGNTL  480
RAPVYSWTHR SADRTNTISS DSINQIPLVK GFRVWGGTSV ITGPGFTGGD ILRRNTFGDF  540
VSLQVNINSP ITQRYRLRFR YASSRDARVI VLTGAASTGV GGQVSVNMPL QKTMEIGENL  600
TSRTFRYTDF SNPFSFRANP DIIGISEQPL FGAGSISSGE LYIDKIEIIL ADATTATFEA  660
EYDLERAQEA VNALFTNTNP RRLKTGVTDY HIDEVSNLVA CLSDEFCLDE KRELLEKVKY  720
AKRLSDERNL LQDPNFTSIN KQPDFISTNE QSNFTSIHEQ SEHGWWGSEN ITIQEGNDVF  780
KENYVILPGT FNECYPTYLY QKIGEAELKA YTRYQLSGYI EDSQDLEIYL IRYNAKHETL  840
DVPGTESVWP LSVESPIGRC GEPNRCAPHF EWNPDLDCSC RDGEKCAHHS HHFSLDIDVG  900
CIDLHENLGV WVVFKIKTQE GHARLGNLEF IEEKPLLGEA LSRVKRAEKK WRDKREKLQL  960
ETKRVYTEAK EAVDALFVDS QYDRLQADTN IGMIHAADKL VHRIREAYLS ELSVIPGVNA  1020
EIFEELEGRI ITAISLYDAR NVVKNGDFNN GLACWNVKGH VDVQQSHHRS VLVIPEWEAE  1080
VSQAVRVCPG RGYILRVTAY KEGYGEGCVT IHEIENNTDE LKFKNCEEEE VYPTDTGTCN  1140
DYTAHQGTAA CNSRNAGYED AYEVDTTASV NYKPTYEEET YTDVRRDNHC EYDRGYVNYP  1200
PVPAGYMTKE LEYFPETDKV WIEIGETEGK FIVDSVELLL MEE                    1243

SEQ ID NO: 42           moltype = DNA  length = 3702
FEATURE                 Location/Qualifiers
misc_feature            1..3702
                        note = Synthetic nucleotide sequence designed for
                        expression in a plant cell encoding TIC868_14.
source                  1..3702
                        mol_type = other DNA
                        organism = synthetic construct
SEQUENCE: 42
atgacgagca accggaagaa cgagaacgag atcatcaacg ccctctcgat ccctgctgtt  60
tcaaaccact ccgcgcagat gaacctgtcc accgacgcgc gcatcgagga ctccctctgc  120
atagccgagg gcaacaacat cgacccattc gtgtcggcca gcacggttca gaccggcatc  180
aacatcgcgg gccgtatcct cggcgtcctc ggtgtcccat cgccggtca gatcgcgtcc  240
ttctactcgt tccttgtggg cgagctgtgg cctcgcggtc gtgacccgtg ggagatcttc  300
ctggagcatg tggagcagtt gatccggcag caagtcacgg agaacacccg cgatactgct  360
ctggccaggc tacagggcct gggaaactcc tttcgggcat accagcagtc actggaggac  420
tggttggaga cagggatga cgcgcgaaca cgctcggtac tctacaccca gtacatcgct  480
ctcgaactcg acttcctgaa cgctatgccg ctgttcgcca tcaggaacca ggaagttcca  540
ctccttatgg tgtacgccca ggccgccaac ttacatctgc tcctgctgcg ggacgccagc  600
ctgttcggct ccgagttcgg actcacatct caagaaatcc agcgttacta cgagcgccaa  660
gtggagaaga cccgtgagta cagtgactac tgcgctcgat ggtacaacac agggctcaac  720
aacctgcgcg gcaccaacgc tgagtcatgg ctccgttaca accagttccg ccgcgacttg  780
actttgggtg tcctagacct ggtggcgcta ttcccgtctt acgacacgcg ggtgtaccca  840
atgaacacta gcgcgcaact cacgcgggag atctacacag acccaatcgg ccggacgaac  900
gcaccctccg gtttcgcatc cacgaattgg ttcaacaaca acgcaccctc cttctcggca  960
atcgaggccg ccgtcatccg ccctcctcac ctgctcgact ttcccgagca gctcacgatc  1020
ttctccgtgc tctcacgctg gtccaacaca cagtacatga actactgggt cgggcaccga  1080
ttggagagta ggacgatccg tggcagcttg agcaccagta cccacggcaa caccaacacc  1140
tccatcaacc cagttacgct acagttcacg agccgcgacg tttaccggac tgagtcgttc  1200
gcgggcatta acatccttct gacaacgccc gtcaacggcg tcccgtgggc ccggttcaac  1260
tggcgtaacc cgttgaactc cctgcgcggg tcattgctct acaccatcgg gtacacgggc  1320
gtcggcaccc agctcttcga cagtgaaact gagctgccgc ccgagaccac ggaacgcccg  1380
aactacgagt cctacagcca ccgcctgtcc aacatccggc tcatctctgg caacacgctg  1440
cgtgcgccgg tgtactcctg gacacaccgc agcgccgacc ggaccaacac gatctcttcc  1500
gactccatta ccagatccc gctcgtgaag ggcttccgtg tgtggggtgg cacgagcgtc  1560
atcaccggtc cgggcttcac cggtggagac atactgcggc gcaacacttt cggcgacttc  1620
gtttcgttgc aagtgaacat caactcgccg atcacccagc gttaccgtct gaggttccgc  1680
tacgcttcaa gccgcgacgc gagggtcatt gtcctgaccg gagccgcgtc cacaggcgtg  1740
ggaggccaag tctcagtcaa catgcctctc cagaagacga tggagatagg cgagaacttg  1800
actagccgaa ccttccggta cactgatttc tcgaaccctt tctcattcag agcgaaccct  1860
gacatcattg ggatctccga gcaaccgctg ttcggtgctg gctccatcag ctctggcgaa  1920
ctgtacatcg acaagattga gatcatcctg gcggatgcga cgaccgcgac gtttgaagct  1980
```

-continued

```
gaatccgacc tcgagcgtgc gcgcaaggcg gtgaacgctc tgttcacgag caccaaccct   2040
cgtggcttga agacggatgt gacggactac cacatcgacc aagtctcgaa cctcgtggag   2100
tgcctgagcg acgagttctg tcttgacaag aagcgcgagc tgctggagga ggtgaagtac   2160
gccaagcgcc tctccgatga gcgcaacctg ctccaagatc ctaccttcac gtcgatttcc   2220
ggccaaaccg accgtggatg gatcggctcg actggcatct ccatccaggg cggcgacgac   2280
atcttcaagg agaactatgt tcggctgccg ggcacggtgg acgagtgtta cccgacgtac   2340
ctctaccaga agatagacga gagtcaactc aagtcctaca cgcggtatca gttacgtggc   2400
tacattgaag actcccagga cttggaaatc tatctcatac ggtacaacgc caagcacgag   2460
accttaagcg tgccgggaac ggagtcgccc tggccaagct ctggcgtgta cccttccggt   2520
aggtgcggcg agcccaaccg ctgtgcacct cgaatcgaat ggaacccgga ccttgactgc   2580
tcttgccggt acggcgagaa gtgcgtccat cattctcacc acttcagctt ggacattgac   2640
gtcggctgca ccgacctcaa tgaagacctc ggagtgtggg tcatcttcaa gatcaagaca   2700
caggacgggc acgcgaaact aggaaacctg gagttcatcg aggagaagcc actcctcggc   2760
aaggcacttt ccagggtcaa gcgggccgag aagaaatgga gggacaagta cgagaaactc   2820
cagctcgaaa caaagcgggt gtacacggag gcaaaggaat ccggcacgc cctgttcgtg   2880
gactctcagt acgacaagct ccaggcgaac acaaacattg gcatcatcca cggtgcggac   2940
aagcaagtgc acaggatacg ggagccttac ctctcggagc tgccggtgat tcctcgatc   3000
aacgcggcga tcttcgagga actgaggggc cacatcttca aggcgtattc tctgtacgac   3060
gcgcgtaacg tcatcaagaa cggcgacttc aacaatgggc tgtcctgctg gaacgttaaa   3120
ggccacgtcg atgtccagca gaaccaccat aggtcagtcc tggtgctgag cgagtgggag   3180
gcggaggtgt cccagaaggt gcgcgtgtgc ccggatcgcg gctacatctt gagggtgaca   3240
gcctacaagg agggctacgg cgagggctgt gtcacgatcc atgagttcga gacgaacacg   3300
gatgtcctga aattccgtaa cttcgtcgag gaggaggtct atcccaacaa caccgtgacc   3360
tgcaacgact acacgaccaa tcagtcggct gagggcagta ccgatgcctg caacagctac   3420
aaccgtggtt acgaagatgg atacgagaac cgctacgagc ccaatccttc ggctcccgtg   3480
aattacactc ccacgtacga ggagggcatg tacactgaca ctcagggcta caaccattac   3540
gtcagcgacc gtggctaccg caaccacacg ccgctcccag cgggctacgt gacgctggag   3600
ctggaatact ttcccgagac agaacaagtg tggatagaga tcggcgagac cgagggcaca   3660
ttcatcgtgg gctctgtgga attgctcctc atggaggagt aa                      3702
```

```
SEQ ID NO: 43          moltype = AA  length = 1200
FEATURE                Location/Qualifiers
REGION                 1..1200
                       note = Amino acid sequence of the chimeric protein variant
                        TIC868_14.
source                 1..1200
                       mol_type = protein
                       organism = synthetic construct
SEQUENCE: 43
MTSNRKNENE IINALSIPAV SNHSAQMNLS TDARIEDSLC IAEGNNIDPF VSASTVQTGI   60
NIAGRILGVL GVPFAGQIAS FYSFLVGELW PRGRDPWEIF LEHVEQLIRQ QVTENTRDTA   120
LARLQGLGNS FRAYQQSLED WLENRDDART RSVLYTQYIA LELDFLNAMP LFAIRNQEVP   180
LLMVYAQAAN LHLLLLRDAS LFGSEFGLTS QEIQRYYERQ VEKTREYSDY CARWYNTGLN   240
NLRGTNAESW LRYNQFRRDL TLGVLDLVAL FPSYDTRVYP MNTSAQLTRE IYTDPIGRTN   300
APSGFASTNW FNNNAPSFSA IEAAVIRPPH LLDFPEQLTI FSVLSRWSNT QYMNYWVGHR   360
LESRTIRGSL STSTHGNTNT SINPVTLQFT SRDVYRTESF AGINILLTTP VNGVPWARFN   420
WRNPLNSLRG SLLYTIGYTG VGTQLFDSET ELPPETTERP NYESYSHRLS NIRLISGNTL   480
RAPVYSWTHR SADRTNTISS DSINQIPLVK GFRVWGGTSV ITGPGFTGGD ILRRNTFGDF   540
VSLQVNINSP ITQRYRLRFR YASSRDARVI VLTGAASTGV GGQVSVNMPL QKTMEIGENL   600
TSRTFRYTDF SNPFSFRANP DIIGISEQPL FGAGSISSGE LYIDKIEIIL ADATTATFEA   660
ESDLERARKA VNALFTSTNP RGLKTDVTDY HIDQVSNLVE CLSDEFCLDK KRELLEEVKY   720
AKRLSDERNL LQDPTFTSIS GQTDRGWIGS TGISIQGGDD IFKENYVRLP GTVDECYPTY   780
LYQKIDESQL KSYTRYQLRG YIEDSQDLEI YLIRYNAKHE TLSVPGTESP WPSSGVYPSG   840
RCGEPNRCAP RIEWNPDLDC SCRYGEKCVH HSHHFSLDID VGCTDLNEDL GVWVIFKIKT   900
QDGHAKLGNL EFIEEKPLLG KALSRVKRAE KKWRDKYEKL QLETKRVYTE AKESVDALFV   960
DSQYDKLQAN TNIGIIHGAD KQVHRIREPY LSELPVIPSI NAAIFEELEG HIFKAYSLYD   1020
ARNVIKNGDF NNGLSCWNVK GHVDVQQNHH RSVLVLSEWE AEVSQKVRVC PDRGYILRVT   1080
AYKEGYGEGC VTIHEFEDNT DVLKFRNFVE EEVYPNNTVT CNDYTTNQSA EGSTDACNSY   1140
NRGYEDGYEN RYEPNPSAPV NYTPTYEEGM YTDTQGYNHC VSDRGYRNHT PLPAGYVTLE   1200
```

```
SEQ ID NO: 44          moltype = DNA  length = 3687
FEATURE                Location/Qualifiers
misc_feature           1..3687
                       note = Synthetic nucleotide sequence designed for
                        expression in a plant cell encoding TIC868_15.
source                 1..3687
                       mol_type = other DNA
                       organism = synthetic construct
SEQUENCE: 44
atgacgagca accggaagaa cgagaacgag atcatcaacg ccctctcgat ccctgctgtt   60
tcaaaccact ccgcgcagat gaacctgtcc accgacgcgc gcatcgagga ctccctctgc   120
atagccgagg gcaacaacat cgacccattc gtgtcggcca gcacggttca gaccggcatc   180
aacatcgcgg gccgtatcct cggcgtcctc ggtgtcccat cgccggtca gatcgcgtcc   240
ttctactcgt tccttgtggg cgagctgtgg cctcgcggtc gtgacccgtg ggagatcttc   300
ctggagcatg tggagcagtt gatccggcag caagtcacgg agaacacccg cgatactgct   360
ctggccaggc tacagggcct gggaaactcc tttcgggcat accagcagtc actggaggac   420
tggttggaga acagggatga cgcgcgaaca cgctcggtac tctacaccca gtacatcgct   480
ctcgaactcg acttcctgaa cgctatgccg ctgttcgcca tcaggaacca ggaagttcca   540
ctccttatgg tgtacgccca ggcgccaaac ttacatctgc tcctgctgcg ggacgccagc   600
```

-continued

```
ctgttcggct ccgagttcgg actcacatct caagaaatcc agcgttacta cgagcgccaa  660
gtggagaaga cccgtgagta cagtgactac tgcgctcgat ggtacaacac agggctcaac  720
aacctgcgcg gcaccaacgc tgagtcatgg ctccgttaca accagttccg ccgcgacttg  780
actttgggtg tcctagacct ggtggcgcta ttccgtctt acgacacacg ggtgtaccca  840
atgaacacta gcgcgcaact cacgcgggag atctacacag acccaatcgg ccggacgaac  900
gcaccctccg gtttcgcatc cacgaattgg ttcaacaaca acgcaccctc cttctcggca  960
atcgaggccg ccgtcatccg ccctcctcac ctgctcgact ttcccgagca gctcacgatc  1020
ttctccgtgc tctcacgctg gtccaacaca cagtacatga actactgggt cgggcaccga  1080
ttggagagta ggacgatccg tggcagcttg agcaccagta cccacggcaa caccaacacc  1140
tccatcaacc cagttacgct acagttcacg agccgcgacg tttaccggac tgagtcgttc  1200
gcgggcatta acatccttct gacaacgccc gtcaacggcg tcccgtgggc ccggttcaac  1260
tggcgtaacc cgttgaactc cctgcgcggg tcattgctct acaccatcgg gtacacgggc  1320
gtcggcaccc agctcttcga cagtgaaact gagctgccgc ccgagaccac ggaacgcccg  1380
aactacgagt cctacagcca ccgcctgtcc aacatccggc tcatctctgg caacacgctg  1440
cgtgcgccgg tgtactcctg gacacaccgc agcgccgacc ggaccaacac gatctcttcc  1500
gactccatta accagatccc gctcgtgaag ggcttccgtg tgtggggtgg cacgagcgtc  1560
atcaccggtc cgggcttcac cggtggagac atactgcggc gcaacacttt cggcgacttc  1620
gtttcgttgc aagtgaacat caactcgccg atcacccagc gttaccgtct gaggttccgc  1680
tacgcttcaa gccgcgacgc gagggtcatt gtcctgaccg gagccgcgtc cacaggcgtg  1740
ggaggccaag tctcagtcaa catgcctctc cagaagacga tggagatagg cgagaacttg  1800
actagccgaa ccttccggta cactgatttc tcgaacccct tctcattcag agcgaaccct  1860
gacatcattg ggatctccga gcaaccgctg ttcggtgctg gctccatcag ctctggcgaa  1920
ctgtacatcg acaagattga gatcatcctg gcggatgcga cggatgctac ctttgaagca  1980
gagtccgact tggaacgtgc acagaaggca gtgaacgcac tcttcacctc aagcaaccag  2040
atcggattga agacagatgt gacagattac cacatcgacc aagtgagcaa cttggtggat  2100
tgcttgtcag atgagttctg cttggatgag aagcgtgaac tctccgagaa ggtgaagcac  2160
gcaaagcgtc tctcagatga acgtaatctc cttcaagacc ctaactttcg tggtatcaat  2220
cgtcagccag atcgtggatg gcgtggatca acagacatca ccatccaggg aggcgatgat  2280
gtgttcaagg agaactacgt gaccctccca ggaaccgtgg atgaatgcta cccaacctac  2340
ctctaccaga agatcgacga gtcaaagctc aaggcttaca cccgttatga actccgtggc  2400
tacatcgaag atagccagga tctcgaaatc tatctcatcc gttacaatgc taagcacgaa  2460
atcgtgaatg tgccaggaac cggctcactc tggccactct cagcacagtc accaatcggc  2520
aagtgcggcg aacccaatcg ctgcgctcct catctcgaat ggaatcccga tctcgactgc  2580
tcctgccgag acggcgagaa gtgtgcacat cactcacacc acttcaccct cgacatcgac  2640
gtgggctgca ccgacctcaa tgaagacctg ggcgtgtggg tgatcttcaa gatcaagacc  2700
caggacggcc acgcacgact gggcaatctg gagtttctgg aggagaagcc actgcttggc  2760
gaggcactgg cacgagtgaa acgagccgag aagaaatggc gagacaaacg tgagaagctg  2820
caactggaga ccaacatcgt gtacaaagag gccaaagagt cagttgacgc cctgtttgtc  2880
aatagccagt atgaccgact gcaagttgac accaacatcg ccatgatcca cgctgcggac  2940
aagcgcgtcc accgcatccg cgaggcttat ctgcccgagc tgagcgtcat tcccggcgtc  3000
aatgccgcga tcttcgagga gttagagggc cgcatcttca ccgcctacag cctctatgac  3060
gcccgcaatg tcattaagaa tggcgacttc aacaatggct actatgctg gaatgtcaaa  3120
gggcacgtgg acgtcgagga gcagaacaat caccgcacgg tcttagtcat acccgagtgg  3180
gaggccgaag tcagccagga agtccgcgtc tgtccaggcg cgggtacat cctgcgggtc  3240
accgcctaca agaggggata cggcgagggt tgtgtcacca tacacgagat agaggacaat  3300
accgacgaac tcaagttcag caattgtgtc gaggaggaag tctatcccaa caataccgta  3360
acctgcaaca actacaccgg aacccaggag gagtatgaag ggacagacc ctcgcggaac  3420
cagggctatg acgaagccta tgggaacaac ccgtcggtgc ctgctgacta tgcgtcggtc  3480
tatgaggaga aatcgtacac ggacgggcgg cgggagaatc cgtgtgagtc gaatcgcggg  3540
tatggtgact acacgccgct accggcgggc tatgtaacga aagacctgga atacttcccg  3600
gagacggaca aagtatggat agagataggc gagacggagg aacgttcat cgtggactcg  3660
gtagagctgc tgctcatgga ggagtga                                      3687
```

SEQ ID NO: 45          moltype = AA   length = 1228
FEATURE                Location/Qualifiers
REGION                 1..1228
                       note = Amino acid sequence of the chimeric protein variant
                       TIC868_15.
source                 1..1228
                       mol_type = protein
                       organism = synthetic construct
SEQUENCE: 45

```
MTSNRKNENE IINALSIPAV SNHSAQMNLS TDARIEDSLC IAEGNNIDPF VSASTVQTGI  60
NIAGRILGVL GVPFAGQIAS FYSFLVGELW PRGRDPWEIF LEHVEQLIRQ QVTENTRDTA  120
LARLQGLGNS FRAYQQSLED WLENRDDART RSVLYTQYIA LELDFLNAMP LFAIRNQEVP  180
LLMVYAQAAN LHLLLLRDAS LFGSEFGLTS QEIQRYYERQ VEKTREYSDY CARWYNTGLN  240
NLRGTNAESW LRYNQFRRDL TLGVLDLVAL FPSYDTRVYP MNTSAQLTRE IYTDPIGRTN  300
APSGFASTNW FNNAPSFSA IEAAVIRPPH LLDFPEQLTI FSVLSRWSNT QYMNYWVGHR  360
LESRTIRGSL STSTHGNTNT SINPVTLQFT SRDVYRTESF AGINILLTTP VNGVPWARFN  420
WRNPLNSLRG SLLYTIGYTG VGTQLFDSET ELPPETTERP NYESYSHRLS NIRLISGNTL  480
RAPVYSWTHR SADRTNTISS DSINQIPLVK GFRVWGGTSV ITGPGFTGGD ILRRNTFGDF  540
VSLQVNINSP ITQRYRLRFR YASSRDARVI VLTGAASTGV GGQVSVNMPL QKTMEIGENL  600
TSRTFRYTDF SNPFSFRANP DIIGISEQPL FGAGSISSGE LYIDKIEIIL ADATDATFEA  660
ESDLERAQKA VNALFTSSNQ IGLKTDVTDY HIDQVSNLVD CLSDEFCLDE KRELSEKVKH  720
AKRLSDERNL LQDPNFRGIN RQPDRGWRGS TDITIQGGDD VFKENYVTLP GTVDECYPTY  780
LYQKIDESKL KAYTRYELRG YIEDSQDLEI YLIRYNAKHE IVNVPGTGSL WPLSAQSPIG  840
KCGEPNRCAP HLEWNPDLDC SCRDGEKCAH HSHHFTLDID VGCTDLNEDL GVWVIFKIKT  900
QDGHARLGNL EFLEEKPLLG EALARVKRAE KKWRDKREKL QLETNIVYKE AKESVDALFV  960
NSQYDRLQVD TNIAMIHAAD KRVHRIREAY LPELSVIPGV NAAIFEELEG RIFTAYSLYD  1020
```

```
ARNVIKNGDF NNGLLCWNVK GHVDVEEQNN HRSVLVIPEW EAEVSQEVRV CPGRGYILRV  1080
TAYKEGYGEG CVTIHEIEDN TDELKFSNCV EEEVYPNNTV TCNNYTGTQE EYEGTYTSRN  1140
QGYDEAYGNN PSVPADYASV YEEKSYTDGR RENPCESNRG YGDYTPLPAG YVTKDLEYFP  1200
ETDKVWIEIG ETEGTFIVDS VELLLMEE                                     1228

SEQ ID NO: 46           moltype = DNA  length = 3600
FEATURE                 Location/Qualifiers
misc_feature            1..3600
                        note = Synthetic nucleotide sequence designed for
                         expression in a plant cell encoding TIC868_29.
source                  1..3600
                        mol_type = other DNA
                        organism = synthetic construct
SEQUENCE: 46
atgacgagca accggaagaa cgagaacgag atcatcaacg ccctctcgat ccctgctgtt  60
tcaaaccact ccgcgcagat gaacctgtcc accgacgcgc gcatcgagga ctccctctgc  120
atagccgagg gcaacaacat cgacccattc gtgtcggcca gcacggttca gaccggcatc  180
aacatcgcg gccgtatcct cggcgtcctc ggtgtcccat tcgccggtca gatcgcgtcc  240
ttctactcgt tccttgtggg cgagctgtgg cctcgcggtc gtgacccgtg ggagatcttc  300
ctggagcatg tggagcagtt gatccggcag caagtcacgg agaacacccg cgatactgct  360
ctggccaggc tacagggcct gggaaactcc tttcgggcat accagtactc actggaggac  420
tggttggaga acagggatga cgcgcgaaca cgctcggtac tctacaccca gtacatcgct  480
ctcgaactcg acttcctgaa cgctatgccg ctgttcgcca tcaggaacca ggaagttcca  540
ctccttatgg tgtacgccca ggcgccaac ttacatctgc tcctgctgcg ggacgccagc  600
ctgttcggct ccgagttcgg actcacatct caagaaatcc agcgttacta cgagcgcaa  660
gtggagaaga cccgtgagta cagtgactac tgcgctcgat ggtacaacac agggctcaac  720
aacctgcgcg gcaccaacgc tgagtcatgg ctccgttaca accagttccg ccgcgacttg  780
actttgggtg tcctagacct ggtggcgcta ttcccgtctt acgacacacg ggtgtaccca  840
atgaacacta gcgcgcaact cacgcgggag atctacacag acccaatcgg ccggacgaac  900
gcaccctccg gtttcgcatc cacgaattgg ttcaacaaca cgcaccctc cttctcggca  960
atcgaggccg ccgtcatccg ccctcctcac ctgctcgact ttcccgagca gctcacgatc  1020
ttctcccagc tctcacgctg gtcccacaca cagtacatga actactggt cgggcaccga  1080
ttggagagta ggacgatccg tggcagcttg agcaccagta cccacggcaa caccaacacc  1140
tccatcaacc cagttacgct acagttcacg agccgcgacg tttaccggac tgagtcgttc  1200
gcgggcatta acatccttct gacaacgccc gtcaacgacg tcccgtgggc ccggttcaac  1260
tggcgtaacc cgttgaactc cctgcgcggg tcattgctct acaccatcgg gtacacgggc  1320
gtcggcaccc agctcttcga cagtgaaact gagctgccgc ccgagaccac ggaacgcccg  1380
aactacgagt cctacagcca ccgcctgtcc aacatccggc tcatctctgg caacacgctg  1440
cgtgcgccgg tgtactcctg gacacaccgc agcgccgaac agcccaacac gatctcttcc  1500
gactccatta accagatccc gctcgtgaag ggcttccgtg tgtggggtgg cacgagcgtc  1560
atcaccggtc cgggcttcac cggtggagac atactcggc gcaacacttt cggcgacttc  1620
gtttcgttgc aagtgaacat caactcgccg atcacccagc gttaccgtct gaggttccgc  1680
tacgcttcaa gccgcgacgc gagggtcatt gtcctgaccg gagccgcgtc cacaggcgtg  1740
ggaggccaag tctcagtcaa catgcctctc cagaagacga tggagatagg cgagaacttg  1800
actagccgaa ccttccggta cactgatttc tcgaaccctt tctcattcag agcgaaccct  1860
gacatcattg ggatctccga gcaaccgctg ttcggtgctg gctccatcag ctctggcgaa  1920
ctgtacatcg acaagattga gatcatcctg gcggatgcga cgttcgagtc cgagtctgac  1980
ctggagcggg ctcagaaggc tgtcaacgaa ctgttcacca gcagcaacca gattgggctc  2040
aagaccgacg tcacggacta tcacattgac caagtgtcca accttgtgga gtgcctgtcc  2100
gacgagttct gcctcgacga gaagaaggag ctgtccgaga aggtcaaaca cgcgaagcgt  2160
ctgagtgacg agcggaattt gctccaggac ccgaacttcc gtggcatcaa ccgccagctc  2220
gaccgtggtt ggcgcgggag tacagacatc accatccagg gaggcgacga tgtgttcaag  2280
gagaactatg tgacgctgct cgggactttc gacgaatgct acccgacgta tctctaccag  2340
aagatagacg agagtaaatt gaaggcgtac acccgctacc agcttcgcgg gtacatcgag  2400
gatagtcagg acctggaaat ctacctgatc cgatacaacg ccaagcacga gacagtgaac  2460
gtgccaggca cgggctcact ttggccattg agcgctccct ctccaatcgg aaagtgcgct  2520
caccactcgc accacttctc tctggacatc gacgtgggct gcaccgacct caacgaggac  2580
ctgggtgtct gggttatctt caagattaag acccaggacg gacatgcccg cctcggcaac  2640
ctggagttcc ttgaggagaa gcctctcgtg ggcgaggccc tcgctcgtgt gaagcgcgcc  2700
gagaagaaat ggcgagacaa gcgggagaca ctggagtggg agaccaacat cgtgtacaag  2760
gaggccaagg agtcagtgga cgcactcttc gtcaacagcc agtacgaccg cctccaggct  2820
gacaccaaca tcgccatgat ccacgcggct gacaagcggg tccacagcat ccgtgaggcg  2880
tacctgcccg agctgtcagt gatccctggt gtgaacgcg cgatcttcga ggaactggag  2940
ggccgcatct tcacagcatt cagcctgtac gatgccagga atgttattaa gaacggtaac  3000
ttcaacaacg gctgagttg ctggaacgtc aagggccatg tggacgtcga ggagcagaac  3060
aaccaccggt ccgtgctggt cgtgccggag tgggaggcag aggtgagcca ggaggtccgc  3120
gtctgccctg tcgcggcta catcctccgt gtgactgcgt acaaggaagg ctacggtgaa  3180
ggctgcgtga ctatccacga gatcgagaac aacaccgacg agctcaagtt ctcgaactgt  3240
gtggaggagg aggtgtaccc gaacaacacc gttacttgca acgactacac tgccacgcaa  3300
gaggagtacg agggcactta cacttcccgg aatcgcggct atgatggcgc gtacgagtcc  3360
aacagcagcg tgcctgcgga ttatgcgtcc gcttacgagg agaaggcgta caccgacgga  3420
cggagggaca acccttgcga gtccaaccgt ggctacggtg actacactcc gctgcccgcc  3480
gggtacgtca ccaaggagct ggagtacttc cggagaccac aaaagtctg gatcgagatc  3540
ggcgagacgg agggcacttt catcgtggac tcggtcgagc tgctactgat ggaggagtga  3600

SEQ ID NO: 47           moltype = AA  length = 1199
FEATURE                 Location/Qualifiers
REGION                  1..1199
                        note = Amino acid sequence of the chimeric protein variant
```

```
                            TIC868_29.
source                      1..1199
                            mol_type = protein
                            organism = synthetic construct
SEQUENCE: 47
MTSNRKNENE IINALSIPAV SNHSAQMNLS TDARIEDSLC IAEGNNIDPF VSASTVQTGI   60
NIAGRILGVL GVPFAGQIAS FYSFLVGELW PRGRDPWEIF LEHVEQLIRQ QVTENTRDTA  120
LARLQGLGNS FRAYQYSLED WLENRDDART RSVLYTQYIA LELDFLNAMP LFAIRNQEVP  180
LLMVYAQAAN LHLLLLRDAS LFGSEFGLTS QEIQRYYERQ VEKTREYSDY CARWYNTGLN  240
NLRGTNAESW LRYNQFRRDL TLGVLDLVAL FPSYDTRVYP MNTSAQLTRE IYTDPIGRTN  300
APSGFASTNW FNNNAPSFSA IEAAVIRPPH LLDFPEQLTI FSQLSRWSHT QYMNYWVGHR  360
LESRTIRGSL STSTHGNTNT SINPVTLQFT SRDVYRTESF AGINILLTTP VNGVPWARFN  420
WRNPLNSLRG SLLYTIGYTG VGTQLFDSET ELPPETTERP NYESYSHRLS NIRLISGNTL  480
RAPVYSWTHR SADRTNTISS DSINQIPLVK GFRVWGGTSV ITGPGFTGGD ILRRNTFGDF  540
VSLQVNINSP ITQRYRLRFR YASSRDARVI VLTGAASTGV GGQVSVNMPL QKTMEIGENL  600
TSRTFRYTDF SNPFSFRANP DIIGISEQPL FGAGSISSGE LYIDKIEIIL ADATFEAESD  660
LERAQKAVNE LFTSSNQIGL KTDVTDYHID QVSNLVECLS DEFCLDEKKE LSEKVKHAKR  720
LSDERNLLQD PNFRGINRQL DRGWRGSTDI TIQGGDDVFK ENYVTLLGTF DECYPTYLYQ  780
KIDESKLKAY TRYQLRGYIE DSQDLEIYLI RYNAKHETVN VPGTGSLWPL SAPSPIGKCA  840
HHSHHFSLDI DVGCTDLNED LGVWVIFKIK TQDGHARLGN LEFLEEKPLV GEALARVKRA  900
EKKWRDKREK LEWETNIVYK EAKESVDALF VNSQYDRLQA DTNIAMIHAA DKRVHSIREA  960
YLPELSVIPG VNAAIFEELE GRIFTAFSLY DARNVIKNGD FNNGLSCWNV KGHVDVEEQN 1020
NHRSVLVVPE WEAEVSQEVR VCPGRGYILR VTAYKEGYGE GCVTIHEIEN NTDELKFSNC 1080
VEEEVYPNNT VTCNDYTATQ EEYEGTYTSR NRGYDGAYES NSSVPADYAS AYEEKAYTDG 1140
RRDNPCESNR GYGDYTPLPA GYVTKELEYF PETDKVWIEI GETEGTFIVD SVELLLMEE  1199

SEQ ID NO: 48             moltype = DNA  length = 3432
FEATURE                   Location/Qualifiers
misc_feature             1..3432
                          note = Recombinant nucleotide sequence used for expression
                           in a bacterial cell encoding TIC869.
source                    1..3432
                          mol_type = other DNA
                          organism = synthetic construct
SEQUENCE: 48
atggagataa ataatcagaa gcaatgcata ccatataatt gcttaagtaa tcctgaggaa   60
gtacttttgg atggggagag gatattacct gatatcgatc cactcgaagt ttctttgtcg  120
cttttgcaat ttcttttgaa taactttgtt ccagggggag gctttatttc aggattagtt  180
gataaaatat gggggggcttt gagaccatct gaatgggact tatttcttgc acagattgaa  240
cggttgattg atcaaagaat agaagcaaca gtaagcagcaa aagcaatcac tgaattagaa  300
ggattaggga gaaattatca aatatacgct gaagcattta aagaatggga atcagatcct  360
gataacgaag cggctaaaag tagagtaatt gatcgctttc gtatacttga tggtctaatt  420
gaagcaaata tcccttcatt tcggataatt ggatttgaag tgccacttt atcggtttat  480
gttcaagcag ctaatctaca tctcgctcta ttgagagatt ctgttatttt tggagagaga  540
tggggattga cgacaaaaaa tgtcaatgat atctataata gacaaattag agaaattcat  600
gaatatagca atcattgcgt agatacgtat aacacagaac tagaacgtct agggtttaga  660
tctatagcgc agtggagaat atataatcag tttagaagag aactaacact aactgtatta  720
gatattgtcg ctctttttccc gaactatgac agtagactgt atccgatcca aacttttttct  780
caattgacaa gagaaattgt tacatcccca gtaagcgaat tttattatgg tgttattaat  840
agtggtaata taattggtac tcttactgaa cagcagataa ggcgaccaca tcttatggac  900
ttctttaact ccatgatcat gtatacatca gataatagac gggaacatta ttggtcagga  960
cttgaaatga cggcttattt tacaggattt gcaggagctc aagtgtcatt cccctttagtc 1020
gggactagag gggagtcagc tccaccatta actgttagaa gtgttaatga tggaatttat 1080
agaatattat cggcaccgtt ttattcagcg ccttttctag gcaccattgt attgggaagt 1140
cgtggagaaa aatttgattt tgcgcttaat aatatttcac ctccgccatc tacaatatac 1200
agacatcctg gaacagtaga ttcactagtc agtataccgc cacaggataa tagcgtacca 1260
ccgcacaggg gatctagtca tcgattaagt catgttacaa tgcgcgcaag ttcccctata 1320
ttccattgga cgcatcgcag cgcaaccact acaaatacaa ttaatccaaa tgctattatc 1380
caaataccac tagtaaaagc atttaacctt cattcaggtg ccactgttgt tagaggacca 1440
gggtttacag gtggagatct cttacgaaga acgaatactg gtacatttgc agacataaga 1500
gtcaatgttc cttcatcact attttcccaa agatatcgcg taaggattcg ttatgcttct 1560
actaccgatt tacaattttt cacgagaatt aatggaactt ctgttaatca aggtaatttc 1620
tcaaaaacga tggatagagg ggataaactg aaatctgaaa actttagaac tgccggattt 1680
agtactcctt ttagattttc aaattttcaa agtacattca cgttgggtac tcaggctttt 1740
tcaaatcagg aagtttatat agatagaatt gaatttgtcc cggcagaagt aacattcgag 1800
gcagaatctg atttagaaag agcacaaaag gcggtgaatg agctgtttac ttcttccaat 1860
caaatcgggt taaaaacaga tgtgacggat tatcatattg atcaagtatc caatttagtt 1920
gagtgtttat ctgatgaatt ttgtctggat gaaaaaaaag aattgtccga gaaagtcaaa 1980
catgcgaagc gacttagtga tgagcgaat ttacttcaag atccaaactt tagagggatc 2040
aatagacaac tagaccgtgg ctggagagga agtacggata ttaccatcca aggaggcgat 2100
gacgtattca aagagaatta cgttacgcta ttgggtacct tgatgagtg ctatccaacg 2160
tatttatatc aaaaaaataga tgagtcgaaa ttaaaagcct atacccgtta ccaattaaga 2220
gggtatatcg aagatagtca agacttagaa atctattaa ttcgctacaa tgccaaacac 2280
gaaacagtaa atgtgccagg tacgggttcc ttatggccga ttcagcccc aagtccaatc 2340
ggaaaatgtg cccatcattc ccatcatttc tccttggaca ttgatgttgg atgtacagac 2400
ttaaatgagg acttaggtgt atgggtgata ttcaagatta agacgcaaga tggccatgca 2460
agactaggaa atctagaatt tctcgaagag aaaccattag taggagaagc actagctcgt 2520
gtgaaaagag cggagaaaaa atggagagac aaacgtgaaa aattggaatg ggaaacaaat 2580
attgtttata agaggcaaaa agaatctgta gatgcttat ttgtaaactc tcaatatgat 2640
```

-continued

```
agattacaag cggataccaa catcgcgatg attcatgcgg cagataaacg cgttcatagc   2700
attcgagaag cttatctgcc tgagctgtct gtgattccgg gtgtcaatgc ggctattttt   2760
gaagaattag aagggcgtat tttcactgca ttctccctat atgatgcgag aaatgtcatt   2820
aaaaatggtg attttaataa tggcttatcc tgctggaacg tgaaagggca tgtagatgta   2880
gaagaacaaa acaaccaccg ttcggtcctt gttgttccgg aatgggaagc agaagtgtca   2940
caagaagttc gtgtctgtcc gggtcgtggc tatatccttc gtgtcacagc gtacaaggag   3000
ggatatggag aaggttgcgt aaccattcat gagatcgaga acaatacaga cgaactgaag   3060
tttagcaact gtgtagaaga ggaagtatat ccaaacaaca cggtaacgtg taatgattat   3120
actgcgactc aagaagaata tgagggtacg tacacttctc gtaatcgagg atatgacgga   3180
gcctatgaaa gcaattcttc tgtaccagct gattatgcat cagcctatga agaaaaagca   3240
tatacagatg gacgaagaga caatccttgt gaatctaaca gaggatatgg ggattacaca   3300
ccactaccag ctggctatgt gacaaaagaa ttagagtact cccagaaac cgataaggta   3360
tggattgaga tcggagaaac ggaaggaaca ttcatcgtgg acagcgtgga attacttctt   3420
atggaggaat ag                                                        3432
```

```
SEQ ID NO: 49          moltype = DNA   length = 3432
FEATURE                Location/Qualifiers
misc_feature           1..3432
                       note = Synthetic nucleotide sequence designed for
                        expression in a plant cell encoding TIC869.
source                 1..3432
                       mol_type = other DNA
                       organism = synthetic construct
SEQUENCE: 49
atggagataa acaaccagaa gcagtgcatt ccgtacaact gcctcagcaa cccgaggag    60
gtgctgctgg acggcgagcg tatcctccca gacatcgacat cactggaggt cagcctgagc   120
ctcctccagt tcctcctcaa taacttcgtg ccaggcggcg gcttcatctc cggcctggtg   180
gacaagatct ggggcgcact ccggccaagt gagtgggatc tgttcctggc ccaaatcgag   240
cgcctgatcg accagaggat cgaggcgacg gtccgcgcca aggcgataac cgagctggag   300
ggcctcggtc gcaactacca gatctacgca gaggcgttca aggagtggga gagcgacccg   360
gacaacgagg cggccaagtc tcgggtgatt gaccgcttcc gcatcctcga cggcctcatc   420
gaagccaaca tccttccttc ccggatcata ggcttcgaag tcccgctcct cagcgtgtac   480
gtgcaagcgg ccaatctcca cctcgcgttg ctccgtgaca gcgtcatctt tggcgagaga   540
tggggcctga cgacgaagaa cgtgaacgac atctacaaca ggcagatccg agagattcac   600
gagtacagca accactgcgt ggacacatac aacacggagc tggagcggct cggcttccgc   660
tcaatcgctc agtggcggat ctacaaccag ttccgccgcg agctgaccct caccgtgctc   720
gacatcgtcg cattgtttcc caattacgac tcacgcctct acccaatcca gactttcagc   780
cagctcacac gcgagattgt gaccagcccg gtgtcagagt tctactacgg cgtcatcaac   840
tcaggcaaca tcatcgggac actgactgaa cagcagatca gacgtccgca cttgatggac   900
ttcttcaact ccatgattat gtacacatca gacaacagga gagagcacta ctggtccggg   960
ttggagatga ctgcttactt caccggcttc gccggtgccc aagtgagctt cccactggtc   1020
ggaactcgtg gcgagtcagc tcctccgcta actgtgcgat ctgtcaacga cgggatctac   1080
agaatactgt cggctccctt ctacagtgcg ccgttcctcg gcaccatcgt cctcggctca   1140
cgtggtgaga agttcgactt cgcactgaac aacattagcc cgccgcctag tacaatctac   1200
aggcaccctg gcaccgtgga ctcactggtt tcgatcccgc cacaagacaa cagtgtgccg   1260
ccacatcgtg gttctagcca caggctctcc catgtgacca tgcgcgcctc ttcaccgatc   1320
tttcactgga cccatcggtc cgctacaacc acaaacacca tcaaacctaa cgccatcatc   1380
caaatcccgc tggtgaaggc gtttaacctc cacagcggcg caactgtcgt gcgcggccct   1440
ggattcaccg gtggtgacct gctccgtcgg accaatactg gcacgttcgc agacatccga   1500
gtgaacgtcc cgtcctcgct gttcagtcag cgctaccgtg tccgcattcg gtacgcttcc   1560
accacggatc tccagttctt tactcgcatc aatgggacga gcgtcaacca gggcaacttc   1620
agcaagacga tggaccgtgg agataagctc aagtccgaga acttccgcac ggctggcttc   1680
tcgacaccgt tcagattcag caacttccag agcactttca cgctgggcac acaggcgttc   1740
tccaaccagg aggtgtacat cgaccgcatc gagttcgtgc ctgctgaggt taccttcgag   1800
gcggaaagcg acctcgaaag ggcccagaag gccgtcaacg agctgttcac ctccagcaac   1860
cagatcggtc tcaagaccga cgtcactgac tatcacattg accaagtcag caacctggtg   1920
gagtgcctca gtgatgagtt ctgcctggat gagaagaagg agcttagcga gaaggtcaag   1980
cacgcaaagc gcttgagcga cgagcgcaac cttctccagg acccgaattt ccgtggtatc   2040
aatagacagc ttgaccgtgg gtggcgcggt agtaccgaca taaccatcca gggtggcgac   2100
gatgtgttca aggagaatta tgttacgctg ctcggtacgt tcgacgagtg ctatcccacg   2160
tacttgtacc agaagattga cgagagcaag ctcaaggcgt acaccgtta ccagctccgt   2220
ggctacatcg aggacagcca ggatctggaa atctacctta tccgtacaa tgctaagcac   2280
gagacagtca acgtgcccgg aacagggtcg ctctggccgc tcagtgctcc gtcgcccatt   2340
ggcaagtgcg cgcaccattc gcatcacttc tcacttgaca ttgacgtggg ctgcaccgac   2400
ctgaacgagg atctgggtgt ctgggtcatc ttcaagatca agacccaaga cggccacgcg   2460
cgcctcggga acctggagtt cctggaggag aagccttttgg taggtgaagc cctggcccgc   2520
gtcaagcgcg cggagaagaa gtggcgcgac aagagggaga agctgggatg ggagaccaac   2580
atcgtgtaca aggaggcgaa ggagtcggtg gacgcactat tcgtgaactc ccagtacgac   2640
cgtctccagg ccgacaccaa catcgccatg atccacgccg ctgacaaacg agttcattcc   2700
attcgtgaag cctatcttcc cgagctgtct gtcataccgg gcgtcaacgc ggccatcttc   2760
gaggagttag agggtcggat ctttacagct ttctcactgt acgatgcccg caacgtcatc   2820
aagaacggcg acttcaacaa cggtctctcc tgttggaacg tgaagggcca cgtggatgtc   2880
gaggagcaga acaaccaccg ctctgtgctt gtggtgcccg agtgggaggc cgaggtgagc   2940
caggagtcc gcgtctgtcc gggtcgcggg tacatcctgc ggctcacccgc ctacaaggag   3000
ggctacggcg aaggctgcgt tactattcac gagattgaga acaataccga cgaactcaag   3060
ttctccaact gtgtcgagga ggaggtgtac ccgaacaaca ccgtgacgtg caacgactac   3120
accgcgacac aggaggaata cgagggcacc tacaccagcc gcaaccgagg ctacgacgga   3180
gcgtacgaga gcaactcgtc cgtgcccgct gattacgcga gtgcgtacga ggagaaggct   3240
tacaccgacg acggcgcga caatccctgc gagagtaacc gtggatacgg agattacacg   3300
```

```
ccgctacccg ctggctacgt cactaaggaa ctggagtact tcccagagac ggacaaggtg   3360
tggatcgaaa tcggcgagac agagggcacg ttcatcgtgg actccgtgga gctgctgctg   3420
atggaggagt ga                                                       3432

SEQ ID NO: 50              moltype = AA   length = 1143
FEATURE                    Location/Qualifiers
REGION                     1..1143
                           note = Amino acid sequence of the chimeric protein TIC869.
source                     1..1143
                           mol_type = protein
                           organism = synthetic construct
SEQUENCE: 50
MEINNQKQCI PYNCLSNPEE VLLDGERILP DIDPLEVSLS LLQFLLNNFV PGGGFISGLV   60
DKIWGALRPS EWDLFLAQIE RLIDQRIEAT VRAKAITELE GLGRNYQIYA EAFKEWESDP   120
DNEAAKSRVI DRFRILDGLI EANIPSFRII GFEVPLLSVY VQAANLHLAL LRDSVIFGER   180
WGLTTKNVND IYNRQIREIH EYSNHCVDTY NTELERLGFR SIAQWRIYNQ FRRELTLTVL   240
DIVALFPNYD SRLYPIQTFS QLTREIVTSP VSEFYYGVIN SGNIIGTLTE QQIRRPHLMD   300
FFNSMIMYTS DNRREHYWSG LEMTAYFTGF AGAQVSFPLV GTRGESAPPL TVRSVNDGIY   360
RILSAPFYSA PFLGTIVLGS RGEKFDFALN NISPPPSTIY RHPGTVDSLV SIPPQDNSVP   420
PHRGSSHRLS HVTMRASSPI FHWTHRSATT TNTINPNAII QIPLVKAFNL HSGATVVRGP   480
GFTGGDLLRR TNTGTFADIR VNVPSSLFSQ RYRVRIRYAS TTDLQFFTRI NGTSVNQGNF   540
SKTMDRGDKL KSENFRTAGF STPFRFSNFQ STFTLGTQAF SNQEVYIDRI EFVPAEVTFE   600
AESDLERAQK AVNELFTSSN QIGLKTDVTD YHIDQVSNLV ECLSDEFCLD EKKELSEKVK   660
HAKRLSDERN LLQDPNFRGI NRQLDRGWRG STDITIQGGD DVFKENYVTL LGTFDECYPT   720
YLYQKIDESK LKAYTRYQLR GYIEDSQDLE IYLIRYNAKH ETVNVPGTGS LWPLSAPSPI   780
GKCAHHSHHF SLDIDVGCTD LNEDLGVWVI FKIKTQDGHA RLGNLEFLEE KPLVGEALAR   840
VKRAEKKWRD KREKLEWETN IVYKEAKESV DALFVNSQYD RLQADTNIAM IHAADKRVHS   900
IREAYLPELS VIPGVNAAIF EELEGRIFTA FSLYDARNVI KNGDFNNGLS CWNVKGHVDV   960
EEQNNHRSVL VVPEWEAEVS QEVRVCPGRG YILRVTAYKE GYGEGCVTIH EIENNTDELK   1020
FSNCVEEEVY PNNTVTCNDY TATQEEYEGT YTSRNRGYDG AYESNSSVPA DYASAYEEKA   1080
YTDGRRDNPC ESNRGYGDYT PLPAGYVTKE LEYFPETDKV WIEIGETEGT FIVDSVELLL   1140
MEE                                                                 1143

SEQ ID NO: 51              moltype = DNA   length = 3513
FEATURE                    Location/Qualifiers
misc_feature               1..3513
                           note = Recombinant nucleotide sequence used for expression
                           in a bacterial cell encoding TIC836.
source                     1..3513
                           mol_type = other DNA
                           organism = synthetic construct
SEQUENCE: 51
atggagaata atattcaaaa tcaatgcgta ccttacaatt gtttaaataa tcctgaagta   60
gaaatattaa atgaagaaag aagtactggc agattaccgt tagatatatc cttatcgctt   120
acacgtttcc ttttgagtga atttgttcca ggtgtgggag ttgcgtttgg attatttgat   180
ttaatatggg gttttataac tccttctgat tggagcttat ttcttttaca gattgaacaa   240
ttgattgagc aaagaataga aacattggaa aggaaccggg caattactac attacgaggg   300
ttagcagata gctatgaaat ttatattgaa gcactaagag agtgggaagc aaatcctaat   360
aatgcacaat taagggaaga tgtgcgtatt cgatttgcta atacagacga cgctttaata   420
acagcaataa ataattttac acttacaagt tttgaaatcc ctctttatc ggtctatgtt    480
caagcggcga atttacattt atcactatta agagacgctg tatcgtttgg gcagggtgg    540
ggactggata tagctactgt taataatcat tataatagat taataaatct tattcataga   600
tatacgaaac attgtttgga cacatacaat caaggattag aaaacttaag aggtactaat   660
actcgacaat gggcaagatt caatcagttt aggagagatt taacacttac tgtattagat   720
atcgttgctc tttttccgaa ctacgatgtt agaacatatc caattcaaac gtcatcccaa   780
ttaacaaggg aaaatttatac aagttcagta attgaggatt ctccagtttc tgctaatata   840
cctaatggtt ttaataggc ggaatttgga gttagaccgc cccatcttat ggactttatg    900
aattctttgt ttgtaactgc agagactgtt agaagtcaaa ctgtgtgggg aggacactta   960
gttagttcac gaaatacggc tggtaaccgt ataaatttcc ctagttacgg ggtcttcaat   1020
cctggtggcg ccatttggat tgcagatgag gatccacgtc cttttatcg gacattatca    1080
gatcctgttt ttgtccgagg aggatttggg aatcctcatt atgtactggg gcttagggga   1140
gtagcatttc aacaaactgg tacgaaccac acccgaacat ttagaaatag tgggaccata   1200
gattctctag atgaaatccc acctcaggat aatagtgggg caccttggaa tgattatagt   1260
catgtattaa atcatgttac agtttgtacg a tggccagtg agatttcagg aagtgattca   1320
tggagagctc caatgttttc ttggacgcac cgtagtgcaa ccctacaaa tacaattgat   1380
ccggagagga ttacacaaat acctttaaca aaatctacta atcttggctc tggaacttct   1440
gtcgttaaag accaggatt tacaggagga gatattcttc gaagaacttc acctggccag   1500
atttcaacct taagagtaaa tattactgca ccattatcag aaagatatcg ggtaagaatt   1560
cgctacgctt ctaccacaaa tttacaattc catacatcaa ttgacggaag acctattaat   1620
caggggaatt tttcagcaac tatgagtagt gggagtaatt tacagtccgg aagctttagg   1680
actgtaggtt ttactactcc gtttaacttt tcaaatggat caagtgtatt tacgttaagt   1740
gctcatgtct tcaattcagg caatgaagtt tatatagatc gaattgaatt tgttccggca   1800
gaagtaacct ttgaggcaga atatgattta gaaagagcgc agaaggcggt gaatgcgctg   1860
tttacgtcta caaaccaact agggctaaaa acaaatgtaa cggattatca tattgatcaa   1920
gtgtccaatt tagttacgta tttatcggat gaattttgtc tggatgaaaa gcgagaattg   1980
tccgagaaag tcaaacatgc gaagcgactc agtgatgaac gcaatttact ccaagattca   2040
aatttcaaag acattaatag gcaaccagaa cgtgggtggg gcggaagtac agggattacc   2100
atccaaggag gggatgacgt atttaagaa aattacgtca cactatcagg tacctttgat    2160
gagtgctatc caacatattt gtatcaaaaa atcgatgaat caaaattaaa agcctttacc   2220
```

```
cgttatcaat taagagggta tatcgaagat agtcaagact tagaaatcta tttaattcgc 2280
tacaatgcaa aacatgaaac agtaaatgtg ccaggtacgg gttccttatg gccgctttca 2340
gcccaaagtc caatcggaaa gtgtggagag ccgaatcgat gcgcgccaca ccttgaatgg 2400
aatcctgact tagattgttc gtgtagggat ggagaaaagt gtgcccatca ttcgcatcat 2460
ttctccttag acattgatgt aggatgtaca gacttaaatg aggacctagg tgtatgggtg 2520
atctttaaga ttaagacgca agatgggcac gcaagactag ggaatctaga gtttctcgaa 2580
gaaaaaccat tagtaggaga agcgctagct cgtgtgaaaa gagcggagaa aaaatggaga 2640
gacaaacgtg aaaaattgga atgggaaaca aatatcgttt ataaagaggc aaaagaatct 2700
gtagatgctt tatttgtaaa ctctcaatat gatcaattac aagcggatac gaatattgct 2760
atgattcatg cggcagataa acgtgttcat agcattcgag aagcttatct gcctgagctg 2820
tctgtgattc cgggtgtcaa tgcggctatt tttgaagaat tagaagggcg tattttcact 2880
gcattctccc tatatgatgc gagaaatgtc attaaaaatg gtgattttaa taatggctta 2940
tcctgctgga acgtgaaagg gcatgtagat gtagaagaac aaaacaacca acgttcggtc 3000
cttgttgttc cggaatggga agcagaagtg tcacaagaag ttcgtgtctg tccgggtcgt 3060
ggctatatcc ttcgtgtcac agcgtacaag gagggatatg gagaaggttg cgtaaccatt 3120
catgagatcg agaacaatac agacgaactg aagtttagca actgcgtaga ggaggaaatc 3180
tatccaaata acacggtaac gtgtaatgat tatactgtaa atcaagaaga atacggaggt 3240
gcgtacactt ctcgtaatcg aggatataac gaagctccat ccgtaccagc tgattatgcg 3300
tcagtctatg aagaaaaatc gtatacagat ggacgtagag agaatccttg tgaatttaac 3360
agagggtata gggattacac gccactacca gttggttatg tgacaaaaga attagaaatac 3420
ttcccagaaa ccgataaggt atggattgag attggagaaa cggaaggaac atttatcgtg 3480
gacagcgtgg aattactcct tatggaggaa taa 3513
```

```
SEQ ID NO: 52          moltype = DNA  length = 3513
FEATURE                Location/Qualifiers
misc_feature           1..3513
                       note = Synthetic nucleotide sequence designed for
                        expression in a plant cell encoding TIC836.
source                 1..3513
                       mol_type = other DNA
                       organism = synthetic construct
SEQUENCE: 52
```

```
atggagaaca acatccagaa ccagtgcgtg ccctacaact gcctgaacaa ccctgaggtt 60
gagatcctga acgaggagcg tagcaccggt aggctcccgc tagacatctc cctgagcctg 120
acccgcttcc tccttagtga gttcgtgccc ggcgtgggcg tggccttcgg cctcttcgac 180
ctcatctggg gcttcatcac tccttccgac tggtccctct tcctccttca gattgagcaa 240
ctgatcgagc agcgcatcga gacccttgag cgcaaccgcg ccatcaccac tctcagaggt 300
ctcgccgact cctacgaaat ctacatcgag gcactccgtg agtgggaggc caacccgaac 360
aatgcccagc tccgcgagga cgtgaggatc agattcgcca acaccgacga tgccctcatc 420
accgccatca caaatttcac cctcacctcc ttcgagatcc ctcttctgtc tgtgtacgtt 480
caagctgcta accttcacct ttccctcctg cgcgacgccg tgagcttcgg ccagggctgg 540
ggcctcgaca tcgccaccgt gaacaatcac tacaaccgcc tcatcaacct catccaccgc 600
tacaccaagc actgccttga cacctacaac cagggccttg agaacctccg tggcaccaac 660
acccgccagt gggcccgctt caaccagttc cgcagagacc tcaccctcac cgtgctcgac 720
atcgtggcac tcttcccaaa ctacgacgtg cgtacctacc ctatccagac ctccagccag 780
ctcaccaggg aaatctacac ctccagcgtg atcgaggact ctcctgtgtc cgccaacatc 840
cctaacggct tcaaccgcgc cgagttcggc gtgcgcctcat ctcacctcat ggacttcatg 900
aactccctct tcgtcactgc cgagaccgtg cgctcccaga ccgtgtgggg cggtcacctc 960
gtgtccagcc gtaacaccgc tggcaacagg atcaacttcc gtcctacgg cgtgttcaac 1020
ccaggcggtc ccatctggat cgccgatgaa gaccctcgtc ctttctaccg taccctgtcc 1080
gaccctgtgt tcgtgcgtgg cggtttcggc aaccctcact acgtgctggg cctgcgtgac 1140
gtggccttcc agcaaaccgg caccaaccac accaggacgt tccgtaactc cggcaccatc 1200
gacagtcttg acgagatccc tccgcaagac aactccggtg caccttggaa cgactactcc 1260
cacgtgctga accacgtgac cttcgtgagg tggcctggcg aaatctccgg ctccgactcc 1320
tggagggctc ctatgttcag ttggacccac aggagcgcta cgcctaccaa caccatcgac 1380
cctgagcgta tcactcagat ccctctgact aagagcacta acctgggcag cggcactagc 1440
gtggtcaagg gccctggctt cactggcggt gacatcctga ggcggactag ccctggccag 1500
atcagcactc tgagggtgaa catcactgct ccgctgagcc agcgttacag ggtcagaatc 1560
cgttacgctt ctactactaa ccttcagttc cacactagca tcgacggccg tccgatcaac 1620
cagggcaact tctctgctac tatgagttct ggcagtaacc tccagtctgg tagtttccgg 1680
actgtcggtt tcactacgcc gttcaacttc tccaacggta gttctgtctt cactctgtct 1740
gctcacgtgt tcaactctgg caacgaggtg tacatcgacc ggatcgagtt cgtccctgct 1800
gaggtgacgt tcgaggccga gtacgacctg agcgggctc agaaggctgt caacgctctg 1860
ttcacttcta ctaaccagct tggtttgaag actaacgtga ccagcaccac cattgatcaa 1920
gtcagtaacc tggtcacgta cctgtctgac gagttctgtc ttgacgagaa gcgggagctg 1980
tctgagaagg tcaagcacgc taagcggctg tctgacgagc ggaacctgct tcaagacagt 2040
aacttcaagg acattaaccg ccagcctgag cgtggtgggg gagggtccac gggtattacg 2100
attcaaggag gtgacgatgt ctttaaggag aactatgtga cgctttcggg tacgtttgat 2160
gagtgctatc caacgtacct ttaccagaag attgacgagt cgaagctgaa ggctttcact 2220
cgttaccagc ttcgtggtta cattgaggac tcgcaagacc tcgaaatcta cctcattcgt 2280
tacaacgcta agcacgagac tgtcaacgtc cctggtacgg gtagtctttg ccgctttct 2340
gctcagtcgc cgattggcaa gtgtggcgag ccgaaccgtt gcgctcctca cttggagtgg 2400
aacccggatc tcgattgctc gtgccgtgac ggtgagaagt gcgcgcacca tagtcatcac 2460
tttagccttg acattgatgt cggttgcacg gatcttaacg aggatctagg agtctgggtg 2520
attttcaaga tcaaaactca ggatgggcac gcgcgtcttg ggaatcttga gttcctggag 2580
gagaagccac ttgtcggtga ggcgcttgcg cgtgtcaagc gtgcggagaa gaaatggcgt 2640
gataagcgtg agaagttgga gtgggagacg aacatcgtgt acaaggaggc gaaggagtcg 2700
gtcgatgcgt tgtttgtcaa tagtcaatac gatcaattgc aagcggatac gaacatcgca 2760
atgattcatg cggcagataa gcgtgtccat tcgattcgtg aggcgtactt gccagagttg 2820
```

```
tcggtcatcc caggagttaa tgcggcaatc tttgaggaat tggagggcag aatcttcacg   2880
gcgttctcgt tgtacgatgc aagaaatgtt attaagaatg gagatttcaa caatgggttg   2940
tcatgctgga atgttaaggg tcacgttgat gttgaagaac agaacaacca gagatcagtg   3000
ttggttgtac cagagtggga ggcagaggtt tcacaagagg tgagagtttg cccaggcaga   3060
ggctacatct tgagagttac agcatacaaa gagggatacg gcgagggtat gttacaatc    3120
cacgaaatcg agaacaatac cgatgagcta aagttctcaa attgtgttga ggaggagatc   3180
tacccgaaca acacggttac ttgtaatgat tacacagtga accaggagga gtatggtggt   3240
gcatacacat caagaaatag aggctacaat gaagcaccat cagttccagc agattatgcc   3300
tcagtttatg aggagaagtc atacacagat ggacgacgtg agaatccatg tgagttcaat   3360
cgaggatacc gagattacac accactacca gttggatacg ttacaaagga actagaaatac  3420
ttcccagaaa cagataaagt atggatagag atcggagaaa cagaaggaac attcatcgtt   3480
gattcagtag aactactact tatggaagaa tga                                3513
```

```
SEQ ID NO: 53        moltype = AA   length = 1170
FEATURE              Location/Qualifiers
REGION               1..1170
                     note = Amino acid sequence of the chimeric protein TIC836.
source               1..1170
                     mol_type = protein
                     organism = synthetic construct
SEQUENCE: 53
MENNIQNQCV PYNCLNNPEV EILNEERSTG RLPLDISLSL TRFLLSEFVP GVGVAFGLFD   60
LIWGFITPSD WSLFLLQIEQ LIEQRIETLE RNRAITTLRG LADSYEIYIE ALREWEANPN   120
NAQLREDVRI RFANTDDALI TAINNFTLTS FEIPLLSVYV QAANLHLSLL RDAVSFGQGW   180
GLDIATVNNH YNRLINLIHR YTKHCLDTYN QGLENLRGTN TRQWARFNQF RRDLTLTVLD   240
IVALFPNYDV RTYPIQTSSQ LTREIYTSSV IEDSPVSANI PNGFNRAEFG VRPPHLMDFM   300
NSLFVTAETV RSQTVWGGHL VSSRNTAGNR INFPSYGVFN PGGAIWIADE DPRPFYRTLS   360
DPVFVRGGFG NPHYVLGLRG VAFQQTGTNH TRTFRNSGTI DSLDEIPPQD NSGAPWNDYS   420
HVLNHVTFVR WPGEISGSDS WRAPMFSWTH RSATPTNTID PERITQIPLT KSTNLGSGTS   480
VVKGPGFTGG DILRRTSPGQ ISTLRVNITA PLSQRYVRI RYASTTNLQF HTSIDGRPIN    540
QGNFSATMSS GSNLQSGSFR TVGFTTPFNF SNGSSVFTLS AHVFNSGNEV YIDRIEFVPA   600
EVTFEAEYDL ERAQKAVNAL FTSTNQLGLK TNVTDYHIDQ VSNLVTYLSD EFCLDEKREL   660
SEKVKHAKRL SDERNLLQDS NFKDINRQPE RGWGGSTGIT IQGGDDVFKE NYVTLSGTFD   720
ECYPTYLYQK IDESKLKAFT RYQLRGYIED SQDLEIYLIR YNAKHETVNV PGTGSLWPLS   780
AQSPIGKCGE PNRCAPHLEW NPDLDCSCRD GEKCAHHSHH FSLDIDVGCT DLNEDLGVWV   840
IFKIKTQDGH ARLGNLEFLE EKPLVGEALA RVKRAEKKWR DKREKLEWET NIVYKEAKES   900
VDALFVNSQY DQLQADTNIA MIHAADKRVH SIREAYLPEL SVIPGVNAAI FEELEGRIFT   960
AFSLYDARNV IKNGDFNNGL SCWNVKGHVD VEEQNNQRSV LVVPEWEAEV SQEVRVCPGR   1020
GYILRVTAYK EGYGEGCVTI HEIENNTDEL KFSNCVEEEI YPNNTVTCND YTVNQEEYGG   1080
AYTSRNRGYN EAPSVPADYA SVYEEKSYTD GRRENPCEFN RGYRDYTPLP VGYVTKELEY   1140
FPETDKVWIE IGETEGTFIV DSVELLLMEE                                     1170
```

```
SEQ ID NO: 54        moltype = DNA   length = 3588
FEATURE              Location/Qualifiers
misc_feature         1..3588
                     note = Chimeric coding sequence encoding TIC713
source               1..3588
                     mol_type = other DNA
                     organism = synthetic construct
SEQUENCE: 54
atggataaca atccgaacat caatgaatgc attccttata attgtgttaag taaccctgaa   60
gtagaagtat taggtggaga aagaatagaa actggttaca ccccaatcga tatttccttg   120
tcgctaacgc aatttctttt gagtgaattt gttcccggtg ctggatttgt gttaggacta    180
gttgatataa tatgggggaat ttttggtccc tctcaatggg acgcatttct tgtacaaatt   240
gaacagttaa ttaaccaaag aatagaagaa ttcgctaaga accaagccat ttctagatta   300
gaaggactaa gcaatcttta tcaaatttac gcagaatctt ttagagagtg ggaagcagat   360
cctactaatc cagcattaag agaagagatg cgtattcaat tcaatgacat gaacagtgcc   420
cttacaaccg ctattcctct tttggcagtt caaaattatc aagttcctct tttatcagta   480
tatgttcaag ctgcaaattt acatttatca gttttgagag atgtttcagt gtttggacaa   540
aggtgggggat ttgatgccgc gactatcaat agtcgttata atgatttaac taggcttatt   600
ggcaactata cagattatgc tgtacgctgg tacaatacgg gattagaacg tgtatgggga   660
ccggattcta gagattgggt aaggtataat caatttagaa gagaattaac actaactgta    720
ttagatatcg ttgctctgtt cccgaattat gatagtagaa gatatccaat tcgaacagtt   780
tcccaattaa caagagaaat ttatacaaac ccagtatcag aaattttga tggtagtttt   840
cgaggctcgg ctcagggcat agaaagaagt attaggagtc cacatttgat ggatatactt   900
aacagtataa ccatctatac ggatgctcat aggggttatt attattggtc agggcatcaa   960
ataatggctt ctcctgtcgg ttttttcgggg ccagaattca cgtttccgct atatggaacc   1020
atgggaaatg cagctccaca acaacgtatt gttgctcaac taggtcaggg cgtgtataga   1080
acattatcgt ccactttata tagaagacct tttaataag ggataaataa tcaacaacta    1140
tctgttcttg acgggacaga atttgcttat ggaacctcct caaatttgcc atccgctgta   1200
tacagaaaaa gcgggaacggt agattcgctg atgaaatac cgccacgaa taacaacgtg    1260
ccacctaggc aaggattttag tcatcgatta agccatgttt caatgtttcg ttcaggcttt   1320
agtaatagta gtgtaagtat aataagagct cctatgttct cttggataca tcgtagtgct   1380
gaatttaata atacagctgg accaaataga attacacaaa taccattggt aaaagcactg   1440
aatcttcatt caggtgttac tgttgttgga gggccaggat ttacaggtgg ggatatcctt   1500
cgtagaacaa atacgggtac atttggagat atacgattaa atattaatgt gccattatcc   1560
caaagatatc gcgtaaggat tcgttatgct tctactacag atttacaatt tttcacgaga   1620
attaatggaa ccactgttaa tattggtaat ttctcaagaa ctatgaatag gggggataat   1680
ttagaatata gaagtttttag aactgcagga tttagtactc cttttaattt tttaaatgcc   1740
```

-continued

```
caaagcacat tcacattggg tgctcagagt ttttcaaatc aggaagttta tatagataga   1800
gtcgaatttg ttccagcaga ggtaacattg gaggcagaat atgatttaga aagagcacaa   1860
aaggcggtga atgctctgtt tacttctaca aatccaagaa gattgaaaac agatgtgaca   1920
gattatcata ttgaccaagt gtccaatatg gtggcatgtt tatcagatga attttgcttg   1980
gatgagaagc gagaattatt tgagaaagtg aaatatgcga agcgactcag tgatgaaaga   2040
aacttactcc aagatccaaa cttcacattc atcagtgggc aattaagttt cgcatccatc   2100
gatggacaat caaacttccc ctctattaat gagctatctg aacatggatg gtggggaagt   2160
gcgaatgtta ccattcagga agggaatgac gtatttaaag agaattacgt cacactaccg   2220
ggtacttta atgagtgtta tccaaattat ttatatcaaa aaataggaga gtcagaatta   2280
aaagcttata cgcgctcatca attaagaggg tatattgaag atagtcaaga tctagagatt   2340
tatttaattc gttacaatgc aaagcatgaa acattggatg ttccaggtac cgattcccta   2400
tggccgcttt cagttgaaag cccaatcgga aggtgcggag aaccaaatcg atgcgcacca   2460
cattttgaat ggaatcctga tctagattgt tcctgcagag atggagaaag atgtgcgcat   2520
cattcccatc atttcacttt ggatattgat gttgggtgca cagacttgca tgagaaccta   2580
ggcgtgtggg tggtattcaa gattaagacg caggaaggtt atgcaagatt aggaaatctg   2640
gaatttatcg aagagaaacc attaattgga gaagcactgt ctcgtgtgaa gagagcggaa   2700
aaaaaatgga gagacaaacg ggaaaaacta caattggaaa caaaacgagt atatacagag   2760
gcaaaagaag ctgtggatgc tttattcgta gattctcaat atgatcaatt acaagcggat   2820
acaaacattg gcatgattca tgcggcagat aaacttgttc atcgaattcg agaggcgtat   2880
ctttcagaat tacctgttat cccaggtgta aatgcggaaa tttttgaaga attagaaggt   2940
cacattatca ctgcaatgtc cttatacgat gcgagaaatg tcgttaaaaa tggtgatttt   3000
aataatggat taacatgttg gaatgtaaaa gggcatgtag atgtacaaca gagccatcat   3060
cgttctgacc ttgttatccc agaatgggaa gcagaagtgt cacaagcagt tcgcgtctgt   3120
ccggggcgtg gctatatcct tcgtgtcaca gcgtacaaag agggatatgg agagggctgc   3180
gtaacgatcc atgaaatcga gaacaataca gacgaactaa aatttaaaaa ctgtgaagaa   3240
gaggaagtgt atccaacgga tacaggaacg tgtaatgatt atactgcaca ccaaggtaca   3300
gcagcatgta attcccgtaa tgctggatat gaggatgcat atgaagttga tactacagca   3360
tctgttaatt acaaaccgac ttatgaagaa gaaacgtata cagatgtacg aagagataat   3420
cattgtgaat atgacagagg gtatgtgaat tatccaccag taccagctgg ttatgtgaca   3480
aaagaattag aatacttccc agaaacagat acagtatgga ttgagattgg agaaacggaa   3540
ggaaagttta ttgtagatag cgtggaacta ctcctcatgg aagaatag          3588
```

```
SEQ ID NO: 55          moltype = AA  length = 1195
FEATURE                Location/Qualifiers
REGION                 1..1195
                       note = Amino acid sequence of the chimeric protein TIC713.
source                 1..1195
                       mol_type = protein
                       organism = synthetic construct
SEQUENCE: 55
MDNNPNINEC IPYNCLSNPE VEVLGGERIE TGYTPIDISL SLTQFLLSEF VPGAGFVLGL   60
VDIIWGIFGP SQWDAFLVQI EQLINQRIEE FARNQAISRL EGLSNLYQIY AESFREWEAD   120
PTNPALREEM RIQFNDMNSA LTTAIPLLAV QNYQVPLLSV YVQAANLHLS VLRDVSVFGQ   180
RWGFDAATIN SRYNDLTRLI GNYTDYAVRW YNTGLERVWG PDSRDWVRYN QFRRELTLTV   240
LDIVALFPNY DSRRYPIRTV SQLTREIYTN PVLENFDGSF RGSAQGIERS IRSPHLMDIL   300
NSITIYTDAH RGYYWSGHQ IMASPVGFSG PEFTFPLYGT MGNAAPQQRI VAQLGQGVYR   360
TLSSTLYRRP FNIGINNQQL SVLDGTEFAY GTSSNLPSAV YRKSGTVDSL DEIPPQNNNV   420
PPRQGFSHRL SHVSMFRSGF SNSSVSIIRA PMFSWIHRSA EFNNTIGPNR ITQIPLVKAL   480
NLHSGVTVVG GPGFTGGDIL RRTNTGTFGD IRLNINVPLS QRYRVRIRYA STTDLQFFTR   540
INGTTVNIGN FSRTMNRGDN LEYRSFRTAG FSTPFNFLNA QSTFTLGAQS FSNQEVYIDR   600
VEFVPAEVTF EAEYDLERAQ KAVNALFTST NPRRLKTDVT DYHIDQVSNM VACLSDEFCL   660
DEKRELFEKV KYAKRLSDER NLLQDPNFTF ISGQLSFASI DGQSNFPSIN ELSEHGWWGS   720
ANVTIQEGND VFKENYVTLP GTFNECYPNY LYQKIGESEL KAYTRYQLRG YIEDSQDLEI   780
YLIRYNAKHE TLDVPGTDSL WPLSVESPIG RCGEPNRCAP HFEWNPDLDC SCRDGERCAH   840
HSHHFTLDID VGCTDLHENL GVWVVFKIKT QEGYARLGNL EFIEEKPLIG EALSRVKRAE   900
KKWRDKREKL QLETKRVYTE AKEAVDALFV DSQYDQLQAD TNIGMIHAAD KLVHRIREAY   960
LSELPVIPGV NAEIFEELEG HIITAMSLYD ARNVVKNGDF NNGLTCWNVK GHVDVQQSHH   1020
RSDLVIPEWE AEVSQAVRVC PGRGYILRVT AYKEGYGEGC VTIHEIENNT DELKFKNCEE   1080
EEVYPTDTGT CNDYTAHQGT AACNSRNAGY EDAYEVDTTA SVNYKPTYEE ETYTDVRRDN   1140
HCEYDRGYVN YPPVPAGYVT KELEYFPETD TVWIEIGETE GKFIVDSVEL LLMEE        1195
```

```
SEQ ID NO: 56          moltype = DNA  length = 3531
FEATURE                Location/Qualifiers
misc_feature           1..3531
                       note = Chimeric coding sequence encoding TIC843.
source                 1..3531
                       mol_type = other DNA
                       organism = synthetic construct
SEQUENCE: 56
atggataaca atccgaacat caatgaatgc attccttata attgtttaag taaccctgaa   60
gtagaagtat taggtggaga aagaatagaa actggttaca ccccaatcga tatttccttg   120
tcgctaacgc aatttctttt gagtgaattt gttcccggtg ctggatttgt gttaggacta   180
gttgatataa tatgggggaat ttttggtccc tctcaatggg acgcatttct tgtacaaatt   240
gaacagttga ttaaccaaag aatagaagaa ttcgctaaga accaagccat ttctagatta   300
gaaggactaa gcaatcttta tcaaatttac gcagaatctt ttagagagtg ggaagcagat   360
cctactaatc cagcattaag agaagagatg cgtattcaat tcaatgacat gaacagtgcc   420
cttacaaccg ctattcctct ttttggcagtt caaaattatc aagttcctct tttatcagta   480
tatgttcaag ctgcaaattt acatttatca gttttgagag atgtttcagt gtttggacaa   540
aggtggggat ttgatgccgc gactatcaat agtcgttata atgatttaac taggcttatt   600
```

```
ggcaactata cagattatgc tgtacgctgg tacaatacgg gattagaacg tgtatgggga   660
ccggattcta gagattgggt aaggtataat caatttagaa gagaattaac actaactgta   720
ttagatatcg ttgctctgtt cccgaattat gatagtagaa gatatccaat tcgaacagtt   780
tcccaattaa caagagaaat ttatacaaac ccagtattag aaaattttga tggtagtttt   840
cgaggctcgg ctcagggcat agaaagaagt attaggagtc cacatttgat ggatatactt   900
aacagtataa ccatctatac ggatgctcat aggggttatt attattggtc agggcatcaa   960
ataatggctt ctcctgtcgg ttttttcgggg ccagaattca cgtttccgct atatggaacc  1020
atgggaaatg cagctccaca acaacgtatt gttgctcaac taggtcaggg cgtgtataga  1080
acattatcgt ccactttata tagaagacct tttaatatag ggataaataa tcaacaacta  1140
tctgttcttg acgggacaga atttgcttat ggaacctcct caaatttgcc atccgctgta  1200
tacagaaaaa gcgggaacggt agattcgctg gatgaaatac cgccacagaa taacaacgtg  1260
ccacctaggc aaggatttag tcatcgatta agccatgttt caatgtttcg ttcaggcttt  1320
agtaatagta gtgtaagtat aataagagct cctatgttct cttggataca tcgtagtgct  1380
gaatttaata atacgattgg accaaataga attacacaaa taccattggt aaaagcactg  1440
aatcttcatt caggtgttac tgttgttgga gggccaggat ttacaggtgg ggatatcctt  1500
cgtagaacaa atacgggtac atttggagat atacgattaa atattaatgt gccattatcc  1560
caaagatatc gcgtaaggat tcgttatgct tctactacag atttacaatt tttcacgaga  1620
attaatggaa ccactgttaa tattggtaat ttctcaacga ctatgaatag ggggataat   1680
ttagaatata gaagttttag aactgcagga tttagtactc cttttaattt tttaaatgcc   1740
caaagcacat tcacattggg tgctcagagt ttttcaaatc aggaagttta tatagataga  1800
gtcgaatttg ttccagcaga ggtaacattt gaggcagaat atgatttaga aagagcgcag  1860
aaggcggtga atgcgctgtt tacgtctaca aaccaactag gtctaaaaac aaatgtaacg  1920
gattatcata ttgatcaagt gtccaattta gttacgtatt tatcggatga attttgtctg  1980
gatgaaaagc gagaattgtc cgagaaagtc aaacatgcga agcgactcag tgatgaacgc  2040
aatttactcc aagattcaaa tttcaaagac attaataggc aaccagaacg tgggtggggc  2100
ggaagtacag ggattaccat ccaaggaggg gatgacgtat ttaaagaaaa ttacgtcaca  2160
ctatcaggta cctttgatga gtgctatcca acatatttgt atcaaaaaat cgatgaatca  2220
aaattaaaag cctttacccg ttatcaatta agagggtata tcgaagatag tcaagactta  2280
gaaatctatt taattcgcta caatgcaaaa catgaaacag taaatgtgcc aggtacgggt  2340
tccttatggc cgctttcagc ccaaagtcca atcggaaagt gcggagagc gaatcgatgc   2400
gcgccacacc ttgaatggaa tcctgactta gattgttcgt gtaggggatgg agaaaagtgt  2460
gcccatcatt cgcatcattt ctccttagac attgatgtag gatgtacaga cttaaatgag  2520
gacctaggtg tatgggtgat ctttaagatt aagacgcaag atgggcacgc aagactaggg  2580
aatctagagt ttctcgaaga gaaaccatta gtaggagaag cgctagctcg tgtgaaaaga  2640
gcggagaaaa aatggagaga caaacgtgaa aaattggaat gggaaacaaa tatcgtttat  2700
aaagaggcaa aagaatctgt agatgcttta tttgtaaact ctcaatatga tcaattacaa  2760
gcggatacga atattgccat gattcatgcg gcagataaac gtgttcatag cattcgagaa  2820
gcttatctgc ctgagctgtc tgtgattccg ggtgtcaatg cggctatttt tgaagaatta  2880
gaagggcgta ttttcactgc attctcccta tatgatgcga gaaatgtcat taaaaatggt  2940
gattttaata atggcttatc ctgctggaac gtgaaaggc atgtagatgt agaagaacaa   3000
aacaaccaac gttcggtcct tgttgttccg aatgggaag cagaagtgtc acaagaagtt   3060
cgtgtctgtc cgggtcgtgg ctatatcctt cgtgtccacg cgtacaagga gggatatgga  3120
gaaggttgcg taaccattca tgagatcgag aacaatacag acgaactgaa gtttagcaac  3180
tgcgtagaag aggaaatcta tccaaataac acggtaacgc gtaatgatta tactgtaaat  3240
caagaagaat acgagggtgc gtacacttct cgtaatcgag gatataacga agctccttcc  3300
gtaccagctg attatgcgtc agtctatgaa gaaaaatcgt atacagatgg acgaagagag  3360
aatccttgtg aatttaacag agggtatagg gattacacgc cactaccagt tggttatgtg  3420
acaaaagaat tagaatactt cccagaaacc gataaggtat ggattgatgag tggagaaacg  3480
gaaggaacat ttatcgtgga cagcgtggaa ttactcctta tggaggaata g            3531
```

SEQ ID NO: 57          moltype = AA  length = 1176
FEATURE                Location/Qualifiers
REGION                 1..1176
                       note = Amino acid sequence of the chimeric protein TIC843.
source                 1..1176
                       mol_type = protein
                       organism = synthetic construct SEQUENCE: 57
```
MDNNPNINEC IPYNCLSNPE VEVLGGERIE TGYTPIDISL SLTQFLLSEF VPGAGFVLGL   60
VDIIWGIFGP SQWDAFLVQI EQLINQRIEE FARNQAISRL EGLSNLYQIY AESFREWEAD  120
PTNPALREEM RIQFNDMNSA LTTAIPLLAV QNYQVPLLSV YVQAANLHLS VLRDVSVFGQ  180
RWGFDAATIN SRYNDLTRLI GNYTDYAVRW YNTGLERVWG PDSRDWVRYN QFRRELTLTV  240
LDIVALFPNY DSRRYPIRTV SQLTREIYTN PVLENFDGSF RGSAQGIERS IRSPHLMDIL  300
NSITIYTDAH RGYYYWSGHQ IMASPVGFSG PEFTFPLYGT MGNAAPQQRI VAQLGQGVYR  360
TLSSTLYRRP FNIGINNQQL SVLDGTEFAY GTSSNLPSAV YRKSGTVDSL DEIPPQNNNV  420
PPRQGFSHRL SHVSMFRSGF SNSSVSIIRA PMFSWIHRSA EFNNTIGPNR ITQIPLVKAL  480
NLHSGVTVVG GPGFTGGDIL RRTNTGTFGD IRLNINVPLS QRYVRIRYA STTDLQFFTR   540
INGTTVNIGN FSRTMNRGDN LEYRSFRTAG FSTPFNFLNA QSTFTLGAQS FSNQEVYIDR  600
VEFVPAEVTF EAEYDLERAQ KAVNALFTST NQLGLKTNVT DYHIDQVSNL VTYLSDEFCL  660
DEKRELSEKV KHAKRLSDER NLLQDSNFKD INRQPERGWG GSTGITIQGG DDVFKENYVT  720
LSGTFDECYP TYLYQKIDES KLKAFTRYQL RGYIEDSQDL EIYLIRYNAK HETVNVPGTG  780
SLWPLSAQSP IGKCGEPNRC APHLEWNPDL DCSCRDGEKC AHHSHHFSLD IDVGCTDLNE  840
DLGVWVIFKI KTQDGHARLG NLEFLEEKPL VGEALARVKR AEKKWRDKRE KLEWETNIVY  900
KEAKESVDAL FVNSQYDQLQ ADTNIAMIHA ADKRVHSIRE AYLPELSVIP GVNAAIFEEL  960
EGRIFTAFSL YDARNVIKNG DFNNGLSCWN VKGHVDVEEQ NNQRSVLVVP EWEAEVSQEV 1020
RVCPGRGYIL RVTAYKEGYG EGCVTIHEIE NNTDELKFSN CVEEIYPNN TVTCNDYTVN  1080
QEEYGGAYTS RNRGYNEAPS VPADYASVYE EKSYTDGRRE NPCEFNRGYR DYTPLPVGYV 1140
TKELEYFPET DKVWIEIGET EGTFIVDSVE LLLMEE                            1176
```

```
SEQ ID NO: 58          moltype = DNA   length = 3501
FEATURE                Location/Qualifiers
misc_feature           1..3501
                       note = Chimeric coding sequence encoding TIC862.
source                 1..3501
                       mol_type = other DNA
                       organism = synthetic construct SEQUENCE: 58
atggataaca atccgaacat caatgaatgc attccttata attgtttaag taaccctgaa   60
gtagaagtat taggtggaga aagaatagaa actggttaca ccccaatcga tatttccttg  120
tcgctaacgc aatttctttt gagtgaattt gttcccggtg ctggatttgt gttaggacta  180
gttgatataa tatgggggaat tttttggtccc tctcaatggg acgcatttct tgtacaaatt  240
gaacagttaa ttaaccaaag aatagaagaa ttcgctagga accaagccat ttctagatta  300
gaaggactaa gcaatcttta tcaaatttac gcagaatctt ttagagagtg ggaagcagat  360
cctactaatc cagcattaag agaagagatg cgtattcaat tcaatgacat gaacagtgcc  420
cttacaaccg ctattcctct tttggcagtt caaaattatc aagttcctct tttatcagta  480
tatgttcaag ctgcaaattt acatttatca gtttttgagag atgtttcagt gtttggacaa  540
aggtggggat ttgatgccgc gactatcaat agtcgttata atgatttaac taggcttatt  600
ggcaactata cagattatgc tgtacgctgg tacaatacgg gattagaacg tgtatgggga  660
ccggattcta gagattgggt aaggtataat caatttagaa gagaattaac actaactgta  720
ttagatatcg ttgctctgtt cccgaattat gatagtagaa gatatccaat tcgaacagtt  780
tcccaattaa caagagaaat ttatacaaac ccagtattag aaaattttga tggtagtttt  840
cgaggctcgg ctcagggcat agaaagaagt attaggagtc cacatttgat ggatatatta  900
aacagtataa ccatctatac ggatgctcat aggggttatt attattggtc agggcatcaa  960
ataatggctt ctcctgtcgg ttttttcgggg ccagaattca cgtttccgct atatggaacc 1020
atgggaaatg cagctccaca acaacgtatt gttgctcaac taggtcaggg cgtgtataga 1080
acattatcgt ccactttata tagaagacct tttaatatag ggataaataa tcaacaacta 1140
tctgttcttg acgggacaga atttgcttat ggaacctcct caaatttgcc atccgctgta 1200
tacagaaaaa gcggaacggt agattcgctg gatgaaatac cgccacagaa taacaacgtg 1260
ccacctaggc aaggatttag tcatcgatta agccatgttt caatgtttcg ttcaggcttt 1320
agtaatagta gtgtaagtat aataagagct cctatgttct cttggataca tcgtagtgct 1380
gaatttaata atataaattgc atcggatagt attactcaaa tccctgcagt gaagggaaac 1440
tttctttta atggttctgt aatttcagga ccaggattta ctggtgggga cttagttaga 1500
tgtacgaatg gatctggatt aactttatat gttacaccgg caccggactt gacgtattct 1560
aaaacatata aaattcgaat tcgttatgct tctacatctc aggtgagatt tggaattgac 1620
ttaggcagtt acactcatag tatttcgtat ttcgataaaa cgatggataa aggaaataca 1680
ttaacgtata attcatttaa tttatcaagt gtcagcagac caattgaaat atcaggaggg 1740
aataaaatcg gggtatccgt cggaggtatt ggctctgggg atgaagttta tatagacaaa 1800
atcgaattta ttccaatgaa aagagcgcag aaggcggtga atgcgctgtt tacgtctaca 1860
aaccaactag ggctaaaaac aaatgtaacg gattatcata ttgatcaagt gtccaattta 1920
gttacgtatt tatcggatga attttgtctg gatgaaaagc gagaattgtc cgagaaagtc 1980
aaacatgcga agcgactcag tgatgaacgc aatttactcc aagattcaaa tttcaaagac 2040
attaataggc aaccagaacg tgggtggggc ggaagtacag ggattaccat ccaaggaggg 2100
gatgacgtat ttaaagaaaa ttacgtcaca ctatcaggta cctttgatga gtgctatcca 2160
acatatttgt atcaaaaaat cgatgaatca aaattaaaag cctttacccg ttatcaatta 2220
agagggtata tcgaagatag tcaagactta gaaatctatt taattcgcta caatgcaaaa 2280
catgaaacag taaatgtgcc aggtacgggt tccttatggc cgctttcagc ccaaagtcca 2340
atcggaaagt gtggagagcc gaatcgatgc gcgccacacc ttgaatggaa tcctgactta 2400
gattgttcgt gtaggatgg agaaaagtgt gcccatcatt cgcatcattt ctccttagac 2460
attgatgtag gatgtacaga cttaaatgag gacctaggtg tatgggtgat ctttaagatt 2520
aagacgcaag atgggcacgc aagactaggg aatctagagt ttctcgaaga aaaaccatta 2580
gtaggagaag cgctagctcg tgtgaaaaga gcggagaaaa aatggagaga caaacgtgaa 2640
aaattggaat gggaaacaaa tatcgtttat aaagaggcaa aagaatctgt agatgcttta 2700
tttgtaaaact ctcaatatga tcaattacaa gcggatacga atattgccat gattcatgcg 2760
gcagtaaaac gtgttcatag cattcgagaa gcttatctgc ctgagctgtc tgtgattccg 2820
ggtgtcaatg cggctatttt tgaagaatta gaagggcgta ttttcactgc attctcccta 2880
tatgatgcga gaaatgtcat taaaaatggt gattttaata atggcttatc ctgctggaac 2940
gtgaaagggc atgtagatgt agaagaacaa aacaaccaac gttcggtcct tgttgttccg 3000
gaatgggaag cagaagtgtc acaagaagtt cgtgtctgtc cgggtcgtgg ctatatcctt 3060
cgtgtcacag cgtacaagga gggatatgga gaaggttgcg taaccattca tgagatcgag 3120
aacaatacag acgaactgaa gtttagcaac tgcgtagagg aggaaatcta tccaaataac 3180
acggtaacgt gtaatgatta tactgtaaat caagaagaat acggaggtgc gtacacttct 3240
cgtaatcgag gatataacga agctccttcc gtaccagctg attatgcgtc agtctatgaa 3300
gaaaaatcgt atacagatgg acgtagagag aatccttgtg aatccttaac ag agggtatagg 3360
gattacacgc cactaccagt tggttatgtg acaaaagaat tagaatactt cccagaaacc 3420
gataaggtat ggattgagat tggagaaacg gaaggaacat ttatcgtgga cagcgtggaa 3480
ttactccta tggaggaata a                                             3501
```

```
SEQ ID NO: 59          moltype = AA   length = 1166
FEATURE                Location/Qualifiers
REGION                 1..1166
                       note = Amino acid sequence of the chimeric protein TIC862.
source                 1..1166
                       mol_type = protein
                       organism = synthetic construct SEQUENCE: 59
MDNNPNINEC IPYNCLSNPE VEVLGGERIE TGYTPIDISL SLTQFLLSEF VPGAGFVLGL   60
VDIIWGIFGP SQWDAFLVQI EQLINQRIEE FARNQAISRL EGLSNLYQIY AESFREWEAD  120
PTNPALREEM RIQFNDMNSA LTTAIPLLAV QNYQVPLLSV YVQAANLHLS VLRDVSVFGQ  180
```

```
RWGFDAATIN SRYNDLTRLI GNYTDYAVRW YNTGLERVWG PDSRDWVRYN QFRRELTLTV   240
LDIVALFPNY DSRRYPIRTV SQLTREIYTN PVLENFDGSF RGSAQGIERS IRSPHLMDIL   300
NSITIYTDAH RGYYYWSGHQ IMASPVGFSG PEFTFPLYGT MGNAAPQQRI VAQLGQGVYR   360
TLSSTLYRRP FNIGINNQQL SVLDGTEFAY GTSSNLPSAV YRKSGTVDSL DEIPPQNNNV   420
PPRQGFSHRL SHVSMFRSGF SNSSVSIIRA PMFSWIHRSA EFNNIIASDS ITQIPAVKGN   480
FLFNGSVISG PGFTGGDLVR CTNGSGLTLY VTPAPDLTYS KTYKIRIRYA STSQVRFGID   540
LGSYTHSISY FDKTMDKGNT LTYNSFNLSS VSRPIEISGG NKIGVSVGGI GSGDEVYIDK   600
IEFIPMERAQ KAVNALFTST NQLGLKTNVT DYHIDQVSNL VTYLSDEFCL DEKRELSEKV   660
KHAKRLSDER NLLQDSNFKD INRQPERGWG GSTGITIQGG DDVFKENYVT LSGTFDECYP   720
TYLYQKIDES KLKAFTRYQL RGYIEDSQDL EIYLIRYNAK HETVNVPGTG SLWPLSAQSP   780
IGKCGEPNRC APHLEWNPDL DCSCRDGEKC AHHSHHFSLD IDVGCTDLNE DLGVWVIFKI   840
KTQDGHARLG NLEFLEEKPL VGEALARVKR AEKKWRDKRE KLEWETNIVY KEAKESVDAL   900
FVNSQYDQLQ ADTNIAMIHA ADKRVHSIRE AYLPELSVIP GVNAAIFEEL EGRIFTAFSL   960
YDARNVIKNG DFNNGLSCWN VKGHVDVEEQ NNQRSVLVVP EWEAEVSQEV RVCPGRGYIL  1020
RVTAYKEGYG EGCVTIHEIE NNTDELKFSN CVEEEIYPNN TVTCNDYTVN QEEYGGAYTS  1080
RNRGYNEAPS VPADYASVYE EKSYTDGRRE NPCEFNRGYR DYTPLPVGYV TKELEYFPET  1140
DKVWIEIGET EGTFIVDSVE LLLMEE                                        1166

SEQ ID NO: 60              moltype = DNA   length = 3549
FEATURE                    Location/Qualifiers
misc_feature               1..3549
                           note = Chimeric coding sequence encoding TIC1099.
source                     1..3549
                           mol_type = other DNA
                           organism = synthetic construct
SEQUENCE: 60
atggataaca atccgaacat caatgaatgc attccttata attgtttaag taaccctgaa   60
gtagaagtat taggtggaga aagaatagaa actggttaca ccccaatcga tatttccttg  120
tcgctaacgc aatttctttt gagtgaattt gttcccggtg ctggatttgt gttaggacta  180
gttgatataa tatgggggaat ttttggtccc tctcaatggg acgcatttct tgtacaaatt  240
gaacagttaa ttaaccaaag aatagaagaa ttcgctagga accaagccat ttctagatta  300
gaaggactaa gcaatcttta tcaaatttac gcagaatctt ttagagagtg ggaagcagat  360
cctactaatc cagcattaag agaagagatg cgtattcaat tcaatgacat gaacagtgcc  420
cttacaaccg ctattcctct tttggcagtt caaaattatc aagttcctct tttatcagta  480
tatgttcaag ctgcaaattt acatttatca gttttgagag agtttcagt gtttggacaa  540
aggtggggat ttgatgccgc gactatcaat agtcgttata atgatttaac taggcttatt  600
ggcaactata cagattatgc tgtacgctgg tacaatacgg gattagaacg tgtatgggga  660
ccggattcta gagattgggt aaggtataat caatttagaa gagaattaac actaactgta  720
ttagatatcg ttgctctgtt cccgaattat gatagtagaa gatatccaat tcgaacagtt  780
tcccaattaa caagagaaat ttatacaaac ccagtattag aaaattttga tggtagtttt  840
cgaggctcgg ctcagggcat agaaagaagt attaggagtc cacatttgat ggatatactt  900
aacagtataa ccatctatac ggatgctcat aggggtatt attattggtc agggcatcaa  960
ataatggctt ctcctgtcgg tttttcgggg ccagaattca cgtttccgct atatggaacc 1020
atgggaaatg cagctccaca acaacgtatt gttgctcaac taggtcaggg cgtgtataga 1080
acattatcgt ccactttata tagaagacct tttaatatag ggataaataa tcaacaacta 1140
tctgttcttg acgggacaga atttgcttat ggaacctcct caaatttgcc atccgctgta 1200
tacagaaaaa gcggaacggt agattcgctg gatgaaatac cgccacagaa taacaacgtg 1260
ccacctaggc aaggatttag tcatcgatta agccatgttt caatgtttcg ttcaggcttt 1320
agtaatagta gtgtaagtat aataagagct cctatgttct cttggataca tcgtagtgct 1380
gaatttaata atataattgc atcggatagt attacacaat accattggt aaaggcatct 1440
gcacctgttt cgggtactac ggtcttaaaa ggtccaggat ttacaggagg gggtatactc 1500
cgaagaacaa ctaatggcac atttggaacg ttaagagtaa cagttaattc accattaaca 1560
caaagatatc gcgtaagagt tcgtttttgct tcatcaggaa atttcagcat aaggatactg 1620
cgtgaaaata cctctatagc ttatcaaaga tttgggagta caatgaacag aggacaggaa 1680
ctaacttacg aatcatttgt cacaagtgag ttcactacta atcagagcga tctgccttt 1740
acatttacac aagctcaaga aaatttaaca atccttgcag aaggtgttag caccggtagt 1800
gaatatttta tagatagaat tgaaatcatc cctgtgaacc cggcacgaga agcagaagag 1860
gatttagaaa gagcgcagaa ggcggtgaat gcgctgttta cgtctacaaa ccaactaggg 1920
ctaaaaacaa atgtaacgga ttatcatatt gatcaagtgt ccaatttagt tacgtatttta 1980
tcggatgaat tttgtctgga tgaaaagcga gaattgtccg agaaagtcaa acatgcgaag 2040
cgactcagtg atgaacgcaa tttactccaa gattcaaatt tcaaagacat taataggcaa 2100
ccagaacgtg ggtggggcgg aagtacaggg attaccatcc aaggagggga tgacgtattt 2160
aaagaaaatt acgtcacact atcaggtacc tttgatgagt gctatccaac atatttgtat 2220
caaaaaatcg atgaatcaaa attaaaagcc tttacccgtt atcaattaag agggtatatc 2280
gaagatagtc aagacttaga aatctattta attcgctaca atgcaaaaca tgaaacagta 2340
aatgtgccag gtacgggttc cttatggccg ctttcagccc aaagtccaat cggaaagtgt 2400
ggagagccga atcgatgcgc gccacacctt gaatggaatc ctgacttaga ttgttcgtgt 2460
agggatggag aaaagtgtgc ccatcattcg catcatttct ccttagacat tgatgtagga 2520
tgtacagact aaatgagga cctaggtgta tgggtgatct ttaagattaa gacgcaagat 2580
gggcacgcaa gactagggaa tctagagttt ctcgaagaaa aaccattagt aggagaagcg 2640
ctagctcgtg tgaaaagagc ggagaaaaaa tggagagaca aacgtgaaaa attggaatgg 2700
gaaacaaata tcgtttataa agaggcaaaa gaatctgtag atgctttatt tgtaaactct 2760
caatatgatc aattacaagc ggatacgaat attgccatga ttcatgcggc agataaacgt 2820
gttcataac ttcgagagc ttatctgcct gagctgtctg ttattccggg tgtcaatgcg 2880
gctattttg aagaattaga agggcgtatt ttcactgcat tctccctata tgatgcgaga 2940
aatgtcatta aaaatggtga tttaataat ggcttatcct gctggaacgt gaaagggcat 3000
gtagatgtag aagaacaaaa caaccaacgt tcggtccttg ttgttccgga atgggaagca 3060
gaagtgtcac aagaagttcg tgtctgtccg ggtcgtggct atatccttcg tgtcacagcg 3120
tacaaggagg gatatggaga aggttgcgta accattcatg agatcgagaa caatacagac 3180
```

-continued

```
gaactgaagt ttagcaactg cgtagaggag gaaatctatc caaataacac ggtaacgtgt   3240
aatgattata ctgtaaatca agaagaatac ggaggtgcgt acacttctcg taatcgagga   3300
tataacgaag ctccttccgt accagctgat tatgcgtcag tctatgaaga aaaatcgtat   3360
acagatggac gtagagagaa tccttgtgaa tttaacagag ggtatagtga ttacacgcca   3420
ctaccagttg gttatgtgac aaaagaatta gaatacttcc cagaaaccga taaggtatgg   3480
attgagattg gagaaacgga aggaacattt atcgtggaca gcgtggaatt actccttatg   3540
gaggaataa                                                          3549

SEQ ID NO: 61          moltype = AA  length = 1182
FEATURE                Location/Qualifiers
REGION                 1..1182
                       note = Amino acid sequence of the chimeric protein TIC1099.
source                 1..1182
                       mol_type = protein
                       organism = synthetic construct
SEQUENCE: 61
MDNNPNINEC IPYNCLSNPE VEVLGGERIE TGYTPIDISL SLTQFLLSEF VPGAGFVLGL   60
VDIIWGIFGP SQWDAFLVQI EQLINQRIEE FARNQAISRL EGLSNLYQIY AESFREWEAD  120
PTNPALREEM RIQFNDMNSA LTTAIPLLAV QNYQVPLLSV YVQAANLHLS VLRDVSVFGQ  180
RWGFDAATIN SRYNDLTRLI GNYTDYAVRW YNTGLERVWG PDSRDWVRYN QFRRELTLTV  240
LDIVALFPNY DSRRYPIRTV SQLTREIYTN PVLENFDGSF RGSAQGIERS IRSPHLMDIL  300
NSITIYTDAH RGYYYWSGHQ IMASPVGFSG PEFTFPLYGT MGNAAPQQRI VAQLGQGVYR  360
TLSSTLYRRP FNIGINNQQL SVLDGTEFAY GTSSNLPSAV YRKSGTVDSL DEIPPQNNNV  420
PPRQGFSHRL SHVSMFRSGF SNSSVSIIRA PMFSWIHRSA EFNNIIASDS ITQLPLVKAS  480
APVSGTTVLK GPGFTGGGIL RRTTNGTFGT LRVTVNSPLT QRYRVRVRFA SSGNFSIRIL  540
RGNTSIAYQR FGSTMNRGQE LTYESFVTSE FTTNQSDLPF TFTQAQENLT ILAEGVSTGS  600
EYFIDRIEII PVNPAREAEE DLERAQKAVN ALFTSTNQLG LKTNVTDYHI DQVSNLVTYL  660
SDEFCLDEKR ELSEKVKHAK RLSDERNLLQ DSNFKDINRQ PERGWGGSTG ITIQGGDDVF  720
KENYVTLSGT FDECYPTYLY QKIDESKLKA FTRYQLRGYI EDSQDLEIYL IRYNAKHETV  780
NVPGTGSLWP LSAQSPIGKC GEPNRCAPHL EWNPDLDCSC RDGEKCAHHS HHFSLDIDVG  840
CTDLNEDLGV WVIFKIKTQD GHARLGNLEF LEEKPLVGEA LARVKRAEKK WRDKREKLEW  900
ETNIVYKEAK ESVDALFVNS QYDQLQADTN IAMIHAADKR VHSIREAYLP ELSVIPGVNA  960
AIFEELEGRI FTAFSLYDAR NVIKNGDFNN GLSCWNVKGH VDVEEQNNQR SVLVVPEWEA 1020
EVSQEVRVCP GRGYILRVTA YKEGYGEGCV TIHEIENNTD ELKFSNCVEE EIYPNNTVTC 1080
NDYTVNQEEY GGAYTSRNRG YNEAPSVPAD YASVYEEKSY TDGRRENPCE FNRGYRDYTP 1140
LPVGYVTKEL EYFPETDKVW IEIGETEGTF IVDSVELLLM EE                    1182

SEQ ID NO: 62          moltype = DNA  length = 3549
FEATURE                Location/Qualifiers
misc_feature           1..3549
                       note = Chimeric coding sequence encoding TIC1099 T507E.
source                 1..3549
                       mol_type = other DNA
                       organism = synthetic construct
SEQUENCE: 62
atggataaca atccgaacat caatgaatgc attccttata attgtttaag taaccctgaa   60
gtagaagtat taggtggaga agaaatagaa actggttaca ccccaatcga tatttccttg  120
tcgctaacgc aatttctttt gagtgaattt gttcccggtg ctggatttgt gttaggacta  180
gttgatataa tatggggaat ttttggtccc tctcaatggg acgcatttct tgtacaaatt  240
gaacagttaa ttaaccaaag aatagaagaa ttcgctagga accaagccat ttctagatta  300
gaaggactaa gcaatcttta tcaaatttac gcagaatctt ttagagagtg ggaagcagat  360
cctactaatc cagcattaag agaagagatg cgtattcaat tcaatgacat gaacagtgcc  420
cttacaaccg ctattcctct tttggcagtt caaaattatc aagttcctct tttatcagta  480
tatgttcaag ctgcaaattt acatttatca gttttgagag atgtttcagt gtttggacaa  540
aggtgggggat ttgatgccgc gactatcaat agtcgttata atgatttaac taggcttatt  600
ggcaactata cagattatgc tgtacgctgg tacaatacgg gattagaacg tgtatgggga  660
ccggattcta gagattgggt aaggtataat caatttagaa gagaattaac actaactgta  720
ttagatatcg ttgctctgtt cccgaattat gatagtagaa gatatccaat tcgaacagtt  780
tcccaattaa caagagaaat ttatacaaac ccagtattac aaaattttga tggtagtttt  840
cgaggctcgg ctcagggcat agaaagaagt attaggagtc cacatttgat ggatatactt  900
aacagtataa ccatctatac ggatgctcat aggggttatt attattggtc agggcatcaa  960
ataatggctt ctcctgtcgg ttttttcgggg ccagaattca cgtttccgct atatggaacc 1020
atgggaaatg cagctccaca acaacgtatt gttgctcaac taggtcaggg cgtgtataga 1080
acattatcgt ccactttata tagaagacct tttaatatag ggataaataa tcaacaacta 1140
tctgttcttg acgggacaga atttgcttat ggaacctcct caaatttgcc atccgctgta 1200
tacagaaaaa gcggaacggt agattcgctg gatgaaatac cgccacgaa taacaacgtg 1260
ccacctaggc aaggatttag tcatcgatta agccatgttt caatgtttcg ttcaggcttt 1320
agtaatagta gtgtaagtat aataagagct cctatgttct cttggatcca tcgtagtgca 1380
gaatttaata atataattgc atcggatagt attacacaat taccattggt aaaggcatct 1440
gcacctgttt cgggtactac ggtcttaaaa ggtccaggat ttacaggagg gggtatactc 1500
cgaagaacaa ctaatggcga atttggaacg ttaagagtaa cagttaattc accattaaca 1560
caaagatatc gcgtaagagt tcgttttgct tcatcaggaa atttcagcat aaggatactg 1620
cgtggaaata cctctatagc ttatcaaaga tttgggagta caatgaacag aggacaggaa 1680
ctaacttacg aatcatttgt cacaagtgag ttcactacta atcagagcga tctgcctttt 1740
acatttacac aagctcaaga aaatttaaca atccttgcag aaggtgttag caccggtagt 1800
gaatatttta tagatagaat tgaaatcatc cctgtgaacc cggcacgaga agcagaagag 1860
gatttagaaa gagcgcagaa ggcggtgaat gcgctgtttta cgtctacaaa ccaactaggg 1920
ctaaaaacaa atgtaacgga ttatcatatt gatcaagtgt ccaatttagt tacgtattta 1980
tcggatgaat tttgtctgga tgaaaagcga gaattgtccg agaaagtcaa acatgcgaag 2040
```

-continued

```
cgactcagtg atgaacgcaa tttactccaa gattcaaatt tcaaagacat taataggcaa   2100
ccagaacgtg ggtggggcgg aagtacaggg attaccatcc aaggagggga tgacgtattt   2160
aaagaaaatt acgtcacact atcaggtacc tttgatgagt gctatccaac atatttgtat   2220
caaaaaatcg atgaatcaaa attaaaagcc tttacccgtt atcaattaag agggtatatc   2280
gaagatagtc aagacttaga aatctattta attcgtacaa atgcaaaaca tgaaacagta   2340
aatgtgccag gtacgggttc cttatggccg ctttcagccc aaagtccaat cggaaagtgt   2400
ggagagccga atcgatgcgc gccacacctt gaatggaatc ctgacttaga ttgttcgtgt   2460
agggatggag aaaagtgtgc ccatcattcg catcatttct ccttagacat tgatgtagga   2520
tgtacagact aaatgagga cctaggtgta tgggtgaact ttaagattaa gacgcaagat   2580
gggcacgcaa gactagggaa tctagagttt ctcgaagaaa aaccattagt aggagaagcg   2640
ctagctcgtg tgaaaagagc ggagaaaaaa tggagagaca aacgtgaaaa attggaatgg   2700
gaaacaaata tcgtttataa agaggcaaaa gaatctgtag atgctttatt tgtaaactct   2760
caatatgatc aattacaagc ggatacgaat attgccatga ttcatgcggc agataaacgt   2820
gttcatagca ttcgagaagc ttatctgcct gagctgtctg tgattccggg tgtcaatgcg   2880
gctatttttg aagaattaga agggcgtatt ttcactgcat tctccctata tgatgcgaga   2940
aatgtcatta aaaatggtga ttttaataat ggcttatcct gctggaacgt gaaagggcat   3000
gtagatgtag aagaacaaaa caaccaacgt tcggtccttg ttgttccgga atgggaagca   3060
gaagtgtcac aagaagttcg tgtctgtccg ggtcgtggct atatccttcg tgtcacagcg   3120
tacaaggagg gatatggaga aggttgcgta accattcatg agatcgagaa caatacagac   3180
gaactgaagt ttagcaactg cgtagaggag gaaatctatc caaataacac ggtaacgtgt   3240
aatgattata ctgtaaatca agaagaatac ggaggtgcgt acacttctcg taatcgagga   3300
tataacgaag ctccttccgt accagctgat tatgcgtcag tctatgaaga aaaatcgtat   3360
acagatggac gtagagagaa tccttgtgaa tttaacagag ggtatagggga ttacacgcca   3420
ctaccagttg gttatgtgac aaaagaatta gaatacttcc cagaaccgaa taaggtatgg   3480
attgagattg gagaaacgga aggaacattc atcgtggaca gcgtggaatt actccttatg   3540
gaggaataa                                                          3549
```

```
SEQ ID NO: 63           moltype = AA   length = 1182
FEATURE                 Location/Qualifiers
REGION                  1..1182
                        note = Amino acid sequence of the chimeric protein TIC1099
                         T507E.
source                  1..1182
                        mol_type = protein
                        organism = synthetic construct
SEQUENCE: 63
MDNNPNINEC IPYNCLSNPE VEVLGGERIE TGYTPIDISL SLTQFLLSEF VPGAGFVLGL    60
VDIIWGIFGP SQWDAFLVQI EQLINQRIEE FARNQAISRL EGLSNLYQIY AESFREWEAD   120
PTNPALREEM RIQFNDMNSA LTTAIPLLAV QNYQVPLLSV YVQAANLHLS VLRDVSVFGQ   180
RWGFDAATIN SRYNDLTRLI GNYTDYAVRW YNTGLERVWG PDSRDWVRYN QFRRELTLTV   240
LDIVALFPNY DSRRYPIRTV SQLTREIYTN PVLENFDGSF RGSAQGIERS IRSPHLMDIL   300
NSITIYTDAH RGYYWSGHQ IMASPVGFSG PEFTFPLYGT MGNAAPQQRI VAQLGQGVYR   360
TLSSTLYRRP FNIGINNQQL SVLDGTEFAY GTSSNLPSAV YRKSGTVDSL DEIPPQNNNV   420
PPRQGFSHRL SHVSMRSGF SNSSVSIIRA PMFSWIHRSA EFNNIIASDS ITQLPLVKAS   480
APVSGTTVLK GPGFTGGGIL RRTTNGEFGT LRVTVNSPLT QRYRVRVRFA SSGNFSIRIL   540
RGNTSIAYQR FGSTMNRGQE LTYESFVTSE FTTNQSDLPF TFTQAENLT ILAEGVSTGS   600
EYFIDRIEII PVNPAREAEE DLERAQKAVN ALFTSTNQLG LKTNVTDYHI DQVSNLVTYL   660
SDEFCLDEKR ELSEKVKHAK RLSDERNLLQ DSNFKDINRQ PERGWGGSTG ITIQGGDDVF   720
KENYVTLSGT FDECYPTYLY QKIDESKLKA FTRYQLRGYI EDSQDLEIYL IRYNAKHETV   780
NVPGTGSLWP LSAQSPIGKC GEPNRCAPHL EWNPDLDCSC RDGEKCAHHS HHFSLDIDVG   840
CTDLNEDLGV WVIFKIKTQD GHARLGNLEF LEEKPLVGEA LARVKRAEKK WRDKREKLEW   900
ETNIVYKEAK ESVDALFVNS QYDQLQADTN IAMIHAADKR VHSIREAYLP ELSVIPGVNA   960
AIFEELEGRI FTAFSLYDAR NVIKNGDFNN GLSCWNVKGH VDVEEQNNQR SVLVVPEWEA  1020
EVSQEVRVCP GRGYILRVTA YKEGYGEGCV TIHEIENNTD ELKFSNCVEE EIYPNNTVTC  1080
NDYTVNQEEY GGAYTSRNRG YNEAPSVPAD YASVYEEKSY TDGRRENPCE FNRGYRDYTP  1140
LPVGYVTKEL EYFPETDKVW IEIGETEGTF IVDSVELLLM EE                     1182
```

```
SEQ ID NO: 64           moltype = DNA   length = 3549
FEATURE                 Location/Qualifiers
misc_feature            1..3549
                        note = Chimeric coding sequence encoding TIC1099 R522K.
source                  1..3549
                        mol_type = other DNA
                        organism = synthetic construct
SEQUENCE: 64
atggataaca atccgaacat caatgaatgc attccttata attgtttaag taaccctgaa    60
gtagaagtat taggtggaga agaaatagaa actggttaca ccccaatcga tatttccttg   120
tcgctaacgc aatttctttt gagtgaattt gttcccggtg ctggatttgt gttaggacta   180
gttgatataa tatggggaat ttttggtccc tctcaatggg acgcatttct tgtacaaatt   240
gaacagttaa ttaaccaaag aatagaagaa ttcgctagga accaagccat ttctagatta   300
gaaggactaa gcaatcttta tcaaatttac gcagaatctt ttagagagtg ggaagcagat   360
cctactaatc cagcattaag agaagagatg cgtattcaat tcaatgacat gaacagtgcc   420
cttacaaccg ctattcctct tttggcagtt caaaattatc aagttcctct tttatcagta   480
tatgttcaag ctgcaaattt acatttatca gttttgagag atgtttcagt gtttggacaa   540
aggtggggat ttgatgccgc gactatcaat agtcgttata atgatttaac taggcttatt   600
ggcaactata cagattatgc tgtacgctgg tacaatacgg gattagaacg tgtatgggga   660
ccggattcta gagattgggt aaggtataat caatttagaa gagaattaac actaactgta   720
ttagatatcg ttgctctgtt cccgaattat gatagtagaa gatatccaat tcgaacagtt   780
tcccaattaa caagagaaat ttatacaaac ccagtattag aaaattttga tggtagtttt   840
```

-continued

```
cgaggctcgg ctcagggcat agaaagaagt attaggagtc cacatttgat ggatatactt  900
aacagtataa ccatctatac ggatgctcat aggggttatt attattggtc agggcatcaa  960
ataatggctt ctcctgtcgg tttttcgggg ccagaattca cgtttccgct atatggaacc  1020
atgggaaatg cagctccaca acaacgtatt gttgctcaac taggtcaggg cgtgtataga  1080
acattatcgt ccactttata tagaagacct tttaatatag ggataaataa tcaacaacta  1140
tctgttcttg acgggacaga atttgcttat ggaacctcct caaatttgcc atccgctgta  1200
tacagaaaaa gcggaacggt agattcgctg gatgaaatac cgccacagaa taacaacgtg  1260
ccacctaggc aaggatttag tcatcgatta agccatgttt caatgtttcg ttcaggcttt  1320
agtaatagta gtgtaagtat aataagagct cctatgttct cttggataca tcgtagtagt  1380
gaatttaata atataattgc atcggatagt attacacaat taccattggt aaaggcatct  1440
gcacctgttt cgggtactac ggtcttaaaa ggtccaggat ttacaggagg gggtatactc  1500
cgaagaacaa ctaatggcac atttggaacg ttaagagtaa cagttaattc accattaaca  1560
caaaaatatc gcgtaagagt tcgttttgct tcatcaggaa atttcagcat aaggatactg  1620
cgtggaaata cctctatagc ttatcaaaga tttgggagta caatgaacag aggacaggaa  1680
ctaacttacg aatcatttgt cacaagtgag ttcactacta atcagagcga tctgcctttt  1740
acatttacac aagctcaaga aaatttaaca atccttgcag aaggtgttag caccggtagt  1800
gaatatttta tagatagaat tgaaatcatc cctgtgaacc cggcacgaga agcagaagag  1860
gatttagaaa gagcgcagaa ggcggtgaat gcgctgttta cgtctacaaa ccaactaggg  1920
ctaaaaacaa atgtaacgga ttatcatatt gatcaagtgt ccaatttagt tacgtatttta  1980
tcggatgaat tttgtctgga tgaaaagcga gaattgtccg agaaagtcaa acatgcgaag  2040
cgactcagtg atgaacgcaa tttactccaa gattcaaatt tcaaagacat taataggcaa  2100
ccagaacgtg ggtggggcgg aagtacaggg attaccatcc aaggagggga tgacgtattt  2160
aaagaaaatt acgtcacact atcaggtacc tttgatgagt gctatccaac atatttgtat  2220
caaaaaatcg atgaatcaaa attaaaagcc tttacccgtt atcaattaag agggtatatc  2280
gaagatagtc aagacttaga aatctatttta attcgctaca atgcaaaaca tgaaacagta  2340
aatgtgccag gtacgggttc cttatggccg ctttcagccc aaagtccaat cggaaagtgt  2400
ggagagccga atcgatgcgc gccacacctt gaatggaatc ctgacttaga ttgttcgtgt  2460
agggatggag aaaagtgtgc ccatcattcg catcatttct ccttagacat tgatgtagga  2520
tgtacagact taaatgagga cctaggtgta tgggtgatct ttaagattaa gacgcaagat  2580
gggcacgcaa gactagggaa tctagagttt ctcgaagaaa aaccattagt aggagaagcg  2640
ctagctcgtg tgaaaagagc ggagaaaaaa tggagagaca aacgtgaaaa attggaatgg  2700
gaaacaaata tcgtttataa agaggcaaaa gaatctgtag atgctttatt tgtaaactct  2760
caatatgatc aattacaagc ggatacgaat attgccatga ttcatgcggc agataaacgt  2820
gttcatagca ttcgagaagc ttatctgcct gagctgtctg tgattccggg tgtcaatgca  2880
gctatttttg aagaattaga agggcgtatt ttcactgcat tctcccctata tgatgcgaga  2940
aatgtcatta aaaatggtga ttttaataat ggcttatcct gctggaacgt gaaagggcat  3000
gtagatgtag aagaacaaaa caaccaacgt tcggtccttg ttgttccgga atgggaagca  3060
gaagtgtcac aagaagttcg tgtctgtccg ggtcgtggct atatccttcg tgtcacacgc  3120
tacaaggagg gatatggaga aggttgcgta accattcatg agatcgagaa caatacagac  3180
gaactgaagt ttagcaactg cgtagaggag gaaatctatc caaataacac ggtaacgtgt  3240
aatgattata ctgtaaatca agaagaatac ggaggtgcgt acacttctcg taatcgagga  3300
tataacgaag ctccttccgt accagctgat tatgcgtcag tctatgaaga aaaatcgtat  3360
acagatggac gtagagagaa tccttgtgaa tttaacagag ggtatagga ttacacgcca  3420
ctaccagttg gttatgtgac aaaagaatta gaatacttcc cagaaaccga taaggtatgg  3480
attgagattg gagaaacgga aggaacattt atcgtggaca gcgtggaatt actccttatg  3540
gaggaataa                                                            3549
```

```
SEQ ID NO: 65            moltype = AA  length = 1182
FEATURE                  Location/Qualifiers
REGION                   1..1182
                         note = Amino acid sequence of the chimeric protein TIC1099
                          R522K.
source                   1..1182
                         mol_type = protein
                         organism = synthetic construct
SEQUENCE: 65
MDNNPNINEC IPYNCLSNPE VEVLGGERIE TGYTPIDISL SLTQFLLSEF VPGAGFVLGL  60
VDIIWGIFGP SQWDAFLVQI EQLINQRIEE FARNQAISRL EGLSNLYQIY AESFREWEAD  120
PTNPALREEM RIQFNDMNSA LTTAIPLLAV QNYQVPLLSV YVQAANLHLS VLRDVSVFGQ  180
RWGFDAATIN SRYNDLTRLI GNYTDYAVRW YNTGLERVWG PDSRDWVRYN QFRRELTLTV  240
LDIVALFPNY DSRRYPIRTV SQLTREIYTN PVLENFDGSF RGSAQGIERS IRSPHLMDIL  300
NSITIYTDAH RGYYWSGHQ IMASPVGFSG PEFTFPLYGT MGNAAPQQRI VAQLGQGVYR  360
TLSSTLYRRP FNIGINNQQL SVLDGTEFAY GTSSNLPSAV YRKSGTVDSL DEIPPQNNNV  420
PPRQGFSHRL SHVSMFRSGF SNSSVSIIRA PMFSWIHRSA EFNNIIASDS ITQLPLVKAS  480
APVSGTTVLK GPGFTGGGIL RRTTNGTFGT LRVTVNSPLT QKYRVRVRFA SSGNFSIRIL  540
RGNTSIAYQR FGSTMNRGQE LTYESFVTSE FTTNQSDLPF TFTQAQENLT ILAEGVSTGS  600
EYFIDRIEII PVNPAREAEE DLERAQKAVN ALFTSTNQLG LKTNVTDYHI DQVSNLVTYL  660
SDEFCLDEKR ELSEKVKHAK RLSDERNLLQ DSNFKDINRQ PERGWGGSTG ITIQGGDDVF  720
KENYVTLSGT FDECPYTLYL QKIDESKLKA FTRYQLRGYI EDSQDLEIYL IRYNAKHETV  780
NVPGTGSLWP LSAQSPIGKC GEPNRCAPHL EWNPDLDCSC RDGEKCAHHS HHFSLDIDVG  840
CTDLNEDLGV WVIFKIKTQD GHARLGNLEF LEEKPLVGEA LARVKRAEKK WRDKREKLEW  900
ETNIVYKEAK ESVDALFVNS QYDQLQADTN IAMIHAADKR VHSIREAYLP ELSVIPGVNA  960
AIFEELEGRI FTAFSLYDAR NVIKNGDFNN GLSCWNVKGH VDVEEQNNQR SVLVVPEWEA  1020
EVSQEVRVCP GRGYILRVTA YKEGYGEGCV TIHEIENNTD ELKFSNCVEE EIYPNNTVTC  1080
NDYTVNQEEY GGAYTSRNRG YNEAPSVPAD YASVYEEKSY TDGRRENPCE FNRGYRDYTP  1140
LPVGYVTKEL EYFPETDKVW IEIGETEGTF IVDSVELLLM EE                      1182
```

```
SEQ ID NO: 66            moltype = DNA  length = 3549
FEATURE                  Location/Qualifiers
```

-continued

```
misc_feature       1..3549
                   note = Chimeric coding sequence encoding TIC1099 K490S.
source             1..3549
                   mol_type = other DNA
                   organism = synthetic construct
SEQUENCE: 66
atggataaca atccgaacat caatgaatgc attccttata attgtttaag taaccctgaa    60
gtagaagtat taggtggaga aagaatagaa actggttaca ccccaatcga tatttccttg   120
tcgctaacgc aatttctttt gagtgaattt gttcccggtg ctggatttgt gttaggacta   180
gttgatataa tatgggggaat ttttggtccc tctcaatggg acgcatttct tgtacaaatt   240
gaacagttaa ttaaccaaag aatagaagaa ttcgctagga accaagccat ttctagatta   300
gaaggactaa gcaatcttta tcaaatttac gcagaatctt ttagagagtg ggaagcagat   360
cctactaatc cagcattaag agaagagatg cgtattcaat tcaatgacat gaacagtgcc   420
cttacaaccg ctattcctct tttggcagtt caaaattatc aagttcctct tttatcagta   480
tatgttcaag ctgcaaattt acatttatca gttttgagag atgtttcagt gtttggacaa   540
aggtgggggat ttgatgccgc gactatcaat agtcgttata atgatttaac taggcttatt   600
ggcaactata cagattatgc tgtacgctgg tacaatacgg gattagaacg tgtatgggga   660
ccggattcta gagattgggt aaggtataat caatttagaa gagaattaac actaactgta   720
ttagatatcg ttgctctgtt cccgaattat gatagtagaa gatatccaat tcgaacagtt   780
tcccaattaa caagagaaat ttatacaaac ccagtattag aaaatttga tggtagtttt   840
cgaggctcgg ctcagggcat agaaagaagt attaggagtc cacatttgat ggatatactt   900
aacagtataa ccatctatac ggatgctcat aggggttatt attattggtc agggcatcaa   960
ataatggctt ctcctgtcgg tttttcggg ccagaattca cgtttccgct atatggaacc   1020
atgggaaatg cagctccaca acaacgtatt gttgctcaac taggtcaggg cgtgtataga   1080
acattatcgt ccactttata tagaagacct tttaatatag ggataaataa tcaacaacta   1140
tctgttcttg acgggacaga atttgcttat ggaacctcct caaatttgcc atccgctgta   1200
tacagaaaaa gcggaacggt agattcgctg gatgaaatac cgccacagaa taacaacgtg   1260
ccacctaggc aaggatttag tcatcgatta agccatgttt caatgtttcg ttcaggcttt   1320
agtaatagta gtgtaagtat aataagagct cctatgttct cttggataca tcgtagtgct   1380
gaatttaata atataattgc atcggatagt attacacaat taccattgt aaaggcatct   1440
gcacctgttt cgggtactac ggtcttatca ggtccaggat ttacaggagg gggtatactc   1500
cgaagaacaa ctaatggcac atttggaacg ttaagagtaa cagttaattc accattaaca   1560
caaagatatc gcgtaagagt tcgttttgct tcatcaggaa atttcagcat aaggatactg   1620
cgtggaaata cctctatagc ttatcaaaga tttgggagta caatgaacag aggacaggaa   1680
ctaacttacg aatcatttgt cacaagtgag ttcactacta atcagagcga tctgcctttt   1740
acatttacac aagctcaaga aaatttaaca atccttgcag aaggtgttag caccggtagt   1800
gaatatttta tagatagaat tgaaatcatc cctgtgaacc cggcacgaga agcagaaagg   1860
gatttagaaa gagcgcagaa ggcggtgaat gcgctgttta cgtctacaaa ccaactaggg   1920
ctaaaaacaa atgtaacgga ttatcatatt gatcaagtgt ccaatttagt tacgtattta   1980
tcggatgaat tttgtctgga tgaaaagcga gaattgtccg agaaagtcaa acatgcgaag   2040
cgactcagtg atgaacgcaa tttactccaa gattcaaatt tcaaagacat taataggcaa   2100
ccagaacgtg ggtggggcgg aagtacaggg attaccatcc aaggagggga tgacgtattt   2160
aaagaaaatt acgtcacact atcaggtacc tttgatgagt gctatccaac atatttgtat   2220
caaaaaatcg atgaatcaaa attaaaagcc tttacccgtt atcaattaag agggtatatc   2280
gaagatagtc aagacttaga aatctattta attcgctaca atgcaaaaca tgaaacagta   2340
aatgtgccag gtacgggttc cttatggccg cttttcagcc caaagtccaat cggaaagtgt   2400
ggagagccga atcgatcgcg cgccacacctt gaatggaatc ctgacttaga ttgttcgtgt   2460
agggatggag aaaagtgtgc ccatcattcg catcatttct ccttagacat tgatgtagga   2520
tgtacagact aaaatgagga cctaggtgta tgggtgatct ttaagattaa gacgcaagat   2580
gggcacgcaa gactagggaa tctagagttt ctcgaagaaa aaccattagt aggagaagcg   2640
ctagctcgtg tgaaaagagc ggagaaaaaa tggagagaca aacgtgaaaa attggaatgt   2700
gaaacaaata tcgtttataa agaggcaaaa gaatctgtag atgctttatt tgtaaactct   2760
caatatgatc aattacaagc ggatacgaat attgccatga ttcatcgcgc agataaacgt   2820
gttcatagca ttcgagaagc ttatctgcct gagctgtctg tgattccggg tgtcaatgcg   2880
gctattttg aagaattaga agggcgtatt ttcactgcat tctccctata tgatgcgaga   2940
aatgtcatta aaaatggtga ttttaataat ggcttatcct gctggaacgt gaaagggcat   3000
gtagatgtag aagaacaaaa caaccaacgt tcggtccttg ttgttccgga atgggaagca   3060
gaagtgtcac aagaagttcg tgtctgtccg ggtcgtggct atatccttcg tgtcacagcg   3120
tacaaggagg gatatgagaa aggttgcgta accattcatg agatcgagaa caatacagac   3180
gaactgaagt ttagcaactg cgtagaggag gaaatctatc caaataacac ggtaacgtgt   3240
aatgattata ctgtaaatca agaagaatac ggaggtgcgt acacttctcg taatcgagga   3300
tataacgaag ctccttccgt accagctgat tatgcgtcag tctatgaaga aaaatcgtat   3360
acagatggac gtagagagaa tccttgtgaa tttaacagag ggtataggga ttacacgcca   3420
ctaccagttg gttatgtgac aaaagaatta gaatacttcc cagaaaccga taaggtatgg   3480
attgagattg gagaaacgga aggaacattt atcgtggaca gcgtggaatt actccttatg   3540
gaggaataa                                                           3549

SEQ ID NO: 67        moltype = AA   length = 1182
FEATURE              Location/Qualifiers
REGION               1..1182
                     note = Amino acid sequence of the chimeric protein TIC1099
                     K490S.
source               1..1182
                     mol_type = protein
                     organism = synthetic construct
SEQUENCE: 67
MDNNPNINEC IPYNCLSNPE VEVLGGERIE TGYTPIDISL SLTQFLLSEF VPGAGFVLGL   60
VDIIWGIFGP SQWDAFLVQI EQLINQRIEE FARNQAISRL EGLSNLYQIY AESFREWEAD   120
PTNPALREEM RIQFNDMNSA LTTAIPLLAV QNYQVPLLSV YVQAANLHLS VLRDVSVFGQ   180
```

-continued

```
RWGFDAATIN SRYNDLTRLI GNYTDYAVRW YNTGLERVWG PDSRDWVRYN QFRRELTLTV  240
LDIVALFPNY DSRRYPIRTV SQLTREIYTN PVLENFDGSF RGSAQGIERS IRSPHLMDIL  300
NSITIYTDAH RGYYYWSGHQ IMASPVGFSG PEFTFPLYGT MGNAAPQQRI VAQLGQGVYR  360
TLSSTLYRRP FNIGINNQQL SVLDGTEFAY GTSSNLPSAV YRKSGTVDSL DEIPPQNNNV  420
PPRQGFSHRL SHVSMFRSGF SNSSVSIIRA PMFSWIHRSA EFNNIIASDS ITQLPLVKAS  480
APVSGTTVLS GPGFTGGGIL RRTTNGTFGT LRVTVNSPLT QRYRVRVRFA SSGNFSIRIL  540
RGNTSIAYQR FGSTMNRGQE LTYESFVTSE FTTNQSDLPF TFTQAQENLT ILAEGVSTGS  600
EYFIDRIEII PVNPAREAEE DLERAQKAVN ALFTSTNQLG LKTNVTDYHI DQVSNLVTYL  660
SDEFCLDEKR ELSEKVKHAK RLSDERNLLQ DSNFKDINRQ PERGWGGSTG ITIQGGDDVF  720
KENYVTLSGT FDECYPTYLY QKIDESKLKA FTRYQLRGYI EDSQDLEIYL IRYNAKHETV  780
NVPGTGSLWP LSAQSPIGKC GEPNRCAPHL EWNPDLDCSC RDGEKCAHHS HHFSLDIDVG  840
CTDLNEDLGV WVIFKIKTQD GHARLGNLEF LEEKPLVGEA LARVKRAEKK WRDKREKLEW  900
ETNIVYKEAK ESVDALFVNS QYDQLQADTN IAMIHAADKR VHSIREAYLP ELSVIPGVNA  960
AIFEELEGRI FTAFSLYDAR NVIKNGDFNN GLSCWNVKGH VDVEEQNNQR SVLVVPEWEA 1020
EVSQEVRVCP GRGYILRVTA YKEGYGEGCV TIHEIENNTD ELKFSNCVEE EIYPNNTVTC 1080
NDYTVNQEEY GGAYTSRNRG YNEAPSVPAD YASVYEEKSY TDGRRENPCE FNRGYRDYTP 1140
LPVGYVTKEL EYFPETDKVW IEIGETEGTF IVDSVELLLM EE                    1182

SEQ ID NO: 68              moltype = DNA   length = 3549
FEATURE                    Location/Qualifiers
misc_feature               1..3549
                           note = Chimeric coding sequence encoding TIC1099 T562R.
source                     1..3549
                           mol_type = other DNA
                           organism = synthetic construct
SEQUENCE: 68
atggataaca atccgaacat caatgaatgc attccttata attgtttaag taaccctgaa   60
gtagaagtat taggtggaga aagaatagaa actggttaca ccccaatcga tatttccttg  120
tcgctaacgc aatttctttt gagtgaattt gttcccggtg ctggatttgt gttaggacta  180
gttgatataa tatgggggaat ttttggtccc tctcaatgag acgcatttct tgtacaaatt  240
gaacagttaa ttaaccaaag aatagaagaa ttcgctagga accaagccat ttctagatta  300
gaaggactaa gcaatcttta tcaaatttac gcagaatctt ttagagagtg ggaagcagat  360
cctactaatc cagcattaag agaagagatg cgtattcaat tcaatgacat gaacagtgcc  420
cttacaaccg ctattcctct tttggcagtt caaaattatc aagttcctct tttatcagta  480
tatgttcaag ctgcaaattt acatttatca gttttgagag agtgtttcagt gtttggacaa  540
aggtggggat ttgatgccgc gactatcaat agtcgttata atgatttaac taggcttatt  600
ggcaactata cagattatgc tgtacgctgg tacaatacgg gattagaacg tgtatggGGa  660
ccggattcta gagattgggt aaggtataat caatttagaa gagaattaac actaactgta  720
ttagatatcg ttgctctgtt cccgaattat gatagtagaa gatatccaat tcgaacagtt  780
tcccaattaa caagagaaat ttatacaaac ccagtattag aaaatttttga tggtagtttt  840
cgaggctcgg ctcagggcat agaaagaagt attaggagtc cacatttgat ggatatactt  900
aacagtataa ccatctatac ggatgctcat aggggttatt attattggtc agggcatcaa  960
ataatggctt ctcctgtcgg ttttttcggg ccagaattca cttttccgct atatggaacc 1020
atgggaaatg cagctccaca acaacgtatt gttgctcaac taggtcaggg cgtgtataga 1080
acattatcgt ccactttata tagaagacct tttaatatag gataaaataa tcaacaacta 1140
tctgttcttg acgggacaga atttgcttat ggaacctcct caaatttgcc atccgctgta 1200
tacagaaaaa gcggaacggt agattcgctg gatgaaatac cgccacagaa taacaacgtg 1260
ccacctaggc aaggatttag tcatcgatta agccatgttt caatgtttcg ttcaggcttt 1320
agtaatagta gtgtaagtat aataagagct cctatgttct cttggataca tcgtagtgct 1380
gaatttaata atataattgc atcggatagt attacacaat taccattggt aaaaggcatct 1440
gcacctgttt cgggtactac ggtcttaaaa ggtccaggat ttacaggagg gggtatactc 1500
cgaagaacaa ctaatggcac atttggaacg ttaagagtaa cagttaattc accattaaca 1560
caaagatatc gcgtaagagt tcgtttttgct tcatcaggaa atttcagcat aaggatactg 1620
cgtgaaaata cctctatagc ttatcaaaga tttgggagta caatgaacag aggacaggaa 1680
ctacgctacg aatcatttgt cacaagtgag ttcactacta atcagagcga tctgcctttt 1740
acatttacac aagctcaaga aaatttaaca atccttgcag aaggtgttag caccggtagt 1800
gaatatttta tagatagaat tgaaatcatc cctgtgaacc cggcacgaga agcagaagag 1860
gatttagaaa gagcgcagaa ggcggtgaat gcgctgttta cgtctacaaa ccaactaggg 1920
ctaaaaacaa atgtaacgga ttatcatatt gatcaagtgt ccaatttagt tacgtatttta 1980
tcggatgaat tttgtctgga tgaaaagcga gaattgtccg agaaagtcaa acatgcgaag 2040
cgactcagtg atgaacgcaa tttactccaa gattcaaatt tcaaagacat taataggcaa 2100
ccagaacgtg ggtggggcgg aagtacaggg attaccatcc aaggaggGGa tgacgtattt 2160
aaagaaaatt acgtcacact atcaggtacc tttgatgagt gctatccaac atatttgtat 2220
caaaaaatcg atgaatcaaa attaaaagcc tttacccgtt atcaattaag agggtatatc 2280
gaagatagtc aagacttaga aatctattta attcgctaca atgcaaaaca tgaaacagta 2340
aatgtgccag gtacgggttc cttatggccg ctttcagccc aaagtccaat cggaaagtgt 2400
ggagagccga atcgatgcgc gccacacctt gaatggaatc ctgacttaga ttgttcgtgt 2460
agggatggag aaaagtgtgc ccatcattcg catcatttct ccttagacat tgatgtagga 2520
tgtacagact aaaatgagga cctaggtgta tgggtgatct ttaagattaa gacgcaagat 2580
gggcacgcaa gactagggaa tctagagttt ctcgaagaaa aaccattagt aggagaagcg 2640
ctagctcgtg tgaaaagagc ggagaaaaaa tggagagaca aacgtgaaaa attggaatgg 2700
gaaacaaata tcgtttataa agaggcaaaa gaatctgtag atgctttatt tgtaaactct 2760
caatatgatc aattacaagc ggatacgaat attgccatga ttcatgcggc agataaacgt 2820
gttcatagca ttcgagaagc ttatctgcct gagctgtctg tgattccggg tgtcaatgcg 2880
gctatttttg aagaattaga agggcgtatt ttcactgcat tctccctata tgatgcgaga 2940
aatgtcatta aaaatggtga tttttaataat ggcttatcct gctggaacgt gaaagggcat 3000
gtagatgtag aagaacaaaa caaccaacgt tcggtccttg ttgttccgga atgggaagca 3060
gaagtgtcac aagaagttcg tgtctgtccg ggtcgtggct atatccttcg tgtcacacgc 3120
tacaaggagg gatatggaga aggttgcgta accattcatg agatcgagaa caatacagac 3180
```

```
gaactgaagt ttagcaactg cgtagaggag gaaatctatc caaataacac ggtaacgtgt   3240
aatgattata ctgtaaatca agaagaatac ggaggtgcgt acacttctcg taatcgagga   3300
tataacgaag ctccttccgt accagctgat tatgcgtcag tctatgaaga aaaatcgtat   3360
acagatggac gtagagagaa tccttgtgaa tttaacagag ggtataggga ttacacgcca   3420
ctaccagttg gttatgtgac aaaagaatta gaatacttcc cagaaaccga taaggtatgg   3480
attgagattg gagaaacgga aggaacattt atcgtggaca gcgtggaatt actccttatg   3540
gaggaataa                                                           3549

SEQ ID NO: 69            moltype = AA  length = 1182
FEATURE                  Location/Qualifiers
REGION                   1..1182
                         note = Amino acid sequence of the chimeric protein TIC1099
                          T526R.
source                   1..1182
                         mol_type = protein
                         organism = synthetic construct
SEQUENCE: 69
MDNNPNINEC IPYNCLSNPE VEVLGGERIE TGYTPIDISL SLTQFLLSEF VPGAGFVLGL   60
VDIIWGIFGP SQWDAFLVQI EQLINQRIEE FARNQAISRL EGLSNLYQIY AESFREWEAD   120
PTNPALREEM RIQFNDMNSA LTTAIPLLAV QNYQVPLLSV YVQAANLHLS VLRDVSVFGQ   180
RWGFDAATIN SRYNDLTRLI GNYTDYAVRW YNTGLERVWG PDSRDWVRYN QFRRELTLTV   240
LDIVALFPNY DSRRYPIRTV SQLTREIYTN PVLENFDGSF RGSAQGIERS IRSPHLMDIL   300
NSITIYTDAH RGYYYWSGHQ IMASPVGFSG PEFTFPLYGT MGNAAPQQRI VAQLGQGVYR   360
TLSSTLYRRP FNIGINNQQL SVLDGTEFAY GTSSNLPSAV YRKSGTVDSL DEIPPQNNNV   420
PPRQGFSHRL SHVSMFRSGF SNSSVSIIRA PMFSWIHRSA EFNNIIASDS ITQLPLVKAS   480
APVSGTTVLK GPGFTGGGIL RRTTNGTFGT LRVTVNSPLT QRYRVRVRFA SSGNFSIRIL   540
RGNTSIAYQR FGSTMNRGQE LRYESFVTSE FTTNQSDLPF TFTQAQENLT ILAEGVSTGS   600
EYFIDRIEII PVNPAREAEE DLERAQKAVN ALFTSTNQLG LKTNVTDYHI DQVSNLVTYL   660
SDEFCLDEKR ELSEKVKHAK RLSDERNLLQ DSNFKDINRQ PERGWGGSTG ITIQGGDDVF   720
KENYVTLSGT FDECYPTYLY QKIDESKLKA FTRYQLRGYI EDSQDLEIYL IRYNAKHETV   780
NVPGTGSLWP LSAQSPIGKC GEPNRCAPHL EWNPDLDCSC RDGEKCAHHS HHFSLDIDVG   840
CTDLNEDLGV WVIFKIKTQD GHARLGNLEF LEEKPLVGEA LARVKRAEKK WRDKREKLEW   900
ETNIVYKEAK ESVDALFVNS QYDQLQADTN IAMIHAADKR VHSIREAYLP ELSVIPGVNA   960
AIFEELEGRI FTAFSLYDAR NVIKNGDFNN GLSCWNVKGH VDVEEQNNQR SVLVVPEWEA   1020
EVSQEVRVCP GRGYILRVTA YKEGYGEGCV TIHEIENNTD ELKFSNCVEE EIYPNNTVTC   1080
NDYTVNQEEY GGAYTSRNRG YNEAPSVPAD YASVYEEKSY TDGRRENPCE FNRGYRDYTP   1140
LPVGYVTKEL EYFPETDKVW IEIGETEGTF IVDSVELLLM EE                      1182

SEQ ID NO: 70            moltype = DNA  length = 3549
FEATURE                  Location/Qualifiers
misc_feature             1..3549
                         note = Chimeric coding sequence encoding TIC1099 S553R.
source                   1..3549
                         mol_type = other DNA
                         organism = synthetic construct
SEQUENCE: 70
atggataaca atccgaacat caatgaatgc attccttata attgtttaag taaccctgaa   60
gtagaagtat taggtggaga aagaatagaa actggttaca ccccaatcga tatttccttg   120
tcgctaacgc aatttctttt gagtgaattt gttcccggtg ctggatttgt gttaggacta   180
gttgatataa tatgggggaat ttttggtccc tctcaatggg acgcatttct tgtacaaatt   240
gaacagttaa ttaaccaaag aatagaagaa ttcgctaaga accaagccat ttctagatta   300
gaaggactaa gcaatcttta tcaaatttac gcagaatctt ttagagagtg ggaagcagat   360
cctactaatc cagcattaag agaagagatg cgtattcaat tcaatgacat gaacagtgcc   420
cttacaaccg ctattcctct tttggcagtt caaaattatc aagttcctct tttatcagta   480
tatgttcaag ctgcaaattt acatttatca gttttgagag atgtttcagt gtttggacaa   540
aggtgggggat ttgatgccgc gactatcaat agtcgttata atgatttaac taggcttatt   600
ggcaactata cagattatgc tgtacgctgg tacaatacgg gattagaacg tgtatgggga   660
ccggattcta gagattgggt aaggtataat caatttagaa gagaattaac actaactgta   720
ttagatatcg ttgctctgtt cccgaattat gatagtagaa gatatccaat tcgaacagtt   780
tcccaattaa caagagaaat ttatacaaac ccagtattag aaaattttga tggtagtttt   840
cgaggctcgg ctcagggcat agaaagaagt attaggagtc cacatttgat ggatatactt   900
aacagtataa ccatctatac ggatgctcat aggggttatt attattggtc agggcatcaa   960
ataatggctt ctcctgtcgg ttttttcgggg ccagaattca cgtttccgct atatggaacc   1020
atgggaaatg cagctccaca acaacgtatt gttgctcaac taggtcaggg cgtgtataga   1080
acattatcgt ccactttata tagaagacct tttaatatag ggtataaataa tcaacaacta   1140
tctgttcttg acgggacaga atttgcttat ggaacctcct caaatttgcc atccgctgta   1200
tacagaaaaa gcgaacggt agattcgctg atgaaatac cgccacgaa taacaacgtg   1260
ccacctaggc aaggatttag tcatcgatta agccatgttt caatgtttcg ttcaggcttt   1320
agtaatagta gtgtaagtat aataagagct cctatgttct cttggataca tcgtagtgct   1380
gaatttaata atataattgc atcggatagt attacacaat taccattggt aaaggcatct   1440
gcacctgttt cgggtactac ggtcttaaaa ggtccaggat ttacaggagg gggtatactc   1500
cgaagaacaa ctaatggcac atttggaacg ttaagagtaa cagttaattc accattaaca   1560
caaagatatc gcgtaagagt tcgttttgct tcatcaggaa atttcagcat aaggatactg   1620
cgtggaaata cctctatagc ttatcaaaga tttgggcgta caatgaacag aggacaggaa   1680
ctaacttacg aatcatttgt cacaagtgag ttcactacta tcagagcga tctgcctttt   1740
acatttacac aagctcaaga aaatttaaca atccttgcag aaggtgttag caccggtagt   1800
gaatatttta tagatagaat tgaaatcatc cctgtgaacc cggcacgaga agcagaagag   1860
gatttagaaa gagcgcagaa ggcggtgaat gcgctgtttac cgtctacaaa ccaactaggg   1920
ctaaaaacaa atgtaacgga ttatcatatt gatcaagtgt ccaatttagt tacgtattta   1980
```

```
tcggatgaat tttgtctgga tgaaaagcga gaattgtccg agaaagtcaa acatgcgaag   2040
cgactcagtg atgaacgcaa tttactccaa gattcaaatt tcaaagacat taataggcaa   2100
ccagaacgtg ggtggggcgg aagtacaggg attaccatcc aaggagggga tgacgtattt   2160
aaagaaaatt acgtcacact atcaggtacc tttgatgagt gctatccaac atatttgtat   2220
caaaaaatcg atgaatcaaa attaaaagcc tttacccgtt atcaattaag agggtatatc   2280
gaagatagtc aagacttaga aatctattta attcgctaca atgcaaaaca tgaaacagta   2340
aatgtgccag gtacgggttc cttatggccg ctttcagccc aaagtccaat cggaaagtgt   2400
ggagagccga atcgatgcgc gccacacctt gaatggaatc ctgacttaga ttgttcgtgt   2460
agggatggag aaaagtgtgc ccatcattcg catcatttct ccttagacat tgatgtagga   2520
tgtacagact aaatgagga cctaggtgta tgggtgatct ttaagattaa gacgcaagat   2580
gggcacgcaa gactagggaa tctagagttt ctcgaagaaa aaccattagt aggagaagcg   2640
ctagctcgtg tgaaaagagc ggagaaaaaa tggagagaca aacgtgaaaa attggaatgg   2700
gaaacaaata tcgtttataa agaggcaaaa gaatctgtag atgctttatt tgtaaactct   2760
caatatgatc aattacaagc ggatacgaat attgccatga ttcatgcggc agataaacgt   2820
gttcatagca ttcgagaagc ttatctgcct gagctgtctg tgattccggg tgtcaatgcg   2880
gctatttttg aagaattaga agggcgtatt ttcactgcat tctccctata tgatgcgaga   2940
aatgtcatta aaaatggtga tttaataat ggcttatcct gctggaacgt gaaagggcat   3000
gtagatgtag aagaacaaaa caaccaacgt tcggtccttg ttgttccgga atgggaagca   3060
gaagtgtcac aagaagttcg tgtctgtccg ggtcgtggct atatccttcg tgtcacagcg   3120
tacaaggagg gatatggaga aggttgcgta accattcatg agatcgagaa caatacagac   3180
gaactgaagt ttagcaactg cgtagaggag gaaatctatc caaataacac ggtaacgtgt   3240
aatgattata ctgtaaatca agaagaatac ggaggtgcgt acacttctcg taatcgagga   3300
tataacgaag ctccttccgt accagctgat tatgcgtcag tctatgaaga aaaatcgtat   3360
acagatggac gtagagagaa tccttgtgaa tttaacagag ggtatggga ttacacgcca   3420
ctaccagttg gttatgtgac aaaagaatta gaatacttcc cagaaccga taaggtatgg   3480
attgagattg gagaaacgga aggaacattt atcgtggaca gcgtggaatt actccttatg   3540
gaggaataa                                                             3549
```

SEQ ID NO: 71        moltype = AA  length = 1182
FEATURE              Location/Qualifiers
REGION               1..1182
                     note = Amino acid sequence of the chimeric protein TIC1099
                      S553R.
source               1..1182
                     mol_type = protein
                     organism = synthetic construct
SEQUENCE: 71
```
MDNNPNINEC IPYNCLSNPE VEVLGGERIE TGYTPIDISL SLTQFLLSEF VPGAGFVLGL   60
VDIIWGIFGP SQWDAFLVQI EQLINQRIEE FARNQAISRL EGLSNLYQIY AESFREWEAD   120
PTNPALREEM RIQFNDMNSA LTTAIPLLAV QNYQVPLLSV YVQAANLHLS VLRDVSVFGQ   180
RWGFDAATIN SRYNDLTRLI GNYTDYAVRW YNTGLERVWG PDSRDWVRYN QFRRELTLTV   240
LDIVALFPNY DSRRYPIRTV SQLTREIYTN PVLENFDGSF RGSAQGIERS IRSPHLMDIL   300
NSITIYTDAH RGYYYWSGHQ IMASPVGFSG PEFTFPLYGT MGNAAPQQRI VAQLGQGVYR   360
TLSSTLYRRP FNIGINNQQL SVLDGTEFAY GTSSNLPSAV YRKSGTVDSL DEIPPQNNNV   420
PPRQGFSHRL SHVSMFRSGF SNSSVSIIRA PMFSWIHRSA EFNNIIASDS ITQLPLVKAS   480
APVSGTTVLK GPGFTGGGIL RRTTNGTFGT LRVTVNSPLT QRYRVRVRFA SSGNFSIRIL   540
RGNTSIAYQR FGRTMNRGQE LTYESFVTSE FTTNQSDLPF TFTQAQENLT ILAEGVSTGS   600
EYFIDRIEII PVNPAREAEE DLERAQKAVN ALFTSTNQLG LKTNVTDYHI DQVSNLVTYL   660
SDEFCLDEKR ELSEKVKHAK RLSDERNLLQ DSNFKDINRQ PERGWGGSTG ITIQGGDDVF   720
KENYVTLSGT FDECYPTYLY QKIDESKLKA FTRYQLRGYI EDSQDLEIYL IRYNAKHETV   780
NVPGTGSLWP LSAQSPIGKC GEPNRCAPHL EWNPDLDCSC RDGEKCAHHS HHFSLDIDVG   840
CTDLNEDLGV WVIFKIKTQD GHARLGNLEF LEEKPLVGEA LARVKRAEKK WRDKREKLEW   900
ETNIVYKEAK ESVDALFVNS QYDQLQADTN IAMIHAADKR VHSIREAYLP ELSVIPGVNA   960
AIFEELEGRI FTAFSLYDAR NVIKNGDFNN GLSCWNVKGH VDVEEQNNQR SVLVVPEWEA   1020
EVSQEVRVCP GRGYILRVTA YKEGYGEGCV TIHEIENNTD ELKFSNCVEE EIYPNNTVTC   1080
NDYTVNQEEY GGAYTSRNRG YNEAPSVPAD YASVYEEKSY TDGRRENPCE FNRGYRDYTP   1140
LPVGYVTKEL EYFPETDKVW IEIGETEGTF IVDSVELLLM EE                       1182
```

SEQ ID NO: 72        moltype = DNA  length = 3549
FEATURE              Location/Qualifiers
misc_feature        1..3549
                     note = Chimeric coding sequence encoding TIC1099 G498D.
source               1..3549
                     mol_type = other DNA
                     organism = synthetic construct
SEQUENCE: 72
```
atggataaca atccgaacat caatgaatgc attccttata attgtttaag taaccctgaa   60
gtagaagtat taggtggaga aagaatagaa actggttaca ccccaatcga tatttccttg   120
tcgctaacgc aatttctttt gagtgaattt gttcccggtg ctggatttgt gttaggacta   180
gttgatataa tatgggggaat ttttggtccc tctcaatggg acgcatttct tgtacaaatt   240
gaacagttaa ttaaccaaag aatagaagaa ttcgctagga accaagccat ttctagatta   300
gaaggactaa gcaatcttta tcaaatttac gcagaatctt ttagagagtg ggaagcagat   360
cctactaatc cagcattaag agaagagatg cgtattcaat tcaatgacat gaacagtgcc   420
cttacaacgc ctattcctct tttggcagtt caaaattatc aagttcctct tttatcagta   480
tatgttcaag ctgcaaattt acatttatca gttttgagag atgtttcagt gtttggacaa   540
aggtggggat ttgatgccgc gactatcaat agtcgttata atgatttaac taggcttatt   600
ggcaactata cagattatgc tgtacgctgg tacaatacgg gattagaacg tgtatgggga   660
ccggattcta gagattgggt aaggtataat caatttagaa gagaattaac actaactgta   720
ttagatatcg ttgctctgtt cccgaattat gatagtagaa gatatccaat tcgaacagtt   780
```

```
tcccaattaa caagagaaat ttatacaaac ccagtattag aaaattttga tggtagtttt  840
cgaggctcgg ctcagggcat agaaagaagt attaggagtc cacatttgat ggatatactt  900
aacagtataa ccatctatac ggatgctcat aggggttatt attattggtc agggcatcaa  960
ataatggctt ctcctgtcgg tttttcgggg ccagaattca cgtttccgct atatggaacc 1020
atgggaaatg cagctccaca acaacgtatt gttgctcaac taggtcaggg cgtgtataga 1080
acattatcgt ccactttata tagaagacct tttaatatag ggataaataa tcaacaacta 1140
tctgttcttg acgggacaga atttgcttat ggaacctcct caaatttgcc atccgctgta 1200
tacagaaaaa gcggaacggt agattcgctg gatgaaatac cgccacgaa taacaacgtg 1260
ccacctaggc aaggatttag tcatcgatta agccatgttt caatgtttcg ttcaggcttt 1320
agtaatagta gtgtaagtat aataagagct cctatgttct cttggataca tcgtagtgct 1380
gaatttaata atataattgc atcggatagt attacacaat taccattggt aaaggcatct 1440
gcacctgttt cgggtactac ggtcttaaaa ggtccaggat ttacaggagg ggatatactc 1500
cgaagaacaa ctaatggcac atttggaacg ttaagagtaa cagttaattc accattaaca 1560
caaagatatc gcgtaagagt tcgttttgct tcatcaggaa atttcagcat aaggatactg 1620
cgtggaaata cctctatagc ttatcaaaga tttgggagta caatgaacag aggacaggaa 1680
ctaacttacg aatcatttgt cacaagtgag ttcactacta atcagagcga tctgcctttt 1740
acatttacac aagctcaaga aaatttaaca atccttgcag aaggtgttag caccggtagt 1800
gaatattta tagatagaat tgaaatcatc cctgtgaacc cggcacgaga agcagaagga 1860
gatttagaaa gagcgcagaa ggcggtgaat gcgctgtta cgtctacaaa ccaactaggg 1920
ctaaaaacaa atgtaacgga ttatcatatt gatcaagtgt ccaatttagt tacgtattta 1980
tcggatgaat tttgtctgga tgaaaagcga gaattgtccg agaaagtcaa acatgcgaag 2040
cgactcagtg atgaacgcaa tttactccaa gattcaaatt tcaaagacat taataggcaa 2100
ccagaacgtg ggtggggcgg aagtacaggg attaccatcc aaggagggga tgacgtattt 2160
aaagaaaatt acgtcacact atcaggtacc tttgatgagt gctatccaac atatttgtat 2220
caaaaaatcg atgaatcaaa attaaaagcc tttacccgtt atcaattaag agggtatatc 2280
gaagatagtc aagacttaga aatctattta attcgctaca atgcaaaaca tgaaacagta 2340
aatgtgccag gtacgggttc cttatggccg ctttcagccc aaagtccaat cggaaagtgt 2400
ggagagccga atcgatgcgc gccacacctt gaatggaatc ctgacttaga ttgttcgtgt 2460
agggatggag aaaagtgtgc ccatcattcg catcatttct ccttagacat tgatgtagga 2520
tgtacagact aaatgagga cctaggtgta tgggtgatct ttaagattaa gacgcaagat 2580
gggcacgcaa gactagggaa tctagagttt ctcgaagaaa aaccattagt aggagaagcg 2640
ctagctcgtg tgaaaagagc ggagaaaaaa tggagagaca aacgtgaaaa attggaatgg 2700
gaaacaaata tcgtttataa agaggcaaaa gaatctgtag atgctttatt tgtaaactct 2760
caatatgatc aattacaagc ggatacgaat attgccataa ttcatgcggc agataaacgt 2820
gttcatagca ttcgagaagc ttatctgcct gagctgtctg tgattccggg tgtcaatgca 2880
gctatttttg aagaattaga agggcgtatt ttcactgcat tctccctata tgatgcgaga 2940
aatgtcatta aaaatggtga tttaataat ggcttatcct gctggaacgt gaaagggcat 3000
gtagatgtag aagaacaaaa caaccaacgt tcggtccttg ttgttccgga atgggaagca 3060
gaagtgtcac aagaagttcg tgtctgtccg ggtcgtgcgt atatccttcg tgtcacagcg 3120
tacaaggagg gatatggaga aggttgcgta accattcatg agatcgagaa caatacagac 3180
gaactgaagt ttagcaactg cgtagaggag gaaatctatc caataacac ggtaacgtgt 3240
aatgattata ctgtaaatca agaagaatac ggaggtgcgt acacttctcg taatcgagga 3300
tataacgaag ctccttccgt accagctgat tatgcgtcag tctatgaaga aaaatcgtat 3360
acagatggac gtagagaga tccttgtgaa tttaacagag ggtatagggga ttacacgcca 3420
ctaccagttg gttatgtgac aaaagaatta gaatacttcc cagaaccga taaggtatgg 3480
attgagattg gagaaacgga aggaacattt atcgtggaca gcgtggaatt actccttatg 3540
gaggaataa                                                         3549
```

SEQ ID NO: 73            moltype = AA  length = 1182
FEATURE                  Location/Qualifiers
REGION                   1..1182
                         note = Amino acid sequence of the chimeric protein TIC1099
                          G498D.
source                   1..1182
                         mol_type = protein
                         organism = synthetic construct
SEQUENCE: 73
MDNNPNINEC IPYNCLSNPE VEVLGGERIE TGYTPIDISL SLTQFLLSEF VPGAGFVLGL   60
VDIIWGIFGP SQWDAFLVQI EQLINQRIEE FARNQAISRL EGLSNLYQIY AESFREWEAD  120
PTNPALREEM RIQFNDMNSA LTTAIPLLAV QNYQVPLLSV YVQAANLHLS VLRDVSVFGQ  180
RWGFDAATIN SRYNDLTRLI GNYTDYAVRW YNTGLERVWG PDSRDWVRYN QFRRELTLTV  240
LDIVALFPNY DSRRYPIRTV SQLTREIYTN PVLENFDGSF RGSAQGIERS IRSPHLMDIL  300
NSITIYTDAH RGYYWSGHQ IMASPVGFSG PEFTFPLYGT MGNAAPQQRI VAQLGQGVYR  360
TLSSTLYRRP FNIGINNQQL SVLDGTEFAY GTSSNLPSAV YRKSGTVDSL DEIPPQNNNV  420
PPRQGFSHRL SHVSMFRSGF SNSSVSIIRA PMFSWIHRSA EFNNIIASDS ITQLPLVKAS  480
APVSGTTVLK GPGFTGGDIL RRTTNGTFGT LRVTVNSPLT QRYRVRVRFA SSGNFSIRIL  540
RGNTSIAYQR FGSTMNRGQE LTYESFVTSE FTTNQSDLPF TFTQAQENLT ILAEGVSTGS  600
EYFIDRIEII PVNPAREAEE DLERAQKAVN ALFTSTNQLG LKTNVTDYHI DQVSNLVTYL  660
SDEFCLDEKR ELSEKVKHAK RLSDERNLLQ DSNFKDINRQ PERGWGGSTG ITIQGGDDVF  720
KENYVTLSGT FDECYPTYLY QKIDESKLKA FTRYQLRGYI EDSQDLEIYL IRYNAKHETV  780
NVPGTGSLWP LSAQSPIGKC GEPNRCAPHL EWNPDLDCSC RDGEKCAHHS HHFSLDIDVG  840
CTDLNEDLGV WVIFKIKTQD GHARLGNLEF LEEKPLVGEA LARVKRAEKK WRDKREKLEW  900
ETNIVYKEAK ESVDALFVNS QYDQLQADTN IAMIHAADKR VHSIREAYLP ELSVIPGVNA  960
AIFEELEGRI FTAFSLYDAR NVIKNGDFNN GLSCWNVKGH VDVEEQNNQR SVLVVPEWEA 1020
EVSQEVRVCP GRGYILRVTA YKEGYGEGCV TIHEIENNTD ELKFSNCVEE EIYPNNTVTC 1080
NDYTVNQEEY GGAYTSRNRG YNEAPSVPAD YASVYEEKSY TDGRRENPCE FNRGYRDYTP 1140
LPVGYVTKEL EYFPETDKVW IEIGETEGTF IVDSVELLLM EE                    1182

SEQ ID NO: 74            moltype = DNA  length = 3549
```

-continued

```
FEATURE              Location/Qualifiers
misc_feature         1..3549
                     note = Chimeric coding sequence encoding TIC1099 K490A.
source               1..3549
                     mol_type = other DNA
                     organism = synthetic construct
SEQUENCE: 74
atggataaca atccgaacat caatgaatgc attccttata attgtttaag taaccctgaa  60
gtagaagtat taggtggaga aagaatagaa actggttaca ccccaatcga tatttccttg  120
tcgctaacgc aatttctttt gagtgaattt gttcccggtg ctggatttgt gttaggacta  180
gttgatataa tatgggggaat tttttggtccc tctcaatggg acgcatttct tgtacaaatt  240
gaacagttaa ttaaccaaag aatagaagaa ttcgctagga accaagccat ttctagatta  300
gaaggactaa gcaatcttta tcaaatttac gcagaatctt ttagagagtg ggaagcagat  360
cctactaatc cagcattaag agaagagatg cgtattcaat tcaatgacat gaacagtgcc  420
cttacaaccg ctattcctct tttggcagtt caaaattatc aagttcctct tttatcagta  480
tatgttcaag ctgcaaattt acatttatca gttttgagag atgtttcagt gtttggacaa  540
aggtggggat ttgatgccgc gactatcaat agtcgttata atgatttaac taggcttatt  600
ggcaactata cagattatgc tgtacgctgg tacaatacgg gattagaacg tgtatgggga  660
ccggattcta gagattgggt aaggtataat caatttagaa gagaattaac actaactgta  720
ttagatatcg ttgctctgtt cccgaattat gatagtagaa gatatccaat tcgaacagtt  780
tcccaattaa caagagaaat ttatacaaac ccagtattag aaaattttga tggtagtttt  840
cgaggctcgg ctcagggcat agaaagaagt attaggagtg cacatttgat ggatatactt  900
aacagtataa ccatctatac ggatgctcat aggggttatt attattggtc agggcatcaa  960
ataatggctt ctcctgtcgg tttttcgggg ccagaattca cgtttccgct atatggaacc  1020
atgggaaatg cagctccaca acaacgtatt gttgctcaac taggtcaggg cgtgtataga  1080
acattatcgt ccactttata tagaagacct tttaatatag ggataaataa tcaacaacta  1140
tctgttcttg acgggacaga atttgcttat ggaacctcct caaatttgcc atccgctgta  1200
tacagaaaaa gcgg0aacggt agattcgctg gatgaaatac cgccacagaa taacaacgtg  1260
ccacctaggc aaggatttag tcatcgatta agccatgttt caatgtttcg ttcaggcttt  1320
agtaatagta gtgtaagtat aataagagct cctatgttct cttggataca tcgtagtgct  1380
gaatttaata atataattgc atcggatagt attacacaat taccattggt aaaggcatct  1440
gcacctgttt cgggtactac ggtcttagca ggtccaggat ttacaggagg gggtatactc  1500
cgaagaacaa ctaatggcac atttggaacg ttaagagtaa cagttaattc accattaaca  1560
caaagatatc gcgtaagagt tcgttttgct tcatcaggaa atttcagcat aaggatactg  1620
cgtggaaata cctctatagc ttatcaaaga tttgggagta caatgaacag aggacaggaa  1680
ctaacttacg aatcatttgt cacaagtgag ttcactacta atcagagcga tctgcctttt  1740
acatttacac aagctcaaga aaatttaaca atccttgcag aaggtgttag caccggtagt  1800
gaatatttta tagatagaat tgaaatcatc cctgtgaacc cggcacgaga agcagaagag  1860
gatttagaaa gagcgcagaa ggcggtgaat gcgctgttta cgtctacaaa ccaactaggg  1920
ctaaaaacaa atgtaacgga ttatcatatt gatcaagtgt ccaatttagt tacgtatttta  1980
tcggatgaat tttgtctgga tgaaaagcga gaattgtccg agaaagtcaa acatgcgaag  2040
cgactcagtg atgaacgcaa tttactccaa gattcaaatt tcaaagacat taataggcaa  2100
ccagaacgtg ggtggggcgg aagtacaggg attaccatcc aaggagggga tgacgtattt  2160
aaagaaaatt acgtcacact atcaggtacc tttgatgagt gctatccaac atatttgtat  2220
caaaaaatcg atgaatcaaa attaaaagcc tttacccgtt atcaattaag agggtatatc  2280
gaagatagtc aagacttaga aatctatttta attcgctaca atgcaaaaca tgaaacagta  2340
aatgtgccag gtacggttc cttatggccg ctttcagccc aaagtccaat cggaaagtgt  2400
ggagagccga atcgatgcgc gccacacctt gaatggaatc ctgacttaga ttgttcgtgt  2460
agggatggag aaaagtgtgc ccatcattcg catcatttct ccttagacat tgatgtagga  2520
tgtacagact aaatgagga cctaggtgta tgggtgatct ttaagattaa gacgcaagat  2580
gggcacgcaa gactagggaa tctagagttt ctcgaagaaa aaccattagt aggagaagcg  2640
ctagctcgtg tgaaaagagc ggagaaaaaa tggagagaca aacgtgaaaa attggaatgg  2700
gaaacaaata tcgtttataa agaggcaaaa gaatctgtag atgctttatt tgtaaactct  2760
caatatgatc aattacaagc ggatacgaat attgccatga ttcatgcggc agataaacgt  2820
gttcatagca ttcgagaagc ttatctgcct gagctgtctg tgattccggg tgtcaatgcg  2880
gctatttttg aagaattaga agggcgtatt ttcactgcat tctccctata tgatgcgaga  2940
aatgtcatta aaaatggtga ttttaataat ggcttatcct gctggaacgt gaaagggcat  3000
gtagatgtag aagaacaaaa caaccaacgt tcggtccttg ttgttccgga atgggaagca  3060
gaagtgtcac aagaagttcg tgtctgtccg ggtcgtggct atatccttcg tgtcacagcg  3120
tacaaggagg gatatggaga aggttgcgta accattcatg agatcgagaa caatacagac  3180
gaactgaagt ttagcaactg cgtagaggag gaaatctatc caataacac ggtaacgtgt  3240
aatgattata ctgtaaatca agaagaatac ggaggtgcgt acacttctcg taatcgagga  3300
tataacgaag ctccttccgt accagctgat tatgcgtcag tctatgaaga aaaatcgtat  3360
acagatggac gtagagagaa tccttgtgaa tttaacagag ggtatagggga ttacacgcca  3420
ctaccagttg gttatgtgac aaaagaatta gaatacttcc cagaaaccga taaggtatgg  3480
attgagattg gagaaacgga aggaacattt atcgtggaca gcgtggaatt actccttatg  3540
gaggaataa                                                          3549
```

```
SEQ ID NO: 75         moltype = AA   length = 1182
FEATURE              Location/Qualifiers
REGION               1..1182
                     note = Amino acid sequence of the chimeric protein TIC1099
                     K490A.
source               1..1182
                     mol_type = protein
                     organism = synthetic construct
SEQUENCE: 75
MDNNPNINEC IPYNCLSNPE VEVLGGERIE TGYTPIDISL SLTQFLLSEF VPGAGFVLGL  60
VDIIWGIFGP SQWDAFLVQI EQLINQRIEE FARNQAISRL EGLSNLYQIY AESFREWEAD  120
```

```
PTNPALREEM RIQFNDMNSA LTTAIPLLAV QNYQVPLLSV YVQAANLHLS VLRDVSVFGQ   180
RWGFDAATIN SRYNDLTRLI GNYTDYAVRW YNTGLERVWG PDSRDWVRYN QFRRELTLTV   240
LDIVALFPNY DSRRYPIRTV SQLTREIYTN PVLENFDGSF RGSAQGIERS IRSPHLMDIL   300
NSITIYTDAH RGYYYWSGHQ IMASPVGFSG PEFTFPLYGT MGNAAPQQRI VAQLGQGVYR   360
TLSSTLYRRP FNIGINNQQL SVLDGTEFAY GTSSNLPSAV YRKSGTVDSL DEIPPQNNNV   420
PPRQGFSHRL SHVSMFRSGF SNSSVSIIRA PMFSWIHRSA EFNNIIASDS ITQLPLVKAS   480
APVSGTTVLA GPGFTGGGIL RRTTNGTFGT LRVTVNSPLT QRYRVRVRFA SSGNFSIRIL   540
RGNTSIAYQR FGSTMNRGQE LTYESFVTSE FTTNQSDLPF TFTQAQENLT ILAEGVSTGS   600
EYFIDRIEII PVNPAREAEE DLERAQKAVN ALFTSTNQLG LKTNVTDYHI DQVSNLVTYL   660
SDEFCLDEKR ELSEKVKHAK RLSDERNLLQ DSNFKDINRQ PERGWGGSTG ITIQGGDDVF   720
KENYVTLSGT FDECYPTYLY QKIDESKLKA FTRYQLRGYI EDSQDLEIYL IRYNAKHETV   780
NVPGTGSLWP LSAQSPIGKC GEPNRCAPHL EWNPDLDCSC RDGEKCAHHS HHFSLDIDVG   840
CTDLNEDLGV WVIFKIKTQD GHARLGNLEF LEEKPLVGEA LARVKRAEKK WRDKREKLEW   900
ETNIVYKEAK ESVDALFVNS QYDQLQADTN IAMIHAADKR VHSIREAYLP ELSVIPGVNA   960
AIFEELEGRI FTAFSLYDAR NVIKNGDFNN GLSCWNVKGH VDVEEQNNQR SVLVVPEWEA  1020
EVSQEVRVCP GRGYILRVTA YKEGYGEGCV TIHEIENNTD ELKFSNCVEE EIYPNNTVTC  1080
NDYTVNQEEY GGAYTSRNRG YNEAPSVPAD YASVYEEKSY TDGRRENPCE FNRGYRDYTP  1140
LPVGYVTKEL EYFPETDKVW IEIGETEGTF IVDSVELLLM EE                     1182

SEQ ID NO: 76              moltype = DNA   length = 3549
FEATURE                    Location/Qualifiers
misc_feature               1..3549
                           note = Chimeric coding sequence encoding TIC1099 E564A.
source                     1..3549
                           mol_type = other DNA
                           organism = synthetic construct
SEQUENCE: 76
atggataaca atccgaacat caatgaatgc attccttata attgtttaag taaccctgaa   60
gtagaagtat taggtggaga aagaatagaa actggttaca ccccaatcga tatttccttg   120
tcgctaacgc aatttctttt gagtgaattt gttcccggtg ctggatttgt gttaggacta   180
gttgatataa tatgggggaat ttttggtccc tctcaatggg acgcatttct tgtacaaatt   240
gaacagttaa ttaaccaaag aatagaagaa ttcgctagga accaagccat ttctagatta   300
gaaggactaa gcaatcttta tcaaatttac gcagaatctt ttagagagtg ggaagcagat   360
cctactaatc cagcattaag agaagagatg cgtattcaat caatgacat gaacagtgcc   420
cttacaaccg ctattcctct tttggcagtt caaaattatc aagttcctct tttatcagta   480
tatgttcaag ctgcaaattt acatttatca gttttgagag atgtttcagt gtttggacaa   540
aggtggggat ttgatgccgc gactatcaat agtcgttata atgatttaac taggcttatt   600
ggcaactata cagattatgc tgtacgctgg tacaatacgg gattagaacg tgtatgggga   660
ccggatccta gagattgggt aaggtataat caatttgaga gagaattaac actaactgta   720
ttagatatcg ttgctctgtt cccgaattat gatagtagaa gatatccaat tcgaacagtt   780
tcccaattaa caagagaaat ttatacaaac ccagtattag aaaattttga tggtagtttt   840
cgaggctcgg ctcagggcat agaaagaagt attaggagtc cacatttgat ggatatactt   900
aacagtataa ccatctatac ggatgctcat aggggtttat tttattggtc aggccatcaa   960
ataatggctt ctcctgtcgg ttttttcgggg ccagaattca cgtttccgct atatggaacc  1020
atgggaaatg cagctccaca acaacgtatt gttgctcaac taggtcaggg cgtgtataga  1080
acattatcgt ccactttata tagaagacct tttaatatag ggataaataa tcaacaacta  1140
tctgttcttg acgggacaga aattgcttat ggaacctcct caaatttgcc atccgctgta  1200
tacagaaaaa gcggaacggt agattcgctg gatgaaaatac cgccacagaa taacaacgtg  1260
ccacctaggc aaggatttag tcatcgatta agccatgttt caatgtttcg ttcaggcttt  1320
agtaatagta gtgtaagtat aataagagct cctatgttct cttggataca tcgtagtgct  1380
gaatttaata atataatgc atcggatagt attacacaat taccattggt aaaggcatct  1440
gcacctgttt cgggtactac ggtcttaaaa ggtccaggat ttacaggagg gggtatactc  1500
cgaagaacaa ctaatggcac atttggaacg ttaagagtaa cagttaattc accattaaca  1560
caaagatatc gcgtaagagt tcgttttgct tcatcaggaa atttcagcat aaggatactg  1620
cgtggaaata cctctatagc ttatcaaaga tttgggagta caatgaacag ggacaggaaa  1680
ctaacttacg catcatttgt cacaagtgag ttcactacta tcagagcga tctgcctttt  1740
acatttacac aagctcaaga aaatttaaca atccttgcag aaggtgttag caccggtagt  1800
gaatatttta tagatagaat tgaaatcatc cctgtgaacc cggcacgaga agcagaagag  1860
gatttagaaa gagcgcagaa ggcggtgaat gcgctgttta cgtctacaaa ccaactaggg  1920
ctaaaaacaa atgtaacgga ttatcatatt gatcaagtgt ccaatttagt tacgtattta  1980
tcggatgaat tttgtctgga tgaaaagcga gaattgtccg agaaagtcaa acatgcgaag  2040
cgactcagtg atgaacgcaa tttactccaa gattcaaatt tcaaagacat taataggcaa  2100
ccagaacgtg ggtggggcgg aagtacaggg attaccatcc aaggaggga tgacgtattt  2160
aaagaaaatt acgtcacact atcaggtacc tttgatgagt gctatccaac atatttgtat  2220
caaaaaatcg atgaatcaaa attaaaagcc tttacccgtt atcaattaag agggtatatc  2280
gaagatagtc aagacttaga aatctattta attcgctaca atgcaaaaca tgaaacagta  2340
aatgtgccag gtacgggttc cttatggccg ctttcagccc aaagtccaat cggaaagtgt  2400
ggagagccga tcgatgcgc gccacacctt gaatggaatc ctgacttaga ttgttcgtgt  2460
agggatggag aaaagtgtgc ccatcattcg catcatttct ccttagacat tgatgtagga  2520
tgtacagact aaaatgagga cctaggtgta tgggtgatct ttaagattaa gacgcaagat  2580
gggcacgcaa gactagggaa tctagagttt ctcgaagaaa aaccattagt aggagaagcg  2640
ctagctcgtg tgaaaagagc ggagaaaaaa tggagagaca aacgtgaaaa attggaatgg  2700
gaaacaaata tcgtttataa agaggcaaaa gaatctgtag atgctttatt tgtaaactct  2760
caatataagc ggatacgaat attgccatga ttcatcgcgc agataaacgt  2820
gttcatagca ttcgagaagc ttatctgcct gagctgtctg tgattccggg tgtcaatgcg  2880
gctatttttg aagaattaga agggcgtatt ttcactgcat tctccctata tgatgcgaga  2940
aatgtcatta aaaatggtga ttttaataat ggcttatcct gctggaacgt gaaagggcat  3000
gtagatgtag aagaacaaaa caaccaacgt tcggtccttg ttgttccgga atgggaagca  3060
gaagtgtcac aagaagttcg tgtctgtccg ggtcgtggct atatccttcg tgtcacagcg  3120
```

```
tacaaggagg gatatggaga aggttgcgta accattcatg agatcgagaa caatacagac  3180
gaactgaagt ttagcaactg cgtagaggag gaaatctatc caaataacac ggtaacgtgt  3240
aatgattata ctgtaaatca agaagaatac ggaggtgcgt acacttctcg taatcgagga  3300
tataacgaag ctccttccgt accagctgat tatgcgtcag tctatgaaga aaaatcgtat  3360
acagatggac gtagagagaa tccttgtgaa tttaacggac ggtataggga ttacacgcca  3420
ctaccagttg gttatgtgac aaaagaatta gaatacttcc cagaaaccga taaggtatgg  3480
attgagattg gagaaacgga aggaacattt atcgtggaca gcgtggaatt actccttatg  3540
gaggaataa                                                          3549
```

```
SEQ ID NO: 77          moltype = AA  length = 1182
FEATURE                Location/Qualifiers
REGION                 1..1182
                       note = Amino acid sequence of the chimeric protein TIC1099
                       E564A.
source                 1..1182
                       mol_type = protein
                       organism = synthetic construct
SEQUENCE: 77
MDNNPNINEC IPYNCLSNPE VEVLGGERIE TGYTPIDISL SLTQFLLSEF VPGAGFVLGL   60
VDIIWGIFGP SQWDAFLVQI EQLINQRIEE FARNQAISRL EGLSNLYQIY AESFREWEAD  120
PTNPALREEM RIQFNDMNSA LTTAIPLLAV QNYQVPLLSV YVQAANLHLS VLRDVSVFGQ  180
RWGFDAATIN SRYNDLTRLI GNYTDYAVRW YNTGLERVWG PDSRDWVRYN QFRRELTLTV  240
LDIVALFPNY DSRRYPIRTV SQLTREIYTN PVLENFDGSF RGSAQGIERS IRSPHLMDIL  300
NSITIYTDAH RGYYYWSGHQ IMASPVGFSG PEFTFPLYGT MGNAAPQQRI VAQLGQGVYR  360
TLSSTLYRRP FNIGINNQQL SVLDGTEFAY GTSSNLPSAV YRKSGTVDSL DEIPPQNNNV  420
PPRQGFSHRL SHVSMFRSGF SNSSVSIIRA PMFSWIHRSA EFNNIIASDS ITQLPLVKAS  480
APVSGTTVLK GPGFTGGGIL RRTTNGTFGT LRVTVNSPLT QRYRVRVRFA SSGNFSIRIL  540
RGNTSIAYQR FGSTMNRGQE LTYASFVTSE FTTNQSDLPF TFTQAQENLT ILAEGVSTGS  600
EYFIDRIEII PVNPAREAEE DLERAQKAVN ALFTSTNQLG LKTNVTDYHI DQVSNLVTYL  660
SDEFCLDEKR ELSEKVKHAK RLSDERNLLQ DSNFKDINRQ PERGWGGSTG ITIQGGDDVF  720
KENYVTLSGT FDECYPTYLY QKIDESKLKA FTRYQLRGYI EDSQDLEIYL IRYNAKHETV  780
NVPGTGSLWP LSAQSPIGKC GEPNRCAPHL EWNPDLDCSC RDGEKCAHHS HHFSLDIDVG  840
CTDLNEDLGV WVIFKIKTQD GHARLGNLEF LEEKPLVGEA LARVKRAEKK WRDKREKLEW  900
ETNIVYKEAK ESVDALFVNS QYDQLQADTN IAMIHAADKR VHSIREAYLP ELSVIPGVNA  960
AIFEELEGRI FTAFSLYDAR NVIKNGDFNN GLSCWNVKGH VDVEEQNNQR SVLVVPEWEA 1020
EVSQEVRVCP GRGYILRVTA YKEGYGEGCV TIHEIENNTD ELKFSNCVEE EIYPNNTVTC 1080
NDYTVNQEEY GGAYTSRNRG YNEAPSVPAD YASVYEEKSY TDGRRENPCE FNRGYRDYTP 1140
LPVGYVTKEL EYFPETDKVW IEIGETEGTF IVDSVELLLM EE                    1182
```

```
SEQ ID NO: 78          moltype = DNA  length = 3534
FEATURE                Location/Qualifiers
misc_feature           1..3534
                       note = Chimeric coding sequence encoding TIC1103.
source                 1..3534
                       mol_type = other DNA
                       organism = synthetic construct
SEQUENCE: 78
atggataaca atccgaacat caatgaatgc attccttata attgtttaag taaccctgaa   60
gtagaagtat taggtggaga aagaatagaa actggttaca ccccaatcga tatttccttg  120
tcgctaacgc aatttctttt gagtgaattt gttcccggtg ctggatttgt gttaggacta  180
gttgtataa tatgggggaat ttttggtccc tctcaatgag acgcatttct tgtacaaatt  240
gaacagttaa ttaaccaaag aatagaagaa ttcgctagga accaagccat ttctagatta  300
gaaggactaa gcaatcttta tcaaatttac gcagaatctt ttagagagtg ggaagcagat  360
cctactaatc cagcattaag agaagagatg cgtattcaat tcaatgacat gaacagtgcc  420
cttacaaccg ctattcctct tttggcagtt caaaattatc aagttcctct tttatcagta  480
tatgttcaag ctgcaaattt acatttatca gttttgagag atgtttcagt gtttggacaa  540
aggtggggat ttgatgccgc gactatcaat agtcgttata atgatttaac taggcttatt  600
ggcaactata cagattatgc tgtacgctgg tacaatacgg gattagaacg tgtatgggga  660
ccggattcta gagattgggt aaggtataat caatttagaa gagaattaac actaactgta  720
ttagatatcg ttgctctgtt cccgaattat gatagtagaa gatatccaat tcgaacagtt  780
tcccaattaa caagagaaat ttatacaaac ccagtattag aaaattttga tggtagtttt  840
cgaggctcgg ctcagggcat agaaagaagt attaggagtc cacatttgat ggatatactt  900
aacagtataa ccatctatac ggatgctcat aggggttatt attattggtc agggcatcaa  960
ataatggctt ctcctgtcgg tttttcgggg ccagaattca tatttccgct atatggaact 1020
atgggaaatg cagctccaca acaacgtatt gttgctcaac taggtcaggg cgtgtataga 1080
acattatcgt ccactttata tagaagacct tttaatatag gtataaataa tcaacaacta 1140
tctgttcttg acgggacaga atttgcttat ggaacctcct caaatttgcc atccgctgta 1200
tacagaaaaa gcggaaacgg tagattcgct gatgaaatac cgccacagaa taacaacgtg 1260
ccacctaggc aaggatttag tcatcgatta agccatgttt caatgtttcg ttcaggcttt 1320
agtaatagta gtgtaagtat aataagagct cctatgttct cttggataca tcgtagtgct 1380
gaatttaata atataattgc atcggatagt attactcaac tacccatggt aaaggcaaat 1440
gctttacttt caggtacttc cgtgataaag ggtcctggat ctacaggggg agatatatta 1500
agaagaacaa gtgttggcag agtaggaaat tttaaggtta acgtaaatgg accattaaca 1560
caacgatatc ttgtaagaat tcgttatgct tctacaactg atgatctat ttacgtctat 1620
cgtgtggagta ccactgtaag taattataga tttaacaaaa caatgaataa gggagcttct 1680
ttaacttacg acattttaa atttgcaagt ttttctaccc ctttcacatt tacaaaaaca 1740
caagatgaat taggaatatc tatacaaaac tttagtagcg gtgaagaagt gtatatagac 1800
aggattgaag tcattccagt aggtacgaca tatgaagcgg aaacggattt agaaagagcg 1860
cagaggcgcg tgaatgcgct gtttacgtct acaaaccaac tagggctaaa aacaaatgta 1920
```

```
acggattatc atattgatca agtgtccaat ttagttacgt atttatcgga tgaatttttgt  1980
ctggatgaaa agcgagaatt gtccgagaaa gtcaaacatg cgaagcgact cagtgatgaa  2040
cgcaatttac tccaagattc aaatttcaaa gacattaata ggcaaccaga acgtgggtgg  2100
ggcggaagta cagggattac catccaagga ggggatgacg tatttaaaga aaaattacgtc  2160
acactatcag gtacctttga tgagtgctat ccaacatatt tgtatcaaaa aatcgatgaa  2220
tcaaaattaa aagcctttac ccgttatcaa ttaagagggt atatcgaaga tagtcaagac  2280
ttagaaatct atttaattcg ctacaatgca aaacatgaaa cagtaaatgt gccaggtacg  2340
ggttccttat ggccgctttc agcccaaagt ccaatcggaa agtgtggaga gccgaatcga  2400
tgcgcgccac accttgaatg gaatcctgac ttagattgtt cgtgtaggga tggagaaaag  2460
tgtgcccatc attcgcatca tttctcctta gacattgatg taggatgtac agacttaaat  2520
gaggacctag gtgtatgggt gatctttaag attaagacgc aagatgggca cgcaagacta  2580
gggaatctag agtttctcga agaaaaacca ttagtaggag aagcgctagc tcgtgtgaaa  2640
agagcggaga aaaaatggag agacaaacgt gaaaaattgg aatgggaaac aaatatcgtt  2700
tataaagagg caaaagaatc tgtagatgct ttatttgtaa actctcaata tgatcaatta  2760
caagcggata cgaatattgc catgattcat gcggcagata aacgtgttca tagcattcga  2820
gaagcttatc tgcctgagct gtctgtgatt ccgggtgtca atgcggctat ttttgaagaa  2880
ttagaagggc gtattttcac tgcattctcc ctatatgatg cgagaaatgt cattaaaaat  2940
ggtgatttta ataatggctt atcctgctgg aacgtgaaag ggcatgtaga tgtagaagaa  3000
caaaacaacc aacgttcggt ccttgttgtt ccggaatggg aagcagaagt gtcacaagaa  3060
gttcgtgtct gtccgggtcg tggctatatc cttcgtgtca cagcgtacaa ggagggatat  3120
ggagaaggtt gcgtaaccat tcatgagatc gagaacaata cagacgaact gaagtttagc  3180
aactgcgtag aggaggaaat ctatccaaat aacacggtaa cgtgtaatga ttatactgta  3240
aatcaagaag aatacggagg tgcgtacact tctcgtaatc gaggatataa cgaagctcct  3300
tccgtaccag ctgattatgc gtcagtctat gaagaaaaat cgtatacaga tggacgtaga  3360
gagaatcctt gtgaatttaa cagagggtat agggattaca cgccactacc agttggttat  3420
gtgacaaaag aattagaata cttcccagaa accgataagg tatggattga gattggagaa  3480
acggaaggaa cattatcgt ggacagcgtg gaattactcc ttatggagga ataa  3534
```

```
SEQ ID NO: 79              moltype = AA  length = 1177
FEATURE                    Location/Qualifiers
REGION                     1..1177
                           note = Amino acid sequence of the chimeric protein TIC1103.
source                     1..1177
                           mol_type = protein
                           organism = synthetic construct
SEQUENCE: 79
MDNNPNINEC IPYNCLSNPE VEVLGGERIE TGYTPIDISL SLTQFLLSEF VPGAGFVLGL  60
VDIIWGIFGP SQWDAFLVQI EQLINQRIEE FARNQAISRL EGLSNLYQIY AESFREWEAD  120
PTNPALREEM RIQFNDMNSA LTTAIPLLAV QNYQVPLLSV YVQAANLHLS VLRDVSVFGQ  180
RWGFDAATIN SRYNDLTRLI GNYTDYAVRW YNTGLERVWG PDSRDWVRYN QFRRELTLTV  240
LDIVALFPNY DSRRYPIRTV SQLTREIYTN PVLENFDGSF RGSAQGIERS IRSPHLMDIL  300
NSITIYTDAH RGYYYWSGHQ IMASPVGFSG PEFTFPLYGT MGNAAPQQRI VAQLGQGVYR  360
TLSSTLYRRP FNIGINNQQL SVLDGTEFAY GTSSNLPSAV YRKSGTVDSL DEIPPQNNNV  420
PPRQGFSHRL SHVSMPRSGF SNSSVSIIRA PMFSWIHRSA EFNNIIASDS ITQLPMVKAN  480
ALLSGTSVIK GPGSTGGDIL RRTSVGRVGN FKVNVNGPLT QRYLVRIRYA STTDLDFYVY  540
RGGTTVSNYR FNKTMNKGAS LTYDIFKFAS FSTPFTFTKT QDELGISIQN FSSGEEVYID  600
RIEVIPVGTT YEAETDLERA QKAVNALFTS TNQLGLKTNV TDYHIDQVSN LVTYLSDEFC  660
LDEKRELSEK VKHAKRLSDE RNLLQDSNFK DINRQPERGW GGSTGITIQG GDDVFKENYV  720
TLSGTFDECY PTYLYQKIDE SKLKAFTRYQ LRGYIEDSQD LEIYLIRYNA KHETVNVPGT  780
GSLWPLSAQS PIGKCGEPNR CAPHLEWNPD LDCSCRDGEK CAHHSHHFSL DIDVGCTDLN  840
EDLGVWVIFK IKTQDGHARL GNLEFLEEKP LVGEALARVK RAEKKWRDKR EKLEWETNIV  900
YKEAKESVDA LFVNSQYDQL QADTNIAMIH AADKRVHSIR EAYLPELSVI PGVNAAIFEE  960
LEGRIFTAFS LYDARNVIKN GDFNNGLSCW NVKGHVDVEE QNNQRSVLVV PEWEAEVSQE  1020
VRVCPGRGYI LRVTAYKEGY GEGCVTIHEI ENNTDELKFS NCVEEEIYPN NTVTCNDYTV  1080
NQEEYGGAYT SRNRGYNEAP SVPADYASVY EEKSYTDGRR ENPCEFNRGY RDYTPLPVGY  1140
VTKELEYFPE TDKVWIEIGE TEGTFIVDSV ELLLMEE                           1177
```

```
SEQ ID NO: 80              moltype = DNA  length = 3597
FEATURE                    Location/Qualifiers
misc_feature               1..3597
                           note = Chimeric coding sequence encoding TIC1101.
source                     1..3597
                           mol_type = other DNA
                           organism = synthetic construct
SEQUENCE: 80
atgaaaaaca gtatcaaatt atcagaactt tggtatttca atgaaagaaa atggaggtat  60
tttatggaga tagtgaataa tcagaatcaa tgcgtgcctt ataattgttt gaataatccc  120
gaaatcgaaa tattagaagg cggaagaata tcagttggta atacccccat tgatatttct  180
ctttcgctta ctcagtttct tttgagtgaa tttgtcccag gtgcggggt tgtattagga  240
ttaattgatt taatatgggg atttgtaggt ccttcccaat gggacgcatt tcttgctcaa  300
gtggaacagt taattaacca agaatagca gaagctgtaa gaaatacagc aattcaggaa  360
ttagagggaa tggcacgggt ttatagaacc tatgctactc tttttgctga gtgggaaaaa  420
gctcctgatg acccagagct aagagaagca ctacgtacac aatttacagc aactgagact  480
tatataagtg gaagaatatc cgtttttaaaa attcaaactt ttgaagtaca gctgttatca  540
gtgtttgccc aagctgcaaa tttacattta tctttattaa gagacgttgt gttttttggg  600
caaaagatggg gttttttcaac gacaaccgta ataattact acaatgattt aacagaaggg  660
attagtacct atacagatta tgctgtacgc tggtacaata cgggattaga acgtgtatgg  720
ggaccggatt ctagagattg ggtaaggtat aatcaattta agagagaatt aacactaact  780
gtattagata tcgttgctct gttcccgaat tatgatagta gaagatatcc aattcgaaca  840
```

```
gtttcccaat taacaagaga aatttataca aacccagtat tagaaaattt tgatggtagt   900
tttcgaggct cggctcaggg catagaaaga agtattagga gtccacattt gatggatata   960
cttaacagta taaccatcta tacgatgctc cataggggtt attattattg gtcagggcat   1020
caaataatgc cttctcctgt cggttttttcg gggccagaat tcacgtttcc gctatatgga   1080
accatgggaa atgcagctcc acaacaacgt attgttgctc aactaggtca gggcgtgtat   1140
agaacattat cgtccacttt atatagaaga ccttttaata tagggataaa taatcaacaa   1200
ctatctgttc ttgacgggac agaatttgct tatggaacct cctcaaattt gccatccgct   1260
gtatacagaa aaagcggaac ggtagattcg ctggatgaaa taccgccaca gaataacaac   1320
gtgccaccta ggcaaggatt tagtcatcga ttaagccatg tttcaatgtt tcgttcaggc   1380
tttagtaata gtagtgtaag tataataaga gctcctatgt tctcttggat acatcgtagt   1440
gctgaattta ataatataat tgcatcggat agtattactc aactacccat ggtaaaggca   1500
aatgctttac tttcaggtac ttccgtgata aagggtcctg gatctacagg gggagatata   1560
ttaagaagaa caagtgttgg cagagtagga aattttaagg ttaacgtaaa tggaccatta   1620
acacaacgat atcttgtaag aattcgttat gcttctacaa ctgatctaga cttttacgtc   1680
tatcgtggag gtaccactgt aagtaattat agatttaaca aaacaatgaa taaggggagct   1740
tctttaactt acgacatttt taaatttgca agttttttcta ccccctttcac atttacaaaa   1800
acacaagatg aattaggaat atctatacaa aactttagta gcggtgaaga agtgtatata   1860
gacaggattg aagtcattcc agtaggtacg acatatgaag cggaaacgga tttagaaaga   1920
gcgcagaagg cggtgaatgc gctgtttacg tctacaaacc aactagggct aaaaacaaat   1980
gtaacggatt atcatattga tcaagtgtcc aatttagtta cgtatttatc ggatgaattt   2040
tgtctggatg aaaagcgaga attgtccgag aaagtcaaac atgcgaagcg actcagtgat   2100
gaacgcaatt tactccaaga ttcaaatttc aaagacatta ataggcaacc agaacgtggg   2160
tggggcggaa gtacagggat taccatccaa ggagggggatg acgtatttaa agaaaattac   2220
gtcacactat caggtacctt tgatgagtgc tatccaacat atttgtatca aaaaatcgat   2280
gaatcaaaat taaaagcctt tacccgttat caattaagag ggtatatcga agatagtcaa   2340
gacttagaaa tctatttaat tcgctacaat gcaaaacatg aaacagtaaa tgtgccaggt   2400
acgggttcct tatggccgct ttcagcccaa agtccaatcg gaaagtgtgg agagccgaat   2460
cgatgcgcgc cacaccttga atggaatcct gacttagatt gttcgtgtag ggatggagaa   2520
aagtgtgccc atcattcgca tcatttctcc ttagacattg atgtaggatg tacagactta   2580
aatgagacc taggtgtatg ggtgatcttt aagattaaga cgcaagatgg gcacgcaaga   2640
ctagggaatc tagagtttct cgaagagaaa ccattagtag gagaagcgct agctcgtgtg   2700
aaaagagcgg agaaaaaatg gagagacaaa cgtgaaaaat tggaatggga aacaaatatc   2760
gtttataaag aggcaaaaga atctgtagat gctttatttg taaactctca atatgatcaa   2820
ttacaagcgg atacgaatat tgccatgatt catgcggcag ataaacgtgt tcatagcatt   2880
cgagaagctt atctgcctga gctgtctgtg attccgggtg tcaatgcggc tattttttgaa   2940
gaattagaag ggcgtatttt cactgcattc tccctatatg atgcgagaaa tgtcattaaa   3000
aatggtgatt ttaataatgg cttatcctgc tggaacgtga aagggcatgt agatgtagaa   3060
gaacaaaaca accaacgttc ggtccttgtt gttccggaat gggaagcaga agtgtcacaa   3120
gaagttcgtg tctgtccggg tcgtggctat atccttcgtg tcacagcgta caaggaggga   3180
tatggagaag gttgcgtaac cattcatgag atcgagaaca atacagacga actgaagttt   3240
agcaactgcg tagaagagga aatctatcca aataacacgg taacgtgtaa tgattatact   3300
gtaaatcaag aagaatacgg aggtgcgtac acttctcgta tcgaggata taacgaagct   3360
ccttccgtac cagctgatta tgcgtcagtc tatgaagaaa aatagtatggat tgagattgga   3420
agagagaatc cttgtgaatt taacagaggg tataggggatt acacgccact accagttggt   3480
tatgtgacaa aagaattaga atacttccca gaaaccgata aggtatggat tgagattgga   3540
gaaacggaag aacatttat cgtggacagc gtggaattac tccttatgga ggaatag       3597
```

SEQ ID NO: 81         moltype = AA  length = 1198
FEATURE               Location/Qualifiers
REGION                1..1198
                      note = Amino acid sequence of the chimeric protein TIC1101.
source                1..1198
                      mol_type = protein
                      organism = synthetic construct
SEQUENCE: 81
MKNSIKLSEL WYFNERKWRY FMEIVNNQNQ CVPYNCLNNP EIEILEGGRI SVGNTPIDIS   60
LSLTQFLLSE FVPGAGFVLG LIDLIWGFVG PSQWDAFLAQ VEQLINQRIA EAVRNTAIQE   120
LEGMARVYRT YATAFAEWEK APDDPELREA LRTQFTATET YISGRISVLK IQTFEVQLLS   180
VFAQAANLHL SLLRDVVFFG QRWGFSTTTV NNYYNDLTEG ISTYTDYAVR WYNTGLERVW   240
GPDSRDWVRY NQFRRELTLT VLDIVALFPN YDSRRYPIRT VSQLTREIYT NPVLENFDGS   300
FRGSAQGIER SIRSPHLMDI LNSITIYTDA HRGYYYWSGH QIMASPVGFS GPEFTFPLYG   360
TMGNAAPQQR IVAQLGQGVY RTLSSTLYRR PFNIGINNQQ LSVLDGTEFA YGTSSNLPSA   420
VYRKSGTVDS LDEIPPQNNN VPPRQGFSHR LSHVSMFRSG FSNSSVSIIR APMFSWIHRS   480
AEFNNIIASD SITQLPMVKA NALLSGTSVI KGPGSTGGDI LRRTSVGRVG NFKVNVNGPL   540
TQRYLVRIRY ASTTDLDFYV YRGGTTVSNY RFNKTMNKGA SLTYDIFKFA SFSTPFTFTK   600
TQDELGISIQ NFSSGEEVYI DRIEVIPVGT TYEAETDLER AQKAVNALFT STNQLGLKTN   660
VTDYHIDQVS NLVTYLSDEF CLDEKRELSE KVKHAKRLSD ERNLLQDSNF KDINRQPERG   720
WGGSTGITIQ GGDDVFKENY VTLSGTFDEC YPTYLYQKID ESKLKAFTRY QLRGYIEDSQ   780
DLEIYLIRYN AKHETVNVPG TGSLWPLSAQ SPIGKCGEPN RCAPHLEWNP DLDCSCRDGE   840
KCAHHSHHFS LDIDVGCTDL NEDLGVVWIF KIKTQDGHAR LGNLEFLEEK PLVGEALARV   900
KRAEKKWRDK REKLEWETNI VYKEAKESVD ALFVNSQYDQ LQADTNIAMI HAADKRVHSI   960
REAYLPELSV IPGVNAAIFE ELEGRIFTAF SLYDARNVIK NGDFNNGLSC WNVKGHVDVE   1020
EQNNQRSVLV VPEWEAEVSQ EVRVCPGRGY ILRVTAYKEG YGEGCVTIHE IENNTDELKF   1080
SNCVEEEIYP NNTVTCNDYT VNQEEYGGAY TSRNRGYNEA PSVPADYASV YEEKSYTDGR   1140
RENPCEFNRG YRDYTPLPVG YVTKELEYFP ETDKVWIEIG ETEGTFIVDS VELLLMEE    1198

SEQ ID NO: 82         moltype = DNA  length = 3573
FEATURE               Location/Qualifiers
misc_feature          1..3573

-continued

```
                             note = Chimeric coding sequence encoding TIC845.
source                       1..3573
                             mol_type = other DNA
                             organism = synthetic construct
SEQUENCE: 82
atgacttcaa ataggaaaaa tgagaatgaa attataaatg ctttatcgat tccaacggta   60
tcgaatcctt ccacgcaaat gaatctatca ccagatgctc gtattgaaga tagcttgtgt  120
gtagccgagg tgaacaatat tgatccattt gttagcgcat caacagtcca aacgggtata  180
aacatagctg gtagaaatatt gggcgtatta ggtgtgccgt ttgctggaca actagctagt  240
ttttatagtt ttcttgttgg ggaattatgt cctagtggca gagatccatg ggaaattttc  300
ctggaacatg tagaacaact tataagacaa caagtaacag aaaatactag gaatacggct  360
attgctcgat tagaaggtct aggaagaggc tatagatctt accagcaggc tcttgaaact  420
tggttagata accgaaatga tgcaagatca agaagcatta ttcttgagcg ctatgttgct  480
ttagaacttg acattactac tgctataccg cttttcaggt tacgaaatga agaagttcca  540
ttattaatgg tatatgctca agctgcaaat ttacacctat tattattgag agacgcatcc  600
ctttttggta gtgaatgggg gatggcatct tccgatgtta accaatatta ccaagaacaa  660
atcagatata cagaggaata ttctaaccat tgcgtacaat ggtataatac agggctaaat  720
aacttaagag ggacaaatgc tgaaagttgg ttgcggtata atcaattccg tagagaccta  780
acgttagggg tattagattt agtagcccta ttcccaagct atgatactcg cacttatcca  840
atcaatacga gtgctcagtt aacaagagaa atttatacag atccaattgg gagaacaaat  900
gcaccttcag gatttgcaag tacgaattgg tttaataata atgcaccatc gttttctgcc  960
atagaggctg ccattttcag gcctccgcat ctacttgatt ttccagaaca acttacaatt 1020
tacagtgcat caagccgttg gagtagcact caacatatga attattgggt gggacatagg 1080
cttaacttcc gcccaatagg agggacatta aatacctcaa cacaaggact tactaataat 1140
acttcaatta atcctgtaac attacagttt acgtctcgag acgtttatag aacagaatca 1200
aatgcaggga caaatatact atttactact cctgtgaatg gagtaccttg ggctagattt 1260
aattttataa accctcagaa tatttatgaa agaggcgcca ctacctcag tcaaccgtat 1320
cagggagttg ggattcaatt atttgattca gaaactgaat taccaccaga aacaacagaa 1380
cgaccaaatt atgaatcata tagtcataga ttatctcata taggactaat cataggaaac 1440
actttgagag caccagtcta ttcttggacg catcgtaggt cagatcgtac gaacataatt 1500
gcatcggata gtattactca aatccctgca gtgaagggaa actttctttt taatggttct 1560
gtaatttcag gaccaggatt tactggtggg gacttagtta gattaaatag tagtggaaat 1620
aacattcaga atagagggta tattgaagtt ccaattcact tcccatcgac atctaccaga 1680
tatcgagttc gtgtacggta tgcttctgta accccgattc acctcaacgt taattggggt 1740
aattcatcca tttttttccaa tacagtacca gctacagcta cgtcattaga taatctacaa 1800
tcaagtgatt ttggttattt tgaaagtgcc aatgctttta catcttcatt aggtaatata 1860
gtaggtgtta gaaattttag tgggactgca ggagtgataa tagacagatt tgaatttatt 1920
ccagttactg caacactcga ggctgaatat aatctggaaa gagcacaaaa ggcggtgaat 1980
gagctgttta cttcttccaa tcaaatcggg ttaaaaacag atgtgacgga ttatcatatt 2040
gatcaagtat ccaatttagt tgagtgttta tctgatgaat tttgtctgga tgaaaaaaaa 2100
gaattgtccg agaaagtcaa acatgcgaag cgacttagtg atgagcggaa tttacttcaa 2160
gatccaaact ttagagggat caatagacaa ctagaccgtg gctggagagg aagtacggat 2220
attaccatcc aaggaggcga tgacgtattc aaagagaatt acgttacgct attgggtacc 2280
tttgatgagt gctatccaac gtatttatat caaaaaatga atgagtcgaa attaaaagcc 2340
tatacccgtt accaattaag agggtatatc gaagatagtc aagacttaga aatctattta 2400
attcgctaca atgccaaaca cgaaacagta aatgtgccag gtacgggttc cttatggccg 2460
ctttcagccc caagtccaat cggaaaatgt gcccatcatt cccatcattt ctccttggac 2520
attgatgttg gatgtacaga cttaaatgag gacttaggtg tatgggtgat attcaagatt 2580
aagacgcaag atggccatgc aagactagga aatctagaat ttctcgaaga gaaaccatta 2640
gtaggagaag cactagctcg tgtgaaaaga gcggagaaaa aatggagaga caaacgtgaa 2700
aaattggaat gggaaacaaa tattgtttat aaagaggcaa aagaatctgt agatgcttta 2760
tttgtaaact ctcaatatga tagattacaa gcggatacca acatcgcgat gattcatgcg 2820
gcagataaac gcgttcatag cattcgagaa gcttatctgc ctgagctgtc tgtgattccg 2880
ggtgtcaatg cggctatttt tgaagaatta gaagggcgta ttttcactgc attctcccta 2940
tatgatgcga gaaatgtcat taaaaatggt gattttaata atggcttatc ctgctggaac 3000
gtgaaagggc atgtagatgt agaagaacaa aacaaccacc gttcggtcct tgttgttccg 3060
gaatgggaag cagaagtgtc acaagaagtt cgtgtctgtc cgggtcgtgg ctatatcctt 3120
cgtgtcacag cgtacaagga gggatatgga gaaggttgcg taaccattca tgagatcgag 3180
aacaatacag acgaactgaa gtttagcaac tgtgtagaag aggaagtata tccaaacaac 3240
acggtaacgt gtaatgatta tactgcgact caagaagaat atgagggtac gtacacttct 3300
cgtaatcgag gatatgacgg agcctatgaa agcaattctt ctgtaccagc tgattatgca 3360
tcagcctatg aagaaaaagc atatacagat ggacgaagag acaatccttg tgaatctaac 3420
agaggatatg gggattacac accactacca gctggctatg tgacaaaaga attagagtac 3480
ttcccagaaa ccgataaggt atggattgag atcggagaaa cggaaggaac attcatcgtg 3540
gacagcgtgg aattacttct tatggaggaa tag                                3573

SEQ ID NO: 83            moltype = AA   length = 1190
FEATURE                  Location/Qualifiers
REGION                   1..1190
                         note = Amino acid sequence of the chimeric protein TIC845.
source                   1..1190
                         mol_type = protein
                         organism = synthetic construct
SEQUENCE: 83
MTSNRKNENE IINALSIPTV SNPSTQMNLS PDARIEDSLC VAEVNNIDPF VSASTVQTGI   60
NIAGRILGVL GVPFAGQLAS FYSFLVGELW PSGRDPWEIF LEHVEQLIRQ QVTENTRNTA  120
IARLEGLGRG YRSYQQALET WLDNRNDARS RSIILERYVA LELDITTAIP LFRIRNEEVP  180
LLMVYAQAAN LHLLLLRDAS LFGSEWGMAS SDVNQYYQEQ IRYTEEYSNH CVQWYNTGLN  240
NLRGTNAESW LRYNQFRRDL TLGVLDLVAL FPSYDTRTYP INTSAQLTRE IYTDPIGRTN  300
```

-continued

```
APSGFASTNW FNNNAPSFSA IEAAIFRPPH LLDFPEQLTI YSASSRWSST QHMNYWVGHR  360
LNFRPIGGTL NTSTQGLTNN TSINPVTLQF TSRDVYRTES NAGTNILFTT PVNGVPWARF  420
NFINPQNIYE RGATTYSQPY QGVGIQLFDS ETELPPETTE RPNYESYSHR LSHIGLIIGN  480
TLRAPVYSWT HRSADRTNII ASDSITQIPA VKGNFLFNGS VISGPGFTGG DLVRLNSSGN  540
NIQNRGYIEV PIHFPSTSTR YRVRVRYASV TPIHLNVNWG NSSIFSNTVP ATATSLDNLQ  600
SSDFGYFESA NAFTSSLGNI VGVRNFSGTA GVIIDRFEFI PVTATLEAEY NLERAQKAVN  660
ELFTSSNQIG LKTDVTDYHI DQVSNLVECL SDEFCLDEKK ELSEKVKHAK RLSDERNLLQ  720
DPNFRGINRQ LDRGWRGSTD ITIQGGDDVF KENYVTLLGT FDECYPTYLY QKIDESKLKA  780
YTRYQLRGYI EDSQDLEIYL IRYNAKHETV NVPGTGSLWP LSAPSPIGKC AHHSHHFSLD  840
IDVGCTDLNE DLGVWVIFKI KTQDGHARLG NLEFLEEKPL VGEALARVKR AEKKWRDKRE  900
KLEWETNIVY KEAKESVDAL FVNSQYDRLQ ADTNIAMIHA ADKRVHSIRE AYLPELSVIP  960
GVNAAIFEEL EGRIFTAFSL YDARNVIKNG DFNNGLSCWN VKGHVDVEEQ NNHRSVLVVP  1020
EWEAEVSQEV RVCPGRGYIL RVTAYKEGYG EGCVTIHEIE NNTDELKFSN CVEEEVYPNN  1080
TVTCNDYTAT QEEYEGTYTS RNRGYDGAYE SNSSVPADYA SAYEEKAYTD GRRDNPCESN  1140
RGYGDYTPLP AGYVTKELEY FPETDKVWIE IGETEGTFIV DSVELLLMEE          1190

SEQ ID NO: 84           moltype = DNA  length = 3567
FEATURE                 Location/Qualifiers
misc_feature            1..3567
                        note = Chimeric coding sequence encoding TIC846.
source                  1..3567
                        mol_type = other DNA
                        organism = synthetic construct
SEQUENCE: 84
atgacttcaa ataggaaaaa tgagaatgaa attataaatg ctttatcgat tccaacggta  60
tcgaatcctt ccacgcaaat gaatctatca ccagatgctc gtattgaaga tagcttgtgt  120
gtagccgagg tgaacaatat tgatccattt gttagcgcat caacagtcca aacgggtata  180
aacatagctg gtagaatatt gggcgtatta ggtgtgccgt ttgctggaca actagctagt  240
ttttatagtt ttcttgttgg ggaattatgg cctagtggca gagatccatg ggaaattttc  300
ctggaacatg tagaacaact tataagacaa caagtaacag aaaatactag gaatacggct  360
attgctcgat tagaaggtct aggaagaggc tatagatctt accagcaggc tcttgaaact  420
tggttagata accgaaatga tgcaagatca agaagcatta ttcttgagcg ctatgttgct  480
ttagaacttg acattactac tgctataccg cttttcagaa tacgaaatga agaagttcca  540
ttattaatgg tatatgctca agctgcaaat ttacacctat tattattgag agacgcatcc  600
cttttggta gtgaatgggg gatggcatct tccgatgtta accaatatta ccaagaacaa  660
atcagatata cagaggaata ttctaaccat tgcgtacaat ggtataatac agggctaaat  720
aacttaagag ggacaaatgc tgaaagttgg ttgcggtata tcaattccg tagagaccta  780
acgttagggg tattagattt agtagcccta ttcccaagct atgatactcg cacttatcca  840
atcaatacga gtgctcagtt aacaagagaa atttatacag atccaattgg gagaacaaat  900
gcaccttcag gatttgcaag tacgaattgg tttaataata atgcaccatc gtttctgcc  960
atagaggctg ccattttcag gcctccgcat ctacttgatt ttccagaaca acttacaatt  1020
tacagtgcat caagccgttg gagtagcact caacatatga attattgggt gggacatagg  1080
cttaacttcc gcccaatagg agggacatta aatacctcaa cacaaggact tactaataat  1140
acttcaatta atcctgtaac attacagttt acgtctcgag acgtttatag aacagaatca  1200
aatgcaggga caaatatact atttactact cctgtgaatg gagtaccttg ggctagattt  1260
aattttataa accctcagaa tatttatgaa agaggcgcca ctacctacag tcaaccgtat  1320
cagggagttg ggattcaatt atttgattca gaaactgaat taccaccaga aacaacagaa  1380
cgaccaaatt atgaatcata tagtcataga ttatctcata taggactaat cataggaaac  1440
actttgagag caccagtcta ttcttggacg catcgtagtg cagatcgtac gaatacgatt  1500
ggaccaaata gaattacaca ataccattg gtaaagcac tgaatcttca ttcaggtgtt  1560
actgttgttg gagggccagg atttacaggt ggagatatcc ttcgaagaac gaatactggc  1620
acatttgcag atatgagagt aaatattact gggccattat cccaaagata tcgtgtaaga  1680
attcgctatg cttctacgac agatttacaa tttttcacga gaatcaatgg aacttctgta  1740
aatcaaggta atttccaaag aactatgaat agaggggata atttagaatc tggaaacttt  1800
aggactgcag gatttagtac gccttttagt ttttcaaatg cgcaaagtac attcacattg  1860
ggtactcagg cttttttcaaa tcaggaagtt tatatagatc gaattgaatt tgtcccggca  1920
gaagtaaacat tcgaggcaga atctgattta gaaagagcac aaaaggcggt gaatgagctg  1980
tttacttctt ccaatcaaat cgggttaaaa acagatgtga cggattatca tattgatcaa  2040
gtatccaatt tagttgagtg tttatctgat gaattttgtc tggatgaaaa aaaagaattg  2100
tccgagaaag tcaaacatgc gaagcgactt agtgatgagc ggaatttact tcaagatcca  2160
aactttagag ggatcaatag acaactagac cgtggctgga gaggaagtac ggatattacc  2220
atccaaggag gcgatgacgt attcaaagag aattacgtta cgctattggg tacctttgat  2280
gagtgctatc caacgtattt atatcaaaaa atagatgagt cgaaattaaa agcctatacc  2340
cgttaccaat taagagggta tatcgaagat agtcaagact tagaaatcta tttaattcgc  2400
tacaatgcca aacacgaaac agtaaatgtg ccaggtacgg gttccttatg gccgctttca  2460
gccccaagtc caatcggaaa atgtgcccat cattcccatc attttctcctt ggacattgat  2520
gttggatgta cagacttaaa tgaggactta ggtgtatggg tgatattcaa gattaagacg  2580
caagatggcc atgcaagact aggaaatcta gaatttctcg aagagaaacc attagtagga  2640
gaagcactag ctcgtgtgaa aagagcggag aaaaaatgga gagcaaacg tgaaaaattg  2700
gaatgggaaa caaatattgt ttataaagag gcaaaagaat ctgtagatgc tttatttgta  2760
aactctcaat atgatagatt acaagcggat accaacatcg cgatgattca tgcggcagat  2820
aaacgcgttc atagcattcg agaagcttat ctgcctgagc tgtctgtgat tccgggtgtc  2880
aatgcggcta ttttgaaga attagaaggg cgtatttca ctgcattctc cctatatgat  2940
gcgagaaatg tcattaaaaa tggtgatttt aataatggct atctcctgtc gaacgtgaaa  3000
gggcatgtag atgtagaaga acaaaacaac caccgttcgg tccttgttgt tccggaatgg  3060
gaagcagaag tgtcacaaga agttcgtgtc tgtccgggtc gtggctatat ccttcgtgtc  3120
acagcgtaca aggagggata tggagaaggt tgcgtaacca ttcatgagat cgagaacaat  3180
acagacgaac tgaagtttag caactgtgta gaagaggaag tatatccaaa caacacggta  3240
acgtgtaatg attatactgc gactcaagaa gaatatgagg gtacgtacac ttctcgtaat  3300
```

```
cgaggatatg acggagccta tgaaagcaat tcttctgtac cagctgatta tgcatcagcc    3360
tatgaagaaa aagcatatac agatggacga agagacaatc cttgtgaatc taacagagga    3420
tatgggggatt acacaccact accagctggc tatgtgacaa aagaattaga gtacttccca    3480
gaaaccgata aggtatggat tgagatcgga gaaacggaag gaacattcat cgtggacagc    3540
gtggaattac ttcttatgga ggaatag                                        3567
```

```
SEQ ID NO: 85            moltype = AA  length = 1188
FEATURE                  Location/Qualifiers
REGION                   1..1188
                         note = Amino acid sequence of the chimeric protein TIC846.
source                   1..1188
                         mol_type = protein
                         organism = synthetic construct
SEQUENCE: 85
MTSNRKNENE IINALSIPTV SNPSTQMNLS PDARIEDSLC VAEVNNIDPF VSASTVQTGI    60
NIAGRILGVL GVPFAGQLAS FYSFLVGELW PSGRDPWEIF LEHVEQLIRQ QVTENTRNTA   120
IARLEGLGRG YRSYQQALET WLDNRNDARS RSIILERYVA LELDITTAIP LFRIRNEEVP   180
LLMVYAQAAN LHLLLLRDAS LFGSEWGMAS SDVNQYYQEQ IRYTEEYSNH CVQWYNTGLN   240
NLRGTNAESW LRYNQFRRDL TLGVLDLVAL FPSYDTRTYP INTSAQLTRE IYTDPIGRTN   300
APSGFASTNW FNNNAPSFSA IEAAIFRPPH LLDFPEQLTI YSASSRWSST QHMNYWVGHR   360
LNFRPIGGTL NTSTQGLTNN TSINPVTLQF TSRDVYRTES NAGTNILFTT PVNGVPWARF   420
NFINPQNIYE RGATTYSQPY QGVGIQLFDS ETELPPETTE RPNYESYSHR LSHIGLIIGN   480
TLRAPVYSWT HRSADRTNTI GPNRITQIPL VKALNLHSGV TVVGGPGFTG GDILRRTNTG   540
TFADMRVNIT GPLSQRYRVR IRYASTTDLQ FFTRINGTSV NQGNFQRTMN RGDNLESGNF   600
RTAGFSTPFS FSNAQSTFTL GTQAFSNQEV YIDRIEFVPA EVTFEAESDL ERAQKAVNEL   660
FTSSNQIGLK TDVTDYHIDQ VSNLVECLSD EFCLDEKKEL SEKVKHAKRL SDERNLLQDP   720
NFRGINRQLD RGWRGSTDIT IQGGDDVFKE NYVTLLGTFD ECYPTYLYQK IDESKLKAYT   780
RYQLRGYIED SQDLEIYLIR YNAKHETVNV PGTGSLWPLS APSPIGKCAH HSHHFSLDID   840
VGCTDLNEDL GVWVIFKIKT QDGHARLGNL EFLEEKPLVG EALARVKRAE KKWRDKREKL   900
EWETNIVYKE AKESVDALFV NSQYDRLQAD TNIAMIHAAD KRVHSIREAY LPELSVIPGV   960
NAAIFEELEG RIFTAFSLYD ARNVIKNGDF NNGLSCWNVK GHVDVEEQNN HRSVLVVPEW  1020
EAEVSQEVRV CPGRGYILRV TAYKEGYGEG CVTIHEIENN TDELKFSNCV EEEVYPNNTV  1080
TCNDYTATQE EYEGTYTSRN RGYDGAYESN SSVPADYASA YEEKAYTDGR RDNPCESNRG  1140
YGDYTPLPAG YVTKELEYFP ETDKVWIEIG ETEGTFIVDS VELLLMEE              1188
```

```
SEQ ID NO: 86            moltype = DNA  length = 3570
FEATURE                  Location/Qualifiers
misc_feature             1..3570
                         note = Chimeric coding sequence encoding TIC858.
source                   1..3570
                         mol_type = other DNA
                         organism = synthetic construct
SEQUENCE: 86
atgacttcaa ataggaaaaa tgagaatgaa attatataaatg ctttatcgat tccaacggta    60
tcgaatcctt ccacgcaaat gaatctatca ccagatgctc gtattgaaga tagcttgtgt   120
gtagccgagg tgaacaatat tgatccattt gttagcgcat caacagtcca aacgggtata   180
aacatagctg gtagaatatt gggcgtatta ggtgtgccta ttgctggaca actagctagt   240
ttttatagtt ttcttgttgg ggaattatgg cctagtggca gagatccatg ggaaattttc   300
ctggaacatg tagaacaact tataagacaa caagtaacag aaaatactag gaatacggct   360
attgctcgat tagaaggtct aggaagaggc tatagatctt accagcaggc tcttgaaact   420
tggttagata accgaaatga tgcaagatca agaagcatta ttcttgagcg ctatgttgct   480
ttagaacttg acattactac tgctataccg ctttttcagaa tacgaaatga agaagttcca   540
ttattaatgg tatatgctca agctgcaaat ttacacctat tattattgag agacgcatcc   600
ctttttggta gtgaatgggg gatggcatct tccgatgtta accaatatta ccaagaacaa   660
atcagatata cagaggaata ttctaaccat tgcgtacaat ggtataaatac agggctaaat   720
aacttaagag ggacaaatgc tgaaagttgg ttgcggtata atcaattccg tagagaccta   780
acgttagggg tattagattt agtagcccta ttcccaagct atgatactcg cacttatcca   840
atcaatacga gtgctcagtt aacaagagaa atttatacag atccaattgg gagaacaaat   900
gcaccttcag gatttgcaag tacgaattgg tttaataata atgcaccatc gttttctgcc   960
atagaggctg ccattttcag gcctccgcat ctacttgatt ttccagaaca acttacaatt  1020
tacagtgcat caagccgttg gagtagcact caacatatga attattgggt gggacatagg  1080
cttaacttcc gcccaatagg agggacatta aatacctcaa cacaaggact tactaataat  1140
acttcaatta atcctgtaac attacagttt acgtctcgag acgtttatag aacagaatca  1200
aatgcaggga caaatatact atttactact cctgtgaatg ggtgaccttg ggctagattt  1260
aattttataa accctcagaa tatttatgaa agaggcgcca ctacctcag tcaaccgtat  1320
cagggagttg ggattcaatt atttgattca gaaactgaat taccaccaga aacaacagaa  1380
cgaccaaatt atgaatcata tagtcataga ttatctcata taggactaat cataggaaac  1440
actttgagag caccagtcta ttcttggacg catcgtagtg cagatcgtac gaatacgatt  1500
ggaccaaata gaattaccca aatcccaatg gtaaaagcat ccgaacttcc tcaaggtacc  1560
actgttgtta gaggaccagg atttactggt ggggatattc ttcgaagaac gaatactggt  1620
ggatttggac cgataagagt aactgttaac ggaccattaa cacaaagata tcgtatagga  1680
ttccgctatg cttcaactgt agattttgat ttctttgtat cacgtggagg tactactgta  1740
aataatttta gattcctacg tacaatgaac agtggagacg aactaaaata cggaaatttt  1800
gtgagacgtg cttttactac aacttttact tttcacacaa ttcaagatat aattcgaacg  1860
tctattcaag gccttagtgg aaatggggaa gtgtatatag ataaaattga aattattcca  1920
gttactgcaa ccttcgaagc agaatatgat ttagaaagag cacaaaaggc ggtgaatgag  1980
ctgtttactt cttccaatca aatcgggtta aaaacagatg tgacggatta tcatattgat  2040
caagtatcca atttagttga gtgtttatct gatgaatttt gtctggatga aaaaaaagaa  2100
ttgtccgaga aagtcaaaca tgcgaagcga cttagtgatg agcggaattt acttcaagat  2160
```

```
ccaaacttta gagggatcaa tagacaacta gaccgtggct ggagaggaag tacggatatt  2220
accatccaag gaggcgatga cgtattcaaa gagaattacg ttacgctatt gggtaccttt  2280
gatgagtgct atccaacgta tttatatcaa aaaatagatg agtcgaaatt aaaagcctat  2340
acccgttacc aattaagagg gtatatcgaa gatagtcaag acttagaaat ctatttaatt  2400
cgctacaatg ccaaacacga aacagtaaat gtgccaggta cgggttcctt atggccgctt  2460
tcagccccaa gtccaatcgg aaaatgtgcc catcattccc atcatttctc cttggacatt  2520
gatgttggat gtacagactt aaatgaggac ttaggtgtat gggtgatatt caagattaag  2580
acgcaagatg gccatgcaag actaggaaat ctagaatttc tcgaagagaa accattagta  2640
ggagaagcac tagctcgtgt gaaaagagcg gagaaaaaat ggagagacaa acgtgaaaaa  2700
ttggaatggg aaacaaatat tgtttataaa gaggcaaaag aatctgtaga tgctttattt  2760
gtaaactctc aatatgatag attacaagcg gataccaaca tcgcgatgat tcatgcggca  2820
gataaacgcg ttcatagcat tcgagaagct tatctgcctg agctgtctgt gattccgggt  2880
gtcaatgcgg ctatttttga agaattagaa gggcgtattt tcactgcatt ctccctatat  2940
gatgcgagaa atgtcattaa aaatggtgat tttaataatg gcttatcctg ctggaacgtg  3000
aaagggcatg tagatgtaga agaacaaaac aaccaccgtt cggtccttgt tgttccggaa  3060
tgggaagcag aagtgtcaca agaagttcgt gtctgtccgg gtcgtggcta tatccttcgt  3120
gtcacagcgt acaaggaggg atatggagaa ggttgcgtaa ccattcatga gatcgagaac  3180
aatacaacg aactgaagtt tagcaactgt gtagaagagg aagtatatcc aaacaacacg  3240
gtaacgtgta atgattatac tgcgactcaa gaagaatatg agggtacgta cacttctcgt  3300
aatcgaggat atgacggagc ctatgaaagc aattcttctg taccagctga ttatgctatca  3360
gcctatgaag aaaaagcata tacagatgga cgaagagaca atccttgtga atctaacaga  3420
ggatatgggg attacacacc actaccagct ggctatgtga caaaagaatt agagtacttc  3480
ccagaaaccg ataaggtatg gattgagatc ggagaaacgg aaggaacatt catcgtggac  3540
agcgtggaat tacttcttat ggaggaatag                                    3570
```

```
SEQ ID NO: 87          moltype = AA   length = 1189
FEATURE                Location/Qualifiers
REGION                 1..1189
                       note = Amino acid sequence of the chimeric protein TIC858.
source                 1..1189
                       mol_type = protein
                       organism = synthetic construct
SEQUENCE: 87
MTSNRKNENE IINALSIPTV SNPSTQMNLS PDARIEDSLC VAEVNNIDPF VSASTVQTGI  60
NIAGRILGVL GVPFAGQLAS FYSFLVGELW PSGRDPWEIF LEHVEQLIRQ QVTENTRNTA  120
IARLEGLGRG YRSYQQALET WLDNRNDARS RSIILERYVA LELDITTAIP LFRIRNEEVP  180
LLMVYAQAAN LHLLLLRDAS LFGSEWGMAS SDVNQYYQEQ IRYTEEYSNH CVQWYNTGLN  240
NLRGTNAESW LRYNQFRRDL TLGVLDLVAL FPSYDTRTYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTQGLTNN TSINPVTLQF TSRDVYRTES NAGTNILFTT PVNGVPWARF  420
NFINPQNIYE RGATTYSQPY QGVGIQLFDS ETELPPETTE RPNYESYSHR LSHIGLIIGN  480
TLRAPVYSWT HRSADRTNTI GPNRITQIPM VKASELPQGT TVVRGPGFTG GDILRRTNTG  540
GFGPIRVTVN GPLTQRYRIG FRYASTVDFD FFVSRGGTTV NNFRFLRTMN SGDELKYGNF  600
VRRAFTTPFT FTQIQDIIRT SIQGLSGNGE VYIDKIEIIP VTATFEAEYD LERAQKAVNE  660
LFTSSNQIGL KTDVTDYHID QVSNLVECLS DEFCLDEKKE LSEKVKHAKR LSDERNLLQD  720
PNFRGINRQL DRGWRGSTDI TIQGGDDVFK ENYVTLLGTF DECYPTYLYQ KIDESKLKAY  780
TRYQLRGYIE DSQDLEIYLI RYNAKHETVN VPGTGSLWPL SAPSPIGKCA HHSHHFSLDI  840
DVGCTDLNED LGVWVIFKIK TQDGHARLGN LEFLEEKPLV GEALARVKRA EKKWRDKREK  900
LEWETNIVYK EAKESVDALF VNSQYDRLQA DTNIAMIHAA DKRVHSIREA YLPELSVIPG  960
VNAAIFEELE GRIFTAFSLY DARNVIKNGD FNNGLSCWNV KGHVDVEEQN NHRSVLVVPE  1020
WEAEVSQEVR VCPGRGYILR VTAYKEGYGE GCVTIHEIEN NTDELKFSNC VEEEVYPNNT  1080
VTCNDYTATQ EEYEGTYTSR NRGYDGAYES NSSVPADYAS AYEEKAYTDG RRDNPCESNR  1140
GYGDYTPLPA GYVTKELEYF PETDKVWIEI GETEGTFIVD SVELLLMEE           1189
```

```
SEQ ID NO: 88          moltype = DNA   length = 3570
FEATURE                Location/Qualifiers
misc_feature           1..3570
                       note = Chimeric coding sequence encoding TIC865.
source                 1..3570
                       mol_type = other DNA
                       organism = synthetic construct
SEQUENCE: 88
atgacttcaa ataggaaaaa tgagaatgaa attatalaatg ccttatcgat tccagctgta  60
tcgaatcatt ccgcacaaat ggatctatcg ctagatgctc gtattgagga ttctttgtgt  120
atagccgagg ggaataatat caatccactt gttagcgcat caacagtcca aacgggtata  180
aacatagctg gtagaatatt gggcgtatta ggtgtgccgt ttgctggaca actagctagt  240
ttttatagtt ttcttgttgg ggaattatgg cctagtggca gagatccatg ggaaattttc  300
ctggaacatg tagaacaact tataaagacaa caagtaacag aaaatactag gaatacggct  360
attgctcgat tagaaggtct aggaagaggc tatagatctt accagcaggc tcttgaaact  420
tggttagata accgaaatga tgcaagatca agaagcatta ttcttgagcg ctatgttgct  480
ttagaacttg acattactac tgctataccg ctttttcagaa tacgaaatga agaagttcca  540
ttattaatgt tatatgctca agctgcaaat ttacacctat tattattgag agacgcatcc  600
cttttttggta gtgaatgggg gatggcatct tccgatgtta accaatatta ccaagaacaa  660
atcagatata cagaggaata ttctaaccat tgcgtacaat ggtataacac agggctaaat  720
aacttaagag ggacaaatgc tgaaagttgg ttgcggtata tcaattccg tagagaccta  780
acgttagggg tattagattt agtagcccta ttcccaagct atgatactcg cacttatcca  840
atcaatacga gtgctcagtt aacaagagaa atttatacag atccaattgg gagaacaaat  900
gcaccttcag gatttgcaag tacgaattgg tttaataata atgcaccatc gttttctgcc  960
atagaggctg ccatttttcag gcctccgcat ctacttgatt ttccagaaca acttacaatt  1020
```

-continued

```
tacagtgcat caagccgttg gagtagcact caacatatga attattgggt gggacatagg 1080
cttaacttcc gcccaatagg agggacatta aatacctcaa cacaaggact tactaataat 1140
acttcaatta atcctgtaac attacagttt acgtctcgtg acgtttatag aacagaatca 1200
aatgcaggga caaatatact atttactact cctgtgaatg gagtaccttg ggctagattt 1260
aattttataa accctcagaa tatttatgaa agaggcgcca ctacctacag tcaaccgtat 1320
cagggagttg ggattcaatt atttgattca gaaactgaat taccaccaga aacaacagaa 1380
cgaccaaatt atgaatcata tagtcataga ttatctcata taggactaat cataggaaac 1440
actttgagag caccagtcta ttcttggacg catcgtagtg cagatcgtac gaacacaatt 1500
gatccggaga ggattactca aataccattg gtaaaagcac atacacttca gtcaggtact 1560
actgttgtaa gagggcccgg gtttacggga ggagatattc ttcgacgaac aagtggagga 1620
ccatttgctt atactattgt taatataaat gggcaattac cccaaaggta tcgtgcaaga 1680
atacgctatg cctctactac aaatctaaga atttacgtaa cggttgcagg tgaacggatt 1740
tttgctggtc aatttaacaa aacaatggat accggtgacc cattaacatt ccaatctttt 1800
agttacgcaa ctattaatac agcttttaca ttcccaatga gccagagtag tttcacagta 1860
ggtgctgata cttttagttc agggaatgaa gtttatatag acagatttga attgattcca 1920
gttactgcaa catttgaagc agaatatgat ttagaaagag cacaaaaggc ggtgaatgag 1980
ctgtttactt cttccaatca aatcgggtta aaaacagatg tgacggatta tcatattgat 2040
caagtatcca atttagttga tgtttatct gatgaatttt gtctggatga aaaaaaagaa 2100
ttgtccgaga aagtcaaaca tgcgaagcga cttagtgatg agcggaattt acttcaagat 2160
ccaaacttta gagggatcaa tagacaacta gaccgtggct ggagaggaag tacgatatt 2220
accatccaag gaggcgatga cgtattcaaa gagaattacg ttacgctatt gggtaccttt 2280
gatgagtgct atccaacgta tttatatcaa aaaatagatg agtcgaaatt aaaagcctat 2340
acccgttacc aattaagagg gtatatcgaa gatagtcaag acttagaaat ctatttaatt 2400
cgctacaatg ccaaacacga aacagtaaat gtgccaggta cgggttcctt atggccgctt 2460
tcagccccaa gtccaatcgg aaaatgtgcc catcattccc atcatttctc cttggacatt 2520
gatgttggat gtacagactt aaatgaggac ttaggtgtat ggttgatatt caagattaag 2580
acgcaagatg gccatgcaag actaggaaat ctagaatttc tcgaagagaa accattagta 2640
ggagaagcac tagctcgtgt gaaaagagcg gagaaaaaat ggagagacaa acgtgaaaaa 2700
ttggaatggg aaacaaatat tgtttataaa gaggcaaaag aatctgtaga tgctttattt 2760
gtaaactctc aatatgatag attacaagcg gataccaaca tcatgatagt tcatgcggca 2820
gataaacgcg ttcatagcat tcgagaagct tatctgcctg agctgtctgt gattccgggt 2880
gtcaatgcgg ctattttga agaattagaa gggcgtattt tcactgcatt ctccctatat 2940
gatgcgagaa atgtcattaa aaatggtgat tttaataatg gcttatcctg ctggaacgtg 3000
aaagggcatg tagatgtaga agaacaaaac aaccaccgtt cggtccttgt tgttccggaa 3060
tgggaagcag aagtgtcaca agaagttcgt gtctgtccgg gtcgtggcta tatccttcgt 3120
gtcacagcgt acaaggaggg atatggagaa ggttgcgtaa ccattcatga gatcgagaac 3180
aatacagacg aactgaagtt tagcaactgt gtagaagagg aagtatatcc aaacaacacg 3240
gtaacgtgta atgattatac tgcgactcaa gaagaatatg agggtacgta cacttctcgt 3300
aatcgaggat atgacggagc ctatgaaagc aattcttctg taccagctga ttatgcatca 3360
gcctatgaag aaaaagcata tacagatgga cgaagagaca atccttgtga atctaacaga 3420
ggatatgggg attacacacc actaccagct ggctatgtga caaaagaatt agagtacttc 3480
ccagaaaccg ataaggtatg gattgagatc ggagaaacgg aaggaacatt catcgtggac 3540
agcgtggaat tacttcttat ggaggaatag                                    3570
```

```
SEQ ID NO: 89          moltype = AA  length = 1189
FEATURE                Location/Qualifiers
REGION                 1..1189
                       note = Amino acid sequence of the chimeric protein TIC865.
source                 1..1189
                       mol_type = protein
                       organism = synthetic construct
SEQUENCE: 89
MTSNRKNENE IINALSIPAV SNHSAQMDLS LDARIEDSLC IAEGNNINPL VSASTVQTGI 60
NIAGRILGVL GVPFAGQLAS FYSFLVGELW PSGRDPWEIF LEHVEQLIRQ QVTENTRNTA 120
IARLEGLGRG YRSYQQALET WLDNRNDARS RSIILERYVA LEDITTAIP LFRIRNEEVP 180
LLMVYAQAAN LHLLLLRDAS LFGSEWGMAS SDVNQYYEQ IRYTEEYSNH CVQWYNTGLN 240
NLRGTNAESW LRYNQFRRDL TLGVLDLVAL FPSYDTRTYP INTSAQLTRE IYTDPIGRTN 300
APSGFASTNW FNNNAPSFSA IEAAIFRPPH LLDFPEQLTI YSASSRWSST QHMNYWVGHR 360
LNFRPIGGTL NTSTQGLTNN TSINPVTLQF TSRDVYRTES NAGTNILFTT PVNGVPWARF 420
NFINPQNIYE RGATTYSQPY QGVGIQLFDS ETELPPETTE RPNYESYSHR LSHIGLIIGN 480
TLRAPVYSWT HRSADRTNTI DPERITQIPL VKAHTLQSGT TVVRGPGFTG GDILRRTSGG 540
PFAYTIVNIN GQLPQRYRAR IRYASTTNLR IYVTVAGERI FAGQFNKTMD TGDPLTFQSF 600
SYATINTAFT FPMSQSSFTV GADTFSSGNE VYIDRFELIP VTATFEAEYD LERAQKAVNE 660
LFTSSNQIGL KTDVTDYHID QVSNLVECLS DEFCLDEKKE LSEKVKHAKR LSDERNLLQD 720
PNFRGINRQL DRGWRGSTDI TIQGGDDVFK ENYVTLLGTF DECYPTLYQ KIDESKLKAY 780
TRYQLRGYIE DSQDLEIYLI RYNAKHETVN VPGTGSLWPL SAPSPIGKCA HHSHHFSLDI 840
DVGCTDLNED LGVWVIFKIK TQDGHARLGN LEFLEEKPLV GEALARVKRA EKKWRDKREK 900
LEWETNIVYK EAKESVDALF VNSQYDRLQA DTNIAMIHAA DKRVHSIREA YLPELSVIPG 960
VNAAIFEELE GRIFTAFSLY DARNVIKNGD FNNGLSCWNV KGHVDVEEQN NHRSVLVVPE 1020
WEAEVSQEVR VCPGRGYILR VTAYKEGYGE GCVTIHEIEN NTDELKFSNC VEEEVYPNNT 1080
VTCNDYTATQ EEYEGTYTSR NRGYDGAYES NSSVPADYAS AYEEKAYTDG RRDNPCESNR 1140
GYGDYTPLPA GYVTKELEYF PETDKVWIEI GETEGTFIVD SVELLLMEE             1189
```

```
SEQ ID NO: 90          moltype = DNA  length = 3564
FEATURE                Location/Qualifiers
misc_feature           1..3564
                       note = Chimeric coding sequence encoding TIC866.
source                 1..3564
                       mol_type = other DNA
```

```
                          organism = synthetic construct
SEQUENCE: 90
atgacttcaa ataggaaaaa tgagaatgaa attataaatg ctttatcgat tccagctgta   60
tcgaatcatt ccgcacaaat gaatctatca accgatgctc gtattgagga tagcttgtgt  120
atagccgagg ggaacaatat cgatccattt gttagcgcat caacagtcca aacgggtatt  180
aacatagctg gtagaatact aggtgtatta ggcgtaccgt ttgctggaca aatagctagt  240
ttttatagtt ttcttgttgg tgaattatgg ccccgcggca gagatccttg ggaaattttc  300
ctagaacatg tcgaacaact tataagacaa caagtaacag aaaatactag ggatacggct  360
cttgctcgat tacaaggttt aggaaattcc tttagagcct atcaacagtc acttgaaagt  420
tggctagaaa accgtgatga tgcaagaacg agaagtgttc tttataccca atatatagcc  480
ttagaacttg attttcttaa tgcgatgccg cttttcgcaa ttagaaacca agaagttcca  540
ttattaatgg tatatgctca agctgcaaat ttacacctat tattattgag agatgcctct  600
cttttggta gtgaatttgg gcttacatcc caagaaattc aacgttatta tgagcgccaa  660
gtggaaaaaa cgagagaata ttctgattat tgcgcaagat ggtataatac gggtttaaat  720
aatttgagag ggacaaatgc tgaaagttgg ttgcgatata atcaattccg tagagactta  780
acgctaggag tattagatct agtggcacta ttcccaagct atgacacgcg tgtttatcca  840
atgaatacca gtgctcaatt aacaagagaa atttatacag atccaattgg gagaacaaat  900
gcaccttcag gatttgcaag tacgaattgg tttaataata atgcaccatc gtttctgcc  960
atagaggctg ccgttattag gcctccgcat ctacttgatt ttccagaaca gcttacaatt 1020
ttcagcgtat taagtcgatg gagtaatact caatatatga attactgggt gggacataga 1080
cttgaatcgc gaacaataag ggggtcatta agtacctcga cacacggaaa taccaatact 1140
tctattaatc ctgtaacatt acagttcaca tctcgagacg tttatagaac agaatcattt 1200
gcagggataa atatacttct aactactcct gtgaatggag taccttgggc tagatttaat 1260
tggagaaatc ccctgaattc tcttagaggt agccttctct atactatagg gtatactgga 1320
gtggggacac aactatttga ttcagaaact gaattaccac cagaaacaac agaacgacca 1380
aattatgaat cttacagtca tagattatct aatataaagc taatatcagg aaacacttg 1440
agagcaccag tatattcttg gacgcaccgt agtgcagatc gtacaaatac cattagttca 1500
gatagcatta ctcaaatacc attggtaaaa gcacatacac ttcagtcagg tactactgtt 1560
gtaagagggc ccgggtttac gggaggagat attcttcgac gaacaagtgg aggaccattt 1620
gcttatacta ttgttaatat aaatgggcaa ttaccccaaa ggtatcgtgc aagaatacgc 1680
tatgcctcta ctacaaatct aagaatttac gtaacggttg caggtgaacg gattttttgct 1740
ggtcaattta acaaaacaat ggataccggt gacccattaa cattccaatc ttttagttac 1800
gcaactatta atacagcttt tacattccca atgagccaga gtagtttcac agtaggtgct 1860
gatactttta gttcagggaa tgaagtttat atagacagat ttgaattgat tccagttact 1920
gcaacatttg aagcagaata tgatttagaa agagcacaga aggcggtgaa tgagctgttt 1980
acttcttcca atcaaatcgg gttaaaaaca gatgtgacgg attatcatat tgatcaagta 2040
tccaatttag ttgagtgttt atctgatgaa ttttgtctgg atgaaaaaaa agaattgtcc 2100
gagaaagtca aacatgcgaa gcgacttagt gatgagcgga atttacttca agatccaaac 2160
tttagaggga tcaatagaca actagaccgt ggctggagga gaagtacgga tattaccatc 2220
caaggaggcg atgacgtatt caaagagaat tacgttacgc tattgggtac ctttgatgag 2280
tgctatccaa cgtatttata tcaaaaaata gatgagtcga aattaaaagc ctataccgt 2340
taccaattaa gagggtatat cgaagatagt caagacttag aaatctattt aattcgctac 2400
aatgccaaac acgaaacagt aaatgtgcca ggtacgggtt ccttatggcc gctttcaccc 2460
ccaagtccaa tcggaaaatg tgcccatcat tcccatcatt tctccttgga cattgatgtt 2520
ggatgtacag acttaaatga ggacttaggt gtatgggtga tattcaagat taagacgcaa 2580
gatggccatg caagactagg aaatctagaa tttctcgaag agaaaccatt agtaggagaa 2640
gcactagctc gtgtgaaaag agcggagaaa aaatgggaga caaacgtgaa aaaattggaa 2700
tgggaaacaa atattgttta taaagaggca aaagaatctg tagatgcttt atttgtaaac 2760
tctcaatatg atagattaca agcggatacc aacatcgcga tgattcatgc ggcagataaa 2820
cgcgttcata gcattcgaga agcttatctg cctgagctgt ctgtgattcc gggtgtcaat 2880
gcggctattt ttgaagaatt agaagggcgt attttcactg cattctccct atatgatgcg 2940
agaaatgtca ttaaaaatgg tgattttaat aatggcttat cctgctggaa cgtgaaaggg 3000
catgtagatg tagaagaaca aaacaaccac cgttcggtcc ttgttgttcc ggaatgggaa 3060
gcagaagtgt cacaagaagt tcgtgtctgt ccgggtcgtg gctatatcct tcgtgtcaca 3120
gcgtacaagg agggatatgg agaaggttgc gtaaccattc atagatatga gaacaataca 3180
gacgaactga agtttagcaa ctgtgtagaa gaggaagtat atccaaacaa cacggtaacg 3240
tgtaatgatt atactgcgac tcaagaagaa tatgagggta cgtacacttc tcgtaatcga 3300
ggatatgacg gagcctatga aagcaattct tctgtaccag ctgattatgc atcagcctat 3360
gaagaaaaag catatacaga tggacgaaga gacaatcctt gtgaatctaa cagaggatat 3420
gggattaca caccactacc agctggctat gtgacaaaag aattagagta cttcccagaa 3480
accgataagg tatggattga gatcggagaa acggaaggaa cattcatcgt ggacagcgtg 3540
gaattacttc ttatggagga atag                                        3564
```

```
SEQ ID NO: 91         moltype = AA  length = 1187
FEATURE               Location/Qualifiers
REGION                1..1187
                      note = Amino acid sequence of the chimeric protein TIC866.
source                1..1187
                      mol_type = protein
                      organism = synthetic construct
SEQUENCE: 91
MTSNRKNENE IINALSIPAV SNHSAQMNLS TDARIEDSLC IAEGNNIDPF VSASTVQTGI   60
NIAGRILGVL GVPFAGQIAS FYSFLVGELW PRGRDPWEIF LEHVEQLIRQ QVTENTRDTA  120
LARLQGLGNS FRAYQQSLED WLENRDDART RSVLYTQYIA LELDFLNAMP LFAIRNQEVP  180
LLMVYAQAAN LHLLLLRDAS LFGSEFGLTS QEIQRYYERQ VEKTREYSDY CARWYNTGLN  240
NLRGTNAESW LRYNQFRRDL TLGVLDLVAL FPSYDTRVYP MNTSAQLTRE IYTDPIGRTN  300
APSGFASTNW FNNNAPSFSA IEAAVIRPPH LLDFPEQLTI FSVLSRWSNT QYMNYWVGHR  360
LESRTIRGSL STSTHGNTNT SINPVTLQFT SRDVYRTESF AGINILLTTP VNGVPWARFN  420
WRNPLNSLRG SLLYTIGYTG VGTQLFDSET ELPPETTERP NYESYSHRLS NIRLISGNTL  480
```

-continued

```
RAPVYSWTHR SADRTNTISS DSITQIPLVK AHTLQSGTTV VRGPGFTGGD ILRRTSGGPF   540
AYTIVNINGQ LPQRYRARIR YASTTNLRIY VTVAGERIFA GQFNKTMDTG DPLTFQSFSY   600
ATINTAFTFP MSQSSFTVGA DTFSSGNEVY IDRFELIPVT ATFEAEYDLE RAQKAVNELF   660
TSSNQIGLKT DVTDYHIDQV SNLVECLSDE FCLDEKKELS EKVKHAKRLS DERNLLQDPN   720
FRGINRQLDR GWRGSTDITI QGGDDVFKEN YVTLLGTFDE CYPTYLYQKI DESKLKAYTR   780
YQLRGYIEDS QDLEIYLIRY NAKHETVNVP GTGSLWPLSA PSPIGKCAHH SHHFSLDIDV   840
GCTDLNEDLG VWVIFKIKTQ DGHARLGNLE FLEEKPLVGE ALARVKRAEK KWRDKREKLE   900
WETNIVYKEA KESVDALFVN SQYDRLQADT NIAMIHAADK RVHSIREAYL PELSVIPGVN   960
AAIFEELEGR IFTAFSLYDA RNVIKNGDFN NGLSCWNVKG HVDVEEQNNH RSVLVVPEWE  1020
AEVSQEVRVC PGRGYILRVT AYKEGYGEGC VTIHEIENNT DELKFSNCVE EEVYPNNTVT  1080
CNDYTATQEE YEGTYTSRNR GYDGAYESNS SVPADYASAY EEKAYTDGRR DNPCESNRGY  1140
GDYTPLPAGY VTKELEYFPE TDKVWIEIGE TEGTFIVDSV ELLLMEE               1187

SEQ ID NO: 92            moltype = DNA   length = 3525
FEATURE                  Location/Qualifiers
misc_feature             1..3525
                         note = Chimeric coding sequence encoding TIC838.
source                   1..3525
                         mol_type = other DNA
                         organism = synthetic construct SEQUENCE: 92
atggaggaaa ataatcaaaa tcaatgcata ccttacaatt gtttaagtaa tcctgaagaa   60
gtacttttgg atggagaacg gatatcaact ggtaattcat caattgatat ttctctgtca  120
cttgttcagt ttctggtatc taactttgta ccagggggag gattttttagt tggattaata  180
gattttgtat ggggaatagt tggcccttct caatgggatg catttctagt acaaattgaa  240
caattaatta atgaaagaat agctgaattt gctcagaagc ctgctattgc taatttagaa  300
ggattaggaa acaatttcaa tatatatgtg gaagcattta aagaatggga agaagatcct  360
aataatccag caaccaggac cagagtaatt gatcgctttc gtatacttga tgggctactt  420
gaaagggaca ttccttcgtt tgcaatttct ggatttgaag tacccctttt atccgtttat  480
gctcaagcgg ccaatctgca tctagctata ttaagagatt ctgtaatttt tggagaaaga  540
tggggattga caacgataaa tgtcaatgaa aactataata gactaattag gcatattgat  600
gaatatgctg atcactgtgc aaatacgtat aatcggggat taaataattt accgaaatct  660
acgtatcaag attggataac atataatcga ttacggagag acttaacatt gactgtatta  720
gatatcgccg ctttctttcc aaactatgac aataggagat atccaattca gtcagttggt  780
caactaacaa gggaaattta tacggaccca ttaattactt ttaatccaca gttacagtct  840
gtagctcaat tacctacttt taacgttatg gaaagcaacg caattagaac tcctcattta  900
tttgatgtat tgaataatct tacaattttt acagattggt ttagtgttgg acgcaacttt  960
tattggggag gacatcgagt aatatctaac cgtataggag gaggtaacat aacatctcct 1020
atatatggaa gggaggcgaa tcaggagcct ccaagatctt ttactttaa tgggcctgtt 1080
tttaggactt tatcaaatcc tactttttaga cctttacagc aaccttggcc agcgccacca 1140
tttaatttac gtggtgttga aggagtagaa ttttctacac ctttaaatag ctttacgtat 1200
cgaggaaggg gtacggttga ttctttaact gagttaccgc ctgaggataa tagtgtgcct 1260
cctcgcgaag gatatagtca tcgtttatgt catgcaactt ttgttcaaag atctggaaatc 1320
ccatttttaa caactggtcc agtattttct tggacgcatc gtagtgctac tgatcgaaat 1380
ataattgcat cggatagtat tactcaaatc cctgcagtga agggaaactt tctttttaat 1440
ggttctgtaa tttcaggacc aggatttact ggtgggggact tagttagatt aaatagtagt 1500
ggaaataaca ttcagaatag agggtatatt gaagttccaa ttcacttccc atcgacatct 1560
accagatatc gagttcgtgt acggtatgct tctgtaaccc cgattcacct caacgttaat 1620
tggggtaatt catccatttt ttccaataca gtaccagcta cagctacgtc attagataat 1680
ctacaatcaa gtgattttgg ttattttgaa agtgccaatg cttttacatc ttcattaggt 1740
aatatagtag gtgttagaaa ttttagtggg actgcaggag tgataataga cagatttgaa 1800
tttattcctg ttactgcaac actcgaggct gaatataatc tagaaagagc gcagaaggcg 1860
gtgaatgcgc tgtttacgtc tacaaaccaa ctagggctaa aaacaaatgt aacgggattat 1920
catattgatc aagtgtccaa tttagttacg tatttatcgg atgaattttg tctggatgaa 1980
aagcagaat tgtccgagaa agtcaaacat gcgaagcgac tcagtgatga acgcaattta 2040
ctccaagatt caaatttcaa agacattaat aggcaaccag aacgtgggtg gggcggaagt 2100
acagggatta ccatccaagg aggggatgac gtatttaaag aaaattacgt cacactatca 2160
ggtacctttg atgagtgcta tccaacatat ttgtatcaaa aaatcgatga atcaaaatta 2220
aaagccttta cccgttatca attaagaggg tatatcgaag atagtcaaga cttagaaatc 2280
tatttaattc gctacaatgc aaaacatgaa acagtaaatg tgccaggtac gggttcctta 2340
tggccgcttt cagcccaaag tccaatcgga aagtgtggag agccgaatcg atgcgcgcca 2400
caccttgaat ggaatcctga cttagattgt tcgtgtaggg atggagaaaa gtgtgcccat 2460
cattcgcatc atttctcctt agacattgat gtaggatgta cagacttaaa tgaggaccta 2520
ggtgtatggg tgatctttaa gattaagacg caagtggcgt acgcaagact agggaaatca 2580
gagtttctcg aagaaaaacc attagtagga gaagcgctag ctcgtgtgaa aagagcggag 2640
aaaaaatgga gagacaaacg tgaaaaattg gaatgggaaa caaatatcgt ttataaagag 2700
gcaaagaat ctgtagatgc tttatttgta aactctcaat atgatcaatt acaagcggat 2760
acgaatattg ccatgattca tgcggcagat aaacgtgttc atagcattcg agaagcttat 2820
ctgcctgagc tgtctgtgat tccgggtgtc aatgcggtca tttttgaaga attagaaggg 2880
cgtatttttca ctgcattctc cctatatgat gcgagaaatg tcattaaaaa tggtgatttt 2940
aataatggct tatcctgctg gaacgtgaaa gggcatgtag atgtagaaga acaaaacaac 3000
caacgttcgg tccttgttgt tccggaatgg gaagcagaag tgtcacaaga gttcgtgtc 3060
tgtccgggtc gtggctatat ccttcgtgtc acagcgtaca aggagggata tggagaaggt 3120
tgcgtaacca ttcatgagat cgagaacaat acagacgaac tgaagtttag caactgcgta 3180
gaggaggaaa tctatccaaa taacacggta acgtgtaatg attatactgt aaatcaagaa 3240
gaatacggag gtgcgtacac ttctcgtaat cgaggatata cgaagctcc ttccgtacca 3300
gctgattatg cgtcagtcta tgaagaaaaa tcgtatacag atggacgtag agagaatcct 3360
tgtgaattta acagagggta tagggattac acgccactac cagttggtta tgtgacaaaa 3420
gaattagaat acttcccaga aaccgataag gtatggattg agattggaga aacggaagga 3480
```

-continued

```
acatttatcg tggacagcgt ggaattactc cttatggagg aatag                    3525

SEQ ID NO: 93          moltype = AA   length = 1174
FEATURE                Location/Qualifiers
REGION                 1..1174
                       note = Amino acid sequence of the chimeric protein TIC838.
source                 1..1174
                       mol_type = protein
                       organism = synthetic construct
SEQUENCE: 93
MEENNQNQCI PYNCLSNPEE VLLDGERIST GNSSIDISLS LVQFLVSNFV PGGGFLVGLI     60
DFVWGIVGPS QWDAFLVQIE QLINERIAEF ARNAAIANLE GLGNNFNIYV EAFKEWEEDP    120
NNPATRTRVI DRFRILDGLL ERDIPSFAIS GFEVPLLSVY AQAANLHLAI LRDSVIFGER    180
WGLTTINVNE NYNRLIRHID EYADHCANTY NRGLNNLPKS TYQDWITYNR LRRDLTLTVL    240
DIAAFFPNYD NRRYPIQSVG QLTREIYTDP LITFNPQLQS VAQLPTFNVM ESNAIRTPHL    300
FDVLNNLTIF TDWFSVGRNF YWGGHRVISN RIGGGNITSP IYGREANQEP PRSFTFNGPV    360
FRTLSNPTFR PLQQPWPAPP FNLRGVEGVE FSTPLNSFTY RGRGTVDSLT ELPPEDNSVP    420
PREGYSHRLC HATFVQRSGT PFLTTGPVFS WTHRSATDRN IIASDSITQI PAVKGNFLFN    480
GSVISGPGFT GGDLVRLNSS GNNIQNRGYI EVPIHFPSTS TRYRVRVRYA SVTPIHLNVN    540
WGNSSIFSNT VPATATSLDN LQSSDFGYFE SANAFTSSLG NIVGVRNFSG TAGVIIDRFE    600
FIPVTATLEA EYNLERAQKA VNALFTSTNQ LGLKTNVTDY HIDQVSNLVT YLSDEFCLDE    660
KRELSEKVKH AKRLSDERNL LQDSNFKDIN RQPERGWGGS TGITIQGGDD VFKENYVTLS    720
GTFDECYPTY LYQKIDESKL KAFTRYQLRG YIEDSQDLEI YLIRYNAKHE TVNVPGTGSL    780
WPLSAQSPIG KCGEPNRCAP HLEWNPDLDC SCRDGEKCAH HSHHFSLDID VGCTDLNEDL    840
GVWVIFKIKT QDGHARLGNL EFLEEKPLVG EALARVKRAE KKWRDKREKL EWETNIVYKE    900
AKESVDALFV NSQYDQLQAD TNIAMIHAAD KRVHSIREAY LPELSVIPGV NAAIFEELEG    960
RIFTAFSLYD ARNVIKNGDF NNGLSCWNVK GHVDVEEQNN QRSVLVVPEW EAEVSQEVRV   1020
CPGRGYILRV TAYKEGYGEG CVTIHEIENN TDELKFSNCV EEEIYPNNTV TCNDYTVNQE   1080
EYGGAYTSRN RGYNEAPSVP ADYASVYEEK SYTDGRRENP CEFNRGYRDY TPLPVGYVTK   1140
ELEYFPETDK VWIEIGETEG TFIVDSVELL LMEE                              1174

SEQ ID NO: 94          moltype = DNA   length = 3558
FEATURE                Location/Qualifiers
misc_feature           1..3558
                       note = Chimeric coding sequence encoding TIC839.
source                 1..3558
                       mol_type = other DNA
                       organism = synthetic construct
SEQUENCE: 94
atggaggaaa ataatcaaaa tcaatgcata ccttacaatt gtttaagtaa tcctgaagaa     60
gtacttttgg atggagaacg gatatcaact ggtaattcat caattgatat ttctctgtca    120
cttgttcagt ttctggtatc taactttgta ccaggggggag gatttttagt tggattaata    180
gattttgtat ggggaatagt tggcccttct caatgggatg catttctagt acaaattgaa    240
caattaatta atgaaagaat agctgaattt gctaggaatg ctgctattgc taatttagaa    300
ggattaggaa acaatttcaa tatatatgtg gaagcattta agaatgggga agaagatcct    360
aataatccag caaccaggac cagagtaatt gatcgctttc gtatacttga tgggctactt    420
gaaagggaca ttccttcgtt tgcaatttct ggatttgaag tacccctttc atccgtttat    480
gctcaagcgg ccaatctgca tctagctata ttaagagatt ctgtaatttt tggagaaaga    540
tggggattga acgataaa tgtcaatgaa aactataata gactaattag gcatattgat    600
gaatatgctg atcactgtgc aaatacgtat aatcggggat taaataattt accgaaatct    660
acgtatcaag attggataac atataatcga ttacggagta acttaacatt gactgtatta    720
gatatcgccg ctttctttcc aaaactatgac aataggagat atccaattca gtcagttggt    780
caactaacaa gggaaattta tacggaccca ttaattactt ttaatccaca gttacagtct    840
gtagctcaat tacctacttt taacgttatg gaaagcaacg caattagaac tcctcattta    900
tttgatgtat tgaataatct tacaattttt acagattggt ttagtgttgg acgcaacttt    960
tattggggag gacatcgagt aatatctaac cgtataggag gaggtaacat aacatctcct   1020
atatatggaa gggaggcgaa tcaggagcct ccaagatctt ttactttaa tgggcctgtt   1080
tttaggactt tatcaaatcc tactttaga cctttacagc aaccttggcc agcgccacca   1140
tttaatttac gtggtgttga aggagtagaa ttttctacac ctttaaatag ctttacgtat   1200
cgaggaaggg gtacggttga ttctttaact gagttaccgc ctgaggataa tagtgtgcct   1260
cctcgcgaag gatatagtca tcgtttatgt catgcaactt ttgttcaaag atctggaacc   1320
ccatttttaa caactggtcc agtattttct tggacgcatc gtagtgctac tgatcgaaat   1380
acaattgatc cagagagaat taatcaaata cctttagtga aaggatttag agtttggggg   1440
ggcacctctg tcattacagg accaggttt acaggagggg atatccttcg aagaaataco   1500
tttggtgatt ttgtatctct acaagtcaat attaattcac caattaccca aagataccgt   1560
ttaagatttc gttacgcttc cagtagggat gcacgagtta gtgtattaac aggagcggca   1620
tccacaggag tgggaggcca agttagtgta aatatgcctc tccagaaaac tatggaaata   1680
ggggagaact taacatctag aacatttaga tataccgatt ttagtaatcc tttttcattt   1740
agagctaatc cagatataat tgggataagt gaacaacctc tatttggtgc aggttctatt   1800
agtagcggtg aactttatat agataaaatt gaaattattc ctgttactgc aacactcgag   1860
gctgaatata atctagaaag agcgcagaag gcggtgaatg cgctgtttac gtctacaaac   1920
caactagggc taaaaacaaa tgtaacggat tatcatattg atcaagtgtc caatttagtt   1980
acgtatttat cggatgaatt ttgtctggat gaaaagcgag aattgtccga gaaagtcaaa   2040
catgcagacg gactcagtga tgaacgcaat ttactccaag attcaaattt caaagacatt   2100
aataggcaac agaacgtgg gtggggcgga agtacaggga ttaccatcca aggaggggat   2160
gacgtattta agaaaattta cgtcacacta tcaggtacct ttgatgagtg ctatccaaca   2220
tatttgtatc aaaaaatcga tgaatcaaaa ttaaagcct ttacccgtta tcaattaaga   2280
gggtatatcg aagatagtca agacttagaa atctatttaa ttcgctacaa tgcaaaacat   2340
gaaacagtaa atgtgccagg tacgggtttcc ttatggccgc tttcagccca aagtccaatc   2400
```

-continued

```
ggaaagtgtg gagagccgaa tcgatgcgcg ccacaccttg aatggaatcc tgacttagat  2460
tgttcgtgta gggatggaga aaaagtgtgcc catcattcgc atcatttctc cttagacatt  2520
gatgtaggat gtacagactt aaatgaggac ctaggtgtat gggtgatctt taagattaag  2580
acgcaagatg ggcacgcaag actagggaat ctagagtttc tcgaagaaaa accattagta  2640
ggagaacgc tagctcgtgt gaaaagagcg gagaaaaaat ggagagacaa acgtgaaaaa  2700
ttggaatggg aaacaaatat cgtttataaa gaggcaaaag aatctgtaga tgctttattt  2760
gtaaactctc aatatgatca attacaagcg gatacgaata ttgccatgat tcatgcggca  2820
gataaacgtg ttcatagcat tcgagaagct tatctgcctg agctgtctgt gattccgggt  2880
gtcaatgcgg ctattttga agaattagaa gggcgtattt tcactgcatt ctccctatat  2940
gatgcgagaa atgtcattaa aaatggtgat tttaataatg cttatcctg ctggaacgtg  3000
aaagggcatg tagatgtaga agaacaaaac aaccaacgtt cggtccttgt tgttccggaa  3060
tgggaagcag aagtgtcaca agaagttcgt gtctgtccgg gtcgtggcta tatccttcgt  3120
gtcacagcgt acaaggaggg atatggagaa ggttgcgtaa ccattcatga gatcgagaac  3180
aatacagacg aactgaagtt tagcaactgc gtagaggagg aaatctatcc aaataacacg  3240
gtaacgtgta atgattatac tgtaaatcaa gaagaatacg gaggtgcgta cacttctcgt  3300
aatcgaggat ataacgaagc tccttccgta ccagctgatt atgcgtcagt ctatgaagaa  3360
aaatcgtata cagatggacg tagagagaat ccttgtgaat ttaacagagg gtataggat  3420
tacacgccac taccagttgg ttatgtgaca aaagaattag aatacttccc agaaaccgat  3480
aaggtatgga ttgagattgg agaaacgaaa ggaacattta tcgtggacag cgtggaatta  3540
ctccttatgg aggaatag                                                 3558
```

```
SEQ ID NO: 95           moltype = AA   length = 1185
FEATURE                 Location/Qualifiers
REGION                  1..1185
                        note = Amino acid sequence of the chimeric protein TIC839.
source                  1..1185
                        mol_type = protein
                        organism = synthetic construct
SEQUENCE: 95
MEENNQNQCI PYNCLSNPEE VLLDGERIST GNSSIDISLS LVQFLVSNFV PGGGFLVGLI   60
DFVWGIVGPS QWDAFLVQIE QLINERIAEF ARNAAIANLE GLGNNFNIYV EAFKEWEEDP  120
NNPATRTRVI DRFRILDGLL ERDIPSFAIS GFEVPLLSVY AQAANLHLAI LRDSVIFGER  180
WGLTTINVNE NYNRLIRHID EYADHCANTY NRGLNNLPKS TYQDWITYNR LRRDLTLTVL  240
DIAAFFPNYD NRRYPIQSVG QLTREIYTDP LITFNPQLQS VAQLPTFNVM ESNAIRTPHL  300
FDVLNNLTIF TDWFSVGRNF YWGGHRVISN RIGGGNITSP IYGREANQEP PRSFTFNGPV  360
FRTLSNPTFR PLQQPWPAPP FNLRGVEGVE FSTPLNSFTY RGRGTVDSLT ELPPEDNSVP  420
PREGYSHRLC HATFVQRSGT PFLTTGPVFS WTHRSATDRN TIDPERINQI PLVKGFRVWG  480
GTSVITGPGF TGGDILRRNT FGDFVSLQVN INSPITQRYR LRFRYASSRD ARVIVLTGAA  540
STGVGGQVSV NMPLQKTMEI GENLTSRTFR YTDFSNPFSF RANPDIIGIS EQPLFGAGSI  600
SSGELYIDKI EIIPVTATLE AEYNLERAQK AVNALFTSTN QLGLKTNVTD YHIDQVSNLV  660
TYLSDEFCLD EKRELSEKVK HAKRLSDERN LLQDSNFKDI NRQPERGWGG STGITIQGGD  720
DVFKENYVTL SGTFDECYPT YLYQKIDESK LKAFTRYQLR GYIEDSQDLE IYLIRYNAKH  780
ETVNVPGTGS LWPLSAQSPI GKCGEPNRCA PHLEWNPDLD CSCRDGEKCA HHSHHFSLDI  840
DVGCTDLNED LGVWVIFKIK TQDGHARLGN LEFLEEKPLV GEALARVKRA EKKWRDKREK  900
LEWETNIVYK EAKESVDALF VNSQYDQLQA DTNIAMIHAA DKRVHSIREA YLPELSVIPG  960
VNAAIFEELE GRIFTAFSLY DARNVIKNGD FNNGLSCWNV KGHVDVEEQN NQRSVLVVPE 1020
WEAEVSQEVR VCPGRGYILR VTAYKEGYGE GCVTIHEIEN NTDELKFSNC VEEEIYPNNT 1080
VTCNDYTVNQ EEYGGAYTSR NRGYNEAPSV PADYASVYEE KSYTDGRREN PCEFNRGYRD 1140
YTPLPVGYVT KELEYFPETD KVWIEIGETE GTFIVDSVEL LLMEE              1185
```

```
SEQ ID NO: 96           moltype = DNA   length = 3519
FEATURE                 Location/Qualifiers
misc_feature            1..3519
                        note = Chimeric coding sequence encoding TIC841.
source                  1..3519
                        mol_type = other DNA
                        organism = synthetic construct
SEQUENCE: 96
atggaggaaa ataatcaaaa tcaatgcata ccttacaatt gtttaagtaa tcctgaagaa   60
gtactttgg atggagaacg gatatcaact ggtaattcat caattgatat ttctctgtca  120
cttgttcagt ttctggtatc taactttgta ccagggggag gattttagt tggattaata  180
gattttgtat ggggaatagt tggcccttct caatgggatg catttctagt acaaattgaa  240
caattaatta atgaaagaat agctgaattt gctaggaatg ctgctattgc taatttagaa  300
ggattaggaa acaatttcaa tatatatgtg gaagcattca atgaatggga agaagatcct  360
aataatccag caaccaggac cagagtaatt gatcgctttc gtatacttga tgggctactt  420
gaaagggaca ttccttcgtt tgcaatttct ggatttgaag taccccttt atccgtttat  480
gctcaagcgg ccaatctgca tctagctata ttaagagatt ctgtaatttt tggagaaaga  540
tggggattga acgataaa tgtcaatgaa aactataata gactaattag gcatattgat  600
gaatatgctg atcactgtgc aaatacgtat aatcggggat taaataattt accgaaatct  660
acgtatcaag attggataac atataatcga ttacggagag acttaacatt gactgtatta  720
gatatcgccg ctttctttcc aaactatgac aataggagat atccaattca gtcagttggt  780
caactaacaa gggaaattta tacggaccca ttaattactt ttaatccaca gttacagtct  840
gtagctcaat tacctacttt taacgttatg gaaagcaacg caattagaac tcctcattta  900
tttgatgtat taaataatct tacaattttt acagattggt ttagtgttgg acgcaacttt  960
tattggggag gacatcgagt aatatctaac cgtataggag gaggtaacat aacatctcct 1020
atatatggaa gggaggcgaa tcaggagcct ccaagatctt ttactttaa tgggcctgtt 1080
tttaggactt tatcaaatcc tactttaga cctttacagc aacctggcc agcgccacca 1140
tttaatttac gtggtgttga aggagtagaa ttttctcac ctttaaatag ctttacgtat 1200
cgaggaaggg gtacggttga ttctttaact gagttaccgc ctgaggataa tagtgtgcct 1260
```

-continued

```
cctcgcgaag gatatagtca tcgtttatgt catgcaactt ttgttcaaag atctggaacc      1320
ccatttttaa caactggtcc agtattttct tggacgcatc gtagtgctac tgatcgaaat      1380
acaattgatc cagagagaat taatcaaata cctttagtga aaggatttag agtttggggg      1440
ggcacctctg tcattacagg accaggattt acaggagggg atatccttag aagaacgaat      1500
actggcacat ttgcagatat gagagtaaat attactgggc cattatccca aagatatcgt      1560
gtaagaattc gctatgcttc tacgacagat ttacaatttt tcacgagaat caatggaact      1620
tctgtaaatc aaggtaattt ccaaagaact atgaatagag gggataattt agaatctgga      1680
aactttagga ctgcaggatt tagtacgcct tttagttttt caaatgcgca aagtacattc      1740
acattgggta ctcaggcttt ttcaaatcag gaagtttata tagatcgaat tgaatttgtc      1800
ccggcagaag taacattcga ggcagaatct gatttagaaa gagcgcagaa ggcggtgaat      1860
gcgctgttta cgtctacaaa ccaactaggg ctaaaaacaa atgtaacgga ttatcatatt      1920
gatcaagtgt ccaatttagt tacgtattta tcggatgaat tttgtctgga tgaaaagcga      1980
gaattgtccg agaaagtcaa acatgcgaag cgactcagtg atgaacgcaa tttactccaa      2040
gattcaaatt tcaaagacat taataggcaa ccagaacgtg ggtggggcgg aagtacaggg      2100
attaccatcc aaggagggga tgacgtattt aaagaaaatt acgtcacact atcaggtacc      2160
tttgatgagt gctatccaac atatttgtat caaaaaatcg atgaatcaaa attaaaagcc      2220
tttacccgtt atcaattaag agggtatatc gaagatagtc aagacttaga aatctattta      2280
attcgctaca atgcaaaaca tgaaacagta aatgtgccag gtacgggttc cttatggccg      2340
ctttcagccc aaagtccaat cggaaagtgt ggagagccga atcgatgcgc gccacacctt      2400
gaatggaatc ctgacttaga ttgttcgtgt agggatggag aaaagtgtgc ccatcattcg      2460
catcatttct ccttagacat tgatgtagga tgtacagact taaatgagga cctaggtgta      2520
tgggtgatct ttaagattaa gacgcaagat gggcacgcaa gactagggaa tctagagttt      2580
ctcgaagaaa aaccattagt aggagaagcg ctagctcgtg tgaaaagagc ggagaaaaaa      2640
tggagagaca aacgtgaaaa attggaatgg gaaacaaata tcgtttataa agaggcaaaa      2700
gaatctgtag atgcttatt tgtaaactct caatatgatc aattacaagc ggatacgaat      2760
attgccatga ttcatgcggc agataaacgt gttcatacga ttcgagaagc ttatctgcct      2820
gagctgtctg tgattccggg tgtcaatgcg gctatttttg aagaattaga agggcgtatt      2880
ttcactgcat tctccctata tgatgcgaga aatgtcatta aaaatggtga tttttaataat      2940
ggcttatcct gctggaacgt gaaagggcat gtagatgtag aagaacaaaa caaccaacgt      3000
tcggtccttg ttgttccgga atgggaagca gaagtgtcac aagaagttcg tgtctgtccca      3060
ggtcgtggct atatccttcg tgtcacagcg tacaaggagg gatatggaga aggttgcgta      3120
accattcatg agatcgagaa caatacagac gaactgaagt ttagcaactg cgtagaggag      3180
gaaatctatc caaataacac ggtaacgtgt aatgattata ctgtaaatca agaagaatac      3240
ggaggtgcgt acacttctcg taatcgagga tataacgaag ctccttccgt accagctgat      3300
tatgcgtcag tctatgaaga aaaatcgtat acagatggac gtagagaaa tccttgtgaa      3360
tttaacagag ggtataggga ttacacgcca ctaccagttg gttatgtgac aaaagaatta      3420
gaatacttcc cagaaaccga taaggtatgg attgagattg gagaaacgga aggaacattt      3480
atcgtggaca gcgtggaatt actccttatg gaggaataa                            3519
```

```
SEQ ID NO: 97          moltype = AA  length = 1172
FEATURE                Location/Qualifiers
REGION                 1..1172
                       note = Amino acid sequence of the chimeric protein TIC841.
source                 1..1172
                       mol_type = protein
                       organism = synthetic construct
SEQUENCE: 97
MEENNQNQCI PYNCLSNPEE VLLDGERIST GNSSIDISLS LVQFLVSNFV PGGGFLVGLI      60
DFVWGIVGPS QWDAFLVQIE QLINERIAEF ARNAAIANLE GLGNNFNIYV EAFKEWEEDP      120
NNPATRTRVI DRFRILDGLL ERDIPSFAIS GFEVPLLSVY AQAANLHLAI LRDSVIFGER      180
WGLTTINVNE NYNRLIRHID EYADHCANTY NRGLNNLPKS TYQDWITYNR LRRDLTLTVL      240
DIAAFFPNYD NRRYPIQSVG QLTREIYTDP LITFNPQLQS VAQLPTFNVM ESNAIRTPHL      300
FDVLNNLTIF TDWFSVGRNF YWGGHRVISN RIGGGNITSP IYGREANQEP PRSFTFNGPV      360
FRTLSNPTFR PLQQPWPAPP FNLRGVEGVE FSTPLNSFTY RGRGTVDSLT ELPPEDNSVP      420
PREGYSHRLC HATFVQRSGT PFLTTGPVFS WTHRSATDRN TIDPERINQI PLVKGFRVWG      480
GTSVITGPGF TGGDILRRTN TGTFADMRVN ITGPLSQRYR VRIRYASTTD LQFFTRINGT      540
SVNQGNFQRT MNRGDNLESG NFRTAGFSTP FSFSNAQSTF TLGTQAFSNQ EVYIDRIEFV      600
PAEVTFEAES DLERAQKAVN ALFTSTNQLG LKTNVTDYHI DQVSNLVTYL SDEFCLDEKR      660
ELSEKVHKAK RLSDERNLLQ DSNFKDINRQ PERGWGGSTG ITIQGGDDVF KENYVTLSGT      720
FDECYPTYLY QKIDESKLKA FTRYQLRGYI EDSQDLEIYL IRYNAKHETV NVPGTGSLWP      780
LSAQSPIGKC GEPNRCAPHL EWNPDLDCSC RDGEKCAHHS HHFSLDIDVG CTDLNEDLGV      840
WVIFKIKTQD GHARLGNLEF LEEKPLVGEA LARVKRAEKK WRDKREKLEW ETNIVYKEAK      900
ESVDALFVNS QYDQLQADTN IAMIHAADKR VHSIREAYLP ELSVIPGVNA AIFEELEGRI      960
FTAFSLYDAR NVIKNGDFNN GLSCWNVKGH VDVEEQNNQR SVLVVPEWEA EVSQEVRVCP      1020
GRGYILRVTA YKEGYGEGCV TIHEIENNTD ELKFSNCVEE EIYPNNTVTC NDYTVNQEEY      1080
GGAYTSRNRG YNEAPSVPAD YASVYEEKSY TDGRRENPCE FNRGYRDYTP LPVGYVTKEL      1140
EYFPETDKVW IEIGETEGTF IVDSVELLLM EE                                   1172
```

```
SEQ ID NO: 98          moltype = DNA  length = 3516
FEATURE                Location/Qualifiers
misc_feature           1..3516
                       note = Chimeric coding sequence encoding TIC842.
source                 1..3516
                       mol_type = other DNA
                       organism = synthetic construct
SEQUENCE: 98
atggcagaga ataatattca aaatcaatgc gtaccttaca attgtttaaa taatcctgaa      60
gtagaaatat taaatgaaga aagaagtact ggcagattac cgttagatat atccttatcg      120
cttacacgtt tccttttgag tgaatttgtt ccaggtgtgg gagttgcgtt tggattattt      180
```

```
gatttaatat ggggttttat aactccttct gattggagct tatttctttt acagattgaa   240
caattgattg agcaaagaat agaaacattg gaaaggaacc gggcaattac tacattacga   300
gggttagcag atagctatga aatttatatt gaagcactaa gagagtggga agcaaatcct   360
aataatgcac aattaaggga agatgtgcgt attcgatttg ctaatacaga cgacgcttta   420
ataacagcaa taaataattt tacacttaca agttttgaaa tccctctttt atcggtctat   480
gttcaagcgg cgaatttaca tttatcacta ttaagagacg ctgtatcgtt tgggcagggt   540
tggggactgg atatagctac tgttaataat cattataata gattaataaa tcttattcat   600
agatatacga aacattgttt ggacacatac aatcaaggat tagaaaactt aagaggtact   660
aatactcgac aatgggcaag attcaatcag tttaggagag atttaacgct aactgtatta   720
gatatcgttg ctcttttttcc gaactacgat gttagaacat atccaattca aacgtcatcc   780
caattaacaa gggaaattta tacaagttca gtaattgagg attctccagt ttctgctaat   840
atacctaatg tgttttaatag ggcggaattt ggagttagac cgccccatct tatggacttt   900
atgaattctt tgtttgtaac tgcagagact gttagaagtc aaactgtgtg gggaggacac   960
ttagttagtt cacgaaatac ggctggtaac cgtataaatt tccctagtta cgggggtcttc  1020
aatcctggtg gcgccatttg gattgcagat gaggatccac gtccttttta tcggacatta  1080
tcagatcctg ttttttgtccg aggaggattt gggaatcctc attatgtact ggggcttagg  1140
ggagtagcat ttcaacaaac tggtacgaac cacacccgaa catttagaaa tagtgggacc  1200
atagattctc tagatgaaat cccacctcag gataatagtg gggcaccttg gaatgattat  1260
agtcatgtat taaatcatgt tacatttgta cgatggccag gtgagatttc aggaagtgat  1320
tcatggagag ctccaatgtt ttcttggacg caccgtagtg caaccccctac aaatacaatt  1380
gatccggaga ggattactca aataccattg gtaaaagcac atacacttca gtcaggtact  1440
actgttgtaa gagggcccgg gtttacggga ggagatattc ttcgacgaac aagtggagga  1500
ccatttgctt atactattgt taatataaat gggcaattac cccaaaggta tcgtgcaaga  1560
atacgctatg cctctactac aaatctaaga atttacgtaa cggttgcagg tgaacggatt  1620
tttgctggtc aatttaacaa aacaatggat accggtgacc cattaacatt ccaatctttt  1680
agttacgcaa ctattaatac agcttttaca ttcccaatgtc gccagagtag tttcacagta  1740
ggtgctgata ctttttagttc agggaatgaa gtttatatag acagatttga attgattcca  1800
gttactgcaa catttgaagc agaatatgat ttagaaagag cacaaaaggc ggtgaatgcg  1860
ctgtttactt ctataaacca aataggggata aaaacagatg tgacggatta tcatattgat  1920
caagtatcca atttagtgga ttgtttatca gatgaatttt gtctggatga aaagcgagaa  1980
ttgtccgaga aagtcaaaca tgcgaagcga ctcagtgatg agcggaattt acttcaagat  2040
ccaaacttca aaggcatcaa taggcaacta gaccgtggtt ggagaggaag tacgggatatt  2100
accatccaaa gaggagatga cgtattcaaa gaaaattatg tcacactacc aggtacctttt  2160
gatgagtgct atccaacata tttgtatcaa aaaatcgatg aatcaaaatt aaaagcctt   2220
acccgttatc aattaagagg gtatatcgaa gatagtcaag acttagaaat ctatttaatt  2280
cgctacaatg caaaacatga aacagtaaat gtgccaggta cgggttcctt atggccgctt  2340
tcagcccaaa gtccaatcgg aaagtgtgga gagccgaatc gatgcgcgcc acaccttgaa  2400
tggaatcctg acttagattg ttcgtgtagg gatggagaaa agtgtgccca tcattcgcat  2460
catttctcct tagacattga tgtaggatgt acagacttaa atgaggacct aggtgtatgg  2520
gtgatcttta agattaagac gcaagatggg cacgcaagac tagggaatct agagtttctc  2580
gaagagaaac cattagtagg agaagcgcta gctcgtgtga aaagagcgga gaaaaaatgg  2640
agagacaaac gtgaaaaatt ggaatgggaa acaaatatcg tttataaaga ggcaaaagaa  2700
tctgtagatg ctttatttgt aaactctcaa tatgatcaat tacaagcgga tacgaatatt  2760
gccatgattc atgcggcaga taaacgtgtt catagcattc gagaagctta tctgcctgag  2820
ctgtctgtga ttccgggtgt caatgcggct attttttgaag aattagaagg gcgtatttttc  2880
actgcattct ccctatatga tgcgagaaat gtcattaaaa atggtgatttt taataatggc  2940
ttatcctgct ggaacgtgaa agggcatgta gatgtagaaa aacaaaacaa ccaacgttcg  3000
gtccttgttg ttccggaatg ggaagcagaa gtgtcacaag aagttcgtgt ctgtccgggt  3060
cgtggctata tccttcgtgt cacagcgtac aaggagggat atggagaagg ttgcgtaacc  3120
attcatgaga tcgagaacaa tacagacgaa ctgaagtttta gcaactgcgt agaagaggaa  3180
atctatccaa ataacacggt aacgtgtaat gattatactg taaatcaaga agaatacggtt  3240
ggtgcgtaca cttctcgtaa tcgaggatat aacgaagctc cttccgtacc agctgattat  3300
gcgtcagtct atgaagaaaa atcgtataca gatggacgaa gagagaatcc ttgtgaatttt  3360
aacagagggg atagggatta cacgccacta ccagttggtt atgtgacaaa agaattagaa  3420
tacttcccag aaaccgataa ggtatggatt gagattggag aaacgaagg aacatttatc  3480
gtggacagcg tggaattact ccttatggag gaataa                              3516
```

```
SEQ ID NO: 99          moltype = AA  length = 1171
FEATURE                Location/Qualifiers
REGION                 1..1171
                       note = Amino acid sequence of the chimeric protein TIC842.
source                 1..1171
                       mol_type = protein
                       organism = synthetic construct
SEQUENCE: 99
MAENNIQNQC VPYNCLNNPE VEILNEERST GRLPLDISLS LTRFLLSEFV PGVGVAFGLF    60
DLIWGFITPS DWSLFLLQIE QLIEQRIETL ERNRAITTLR GLADSYEIYI EALREWEANP   120
NNAQLREDVR IRFANTDDAL ITAINNFTLT SFEIPLLSVY VQAANLHLSL LRDAVSFGQG   180
WGLDIATVNN HYNRLINLIH RYTKHCLDTY NQGLENLRGT NTRQWARFNQ FRRDLTLTVL   240
DIVALFPNYD VRTYPIQTSS QLTREIYTSS VIEDSPVSAN IPNGFNRAEF GVRPPHLMDF   300
MNSLFVTAET VRSQTVWGGH LVSSRNTAGN RINFPSYGVF NPGGAIWIAD EDPRPFYRTL   360
SDPVFVRGGF GNPHYVLGLR GVAFQQTGTN HTRTFRNSGT IDSLDEIPPQ DNSGAPWNDY   420
SHVLNHVTFV RWPGEISGSD SWRAPMFSWT HRSATPTNTI DPERITQIPL VKAHTLQSGT   480
TVVRGPGFTG GDILRRTSGG PFAYTIVNIN GQLPQRYRAR IRYASTTNLR IYVTVAGERI   540
FAGQFNKTMD TGDPLTFQSF SYATINTAFT FPMSQSSFTV GADTFSSGNE VYIDRFELIP   600
VTATFEAEYD LERAQKAVNA LFTSINQIGI KTDVTDYHID QVSNLVDCLS DEFCLDEKRE   660
LSEKVKHAKR LSDERNLLQD PNFKGINRQL DRGWRGSTDI TIQRGDDVFK ENYVTLPGTF   720
DECYPTYLYQ KIDESKLKAF TRYQLRGYIE DSQDLEIYLI RYNAKHETVN VPGTGSLWPL   780
SAQSPIGKCG EPNRCAPHLE WNPDLDCSCR DGEKCAHHSH HFSLDIDVGC TDLNEDLGVW   840
```

```
VIFKIKTQDG HARLGNLEFL EEKPLVGEAL ARVKRAEKKW RDKREKLEWE TNIVYKEAKE    900
SVDALFVNSQ YDQLQADTNI AMIHAADKRV HSIREAYLPE LSVIPGVNAA IFEELEGRIF    960
TAFSLYDARN VIKNGDFNNG LSCWNVKGHV DVEEQNNQRS VLVVPEWEAE VSQEVRVCPG   1020
RGYILRVTAY KEGYGEGCVT IHEIENNTDE LKFSNCVEEE IYPNNTVTCN DYTVNQEEYG   1080
GAYTSRNRGY NEAPSVPADY ASVYEEKSYT DGRRENPCEF NRGYRDYTPL PVGYVTKELE   1140
YFPETDKVWI EIGETEGTFI VDSVELLLME E                                  1171

SEQ ID NO: 100         moltype = DNA  length = 3444
FEATURE                Location/Qualifiers
misc_feature           1..3444
                       note = Chimeric coding sequence encoding TIC850.
source                 1..3444
                       mol_type = other DNA
                       organism = synthetic construct
SEQUENCE: 100
atggagaata atattcaaaa tcaatgcgta cctacaatt gtttaaataa tcctgaagta    60
gaaatattaa atgaagaaag aagtactggc agattaccgt tagatatatc cttatcgctt   120
acacgtttcc ttttgagtga atttgttcca ggtgtgggag ttgcgtttgg attatttgat   180
ttaatatggg gttttataac tccttctgat tggagcttat ttcttttaca gattgaacaa   240
ttgattgagc aaagaataga aacattggaa aggaaccggg caattactac attacgaggg   300
ttagcagata gctatgaaat ttatattgaa gcactaagag agtgggaagc aaatcctaat   360
aatgcacaat taagggaaga tgtgcgtatt cgatttgcta atacagacga cgctttaata   420
acagcaataa ataattttac acttacaagt tttgaaatcc ctcttttatc ggtctatgtt   480
caagcggcga atttacattt atcactatta agagacgctg tatcgtttgg gcagggttgg   540
ggactggata tagctactgt taataatcat tataatagat taataaatct tattcataga   600
tatacgaaac attgtttgga cacatacaat caaggataag aaaacttaag aggtactaat   660
actcgacaat gggcaagatt caatcagttt aggagagatt taacgctaac tgtattagat   720
atcgttgctc tttttccgaa ctacgatgtt agaacatatc caattcaaac gtcatcccaa   780
ttaacaaggg aaatttatac aagttcagta attgaggatt ctccagtttc tgctaatata   840
cctaatggtt ttaatagggc ggaatttgga gttagaccgc cccatcttat ggactttatg   900
aattctttgt ttgtaactgc agagactgtt agaagtcaaa ctgtgtgggg aggacactta   960
gttagttcac gaaatacggc tggtaaccgt ataaatttcc ctagttacgg ggtcttcaat  1020
cctggtggcg ccatttggat tgcagatgag gatccacgtc cttttttatcg gacattatca  1080
gatcctgttt ttgtccgagg aggatttggg aatcctcatt atgtactggg gcttagggga  1140
gtagcatttc aacaaactgg tacgaaccac acccgaacat ttagaaatag tgggaccata  1200
gattctctag atgaaatccc acctcaggat aatagtgggg caccttggaa tgattatagt  1260
catgtattaa atcatgttac atttgtacga tggccaggtg agatttcagg aagtgattca  1320
tggagagctc caatgttttc ttggacgcac cgtagtgcaa ccccctacaaa tacaattgat  1380
ccggagagga ttactcaaat accattggta aaagcacata cacttcagtc aggtactact  1440
gttgtaagag ggcccggggtt tacgggagga gatatccttc gaagaacgaa tactggcaca  1500
tttgcagata tgagagtaaa tattactggg ccattatccc aaagatatcg tgtaagaatt  1560
cgctatgctt ctacgacaga tttacaattt ttcacgagaa tcaatggaac ttctgtaaat  1620
caaggtaatt tccaaagaac tatgaataga ggggataatt tagaatctgg aaactttagg  1680
actgcaggat ttagtacgcc ttttagtttt tcaaatgcgc aaagtacatt cacattgggt  1740
actcaggctt tttcaaatca ggaagtttat atagatcgaa ttgaatttgt cccggcagaa  1800
gtaacattcg aggcagaatc tgatttagaa agagcacaaa aggcggtgaa tgagctgttt  1860
acttcttcca atcaaatcgg gttaaaaaca gatgtgacgg attatcatat tgatcaagta  1920
tccaatttag ttgagtgttt atctgatgaa ttttgtctgg atgaaaaaaa agaattgtcc  1980
gagaaagtca aacatgcgaa gcgacttagt gatgagcgga atttacttca agatccaaac  2040
tttgaggga tcaatagaca actagaccgt ggctggagag gaagtacgga tattaccatc  2100
caaggaggcg atgacgtatt caaagagaat tacgttacgc tcttttgatgag  2160
tgctatccaa cgtatttata tcaaaaaata gatgagtcga aattaaaagc ctatacccgt  2220
taccaattaa gagggtatat cgaagatagt caagacttag aaatctattt aattcgctac  2280
aatgccaaac acgaaacagt aaatgtgcca ggtacgggtt ccttatggcc gctttcagcc  2340
ccaagtccaa tcggaaaatg tgcccatcat tcccatcatt tctccttga cattgatgtt  2400
ggatgtacag acttaaatga ggacttaggt gtatgggtga tattcaagat taagacgcaa  2460
gatgccatg caagactagg aaatctagaa tttctcgaag agaaaccatt agtaggagaa  2520
gcactagctc gtgtgaaaag agcggagaaa aaatggagag acaaacgtga aaaattggaa  2580
tgggaaacaa atattgttta taaagaggca aagaatctgt tagatgcttt atttgtaaac  2640
tctcaatatg atagattaca agcggatacc aacatcgcga tgattcatgc ggcagataaa  2700
cgcgttcata gcattcgaga agcttatctg cctgagctgt ctgtgattcc gggtgtcaat  2760
gcggctattt tgaagaatt agaagggcgt attttcactg cattctccct atatgatgcg  2820
agaaatgtca ttaaaaatgg tgattttaat aatggcttat cctgctggaa cgtgaaaggg  2880
catgtagatg tagaagaaca aaacaaccac cgttcggtcc ttgttgttcc ggaatgggaa  2940
gcagaagtgt cacaagaagt tcgtgtctgt ccgggtcgtg ctatatcct tcgtgtcaca  3000
gcgtacaagg agggatatgg agaaggttgc gtaaccattc atgagatcga gaacaataca  3060
gacgaactga gtttagcaa ctgtgtagaa gaggaagtat atccaaacaa cacggtaacg  3120
tgtaatgatt atactgcgac tcaagaagaa tatgagggta cgtacacttc tcgtaactga  3180
ggatatgacg gagcctatga aagcaattct tctgtaccag ctgattatgc atcagcctat  3240
gaagaaaaag catatacaga tggacgaaga gacaatcctt gtgaatctaa cagaggatat  3300
ggggattaca caccactacc agctggctat gtgacaaaag aattagagta cttcccagaa  3360
accgataagg tatggattga gatcggagaa acgaaggaa cattcatcgt ggacagcgtg  3420
gaattacttc ttatggagga atag                                         3444

SEQ ID NO: 101         moltype = AA  length = 1147
FEATURE                Location/Qualifiers
REGION                 1..1147
                       note = Amino acid sequence of the chimeric protein TIC850.
source                 1..1147
```

-continued

```
                        mol_type = protein
                        organism = synthetic construct
SEQUENCE: 101
MENNIQNQCV PYNCLNNPEV EILNEERSTG RLPLDISLSL TRFLLSEFVP GVGVAFGLFD    60
LIWGFITPSD WSLFLLQIEQ LIEQRIETLE RNRAITTLRG LADSYEIYIE ALREWEANPN   120
NAQLREDVRI RFANTDDALI TAINNFTLTS FEIPLLSVYV QAANLHLSLL RDAVSFGQGW   180
GLDIATVNNH YNRLINLIHR YTKHCLDTYN QGLENLRGTN TRQWARFNQF RRDLTLTVLD   240
IVALFPNYDV RTYPIQTSSQ LTREIYTSSV IEDSPVSANI PNGFNRAEFG VRPPHLMDFM   300
NSLFVTAETV RSQTVWGGHL VSSRNTAGNR INFPSYGVFN PGGAIWIADE DPRPFYRTLS   360
DPVFVRGGFG NPHYVLGLRG VAFQQTGTNH TRTFRNSGTI DSLDEIPPQD NSGAPWNDYS   420
HVLNHVTFVR WPGEISGSDS WRAPMFSWTH RSATPTNTID PERITQIPLV KAHTLQSGTT   480
VVRGPGFTGG DILRRTNTGT FADMRVNITG PLSQRYRVRI RYASTTDLQF FTRINGTSVN   540
QGNFQRTMNR GDNLESGNFR TAGFSTPFSF SNAQSTFTLG TQAFSNQEVY IDRIEFVPAE   600
VTFEAESDLE RAQKAVNELF TSSNQIGLKT DVTDYHIDQV SNLVECLSDE FCLDEKKELS   660
EKVKHAKRLS DERNLLQDPN FRGINRQLDR GWRGSTDITI QGGDDVFKEN YVTLLGTFDE   720
CYPTYLYQKI DESKLKAYTR YQLRGYIEDS QDLEIYLIRY NAKHETVNVP GTGSLWPLSA   780
PSPIGKCAHH SHHFSLDIDV GCTDLNEDLG VWVIFKIKTQ DGHARLGNLE FLEEKPLVGE   840
ALARVKRAEK KWRDKREKLE WETNIVYKEA KESVDALFVN SQYDRLQADT NIAMIHAADK   900
RVHSIREAYL PELSVIPGVN AAIFEELEGR IFTAFSLYDA RNVIKNGDFN NGLSCWNVKG   960
HVDVEEQNNH RSVLVVPEWE AEVSQEVRVC PGRGYILRVT AYKEGYGEGC VTIHEIENNT  1020
DELKFSNCVE EEVYPNNTVT CNDYTATQEE YEGTYTSRNR GYDGAYESNS SVPADYASAY  1080
EEKAYTDGRR DNPCESNRGY GDYTPLPAGY VTKELEYFPE TDKVWIEIGE TEGTFIVDSV  1140
ELLLMEE                                                           1147

SEQ ID NO: 102          moltype = DNA   length = 3447
FEATURE                 Location/Qualifiers
misc_feature            1..3447
                        note = Chimeric coding sequence encoding TIC859.
source                  1..3447
                        mol_type = other DNA
                        organism = synthetic construct
SEQUENCE: 102
atggagaata atattcaaaa tcaatgcgta ccttacaatt gtttaaataa tcctgaagta    60
gaaatattaa atgaagaaag aagtactggc agattaccgt tagatatatc cttatcgctt   120
acacgtttcc ttttgagtga atttgttcca ggtgtgggag ttgcgtttgg attatttgat   180
ttaatatggg gttttataac tcctcctgat tggagcttat ttctttaca gattgaacaa    240
ttgattgagc aaagaataga aacattgaa aggaaccggg caattactac attacgaggg     300
ttagcagata gctatgaaat ttatattgaa gcactaagag agtgggaagc aaatcctaat    360
aatgcacaat taagggaaga tgtgcgtatt cgatttgcta atacagacga cgctttaata   420
acagcaataa ataattttac acttacaagt tttgaaatcc ctcttttatc ggtctatgtt    480
caagcggcga atttacattt atcactatta agagacgctg tatcgtttgg gcagggttgg    540
ggactggata tagctactgt taataatcat tataatagat taataaatct tattcataga   600
tatcgaaac attgtttgga cacatacaat caaggtactg aaaacttaag aggtactaat    660
actcgacaat gggcaagatt caatcagttt aggagagatt taacgctaac tgtattagat   720
atcgttgctc tttttccgaa ctacgatgtt agaacatatc caattcaaac gtcatcccaa   780
ttaacaaggg aaatttatac aagttcagta attgaggatt ctccagtttc tgctaatata   840
cctaatggtt ttaatagggc ggaatttgga gttagaccgc cccatcttat ggactttatg   900
aattctttgt ttgtaactgc agagactgtt agaagtcaaa ctgtgtgggg aggacactta   960
gttagttcac gaaatacggc tggtaaccgt ataaatttcc ctagttacgg ggtcttcaat  1020
cctggtggcg ccatttggat tgcagatgag gatccacgtc cttttttatcg gacattatca  1080
gatcctgttt ttgtccgagg aggatttggg aatcctcatt atgtactggg gcttagggga  1140
gtagcatttc aacaaactgg tacgaaccac acccgaacat ttagaaatag tgggaccata  1200
gattctctag atgaaatccc acctcaggat aatagtgggg caccttggaa tgattatagt  1260
catgtattaa atcatgttac atttgtacga tggccaggtg agatttcagg aagtgattca  1320
tggagagctc caatgttttc ttggacgcac cgtagtgcaa cccctacaaa cgaagttcgt  1380
gtatctagaa ttacacaatt accgatggtg aaggcgcata cgcttcatgc gggagctact  1440
gttgttagag accaggatt tacaggagga gatatactcc gaagaactac ttcaggctca  1500
tttggggata tgagaataac aaattttca agttcatcat cgaggtatcg tgtaagaata  1560
cgttatgctt ctactacaga tttacaattt ttcttgagtg ttggaggaac ccctgtcaat  1620
gtagccgatt tcccgaaaac catagataga ggggaaaact tagaatatgg aagcttttaga  1680
acggcaggtt ttactacccc tttagttttt gtaagttcaa caaataatt cacattaggt   1740
gttcagagtg tttcttcagg taacgagatt tttgtagatc gaattgaatt tgttccggca  1800
gatgcaacct ttgaggcaga atatgattta gaaagagcac aaaaggcggt gaatgagctg  1860
tttacttctt ccaatcaaat cgggttaaaa acagatgtga cagattatca tattgatcaa  1920
gtatccaatt tagttgagtg tttatctgat gaattttgtc tggatgaaaa aaaagaattg  1980
tccgagaaag tcaaacatgc gaagcgactt agtgatgagc ggaatttact tcaagatcca  2040
aactttagag ggatcaatag acaactagac cgtggctgga gaggaagtac ggatattacc  2100
atccaaggag gcgatgacgt attcaaagag aattacgtta cgcttattgg gtacttttgat  2160
gagtgctatc caacgtattt atatcaaaaa atagatgagt cgaaattaaa agcctatacc  2220
cgttaccaat taagagggta tatcgaagat agtcaagact tagaaatcta tttaattcgc  2280
tacaatgcca aacacgaaac agtaaatgtg ccaggtacgg gttccttatg gccgctttca  2340
gccccaagtc caatcggaaa atgtgcccat cattcccatc atttctcctt ggacattgat  2400
gttggatgta cagacttaaa tgaggactta ggtgtatggg tgatattcaa gattaagacg  2460
caagatggcc atgcaagact aggaaatcta gaatttctcg agagaaaacc attagtagga  2520
gaagcactag ctcgtgtgaa aagagcggag aaaaaatgga gagacaaacg tgaaaaattg  2580
gaatgggaaa caaatattgt ttataaagag gcaaaagaat ctgtagatgc tttatttgta  2640
aactctcaat atgatagatt acaagcggat accaacatcg cgatgattca tgcggcagat  2700
aaacgcgttc atagcattcg agaagcttat ctgcctgagc tgtctgtgat tccgggtgtc  2760
aatgcggcta tttttgaaga attagaaggg cgtattttca ctgcattctc cctatatgat  2820
```

-continued

```
gcgagaaatg tcattaaaaa tggtgatttt aataatggct tatcctgctg gaacgtgaaa   2880
gggcatgtag atgtagaaga acaaaacaac caccgttcgg tccttgttgt tccggaatgg   2940
gaagcagaag tgtcacaaga agttcgtgtc tgtccgggtc gtggctatat ccttcgtgtc   3000
acagcgtaca aggagggata tggagaaggt tgcgtaacca ttcatgagat cgagaacaat   3060
acagacgaac tgaagtttag caactgtgta gaagaggaag tatatccaaa caacacggta   3120
acgtgtaatg attatactgc gactcaagaa gaatatgagg gtacgtacac ttctcgtaat   3180
cgaggatatg acggagccta tgaaagcaat tcttctgtac cagctgatta tgcatcagcc   3240
tatgaagaaa aagcatatac agatggacga agagacaatc cttgtgaatc taacagagga   3300
tatgggggatt acacaccact accagctggc tatgtgacaa aagaattaga gtacttccca   3360
gaaaccgata aggtatggat tgagatcgga gaaacggaag gaacattcat cgtggacagc   3420
gtggaattac ttcttatgga ggaatag                                       3447
```

SEQ ID NO: 103      moltype = AA  length = 1148
FEATURE            Location/Qualifiers
REGION              1..1148
                      note = Amino acid sequence of the chimeric protein TIC859.
source              1..1148
                      mol_type = protein
                      organism = synthetic construct

```
SEQUENCE: 103
MENNIQNQCV PYNCLNNPEV EILNEERSTG RLPLDISLSL TRFLLSEFVP GVGVAFGLFD   60
LIWGFITPSD WSLFLLQIEQ LIEQRIETLE RNRAITTLRG LADSYEIYIE ALREWEANPN   120
NAQLREDVRI RFANTDDALI TAINNFTLTS FEIPLLSVYV QAANLHLSLL RDAVSFGQGW   180
GLDIATVNNH YNRLINLIHR YTKHCLDTYN QGLENLRGTN TRQWARFNQF RRDLTLTVLD   240
IVALFPNYDV RTYPIQTSSQ LTREIYTSSV IEDSPVSANI PNGFNRAEFG VRPPHLMDFM   300
NSLFVTAETV RSQTVWGGHL VSSRNTAGNR INFPSYGVFN PGGAIWIADE DPRPFYRTLS   360
DPVFVRGGFG NPHYVLGLRG VAFQQTGTNH TRTFRNSGTI DSLDEIPPQD NSGAPWNDYS   420
HVLNHVTFVR WPGEISGSDS WRAPMFSWTH RSATPTNEVR VSRITQLPMV KAHTLHAGAT   480
VVRGPGFTGG DILRRTTSGS FGDMRITNFS SSSSRYRVRI RYASTTDLQF FLSVGGTPVN   540
VADFPKTIDR GENLEYGSFR TAGFTTPFSF VSSTNNFTLG VQSVSSGNEI FVDRIEFVPA   600
DATFEAEYDL ERAQKAVNEL FTSSNQIGLK TDVTDYHIDQ VSNLVECLSD EFCLDEKKEL   660
SEKVKHAKRL SDERNLLQDP NFRGINRQLD RGWRGSTDIT IQGGDDVFKE NYVTLLGTFD   720
ECYPTYLYQK IDESKLKAYT RYQLRGYIED SQDLEIYLIR YNAKHETVNV PGTGSLWPLS   780
APSPIGKCAH HSHHFSLDID VGCTDLNEDL GVWVIFKIKT QDGHARLGNL EFLEEKPLVG   840
EALARVKRAE KKWRDKREKL EWETNIVYKE AKESVDALFV NSQYDRLQAD TNIAMIHAAD   900
KRVHSIREAY LPELSVIPGV NAAIFEELEG RIFTAFSLYD ARNVIKNGDF NNGLSCWNVK   960
GHVDVEEQNN HRSVLVVPEW EAEVSQEVRV CPGRGYILRV TAYKEGYGEG CVTIHEIENN   1020
TDELKFSNCV EEEVYPNNTV TCNDYTATQE EYEGTYTSRN RGYDGAYESN SSVPADYASA   1080
YEEKAYTDGR RDNPCESNRG YGDYTPLPAG YVTKELEYFP ETDKVWIEIG ETEGTFIVDS   1140
VELLLMEE                                                            1148
```

SEQ ID NO: 104      moltype = DNA  length = 3612
FEATURE            Location/Qualifiers
misc_feature       1..3612
                      note = Chimeric coding sequence encoding TIC861.
source              1..3612
                      mol_type = other DNA
                      organism = synthetic construct

```
SEQUENCE: 104
atgaaactaa agaatccaga taagcatcaa agtttttcta gcaatgcgaa agtagataaa   60
atctctacgg attcactaaa aaatgaaaca gatatagaat tacaaaacat taatcatgaa   120
gattgtttga aaatatctga gtatgaaaat gtagagccgt ttgttagtgc atcaacaatt   180
caaacaggta ttagtattgc gggtaaaata cttggcaccc taggcgttcc ttttgcagga   240
caagtagcta gtctttatag ttttatctta ggtgagtat ggcctaaggg gaaaaatcaa    300
tgggaaatct ttatggaaca tgtagaagag attattaatc aaaaaatatc aacttatgca   360
agaaataaag cacttacaga cttgaaagga ttaggagatg ccttagctgt ctaccatgaa   420
tcgcttgaaa gttgggttgg aaatcgtaag aacacaaggg ctaggagtgt tgtcaagagc   480
caatatatcg cattagaatt gatgttcgtt cagaaactac cttcttttgc agtgtctgga   540
gaggaggtac cattattacc gatatatgcc caagctgcaa atttacattt gttgctatta   600
agagatgcat ctatttttgg aaaagagtgg ggattatcat cttcagaaat ttcaacattt   660
tataaccgtc aagtcgaacg agcaggagat tattccgacc attgtgtgaa atggtatagt   720
acaggtctaa ataacttgag gggtacaaat gccgaaagct gggttcgtta taatcaattt   780
cgtaaagata tgacattaat ggtacttgat ttagtcgcac tattcccaag ctatgataca   840
cttgtatatc caattaaaac tacttctcaa cttacaagga aagtatatac agacgcaatt   900
gggacagtac atccgaatgc aagttttgca agtacgactt ggtataataa taatgcccct   960
tcgttctcta ccatagagtc tgctgttgtt cgaaacccgc atctactcga ttttctagaa   1020
caagttacaa tttacagctt attaagtagg tggagtaaca ctcagtatat gaatatgtgg   1080
ggaggacata gacttgaatt ccgaacaatc ggaggaatgt taaatacctc aacacaagga   1140
tctactaata cttctattaa tcctgtaaca ttaccgttca cgtctcgaga cgtctctagg   1200
actgaatcat tggcagggct gaatctattt ttaactcaac ctgttaatgg agtacctagg   1260
gttgattttc attggaaatt cgtcacacat ccgatcgcat ctgataattt ctattatcca   1320
gggtatgctg gaattgggac gcaattacaa gattcagaaa atgaattacc acctgaaaca   1380
acaggacagc caaattatga atcatatagt catagattat ctcatatagg actcatttca   1440
gcatcccatg tgaaagcatt ggtatattct tggacgcatc ggtatagaa tcgtacaaac   1500
acaattgatc cagagagaat taatcaaata cctttagtga aaggatttag agtttggggg   1560
ggcacctctg tcattacagg accaggattt acaggagggg atatccttcg aagaaatacc   1620
tttggtgatt ttgtatctct acaagtcaat attaattcac caattaccca aagataccgt   1680
ttaagatttc gttacgcttc cagtagggat gcacgagtta tagtattaac aggagcggca   1740
tccacaggag tgggaggcca agttagtgta aatatgcctc ttcagaaaac tatggaaata   1800
```

-continued

```
ggggagaact taacatctag aacatttaga tataccgatt ttagtaatcc ttttcattt    1860
agagctaatc cagatataat tgggataagt gaacaacctc tatttggtgc aggttctatt    1920
agtagcggtg aactttatat agataaaatt gaaattattc tagcagatgc aacatttgaa    1980
gcagaatctg atttagaaag agcacaaaag gcggtgaatg agctgtttac ttcttccaat    2040
caaatcgggt taaaaacaga tgtgacggat tatcatattg atcaagtatc caatttagtt    2100
gagtgtttat ctgatgaatt ttgtctggat gaaaaaaaag aattgtccga gaaagtcaaa    2160
catgcgaagc gacttagtga tgagcggaat ttacttcaag atccaaactt tagagggatc    2220
aatagacaac tagaccgtgg ctggagagga agtacggata ttaccatcca aggaggcgat    2280
gacgtattca aagagaatta cgttacgcta ttgggtacct ttgatgagtg ctatccaacg    2340
tatttatatc aaaaaataga tgagtcgaaa ttaaaagcct atacccgtta ccaattaaga    2400
gggtatatcg aagatagtca agacttagaa atctatttaa ttcgctacaa tgccaaacac    2460
gaaacagtaa atgtgccagg tacgggttcc ttatggccgc tttcagcccc aagtccaatc    2520
ggaaaatgtg cccatcattc ccatcatttc tccttggaca ttgatgttgg atgtacagac    2580
ttaaatgagg acttaggtgt atgggtgata ttcaagatta gacgcaaga tggccatgca    2640
agactaggaa atctagaatt tctcgaagag aaaccattag taggagaagc actagctcgt    2700
gtgaaaagc cggagaaaaa atggagagac aaacgtgaaa aattggaatg ggaaacaaat    2760
attgtttata aagaggcaaa agaatctgta gatgctttat ttgtaaactc tcaatatgat    2820
agattacaag cggataccaa catcgcgatg attcatgcgg cagataaacg cgttcatagc    2880
attcgagaag cttatctgcc tgagctgtct gtgattccgg gtgtcaatgc ggctattttt    2940
gaagaattag aagggcgtat tttcactgca ttctccctat atgatgcgag aaatgtcatt    3000
aaaaatggtg attttaataa tggcttatcc tgctggaacg tgaaagggca tgtagatgta    3060
gaagaacaaa acaaccaccg ttcggtcctt gttgttccgg aatgggaagc agaagtgtca    3120
caagaagttc gtgtctgtcc gggtcgtggc tatatccttc gtgtcacagc gtacaaggag    3180
ggatatggag aaggttgcgt aacccattcat gagatcgaga acaatacaga cgaactgaag    3240
tttagcaact gtgtagaaga ggaagtatat ccaaacaaca cggtaacgtg taatgattat    3300
actgcgactc aagaagaata tgagggtacg tacacttctc gcaatcgagg atatgacgga    3360
gcctatgaaa gcaattcttc tgtaccagct gattatgcat cagcctatga agaaaaagca    3420
tatacagatg gacgaagaga caatccttgt gaatctaaca gaggatatgg ggattacaca    3480
ccactaccag ctggctatgt gacaaaagaa ttagagtact tcccagaaac cgataaggta    3540
tggattgaga tcgagaaac ggaaggaaca ttcatcgtgg acagcgtgga attacttctt    3600
atggaggaat ag                                                        3612
```

```
SEQ ID NO: 105          moltype = AA   length = 1203
FEATURE                 Location/Qualifiers
REGION                  1..1203
                        note = Amino acid sequence of the chimeric protein TIC861.
source                  1..1203
                        mol_type = protein
                        organism = synthetic construct
SEQUENCE: 105
MKLKNPDKHQ SFSSNAKVDK ISTDSLKNET DIELQNINHE DCLKISEYEN VEPFVSASTI   60
QTGISIAGKI LGTLGVPFAG QVASLYSFIL GELWPKGKNQ WEIFMEHVEE IINQKISTYA   120
RNKALTDLKG LGDALAVYHE SLESWVGNRK NTRARSVVKS QYIALELMFV QKLPSFAVSG   180
EEVPLLPIYA QAANLHLLLL RDASIFGKEW GLSSSEISTF YNRQVERAGD YSDHCVKWYS   240
TGLNNLRGTN AESWVRYNQF RKDMTLMVLD LVALFPSYDT LVYPIKTTSQ LTREVYTDAI   300
GTVHPNASFA STTWYNNNAP SFSTIESAVV RNPHLLDFLE QVTIYSLLSR WSNTQYMNMW   360
GGHRLEFRTI GGMLNTSTQG STNTSINPVT LPFTSRDVTR TESLAGLNLF LTQPVNGVPR   420
VDFHWKFVTH PIASDNFYYP GYAGIGTQLQ DSENELPPET TGQPNYESYS HRLSHIGLIS   480
ASHVKALVYS WTHRSADRTN TIDPERINQI PLVKGFRVWG GTSVITGPGF TGGDILRRNT   540
FGDFVSLQVN INSPITQRYR LRFRYASSRD ARVIVLTGAA STGVGGQVSV NMPLQKTMEI   600
GENLTSRTFR YTDFSNPFSF RANPDIIGIS EQPLFGAGSI SSGELYIDKI EIILADATFE   660
AESDLERAQK AVNELFTSSN QIGLKTDVTD YHIDQVSNLV ECLSDEFCLD EKKELSEKVK   720
HAKRLSDERN LLQDPNFRGI NRQLDRGWRG STDITIQGGD DVFKENYVTL LGTFDECYPT   780
YLYQKIDESK LKAYTRYQLR GYIEDSQDLE IYLIRYNAKH ETVNVPGTGS LWPLSAPSPI   840
GKCAHHSHHF SLDIDVGCTD LNEDLGVWVI FKIKTQDGHA RLGNLEFLEE KPLVGEALAR   900
VKRAEKKWRD KREKLEWETN IVVYKEAKESV DALFVNSQYD RLQADTNIAM IHAADKRVHS   960
IREAYLPELS VIPGVNAAIF EELEGRIFTA FSLYDARNVI KNGDFNNGLS CWNVKGHVDV   1020
EEQNNHRSVL VVPEWEAEVS QEVRVCPGRG YILRVTAYKE GYGEGCVTIH EIENNTDELK   1080
FSNCVEEEVY PNNTVTCNDY TATQEEYEGT YTSRNRGYDG AYESNSSVPA DYASAYEEKA   1140
YTDGRRDNPC ESNRGYGDYT PLPAGYVTKE LEYFPETDKV WIEIGETEGT FIVDSVELLL   1200
MEE                                                                  1203
```

```
SEQ ID NO: 106          moltype = DNA   length = 3432
FEATURE                 Location/Qualifiers
misc_feature            1..3432
                        note = Chimeric coding sequence encoding TIC848.
source                  1..3432
                        mol_type = other DNA
                        organism = synthetic construct
SEQUENCE: 106
atggagataa ataatcagaa gcaatgcata ccatataatt gcttaagtaa tcctgaggaa    60
gtacttttgg atggggagag gatattacct gatatcgatc cactcgaagt ttctttgtcg   120
cttttgcaat ttctttgaa taactttgtt ccagggggag ctttatttc aggattagtt   180
gataaaatat gggggctt gagaccatct gaatggatt tatttcttgc acagattgaa   240
cggttgattg atcaaagaat agaagcaaca gtaagcagca aagcaatcac tgaattagaa   300
ggattaggga gaaattatca aatatacgct gaagcattta agaatgggga tcagatcct   360
gataacgaag cggctaaaag tagagtaatt gatcgctttc gtacttga tggtctaatt   420
gaagcaaata tcccttcatt tcggataatt ggatttgaag tgccactttt atcggtttat   480
gttcaagcag ctaatctaca tctcgctcta ttgagagatt ctgttattttt tggagagaga   540
```

```
tggggattga cgacaaaaaa tgtcaatgat atctataata gacaaattag agaaattcat   600
gaatatagca atcattgcgt agatacgtat aacacagaac tagaacgtct agggtttaga   660
tctatagcgc agtggagaat atataatcag tttagaagag aactaacact aactgtatta   720
gatattgtcg ctcttttccc gaactatgac agtagactgt atccgatcca aactttttct   780
caattgacaa gagaaattgt tacatcccca gtaagcgaat tttattatgg tgttattaat   840
agtggtaata taattggtac tcttactgaa cagcagataa ggcgaccaca tcttatggac   900
ttctttaact ccatgatcat gtatacatca gataatagac gggaacatta ttggtcagga   960
cttgaaatga cggcttattt tacaggattt gcaggagctc aagtgtcatt ccctttagtc  1020
gggactagag gggagtcagc tccaccatta actgttagaa gtgttaatga tggaatttat  1080
agaatattat cggcaccgtt ttattcagcg ccttttctag gcaccattgt attgggaagt  1140
cgtggagaaa aatttgattt tgcgcttaat aatatttcac ctccgccatc tacaatatac  1200
agacatcctg gaacagtaga ttcactagtc agtataccgc cacaggataa tagcgtacca  1260
ccgcacaggg gatctagtca tcgattaagt catgttacaa tgcgcgcaag ttcccctata  1320
ttccattgga cgcatcgcag cgcaaccact acaaatacaa ttaatccaaa tgctattatc  1380
caaataccac tagtaaaatc tactaatctt ggctctggaa cttctgtcgt taaaggacca  1440
ggatttacag gaggagatat tcttcgaaga acttcacctg gccagatttc aaccttaaga  1500
gtaaatatta ctgcaccatt atcacaaaga tatcgggtaa gaattcgcta cgcttctacc  1560
acaaatttac aattccatac atcaattgac ggaagaccta ttaatcaggg gaattttca   1620
gcaactatga gtagtgggag taatttacag tccggaagct ttaggactgt aggttttact  1680
actccgttta acttttcaaa tggatcaagt gtatttacgt taagtgctca tgtcttcaat  1740
tcaggcaatg aagtttatat agatcgaatt gaatttgttc cggcagaagt aacctttgag  1800
gcagaaatg atttagaaag agcacaaaag gcggtgaatg agctgtttac ttcttccaat  1860
caaatcgggt taaaaacaga tgtgacggat tatcatattg atcaagtatc caatttagtt  1920
gagtgtttat ctgatgaatt ttgtctggat gaaaaaaaag aattgtccga gaaagtcaaa  1980
catgcgaagc gacttagtga tgagcggaat ttacttcaag atccaaactt tagagggatc  2040
aatagacaac tagaccgtgg ctggagagga agtacggata tcaccatcca aggaggcgat  2100
gacgtattca aagagaatta cgttacgcta ttgggtacct ttgatgagtg ctatccaacg  2160
tatttatatc aaaaaaataga tgagtcgaaa ttaaaagcct atacccgtta ccaattaaga  2220
gggtatatcg aagatagtca agacttagaa atctatttaa ttcgctacaa tgccaaacac  2280
gaaacagtaa atgtgccagg tacgggttcc ttatggccgc tttcagcccc aagtccaatc  2340
ggaaaatgtg cccatcattc ccatcatttc tccttggaca ttgatgttgg atgtacagac  2400
ttaaatgagg acttaggtgt atgggtgata ttcaagatta gacgcaaga tggccatgca  2460
agactaggaa atctagaatt tctcgaagag aaaccattag taggagaagc actagctcgt  2520
gtgaaaagag cggagaaaaa atggagagac aaacgtgaaa aattggaatg ggaaacaaat  2580
attgtttata aagaggcaaa agaatctgta gatgctttat ttgtaaactc tcaatatgat  2640
agattacaag cggataccaa catcgcgatg attcatgcgg cagataaacg cgttcatagc  2700
attcgagaag cttatctgcc tgagctgtct gtgattccgg gtgtcaatgc ggctattttt  2760
gaagaattag aagggcgtat tttcactgca ttctccctat atgatgcgag aaatgtcatt  2820
aaaaatggtg attttaataa tggcttatcc tgctggaacg tgaaagggca tgtagatgta  2880
gaagaacaaa acaaccaccg ttcggtcctt gttgttccgg aatgggaagc agaagtgtca  2940
caagaagttc gtgtctgtcc gggtcgtggc tatatccttc gtgtcacagc gtacaaggag  3000
ggatatggag aaggttgcgt aaccattcat gagatcgaga acaatacaga cgaactgaag  3060
tttagcaact gtgtagaaga ggaagtatat ccaaacaaca cggtaacgtg taatgattat  3120
actgcgactc aagaagaata tgagggtacg tacacttctc gtaatcgagg atatgacgga  3180
gcctatgaaa gcaattcttc tgtaccagct gattatgcat cagcctatga agaaaaagca  3240
tatacagatg gacgaagaga caatccttgt gaatctaaca gaggatatgg ggattacaca  3300
ccactaccag ctggctatgt gacaaaagaa ttagagtact cccagaaac cgataaggta  3360
tggattgaga tcggagaaac ggaaggaaca ttcatcgtgg acagcgtgga attacttctt  3420
atggaggaat ag                                                      3432
```

```
SEQ ID NO: 107        moltype = AA  length = 1143
FEATURE               Location/Qualifiers
REGION                1..1143
                      note = Amino acid sequence of the chimeric protein TIC848.
source                1..1143
                      mol_type = protein
                      organism = synthetic construct SEQUENCE: 107
MEINNQKQCI PYNCLSNPEE VLLDGERILP DIDPLEVSLS LLQFLLNNFV PGGGFISGLV   60
DKIWGALRPS EWDLFLAQIE RLIDQRIEAT VRAKAITELE GLGRNYQIYA EAFKEWESDP  120
DNEAAKSRVI DRFRILDGLI EANIPSFRII GFEVPLLSVY VQAANLHLAL LRDSVIFGER  180
WGLTTKNVND IYNRQIREIH EYSNHCVDTY NTELERLGFR SIAQWRIYNQ FRRELTLTVL  240
DIVALFPNYD SRLYPIQTFS QLTREIVTSP VSEFYYGVIN SGNIIGTLTE QQIRRPHLMD  300
FFNSMIMYTS DNRREHYWSG LEMTAYFTGF AGAQVSFPLV GTRGESAPPL TVRSVNDGIY  360
RILSAPFYSA PFLGTIVLGS RGEKFDFALN NISPPPSTIY RHPGTVDSLV SIPPQDNSVP  420
PHRGSSHRLS HVTMRASSPI FHWTHRSATT TNTINPNAII QIPLVKSTNL GSGTSVVKGP  480
GFTGGDILRR TSPGQISTLR VNITAPLSQR YRVRIRYAST TNLQFHTSID GRPINQGNFS  540
ATMSSGSNLQ SGSFRTVGFT TPFNFSNGSS VFTLSAHVFN SGNEVYIDRI EFVPAEVTFE  600
AEYDLERAQK AVNELFTSSN QIGLKTDVTD YHIDQVSNLV ECLSDEFCLD EKKELSEKVK  660
HAKRLSDERN LLQDPNFRGI NRQLDRGWRG STDITIQGGD DVFKENYVTL LGTFDECYPT  720
YLYQKIDESK LKAYTRYQLR GYIEDSQDLE IYLIRYNAKH ETVNVPGTGS LWPLSAPSPI  780
GKCAHHSHHF SLDIDVGCTD LNEDLGVWVI FKIKTQDGHA RLGNLEFLEE KPLVGEALAR  840
VKRAEKKWRD KREKLEWETN IVYKEAKESV DALFVNSQYD RLQADTNIAM IHAADKRVHS  900
IREAYLPELS VIPGVNAAIF EELEGRIFTA FSLYDARNVI KNGDFNNGLS CWNVKGHVDV  960
EEQNNHRSVL VVPEWEAEVS QEVRVCPGRG YILRVTAYKE GYGEGCVTIH EIENNTDELK  1020
FSNCVEEEVY PNNTVTCNDY TATQEEYEGT YTSRNRGYDG AYESNSSVPA DYASAYEEKA  1080
YTDGRRDNPC ESNRGYGDYT PLPAGYVTKE LEYFPETDKV WIEIGETEGT FIVDSVELLL  1140
MEE                                                                1143
```

-continued

```
SEQ ID NO: 108           moltype = DNA   length = 3429
FEATURE                  Location/Qualifiers
misc_feature             1..3429
                         note = Chimeric coding sequence encoding TIC849.
source                   1..3429
                         mol_type = other DNA
                         organism = synthetic construct
SEQUENCE: 108
atggagataa ataatcagaa gcaatgcata ccatataatt gcttaagtaa tcctgaggaa  60
gtacttttgg atggggagag gatattacct gatatcgatc cactcgaagt ttctttgtcg  120
cttttgcaat ttcttttgaa taactttgtt ccaggggggag gctttatttc aggattagtt  180
gataaaatat gggggggcttt gagaccatct gaatgggact tatttcttgc acagattgaa  240
cggttgattg atcaaagaat agaagcaaca gtaagagcaa aagcaatcac tgaattagaa  300
ggattaggga gaaattatca aatatacgct gaagcattta aagaatggga atcagatcct  360
gataacgaag cggctaaaag tagagtaatt gatcgctttc gtatacttga tggtctaatt  420
gaagcaaata tcccttcatt tcggataatt ggatttgaag tgccactttt atcggtttat  480
gttcaagcag ctaatctaca tctcgctcta ttgagagatt ctgttatttt tggagagaga  540
tggggattga cgacaaaaaa tgtcaatgat atctataata gacaaattag agaaattcat  600
gaatatagca atcattgcgt agatacgtat aacacagaac tagaacgtct agggtttaga  660
tctatagcgc agtggagaat atataatcag tttagaagag aactaacact aactgtatta  720
gatattgtcg ctcttttccc gaactatgac agtagagtgt atccgatcca aacttttct  780
caattgacaa gagaaattgt tacatcccca gtaagcgaat tttattatgg tttgttattaat  840
agtggtaata taattggtac tcttactgaa cagcagataa ggcgaccaca tcttatggac  900
ttctttaact ccatgatcat gtatacatca gataatagac gggaacatta ttggtcagga  960
cttgaaatga cggcttattt tacaggattt gcaggagctc aagtgtcatt cccctttagtc  1020
gggactagag gggagtcagc tccaccatta actgttagaa gtgttaatga tggaatttat  1080
agaatattat cggcaccgtt ttattcagcg cctttctag gcaccattgt attgggaagt  1140
cgtggagaaa aatttgattt tgcgcttaat aatatttcac ctccgccatc tacaatatac  1200
agacatcctg gaacagtaga ttcactagtc agtataccgc cacaggataa tagcgtacca  1260
ccgcacaggg gatctagtca tcgattaagt catgttacaa tgcgcgcaag ttcccctata  1320
ttccattgga cgcatcgcag cgcaaccact acaaatacaa ttaatccaaa tgctattatc  1380
caaataccac tagtaaaagc atttaacctt cattcaggtg ccactgttgt tagaggacca  1440
gggtttacag gtggagatat ccttcgtaga acaaatacgg gtacatttgg agatatacga  1500
ttaaatatta atgtgccatt atcccaaaga tatcgcgtaca ggattcgtta tgcttctact  1560
acagatttac aatttttcac gagaattaat ggaaccactg ttaatattgg taatttctca  1620
agaactatga ataggggga taatttagaa tatagaagtt ttagaactgc aggatttagt  1680
actccttta atttttaaa tgcccaaagc acattcacat tgggtgctca gagttttca  1740
aatcaggaag tttatataga tagagtcgaa tttgttccag cagaggtaac atttgaggca  1800
gaatatgatt tagaaagagc acaaaaggcg gtgaatgagc tgtttacttc ttccaatcaa  1860
atcgggttaa aaacagatgt gacggattat catattgatc aagtatccaa tttagttgag  1920
tgtttatctg atgaatttg tctggatgaa aaaaaagaat tgtccgagaa agtcaaacat  1980
gcgaagcgac ttagtgatga gcggaattta cttcaagatc caaactttag agggatcaat  2040
agacaactag accgtggctg gagaggaagt acggatatta ccatccaagg aggcgatgac  2100
gtattcaaag agaattacgt tacgctattg ggtacctttg atgagtgcta tccaacgtat  2160
ttatatcaaa aaatagatga gtcgaaatta aaagcctata cccgttacca attaagaggg  2220
tatatcgaag atagtcaaga cttagaaatc tatttaattc gctacaatgc caaacacgaa  2280
acagtaaatg tgccaggtac gggttcctta tggccgcttt cagccccaag tccaatcgga  2340
aaatgtgccc atcattccca tcatttctcc ttggacattg atgttggatg tacagactta  2400
aatgaggact taggtgtatg ggtgatattc aagattaaga cgcaagatgg ccatgcaaga  2460
ctaggaaatc tagaatttct cgaagagaaa ccattagtag gagaagcact agctcgtgtg  2520
aaaagacgg agaaaaaatg gagagacaaa cgtgaaaaat tggaatggga aacaaatatt  2580
gtttataaag aggcaaaaga atctgtagat gctttatttg taaactctca atatgtataga  2640
ttacaagcgg ataccaacat cgcgatgatt catcggcag ataaacgcgt tcatagcatt  2700
cgagaagctt atctgcctga gctgtctgtg attccgggtg tcaatgcggc tattttgaa  2760
gaattagagg ggcgtatttt cactgcattc tccctatatg atgcgagaaa tgtcattaaa  2820
aatggtgatt ttaataatgg cttatcctgc tggaacgtga aagggcatgt agatgtagaa  2880
gaacaaaaca accaccgttc ggtccttgtt gttccggaat gggaagcaga agtgtcacaa  2940
gaagttcgtg tctgtccggg tcgtggctat atccttcgtg tcacagcgta caaggaggga  3000
tatggagaag gttgcgtaac cattcatgag atcgagaaca atacagacga gctgaagttt  3060
agcaactgtg tagaagagga agtatatcca aacaacacgg taacgtgtaa tgattatact  3120
gcgactcaag aagaatatga gggtacgtac acttctcgta tcgaggata tgacggagcc  3180
tatgaaagca attcttctgt accagctgat tatgcatcag cctatgaaga aaaagcatat  3240
acagatggac gaagagacaa tccttgtgaa tctaacagag gatatgggga ttacacacca  3300
ctaccagctg gctatgtgac aaaagaatta gagtacttcc cagaaccgga taaggtatgg  3360
attgagatcg gagaaacgga aggaacattc atcgtggaca gcgtggaatt acttcttatg  3420
gaggaatag                                                         3429

SEQ ID NO: 109           moltype = AA   length = 1142
FEATURE                  Location/Qualifiers
REGION                   1..1142
                         note = Amino acid sequence of the chimeric protein TIC849.
source                   1..1142
                         mol_type = protein
                         organism = synthetic construct
SEQUENCE: 109
MEINNQKQCI PYNCLSNPEE VLLDGERILP DIDPLEVSLS LLQFLLNNFV PGGGFISGLV  60
DKIWGALRPS EWDLFLAQIE RLIDQRIEAT VRAKAITELE GLGRNYQIYA EAFKEWESDP  120
DNEAAKSRVI DRFRILDGLI EANIPSFRII GFEVPLLSVY VQAANLHLAL LRDSVIFGER  180
WGLTTKNVND IYNRQIREIH EYSNHCVDTY NTELERLGFR SIAQWRIYNQ FRRELTLTVL  240
```

-continued

```
DIVALFPNYD SRLYPIQTFS QLTREIVTSP VSEFYYGVIN SGNIIGTLTE QQIRRPHLMD   300
FFNSMIMYTS DNRREHYWSG LEMTAYFTGF AGAQVSFPLV GTRGESAPPL TVRSVNDGIY   360
RILSAPPYSA PFLGTIVLGS RGEKFDFALN NISPPPSTIY RHPGTVDSLV SIPPQDNSVP   420
PHRGSSHRLS HVTMRASSPI FHWTHRSATT TNTINPNAII QIPLVKAFNL HSGATVVRGP   480
GFTGGDILRR TNTGTFGDIR LNINVPLSQR YRVRIRYAST TDLQFFTRIN GTTVNIGNFS   540
RTMNRGDNLE YRSFRTAGFS TPFNFLNAQS TFTLGAQSFS NQEVYIDRVE FVPAEVTFEA   600
EYDLERAQKA VNELFTSSNQ IGLKTDVTDY HIDQVSNLVE CLSDEFCLDE KKELSEKVKH   660
AKRLSDERNL LQDPNFRGIN RQLDRGWRGS TDITIQGGDD VFKENYVTLL GTFDECYPTY   720
LYQKIDESKL KAYTRYQLRG YIEDSQDLEI YLIRYNAKHE TVNVPGTGSL WPLSAPSPIG   780
KCAHHSHHFS LDIDVGCTDL NEDLGVWVIF KIKTQDGHAR LGNLEFLEEK PLVGEALARV   840
KRAEKKWRDK REKLEWETNI VYKEAKESVD ALFVNSQYDR LQADTNIAMI HAADKRVHSI   900
REAYLPELSV IPGVNAAIFE ELEGRIFTAF SLYDARNVIK NGDFNNGLSC WNVKGHVDVE   960
EQNNHRSVLV VPEWEAEVSQ EVRVCPGRGY ILRVTAYKEG YGEGCVTIHE IENNTDELKF   1020
SNCVEEEVYP NNTVTCNDYT ATQEEYEGTY TSRNRGYDGA YESNSSVPAD YASAYEEKAY   1080
TDGRRDNPCE SNRGYGDYTP LPAGYVTKEL EYFPETDKVW IEIGETEGTF IVDSVELLLM   1140
EE                                                                  1142

SEQ ID NO: 110          moltype = DNA  length = 3570
FEATURE                 Location/Qualifiers
misc_feature            1..3570
                        note = Chimeric coding sequence encoding TIC847.
source                  1..3570
                        mol_type = other DNA
                        organism = synthetic construct
SEQUENCE: 110
atgacttcaa ataggaaaaa tgagaatgaa attatataatg ctttatcgat tccaacggta   60
tcgaatcctt ccacgcaaat gaatctatca ccagatgctc gtattgaaga tagcttgtgt   120
gtagccgagg tgaacaatat tgatccattt gttagcgcat caacagtcca aacgggtata   180
aacatagctg gtagaatatt gggcgtatta ggtgtgccgt ttgctggaca actagctagt   240
tttatagtt ttcttgttgg ggaattatgg cctagtgaca gagatccatg ggaaattttc   300
ctggaacatg tagaacaact tataagacaa caagtaacag aaaatactag gaatacggct   360
attgctcgat tagaaggtct aggaagaggc tatagatctt accagcaggc tcttgaaact   420
tggttagata accgaaatga tgcaagatca agaagcatta ttcttgagcg ctatgttgct   480
ttagaacttg acattactac tgctataccg cttttcagaa tacgaaatga agaagttcca   540
ttattaatgg tatatgctca agctgcaaat ttacacctat tattattgag agacgcatcc   600
cttttttggta gtgaatgggg gatggcatct tccgatgtta accaatatta ccaagaacaa   660
atcagatata cagaggaata ttctaaccat tgcgtacaat ggtataatac agggctaaat   720
aacttaagag ggacaaatgc tgaaagttgg ttgcggtata atcaattccg tagagaccta   780
acgttagggg tattagattt agtagcccta ttcccaagct atgatactcg cacttatcca   840
atcaatacga gtgctcagtt aacaagagaa atttatacag atccaattgg gagaacaaat   900
gcaccttcag gatttgcaag tacgaattgg tttaataata atgcaccatc gttttctgcc   960
atagaggctg ccattttcag gcctccgcat ctacttgatt ttccagaaca acttacaatt   1020
tacagtgcat caagccgttg gagtagcact caacatatga attattgggt gggacatagg   1080
cttaacttcc gcccaatagg agggacatta aatacctcaa cacaaggact tactaataat   1140
acttcaatta atcctgtaac attacagttt acgtctcgag acgtttatag aacagaatca   1200
aatgcaggga caaatatact atttactact cctgtgaatg gagtaccttg ggctagattt   1260
aattttataa accctcagaa tatttatgaa agaggcgtca ctacctacag tcaaccgtat   1320
cagggagttg ggattcaatt atttgattca gaaactgaat taccaccaga aacaacagaa   1380
cgaccaaatt atgaatcata tagtcataga ttatctcata taggactaat cataggaaac   1440
actttgagag caccagtcta ttcttggacg catcgtagtg cagatcgtac gaatacgatt   1500
ggaccaaata gaattacaca aataccattg gtaaaggcgc atacccctca atcgggtacc   1560
actgtagtaa aagggccagg gtttacagga ggggatatcc tccgtcgaac aagtggagga   1620
ccatttgctt ttagtaatgt taatctagat tttaacttgt cacaaaggta tcgtgctaga   1680
attcgttatg cctctactac taacctaaga atttacgtaa cggttgcagg tgaacgaatt   1740
tttgctggtc aatttgacaa aactatggat gctggtgccc cattaacatt ccaatctttt   1800
agttacgcaa ctattaatac agcttttaca ttcccagaaa gatcgagcag cttgactgta   1860
ggtgccgata cgtttagttc aggtaatgaa gtttatgtag atagatttga attaatccca   1920
gttactgcaa ccttcgaggc agaatctgat ttagaaagag cacaaaaggc ggtgaatgag   1980
ctgtttactt cttccaatca aatcgggtta aaaacagatg tgacggatta tcatattgat   2040
caagtatcca atttagttga gtgtttatct gatgaatttt gtctggatga aaaaaaagaa   2100
ttgtccgaga aagtcaaaca tgcgaagcga cttagtgatg agcggaattt acttcaagat   2160
ccaaacttta gagggatcaa tagacaacta gaccgtggct ggagaggaag tacgggatatt   2220
accatccaag gaggcgatga cgtattcaaa gagaattacg ttacgctatt gggtaccttt   2280
gatgagtgct atccaacgta tttatatcaa aaaatagatg agtcgaaatt aaaagcctat   2340
acccgttacc aattaagagg gtatatcgaa gatagtcaag acttagaaat ctatttaatt   2400
cgctacaatg ccaaacacga aacagtaaat gtgccaggta cgggttcctt atggccgctt   2460
tcagccccaa gtccaatcgg aaaatgtgcc catcattccc atcatttctc cttggacatt   2520
gatgttggat gtacagactt aaatgaggac ttaggtgtat gggtgatatt caagattaag   2580
acgcaagatg gccatgcaag actagaattc ctagaatttc tcgaagagaa accattagta   2640
ggagaagcac tagctcgtgt gaaaagagcg gagaaaaaat ggagagacaa acgtgaaaaa   2700
ttggaatggg aaacaaatat tgtttataaa gaggcaaaag aatctgtaga tgctttattt   2760
gtaaactctc aatatgatag attacaagcg gataccaaca tcgcgatgat tcatgcggca   2820
gataaacgcg ttcatagcat tcgagaagct tatctgcctg agctgtctgt gattccgggt   2880
gtcaatgcgg ctattttga gaattacaa gggcatgttg atgtcgaaga gcagaaccat   2940
gatgcgagaa atgtcattaa aaatggtgat tttaataatg gcttatcctg ctggaacgtg   3000
aaagggcatg tagatgtaga agaacaaaac aaccaccgtt cggtccttgt tgttccggaa   3060
tgggaagcag aagtgtcaca agaagttcgt gtctgtccgg tcgtggctaa tatccttcgt   3120
gtcacagcgt acaaggaggg atatggagaa ggttgcgtaa ccattcatga gatcgagaac   3180
aatacagacg aactgaagtt tagcaactgt gtagaagagg aagtatatcc aaacaacacg   3240
```

```
gtaacgtgta atgattatac tgcgactcaa gaagaatatg agggtacgta cacttctcgt   3300
aatcgaggat atgacggagc ctatgaaagc aattcttctg taccagctga ttatgcatca   3360
gcctatgaag aaaaagcata tacagatgga cgaagagaca atccttgtga atctaacaga   3420
ggatatgggg attacacacc actaccagct ggctatgtga caaaagaatt agagtacttc   3480
ccagaaaccg ataaggtatg gattgagatc ggagaaacgg aaggaacatt catcgtggac   3540
agcgtggaat tacttcttat ggaggaatag                                     3570

SEQ ID NO: 111          moltype = AA  length = 1189
FEATURE                 Location/Qualifiers
REGION                  1..1189
                        note = Amino acid sequence of the chimeric protein TIC847.
source                  1..1189
                        mol_type = protein
                        organism = synthetic construct
SEQUENCE: 111
MTSNRKNENE IINALSIPTV SNPSTQMNLS PDARIEDSLC VAEVNNIDPF VSASTVQTGI    60
NIAGRILGVL GVPFAGQLAS FYSFLVGELW PSGRDPWEIF LEHVEQLIRQ QVTENTRNTA    120
IARLEGLGRG YRSYQQALET WLDNRNDARS RSIILERYVA LELDITTAIP LFRIRNEEVP    180
LLMVYAQAAN LHLLLLRDAS LFGSEWGMAS SDVNQYYQEQ IRYTEEYSNH CVQWYNTGLN    240
NLRGTNAESW LRYNQFRRDL TLGVLDLVAL FPSYDTRTYP INTSAQLTRE IYTDPIGRTN    300
APSGFASTNW FNNNAPSFSA IEAAIFRPPH LLDFPEQLTI YSASSRWSST QHMNYWVGHR    360
LNFRPIGGTL NTSTQGLTNN TSINPVTLQF TSRDVYRTES NAGTNILFTT PVNGVPWARF    420
NFINPQNIYE RGATTYSQPY QGVGIQLFDS ETELPPETTE RPNYESYSHR LSHIGLIIGN    480
TLRAPVYSWT HRSADRTNTI GPNRITQIPL VKAHTLQSGT TVVKGPGFTG GDILRRTSGG    540
PFAFSNVNLD FNLSQRYRAR IRYASTTNLR IYVTVAGERI FAGQFDKTMD AGAPLTFQSF    600
SYATINTAFT FPERSSSLTV GADTFSSGNE VYVDRFELIP VTATFEAESD LERAQKAVNE    660
LFTSSNQIGL KTDVTDYHID QVSNLVECLS DEFCLDEKKE LSEKVKHAKR LSDERNLLQD    720
PNFRGINRQL DRGWRGSTDI TIQGGDDVFK ENYVTLLGTF DECYPTYLYQ KIDESKLKAY    780
TRYQLRGYIE DSQDLEIYLI RYNAKHETVN VPGTGSLWPL SAPSPIGKCA HHSHHFSLDI    840
DVGCTDLNED LGVWVIFKIK TQDGHARLGN LEFLEEKPLV GEALARVKRA EKKWRDKREK    900
LEWETNIVYK EAKESVDALF VNSQYDRLQA DTNIAMIHAA DKRVHSIREA YLPELSVIPG    960
VNAAIFEELE GRIFTAFSLY DARNVIKNGD FNNGLSCWNV KGHVDVEEQN NHRSVLVVPE    1020
WEAEVSQEVR VCPGRGYILR VTAYKEGYGE GCVTIHEIEN NTDELKFSNC VEEEVYPNNT    1080
VTCNDYTATQ EEYEGTYTSR NRGYDGAYES NSSVPADYAS AYEEKAYTDG RRDNPCESNR    1140
GYGDYTPLPA GYVTKELEYF PETDKVWIEI GETEGTFIVD SVELLLMEE               1189

SEQ ID NO: 112          moltype = DNA  length = 3588
FEATURE                 Location/Qualifiers
misc_feature            1..3588
                        note = Synthetic DNA sequence for expression in plants
                         encoding TIC713.
source                  1..3588
                        mol_type = other DNA
                        organism = synthetic construct
SEQUENCE: 112
atggataaca acccaaacat caacgaatgc attccgtaca actgcctgag caaccctgag   60
gtggaggtgc taggtggcga gcgcatcgaa acgggttaca cgccgattga catctccctg   120
tccctcaccc agttcctcct tagcgagttc gtgccgggcg cgggtttcgt gctgggcctc   180
gttgacatca tctgggggat cttcggtccc tcccaatggg atgcgttcct ggtgcagatc   240
gagcagctta tcaaccagcg gatcgaagag ttcgctagga accaggccat cagccgcctc   300
gaaggtctca gcaacctcta tcaaatctac gctgagtcct tccgcgagtg ggaggcggac   360
cccaccaacc ctgccctccg cgaggaaatg cgtatccaat tcaatgacat gaacagcgcc   420
ctgaccacgg cgatcccgct gctggccgtc cagaactacc aggtccccct gctcagcgtc   480
tacgtccagg ccgctaacct ccacctcagc gtgctgcgcg acgtctccgt cttcggccag   540
aggtggggggt tcgacgcggc gacgatcaac agccgctaca agacctgac ccggctgatc   600
gggaactaca cggactacgc tgtccggtgg tacaacaccg gcctggagcg cgtgtgggga   660
ccagactccc gtgactgggt ccggtacaac cagttccgta gggaactcac tctgacggtc   720
ctggacatcg tggctctgtt cccgaactac gacagccgcc gctacccat ccggactgtg   780
tcccaactga cccgcgaaat ctacacgaac cctgtccttg agaacttcga tgggagcttc   840
cgtggctccg cccagggcat cgagcgctcc atccgctccc cgcacctcat ggacatcctc   900
aactccatca cgatctacac cgacgcccat cgcggctact attactggtc cggccaccag   960
atcatggcca gccccgtggg cttctccggc cccgagttca ccttcccgct ctacggcacg   1020
atgggcaacg ccgctcctca gcaacgcatc gtggcccagc tcggccaggg cgtgtacagg   1080
accctctcca gcaccctcta caggcgtcct ttcaacatcg gcatcaacaa tcagcaactc   1140
tccgtgctcg acgggactga gttcgcctac ggcaccagca gcaacctgcc tagcgccgtg   1200
taccgcaaga gcggcaccgt ggacagcctg acgagatcc ctccgcagaa caacaacgtg   1260
cctccgaggc aaggcttcag ccacaggctg agccacgtga gcatgttccg tagcggcttc   1320
agcaacagct ctgtgagcat catcagggcc ccgatgttct cctggattca caggagcgcc   1380
gagttcaaca ataccatcgg cccgaacagg atcacccaga tccctctggt gaaggccctg   1440
aacctgcact ctggcgtcac cgtcgttggc ggtcctggct tcaccggtgg ggacatcctg   1500
aggcgtacca acaccggaac cttcggtgac atcaggctga acatcaacgt ccctctgtct   1560
cagaggtaca gggtcaggat caggtacgcc tctaccactg accttcagtt ctttaccagg   1620
atcaacggta ctactgtcaa catcggtaac ttcagccgca ctatgaacag gggtgacaac   1680
ctggagtacc gtagtttccg tactgctgga ttctctactc ctttcaactt cctgaacgct   1740
cagtctactt tcactctggg tgctcagtct ttctcgaacc aggaggtcta catcgaccgt   1800
gtcgagttcg tcccggctga ggtcactttc gaggctgagt acgacctgga gcgcgctcaa   1860
aaggctgtca acgctctgtt cacttctact aacccgcgca gactgaagac tgacgtcact   1920
gactaccaca tcgaccaagt ctcgaacatg gtcgcttgcc tgtctgacga gttctgcctg   1980
gacgagaagc gtgagctgtt cgagaaggtc aagtacgcta agcgtctgtc tgacgagcgt   2040
```

```
aacctgctcc aggacccgaa cttcactttc atctcgggtc aactgtcgtt tgctagtatt  2100
gacggtcagt cgaactttcc gtcgattaac gagctgtcgg agcacggttg gtggggtagt  2160
gctaacgtca ctatccagga gggtaacgac gtctttaagg agaactacgt cactctgccg  2220
ggtactttca acgagtgcta cccgaactac ctttaccaga agattggtga gtcggagctt  2280
aaggcttaca ctcgttacca gcttcgtggt tacattgagg actcgcagga ccttgaaatc  2340
taccttattc ggtacaatgc caaacacgag actcttgacg tccctgggac ggatagtctt  2400
tggccgcttt cggtcgagtc gccgattggg cggtgcgggg agccgaatcg ttgcgctccg  2460
cactttgagt ggaatccaga ccttgattgc tcatgccggg atggggagcg gtgcgctcac  2520
catagtcacc actttacgct tgatattgat gtcgggtgca cggatcttca cgagaatctt  2580
ggggtctggg tcgtgtttaa gattaagacg caagaggggt acgcgcggct tgggaatctt  2640
gagtttattg aggaaaagcc acttattggt gaggcgcttt cacgggtcaa gcgggcggaa  2700
aagaaatgga gggataagcg ggagaagctc caattggaga cgaagcgggt ctacacggag  2760
gcgaaggagg cggtcgatgc gctgtttgtc gatagtcaat acgatcaatt gcaagcggat  2820
acgaacattg ggatgattca cgcggcagat aagttggtcc accggattag agaggcgtac  2880
ttgtcagagt tgccagtcat tccagggggt aatgcgggaga ttttcgagga attggaggggg  2940
cacatcataa cggcgatgag tctgtacgat gcgagaaatg ttgtaaagaa tggtgatttc  3000
aacaatgggt tgacgtgctg gaatgttaag ggccacgttg atgttcaaca atcacatcat  3060
cggtcggatc tcgttattcc agagtgggag gcggaggttt cacaagcagt tagagtttgc  3120
ccagggagag gttacatcct aagagttacg gcatacaagg agggctatgg agaaggatgc  3180
gttacgatcc atgagattga gaacaatacg gatgagctaa agtttaagaa ttgtgaggaa  3240
gaagaagttt acccaacgga tacgggaaca tgcaacgatt acacagcaca tcaaggaaca  3300
gcagcatgta attcacgaaa tgccgggtat gaagatgctt acgaagttga tcaaacagca  3360
tcagttaatt acaagccaac atacgaagaa gaaacataca cagatgttcg acgagataat  3420
cattgtgagt atgatcgagg gtatgtaaat tatccaccag ttccagccgg gtatgtcaca  3480
aaggaactag aatactttcc agaaacagat acagtatgga tagagatcgg agaaacagaa  3540
ggaaagttca tagtggactc agtagaacta ttactgatgg aagaatga             3588
```

SEQ ID NO: 113          moltype = DNA   length = 3588
FEATURE                 Location/Qualifiers
misc_feature            1..3588
                        note = Synthetic DNA sequence for expression in plants
                         encoding TIC713.
source                  1..3588
                        mol_type = other DNA
                        organism = synthetic construct
SEQUENCE: 113

```
atggataaca acccaaacat caacgaatgc attccgtaca actgcctgag caaccctgag   60
gtggaggtgc taggtggcga gcgcatcgaa acgggttaca cgccgattga catctccctg  120
tccctcaccc agttcctcct tagcgagttc gtgccgggcg cgggtttcgt gctgggcctc  180
gttgacatca tctgggggat cttcggtccc tcccaatggg atgcgttcct ggtgcagatc  240
gagcagctta tcaaccagcg gatcgaagag ttcgctagga accaggccat cagccgcctc  300
gaaggtctca gcaacctcta tcaaatctac gctgagtcct ccgcgagtg ggaggcggac  360
cccaccaacc ctgccctccg cgaggaaatg cgtatccaat caatgacat gaacagcgcc  420
ctgaccacgg cgatcccgct gctggccgtc cagaactacc aggtcccct gctcagcgtc  480
tacgtccagg ccgctaacct ccacctcagc gtgctgcgcg acgtctccgt cttcggccag  540
aggtgggggt tcgacgcggc gacgatcaac agccgctaca acgacctgac ccggctgatc  600
gggaactaca cggactacgc tgtccggtgg tacaacaccg gctcgaggcg cgtgtgggga  660
ccagactccc gtgactgggt ccggtacaac cagttccgta gggaactcac tctgacggtc  720
ctggacatcg tggctctgtt cccgaactac gacagccgcc gctaccccat ccggactgtg  780
tcccaactga cccgcgaaat ctacacgaac cctgtccttg agaacttcga tgggagcttc  840
cgtcggctccg cccagggcat cgagcgctcc atccgctccc cgcacctcat ggacatcctc  900
aactccatca cgatctacac cgacgcccat cgcggctact attactggtc cggccaccag  960
atcatggcca gcccggtggg cttctccggc cccgagttca cctcccctct ctacggcacg 1020
atgggcaacg ccgctcctca gcaacgcatc gtggcccagc tcggccaggg cgtgtacagg 1080
accctctcca gcaccctcta caggcgtcct ttcaacatcg gcatcaacaa tcagcaactc 1140
tccgtgctcg acgggactga gttcgcctac ggcaccagca gcaacctgcc tagcgccgtg 1200
taccgcaaga gcggcaccgt ggacagcctg gacgagatcc ctccgcagaa caacaacgtg 1260
cctccgaggc aaggcttcag ccacaggctg agccacgtga gcatgttccg tagcggcttc 1320
agcaacgct ctgtgagcat catcaggggcc ccgatgttct cctggattca caggagcgcc 1380
gagttcaaca ataccatcgg cccgaacagg atcacccaga tccctctggt gaaggccgccca 1440
aacctgcact ctggcgtcac cgtcgttggc ggtcctggct tcaccggtgg ggacatcctg 1500
aggcgtacca acaccggaac cttcggtgac atcaggctga acatcaacgt ccctctgtct 1560
cagaggtaca gggtcaggat caggtacgcc tctaccactg accttcagtt ctttaccagg 1620
atcaacggta ctactgtcaa catcggtaac ttcagccgca ctatgaacag gggtgacaac 1680
ctggagtacc gtagtttccg tactgctgga ttctctactc ctttcaactt cctgaacgct 1740
cagtctactt tcactctggg tgctcagtct ttctcgaacc aggaggtcta catcgaccgt 1800
gtcgagttcg tcccggctga ggtcactttc gaggctgagt acgacctgga gcgcgctcaa 1860
aaggctgtca acgctctgtt cacttctact aacccgcgca gactgaagac tgacgtcact 1920
gactaccaca tcgaccaagt ctcgaacatg gtcgcttgcc tgtctgacga gttctgcctg 1980
gacgagaagc gtgagctgtt cgagaaggtc aagtacgcta agcgtctgtc tgacgagcgt 2040
aacctgctcc aggacccgaa cttcactttc atctcgggtc aactgtcgtt tgctagtatt 2100
gacggtcagt cgaactttcc gtcgattaac gagctgtcgg agcacggttg gtggggtagt 2160
gctaacgtca ctatccagga gggtaacgac gtctttaagg agaactacgt cactctgccg 2220
ggtactttca acgagtgcta cccgaactac ctttaccaga agattggtga gtcggagctt 2280
aaggcttaca ctcgttacca gcttcgtggt tacattgagg actcgcagga ccttgaaatc 2340
taccttattc ggtacaatgc caaacacgag actcttgacg tccctgggac ggatagtctt 2400
tggccgcttt cggtcgagtc gccgattggg cggtgcgggg agccgaatcg ttgcgctccg 2460
cactttgagt ggaatccaga ccttgattgc tcatgccggg atggggagcg gtgcgctcac 2520
catagtcacc actttacgct tgatattgat gtcgggtgca cggatcttca cgagaatctt 2580
```

-continued

```
ggggtctggg tcgtgtttaa gattaagacg caagaggggt acgcgcggct tgggaatctt   2640
gagtttattg aggaaaagcc acttattggt gaggcgcttt cacgggtcaa gcgggcggaa   2700
aagaaatgga gggataagcg ggagaagctc caattggaga cgaagcgggt ctacacggag   2760
gcgaaggagg cggtcgatgc gctgtttgtc gatagtcaat acgatcaatt gcaagcggat   2820
acgaacattg ggatgattca cgcggcagat aagttggtcc accggattag agaggcgtac   2880
ttgtcagagt tgccagtcat tccaggggtt aatgcggaga ttttcgagga attggaggggg  2940
cacatcataa cggcgatgag tctgtacgat gcgagaaatg ttgtaaagaa tggtgatttc   3000
aacaatgggt tgacgtgctg gaatgttaag ggccacgttg atgttcaaca atcacatcat   3060
cggtcggatc tcgttattcc agagtgggag gcggaggttt cacaagcagt tagagtttgc   3120
ccagggagag gttacatcct aagagttacg gcatacaagg agggctatgg agaaggatgc   3180
gttacgatcc atgagattga gaacaatacg gatgagctaa agtttaagaa ttgtgaggaa   3240
gaagaagttt acccaacgga tacgggaaca tgcaacgatt acacagcaca tcaaggaaca   3300
gcagcatgta attcacgaaa tgccgggtat gaagatgctt acgaagttga tacaacagca   3360
tcagttaatt acaagccaac atacgaagaa gaaacataca cagatgttcg acgagataat   3420
cattgtgagt atgatcgagg gtatgtaaat tatccaccag ttccagccgg gtatgtcaca   3480
aaggaactag aatactttcc agaaacagat acagtatgga tagagatcgg agaaacagaa   3540
ggaaagttca tagtggactc agtagaacta ttactgatgg aagaatag             3588
```

SEQ ID NO: 114          moltype = DNA  length = 3531
FEATURE                 Location/Qualifiers
misc_feature           1..3531
                       note = Synthetic DNA sequence for expression in plants
                        encoding TIC843.
source                 1..3531
                       mol_type = other DNA
                       organism = synthetic construct
SEQUENCE: 114

```
atggataaca acccaaacat caacgaatgc attccgtaca actgcctgag caaccctgag   60
gtggaggtgc taggtggcga gcgcatcgaa acgggttaca cgccgattga catctccctg   120
tccctcaccc agttcctcct tagcgagttc gtgccgggcg cgggtttcgt gctgggcctc   180
gttgacatca tctgggggat cttcggtccc tcccaatggg atgcgttcct ggtgcagatc   240
gagcagctta tcaaccagcg gatcgaagag ttcgctagga accaggccat cagccgcctc   300
gaaggtctca gcaacctcta tcaaatctac gctgagtcct tccgcgagtg ggaggcggac   360
cccaccaacc ctgccctccg cgaggaaatg cgtatccaat tcaatgacat gaacagcgcc   420
ctgaccacgg cgatcccgct gctggccgtc cagaactacc aggtccccct gctcagcgtc   480
tacgtccagg ccgctaacct ccacctcagc gtgctgcgcg acgtctccgt cttcggccag   540
aggtggggggt tcgacgcggc gacgatcaac agccgctaca acgacctgac ccggctgatc   600
gggaactaca cggactacgc tgtccggtgg tacaacaccg gcctggagcg cgtgtgggga   660
ccagactccc gtgactgggt ccggtacaac cagttccgta gggaactcac tctgacggtc   720
ctggacatcg tggctctgtt cccgaactac gacagccgcc gctacccccat ccggactgtg   780
tcccaactga cccgcgaaat ctacacgaac cctgtccttg agaacttcga tgggagcttc   840
cgtggctccg cccagggcat cgagcgctcc atccgctccc cgcacctcat ggacatcctc   900
aactccatca cgatctacac cgacgcccat cgcggctact attactggtc cggccaccag   960
atcatggcca gcccccgtggg cttctccggc cccgagttca ccttcccgct ctacggcacg   1020
atgggcaacg ccgctcctca gcaacgcatc gtggcccagc tcggccaggg cgtgtacagg   1080
accctctcca gcaccctcta caggcgtcct ttcaacatcg gcatcaacaa tcagcaactc   1140
tccgtgctcg acgggactga gttcgcctac ggcaccagca gcaacctgcc tagcgccgtg   1200
taccgcaaga gcggcaccgt ggacagcctg gacgagatcc ctccgcagaa caacaacgtg   1260
cctccgaggc aaggcttcag ccacaggctg agccacgtga gcatgttccg tagcggcttc   1320
agcaacagct ctgtgagcat catcaggggcc ccgatgttct cctggattca caggagcgcc   1380
gagttcaaca ataccatcgg cccgaacagg atcacccagg tccctctggt gaaggccctg   1440
aacctgcact ctggcgtcac cgtcgttggc ggtcctggct tcaccggtgg ggacatcctg   1500
aggcgtacca acaccggaac cttcggtgac atcaggctga acatcaacgt ccctctgtct   1560
cagaggtaca gggtcaggat caggtacgcc tctaccactg accttcagtt ctttaccagg   1620
atcaacggta ctactgtcaa catcggtaac ttcagccgca ctatgaacgg gggtgacaac   1680
ctggagtacc gtagtttccg tactgctgga ttctctactc cttttcaactt cctgaacgct   1740
cagtctactt tcactctggg tgctcagtct ttctcgaacc aggaggtcta catcgaccgt   1800
gtcgagttcc tcccggctga ggtcactttc gaggctgagt acgaccttga gagagcgcag   1860
aaggccgtga accgcgctgtt cacctcgact aaccagttgg gactcaagac aaatgtcact   1920
gactaccaca tcgaccaagt gagtaatctc gttacctacc tgtcggacga gttctgcctg   1980
gatgagaaga gggaactgtc tgagaaagtg aagcacgcaa agcgcctctc ggatgagagg   2040
aacctcctcc aggattccaa cttcaaggac atcaaccggc agccggaaag aggctggggt   2100
ggctccaccg gcattactat ccaggcggc gacgatgtgt caaggagaa ctacgtcaca   2160
ctctcaggca cttttcgacga gtgttacccg acgtacctgt accagaagat tgatgagtcc   2220
aagctgaagg cattcacccg ctatcagctt cgcggttaca ttgaagattc ccaggacctt   2280
gagatctacc tcatcaggta caacgccaag cacgagacgg tcaacgtgcc cggcacgggg   2340
tccctgtggc cgttgtctgc ccaatctccc atcgggaagt gcggtgagcc gaaccgttgc   2400
gccccgcacc tggagtggaa ccctgacctg gattgctcct gtaggatggg cgagaagtgc   2460
gctcaccatt cccaccactt ctcgctggac atcgacgtgg ggtgcacgga tctcaacgag   2520
gatctcggag tctgggtcat cttcaagatc aagacgcagg acggacacgc tcgcctcggc   2580
aatctcgagt ttcttgagga aaagccgctc gtaggtgagg cgctcgccag ggtaaagcgc   2640
gcggagaaga agtggaggga taagcgtgag aaacttgaat gggagacaaa catcgtctac   2700
aaggaagcaa aggagtcagt tgatgcactg ttcgtcaact ctcagtatga ccagttgcag   2760
gccgatacca acatcgcgat gatccacgcc gctgacaagc gcttcactc gatccgcgag   2820
gcgtacctcc ctgagctttc cgtcatcccca ggcgtcaatg cggccatctt cgaggaactt   2880
gaggggccggga tcttcaccgc tttctcgctc tacgacgcta gaaacgtcat caagaacggc   2940
gacttcaaca atggcctgag ctgctggaat gtgaagggtc atgtggatgt cgaagagcag   3000
aacaatcagc gttctgtgct cgtggtcccc gaatgggaag ctgaggtttc ccaagaagtg   3060
agagtgtgcc caggacgcgg ttacattctc cgtgttacgg cgtacaagga gggctatggc   3120
```

```
gaaggctgcg tgaccattca tgagatcgag aacaacacgg atgagctgaa gttctcaaac  3180
tgcgtcgagg aagaaatcta ccctaacaac actgtgacct gtaacgacta cacggtgaac  3240
caggaagagt acggcggcgc ttacactagc cgcaaccgtg ggtacaacga ggccccatcg  3300
gtccctgctg actacgcatc cgtctacgag gagaagtctt acactgacgg gagacgggag  3360
aaccctgcg agttcaaccg gggttacagg gattacacgc ctctgcccgt tggctatgtc   3420
actaaggagc tggagtattt cccggagact gataaagtct ggatcgagat cggggagact  3480
gaagggactt tcatcgtcga ttccgtggag ctgcttctga tggaggagtg a            3531
```

SEQ ID NO: 115          moltype = DNA  length = 3501
FEATURE                 Location/Qualifiers
misc_feature            1..3501
                        note = Synthetic DNA sequence for expression in plants
                         encoding TIC862.
source                  1..3501
                        mol_type = other DNA
                        organism = synthetic construct
SEQUENCE: 115

```
atggacaaca acccgaacat caacgagtgc atcccgtaca actgcctgag caaccctgag  60
gtggaggtgc taggcggtga gcgcatcgag accggctaca cgcctatcga catctccctg  120
agcctgaccc agttcctcct tagcgagttc gtgcccggcg cgggcttcgt gctcggcctc  180
gtggacatca tctggggcat cttcggcccg tcccagtggg acgccttcct cgtgcagatc  240
gagcagctca tcaaccagcg catcgaggag ttcgcccgca accaggccat ctcccgcctg  300
gagggcctct ccaacctcta ccagatctac gccgagtcct tccgcgagtg ggaggccgac  360
ccgaccaacc cggccctccg cgaggaaatg cgtatccagt tcaacgacat gaactccgcc  420
ctcaccactg ccatcccgct cctggccgtg cagaactacc aagtgcctct cctgtccgtg  480
tacgtccaag ctgcgaacct ccacctctcc gtgctgccga acgtctccgt cttcggccag  540
cgctggggct tcgacgctgc gaccatcaac tcccgctaca acgacctgac ccgcctgatc  600
ggcaactaca ccgactacgc tgtccgctgg tacaacaccg gcctggagcg cgtctggggc  660
cctgactcca gggactgggt ccgctacaac cagttccgcc gggagctgac cctgactgtc  720
ctggacatcg tcgctctgtt ccctaactac gatagccgcc gctaccctat caggactgtc  780
agccagctta ctaggggaaat ctacactaac cctgtccttg agaacttcga tggttccttc  840
cgtggtagcg ctcagggtat tgagcggagc attcggagcc cgcaccttat ggacattctt  900
aactctatta ctatctacac ggatgctcac cgtggttact attactggtc tggtcaccag  960
attatggcta gtccggtcgg tttctctggg ccggagttca cgttcccgct ttatgggacg  1020
atgggcaacg cggcaccgca gcaacgtatt gtggcgcagc ttgggcaagg cgtttatcgt  1080
acgctttctt cgacattgta cagacgtccg tttaacattg ggatcaataa ccagcaattg  1140
tctgttctgg atggaacaga atttgcgtat ggaacatctt cgaatttgcc atctgcggtt  1200
tatcgtaagt ctggaacagt tgacagtctc gatgagattc caccacagaa caacaacgtt  1260
ccaccaagac agggattcag tcacagatta agccacgtta gtatgtttag atcaggcttc  1320
tcgaactcat cagtatcaat catacgagca ccaatgttct cgtggataca ccgctcggca  1380
gagttcaaca acatcatcgc ctccgacagc atcacccaga tcccggccgt gaagggcaac  1440
ttcctcttca acggctccgt catctccggc cctggcttca ccggcggcga tctcgtcgcg  1500
tgcacgaatg gttccggcct caccctgtac gtgacgcctg cgcccgacct cacctactcc  1560
aagacctaca agattcgcat tcgctatgcc tccacctccc aagtgcgctt tggcatcgac  1620
ctcggctcct acactcactc catctcctac ttcgacaaga cgatggacaa aggcaacacc  1680
ctcacctaca actccttcaa cctctcctcc gtgtcccgcc ctatcgagat cagcggcggc  1740
aacaagatcg gtgtctcggt cggcggcatc ggctctggcg acgaggtgta catcgacaag  1800
atcgagttca tcccgatgga gcgcgcccag aaggccgtga acgccctctt cactagcact  1860
aaccagctcg gcctcaagac taacgtgacc gactaccaca ttgaccaagt gagcaaccta  1920
gtgacctacc ttagcgacga gttctgcctt gacgagaagc gtgagctgag cgagaaggtg  1980
aagcagccca agcgcctctc cgacgagcgc aacctcctcc aggactccaa cttcaaggac  2040
atcaaccgcc agcccgagcg cggctggggc ggtagcaccg gcatcaccat ccagggcggt  2100
gacgatgtgt tcaaggagaa ctacgtgacc ctctccggca ccttcgacga gtgctacccg  2160
acctacctct accagaagat cgacgagtcc aagctcaagg cgttcacccg ctaccagctt  2220
cgcggctaca tcgaggactc ccaggatctg gagatctacc tcatccgcta caacgccaag  2280
cacgagaccg tgaacgtgcc cggcaccggc tccctctggc cgctctccgc ccagagccct  2340
atcggcaagt gcggcgagcc caaccgctgc gcgcctcacc tggagtggaa ccctgacctc  2400
gactgctcct gccgcgacgg cgagaagtgc gcccaccata gccaccactt ctctctcgac  2460
atcgacgtgg gctgcaccga cctcaacgag gatctgggcg tgtgggtgat cttcaagatc  2520
aagaaccagg acggccacgc caggctgggc aacctggagt tcctggagga gaagcctcca  2580
gtgggtgagg ccctggccag ggtcaagagg gctgagaaga aatggaggga caagagggag  2640
aagctggagt gggagaccaa catcgtgtac aaggaggcta aggagtccgt ggacgctctg  2700
ttcgtcaact ctcagtacga tcagctccag gctgacacca acatcgctat gatccacgct  2760
gcggataaga gggtccactc tatcagggag gcttacctgc ctgagctttc tgtcatccct  2820
ggtgtcaacg cggcaatctt cgaggaactt gagggccgca tcttcactgc gttctcgctt  2880
tacgatcgc ggaacgtcat taagaacggt gacttcaaca atggtctttc gtgctcggaac  2940
gtcaagggtc atgtcgatgt cgaggaacag aacaaccagc ggtcggtcct tgtcgttccc   3000
gagtgggagg ccgaggtctc gcaagaggtc cgggtctgcc ctgggcgcgg gtacattctt  3060
cgtgtcactg cgtacaagga gggctacggc gagggctgcg ttactattca tgagattgag  3120
aacaatacgg atgagcttaa gtttagtaac tgtgttgagg aggagatcta cccgaacaat  3180
acggttacgt gcaatgatta cacggtgaac caggaggaat acggcggagc atacacctca  3240
cgtaatagag ggtacaatga ggcaccgtca gttccggcag attatgcctc agtttatgag  3300
gagaagtcct acacggatgg aagacgcgag aatccatgtg agtttaatag aggataccga  3360
gactacacac cactcccagt tggatacgtt acaaaggagt tggaatactt cccagaaaca  3420
gataaagttt ggatagagat cggagaaaca gaaggaacct tcatcgtgga cagtgtagaa  3480
ctgctgctga tggaagaatg a                                             3501
```

SEQ ID NO: 116          moltype = DNA  length = 3549
FEATURE                 Location/Qualifiers

```
misc_feature        1..3549
                    note = Synthetic DNA sequence for expression in plants
                     encoding TIC1099.
source              1..3549
                    mol_type = other DNA
                    organism = synthetic construct
SEQUENCE: 116
atggacaaca accccaacat caatgagtgc atcccttaca actgcctcag caaccccgag    60
gtggaggtgc tcggcggtga gcggatcgag accgggtaca ctcctatcga catcagcctg   120
tccctgacac agttccttct ctccgagttc gtcccaggcg cgggctttgt cctgggcctt   180
gtggacatca tctggggaat cttcgggcca tctcagtggg acgcgtttct tgtgcagata   240
gagcaactta ttaaccagag gatcgaggag ttcgcgcgca atcaggctat ctcacgcctc   300
gaagggcttt ccaatctgta ccagatctac gcggagtcgt tccgggaatg ggaggcggac   360
cctaccaacc cggcgctgcg cgaggaaatg aggatccagt tcaacgatat gaactcggct   420
ctgaccacgg ccatccctct gctcgccgtg cagaattacc aagtcccgct cctttccgtg   480
tacgtccagg ctgccaacct ccatctgtcg gtcctccgtg acgtgagcgt gttcggtcag   540
cgttggggct tcgatgccgc gactatcaac agccggtaca acgacttgac taggcttatc   600
gggaactaca cagactacgc tgtcagatgg tacaataccg gcctggagag agtgtggggc   660
cccgactccc gcgactgggt gagatacaat cagttccgcc gcgagcttac cctcactgtc   720
ctggacatcg tggccctctt cccaaattac gatagccgcc gttacccgat caggactgtg   780
agtcagttga cccgtgaaat ctacaccaac ccggtcttgg agaactttga cggttccttc   840
cggggttccg cacaaggaat cgagcggagc atccgctcct cacacctgat ggacatcctg   900
aactcaatta ccatctacac ggatgcccac cgaggctact attactggag tggtcaccaa   960
atcatggcca gccctgtggg cttctcgggg ccggagttca cgttcccgct gtacggtacg  1020
atgggcaacg ctgcacctca gcaaaggatc gttgcccaac tgggtcaggg cgtttacaga  1080
accttgtcga gcacactgta ccggaggccg ttcaacatcg gcatcaataa ccagcagctg  1140
agcgttctcg acggcacgga gttcgcctac ggaactagca gcaacctccc gagtgcagtg  1200
taccggaagt ccgggaccgt ggatagcctg gacgaaatcc cacctcagaa caacaacgtc  1260
cctcctcggc aaggcttctc ccaccgcctt agccatgttt ccatgttccg gtcgggattc  1320
agtaactcca gcgtctctat catcaaggct cccatgttca gctggattca taggtccgct  1380
gagttcaaca acatcattgc ctccgactca atcactcagc tccctctggt gaaggcgtct  1440
gcgccagtca gtggaaccac cgtactcaag ggccccggct tcaccggcgg cggaatcctt  1500
cgtaggacca ctaacggcac tttcggtact ctgcgtgtca ctgtcaatag cccgctcact  1560
cagcgctacc gtgtaagggt tcgattcgcc agctccggca acttctcaat aaggatcttg  1620
cgcggaaaca catctatcgc ataccagcgc ttcggctcaa cgatgaacag gggccaagag  1680
ctgacttacg agagcttcgt gacctcagag ttcaccacta accagtccga tctacctttc  1740
accttcaccc aggctcagga gaacctcaca attcttgccg aaggcgtgag cactggcagt  1800
gagtatttca tcgaccggat cgagatcata ccagtcaacc cagcacgtga ggctgaggaa  1860
gacctcgaac gcgcgcagaa ggcagtcaac gccctcgtta ccagcaccaa tcagttgggt  1920
cttaagacga atgttaccga ttaccatatc gaccaagtta gtaatcttgt tacataccgc  1980
tctgatgagt tctgcttgga cgaaaagcgt gaactctccg agaaggtcaa acacgcgaag  2040
cgcctctctg atgagcgcaa ccttctgcaa gactcgaact tcaaggacat taacaggcaa  2100
ccggaaagag gttggggcgg tagtaccggc attacgatcc agggcgggag cgatgtttc   2160
aaggagaact acgttaccct tagcggcacg tttgacgagt gctaccctac ctatctctat  2220
cagaagatcg acgagagcaa gctcaaggcg tttacccgtt accagctccg tggctacatt  2280
gaggactctc aggatctcga aatctacttg atccggtaca acgcgaagca cgagaccgtc  2340
aacgtccctg ggacagggtc gctgtggccc ctctctgccc aatctccgat tggaaagtgc  2400
ggcgagccaa accggtgtgc tcctcacctg gagtggaatc ccgatctgga ttgctcgtcg  2460
agggacggtg agaagtgtgc acaccattca caccacttct ccctcgacat cgacgtgggc  2520
tgtacggatc tgaacgagga tcttgggggtt tgggttatct tcaagattaa gactcaggat  2580
ggacacgcgc gcctcggcaa cctggagttc ctcgaggaaa agcctctcgt gggcgaggcg  2640
ctggcccgcg ttaagcgagc tgagaagaag tggcgggaca aacgcgagaa gctagagtgg  2700
gaaacgaaca tcgtttacaa ggaagccaag gaatctgtgg atgccctctt cgtgaactct  2760
cagtacgacc aactccaggc cgacaccaac atcgccatga tccatgctgc cgacaagcgc  2820
gtgcacagca tccgggaagc gtacctgcct gagctgagcg ttattccggg tgtgaacgct  2880
gcgatcttcg aggaactcga aggcagaatc ttcaccgcat tctccctgta cgatgctagg  2940
aatgttatca agaacgggga cttcaacaat gggctctcct gttggaacgt taagggccat  3000
gtggacgtgg aggaacagaa taaccagagg tctgtcctcg tggtccctga gtgggaggct  3060
gaggtttcac aggaggttcg ggtctgcccg ggtaggggt acattctccg ggttaccgcc   3120
tacaaggagg gctacgccga gggctgtgtg accataccg agatcgagaa taacaccgat  3180
gagttgaagt ttagcaactg cgtcgaggag gaaatctacc ccaacaatac ggttacctgc  3240
aacgactaca ctgtcaacca ggaggagtat ggcggagctt acacatcccg gaaccgaggc  3300
tacaacgagg ccccatctgt cccggcggac tatgcgtcgg tgtacgagga gaagtcctac  3360
accgatggcc gtagggagaa tccgtgcgag tttaaccgtg gctaccgcga ctacacgcct  3420
ttgcccgtcg gttatgtcac taaggaactg gaatactttc ccgagacgga caaggtgtgg  3480
attgagatcg gtgagactga gggcacgttt atcgttgact cggtggagct gttgctcatg  3540
gaggagtga                                                          3549

SEQ ID NO: 117    moltype = DNA  length = 3534
FEATURE           Location/Qualifiers
misc_feature      1..3534
                  note = Synthetic DNA sequence for expression in plants
                   encoding TIC1103.
source            1..3534
                  mol_type = other DNA
                  organism = synthetic construct
SEQUENCE: 117
atggacaaca acccgaacat caacgagtgc atcccgtaca actgcctgag caaccccggag   60
gttgaggtgc tgggcggtga gcgcatcgag accggctaca cgcctatcga catctccctg  120
```

```
agcctgaccc agttcctcct tagcgagttc gtgccgggcg cgggcttcgt gctcggcctc   180
gtggacatca tctgggggcat cttcggcccg tcccagtggg acgccttcct cgtgcagatc   240
gagcagctca tcaaccagcg catcgaggag ttcgcccgca accaggccat ctcccgcctg   300
gagggtctgt ccaacctcta ccaaatctac gccgagtcct tccgcgagtg ggaggccgac   360
ccgaccaacc cggccctccg cgaggagatg cggattcagt tcaacgacat gaactccgca   420
ctcaccaccg ccatcccgct cctggccgtg cagaactacc aagtgccgct cctgtccgtg   480
tacgtgcaag ccgcgaacct ccacctctcc gtgctccgcg acgtctccgt gttcggccag   540
cgctgggggct tcgacgccgc gaccatcaac tcccgctaca cgacctcac ccgcctcatc   600
ggcaactaca ccgactacgc cgtgcgctgg tacaacaccg gcctggagcg cgtgtggggc   660
ccggactccc gcgactgggt gcgctacaac cagttccgcc gcgagctgac cctcaccgtg   720
ctcgacatcg tggccctctt cccgaactac gactccaggc gctacccgat ccgcaccgtg   780
tcccagctca cccgcgaaat ctacaccaac ccggtgctgg agaacttcga cggctccttc   840
cgggggctccg cccagggcat cgagcgctcc atccgctccc cgcacctcat ggacatcctc   900
aactccatca ccatctacac cgacgcccac aggggctact actactggtc cggccaccag   960
atcatggcca gcccggtggg cttctccggc ccggagttca ccttcccgct ctacggcact  1020
atgggcaacg ccgcgcccca gcaaaggatc gtggcccagc tcggccaggg cgtgtaccgc  1080
accctcagct ctaccctgta caggcggccc ttcaacatcg gcatcaacaa ccagcaactg  1140
agcgtgctgg acggcaccga gttcgcctac ggcaccagca gcaacctgcc cagcgccgtg  1200
taccgcaaga gcggcaccgt ggacagcctg gacgagatcc cgccgcagaa caacaacgtg  1260
ccgccgcgcc agggcttcag ccacaggctg agccacgtga gcatgttccg cagcggcttc  1320
agcaacagct ctgtgagcat catcagggct cccatgttct cctggattca caggagcgcg  1380
gagttcaaca acatcattgc gagcgactct atcacccagc tcccgatggt gaaggcgaac  1440
gcgctgctga gcggcaccag cgtcatcaag ggccctggca gcaccggcgg ggacatcctg  1500
aggcggacgt ctgtgggcag ggtcgggaac ttcaaggtca acgtcaacgg gccgctgacg  1560
cagcgctacc tggtccgcat ccgctacgcg agcacgactg acctggactt ctacgtttac  1620
cggggcggta cgactgtcag caactaccgg ttcaacaaga cgataacaa gggcgcgtct  1680
ctgacgtacg acatcttcaa gttcgcgtct ttcagcacgc ccttcacgtt cacgaagacg  1740
caagacgagc tggggatcag tatccagaac ttcagcagcg cgaggaggt gtacattgac  1800
cggattgagg tcattcccgt cgggacgact tacgaggcgg agacggacct ggagcgggcg  1860
cagaaggcgg tcaacgcgct gttcacgagc acgaaccagc tcggcctcaa gacgaacgtc  1920
actgactacc acattgacca agtctcgaac ctggtcactt acctgtcgga cgagttctgc  1980
ctggacgaga agcggggagct gtcggagaag gtcaagcacg cgaagcggct gtcggacgag  2040
cggaacctgc tccaggactc gaacttcaag gacatcaacc ggcagccaga gcggggctgg  2100
ggcggcagca ccgggattac tatccagggc ggtgacgag tctttaagga gaactacgtc  2160
actctttcgg gcactttcga cgagtgctac ccaacttacc tttaccagaa gattgacgag  2220
tcgaagctca aggcgtttac tcgctaccaa cttcgcgggt acattgagga cagtcaggat  2280
cttgaaatct accttatccg ctacaacgcg aagcacgaga ctgtcaacgt cccagggact  2340
gggtcgctct ggccactctc ggctcaatcg ccaattggga agtgcggtga gccaaacaga  2400
tgcgctccac accttgagtg gaatccagac cttgactgct cgtcgcagaga cggtgagaag  2460
tgcgctcacc atagtcatca cttcagtctt gacatcgacg tcggttgcac tgatctgaat  2520
gaggatcttg gtgtctgggt catcttcaag attaagactc aagatggtca tgctagactc  2580
ggcaacttgg agttcctgga ggagaagcca ttggtcggtg aggctttggc tagagtcaag  2640
cgcgctgaga agaaatggag agataagagg gagaagctgg agtggggaac caacatcgtg  2700
tacaaggagg ctaaagagtc agtcgatgct ctgttcgtca atagccagta cgatcagctc  2760
caagctgaca caaacatcgc tatgattcat gctgccgata agagggtcca tagtatccgt  2820
gaggcttatc tgcctgagtt gtcagtcata cctggtgtga atgctgccat cttcgaggag  2880
ctggaaggtc gcatcttcac agcgttcagt ctgtacgatg cacgtaacgt catcaagaac  2940
ggtgacttca caaacggtct gtcctgctgg aatgtgaaag gccacgtgga tgtggaggaa  3000
cagaacaacc agcgttcagt gctcgtcgta cctgagtggg aggcagaggt gtcacaggag  3060
gtgcgtgtgt gccctggacg tggctacatc ctccgtgtta cagcatacaa ggagggatac  3120
ggcgaaggat gtgtgaccat ccacgagatc gagaacaaca cagatgaact aaagttcagc  3180
aattgtgttg aggaggaaat ctacccgaac aacacagtga catgcaacga ctacacagtg  3240
aaccaggaag aatacggagg agcatacaca tcacgtaacc gaggatacaa cgaggcacct  3300
tcagttccgg ccgactacgc ctcagtttac gaggagaagt catacacaga tggacgaagg  3360
gagaaccctt gtgagttcaa tcgaggctac cgagactaca caccttttgcc tgtgggctac  3420
gtgacaaagg agctggaata cttccctgaa acagacaaag tatggatcga gatcggagaa  3480
acagaaggaa cattcatcgt ggactccgtg gagctgctgc tgatgggagga gtga       3534
```

```
SEQ ID NO: 118          moltype = DNA  length = 3573
FEATURE                 Location/Qualifiers
misc_feature            1..3573
                        note = Synthetic DNA sequence for expression in plants
                         encoding TIC845.
source                  1..3573
                        mol_type = other DNA
                        organism = synthetic construct
SEQUENCE: 118
atgaccagca accggaagaa cgagaacgag atcatcaacg ccctgagcat ccgaccgtg    60
agcaaccta gcacccagat gaacctgagc cctgacgctc gcatcaggga ctccctctgc   120
gtggctgagg tgaacaacat cgacccgttc gtgtccgcct ccaccgtgca gaccggcatc   180
aacatcgcgg gccgcatcct cggcgtgctc ggcgtgccct ttgcgggcca gctcgcctcc   240
ttctactcct tcctcgtggg agagctgtgg ccctccggcc gcgacccgtg ggagatcttc   300
ctggagcacg tggagcagct catccgccag caagtcaccg agaacacccg caacaccgcc   360
atcgcccgac tggaggggcct gggcgtggcc taccgctcct accagcaagc cctggagacc   420
tggctcgaca accgcaacga cgcccgctcc cgctccatca tcctggagcg ctacgtcgcc   480
ctggaactgg acatcaccac tgccatccca ctcttccgca tcaggaacga ggaggtgcct   540
ctgctgatgt gtacgcccca ggctgcgaac ctgcacctgc tgctgctgcg cgacgcaagc   600
ctgtttggct ccgagtgggg tatggcaagc tccgacgtca accagtacta ccaggagcag   660
atccgctaca ccgaggagta cagcaaccac tgcgtccagt ggtacaacac cggtctgaac   720
```

```
aatctcagag ggaccaacgc tgagagctgg ctgcgctaca accagttccg gcgggatctg   780
accctaggtg tcctggatct ggtcgctctg ttcccgagct acgataccag gacgtaccct   840
atcaacacct ctgctcagct taccagggag atctacactg atcctatcgg taggactaac   900
gctcctagtg gtttcgccag cactaactgg ttcaacaaca acgcgcctag tttctctgcc   960
atcgaggcgg cgatcttccg gcctcctcac ctcctcgact tcccgagca gcttactatc    1020
tactctgcgt cttcgcggtg gtcttcgact cagcacatga actactgggt tggtcaccgg   1080
cttaacttcc gcccgattgg aggaactctt aacaccagta cgcaaggtct tacgaacaac   1140
acttccatca acccggttac gttgcagttc acgtctcggg acgtttaccg gacggagtcg   1200
aatgctggga cgaacatcct gttcacgaca ccggtgaatg gtgttccgtg ggcacgtttc   1260
aacttcatca acccgcagaa catctacgag cgtggagcaa cgacatactc gcaaccatac   1320
caaggcgttg gcatccaact gtttgactcg gagacggaac tgccaccaga gacgacagaa   1380
cgtccgaatt acgagtcata ctcacacaga ctatcacaca ttggactcat tatcggaaac   1440
acactgagag caccagtgta ctcatggaca catcggtcag cagatcgtac gaacatcatc   1500
gcctccgact ccatcaccca gattccggct gtgaagggca acttcctgtt caacggcagc   1560
gtcatctccg gccctgggtt caccggcggc gatctcgtca gactcaactc ctccggcaac   1620
aacatccaga atcgtggcta cattgaggtt cccatccact tcccatccac ctccaccgc    1680
tatcgcgtgc gcgtgcgcta cgcatccgtg actccgatcc atctcaacgt caactggggc   1740
aactcctcca tcttctccaa caccgtgccc gccaccgcga cctcccttga caacctccag   1800
agcagcgact tcggctactt cgagtctgcc aatgccttca cctcctcctt gggcaacatc   1860
gtaggtgtga ggaacttctc cggcactgcg ggcgtcatca tcgaccgctt cgagttcatc   1920
cctgtgaccg ccactctgga agccgagtac aacctcgagc gtgcccagaa ggcagtgaat   1980
gagctgttca cgagcagcaa tcagatcggg ctcaagaccg acgtgaccga ctaccacatc   2040
gaccaagtca gcaatctggt ggagtgtctc agcgacgagt tctgcctgga cgagaagaag   2100
gaactcagcg agaaggtgaa gcacgccaaa cgtctgtccg acgaacgcaa tctgctgcaa   2160
gatccgaact tcagagggat caacaggcaa ctggaccgtg ggtggcgtgg gtccaccgac   2220
atcaccatcc aaggcggcga cgacgtcttc aaggagaact acgtcactct gctgggcacc   2280
ttcgacgagt gctatccgac ctacctgtac cagaagatcg acgagagcaa gctcaaggcg   2340
tacacccgct accaactcag aggctacatc gaagactccc aggatctgga aatctacctc   2400
attcgctaca acgcgaagca cgagactgtc aacgtgcccg gcactggcag cctgtggccg   2460
ctctcgcgc cgagccctat cggaaagtgt gcgcaccact cccaccactt cagcttggac   2520
atcgacgtgg gttgcacgga cctcaacgaa gacctgggtg tctgggtgat cttcaagatc   2580
aagacgcaag acggacacgc gagactcggc aatctggagt tcctggagga gaagcctctg   2640
gtcggcgaag ctctcgccag ggtgaagcgc gccgagaaga agtggcgcga caagcgggag   2700
aagctggagt gggagacgaa catcgtgtac aaggagcgca aggagtccgt ggacgccctc   2760
tttgtgaaca gccagtacga ccgcctccaa gcagcacaca acattgccat gatccacgcc   2820
gccgacaagc gcgtgcactc catcaggag gcgtatctcc ctgaactcag cgtgattcct   2880
ggcgtgaatg ctgccatctt cgaggagctt gagggtcgca tcttcaccgc attcagcctc   2940
tacgacgcca ggaacgtcat caagaacgga gacttcaaca acgggctgtc ctgctggaac   3000
gtcaaaggtc acgttgacgt ggaggagcag aacaaccatc gcagcgtcct cgtcgtccct   3060
gagtgggaag ctgaggtcag ccaagaagtc agggtctgcc ctggtcgcgg ctacatcctc   3120
agggtgaccg cctacaagga agggtatggt gaagggtgtg tcacgatcca tgagattgag   3180
aacaacacgg acgaactcaa gttcagcaac tgcgtcgagg aggaggtcta tccgaacaac   3240
acggtcacct gcaacgacta cactgccact caggaggagt acgaggggaac ctacactagc   3300
cgcaaccgtg gctacgatgg agcctacgag tccaactcct ccgttccgc tgactacgca    3360
agcgcctacg aggagaaggc gtacacggac gggcggcgcg acaacccgtg cgagtccaat   3420
cgtggctacg gtgactacac tccgcttccc gctggttacg tgaccaagga acttgagtac   3480
ttccctgaga ccgacaaggt ctggatcgag ataggtgaga ccgaaggcac gttcatcgtt   3540
gactccgtcg aactgctgct catggaggag tga                                3573
```

```
SEQ ID NO: 119           moltype = DNA  length = 3567
FEATURE                  Location/Qualifiers
misc_feature            1..3567
                         note = Synthetic DNA sequence for expression in plants
                         encoding TIC846.
source                  1..3567
                         mol_type = other DNA
                         organism = synthetic construct
SEQUENCE: 119
atgaccagca accggaagaa cgagaacgag atcatcaacg ccctgagcat ccgaccgtg     60
agcaaccta gcaccagat gaacctgagc cctgacgctc gcatcgagga ctccctctgc    120
gtggctgagt gaacaacat cgaccgttc gtgtccgcct ccaccgtgca gaccggcatc    180
aacatcgcgg gccgcatcct cggcgtgctc ggcgtgcct ttgcgggcca gctcgcctcc   240
ttctactcct tcctcgtggg agagctgtgg ccctccggcc gcgaccgtg ggagatcttc    300
ctggacacg tggagcagct catccgccag caagtcaccg agaacaccg caacaccgcc   360
atcgcccgcc tggagggcct gggccgtggc taccgctcct accagcaagc cctggagacc   420
tggctcgaca accgcaacga cgcccgctcc cgctccatca tcctggagcg ctacgtcgcc   480
ctggaactgg acatcaccac tgccatccca ctcttccgca tcaggaacga ggaggtgcct   540
ctgctgatgg tgtacgccca ggctgcgaac ctgcacctgc tgctgctgcg cgacgcaagc   600
ctgtttggct ccgagtgggg tatggcaagc tccgacgtca accagtacta ccaggagcag   660
atccgctaca ccgaggagta cagcaaccac tgcgtccagt ggtacaacac cggtctgaac   720
aatctcagag ggaccaacgc tgagagctgg ctgcgctaca accagttccg gcgggatctg   780
accctaggtg tcctggatct ggtcgctctg ttcccgagct acgataccag gacgtaccct   840
atcaacacct ctgctcagct taccagggag atctacactg atcctatcgg taggactaac   900
gctcctagtg gtttcgccag cactaactgg ttcaacaaca acgcgcctag tttctctgcc   960
atcgaggcgg cgatcttccg gcctcctcac ctcctcgact tcccgagca gcttactatc    1020
tactctgcgt cttcgcggtg gtcttcgact cagcacatga actactgggt tggtcaccgg   1080
cttaacttcc gcccgattgg aggaactctt aacaccagta cgcaaggtct tacgaacaac   1140
acttccatca acccggttac gttgcagttc acgtctcggg acgtttaccg gacggagtcg   1200
aatgctggga cgaacatcct gttcacgaca ccggtgaatg gtgttccgtg ggcacgtttc   1260
```

-continued

```
aacttcatca acccgcagaa catctacgag cgtggagcaa cgacatactc gcaaccatac  1320
caaggcgttg gcatccaact gtttgactcg gagacggaac tgccaccaga gacgacagaa  1380
cgtccgaatt acgagtcata ctcacacaga ctatcacaca ttggactcat tatcggaaac  1440
acactgagag caccagtgta ctcatggaca catcggtcag cagatcgtac gaacaccatc  1500
ggtcccaacc gcatcactca gatcccgctc gtgaaggcac tgaacctgca cagcggagtg  1560
accgtggtgg gcggccctgg cttcaccggc ggcgacattc ttcgccgcac gaacacaggc  1620
accttcgctg acatgcgtgt gaacatcacc ggcccactca gccaacgcta ccgcgttcgc  1680
atccgctacg ccagcaccac cgatctccag ttcttcaccc gcatcaatgg cacgtctgtg  1740
aaccagggca acttccagcg caccatgaac cgtggcgaca acctcgaatc tggcaacttc  1800
cgcactgcgg gcttctcgac gcccttctcc ttctccaacg cgcagtccac cttcaccttg  1860
ggcactcagg cgttctccaa ccaggaggtg tacatcgaca ggatcgagtt cgtaccagcc  1920
gaagtgacct tcgaggccga gtccgatctc gagcgtgccc agaaggcagt gaatgagctg  1980
ttcacgagca gcaatcagat cgggctcaag accgacgtga ccgactacca catcgaccag  2040
gtcagcaatc tggtggagtg tctcagcgac gagttctgcc tggacgagaa gaaggaactc  2100
agcgagaagg tgaagcacgc caaacgtctg tccgacgaac gcaatctgct gcaagatccg  2160
aacttcagag ggatcaacag gcaactggac cgtgggtggc gtgggtccac cgacatcacc  2220
atccaaggcg gcgacgacgt cttcaaggag aactacgtca ctctgctggg cacgttcgac  2280
gagtgctatc cgacctacct gtaccagaag atcgacgaga gcaagctcaa ggcgtacacc  2340
cgctaccaac tcagaggcta catcgaagac tcccaggatc tggaaatcta cctcattcgc  2400
tacaacgcga agcacgagac tgtcaacgtg cccggcactg gcagcctgtg gccgctctcc  2460
gcgccgagcc ctatcggaaa gtgtgcgcac cactcccacc acttcagctt ggacatcgac  2520
gtgggttgca cggacctcaa cgaagacctg ggtgtctggg tgatcttcaa gatcaagacg  2580
caagacggac acgcgagact cggcaatctg gagttcctgg aggagaagcc tctggtcggc  2640
gaagctctcg ccagggtgaa gcgcgccgag aagaagtggc gcgacaagcg ggagaagctg  2700
gagtgggaga cgaacatcgt gtacaaggag gccaaggagt ccgtggacgc cctctttgtg  2760
aacagccagt acgaccgcct ccaagcagac accaacattg tcgccgtcca cgccgccaag  2820
aagcgcgtgc actccatcag ggaggcgtat ctccctgaac tcagcgtgat tcctggcgtg  2880
aatgctgcca tcttcgagga gcttgagggt cgcatcttca ccgcattcag cctctacgac  2940
gccaggaacg tcatcaagaa cggagacttc aacaacgggc tgtcctgctg gaacgtcaaa  3000
ggtcacgttg acgtggagga gcagaacaac catcgcaacg tcctcgtcgt ccctgagtgg  3060
gaagctgagg tcagccaaga agtcagggtc tgccctggtc gcggctacat cctcagggtg  3120
accgcctaca aggaagggta tggtgaaggg tgtgtcacga tccatgagat tgagaacaac  3180
acggacgaac tcaagttcag caactgcgtc gaggaggagg tctatccgaa caacacggtc  3240
acctgcaacg actacactgc cactcaggag gagtacgagg gaacctacac tagccgcaac  3300
cgtgcgctacg atggagccta cgagtccaac tcctccgttc ccgctgacta cgcaagcgcc  3360
tacgaggaga aggcgtacac ggacgggcgg cgcgacaacc cgtgcgagtc caatcgtggc  3420
tacggtgact acactccgct tcccgctggt tacgtgacca aggaacttga gtacttccct  3480
gagaccgaca aggtctggat cgagataggt gagaccgaag gcacgttcat cgttgactcc  3540
gtcgaactgc tgctcatgga ggagtga                                      3567
```

```
SEQ ID NO: 120          moltype = DNA  length = 3570
FEATURE                 Location/Qualifiers
misc_feature           1..3570
                        note = Synthetic DNA sequence for expression in plants
                         encoding TIC858.
source                 1..3570
                        mol_type = other DNA
                        organism = synthetic construct
SEQUENCE: 120
atgaccagca accggaagaa cgagaacgag atcatcaacg ccctgagcat cccgaccgtg  60
agcaaccctca gcacccagat gaacctgagc cctgacgctc gcatcgagga ctccctctgc  120
gtggctgagg tgaacaacat cgacccgttc gtgtccgcct ccaccgtgca gaccggcatc  180
aacatcgcgg gccgcatcct cggcgtgctc ggcgtgccct ttgcgggcca gctcgcctcc  240
ttctactcct tcctcgtggg agagctgtgg ccctccggcc gcgacccgtg ggagatcttc  300
ctggacacg tggagcagct catccgccag caagtcaccg agaacacccg caacaccgcc  360
atcgcccgcc tggagggcct gggccgtggc taccgctcct accagcaagc cctggagacc  420
tggctcgaca accgcaacga cgcccgctcc cgctccatca tcctggagcg ctacgtcgcc  480
ctggaactgg acatcaccac tgccatccca ctcttccgca tcaggaacga ggaggtgcct  540
ctgctgatgg tgtacgccca ggctgcgaac ctgcacctgc tgctgctgcg cgacgcaagc  600
ctgtttggct ccgagtgggg tatggcaagc tccgacgtca accagtacta ccaggagcag  660
atccgctaca ccgaggagta cagcaaccac tgcgtccagt ggtacaacac cggtctgaac  720
aatctcagag ggaccaacgc tgagagctgg ctgcgctaca accagttccg gcgggatctg  780
accctaggtg tcctggatct ggtcgctctg ttcccgagct acgataccag gacgtaccct  840
atcaacaccct ctgctcagct taccaggag atctacactg atcctatcgg taggactaac  900
gctcctagtg gtttcgccag cactaactgg ttcaacaaca acgcgcctag tttctctgcc  960
atcgaggcgg cgatcttccg gcctcctcac ctcctcgact tcccggagca gcttactatc  1020
tactctgcgt cttcgcggtg gtcttcgact cagcacatga actactgggt tggtcaccgg  1080
cttaacttcc gcccgattgg aggaactctt aacaccagta cgcaaggtct tacgaacaac  1140
acttccatca acccggttac gttgcagttc acgtctcggg acgtttaccg gacggagtcg  1200
aatgctggga cgaacatcct gttcacgaca ccggtgaatg gtgttccgtg ggcacgtttc  1260
aacttcatca acccgcagaa catctacgag cgtggagcaa cgacatactc gcaaccatac  1320
caaggcgttg gcatccaact gtttgactcg gagacggaac tgccaccaga gacgacagaa  1380
cgtccgaatt acgagtcata ctcacacaga ctatcacaca ttggactcat tatcggaaac  1440
acactgagag caccagtgta ctcatggaca catcggtcag cagatcgtac gaacaccatc  1500
ggtccgaacc gcatcactca gatccctatg gtcaaggctt ccgaacttcc tcaaggaacc  1560
accgtggtgc gtgcccagg cttcacaggc ggcgacattc tccgccgcac gaacactggc  1620
ggcttcggcc cgattcgtgt gacagtcaat ggtccgctga cccaacgcta tcgcataggc  1680
tttcgctacg cctccaccgt tgacttcgac ttcttcgtgt cgcgtggtgg tacgaccgtc  1740
aacaacttcg gcttccttcg caccatgaac tcaggagacg agttgaagta cggcaacttc  1800
```

-continued

```
gtacgccgcg ccttcaccac gccgttcacc ttcacccaga tccaggacat catcaggacc   1860
agcatccaag gtctctctgg caatggcgaa gtgtacatcg acaagatcga gatcatccca   1920
gtgactgcga cctttgaagc agagtacgat ctcgagcgtg cccagaaggc agtgaatgag   1980
ctgttcacga gcagcaatca gatcgggctc aagaccgacg tgaccgacta ccacatcgac   2040
caagtcagca atctggtgga gtgtctcagc gacgagttct gcctggacga gaagaaggaa   2100
ctcagcgaga aggtgaagca cgccaaacgt ctgtccgacg aacgcaatct gctgcaagat   2160
ccgaacttca gagggatcaa caggcaactg gaccgtgggt ggcgtgggtc caccgacatc   2220
accatccaag gcggcgacga cgtcttcaag gagaactacg tcactctgct gggcaccttc   2280
gacgagtgct atccgaccta cctgtaccag aagatcgacg agagcaagct caaggcgtac   2340
acccgctacc aactcagagg ctacatcgaa gactcccagg atctggaaat ctacctcatt   2400
cgctacaacg cgaagcacga gactgtcaac gtgcccggca ctggcagcct gtggccgctc   2460
tccgcgccga gccctatcgg aaagtgtgcg caccactccc accacttcag cttggacatc   2520
gacgtgggtt gcacggacct caacgaagac ctgggtgtct gggtgatctt caagatcaag   2580
acgcaagacg gacacgcgag actcggcaat ctggagttcc tggaggagaa gcctctggtc   2640
ggcgaagctc tcgccagggt gaagcgcgcc gagaagaagt ggcgcgacaa gcgggagaag   2700
ctggagtggg agacgaacat cgtgtacaag gaggccaagg agtccgtgga cgccctcttt   2760
gtgaacagcc agtacgaccg cctccaagca gacaccaaca ttgccatgat ccacgccgcc   2820
gacaagcgcg tgcactccat cagggaggcg tatctccctg aactcagcgt gattcctggc   2880
gtgaatgctg ccatcttcga ggagcttgag ggtcgcatct tcaccgcatt cagcctctac   2940
gacgccagga acgtcatcaa gaacggagac ttcaacaacg ggctgtcctg ctggaacgtc   3000
aaaggtcacg ttgacgtgga ggagcagaac aaccatcgca gcgtcctcgt cgtccctgag   3060
tgggaagctg aggtcagcca agaagtcagg gtctgcccga gtcgcggcta catcctcagg   3120
gtgaccgcct acaaggaagg gtatggtgaa gggtgtgtca cgatccatga gattgagaac   3180
aacacggacg aactcaagtt cagcaactgc gtcgaggagg aggtctatcc gaacaacacg   3240
gtcacctgca acgactacac tgccactcag gaggagtacg agggaaccta cactagccgc   3300
aaccgtggct acgatggagc ctacgagtcc aactcctccg ttcccgctga ctacgcaagc   3360
gcctacgagc agaaggcgta cacggacggg cggcgcgaca acccgtgcga gtccaatcgt   3420
ggctacggtg actacactcc gcttcccgct ggttacgtga ccaaggaact tgagtacttc   3480
cctgagaccg acaaggtctg gatcgagata ggtgagaccg aaggcacgtt catcgttgac   3540
tccgtcgaac tgctgctcat ggaggagtga                                    3570
```

SEQ ID NO: 121          moltype = DNA  length = 3564
FEATURE                 Location/Qualifiers
misc_feature           1..3564
                        note = Synthetic DNA sequence for expression in plants
                         encoding TIC866.
source                  1..3564
                        mol_type = other DNA
                        organism = synthetic construct
SEQUENCE: 121

```
atgacgtcca accggaagaa cgagaacgag atcatcaacg cgctgtcaat cccggcggtg   60
tccaaccact cggcccagat gaacctgtcc acggacgcca ggatcgagga cagcctctgc   120
atcgccgagg gcaacaacat tgaccgcttc gttagcgcca gcaccgtcca gaccggcatt   180
aacatcgcgg gccgcatcct cggcgttctg ggcgtcccgt tcgcgggcca gatcgcctca   240
ttctacagct tcctggtggg agagctgtgg ccgcgtgggc gcgacccgtg ggagatcttc   300
ctggagcacg tggagcagct catcaggcag caagtcaccg agaacacacg agacaccgca   360
ttggcggcaa tccagggcct gggcaactca ttccgcgcgt accagcagag cctggaggac   420
tggctggaga accgagacga cgcgcgcact cgctccgtcc tgtacacgca gtacatcgcc   480
cttgagctgg acttcctcaa cgcgatgcca ctgttcgcca tccggaacca ggaggtgccg   540
ctcctcatgg tgtacgctca ggctgccaac ctccacctgc tgctgctgcg ggacgcatcc   600
ctgttcgggt cggagttcgg cctgacctcc caggagattc agcgctacta ggacgggcaa   660
gtggagaaga caagggagta cagtgattat tgcgcccgct ggtacaacac cgggttgaac   720
aacttgcgag gcaccaacgc ggagtcatgg ctccgctaca atcagttccg gcgagacctc   780
acgctggggc tgctcgacct cgtggccctc ttcccttcgt acgacacgcg cgtgtaccca   840
atgaacacca gcgccagct cacgcgcgaa atctcacacg accctatcgg tcgtacaaat   900
gcaccgtcgg gcttcgcctc gacaaactgg tttaacaata acgcgccttc tttctcagca   960
atcgaggccg ctgtgattcg gcctccgcat ctgctcgatt tcccggagca gcttactatc   1020
ttctctgttc tcagccgctg gagcaacaca cagtacatga actattgggt cgggcaccgt   1080
ctggagagcc gcactattcg aggctcactg tcaaccagca cacacgggaa caccaacacc   1140
agcatcaacc cggtcaccct gcaattcact tcccgcgatg tgtacaggac ggagagtttc   1200
gcgggcatta acattctgct cactactccg gtcaacggtg tcccgtgggc ccgcttcaac   1260
tggaggaatc cgctgaacag cctgcgtggc tcccttctct acacaatcgg ttacacgggt   1320
gtcggcaccc agctcttcga ctctgaaacc gagctgccac ctgaaactac agagcgacct   1380
aactacgagt cctacagtca ccgtctgagc aacatcggc taatcagcgg gaacactctt   1440
cgagcgccgg tgtactcctg gacccacaga tcagcagacc ggaccaacac tatctcgtcc   1500
gactccatca cccagatccc tctcgtgaag gctcacaccc ttcagagcgg gacgaccgtg   1560
gtgcgcgggc cgggcttcac cggtggcgac atcctgcgac gtacttccgg cggtccattc   1620
gcatacacaa tcgtgaacat caaccgacag ctcccgcagc gttaccgggc caggataaga   1680
tacgccagca caacgaacct ccggatctac gtgaccgtgg ctggcgaacg gatctttgct   1740
ggtcagttca ataagacaat ggacacgggc gaccgctga cgttccaatc gttctctgtac   1800
gcgaccatca atacggcatt cacgtttccg atgtcccagt cctccttcac agtcggtgct   1860
gatacgttca gctccgggaa cgaggtgtac atcgaccgct tgaactaat tccggtcacc   1920
gcgacgttcg aggctgagta cgatttggag cgcgcgcaga aggcagtcaa tgagctgttc   1980
acttccagca accagatcgg cctcaagacc gatgtgaccg actaccacat cgaccaagtg   2040
tcgaacctgg tggagtgcct gagtgacgag ttctgcttgg acgagaagaa gggagctgtct   2100
gagaaggtca aacatgctaa gaggctgtca gacgagcgta acctccttca agatcctaac   2160
ttccgtggca tcaaccgcca actggatcgc gggtggcgag gcagtacaga catcaccatc   2220
cagggaggcg atgacgtctt caaggagaac tacgttacgc tgctgggcac gttcgacgaa   2280
tgctaccccga cttacctgta ccagaagatc gacgagagca gttgaaggc ttacacccgt   2340
```

```
taccagctca gaggttacat tgaggactcc caggatctgg aaatctacct gatccgctac  2400
aacgctaagc acgagaccgt gaatgtgccc ggcactggtt ccctgtggcc gctgtcggct  2460
ccgtcgccca tcggcaagtg cgcccaccac tcccaccact tcagtctgga cattgacgtc  2520
ggctgcaccg acctaaatga ggacttgggt gtctgggtta tcttcaagat caagacccag  2580
gacgggcacg ctcgtcttgg caacttggag tttctgacgg agaagccgct ggtcggcgag  2640
gccctggccc gagtaaagcg ggccgagaag aagtggcgcg ataagcggga gaagctggag  2700
tgggagacca acatcgtgta caaggaggca aaggagagcg tggacgccct cttcgttaat  2760
tcgcagtacg accggttgca agctgacaca aacatcgcta tgatccacgc cgccgacaag  2820
agggtccact ccatcaggga ggcttacctg ccggaattgt cggtgatccc tggcgtgaat  2880
gctgccatct ttgaggagct ggagggacgg atcttcacag cgttctccct gtacgatgct  2940
aggaacgtca tcaagaacgg cgacttcaac aacggtctga gctgctggaa cgtgaagggc  3000
catgtggacg tggaggagca gaacaaccac cgcagcgtgc tggtcgtgcc cgagtgggaa  3060
gcggaggtca gccaggaggt gcgtgtctgc cctggacgcg gctacatcct gcgggtgacc  3120
gcgtacaagg agggctacgg cgaaggatgc gttaccatcc acgagattga gaacaatacg  3180
gacgagctta agtttagcaa ctgcgtggag gaggaggtgt acccgaataa cacggtgacc  3240
tgcaacgact acacggccac ccaagaggaa tacgaaggca cctacaccag ccgcaaccgt  3300
ggctacgacg gtgcctacga gagcaacagc tccgtgcccg ctgactacgc ttcggcctac  3360
gaggagaagg cgtacactga cggcagacgc gacaacccct gcgagagcaa cagaggctac  3420
ggtgactaca cgccgctccc ggctggctac gtcaccaagg aactggagta cttcccggag  3480
accgacaagg tgtggataga gataggcgag accgagggca ctttcatcgt cgatagcgtc  3540
gagcttcttc tgatggagga gtga                                        3564
```

SEQ ID NO: 122          moltype = DNA  length = 3525
FEATURE                 Location/Qualifiers
misc_feature           1..3525
                        note = Synthetic DNA sequence for expression in plants
                        encoding TIC838.
source                 1..3525
                        mol_type = other DNA
                        organism = synthetic construct
SEQUENCE: 122

```
atggaggaga acaaccagaa ccagtgcatc ccgtacaact gcctgagcaa ccctgaggag  60
gtgctcctag acggtgagcg catctccacc ggcaactcta gcatcgacat ctccctgagc  120
ctagtgcagt tcctagtgag caacttcgtg cccggcggtg gcttcctcgt gggcctcatc  180
gacttcgtgt ggggcatcgt gggcccgtcc cagtgggacg ccttcctcgt gcagatcgag  240
cagctcatca cgagcgcat cgccgagttc gcccgcaacg ccgctatcgc caacctggag  300
ggcctcggca acaatttcaa catctacgtg gaggcgttca aggagtggga ggaagacccg  360
aacaatcccg ccacccgcac ccgcgtgatc gaccgcttcc gcatcctcga cggcctcctg  420
gagcgcgaca tcccgtcctt cgccatctcc ggcttcgagg tgccgctcct gtccgtgcac  480
gcccaggccg ctaacctcca cctcgccatc ctccgcgact ccgtgatctt cggcgagcgc  540
tggggcctca ccactatcaa cgtgaacgag aactacaacc gcctcatccg ccacatcgac  600
gagtacgctg accactgcgc caacacctac aacaggggcc tcaacaatct gcccaagtcc  660
acctaccagg actggatcac ctacaacagg ctgaggcgcg acctgacccg gaccgtgctg  720
gacatcgctg cgttcttccc gaactacgac aacaggcgct accccatcca gagcgtcggc  780
cagctcacca gggagatcta caccgatccg ctcatcacct caaccctca gctccagtcc  840
gtcgctcagc tccctacctt caacgtcatg gagtccaacg ctatccgcac ccctcacctg  900
ttcgatgtcc tgaacaatct taccatcttc accgattggt tctccgtcgg caggaacttc  960
tactggggcg gtcacagggt cattagcaac aggatcggcg gtggcaacat taccagccct  1020
atctacggca gggaggctaa ccaggagcct ccgaggagct tcactttcaa cggtcctgtc  1080
ttccggactc ttagcaaccc tactttccgg cctcttcagc aaccttggcc cgcgccgcca  1140
ttcaaccttc ggggtgtcga gggtgtcgag ttcagcactc cgcttaacag cttcacttac  1200
cggggtagag gcactgtcga tagccttact gaacttccgc cagaagataa cagcgtcccg  1260
ccacgtgaag ggtacagcca ccgtctttgt cacgcgactt cgtccagcg tagtgggact  1320
ccgttcctta cgacagggcc ggtctttagt tggacgcatc gctctgcgac ggacagaaac  1380
attatcgcgt ctgacagtat tacgcaaatt ccggcggtta agggcaactt cctcttcaat  1440
gggtctgtta tttctgggcc aggggtttacg ggcggagatt tggttcgttt gaacagcagc  1500
gggaacaaca tccagaacag aggctacatt gaagtgccaa tccacttccc atctacgagc  1560
acgcgctatc gcgttagagt tcgatacgca tcggttacac caatccacct gaatgttaat  1620
tggggaaatt catcaatctt ctcgaacaca gttccagcaa cagcaacatc attagacaat  1680
ttgcaatcat cagatttcgg atacttcgaa tcggcaaacg cattcacatc gtcgttgggc  1740
aacatcgtag gagtacgcaa cttctcgggc accgccggcg tgatcattga ccgcttcgag  1800
tttatcccgg tcactgctac gctggaggcg gaatacaacc ttgagagagc gcagaaggcc  1860
gtgaacgcgc tgttcacctc gactaaccag ttgggactca agacaaatgt cactgactac  1920
cacatcgacc aagtgagtaa tctcgttacc tacctgtcag acagttctg cctggatgag  1980
aagagggaac tgtctgagaa agtgaagcac gcaaagcgcc tctcggatga gaggaacctc  2040
ctccaggatt ccaacttcaa ggacatcaac cggcagccgg aaagaggctg gggtggctcc  2100
accggcatta ctatccaggg cggcgacgat gtgttcaagg agaactacgt cacactctca  2160
ggcactttcg acgagtgtta cccgacgtac ctgtaccaga agattgatga gtccaagctg  2220
aaggcattca cccgctatca gcttcgcggt tacattgaag attcccagga ccttgagatc  2280
tacctcatca ggtacaacgc caagcacgag acggtcaacg tgcccggcac gggttccctg  2340
tggccgttgt ctgcccaatc tcccatcggg aagtgcggtg agccgaaccg ttgcgccccg  2400
cacctggagt ggaaccctga cctggattgc tcctgtaggg atggcgagaa gtgcgctcac  2460
cattccacc acttctcgct ggacatcgac gtgggggtgca cggatctcaa cgaggatctc  2520
ggagtctggg tcatcttcaa gatcaagacg caggacgac acgctcgcct cggcaatctg  2580
gagtttcttt aggaaaagcc gctcgtaggg gaggcgctcg ccagggtaaa gcgcgcggag  2640
aagaagtgga gggataagcg tgagaaactt gaatgggaga caaacatcgt ctacaaggaa  2700
gcaaaggagt cagttgatgc actgttcgtc aactctcagt atgaccagtt gcaggccgat  2760
accaacatcg cgatgatcca cgccgctgac aagcgcgttc actcgatccg cgaggcgtac  2820
ctccctgagc tttccgtcat cccaggcgtc aatgcggcca tcttcgagga acttgagggc  2880
```

-continued

```
cggatcttca ccgctttctc gctctacgac gctagaaacg tcatcaagaa cggcgacttc   2940
aacaatggcc tgagctgctg gaatgtgaag ggtcatgtgg atgtcgaaga gcagaacaat   3000
cagcgttctg tgctcgtggt ccccgaatgg gaagctgagg tttcccaaga agtgagagtg   3060
tgcccaggac gcggttacat tctccgtgtt acggcgtaca aggagggcta tggcgaaggc   3120
tgcgtgacca ttcatgagat cgagaacaac acggatgagc tgaagttctc aaactgcgtc   3180
gaggaagaaa tctaccctaa caacactgtg acctgtaacg actacacggt gaaccaggaa   3240
gagtacggcg gcgcttacac tagccgcaac cgtgggtaca acgaggcccc atcggtccct   3300
gctgactacg catccgtcta cgaggagaag tcttacactg acgggagacg ggagaacccc   3360
tgcgagttca accggggtta cagggattac acgcctctgc ccgttggcta tgtcactaag   3420
gagctggagt atttcccgga gactgataaa gtctggatcg agatcgggga gactgaaggg   3480
actttcatcg tcgattccgt ggagctgctt ctgatggagg agtga          3525
```

SEQ ID NO: 123          moltype = DNA  length = 3519
FEATURE                 Location/Qualifiers
misc_feature            1..3519
                        note = Synthetic DNA sequence for expression in plants
                         encoding TIC841.
source                  1..3519
                        mol_type = other DNA
                        organism = synthetic construct

SEQUENCE: 123

```
atggaggaga acaaccagaa ccagtgcatc ccgtacaact gcctgagcaa ccctgaggag   60
gtgctcctag acggtgagcg catctccacc ggcaactcta gcatcgacat ctccctgagc   120
ctagtgcagt tcctagtgag caacttcgtg cccggcggtg gcttcctcgt gggcctcatc   180
gacttcgtgt ggggcatcgt gggcccgtcc cagtgggacg ccttcctcgt gcagatcgag   240
cagctcatca acgagcgcat cgccgagttc gcccgcaacg ccgctatcgc caacctggag   300
ggcctcggca acaatttcaa catctacgtg gaggcgttca aggagtggga ggaagacccg   360
aacaatcccg ccacccgcac ccgcgtgatc gaccgcttcc gcatcctcga cggcctcctg   420
gagcgcgaca tcccgtcctt cgccatctcc ggcttcgagg tgccgctcct gtccgtgtac   480
gcccaggccg ctaacctcca cctcgccatc ctccgcgact ccgtgatctt cggcgagcgc   540
tggggcctca ccactatcaa cgtgaacgag aactacaacc gcctcatccg ccacatcgac   600
gagtacgctg accactgcgc caacacctac aacaggggcc tcaacaatct gcccaagtcc   660
acctaccagg actggatcac ctacaacagg ctgaggcgcg acctgaccct gaccgtgctg   720
gacatcgctg cgttcttccc gaactacgac aacaggcgct accccatcca gagcgtcggc   780
cagctcacca gggagatcta caccgatccg ctcatcacct tcaaccctca gctccagtca   840
gtcgctcagc tccctacctt caacgtcatg gagtccaacg ctatccgcac ccctcacctg   900
ttcgatgtcc tgaacaatct taccatcttc accgattggt tctccgtcgg caggaacttc   960
tactgggcg gtcacagggt cattagcaac aggatcggcg gtggcaacat taccagccct   1020
atctacgca gggaggctaa ccaggagcct ccgaggagct tcactttcaa cggtcctgtc   1080
ttccggactc ttagcaaccc tactttccgg cctcttcagc aaccttggcc cgcgccgcca   1140
ttcaaccttc ggggtgtcga gggtgtcgag ttcagcactc cgcttaacag cttcacttac   1200
cggggtagag gcactgtcga tagccttact gaacttccgc cagaagataa cagcgtcccg   1260
ccacgtgaag ggtacagcca ccgtctttgt cacgcgactt tcgtccagcg tagtgggact   1320
ccgttcctta cgacagggcc ggtctttagt tggacgcatc gctctgcgac ggacagaaac   1380
accatcgacc cggagcgcat caaccagatc cctctcgtga agggcttccg cgtgtggggc   1440
ggcacctccg tcatcaccgg ccctggcttc accggcggcg acattcttcg ccgcacgaac   1500
acaggcacct tcgctgacat gcgtgtgaac atcaccggcc cactcagcca acgctaccgc   1560
gttcgcatcc gctacgccag caccaccgat ctccagttct tcacccgcat caatggcacg   1620
tctgtgaacc agggcaactt ccagcgcacc atgaaccgtg gcgacaacct cgaatctggc   1680
aacttccgca ctgcgggctt ctcgacgccc ttctccttct ccaacgcgca gtccaccttc   1740
accttgggca ctcaggcgtt ctccaaccag gaggtgtaca tcgacaggat cgagttcgta   1800
ccagccgaag tgaccttcga ggccgagtcc gatctcgagc gcgcccagaa ggccgtgaac   1860
gccctcttca ctagcactaa ccagctcggc ctcaagacta acgtgaccga ctaccacatt   1920
gaccaagtga gcaacctagt gacctacctt agcgacgagt tctgccttga cgagaagcgt   1980
gagctgagcg agaaggtgaa cacgccaag cgcctctccg acgagcgcaa cctcctccag   2040
gactccaact tcaaggacat caaccgccag cccgagcgcg gctggggcgg tagcaccggc   2100
atcaccatcc agggcggtga cgatgtgttc aaggagaact acgtgaccct ctccggcacc   2160
ttcgacgagt gctacccgac ctacctctac cagaagatcg acgagtccaa gctcaaggcg   2220
ttcacccgct accagcttcg cggctacatc gaggactccc aggatctgga gatctacctc   2280
atccgctaca acgccaagca cgagaccgtg aacgtgcccg gcaccggctc cctctcgccg   2340
ctctccgccc agagccctat cggcaagtgc ggcgagccca accgctgcgc gcctcacctg   2400
gagtggaacc ctgacctcga ctgctcctgc gcgacggcg agaagtgcgc gccaccatagc   2460
caccacttct ctctcgacat cgacgtgggc tgcaccgacc tcaacgagga tctgggcgtg   2520
tgggtgatct tcaagatcaa gacccaggac ggcacgcca ggctgggcaa cctggagttc   2580
ctggaggaga agcctctggt gggtgaggcc ctggccaggg tcaagagggc tgagaagaaa   2640
tggagggaca agaggagaa gctgagtgg gagaccaaca tcgtgtacaa ggaggctaag   2700
gagtccgtgg acgctctgtt cgtcaactct cagtacgatc agctccaggc tgacaccaac   2760
atcgctatga tccacgctgc ggataagagg gtccactcta tcagggaggc ttacctgcct   2820
gagctttctg tcatccctgg tgtcaacgcg gcaatcttcg aggaacttga gggccgcatc   2880
ttcactgcgt tctcgcttta cgatgcgcg aacgtcatta agaacggtga cttcaacaat   2940
ggtctttcgt gctggaacgt caagggtcat gtcgatgtcg aggaacagaa caaccagcgg   3000
tcggtccttg tcgttcccga gtgggaggcc gaggtctcgc aagaggtccg ggtctgccct   3060
gggcgcgggt acattcttcg tgtcactgcg tacaaggagg ctacggcga gggctgcgtt   3120
actattcatg agattgagaa caatacggat gagcttaagt ttagtaactg tgttgaggag   3180
gagatctacc cgaacaatac ggttacgtgc aatgattaca cggtgaacca ggaggaatac   3240
ggcggagcat acacctcacg taatagaggg tacaatgagg caccgtcagt ccggcagat   3300
tatgcctcag tttatgagga gaagtcctac acgatggaa gacgcgagaa tccatgtgag   3360
tttaatagag gataccgaga ctacacacca ctcccagttg gatacgttac aaaggagttg   3420
gaatacttcc cagaaacaga taaagtttgg atagagatcg gagaaacaga aggaaccttc   3480
```

```
atcgtggaca gtgtagaact gctgctgatg gaagaatga                      3519

SEQ ID NO: 124          moltype = DNA   length = 3516
FEATURE                 Location/Qualifiers
misc_feature            1..3516
                        note = Synthetic DNA sequence for expression in plants
                         encoding TIC842.
source                  1..3516
                        mol_type = other DNA
                        organism = synthetic construct
SEQUENCE: 124
atggctgaga acaacatcca gaaccagtgc gtgccctaca actgcctgaa caaccctgag    60
gtggagatcc tgaacgagga gcgtagcacc ggtaggctcc cgctagacat ctccctgagc   120
ctgacccgct tcctccttag cgagttcgtg cccggcgtgg gcgtggcctt cggcctcttc   180
gacctcatct ggggcttcat cacgccgtcc gactggtccc tcttcctcct ccagatcgag   240
cagctcatcg agcagcgcat cgagaccctg gagcgcaacc gcgccatcac cactctgcgc   300
ggcctcgccg actcctacga aatctacatc gaggccctcc gcgagtggga ggccaacccg   360
aacaatgccc agctccgcga ggacgtgcgg attcgcttcg ccaacaccga cgatgccctc   420
atcaccgcca tcaacaactt caccctcacc tccttcgaga tcccgctgct cagcgtgtac   480
gtgcaagccg ctaacctcca cctctccctc ctgcgcgacg ccgtgagctt cggccagggc   540
tggggcctcg acatcgccac cgtgaacaat cactacaacc gcctcatcaa cctcatccac   600
cgctacacca agcactgcct cgacacctac aaccagggcc tggagaacct gcgcggcacc   660
aacacccgcc agtgggcccg cttcaaccag ttccgccgcg acctcaccct caccgtgctc   720
gacatcgtgg ccctgttccc taactacgac gtccgcacct acccgatcca gacctccagc   780
cagctcacga gggaaatcta cacctccagc gtgatcgagg acagcccggt gtccgccaac   840
atcccgaacg gcttcaaccg cgccgagttc ggcgtgcgcc tcacctcacct catggacttc   900
atgaactccc tcttcgtcac tgccgagacc gtgcgctccc agaccgtgtg gggcggtcac   960
ctcgtgtcca gccgcaacac cgctggcaac cgcatcaact tcccgtccta cggcgtgttc  1020
aaccctggcg gtgccatctg gatcgccgac gaggacccga ggcccttcta ccgcaccctg  1080
tccgaccctg tgttcgtgcg cggcggtttc ggcaaccctc actacgtgct gggcctgagg  1140
ggcgtggcct tccagcaaac cggcaccaac cacacccgca ccttccgcaa ctccggcacc  1200
atcgactccc tggacgagat ccctcctcag gacaactccg gcgccccttg gaacgactac  1260
tcccacgtgc tgaaccacgt gaccttcgtg aggtggcctg gcgagatcag cggcagcgac  1320
tcctggaggg ccctatgtt ctcctggacc cacaggagcg ccaccccgac caacaccatc  1380
gaccctgagc gcatcaccca gatccctctg gtgaaggccc acactctcca gagcggcact  1440
actgtcgttc gcggccctgg cttcactggc ggtgacatcc tgaggcggac tagcggcggt  1500
cctttcgctt acactatcgt caacatcaac ggccagctcc ctcagcgcta cagggcccgc  1560
atccgctacg ccagcactac taacctgagg atctacgtca ctgtcgctgg cgagcgcatc  1620
ttcgccgggc agttcaacaa gacgatggac actggtgacc cgctgacttt ccagtctttc  1680
tcttacgcta ctatcaacac tgctttcact ttcccgatga gtcagtcttc gttcactgtc  1740
ggtgctgaca ctttctcttc gggcaacgag gtgtacatcg accggttcga gctgatcccg  1800
gtcactgcta ctttcgaggc tgagtacgac ctggagcggg ctcagaaggc tgtcaacgct  1860
ctgttcactt ctatcaacca gatcggtatt aagacggacg tcacggacta ccacattgac  1920
caagtcagca acctggtgga ctgcctgtct gacgagttct gcctggacga gaagcgggag  1980
ctgtctgaga aggtcaagca cgctaagcgg ctgtctgacg agcggaacct gctccaaagac  2040
ccgaacttta agggtattaa ccgccagctc gaccgtggtt ggcgcggtag tacggacatt  2100
acgattcagc gcggtgacga tgtcttcaag gagaactacg tcacgctgcc gggtaccttc  2160
gacgagtgct acccgacgta cctttaccag aagattgatg agtctaagct caaggcgttt  2220
acgcgctacc agcttcgtgg ttacattgag gatagtcagg atcttgaaat ctaccttatt  2280
cgttacaacg ctaagcacga gacggtcaac gtgccgggta cgggctctct ttggccgctt  2340
tctgctcagt ctccgattgg gaagtgcggt gagccgaacc gttgcgcgcc gcaccttgag  2400
tggaacccgg atcttgattg ctcgtgccgt gatggcgaga agtgcgcgca ccatagtcat  2460
cacttcagtc ttgacattga tgtcgggtgc acggatctta acgaggatct tggcgtgtgg  2520
gtgatcttca agattaagac gcaagatggg cacgcgcgtc ttgggaacct tgagtttctt  2580
gaggagaagc cacttgtcgg cgaggcgctt gcgcgtgtca agcgtgcgga gaagaaatgg  2640
cgtgataagc gtgagaagtt ggagtgggag acgaacattg tgtacaagga ggcgaaggag  2700
tcggtcgatg cgttgttcgt caacagtcag tacgatcagt tgcaagcgga tacgaacatc  2760
gccatgattc atgcggcaga taagcgtgtc cattcgatca gggaggcgta cctgccagag  2820
ttgtcggtca ttccaggcgt caatgcggca atcttcgagg aattggaggg cagaatcttc  2880
acggcattct cgctgtacga tgcaaggaat gtgattaaga atggcgattt caacaacggg  2940
ctgtcgtgct ggaatgttaa gggccatgtt gatgttgagg aacagaacaa ccagagatca  3000
gtgttggtcg taccagagtg ggaggcagag gtttcacaag aggtgagagt ctgcccaggg  3060
cgcggctaca tcttgagagt taccgcctac aaggagggat acggcgaggg atgtgtgaca  3120
attcacgaaa tcgagaacaa cacagacgag ctaaagttct caaactgtgt cgaggaagaa  3180
atctacccga ataacacagt cacatgcaat gattacacag tgaaccagga agaatacgga  3240
ggagcataca catcacgcaa tagaggatac aatgaagcac caagcgttcc agcagactac  3300
gcctcagtgt acgaggagaa gtcatacaca gacggacgaa gggagaatcc atgtgagttc  3360
aatcgaggat accgagatta cacaccactt ccagttggat acgttaccaa ggaactcgaa  3420
tacttcccag aaacagacaa agtgtggatc gaaatcggcg aaaccgaagg cacattcatc  3480
gtggactcag tcgaactgct gctgatggag gagtga                            3516

SEQ ID NO: 125          moltype = DNA   length = 3444
FEATURE                 Location/Qualifiers
misc_feature            1..3444
                        note = Synthetic DNA sequence for expression in plants
                         encoding TIC850.
source                  1..3444
                        mol_type = other DNA
                        organism = synthetic construct
```

```
SEQUENCE: 125
atggagaaca acatccagaa ccagtgcgtg ccctacaact gcctgaacaa ccctgaggtt    60
gagatcctga acgaggagcg tagcaccggt aggctcccgc tagacatctc cctgagcctg   120
acccgcttcc tccttagtga gttcgtgccc ggcgtgggcg tggccttcgg cctcttcgac   180
ctcatctggg gcttcatcac tccttccgac tggtccctct tcctccttca gattgagcaa   240
ctgatcgagc agcgcatcga gacccttgag cgcaaccgcg ccatcaccac tctcagaggt   300
ctcgccgact cctacgaaat ctacatcgag gcactccgtg agtgggaggc caacccgaac   360
aatgcccagc tccgcgagga cgtgaggatc agattcgcca acaccgacga tgccctcatc   420
accgccatca acaatttcac cctcacctcc ttcgagatcc ctcttctgtc tgtgtacgtt   480
caagctgcta accttcacct ttccctcctg cgcgacgccg tgagcttcgg ccagggctgg   540
ggcctcgaca tcgccaccgt gaacaatcac tacaaccgcc tcatcaacct catccaccgc   600
tacaccaagc actgccttga cacctacaac cagggccttg agaacctccg tggcaccaac   660
acccgccagt gggcccgctt caaccagttc cgcagagacc tcaccctcac cgtgctcgac   720
atcgtggcac tcttcccaaa ctacgacgtg cgtacctacc ctatccagac ctccagccag   780
ctcaccaggg aaatctacac ctccagccgt atcgaggact ctcctgtgtc cgccaacatc   840
cctaacggct tcaaccgcgc cgagttcggc gtgcgccctc ctcacctcat ggacttcatg   900
aactccctct tcgtcactgc cgagaccgtg cgctcccaga ccgtgtgggg cggtcacctc   960
gtgtccagcc gtaacaccgc tggcaacagg atcaacttcc cgtcctacgg cgtgttcaac  1020
ccaggcggtg ccatctggat cgccgatgaa gaccctcgtc ctttctaccg taccctgtcc  1080
gaccctgtgt tcgtgcgtgg cggtttcggc aaccctcact acgtgctggg cctgcgtggc  1140
gtggccttcc agcaaaccgg caccaaccac accaggacgt tccgtaactc cggcaccatc  1200
gacagtcttg acgagatccc tccgcaagac aactccggtc accttggaa cgactactcc  1260
cacgtgctga accacgtgac cttcgtgagg tggcctggcg aaatctccgg ctccgactcc  1320
tggagggctc ctatgttcag ttggacccac aggagcgcta cgcctaccaa caccatcgat  1380
cctgaacgca tcactcagat ccctctcgtc aaggctcaca ccctccagtc aggcaccacc  1440
gtggtgcgcg gccctggctt caccggcggc gacatccttc gccgcacgaa caccggcacc  1500
tttgcagaca tgagggtcaa catcaccggt cctctctccc aacgctatcg cgtccgcatt  1560
cgctatgcct cgaccaccga tctacagttc ttcacccgga tcaatggcac gtctgtgaac  1620
cagggcaact tccaacgcac gatgaaccgt ggtgacaacc tggagtccgg gaacttccga  1680
actgctggct tctccacgcc cttcagcttc tccaatgcca agtccaccct cactcttggc  1740
acccaagcgt tcagcaacca ggaagtgtac atcgaccgca ttgagtttgt tcccgctggc  1800
gtgaccttcg aggccgagtc tgatctcgag cgtgcccaga aggcagtgaa tgagctgttc  1860
acgagcagca atcagatcgg gctcaagacc gacgtgaccg actaccacat cgaccaagtc  1920
agcaatctgg tggagtgtct cagcgacgag ttctgcctgg acgagaagaa ggaactcagc  1980
gagaaggtga agcacgccaa acgtctgtcc gacgaacgca atctgctgca agatccgaac  2040
ttcagaggga tcaacaggca actggaccgt gggtggcgtg ggtccaccga catcaccatc  2100
caaggcggcg acgacgtctt caaggagaac tacgtcactc tgctgggcac cttcgacgag  2160
tgctatccga cctacctgta ccagaagatc gacgagagca agctcaaggc gtacaccgc  2220
taccaactca gaggctacat cgaagactcc caggatctgg aaatctacct cattcgctac  2280
aacgcgaagc acgagactgt caacgtgccc ggcactggca gcctgtggcc gctctccgcg  2340
ccgagccta tcggaaagtg tgcgcaccac tccaccact tcagcttgga catcgacgtg  2400
ggttgcacgg acctcaacga agacctgggt gtctgggtga tcttcaagat caagacgcaa  2460
gacggacacg cgagactcgg caatctggag ttcctggagg agaagcctct ggtcggcgaa  2520
gctctcgcca gggtgaagcg cgccgagaag aagtggcgcg acaagcggga gaagctggag  2580
tgggagacga acatcgtgta caaggaggcc aaggagtccg tggacgccct cttgtgaac  2640
agccagtacg accgcctcca agcagacacc aacattgcca tgatccacgc cgccgacaag  2700
cgcgtgcact ccatcaggga ggcgtatctc cctgaactca gcgtgattcc tggcgtgaat  2760
gctgccatct tcgaggagct tgagggtcgc atcttcaccg cattcagcct ctacgacgcc  2820
aggaacgtca tcaagaacgg agacttcaac aacgggctgt cctgctggaa cgtcaaaggt  2880
cacgttgacg tggaggagca gaacaaccat cgcagcgtcc tcgtcgtccc tgagtgggaa  2940
gctgaggtca gccaagaagt cagggtctgc cctggtcgcg gctacatcct cagggtgacc  3000
gcctacaagg aagggtatgg tgaagggtgt gtcacgatcc atgagattga gaacaacacg  3060
gacgaactca agttcagcaa ctgcgtcgag gaggaggtct atccgaacaa cacggtcacc  3120
tgcaacgact acactgccac tcaggaggag tacgagggaa cctacactag ccgcaaccgt  3180
ggctacgatg gagcctacga gtccaactcc tccgttcccg ctgactacgc aagcgcctac  3240
gaggagaagg cgtacacgga cgggcggcgc gacaacccgt gcgagtccaa tcgtggctac  3300
ggtgactaca ctccgcttcc cgctggttac gtgaccaagg aacttgagta cttccctgag  3360
accgacaagg tctggatcga gataggtgag accgaaggca cgttcatcgt tgactccgtc  3420
gaactgctgc tcatggagga gtga                                        3444

SEQ ID NO: 126       moltype = DNA  length = 3447
FEATURE              Location/Qualifiers
misc_feature        1..3447
                    note = Synthetic DNA sequence for expression in plants
                     encoding TIC859.
source              1..3447
                    mol_type = other DNA
                    organism = synthetic construct
SEQUENCE: 126
atggagaaca acatccagaa ccagtgcgtg ccctacaact gcctgaacaa ccctgaggtt    60
gagatcctga acgaggagcg tagcaccggt aggctcccgc tagacatctc cctgagcctg   120
acccgcttcc tccttagtga gttcgtgccc ggcgtgggcg tggccttcgg cctcttcgac   180
ctcatctggg gcttcatcac tccttccgac tggtccctct tcctccttca gattgagcaa   240
ctgatcgagc agcgcatcga gacccttgag cgcaaccgcg ccatcaccac tctcagaggt   300
ctcgccgact cctacgaaat ctacatcgag gcactccgtg agtgggaggc caacccgaac   360
aatgcccagc tccgcgagga cgtgaggatc agattcgcca acaccgacga tgccctcatc   420
accgccatca acaatttcac cctcacctcc ttcgagatcc ctcttctgtc tgtgtacgtt   480
caagctgcta accttcacct ttccctcctg cgcgacgccg tgagcttcgg ccagggctgg   540
ggcctcgaca tcgccaccgt gaacaatcac tacaaccgcc tcatcaacct catccaccgc   600
```

-continued

```
tacaccaagc actgccttga cacctacaac cagggccttg agaacctccg tggcaccaac  660
acccgccagt gggcccgctt caaccagttc cgcagagacc tcaccctcac cgtgctcgac  720
atcgtggcac tcttcccaaa ctacgacgtg cgtacctacc ctatccagac ctccagccag  780
ctcaccaggg aaatctacac ctccagcgtg atcgaggact ctcctgtgtc cgccaacatc  840
cctaacggct tcaaccgcgc cgagttcggc gtgcgccctc ctcacctcat ggacttcatg  900
aactccctct tcgtcactgc cgagaccgtg cgctcccaga ccgtgtgggg cggtcacctc  960
gtgtccagcc gtaacaccgc tggcaacagg atcaacttcc cgtcctacgg cgtgttcaac  1020
ccaggcggtg ccatctggat cgccgatgaa gaccctcgtc ctttctaccg taccctgtcc  1080
gaccctgtgt tcgtgcgtgg cggtttcggc aaccctcact acgtgctggg cctgcgtggc  1140
gtggccttcc agcaaaccgg caccaaccac accaggacgt tccgtaactc cggcaccatc  1200
gacagtcttg acgagatccc tccgcaagac aactccggtg caccttggaa cgactactcc  1260
cacgtgctga accacgtgac cttcgtgagg tggcctggcg aaatctccgg ctccgactcc  1320
tggagggctc ctatgttcag ttggacccac aggagcgcta cgcctaccaa cgaggtccgt  1380
gtgtcccgca tcacccagct ccctatggtg aaggctcaca cccttcacgc tggtgccaca  1440
gtagtcagag gtccgggctt cactggcggc gacattcttc gccgcaccac ctccggctcc  1500
ttcggcgaca tgaggatcac caacttcagc tcctcctcca gtcgctatcg cgttcgtatt  1560
cgctacgcct ccaccaccga cctccagttc ttcctgtccg ttggcggcac gcctgtgaat  1620
gtggcagact tcccgaagac catcgaccgt ggcgagaacc tggagtacgg cagctttcgc  1680
actgctggct tcaccactcc gttcagcttc gtctcctcca ccaacaactt cacactaggc  1740
gtgcagtctg tctcctccgg caacgagatc ttcgtggatc ggatcgagtt cgtaccagcc  1800
gacgcgacct tcgaagccga gtacgatctc gagcgtgccc agaaggcagt gaatgagctg  1860
ttcacgagca gcaatcagat cgggctcaag accgacgtga cgactacca catcgaccaa  1920
gtcagcaatc tggtggagtg tctcagcgac gagttctgcc tggacgagaa gaaggaactc  1980
agcgagaagg tgaagcacgc caaacgtctg tccgacgaac gcaatctgct gcaagatccg  2040
aacttcagag ggatcaacag gcaactggac cgtgggtggc gtgggtccac cgacatcacc  2100
atccaaggcg gcgacgacgt cttcaaggag aactacgtca ctctgctggg caccttcgac  2160
gagtgctatc cgacctacct gtaccagaag atcgacgaga gcaagctcaa ggcgtacacc  2220
cgctaccaac tcagaggcta catcgaagac tcccaggatc tggaaatcta cctcattcgc  2280
tacaacgcga agcacgagac tgtcaacgtg cccggcactg gcagcctgtg gccgctctcc  2340
gcgccgagcc ctatcggaaa gtgtgcgcac cactcccacc acttcagctt ggacatcgac  2400
gtgggttgca cggacctcaa cgaagacctg ggtgtctggg tgatcttcaa gatcaagacg  2460
caagacggac acgcgagact cggcaatctg gagttcctgg aggagaagcc tctggtcggc  2520
gaagctctcg ccagggtgaa gcgcgccgag aagaagtggc gcgacaagcg ggagaagctg  2580
gagtgggaga cgaacatcgt gtacaaggag gccaaggagt ccgtggacgc cctctttgtg  2640
aacagccagt acgaccgcct ccaagcagac accaacattg ccatgatcca cgccgccgac  2700
aagcgcgtgc actccatcag ggaggcgtat ctccctgaac tcagcgtgat tcctggccgtg  2760
aatgctgcca tcttcgagga gcttgagggt cgcatcttca ccgcattcag cctctacgac  2820
gccaggaacg tcatcaagaa cggagacttc aacaacgggc tgtcctgctg gaacgtcaaa  2880
ggtcacgttg acgtggagga gcagaacaac catcgcaacg tcctcgtcgt ccctgagtgg  2940
gaagctgagg tcagccaaga agtcagggtc tgccctggtc gcggctacat cctcagggtg  3000
accgcctaca aggaagggta tggtgaaggg tgtgtcacga tccatgagat tgagaacaac  3060
acggacgaac tcaagttcag caactgcgtc gaggaggagg tctatccgaa caacacggtc  3120
acctgcaacg actacactgc cactcaggag gagtacgagg gaacctacac tagccgcaac  3180
cgtggctacg atggagccta cgagtccaac tcctccgttc ccgctgacta cgcaagcgcc  3240
tacgaggaga aggcgtacac ggacgggcgg cgcgacaacc cgtgcgagtc caatcgtggc  3300
tacggtgact acactccgct tcccgctggt tacgtgacca aggaacttga gtacttcct  3360
gagaccgaca aggtctggat cgagataggt gagaccgaag gcacgttcat cgttgactcc  3420
gtcgaactgc tgctcatgga ggagtga                                       3447

SEQ ID NO: 127       moltype = DNA  length = 3612
FEATURE              Location/Qualifiers
misc_feature        1..3612
                     note = Synthetic DNA sequence for expression in plants
                     encoding TIC861.
source              1..3612
                     mol_type = other DNA
                     organism = synthetic construct
SEQUENCE: 127
atgaagctca agaaccctga caagcaccag tccttctcta gcaacgcgaa ggtggacaag  60
atcagcactg actccctcaa gaacgagact gacatcgagc ttcagaacat caaccacgag  120
gactgcctca agatcagcga gtacgagaac gtggaaccct tcgtgagcgc ctccaccatc  180
cagaccggca tctccattgc cgggaagatc ctcggcaccc tcggcgtacc cttcgcgggc  240
caagtggcct ccctctactc cttcatcctc ggcgaactgt ggcccaaagg caagaaccag  300
tgggagatct tcatggagca cgtggaggag atcatcaagc agaagatcag cacctatgcc  360
cgcaacaagg ccctcaccga cctcaagggc ctcggcgacg ccctcgccgt gtaccacgag  420
tccctggagt cctgggtcgg caaccgcaag aacacccgcg ccgctccgt ggtgaagtcc  480
cagtacatcg ccctggagct gatgttcgtg cagaagctcc gtccttcgc cgtgagcggc  540
gaggaggtgc cgctcctgcc catctacgcc caggccgcta acctccacct cctgctcctg  600
cgcgacgcct ccatcttcgg caaggagtgg ggcctctcac gctccgagat cagcaccttc  660
tacaaccgcc aagtggaacg cgctggcgac tactccgatc actccgtgaa gtggtacagc  720
accgcctca acaacctgcg cggcaccaac gctgagagct gggtgcgcta caaccagttc  780
cgcaaggaca tgaccctgat ggtcctggat ctggtcgcac tgttcccgag ctacgacact  840
ctggtgtacc cgatcaagac caccagccag ctcaccaggg aggtgtacac cgacgctatc  900
ggcactgtac atcctaatgc gagcttcgcc agcaccacct ggtacacaaa cacgctcct  960
tccttcagca ccatcgagag cgctgtggtg aggaatcctc acctgcttga cttcctggag  1020
caagtcacca tctacagcct gctttctagg tggtccaaca cccagtacat gaacatgtgg  1080
ggcggtcaca ggctggagtt ccgcaccatc ggcggtatgc tgaacacctc tactcaggga  1140
agtaccaaca cttccatcaa ccctgtcact ctgcctttca cttctaggga cgtttacagg  1200
actgagtccc tggctggact taacctgttc cttactcagc ctgtcaacgg tgtcccgagg  1260
```

```
gtggacttcc actggaagtt cgtcactcat cccatcgcgt ctgacaactt ctactaccct   1320
ggttacgcgg gtatcggtac tcagctccag gacagtgaga atgagttgcc gccggagacg   1380
accggtcagc cgaactacga gtcttacagt cacaggcttt ctcacatcgg tctcatctct   1440
gcgtctcatg tcaaagcgct tgtgtactcg tggacgcatc gctcagcgga tcgcacgaat   1500
accatcgacc cagagcgcat caaccagatc ccgctcgtga agggcttccg cgtgtggggc   1560
ggcacctccg tcatcaccgg tccgggcttc accggcggcg acatcctccg ccgcaacacc   1620
ttcggcgact tcgtgtcact ccaagtgaac atcaacagcc cgatcaccca gcgctatcgc   1680
ctccgcttcc gctacgcctc ctcccgcgac gctagagtga tcgtgctcac cggagcggcg   1740
tccacaggcg taggcggcca agtgtctgtg aacatgccgc tccagaagac tatggagatt   1800
ggtgagaacc tcacctctcg caccttccgc tacaccgact tctccaatcc gttctccttc   1860
agagccaacc cagacatcat cggcatctcc gagcagcctc tctttggcgc tggctccatc   1920
tcctccggcg agctgtacat cgacaagatt gagatcatcc ttgccgacgc caccttcgaa   1980
gctgagtccg atctcgagcg tgcccagaag gcagtgaatg agctgttcac gagcagcaat   2040
cagatcgggc tcaagaccga cgtgaccgac taccacatcg accaagtcag caatctggtg   2100
gagtgtctca gcgacgagtt ctgcctggac gagaagaagg aactcagcga gaaggtgaag   2160
cacgccaaac gtctgtccga cgaacgcaat ctgctgcaag atccgaactt cagagggatc   2220
aacaggcaac tggaccgtgg gtggcgtggg tccaccgaca tcaccatcca aggcggcgac   2280
gacgtcttca aggagaacta cgtcactctg ctgggcacct tcgacgagtg ctatccgacc   2340
tacctgtacc agaagatcga cgagagcaag ctcaaggcgt acacccgcta ccaactcaga   2400
ggctacatcg aagactccca ggatctggaa atctacctca ttcgctacaa cgcgaagcac   2460
gagactgtca acgtgcccgg cactggcagc ctgtggccgc tctccgcgcc gagccctatc   2520
ggaaagtgtg cgcaccactc ccaccacttc agcttggaca tcgacgtggg ttgcacggac   2580
ctcaacgaag acctgggtgt ctgggtgatc ttcaagatca agacgcaaga cggacacgcg   2640
agactcggca atctggagtt cctggaggag aagcctctgg tcggcgaagc tctcgccagg   2700
gtgaagcgcg ccgagaagaa gtggcgcgac aagcgggaga agctggagtg ggagacgaac   2760
atcgtgtaca aggaggccaa ggagtccgtg gacgccctct ttgtgaacag ccagtacgac   2820
cgcctccaag cagacaccaa cattgccatg atccacgccg ccgacaagcg cgtgcactcc   2880
atcagggagg cgtatctccc tgaactcagc gtgattcctg gcgtgaatgc tgccatcttc   2940
gaggagcttg agggtcgcat cttcaccgca ttcagcctct acgacgccag gaacgtcatc   3000
aagaacgagg acttcaacaa cgggctgtcc tgctggaaca tcaaaggtca cgttgacgtg   3060
gaggagcaga acaaccatcg cagcgtcctc gtcgtccctg agtgggaagc tgaggtcagc   3120
caagaagtca gggtctgccc tggtcgcggc tacatcctca gggtgaccgc ctacaaggaa   3180
gggtatggta aagggtgtgt cacgatccat gagattgaga acaacacgga cgaactcaag   3240
ttcagcaact gcgtcgagga ggaggtctat ccgaacaaca cggtcacctg caacgactac   3300
actgccactc aggaggagta cgaggaacc tacactagcc gcaaccgtgg ctacgatgga   3360
gcctacgagt ccaactcctc cgttcccgct gactacgcaa gcgcctacga gggagaaggcg   3420
tacacggacg ggcggcgcga caacccgtgc gagtccaatc gtggctacgg tgactacact   3480
ccgcttcccg ctggttacgt gaccaaggaa cttgagtact tccctgagac cgacaaggtc   3540
tggatcgaga taggtgagac cgaaggcacg ttcatcgttg actccgtcga actgctgctc   3600
atggaggagt ga                                                      3612
```

```
SEQ ID NO: 128          moltype = DNA  length = 3432
FEATURE                 Location/Qualifiers
misc_feature            1..3432
                        note = Synthetic DNA sequence for expression in plants
                         encoding TIC848.
source                  1..3432
                        mol_type = other DNA
                        organism = synthetic construct
SEQUENCE: 128
atggagatca acaaccagaa gcagtgcatc ccgtacaact gcctgagcaa ccctgaggag     60
gtgctcctag acggtgagcg catcctccct gacatcgacc cgctggaggt gagcctgagc    120
ctcctccagt tcctgctgaa caacttcgtg cccggcggtg gcttcatctc cgggctcgtg    180
gacaagatct ggggcgcgct ccgcccgtcc gagtgggatc tcttcctcgc ccagatcgag    240
cgcctcatcg accagcgcat cgaggccacc gtgcgcgaca aggccatcac cgagctggag    300
ggcctgggcc gcaactacca aatctacgcc gaggcgttca aggagtggga gtccgacccg    360
gacaacgagg ccgctaagtc ccgcgtgatc gaccgcttcc gcatcctcga cggcctcatc    420
gaggccaaca tcccgtcctt ccgcatcatt ggcttcgagg tgccgctgct gtccgtgtac    480
gtgcaagccg ctaacctcca cctcgccctc ctgcgcgact ccgtgatctt cggcgagcgc    540
tggggcctca ccactaagaa cgtgaacgac atctacaacc gccagatccg cgagatccac    600
gaatactcca accactgcgt ggacacctac aacaccgagc tggagcgcct cggcttccgc    660
tccatcgccc agtggcgcat ctacaaccag ttcgccgcgc agctgaccct gaccgtcctg    720
gacatcgtgg ccctgttccc gaactacgac agccgcctct acccgatcca gaccttctcc    780
cagctcaccc gcgagatcgt gaccagcccg gtgtccgagt tctactatgg cgtcatcaac    840
tccggcaaca tcattggcac cctcaccgag cagcaaatcc gccgcccgca cctgatggac    900
ttcttcaact ccatgattat gtacacctcc gacaaccgcc gcgagcacta ctggtccggc    960
ctggagatga ccgcctactt caccggcttc gcgggcgcgc aagtgtcctt cccgctcgtg   1020
ggcaccaggg gcgagtccgc gccgcctctc accgtgaggt ccgtgaacga cggcatctac   1080
cgcatcctca gcgcgcgtt ctacagcgcg ccgttcctgg gcaccatcgt gctgggcagc   1140
cgtggcgaga agttcgactt cgccctgaac aacatcagcc ctccgcctag caccatctac   1200
aggcaccctg gcaccgtgga cagcctggtg agcatccctc ctcaagacaa cagcgtgcct   1260
ccgcacaggg gcagctctca caggctgagc cacgtgacca tgaggccag ctctcctatc    1320
ttccactgga cccacaggag cgccaccact accaacacca tcaaccctaa cgctatcatt   1380
cagatcccgc tggtgaagtc caccaacctc ggctccggca cctccgtggt gaagggtcag   1440
ggcttcactg gcggcgacat cctccgccgc accagccctg gccaaatctc caccctccgt   1500
gtgaacatca tcgctccact gtcccaacgc tatcgcgtac ggattcgtta cgcatccacc   1560
accaacctcc agtccacacac ctccattgac ggccgaccga tcaaccaggg caacttctcc   1620
gctacgatgt cctccgggtc caatctccag tctgggagct ttcgcactgt cggcttcacc   1680
actccgttca acttctccaa tggctcctcc gtgttcacac tttcggcgca cgtcttcaac   1740
```

```
tctggcaacg aagtgtacat cgacaggatc gagtttgttc ccgcagaggt gaccttcgaa   1800
gccgagtacg atctcgagcg tgcccagaag gcagtgaatg agctgttcac gagcagcaat   1860
cagatcgggc tcaagaccga cgtgaccgac taccacatcg accaagtcag caatctggtg   1920
gagtgtctca gcgacgagtt ctgcctggac gagaagaagg aactcagcga gaaggtgaag   1980
cacgccaaac gtctgtccga cgaacgcaat ctgctgcaag atccgaactt cagagggatc   2040
aacaggcaac tggaccgtgg gtggcgtggg tccaccgaca tcaccatcca aggcggcgac   2100
gacgtcttca aggagaacta cgtcactctg ctgggcacct tcgacgagtg ctatccgacc   2160
tacctgtacc agaagatcga cgagagcaag ctcaaggcgt acacccgcta ccaactcaga   2220
ggctacatcg aagactccca ggatctggaa atctacctca ttcgctacaa cgcgaagcac   2280
gagactgtca acgtgcccgg cactggcagc ctgtggccgc tctccgcgcc gagccctatc   2340
ggaaagtgtg cgcaccactc ccaccacttc agcttggaca tcgacgtggg ttgcacggac   2400
ctcaacgaag acctgggtgt ctgggtgatc ttcaagatca agacgcaaga cggacacgcg   2460
agactcggca atctggagtt cctggaggag aagcctctgg tcggcgaagc tctcgccagg   2520
gtgaagcgcg ccgagaagaa gtggccgcac aagcgggaga agctggagtg ggagacgaac   2580
atcgtgtaca aggaggccaa ggagtccgtg gacgccctct ttgtgaacag ccagtacgac   2640
cgcctccaag cagacaccaa cattgccatg atccacgccg ccgacaagcg cgtgcactcc   2700
atcagggagg cgtatctccc tgaactcagc gtgattcctg gcgtgaatgc tgccatcttc   2760
gaggacgttg agggtcgcat cttcaccgca ttcagcctct acgacgccag gaacgtcatc   2820
aagaacggag acttcaacaa cgggctgtcc tgctggaacg tcaaaggtca cgttgacgtg   2880
gaggagcaga acaaccatcg cagcgtcctc gtcgtccctg agtgggaagc tgaggtcagc   2940
caagaagtca gggtctgccc tggtcgcggc tacatcctca gggtgaccgc ctacaaggaa   3000
gggtatggtg aagggtgtgt cacgatccat gagattgaaa caaacacgga cgaactcaag   3060
ttcagcaact gcgtcgagga ggaggtctat ccgaacaaca cggtcacctg caacgactac   3120
actgccactc aggaggagta cgagggaacc tacactagcc gcaaccgtgg ctacgatgga   3180
gcctacgagt ccaactcctc cgttcccgct gactacgcaa gcgcctacga ggagaaggcg   3240
tacacggacg ggcggcgcga caacccgtgc gagtccaatc gtggctacgg tgactacact   3300
ccgcttcccg ctggttacgt gaccaaggaa cttgagtact tccctgagac cgacaaggtc   3360
tggatcgaga taggtgagac cgaaggcacg ttcatcgttg actccgtcga actgctgctc   3420
atggaggagt ga                                                       3432
```

```
SEQ ID NO: 129          moltype = DNA  length = 3429
FEATURE                 Location/Qualifiers
misc_feature            1..3429
                        note = Synthetic DNA sequence for expression in plants
                         encoding TIC849.
source                  1..3429
                        mol_type = other DNA
                        organism = synthetic construct
SEQUENCE: 129
atggagatca acaaccagaa gcagtgcatc ccgtacaact gcctgagcaa ccctgaggag   60
gtgctcctag acggtgagcg catcctccct gacatcgacc cgctggaggt gagcctgagc   120
ctcctccagt tcctgctgaa caacttcgtg cccggcggtg gcttcatctc cgggctcgtg   180
gacaagatct ggggcgcgct ccgcccgtcc gagtgggatc tcttcctcgc ccagatcgag   240
cgcctcatcg accagcgcat cgaggccacc gtgcgcgcca aggccatcac cgagctggag   300
ggcctgggcc gcaactacca aatctacgcc gaggcgttca aggagtggga gtccgacccg   360
gacaacgagg ccgctaagtc ccgcgtgatc gaccgcttcc gcatcctcga cggcctcatc   420
gaggccaaca tcccgtcctt ccgcatcatt ggcttcgagc tgccgctgct gtccgtgtac   480
gtgcaagccg ctaacctcca cctcgccctc ctgcgcgact ccgtgatctt cggcgagcgc   540
tggggcctca ccactaagaa cgtgaacgac atctacaacc gccagatccg cgagatccac   600
gaatactcca accactgcgt ggacacctac aacaccgagc tggagcgcct cggcttccgc   660
tccatcgccc agtggcgcat ctacaaccag ttccgccgcg agctgaccct gaccgtcctg   720
gacatcgtgg ccctgttccc gaactacgac agccgcctct acccgatcca gaccttctcc   780
cagctcaccc gcgagatcgt gaccagcccg gtgtccgagt ctactatgg cgtcatcaac   840
tccggcaaca tcattggcac cctcaccgag cagcaaatcc gccgcccgca cctgatggac   900
ttcttcaact ccatgattat gtacacctcc gacaaccgcc gcgagcacta ctggtccggc   960
ctggagatga ccgcctactt caccggcttc gcgggcgcgc aagtgtcctt cccgctcgtg   1020
ggcaccaggg gcgagtccgc gccgcctctc accgtgaggt ccgtgaacga cggcatctac   1080
cgcatcctca gcgcgccgtt ctacagcgcg ccgttcctgg gcaccatcgt gctgggcagc   1140
cgtggcgaga agttcgactt cgccctgaac aacatcagcc ctccgcctag caccatctac   1200
aggcaccctg gcaccgtgga cagcctggtg agcatccctc ctcaagacaa cagcgtgcct   1260
ccgcacaggg gcagctctca caggctgagc cacgtgacca tgaggccag ctctcctatc   1320
ttccactgga cccacaggag cgccaccact accaacacca tcaaccctaa cgctatcatt   1380
cagatcccgc tggtgaaggc gttcaacctg cacagcggtg ccaccgtggt gcgcggacct   1440
ggcttcaccg gcggcgacat cctttgccgc accaaccacg caccttttgg tgacattcgc   1500
ctcaacatca acgtgccact gtcccaacgc tatcgcgttc gtattcgtta cgcctccacc   1560
accgatcttc agttcttcac tcgcatcaat ggcaccaccg tgaacattgg gaacttctct   1620
cgaaccatga accgtggtga caacctggag taccgcagct tccggactgc tggcttcagc   1680
acgccgttca acttcctcaa cgcccagtcc accttcactc taggtgcaca gtccttctcc   1740
aaccaggaag tgtacatcga ccgcgttgag tttgtgcccg ctgaggtcac gttcgaagcg   1800
gagtacgacc tcgagcgtgc ccagaaggca gtgaatgagc tgttcacgag cagcaatcag   1860
atcgggctca gaccgacgt gaccgactac cacatcgacc aagtcagcaa tctggtggag   1920
tgtctcagcg acgagttctg cctggacgag aagaaggaac tcagcgagaa ggtgaagcac   1980
gccaaacgtc tgtccgacga acgcaatctg ctgcaagatc gaacttcag agggatcaac   2040
aggcaactgg accgtgggtg gcgtgggtcc accgacatca tccaaggcgg cggcgacgac   2100
gtcttcaagg agaactacgt cactctgctg ggcaccttcg acgagtgcta tccgacctac   2160
ctgtaccaga agatcgacga gagcaagctc aaggcgtaca cccgctacca actcagaggc   2220
tacatcgaag actcccagga tctggaaatc tacctcattc gctacaacgc gaagcacgag   2280
actgtcaacg tgcccggcac tggcagcctg tggccgctct ccgcgccgag ccctatcgga   2340
aagtgtgcgc accactccca ccacttcagc ttggacatcg acgtgggttg cacggacctc   2400
```

-continued

```
aacgaagacc tgggtgtctg ggtgatcttc aagatcaaga cgcaagacgg acacgcgaga   2460
ctcggcaatc tggagttcct ggaggagaag cctctggtcg gcgaagctct cgccagggtg   2520
aagcgcgccg agaagaagtg gcgcgacaag cgggagaagc tggagtggga gacgaacatc   2580
gtgtacaagg aggccaagga gtccgtggac gccctctttg tgaacagcca gtacgaccgc   2640
ctccaagcag acaccaacat tgccatgatc cacgccgcca acaagcgcgt gcactccatc   2700
agggaggcgt atctccctga actcagcgtg attcctggcg tgaatgctgc catcttcgag   2760
gagcttgagg tcgcatctt caccgcattc agcctctacg acgccaggaa cgtcatcaag   2820
aacgagact tcaacaacgg gctgtcctgc tggaacgtca aaggtcacgt tgacgtggag   2880
gagcagaaca accatcgcag cgtcctcgtc gtccctgagt gggaagctga ggtcagccaa   2940
gaagtcaggg tctgccctgg tcgcggctac atcctcaggg tgaccgccta caaggaaggg   3000
tatggtgaag ggtgtgtcac gatccatgag attgagaaca acacggacga actcaagttc   3060
agcaactgcg tcgaggagga ggtctatccg aacaacacgg tcacctgcaa cgactacact   3120
gccactcagg aggagtacga gggaacctac actagccgca accgtggcta cgatggagcc   3180
tacgagtcca actcctccgt tcccgctgac tacgcaagcg cctacgagga gaaggcgtac   3240
acggacgggc ggcgcgacaa cccgtgcgag tccaatcgtg gctacggtga ctacactccg   3300
cttcccgctg gttacgtgac caaggaactt gagtacttcc ctgagaccga caaggtctgg   3360
atcgagatag gtgagaccga aggcacgttc atcgttgact ccgtcgaact gctgctcatg   3420
gaggagtga                                                           3429
```

SEQ ID NO: 130            moltype = DNA  length = 3570
FEATURE                   Location/Qualifiers
misc_feature             1..3570
                         note = Synthetic DNA sequence for expression in plants
                          encoding TIC847.
source                   1..3570
                         mol_type = other DNA
                         organism = synthetic construct
SEQUENCE: 130

```
atgaccagca accggaagaa cgagaacgag atcatcaacg ccctgagcat cccgaccgtg   60
agcaacccta gcaccagat gaacctgagc cctgacgctc gcatcgagga ctccctctgc   120
gtggctgagg tgaacaacat cgacccgttc gtgtccgcct ccaccgtgca gaccggcatc   180
aacatcgcgg gccgcatcct cggcgtgctc ggcgtgcct ttgcgggcca gctcgcctcc   240
ttctactcct tcctcgtggg agagctgtgg ccctccggcc gcgacccgtg ggagatcttc   300
ctggagcacg tggagcagct catccgccag caagtcaccg agaacacccg caacaccgcc   360
atcgcccgcc tggagggcct gggccgtggc taccgctcct accagcaagc cctggagacc   420
tggctcgaca accgcaacga cgcccgctcc cgctccatca tcctggagcg ctacgtcgcc   480
ctggaactgg acatcaccac tgccatccca ctcttccgca tcaggaacga ggaggtgcct   540
ctgctgatgg tgtacgccca ggctgcgaac ctgcacctgc tgctgctgcg cgacgcaagc   600
ctgtttggct ccgagtgggg tatggcaagc tccgacgtca accagtacta ccaggagcag   660
atccgctaca ccgaggagta cagcaaccac tgcgtccagt ggtacaacac cggtctgaac   720
aatctcagag ggaccaacgc tgagagctgg ctgcgctaca accagttccg gcgggatctg   780
accctaggtg tcctggatct ggtcgctctg ttcccgagct acgataccag gacgtaccct   840
atcaacacct ctgctcagct taccagggag atctacactg atcctatcgg taggactaac   900
gctcctagtg gtttcgccag cactaactgg ttcaacaaca acgcgcctag tttctctgcc   960
atcgaggcgg cgatcttccg gcctcctcac ctcctcgact tcccggagca gcttactatc   1020
tactctgcgt cttcgcggtg gtcttcgact cagcacatga actactgggt tggtcaccgg   1080
cttaacttcc gcccgattgg aggaactctt aacaccagta cgcaaggtct tacgaacaac   1140
acttccatca acccggttac gttgcagttc acgtctcggg acgtttaccg gacggagtcg   1200
aatgctggga cgaacatcct gttcacgaca ccggtgaatg tgttccgtg ggcacgtttc   1260
aacttcatca acccgcagaa catctacgag cgtggagcaa cgacatactc gcaaccatac   1320
caaggcgttg gcatccaact gtttgactcg gagacggaac tgccaccaga gacgacagaa   1380
cgtccgaatt acgagtcata tctcacacaga ctatcacaca ttggactcat tatcggaaac   1440
acactgagag caccagtgta ctcatggaca catcggtcag cagatcgtac gaacaccatc   1500
ggtcctaacc gtatcaccca gattcctctc gtgaaggccc acaccctcca gtccggcacc   1560
accgtggtga agggaccggg cttcaccggc ggcgacatcc tccgccgcac ctctggcggc   1620
ccgttcgcgt tctccaacgt gaacctcgac ttcaacctct cccaacgcta cagagcacgc   1680
atacgctacg cctccaccac caacctacgc atctacgtga ccgtggctgg cgaacgcatc   1740
ttcgctgggc agtttgacaa gactatggac gctggcgcac ctcttacctt ccagtccttc   1800
tcctacgcca ccatcaacac cgcgttcacc ttcccagagc gctcctcctc cttgaccgtg   1860
ggtgccgaca ccttcagcag cggcaatgag gtgtacgtgg atcgcttcga actcatccca   1920
gtgaccgcca ccttcgaggc cgagtcggat ctcgagcgtg cccagaaggc agtgaatgag   1980
ctgttcacga gcagcaatca gatcgggctc aagaccgacg tgaccgacta ccacatcgac   2040
caagtcagca atctggtgga gtgtctcagc gacgagttct gcctggacga gaagaaggaa   2100
ctcagcgaga aggtgaagca cgccaaacgt cgtgtccggca aacgcaatct gctgcaagat   2160
ccgaacttca gagggatcaa caggcaactg gaccgtgggt ggcgtgggtc caccgacatc   2220
accatccaag gcggcgacga cgtcttcaag gagaactacg tcactctgct gggcacctttc   2280
gacgagtgct atccgaccta cctgtaccag aagatcgacg agagcaagct caaggcgtac   2340
accccgctacc aactcagagg ctacatcgaa gactcccagg atctggaaat ctacctcatt   2400
cgctacaacg cgaagcacga gactgtcaac gtgcccggca ctggcagcct gtggccgatc   2460
tccgcgccga gccctatcgg aaagtgtgcg caccactccc accacttcag cttggacatc   2520
gacgtgggtt gcacggacct caacgaagac ctgggtgtct gggtgatctt caagatcaag   2580
acgcaagacg gacacgcgag actcggcaat ctggagttcc tggaggagaa gcctctggtc   2640
ggcgaagctc tcgccagggt gaagcgcgcc gagaagaagt ggcgcgacaa gcgggagaag   2700
ctggagtggg agacgaacat cgtgtacaag gaggccaagga gtccgtggac gccctctttg   2760
gtgaacagca gtacgaccg cctccaagca gacaccaaca ttgccatgat ccacgccgcc   2820
aacaagcgcg tgcactccat cagggaggcg tatctccctg aactcagcgt gattcctggc   2880
gtgaatgctg ccatcttcga ggagcttgag ggtcgcatct tcaccgcatt cagcctctac   2940
gacgccagga acgtcatcaa gaacggagac ttcaacaacg gggctgtcctg ctggaacgtc   3000
aaaggtcacg ttgacgtgga gggagcagaac aaccatcgca gcgtcctcgt cgtccctgag   3060
```

-continued

```
tgggaagctg aggtcagcca agaagtcagg gtctgccctg gtcgcggcta catcctcagg  3120
gtgaccgcct acaaggaagg gtatggtgaa gggtgtgtca cgatccatga gattgagaac  3180
aacacggacg aactcaagtt cagcaactgc gtcgaggagg aggtctatcc gaacaacacg  3240
gtcacctgca acgactacac tgccactcag gaggagtacg agggaaccta cactagccgc  3300
aaccgtggct acgatggagc ctacgagtcc aactcctccg ttcccgctga ctacgcaagc  3360
gcctacgagg agaaggcgta cacggacggg cggcgcgaca acccgtgcga gtccaatcgt  3420
ggctacggtg actacactcc gcttcccgct ggttacgtga ccaaggaact tgagtacttc  3480
cctgagaccg acaaggtctg gatcgagata ggtgagaccg aaggcacgtt catcgttgac  3540
tccgtcgaac tgctgctcat ggaggagtga                                    3570
```

CHIMERIC INSECTICIDAL PROTEINS TOXIC OR INHIBITORY TO LEPIDOPTERAN PESTS

REFERENCE TO RELATED APPLICATION

This application is a divisional of U.S. patent application Ser. No. 17/698,936, filed Mar. 18, 2022, which is a divisional of U.S. patent application Ser. No. 16/658,938, filed Oct. 21, 2019, now U.S. Pat. No. 11,286,284, which is a continuation of U.S. patent application Ser. No. 15/656,616, filed Jul. 21, 2017, now U.S. Pat. No. 10,487,123, which is a continuation-in-part of U.S. patent application Ser. No. 14/884,469 filed Oct. 15, 2015, now U.S. Pat. No. 10,233, 217, which claims the benefit of U.S. provisional application No. 62/064,989, filed Oct. 16, 2014, which is herein incorporated by reference in its entirety.

INCORPORATION OF SEQUENCE LISTING

A computer readable form of the Sequence Listing is filed with this application by electronic submission and is incorporated into this application by reference in its entirety. The Sequence Listing is contained in the file created on Mar. 13, 2024, having the file name MONS476USCP1D2_ST26.xml, and which is 515,400 bytes in size (as measured in the MS-Windows® operating system).

FIELD OF THE INVENTION

The invention generally relates to the field of insect inhibitory proteins. A novel class of chimeric insecticidal proteins exhibiting insect inhibitory activity against agriculturally-relevant pests of crop plants and seeds is disclosed in this application. In particular, the disclosed class of proteins exhibits insecticidal activity against the Lepidopteran order of insect pests. Plants, plant parts, and seeds containing a recombinant nucleic acid molecule encoding one or more of the disclosed toxin proteins are provided.

BACKGROUND OF THE INVENTION

Improving crop yield from agriculturally-significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts with respect to food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the order Lepidoptera, are considered a major cause of damage to field crops, thereby decreasing crop yields in infested areas. Lepidopteran pest species which negatively impact agriculture include, but are not limited to, fall armyworm (Spodoptera frugiperda), beet armyworm (Spodoptera exigua), bertha armyworm (Mamestra configurata), black cutworm (Agrotis ipsilon), cabbage looper (Trichoplusia ni), soybean looper (Chrysodeixis includens), velvetbean caterpillar (Anticarsia gemmatalis), green cloverworm (Hypena scabra), tobacco budworm (Heliothis virescens), granulate cutworm (Agrotis subterranea), armyworm (Pseudaletia unipuncta), western cutworm (Agrotis orthogonia), European corn borer (Ostrinia nubilalis), navel orangeworm (Amyelois transitella), corn root webworm (Crambus caliginosellus), sod webworm (Herpetogramma licarsisalis), sunflower moth (Homoeosoma electellum), lesser cornstalk borer (Elasmopalpus lignosellus), codling moth (Cydia pomonella), grape berry moth (Endopiza viteana), oriental fruit moth (Grapholita molesta), sunflower bud moth (Suleima helianthana), diamondback moth (Plutella xylostella), pink bollworm (Pectinophora gossypiella), pink stem borer (Sesamia inferens), gypsy moth (Lymantria dispar), cotton leaf worm (Alabama argillacea), fruit tree leaf roller (Archips argyrospila), European leafroller (Archips rosana), Asiatic rice borer, or rice stem borer (Chilo suppressalis), rice leaf roller (Cnaphalocrocis medinalis), corn root webworm (Crambus caliginosellus), bluegrass webworm (Crambus teterrellus), southwestern corn borer (Diatraea grandiosella)), sugarcane borer (Diatraea saccharalis), spiny bollworm (Earias insulana), spotted bollworm (Earias vittella), Old World cotton bollworm (Helicoverpa armigera), corn earworm, soy podworm or cotton bollworm (Helicoverpa zea), sod webworm (Herpetogramma licarsisalis), European grape vine moth (Lobesia botrana), citrus leafminer (Phyllocnistis citrella), large white butterfly (Pieris brassicae), imported cabbageworm, or small white butterfly (Pieris rapae), tobacco cutworm, or cluster caterpillar (Spodoptera litura), and tomato leafminer (Tuta absoluta).

Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus Bacillus, was discovered and developed as a biological pest control agent. Strains of the bacterium Bacillus thuringiensis (Bt) have been used as a source for insecticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other Bacillus and a diversity of other bacterial species, such as Brevibacillus laterosporus, Lysinibacillus sphaericus ("Ls" formerly known as Bacillus sphaericus) and Paenibacillus popilliae.

Crystalline and secreted soluble insecticidal protein toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein.

The use of transgenic plants expressing insecticidal proteins has been globally adopted. For example, in 2012, 26.1 million hectares were planted with transgenic crops expressing Bt toxins (James, C., Global Status of Commercialized Biotech/GM Crops: 2012. ISAAA Brief No. 44). The global use of transgenic insect-protected crops and the limited number of insecticidal proteins used in these crops has created a selection pressure for existing insect alleles that impart resistance to the currently-utilized insecticidal proteins.

The development of resistance in target pests to insecticidal proteins creates the continuing need for discovery and development of new forms of insecticidal proteins that are useful for managing the increase in insect resistance to transgenic crops expressing insecticidal proteins. New insecticidal proteins with improved efficacy and which exhibit control over a broader spectrum of susceptible insect species will reduce the number of surviving insects which can develop resistance alleles. In addition, the use in one plant of two or more transgenic insecticidal proteins toxic to the same insect pest and displaying different modes of action reduces the probability of resistance in any single target insect species.

Consequently, there is a critical need to identify additional insecticidal proteins with improved insecticidal properties such as increased efficacy against a broader spectrum of target insect pests species and different modes of action compared to the toxins currently used in agricultural practices. To meet this need, the present invention discloses novel Cry1 chimeric insecticidal proteins that exhibit activity against significant target Lepidopteran pest species.

Members of the family of Cry1 crystal proteins are known in the art to exhibit bioactivity against Lepidopteran pests. The precursor form of Cry 1 crystal proteins consists of two approximately equal-sized segments. The carboxy-terminal portion of the precursor protein, known as the protoxin segment, stabilizes crystal formation and exhibits no insecticidal activity. The amino-terminal half of the precursor protein comprises the toxin segment of the Cry1 protein and, based on alignment of conserved or substantially conserved sequences within Cry1 family members, can be further sub-divided into three structural domains, domain I, domain II, and domain III. Domain I comprises about the first third of the active toxin segment and has been shown to be essential for channel formation. Domains II and III have both been implicated in receptor binding and insect species specificity, depending on the insect and insecticidal protein being examined.

The likelihood of arbitrarily creating a chimeric protein with enhanced properties from the assortment of the domain structures of the numerous native insecticidal proteins known in the art is remote. This is a result of the complex nature of protein structure, oligomerization, and activation (including correct proteolytic processing of the chimeric precursor, if expressed in such a form) required to release an insecticidal protein segment. Only by careful selection of protoxins and specific targets within each parental protein for the creation of a chimeric structure can functional chimeric insecticidal toxins be constructed that exhibit improved insecticidal activity in comparison to the parental proteins from which the chimeras are derived. It is known in the art that reassembly of the protoxin and toxin domains I, II and III of any two or more toxins that are different from each other often results in the construction of proteins that exhibit faulty crystal formation or the complete lack of any detectable insecticidal activity directed to a preferred target insect pest species. Only by trial and error are effective insecticidal chimeras designed, and even then, the skilled artisan is not certain to end up with a chimera that exhibits insecticidal activity that is equivalent to or improved in comparison to any single parental toxin protein from which the constituent protoxin or toxin domains of the chimera may have been derived. For example, the literature reports numerous examples of the construction or assembly of chimeric proteins from two or more crystal protein precursors. See, e.g. Jacqueline S. Knight, et al. "A Strategy for Shuffling Numerous *Bacillus thuringiensis* Crystal Protein Domains." *J. Economic Entomology*, 97 (6) (2004): 1805-1813; Bosch, et al. (U.S. Pat. No. 6,204,246); Malvar and Gilmer (U.S. Pat. No. 6,017,534). In each of these examples, many of the resultant chimeras failed to exhibit insecticidal or crystal forming properties that were equivalent to or improved in comparison to the precursor proteins from which the components of the chimeras were derived.

SUMMARY OF THE INVENTION

Recombinant nucleic acid molecules are provided that encode chimeric insecticidal proteins toxic to Lepidopteran species of plant pests. Each of the chimeric insecticidal proteins can be used alone or in combination with each other and with other insecticidal proteins and insect inhibitory agents in formulations and in planta; thus providing alternatives to insecticidal proteins and insecticidal chemistries currently in use in agricultural systems.

In certain embodiments disclosed herein is a chimeric insecticidal protein comprising an amino acid sequence as set forth in any of SEQ ID NOs: 21, 10, 28, 7, 4, 13, 16, 19, 23, 25, 30, 33, 36, 39, 41, 43, 45, 47, 50, 53, 55, 57, 59, 61, 63, 65, 67, 69, 71, 73, 75, 77, 79, 81, 83, 85, 87, 89, 91, 93, 95, 97, 99, 101, 103, 105, 107, 109, or 111. In certain embodiments disclosed herein is a chimeric insecticidal protein comprising SEQ ID NO: 93. This chimeric insecticidal protein exhibits inhibitory activity against an insect species of the order *Lepidoptera* such as, but not limited to, *Anticarsia gemmatalis, Diatraea saccharalis, Elasmopalpus lignosellus, Helicoverpa zea, Heliothis virescens, Chrysodeixis includens, Spodoptera cosmioides, Spodoptera eridania, Spodoptera frugiperda, Spodoptera exigua, Helicoverpa armigera, Spodoptera litura, Pectinophora gossypiella, Diatraea grandiosella, Earias vitella, Helicoverpa gelotopeon*, and *Rachiplusia nu*.

In another embodiment, a polynucleotide encoding a chimeric insecticidal protein, wherein the polynucleotide is operably linked to a heterologous promoter and the chimeric insecticidal protein comprises the amino acid sequence as set forth in any of SEQ ID NOs: 21, 10, 28, 7, 4, 13, 16, 19, 23, 25, 30, 33, 36, 39, 41, 43, 45, 47, 50, 53, 55, 57, 59, 61, 63, 65, 67, 69, 71, 73, 75, 77, 79, 81, 83, 85, 87, 89, 91, 93, 95, 97, 99, 101, 103, 105, 107, 109, or 111 is disclosed. In another embodiment, a polynucleotide encoding a chimeric insecticidal protein, wherein the polynucleotide is operably linked to a heterologous promoter and the chimeric insecticidal protein comprises the amino acid sequence SEQ ID NO: 93. A polynucleotide encoding a chimeric insecticidal protein, wherein the polynucleotide comprises a nucleotide sequence that optionally: hybridizes under stringent conditions to the reverse complement of the polynucleotide sequence as set forth in any of SEQ ID NOs: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 113, 114, 115, 116, 117, 118, 119, 120, 121, 122, 123, 124, 125, 126, 127, 128, 129, or 130; or encodes the chimeric insecticidal protein comprising an amino acid sequence as set forth in any of SEQ ID NOs: 21, 10, 28, 7, 4, 13, 16, 19, 23, 25, 30, 33, 36, 39, 41, 43, 45, 47, 50, 53, 55, 57, 59, 61, 63, 65, 67, 69, 71, 73, 75, 77, 79, 81, 83, 85, 87, 89, 91, 93, 95, 97, 99, 101, 103, 105, 107, 109, or 111 is also contemplated. A polynucleotide encoding a chimeric insecticidal protein, wherein the polynucleotide comprises a nucleotide sequence that optionally hybridizes under stringent conditions to the reverse complement of a polynucleotide sequence of SEQ ID NO: 92 or 122, or encodes the chimeric insecticidal protein comprises the amino acid sequence SEQ ID NO: 93.

In other embodiments disclosed herein is a host cell comprising the polynucleotide set forth in any of SEQ ID NO: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 113, 114, 115, 116, 117, 118, 119, 120, 121, 122, 123, 124, 125, 126, 127, 128, 129, or 130; wherein the host cell is selected from the group consisting of a bacterial host cell or a plant host cell. In other embodiments disclosed herein is a host cell comprising the polynucleotide SEQ ID NOs: 92 or 122, wherein the host cell is selected from the group consisting of a bacterial host cell or a plant host cell. Contemplated bacterial host include *Agrobacterium, Rhizobium, Bacillus, Brevibacillus, Escherichia, Pseudomonas, Klebsiella,* and *Erwinia*; and wherein the *Bacillus* species is a *Bacillus cereus* or a *Bacillus thuringiensis*, said *Brevibacillus* is a *Brevibacillus laterosperous*, and said *Escherichia* is *an Escherichia coli*. Contemplated plant cells include monocots and dicots.

Other embodiments disclosed herein include insect inhibitory compositions comprising a chimeric insecticidal protein comprising an amino acid sequence as set forth in any of SEQ ID NOs: 21, 10, 28, 7, 4, 13, 16, 19, 23, 25, 30, 33, 36, 39, 41, 43, 45, 47, 50, 53, 55, 57, 59, 61, 63, 65, 67, 69, 71, 73, 75, 77, 79, 81, 83, 85, 87, 89, 91, 93, 95, 97, 99, 101, 103, 105, 107, 109, or 111. Other embodiments disclosed herein include insect inhibitory compositions comprising a chimeric insecticidal protein comprising an amino acid sequence SEQ ID NO: 93. In certain embodiments, the insect inhibitory composition further comprises at least one insect inhibitory agent different from the chimeric insecticidal protein. Contemplated insect inhibitory agents different from the chimeric insecticidal protein include an insect inhibitory protein, an insect inhibitory dsRNA molecule, and an insect inhibitory chemistry. These insect inhibitory agents different from the chimeric insecticidal protein can exhibit activity against one or more pest species of the orders *Lepidoptera*, Coleoptera, Hemiptera, Homoptera, or Thysanoptera.

In yet another embodiment, disclosed herein is a seed comprising an insect inhibitory effective amount of: a chimeric insecticidal protein comprising the amino acid sequence as set forth in any of SEQ ID NOs: 21, 10, 28, 7, 4, 13, 16, 19, 23, 25, 30, 33, 36, 39, 41, 43, 45, 47, 50, 53, 55, 57, 59, 61, 63, 65, 67, 69, 71, 73, 75, 77, 79, 81, 83, 85, 87, 89, 91, 93, 95, 97, 99, 101, 103, 105, 107, 109, or 111; or a polynucleotide set forth in any of SEQ ID NOs:1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 113, 114, 115, 116, 117, 118, 119, 120, 121, 122, 123, 124, 125, 126, 127, 128, 129, or 130. Another embodiment, disclosed herein is a seed comprising an insect inhibitory effective amount of a chimeric insecticidal protein comprising the amino acid sequence SEQ ID NO: 93, or a polynucleotide of SEQ ID NOs: 92 or 122.

Methods of controlling a Lepidopteran pest comprising contacting the Lepidopteran pest with an inhibitory amount of a chimeric insecticidal protein of the invention are also contemplated.

In another embodiment, disclosed herein is a transgenic plant cell, plant or plant part comprising a chimeric insecticidal protein, wherein: the chimeric insecticidal protein comprises any amino acid sequence set forth in any of SEQ ID NOs: 21, 10, 28, 7, 4, 13, 16, 19, 23, 25, 30, 33, 36, 39, 41, 43, 45, 47, 50, 53, 55, 57, 59, 61, 63, 65, 67, 69, 71, 73, 75, 77, 79, 81, 83, 85, 87, 89, 91, 93, 95, 97, 99, 101, 103, 105, 107, 109, or 111; or the chimeric insecticidal protein comprises a protein having: at least 94% identical to SEQ ID NOs:21, 10; at least 93% identical to SEQ ID NO:28; at least 87% identical to SEQ ID NO:7; at least 90% identity to SEQ ID NO:4; at least 91% identical to SEQ ID NO:13; at least 64% identical to SEQ ID NO:16; at least 66% identical to SEQ ID NO:19; at least 86% identical to SEQ ID NO:23; at least 91% identical to SEQ ID NO:25; at least 94% identical to SEQ ID NO:30; at least 91% identical to SEQ ID NO:33; at least 64% identical to SEQ ID NO:36; at least 66% identical to SEQ ID NO:39; at least 94% identical to SEQ ID NO:41; at least 84% identical to SEQ ID NO:43; at least 93% identical to SEQ ID NO:45; at least 94% identical to SEQ ID NO:47; at least 91% identical to SEQ ID NO:50; or at least 93% identical to SEQ ID NO:53; or at least 87% identity to SEQ ID NOs:85, 93, 105; or at least 85% identity to SEQ ID NOs:55, 57, 59, 61, 63, 65, 67, 69, 71, 73, 75, 77, 79; or at least 88% identity to SEQ ID NOs: 91, 87, 89; or at least 89% identity to SEQ ID NOs: 107, 111; or at least 90% identity to SEQ ID NO: 97; at least 91% identity to SEQ ID NO: 109; or at least 93% identity to SEQ ID NO:83; or at least 94% identity to SEQ ID NOs:91 or 103; or at least 95% identity to SEQ ID NOs:95, 101; or at least 98% identity to SEQ ID NO:99. In another embodiment disclosed hercin, is a transgenic plant cell, plant or plant part comprising a chimeric insecticidal protein, wherein: the chimeric insecticidal protein comprises the amino acid sequence of SEQ ID NO:93, or the chimeric insecticidal protein comprises a protein having at least 87% identity to SEQ ID NO:93. Methods of controlling a Lepidopteran pest which comprise exposing the pest to this transgenic plant cell, plant or plant part, wherein said plant cell, plant or plant part expresses a Lepidopteran inhibitory amount of the chimeric insecticidal protein are also contemplated.

In other embodiments herein, commodity products derived from the plant cell, plant, or plant part wherein the product comprises a detectable amount of the chimeric insecticidal protein are provided. Contemplated commodity products include plant biomass, oil, meal, animal feed, flour, flakes, bran, lint, hulls, and processed sced.

Yet another method disclosed herein is a method of producing a seed comprising a chimeric insecticidal protein, the method comprising: planting at least one seed comprising a chimeric insecticidal protein; growing plants from said seed; and harvesting seed from said plants, wherein said harvested seed comprises the chimeric insecticidal protein.

Recombinant polynucleotide molecules encoding a chimeric insecticidal protein, comprising a nucleotide sequence selected from the group consisting of SEQ ID NOs: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 113, 114, 115, 116, 117, 118, 119, 120, 121, 122, 123, 124, 125, 126, 127, 128, 129, or 130; recombinant polynucleotide molecules encoding a chimeric insecticidal protein comprising a nucleotide sequence of SEQ ID NOs:92 or 122; and optionally a polynucleotide sequence encoding an insect inhibitory agent different from the chimeric insecticidal protein are also contemplated herein.

Another recombinant nucleic acid molecule contemplated herein comprises a heterologous promoter operably linked to a polynucleotide segment encoding a chimeric insecticidal proteins, wherein: the chimeric insecticidal protein comprises any amino acid sequence set forth in any of SEQ ID NOs: 21, 10, 28, 7, 4, 13, 16, 19, 23, 25, 30, 33, 36, 39, 41, 43, 45, 47, 50, 53, 55, 57, 59, 61, 63, 65, 67, 69, 71, 73, 75, 77, 79, 81, 83, 85, 87, 89, 91, 93, 95, 97, 99, 101, 103, 105, 107, 109, or 111; or the chimeric insecticidal protein comprises a protein having: at least 94% identical to SEQ ID NOs:21, 10; at least 93% identical to SEQ ID NO:28; at least 87% identical to SEQ ID NO:7; at least 90% identity to SEQ ID NO:4; at least 91% identical to SEQ ID NO:13; at least 64% identical to SEQ ID NO:16; at least 66% identical to SEQ ID NO:19; at least 86% identical to SEQ ID NO:23; at least 91% identical to SEQ ID NO:25; at least 94% identical to SEQ ID NO:30; at least 91% identical to SEQ ID NO:33; at least 64% identical to SEQ ID NO:36; at least 66% identical to SEQ ID NO:39; at least 94% identical to SEQ ID NO:41; at least 84% identical to SEQ ID NO:43; at least 93% identical to SEQ ID NO:45; at least 94% identical to SEQ ID NO:47; at least 91% identical to SEQ ID NO:50; or at least 93% identical to SEQ ID NO:53; or at least 87% identity to SEQ ID NOs:85, 93, 105; or at least 85% identity to SEQ ID NOs:55, 57, 59, 61, 63, 65, 67, 69, 71, 73, 75, 77, 79; or at least 88% identity to SEQ ID NOs:91, 87, 89; or at least 89% identity to SEQ ID NOs: 107, 111; or at least 90% identity to SEQ ID NO:97; or at least 91% identity to SEQ ID NO:109; or at least 93% identity to SEQ ID NO:83; or at least 94% identity to SEQ ID NOs:91, 103; or at least 95% identity to SEQ ID NOs:95, 101; or at least 98% identity to SEQ ID NO:99; or the polynucleotide segment hybridizes to a polynucleotide having a nucleotide sequence as set forth in any of SEQ ID NOs: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 113, 114, 115, 116, 117, 118, 119, 120, 121, 122, 123, 124, 125, 126, 127, 128, 129, or 130. Another recombinant nucleic acid molecule contemplated herein comprises a heterologous promoter operably linked to a polynucleotide segment encoding a chimeric insecticidal proteins, wherein the chimeric insecticidal protein comprises the amino acid sequence of SEQ ID NO:93, or the chimeric insecticidal protein comprises a protein having at least 87% identity to SEQ ID NO:93; or the polynucleotide segment hybridizes to a polynucleotide having a nucleotide sequence of SEQ ID NOs:92 or 122

Other embodiments, features, and advantages of the invention will be apparent from the following detailed description, examples, and claims.

BRIEF DESCRIPTION OF THE SEQUENCES

SEQ ID NO: 1 is a recombinant DNA sequence encoding TIC1100 used for expression in a bacterial cell.

SEQ ID NO: 2 is a synthetic DNA sequence encoding TIC1100 for expression in a plant cell.

SEQ ID NO: 3 is a synthetic DNA sequence encoding TIC1100 for expression in a plant cell.

SEQ ID NO: 4 is the amino acid sequence of TIC1100.

SEQ ID NO: 5 is a recombinant DNA sequence encoding TIC860 used for expression in a bacterial cell.

SEQ ID NO: 6 is a synthetic DNA sequence encoding TIC860 for expression in a plant cell.

SEQ ID NO: 7 is the amino acid sequence of TIC860.

SEQ ID NO: 8 is a recombinant DNA sequence encoding TIC867 used for expression in a bacterial cell.

SEQ ID NO: 9 is a synthetic DNA sequence encoding TIC867 for expression in a plant cell.

SEQ ID NO: 10 is the amino acid sequence of TIC867.

SEQ ID NO: 11 is a recombinant DNA sequence encoding TIC867_20 used for expression in a bacterial cell.

SEQ ID NO: 12 is a synthetic DNA sequence encoding TIC867_20 for expression in a plant cell.

SEQ ID NO: 13 is the amino acid sequence of TIC867_20.

SEQ ID NO: 14 is a recombinant DNA sequence encoding TIC867_21 used for expression in a bacterial cell.

SEQ ID NO: 15 is a synthetic DNA sequence encoding TIC867_21 for expression in a plant cell.

SEQ ID NO: 16 is the amino acid sequence of TIC867_21.

SEQ ID NO: 17 is a recombinant DNA sequence encoding TIC867_22 used for expression in a bacterial cell.

SEQ ID NO: 18 is a synthetic DNA sequence encoding TIC867_22 for expression in a plant cell.

SEQ ID NO: 19 is the amino acid sequence of TIC867_22.

SEQ ID NO: 20 is a synthetic DNA sequence encoding TIC867_23 for expression in the plant cell.

SEQ ID NO: 21 is the amino acid sequence of TIC867_23.

SEQ ID NO: 22 is a synthetic DNA sequence encoding TIC867_24 for expression in a plant cell.

SEQ ID NO: 23 is the amino acid sequence of TIC867_24.

SEQ ID NO: 24 is a synthetic DNA sequence encoding TIC867_24 for expression in a plant cell.

SEQ ID NO: 25 is the amino acid sequence of TIC867_25.

SEQ ID NO: 26 is a recombinant DNA sequence encoding TIC868 used for expression in a bacterial cell.

SEQ ID NO: 27 is a synthetic DNA sequence encoding TIC868 for expression in a plant cell.

SEQ ID NO: 28 is the amino acid sequence of TIC868.

SEQ ID NO: 29 is a synthetic DNA sequence encoding TIC868_9 for expression in a plant cell.

SEQ ID NO: 30 is the amino acid sequence of TIC868_9.

SEQ ID NO: 31 is a recombinant DNA sequence encoding TIC868_10 used for expression in a bacterial cell.

SEQ ID NO: 32 is a synthetic DNA sequence for expression in the plant cell encoding the TIC868 variant, TIC868_10.

SEQ ID NO: 33 is the amino acid sequence of TIC868_10.

SEQ ID NO: 34 is a recombinant DNA sequence encoding TIC868_11 used for expression in a bacterial cell.

SEQ ID NO: 35 is a synthetic DNA sequence encoding TIC868_11 for expression in a plant cell.

SEQ ID NO: 36 is the amino acid sequence of TIC868_11.

SEQ ID NO: 37 is a recombinant DNA sequence encoding TIC868_12 used for expression in a bacterial cell.

SEQ ID NO: 38 is a synthetic DNA sequence encoding TIC868_12 for expression in the plant cell.

SEQ ID NO: 39 is the amino acid sequence of TIC868_12.

SEQ ID NO: 40 is a synthetic DNA sequence encoding TIC868_13 for expression in the plant cell.

SEQ ID NO: 41 is the amino acid sequence of TIC868_13.

SEQ ID NO: 42 is a synthetic DNA sequence encoding TIC868_14 for expression in a plant cell.

SEQ ID NO: 43 is the amino acid sequence of TIC868_14.

SEQ ID NO: 44 is a synthetic DNA sequence encoding TIC868_15 for expression in a plant cell.

SEQ ID NO: 45 is the amino acid sequence of TIC868_15.

SEQ ID NO: 46 is a synthetic DNA sequence encoding TIC868_29 for expression in a plant cell.

SEQ ID NO: 47 is the amino acid sequence of TIC868_29.

SEQ ID NO: 48 is a recombinant DNA sequence encoding TIC869 used for expression in a bacterial cell.

SEQ ID NO: 49 is a synthetic DNA sequence encoding TIC869 for expression in a plant cell.

SEQ ID NO: 50 is the amino acid sequence of TIC869.

SEQ ID NO: 51 is a recombinant DNA sequence encoding TIC836 used for expression in a bacterial cell.

SEQ ID NO: 52 is a synthetic DNA sequence encoding TIC836 for expression in a plant cell.

SEQ ID NO: 53 is the amino acid sequence of TIC836.

SEQ ID NO: 54 is a DNA sequence encoding a chimeric TIC713 amino acid sequence.

SEQ ID NO: 55 is the TIC713 amino acid sequence translated from the open reading frame set forth in SEQ ID NO: 54.

SEQ ID NO: 56 is a DNA sequence encoding a chimeric TIC843 amino acid sequence.

SEQ ID NO: 57 is the TIC843 amino acid sequence translated from the open reading frame set forth in SEQ ID NO: 56.

SEQ ID NO: 58 is a DNA sequence encoding a chimeric TIC862 amino acid sequence.

SEQ ID NO: 59 is the TIC862 amino acid sequence translated from the open reading frame set forth in SEQ ID NO: 58.

SEQ ID NO: 60 is a DNA sequence encoding a chimeric TIC1099 amino acid sequence.

SEQ ID NO: 61 is the TIC1099 amino acid sequence translated from the open reading frame set forth in SEQ ID NO: 60.

SEQ ID NO: 62 is a DNA sequence encoding a chimeric TIC1099-T507E amino acid sequence.

SEQ ID NO: 63 is the TIC1099-T507E amino acid sequence translated from the open reading frame set forth in SEQ ID NO: 62.

SEQ ID NO: 64 is a DNA sequence encoding a chimeric TIC1099-R522K amino acid sequence.

SEQ ID NO: 65 is the TIC1099-R522K amino acid sequence translated from the open reading frame set forth in SEQ ID NO: 64.

SEQ ID NO: 66 is a DNA sequence encoding a chimeric TIC1099-K490S amino acid sequence.

SEQ ID NO: 67 is the TIC1099-K490S amino acid sequence translated from the open reading frame set forth in SEQ ID NO: 66.

SEQ ID NO: 68 is a DNA sequence encoding a chimeric TIC1099-T562R amino acid sequence.

SEQ ID NO: 69 is the TIC1099-T562R amino acid sequence translated from the open reading frame set forth in SEQ ID NO: 68.

SEQ ID NO: 70 is a DNA sequence encoding a chimeric TIC1099-S553R amino acid sequence.

SEQ ID NO: 71 is the TIC1099-S553R amino acid sequence translated from the open reading frame set forth in SEQ ID NO: 70.

SEQ ID NO: 72 is a DNA sequence encoding a chimeric TIC1099-G498D amino acid sequence.

SEQ ID NO: 73 is the TIC1099-G498D amino acid sequence translated from the open reading frame set forth in SEQ ID NO: 72.

SEQ ID NO: 74 is a DNA sequence encoding a chimeric TIC1099-K490A amino acid sequence.

SEQ ID NO: 75 is the TIC1099-K490A amino acid sequence translated from the open reading frame set forth in SEQ ID NO: 74.

SEQ ID NO: 76 is a DNA sequence encoding a chimeric TIC1099-E564A amino acid sequence.

SEQ ID NO: 77 is the TIC1099-E564A amino acid sequence translated from the open reading frame set forth in SEQ ID NO: 76.

SEQ ID NO: 78 is a DNA sequence encoding a chimeric TIC1103 amino acid sequence.

SEQ ID NO: 79 is the TIC1103 amino acid sequence translated from the open reading frame set forth in SEQ ID NO: 78.

SEQ ID NO: 80 is a DNA sequence encoding a chimeric TIC1101 amino acid sequence.

SEQ ID NO: 81 is the TIC1101 amino acid sequence translated from the open reading frame set forth in SEQ ID NO: 80.

SEQ ID NO: 82 is a DNA sequence encoding a chimeric TIC845 amino acid sequence.

SEQ ID NO: 83 is the TIC845 amino acid sequence translated from the open reading frame set forth in SEQ ID NO: 82.

SEQ ID NO: 84 is a DNA sequence encoding a chimeric TIC846 amino acid sequence.

SEQ ID NO: 85 is the TIC846 amino acid sequence translated from the open reading frame set forth in SEQ ID NO: 84.

SEQ ID NO: 86 is a DNA sequence encoding a chimeric TIC858 amino acid sequence.

SEQ ID NO: 87 is the TIC858 amino acid sequence translated from the open reading frame set forth in SEQ ID NO: 86.

SEQ ID NO: 88 is a DNA sequence encoding a chimeric TIC865 amino acid sequence.

SEQ ID NO: 89 is the TIC865 amino acid sequence translated from the open reading frame set forth in SEQ ID NO: 88.

SEQ ID NO: 90 is a DNA sequence encoding a chimeric TIC866 amino acid sequence.

SEQ ID NO: 91 is the TIC866 amino acid sequence translated from the open reading frame set forth in SEQ ID NO: 90.

SEQ ID NO: 92 is a DNA sequence encoding a chimeric TIC838 amino acid sequence.

SEQ ID NO: 93 is the TIC838 amino acid sequence translated from the open reading frame set forth in SEQ ID NO: 92.

SEQ ID NO: 94 is a DNA sequence encoding a chimeric TIC839 amino acid sequence.

SEQ ID NO: 95 is the TIC839 amino acid sequence translated from the open reading frame set forth in SEQ ID NO: 94.

SEQ ID NO: 96 is a DNA sequence encoding a chimeric TIC841 amino acid sequence.

SEQ ID NO: 97 is the TIC841 amino acid sequence translated from the open reading frame set forth in SEQ ID NO: 96.

SEQ ID NO: 98 is a DNA sequence encoding a chimeric TIC842 amino acid sequence.

SEQ ID NO: 99 is the TIC842 amino acid sequence translated from the open reading frame set forth in SEQ ID NO: 98.

SEQ ID NO: 100 is a DNA sequence encoding a chimeric TIC850 amino acid sequence.

SEQ ID NO: 101 is the TIC850 amino acid sequence translated from the open reading frame set forth in SEQ ID NO: 100.

SEQ ID NO: 102 is a DNA sequence encoding a chimeric TIC859 amino acid sequence.

SEQ ID NO: 103 is the TIC859 amino acid sequence translated from the open reading frame set forth in SEQ ID NO: 102.

SEQ ID NO: 104 is a DNA sequence encoding a chimeric TIC861 amino acid sequence.

SEQ ID NO: 105 is the TIC861 amino acid sequence translated from the open reading frame set forth in SEQ ID NO: 104.

SEQ ID NO: 106 is a DNA sequence encoding a chimeric TIC848 amino acid sequence.

SEQ ID NO: 107 is the TIC848 amino acid sequence translated from the open reading frame set forth in SEQ ID NO: 106.

SEQ ID NO: 108 is a DNA sequence encoding a chimeric TIC849 amino acid sequence.

SEQ ID NO: 109 is the TIC849 amino acid sequence translated from the open reading frame set forth in SEQ ID NO: 108.

SEQ ID NO: 110 is a DNA sequence encoding a chimeric TIC847 amino acid sequence.

SEQ ID NO: 111 is the TIC847 amino acid sequence translated from the open reading frame set forth in SEQ ID NO: 110.

SEQ ID NO: 112 is a synthetic DNA sequence for expression in the plant cell encoding TIC713.

SEQ ID NO: 113 is a synthetic DNA sequence for expression in the plant cell encoding TIC713.

SEQ ID NO: 114 is a synthetic DNA sequence for expression in the plant cell encoding TIC843.

SEQ ID NO: 115 is a synthetic DNA sequence for expression in the plant cell encoding TIC862.

SEQ ID NO: 116 is a synthetic DNA sequence for expression in the plant cell encoding TIC1099.

SEQ ID NO: 117 is a synthetic DNA sequence for expression in the plant cell encoding TIC1103.

SEQ ID NO: 118 is a synthetic DNA sequence for expression in the plant cell encoding TIC845.

SEQ ID NO: 119 is a synthetic DNA sequence for expression in the plant cell encoding TIC846.

SEQ ID NO: 120 is a synthetic DNA sequence for expression in the plant cell encoding TIC858.

SEQ ID NO: 121 is a synthetic DNA sequence for expression in the plant cell encoding TIC866.

SEQ ID NO: 122 is a synthetic DNA sequence for expression in the plant cell encoding TIC838.

SEQ ID NO: 123 is a synthetic DNA sequence for expression in the plant cell encoding TIC841.

SEQ ID NO: 124 is a synthetic DNA sequence for expression in the plant cell encoding TIC842.

SEQ ID NO: 125 is a synthetic DNA sequence for expression in the plant cell encoding TIC850.

SEQ ID NO: 126 is a synthetic DNA sequence for expression in the plant cell encoding TIC859.

SEQ ID NO: 127 is a synthetic DNA sequence for expression in the plant cell encoding TIC861.

SEQ ID NO: 128 is a synthetic DNA sequence for expression in the plant cell encoding TIC848.

SEQ ID NO: 129 is a synthetic DNA sequence for expression in the plant cell encoding TIC849.

SEQ ID NO: 130 is a synthetic DNA sequence for expression in the plant cell encoding TIC847.

DETAILED DESCRIPTION OF THE INVENTION

The problem in the art of agricultural pest control can be characterized as a need for new insecticidal proteins that are efficacious against target pests, exhibit broad spectrum toxicity against target pest species, are capable of being expressed in plants without causing undesirable agronomic issues, and provide an alternative mode of action compared to current toxins that are used commercially in plants. Novel chimeric insecticidal proteins are disclosed herein, and address each of these needs, particularly against a broad spectrum of Lepidopteran insect pests.

In order to avoid the development of, or circumvent insect resistance against currently used insecticidal proteins, new insecticidal proteins with different modes-of-action (MOA), as well as a broad spectrum and efficacy, are needed for *Lepidoptera* control. One way to address this need is to discover new insecticidal proteins from different biological sources, preferably from bacteria, fungi or plants. Another approach is to interchange segments between various Bt proteins that exhibit structural similarities to create new chimeric Bt proteins having insect inhibitory properties. The likelihood of creating a chimeric protein with enhanced properties from the re-assortment of the domain structures of numerous native insecticidal crystal proteins known in the art is known in the art to be remote. See, e.g. Jacqueline S. Knight, et al. "A Strategy for Shuffling Numerous *Bacillus thuringiensis* Crystal Protein Domains." *J. Economic Entomology*, 97 (6) (2004): 1805-1813.

Disclosed herein are recombinant nucleic acid molecule sequences that encode novel chimeric insecticidal proteins. These insecticidal proteins address the ongoing need in the art to engineer additional toxic insecticidal proteins with improved insecticidal properties such as increased efficacy against a broader spectrum of target insect pests species and different modes of action. Members of this group of proteins, including the exemplary proteins disclosed herein, exhibit insecticidal activity against Lepidopteran insect pest species.

The term "segment" or "fragment" is used in this application to describe consecutive amino acid or nucleic acid sequences that are shorter than the complete amino acid or nucleic acid sequence describing a disclosed chimeric insecticidal protein. A segment or fragment exhibiting insect inhibitory activity is also disclosed in this application if alignment of such segment or fragment, with the corresponding section of the chimeric insecticidal protein, results in amino acid sequence identity of any fraction percentage from about 65 to about 100 percent between the segment or fragment and the corresponding section of the chimeric insecticidal protein.

Reference in this application to the terms "active" or "activity", "pesticidal activity" or "pesticidal", or "insecticidal activity", "insect inhibitory" or "insecticidal" refer to efficacy of a toxic agent, such as an insecticidal protein, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of the insecticidal protein) or killing (causing the morbidity, mortality, or reduced fecundity of) a pest. These terms are intended to include the result of providing a pesticidally effective amount of an insecticidal protein to a pest where the exposure of the pest to the insecticidal protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the insecticidal protein in or on the plant. In general, pesticidal activity refers to the ability of an insecticidal protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera. The insecticidal protein can be produced by the plant or can be applied to the plant or to the environment within the location where the plant is located. The terms "bioactivity", "effective", "efficacious" or variations thereof are also terms interchangeably utilized in this application to describe the effects of the chimeric insecticidal proteins of the present invention on target insect pests.

A pesticidally effective amount of a toxic agent, when provided in the diet of a target pest, exhibits pesticidal activity when the toxic agent contacts the pest. A toxic agent can be an insecticidal protein or one or more chemical agents known in the art. Insecticidal chemical agents and insecticidal protein agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Insecticidal protein agents include the chimeric insecticidal proteins set forth in this application, as well as other proteinaceous toxic agents including those that target Lepidopteran pest species, as well as protein toxins that are used to control other plant pests such as Cry proteins available in the art for use in controlling Coleopteran, Thysanopteranm, Hemipteran and Homopteran species.

It is intended that reference to a pest, particularly a pest of a crop plant, means insect pests of crop plants, particularly those Lepidopteran insect pests that are controlled by the disclosed chimeric insecticidal proteins. However, reference to a pest can also include Coleopteran, Hemipteran and Homopteran insect pests of plants, as well as nematodes and fungi when toxic agents targeting these pests are co-localized or present together with the chimeric insecticidal protein, or a protein that is 65 to about 100 percent identical to the chimeric insecticidal protein.

The chimeric insecticidal proteins disclosed herein exhibit insecticidal activity towards insect pests from the Lepidopteran insect species, including adults, pupae, larvae, and neonates, as well as Hemipteran insect species, including adults and nymphs. The insects of the order Lepidoptera include, but are not limited to, armyworms, cutworms, loopers, and heliothines in the Family Noctuidae, e.g., fall armyworm (Spodoptera frugiperda), bect armyworm (Spodoptera exigua), bertha armyworm (Mamestra configurata), black cutworm (Agrotis ipsilon), cabbage looper (Trichoplusia ni), soybean looper (Pseudoplusia includens), velvetbean caterpillar (Anticarsia gemmatalis), green cloverworm (Hypena scabra), tobacco budworm (Heliothis virescens), granulate cutworm (Agrotis subterranea), armyworm (Pseudaletia unipuncta), western cutworm (Agrotis orthogonia); borers, casebearers, webworms, coneworms, cabbageworms and skeletonizers from the Family Pyralidae, e.g., European corn borer (Ostrinia nubilalis), navel orangeworm (Amyelois transitella), corn root webworm (Crambus caliginosellus), sod webworm (Herpetogramma licarsisalis), sunflower moth (Homoeosoma electellum), lesser cornstalk borer (Elasmopalpus lignosellus); leafrollers, budworms, seed worms, and fruit worms in the Family Tortricidac, e.g., codling moth (Cydia pomonella), grape berry moth (Endopiza viteana), oriental fruit moth (Grapholita molesta), sunflower bud moth (Suleima helianthana); and many other economically important Lepidoptera, e.g., diamondback moth (Plutella xylostella), pink bollworm (Pectinophora gossypiella) and gypsy moth (Lymantria dispar). Other insect pests of order Lepidoptera include, e.g., Alabama argillacea (cotton leaf worm), Archips argyrospila (fruit tree leaf roller), Archips rosana (European leafroller) and other Archips species, Chilo suppressalis (Asiatic rice borer, or rice stem borer), Cnaphalocrocis medinalis (rice leaf roller), Crambus caliginosellus (corn root webworm), Crambus teterrellus (bluegrass webworm), Diatraea grandiosella (southwestern corn borer), Diatraea saccharalis (surgarcane borer), Earias insulana (spiny bollworm), Earias vittella (spotted bollworm), Helicoverpa armigera (American bollworm), Helicoverpa zea (corn earworm or cotton bollworm), Heliothis virescens (tobacco budworm), Herpetogramma licarsisalis (sod webworm), Lobesia botrana (European grape vine moth), Phyllocnistis citrella (citrus leafminer), Pieris brassicae (large white butterfly), Pieris rapae (imported cabbageworm, or small white butterfly), Plutella xylostella (diamondback moth), Spodoptera exigua (bect armyworm), Spodoptera litura (tobacco cutworm, cluster caterpillar), and Tuta absoluta (tomato leafminer).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further in the Examples, through a chimeragenesis effort about eight hundred and forty four (844) nucleotide sequences that encode chimeric insecticidal proteins were constructed from the protoxin and toxin domains of known insecticidal toxins (referred to herein as the "parent proteins"), and expressed and tested in bioassay for Lepidopteran activity. A small number of the constructed chimeric insecticidal proteins exhibited improved Lepidopteran activity or an enhanced Lepidopteran spectrum compared to the parent proteins from which its toxin components were derived.

These novel chimeric insecticidal proteins with improved Lepidopteran activity or an enhanced Lepidopteran spectrum were constructed from the following insecticidal parent protein protoxin and toxin domains: Cry1Ah (Domain I), Cry1Bb1 (Domains I and II), Cry 1Be2 (Domains I and II), Cry1Ja1 (Domains I and II), Cry1Fa1 (Domains I and II), Cry1Ac (Domain II and protoxin), Cry1Ca (Domain III and protoxin), Cry1Ka (Domain III and protoxin), Cry1Jx (Domain III), Cry1Ab (Domain III), Cry1Ab3 (protoxin), Cry1Da1 (protoxin), Cry4 (protoxin), Cry9 (protoxin), Cry1Bc (protoxin), and Cry1Ka (protoxin).

Specifically, the novel chimeric insecticidal proteins of this invention with improved Lepidopteran activity or an enhanced Lepidopteran spectrum comprise the following protoxin and domain combinations: TIC1100/SEQ ID NO:4 (Domain I-Cry1Ah, Domain II-Cry 1Ac, Domain III-Cry1Ca, Protoxin-Cry1Ac), TIC860/SEQ ID NO:7 (Domain I-Cry1Bb1, Domain II-Cry1BB1, Domain III-Cry1Ca, Protoxin-Cry1Ac), TIC867/SEQ ID NO: 10 (Domain I-Cry1Bc2, Domain II-Cry1Bc2, Domain III-Cr1Ka, Protoxin-Cry1Ab3), TIC868/SEQ ID NO:28 (Domain I-Cry 1Bc2, Domain II-Cry1Be2, and Domain III-Cry 1Ca, Protoxin-Cry1Ab3), TIC869/SEQ ID NO:50 (Domain I-Cry1Ja1, Domain II-Cry1Ja1, Domain III-Cry1Jx, Protoxin-Cry1Ab3) and TIC836/SEQ ID NO:53 (Domain I-Cry1Fa1, Domain II-Cry1Fa1, Domain III-Cry1Ab, Protoxin-Cry1Ac).

Variants in which amino acid substitutions or alternate protoxin domains were introduced were also constructed for the chimeric insecticidal proteins TIC867 and TIC868. Specifically, these variants of TIC867 and TIC868 comprise the following amino acid substitutions or alternate protoxin domains: TIC867_20/SEQ ID NO:13 (alternate protoxin domain Cry1Da1), TIC867_21/SEQ ID NO:16 (alternate protoxin domain Cry4), TIC867_22/SEQ ID NO:19 (alternate protoxin domain Cry9), TIC867_23/SEQ ID NO:21 (alternate protoxin domain Cry1Bc), TIC867_24/SEQ ID NO:23 (alternate protoxin domain Cry1Ka), TIC867_25/ SEQ ID NO: 25 (alternate protoxin domain Cry1Ka), TIC868_9/SEQ ID NO:30 (amino acid modification N240S_Y343Q_N349T), TIC868_10/SEQ ID NO:33 (alternate protoxin domain Cry1Da1), TIC868_11/SEQ ID NO:36 (alternate protoxin domain Cry4), TIC868_12/SEQ ID NO:39 (alternate protoxin domain Cry 9), TIC868_13/SEQ ID NO:41 (alternate protoxin domain Cry1Bc), TIC868_14/ SEQ ID NO:43 (alternate protoxin domain Cry1Ka), TIC868_15/SEQ ID NO:45 (alternate protoxin domain Cry1Ca), and TIC868_29/SEQ ID NO:47 (amino acid modification Q136Y_Y343Q_N349T).

As demonstrated in the Examples, each of these TIC867 and TIC868 variants altered the Lepidopteran activity and/or reduced the Lepidopteran activity spectrum of the parent chimeric insecticidal protein, thus indicating that the alternate protoxin domain and the amino acid substitutions had a direct consequence on the insecticidal activity and spectrum of the chimeric insecticidal proteins TIC867 and TIC868.

Many of the chimeric insecticidal proteins demonstrate insecticidal activity against multiple Lepidopteran insect pest species. Specifically, the novel chimeric insecticidal proteins disclosed in this application exhibited activity against one or more of the following Lepidopteran insect pests, Velvet bean caterpillar (VBC, *Anticarsia gemmatalis*), Sugarcane borer (SCB, *Diatraea saccharalis*), Lesser cornstalk borer (LSCB, *Elasmopalpus lignosellus*), Corn earworm (CEW, *Helicoverpa zea*), Soybean pod worm (SPW, *Helicoverpa zea*), Cotton bollworm (CBW, *Helicoverpa zea*), Tobacco budworm (TBW, *Heliothis virescens*), Soybean looper (SBL, *Chrysodeixis includens*), Black armyworm (BLAW, *Spodoptera cosmioides*), Southern armyworm (SAW, *Spodoptera eridania*), Fall armyworm (FAW, *Spodoptera frugiperda*), Bect armyworm (BAW, *Spodoptera exigua*), Old World bollworm (OBW, *Helicoverpa armigera*), Oriental leafworm (OLW, *Spodoptera litura*), Pink bollworm (PBW, *Pectinophora gossypiella*), Southwestern Corn Borer (SWCB, *Diatraea grandiosella*), Spotted bollworm (SBW, *Earias vitella*), American bollworm (SABW, *Helicoverpa gelotopeon*), and Sunflower looper (SFL, *Rachiplusia nu*). Thus, the exemplary proteins described in this application are related by common function and exhibit insecticidal activity towards insect pests from the *Lepidoptera* insect species including adults, larvae and pupae.

Proteins that resemble the chimeric insecticidal proteins can be identified by comparison to each other using various computer based algorithms known in the art. For example, amino acid sequence identities of proteins related to the chimeric insecticidal proteins can be analyzed using a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of the subject protein). Other alignment algorithms are also available in the art, provide results similar to those obtained using Clustal W alignment and are contemplated in this application.

It is intended that a query protein exhibiting insect inhibitory activity is disclosed in this application if alignment of such query protein with the subject chimeric insecticidal proteins set forth in SEQ ID NOs: 4, 7, 10, 13, 16, 19, 21, 23, 25, 28, 30, 33, 36, 39, 41, 43, 45, 47, 50, 53, 55, 57, 59, 61, 63, 65, 67, 69, 71, 73, 75, 77, 79, 81, 83, 85, 87, 89, 91, 93, 95, 97, 99, 101, 103, 105, 107, 109, and 111 and results in at least about 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% amino acid sequence identity (or any fraction percentage in this range) between the query and subject protein. It is intended that a query protein exhibiting insect inhibitory activity is disclosed in this application if alignment of such query protein with the subject chimeric insecticidal proteins SEQ ID NO:93 and results in at least about 87%, 88%, 89%, 90%, 91%, 92%, 93%, 94%, 95%, 96%, 97%, 98%, 99%, or about 100% amino acid sequence identity (or any fraction percentage in this range) between the query and subject protein.

As described further in the Examples of this application, synthetic or artificial sequences encoding the chimeric insecticidal proteins were designed for use in plants. Exemplary synthetic nucleotide sequences that were designed for use in plants are set forth in SEQ ID NOs:2 and 3 (TIC1100), SEQ ID NO:6 (TIC860), SEQ ID NO:9 (TIC867), SEQ ID NO: 12 (TIC867_20), SEQ ID NO:15 (TIC867_21), SEQ ID NO:18 (TIC867_22), SEQ ID NO:20 (TIC867_23), SEQ ID NO:22 (TIC867_24), SEQ ID NO:24 (TIC867_25), SEQ ID NO:27 (TIC868), SEQ ID NO:29 (TIC868_9), SEQ ID NO:32 (TIC868_10), SEQ ID NO:35 (TIC868_11), SEQ ID NO:38 (TIC868_12), SEQ ID NO:40 (TIC868_13), SEQ ID NO:42 (TIC868_14), SEQ ID NO:44 (TIC868_15), SEQ ID NO:46 (TIC868_29), SEQ ID NO:49 (TIC869) and SEQ ID NO:52 (TIC836), SEQ ID NO:112 and 113 (TIC713), SEQ ID NO:114 (TIC843), SEQ ID NO:115 (TIC862), SEQ ID NO:116 (TIC1099), SEQ ID NO:117 (TIC1103), SEQ ID NO:118 (TIC845), SEQ ID NO:119 (TIC846), SEQ ID NO:120 (TIC858), SEQ ID NO:121 (TIC866), SEQ ID NO:122 (TIC838), SEQ ID NO:123 (TIC841), SEQ ID NO:124 (TIC842), SEQ ID NO:125 (TIC850), SEQ ID NO: 126 (TIC859), SEQ ID NO: 127 (TIC861), SEQ ID NO: 128 (TIC848), SEQ ID NO:129 (TIC849), and SEQ ID NO:130 (TIC847). An exemplary synthetic nucleotide sequence that was designed for use in plants is SEQ ID NO:122 (TIC838).

For expression in plant cells, the chimeric insecticidal proteins can be expressed to reside in the cytosol or targeted to various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the chloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5, -bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.* 210:437-442, 1987) or the *Petunia hybrida* EPSPS CTP (CTP4) (see, della-Cioppa et al., *Proc. Natl. Acad. Sci. USA* 83:6873-6877, 1986) has been shown to target heterologous EPSPS protein sequences to chloroplasts in transgenic plants (see, U.S. Pat. Nos. 5,627,061; 5,633,435; and 5,312,910; and EP 0218571; EP 189707; EP 508909; and EP 924299). For targeting the chimeric insecticidal proteins to the chloroplast, a sequence encoding a chloroplast transit peptide is placed 5' in operable linkage and in frame to a synthetic coding sequence encoding the chimeric insecticidal protein that has been designed for optimal expression in plant cells.

Expression cassettes and vectors containing these synthetic or artificial nucleotide sequences were constructed and introduced into corn, cotton, and soybean plant cells in accordance with transformation methods and techniques which are known in the art. Transformed cells were regenerated into transformed plants that were observed to be expressing the chimeric insecticidal protein. To test pesticidal activity, bioassays were performed in the presence of Lepidopteran pest larvae using plant leaf disks obtained from the transformed plants. Recombinant nucleic acid molecule compositions that encode the chimeric insecticidal proteins are contemplated. For example, the chimeric insecticidal proteins can be expressed with recombinant DNA constructs in which a polynucleotide molecule with an ORF encoding a chimeric insecticidal protein is operably linked to genetic expression elements such as a promoter and any other regulatory element necessary for expression in the system for which the construct is intended. Non-limiting examples include a plant-functional promoter operably linked to the synthetic chimeric insecticidal protein encoding sequences for expression of the chimeric insecticidal protein in plants or a Bt-functional promoter operably linked to a chimeric insecticidal protein encoding sequence for expression of the protein in a Bt bacterium or other *Bacillus* species. Other elements can be operably linked to the chimeric insecticidal proteins encoding sequences including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites.

Exemplary recombinant polynucleotide molecules provided herein include, but are not limited to, a heterologous promoter operably linked to a polynucleotide such as SEQ ID NOs: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 113, 114, 115, 116, 117, 118, 119, 120, 121, 122, 123, 124, 125, 126, 127, 128, 129, and 130; that encodes the polypeptide or protein having the amino acid sequence as set forth in SEQ ID NOs: 4 (TIC1100), 7 (TIC860), 10 (TIC867), 13 (TIC867_20), 16 (TIC867_21), 19 (TIC867_22), 21 (TIC867_23), 23 (TIC867_24), 25 (TIC867_25), 28 (TIC868), 30 (TIC868_9), 33 (TIC868_10), 36 (TIC868_11), 39 (TIC867_12), 41 (TIC867_13), 43 (TIC867_14), 45 (TIC867_15), 47 (TIC867_29), 50 (TIC869), 53 (TIC836), 55 (TIC713), 57 (TIC843), 59 (TIC862), 61 (TIC1099), 63 (TIC1099-T507E), 65 (TIC1099-R522K), 67 (TIC1099-K490S), 69 (TIC1099-T562R), 71 (TIC1099-S533R), 73 (TIC1099-G498D), 75 (TIC1099-K490A), 77 (TIC1099-E564A), 79 (TIC1103), 81 (TIC1101), 83 (TIC845), 85 (TIC846), 87 (TIC858), 89 (TIC865), 91 (TIC866), 93 (TIC838), 95 (TIC839), 97 (TIC841), 99 (TIC842), 101 (TIC850), 103 (TIC859), 105 (TIC861), 107 (TIC848), 109 (TIC849), and 111 (TIC847). Exemplary recombinant polynucleotide molecules provided herein include, but are not limited to, a heterologous promoter operably linked to a polynucleotide such as SEQ ID NOs:92 or 122, that encodes the polypeptide or protein having the amino acid sequence as set forth in SEQ ID NOs:93 (TIC838). A heterologous promoter can also be operably linked to synthetic DNA coding sequences encoding a plastid targeted chimeric insecticidal protein and untargeted chimeric insecticidal protein. It is contemplated that the codons of a recombinant nucleic acid molecule encoding for a chimeric insecticidal protein disclosed herein can be substituted by synonymous codons (known in the art as a silent substitution).

A recombinant DNA molecule or construct comprising a chimeric insecticidal protein encoding sequence can further comprise a region of DNA that encodes for one or more toxic agents which can be configured to concomitantly express or co-express with a DNA sequence encoding a chimeric insecticidal protein, a protein different from a chimeric insecticidal protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA molecule or construct can be assembled so that all proteins or dsRNA molecules are expressed from one promoter or each protein or dsRNA molecule is under separate promoter control or some combination thereof. The proteins of this invention can be expressed from a multi-gene expression system in which a chimeric insecticidal protein is expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked expression cassettes, each expressing a different protein or other toxic agent such as one or more dsRNA molecules.

Recombinant nucleic acid molecules or recombinant DNA constructs comprising chimeric insecticidal protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a chimeric insecticidal protein encoding sequence in a host cell, or subsequent expression of the encoded polypeptide. An exogenous recombinant polynucleotide or recombinant DNA construct that comprises chimeric insecticidal protein sequence encoding sequence and that is introduced into a host cell is referred herein as a "transgene".

Transgenic bacteria, transgenic plant cells, transgenic plants, and transgenic plant parts that contain a polynucleotide that encodes any one or more of the chimeric insecticidal proteins are provided herein. The term "bacterial cell" or "bacterium" can include, but is not limited to, an *Agrobacterium*, a *Bacillus*, an *Escherichia*, a *Salmonella*, a *Pseudomonas*, or a *Rhizobium* cell. The term "plant cell" or "plant" can include but is not limited to a dicotyledonous cell or a monocotyledonous cell. Contemplated plants and plant cells include, but are not limited to, alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise *Lepidoptera*-inhibitory amounts of a chimeric insecticidal proteins are provided. Such plants can be made by introducing a polynucleotide that encodes the chimeric insecticidal proteins provided in this application into a plant cell, and selecting a plant derived from said plant cell that expresses an insect or *Lepidoptera*-inhibitory amount of the chimeric insecticidal protein. Plants can be derived from the plant cells by regeneration, seed, pollen, or meristem transformation techniques. Methods for transforming plants are known in the art. For example, *Agrobacterium*-mediated transformation is described in U.S. Patent Application Publications 2009/0138985A1 (soybean), 2008/0280361A1 (soybean), 2009/0142837A1 (corn), 2008/0282432 (cotton), and 2008/0256667 (cotton).

Plants expressing the chimeric insecticidal proteins can be crossed by breeding with transgenic events expressing other insecticidal proteins and/or expressing other transgenic traits such as other insect control traits, herbicide tolerance genes, genes conferring yield or stress tolerance traits, and the like, or such traits can be combined in a single vector so that the traits are all linked.

Processed plant products, wherein the processed product comprises a detectable amount of a chimeric insecticidal protein, an insect inhibitory segment or fragment thereof, or any distinguishing portion thereof, are also disclosed in this application. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a chimeric insecticidal protein.

Methods of controlling insects, in particular *Lepidoptera* infestations of crop plants, with the chimeric insecticidal proteins are also disclosed in this application. Such methods can comprise growing a plant comprising an insect—or *Lepidoptera*-inhibitory amount of the chimeric insecticidal protein. In certain embodiments, such methods can further comprise any one or more of: (i) applying any composition comprising or encoding a chimeric insecticidal protein to a plant or a seed that gives rise to a plant; and (ii) transforming a plant or a plant cell that gives rise to a plant with a polynucleotide encoding a chimeric insecticidal protein. In general, it is contemplated that chimeric insecticidal protein can be provided in a composition, provided in a microorganism, or provided in a transgenic plant to confer insect inhibitory activity against Lepidopteran insects.

In certain embodiments, the chimeric insecticidal protein is the insecticidally active ingredient of an insect inhibitory composition prepared by culturing recombinant *Bacillus* or any other recombinant bacterial cell transformed to express a chimeric insecticidal protein under conditions suitable for expression. Such a composition can be prepared by desiccation, lyophilization, homogenization, extraction, filtration, centrifugation, sedimentation, or concentration of a culture of such recombinant cells expressing/producing the chimeric insecticidal protein. Such a process can result in a *Bacillus* or other entomopathogenic bacterial cell extract, cell suspension, cell homogenate, cell lysate, cell supernatant, cell filtrate, or cell pellet. By obtaining the chimeric insecticidal protein so produced, a composition that includes the chimeric insecticidal protein can include bacterial cells, bacterial spores, and parasporal inclusion bodies and can be formulated for various uses, including as agricultural insect inhibitory spray products or as insect inhibitory formulations in diet bioassays.

The aforementioned compound or formulation can further comprise an agriculturally-acceptable carrier, such as a bait, a powder, dust, pellet, granule, spray, emulsion, a colloidal suspension, an aqueous solution, a *Bacillus* spore or crystal preparation or a seed treatment. The compound or formulation can also further comprise a recombinant plant cell, plant tissue, seed or plant transformed to express one or more of the proteins; or bacterium transformed to express one or more of the proteins. Depending on the level of insect inhibitory or insecticidal inhibition inherent in the recombinant polypeptide and the level of compound or formulation to be applied to a plant or diet assay, the compound or formulation can include various by weight amounts of the recombinant polypeptide, e.g. from 0.0001% to 0.001% to 0.01% to 1% to 99% by weight of the recombinant polypeptide.

In an embodiment, in order to reduce the likelihood of resistance development, an insect inhibitory composition or transgenic plant comprising a chimeric insecticidal protein can further comprise at least one additional toxic agent that exhibits insect inhibitory activity against the same Lepidopteran insect species, but which is different from the chimeric insecticidal protein. Possible additional toxic agents for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Such additional polypeptide(s) for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ac, Cry1B (U.S. patent Publication Ser. No. 10/525,318), Cry1C (U.S. Pat. No. 6,033,874), Cry1D, Cry1E, Cry1F, and Cry1A/F chimeras (U.S. Pat. Nos. 7,070,982; 6,962,705; and 6,713, 063), Cry1G, Cry1H, Cry1I, Cry1J, Cry1K, Cry1L, Cry2A, Cry2Ab (U.S. Pat. No. 7,064,249), Cry2Ac, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, AXMI-209 (U.S. Patent Publication 2011-0030096 A1), AXMI-218, AXMI-220 (U.S. Patent Publication 2014-0245491 A1), AXMI-2212, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1); and the like.

In other embodiments, an insect inhibitory composition or transgenic plant can further comprise at least one additional toxic agent that exhibits insect inhibitory activity to an insect pest that is not inhibited by the chimeric insecticidal proteins of the present invention (such as Colcopteran, Hemipteran and Homopteran pests), in order to expand the spectrum of insect inhibition obtained.

Such additional toxic agent for the control of Coleopteran pests may be selected from the group consisting of an insect inhibitory protein, such as, but not limited to, Cry3Bb (U.S.

Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), axmi207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), CHIPs (U.S. Patent Application Publication No. 2010/0017914), IP3 and variants thereof (U.S. Patent Publication 2012-0210462 A1), and ω-Hexatoxin-Hvla (U.S. Patent Application Publication US2014-0366227 A1).

Such additional toxic agent for the control of Hemipteran pests may be selected from the group consisting of Hemipteran-active proteins such as, but not limited to, TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1). Additional polypeptides for the control of Coleopteran, Lepidopteran, and Hemipteran insect pests can be found on the *Bacillus thuringiensis* toxin nomenclature website maintained by Neil Crickmore (on the world wide web at btnomenclature.info).

Chimeric insecticidal protein-encoding sequences and sequences having a substantial percentage identity to the chimeric insecticidal proteins can be identified using methods known to those of ordinary skill in the art such as polymerase chain reaction (PCR), thermal amplification and hybridization. For example, the chimeric insecticidal proteins can be used to produce antibodies that bind specifically to related proteins, and can be used to screen for and to find other proteins that are closely related.

Furthermore, nucleotide sequences encoding the chimeric insecticidal proteins can be used as probes and primers for screening to identify other members of the class using thermal-cycle or isothermal amplification and hybridization methods. For example, oligonucleotides derived from sequences as set forth in SEQ ID NO:2 can be used to determine the presence or absence of a chimeric insecticidal transgene in a deoxyribonucleic acid sample derived from a commodity product. Given the sensitivity of certain nucleic acid detection methods that employ oligonucleotides, it is anticipated that oligonucleotides derived from sequences as set forth in any of SEQ ID NO:2 can be used to detect the respective chimeric insecticidal protein in commodity products derived from pooled sources where only a fraction of the commodity product is derived from a transgenic plant containing any of SEQ ID NO:2.

Furthermore, nucleotide sequences encoding the chimeric insecticidal proteins can be used as probes and primers for screening to identify other members of the class using thermal-cycle or isothermal amplification and hybridization methods. For example, oligonucleotides derived from sequences as set forth in SEQ ID NO:122 can be used to determine the presence or absence of a chimeric insecticidal transgene in a deoxyribonucleic acid sample derived from a commodity product. Given the sensitivity of certain nucleic acid detection methods that employ oligonucleotides, it is anticipated that oligonucleotides derived from sequences as set forth in any of SEQ ID NO: 122 can be used to detect the respective chimeric insecticidal protein in commodity products derived from pooled sources where only a fraction of the commodity product is derived from a transgenic plant containing any of SEQ ID NO:122.

EXAMPLES

In view of the foregoing, those of skill in the art will appreciate that the following disclosed embodiments are merely representative of the invention, which may be embodied in various forms. Thus, specific structural and functional details disclosed herein are not to be interpreted as limiting.

Example 1

Creation and Cloning of Lepidopteran-Active Novel Chimeric Insecticidal Protein Coding Sequences This Example illustrates the creation of the novel chimeric insecticidal proteins and the cloning and expressing of the chimeric insecticidal proteins.

Recombinant nucleic acid sequences were constructed from known Cry protein genes to produce polynucleotide sequences encoding novel chimeric insecticidal proteins. The resulting polynucleotide sequences were cloned into a *Bacillus thuringiensis* (Bt) expression plasmid vector. After confirmation of the polynucleotide sequence, the expression plasmid was transformed into Bt and expressed. Preparations of the expressed novel chimeric proteins were assayed for activity against various Lepidopteran pests.

Many polynucleotide sequences encoding chimeric insecticidal proteins were produced and tested in bioassay. Not all of the chimeric insecticidal proteins demonstrated activity. Only a few of the chimeric insecticidal proteins were selected based upon their activity to specific *Lepidoptera* demonstrated in bioassay such as TIC838 (SEQ ID NO:93). Amino acid variants in which amino acid substitutions, or alternate protoxin domains, were introduced were also produced based upon the original chimeric insecticidal proteins TIC867 and TIC868. The components of the chimeric insecticidal proteins (domains I, II and III and the protoxin) of the present invention are presented in Table 1. The amino acid substitutions in the TIC868 variants relative to the original TIC868 protein sequence are also presented.

TABLE 1

Novel chimeric pesticidal proteins and their components.

| Toxin | PRT SEQ ID NO: | Dom1 | Dom2 | Dom3 | Protox | Amino Acid Modifications* |
|---|---|---|---|---|---|---|
| TIC1100 | 4 | Cry1Ah | Cry1Ac | Cry1Ca | Cry1Ac | |
| TIC860 | 7 | Cry1Bb1 | Cry1Bb1 | Cry1Ca | Cry1Ac | |
| TIC867 | 10 | Cry1Be2 | Cry1Be2 | Cry1Ka | Cry1Ab3 | |
| TIC867_20 | 13 | Cry1Be2 | Cry1Be2 | Cry1Ka | Cry1Da1 | |

TABLE 1-continued

Novel chimeric pesticidal proteins and their components.

| Toxin | PRT SEQ ID NO: | Dom1 | Dom2 | Dom3 | Protox | Amino Acid Modifications* |
|---|---|---|---|---|---|---|
| TIC867_21 | 16 | Cry1Be2 | Cry1Be2 | Cry1Ka | Cry4 | |
| TIC867_22 | 19 | Cry1Be2 | Cry1Be2 | Cry1Ka | Cry9 | |
| TIC867_23 | 21 | Cry1Be2 | Cry1Be2 | Cry1Ka | Cry1Be | |
| TIC867_24 | 23 | Cry1Be2 | Cry1Be2 | Cry1Ka | Cry1Ka | |
| TIC867_25 | 25 | Cry1Be2 | Cry1Be2 | Cry1Ka | Cry1Ca | |
| TIC868 | 28 | Cry1Be2 | Cry1Be2 | Cry1Ca | Cry1Ab3 | |
| TIC868_9 | 30 | Cry1Be2 | Cry1Be2 | Cry1Ca | Cry1Ab3 | N240S_Y343Q_N349T |
| TIC868_10 | 33 | Cry1Be2 | Cry1Be2 | Cry1Ca | Cry1Da1 | |
| TIC868_11 | 36 | Cry1Be2 | Cry1Be2 | Cry1Ca | Cry4 | |
| TIC868_12 | 39 | Cry1Be2 | Cry1Be2 | Cry1Ca | Cry9 | |
| TIC868_13 | 41 | Cry1Be2 | Cry1Be2 | Cry1Ca | Cry1Be | |
| TIC868_14 | 43 | Cry1Be2 | Cry1Be2 | Cry1Ca | Cry1Ka | |
| TIC868_15 | 45 | Cry1Be2 | Cry1Be2 | Cry1Ca | Cry1Ca | |
| TIC868_29 | 47 | Cry1Be2 | Cry1Be2 | Cry1Ca | Cry1Ab3 | Q136Y_Y343Q_N349T |
| TIC869 | 50 | Cry1Ja1 | Cry1Ja1 | Cry1Jx | Cry1Ab3 | |
| TIC836 | 53 | Cry1Fa1 | Cry1Fa1 | Cry1Ab | Cry1Ac | |
| TIC838 | 93 | Cry1Ca | Cry1Cb | Cry1Ac | Cry1Ac | |

*The amino acid mutations are identified using the standard IUPAC amino acid code. See IUPAC-IUB Joint Commission on Biochemical Nomenclature. Nomenclature and Symbolism for Amino Acids and Peptides. Eur. J. Biochem. 138: 9-37 (1984). The first amino acid sequence abbreviation indicates the original amino acid in the given scaffold protein, the number represents the position of the amino acid, and the second amino acid sequence abbreviation indicates the amino acid placed in that position in the improved variant protein.

Example 2

The Novel Chimeric Insecticidal Proteins Demonstrate Activity Against Lepidopteran Pests This Example illustrates the testing of the chimeric insecticidal proteins described in Example 1 and the Lepidopteran activity observed for the chimeric insecticidal proteins.

Polynucleotide sequences encoding chimeric insecticidal proteins were expressed in Bt. The expressed chimeric insecticidal proteins were then assayed against a variety of *Lepidoptera* known to be pests of corn, sugarcane, soybean and cotton, as well as other crop plants. Specifically, the insecticidal proteins were assayed for activity against Velvetbean caterpillar (VBC, *Anticarsia gemmatalis*), Sugarcane borer (SCB, *Diatraea saccharalis*), Lesser cornstalk borer (LSCB, *Elasmopalpus lignosellus*), Corn earworm (CEW, *Helicoverpa zea*), Tobacco budworm (TBW, *Heliothis virescens*), Soybean looper (SBL, *Chrysodeixis includens*), Black armyworm (BLAW, *Spodoptera cosmioides*), Southern armyworm (SAW, *Spodoptera eridania*), Fall armyworm (FAW, *Spodoptera frugiperda*), Beet armyworm (BAW, *Spodoptera exigua*), Old World bollworm (OBW, *Helicoverpa armigera*), Oriental leafworm (OLW, *Spodoptera litura*), Pink bollworm (PBW, *Pectinophora gossypiella*), Black cutworm (BCW, *Agrotis ipsilon*), Southwestern Corn Borer (SWCB, *Diatraea grandiosella*), Spotted bollworm (SBW, *Earias vitella*), and European corn borer (ECB, *Ostrinia nubilalis*). Corn earworm (CEW, *Helicoverpa zea*) is also referred to as Soybean pod worm (SPW) and Cotton bollworm (CBW). Activity was determined through a combination of mortality and stunting scores as well as MIC50 scores. MIC50 refers to a molt inhibition concentration wherein both the dead larvae and L1 larvae (larvae that failed to molt to second instars) are factored into the score. Table 2 shows the activity of each chimeric insecticidal protein. A '+' sign indicates activity observed to the specific insect pest.

TABLE 2

Bioassay activity against selected Lepidoptera.

| Toxin | PRT SEQ ID NO: | VBC | SCB | LSCB | CEW SPW CBW | BLAW | TBW | SBL | SAW | FAW | BAW | OBW | OLW | PBW | BCW | SWCB | ECB | SBW |
|---|---|---|---|---|---|---|---|---|---|---|---|---|---|---|---|---|---|---|
| TIC1100 | 4 | + | + | | | + | | + | | + | | | + | + | | | | |
| TIC860 | 7 | + | + | + | | + | + | + | + | + | + | | + | + | | + | | + |
| TIC867 | 10 | + | + | | | + | | + | | + | + | + | + | | | + | | |
| TIC867_20 | 13 | | | | | | | | | | | | | | | | | |
| TIC867_21 | 16 | | | | + | | | | | | | | | | | | | |
| TIC867_22 | 19 | | | | + | | | | | + | | | | | | | | |
| TIC868 | 28 | + | + | | | + | | + | | + | + | | + | + | | + | | + |
| TIC868_10 | 33 | | | | | | | | | + | | | | | | | | |
| TIC868_11 | 36 | | | | | | | | | + | | | | | | | | |
| TIC868_12 | 39 | | | | | | | | | + | | | | | | | | |
| TIC869 | 50 | + | + | | | | | + | | + | | | | | | + | | |
| TIC836 | 53 | + | | | | + | | + | + | + | | | | | | | | |
| TIC838 | 93 | + | + | | | | + | + | + | + | + | | | | | + | | |

As can be seen in Table 2 above, most of the chimeric insecticidal proteins exhibited activity against one or more Lepidopteran pest species.

Example 3

Synthesis of Genes Encoding Chimeric Insecticidal Proteins and for Expression in Plants This Example illustrates the synthesis of polynucleotides encoding the chimeric insecticidal proteins for expression in plants.

Synthetic coding sequences were constructed for use in expression of the chimeric insecticidal proteins in plants. The synthetic sequences were designed and synthesized according to methods generally described in U.S. Pat. No. 5,500,365, avoiding certain inimical problem sequences such as ATTTA and A/T rich plant polyadenylation sequences while preserving the amino acid sequence of the chimeric insecticidal protein. The nucleotide sequences for these genes encoding the chimeric insecticidal proteins for expression in plants are listed in Table 3. The nucleotide sequence for the gene encoding the TIC838 chimeric insecticidal protein for expression in plants is presented as SEQ ID NO:3

TABLE 3

Polynucleotide Sequences Encoding Chimeric Insecticidal Proteins Designed for Use in Plants.

| Insecticidal Protein | DNA SEQ ID NO: | PRT SEQ ID NO: |
|---|---|---|
| TIC1100 | 2 | 4 |
| TIC1100 | 3 | 4 |
| TIC860 | 6 | 7 |
| TIC867 | 9 | 10 |
| TIC867_20 | 12 | 13 |
| TIC867_21 | 15 | 16 |
| TIC867_22 | 18 | 19 |
| TIC867_23 | 20 | 21 |
| TIC867_24 | 22 | 23 |
| TIC867_25 | 24 | 25 |
| TIC868 | 27 | 28 |
| TIC868_9 | 29 | 30 |
| TIC868_10 | 32 | 33 |
| TIC868_11 | 35 | 36 |
| TIC868_12 | 38 | 39 |
| TIC868_13 | 40 | 41 |
| TIC868_14 | 42 | 43 |
| TIC868_15 | 44 | 45 |
| TIC868_29 | 46 | 47 |
| TIC869 | 49 | 50 |
| TIC836 | 52 | 53 |
| TIC838 | 122 | 93 |

Example 4

Expression Cassettes for the Expression of Chimeric Insecticidal Proteins in Plants This Example illustrates the construction of expression cassettes comprising polynucleotide sequences designed for use in plants which encode chimeric insecticidal proteins.

A variety of plant expression cassettes were constructed with the polynucleotide sequences encoding the chimeric insecticidal proteins designed for plant expression provided in Table 3. Such expression cassettes are useful for transient expression in plant protoplasts or transformation of plant cells. Typical expression cassettes were designed with respect to the eventual placement of the protein within the cell. One set of expression cassettes was designed in a manner to allow the protein to be translated and remain in the cytosol. Another set of expression cassettes was designed to have a transit peptide contiguous with the toxin protein to allow targeting to an organelle of the cell such as the chloroplast or plastid. All expression cassettes were designed to begin at the 5' end with a promoter, which can be comprised of multiple promoter elements, enhancer elements, or other expression elements known to those of ordinary skill in the art operably linked to boost the expression of the transgene. The promoter sequence was usually followed contiguously with one or more leader sequences 3' to the promoter. An intron sequence was usually provided 3' to the leader sequence to improve expression of the transgene. A coding sequence for the toxin or transit peptide and coding sequence for the toxin was usually located 3' to the operably linked promoter, leader and intron configuration. A 3'UTR sequence was usually provided 3' of the coding sequence to facilitate termination of transcription and to provide sequences important for the polyadenylation of the resulting transcript. All of the elements described above were operably linked and arranged sequentially, often with additional sequences provided for the construction of the expression cassette.

The binary transformation vector typically is comprised of T-DNA consisting of two transgene cassettes; one for the selection of transformed plant cells using a selectable marker such as glyphosate or an antibiotic such as spectinomycin. The T-DNA is flanked by a right and left border sequence derived from *Agrobacterium tumefaciens* used for stable integration of the T-DNA into the plant host chromosomal DNA.

Example 5

Lepidopteran Activity of the Chimeric Insecticidal Proteins in Stably Transformed Corn This Example illustrates the inhibitory activity exhibited by the chimeric insecticidal proteins against Lepidopteran pests when expressed in corn plants and provided as a diet to the respective corn insect pest.

Corn variety LH244 was transformed with the binary transformation vectors described in Example 4 using an *Agrobacterium*-mediated transformation method. The transformed cells were induced to form plants by methods known in the art. Bioassays using plant leaf disks were performed analogous to those described in U.S. Pat. No. 8,344,207. A non-transformed LH244 plant was used to obtain tissue to be used as a negative control. Multiple transformation events from each binary vector were assessed against Corn earworm (CEW, *Helicoverpa zea*), Fall armyworm (FAW, *Spodoptera frugiperda*), Black cutworm (BCW, *Agrotis ipsilon*) and Southwestern Corn Borer (SWCB, *Diatraea grandiosella*).

Leaf disc bioassay was performed on $R_0$ and $F_1$ generation transgenic plants. In addition, leaf damage ratings were assessed for whole transgenic $F_1$ plants expressing certain chimeric insecticidal proteins infested with the Lepidopteran insect pests. $F_1$ transgenic events expressing TIC860 and TIC868 were also assessed for activity in the field against FAW, CEW, and SWCB. The assay results are shown in Table 4. A '+' sign indicates activity observed to the specific insect pest. As can be seen in Table 4, most of the chimeric insecticidal proteins and many of the chimeric insecticidal protein variants demonstrated activity against one or more Lepidopteran pest species.

TABLE 4

Bioassay activity of chimeric insecticidal proteins from stably transformed corn leaf tissue.

| Toxin | PRT SEQ ID NO: | VBC | SCB | LSCB | CEW SPW CBW | BLAW | TBW | SBL | SAW | FAW | BAW | OBW | OLW | PBW | BCW | SWCB | ECB | SBW |
|---|---|---|---|---|---|---|---|---|---|---|---|---|---|---|---|---|---|---|
| TIC1100 | 4 | + | + | | | + | | | + | | + | | + | + | | | | |
| TIC860 | 7 | + | + | + | | + | + | + | + | + | + | | + | + | | + | | + |
| TIC867 | 10 | + | + | | | + | + | | + | + | + | | + | | | + | | |
| TIC867_20 | 13 | NT | NT | NT | | NT | NT | NT | NT | | NT | NT | NT | NT | NT | NT | NT | NT |
| TIC867_21 | 16 | NT | NT | NT | + | NT | NT | NT | NT | | NT | NT | NT | NT | NT | NT | NT | NT |
| TIC867_22 | 19 | NT | NT | NT | + | NT | NT | NT | NT | + | NT | NT | NT | NT | NT | NT | NT | NT |
| TIC868 | 28 | + | + | | | + | | + | + | + | + | | + | + | | + | | + |
| TIC868_10 | 33 | NT | NT | NT | + | NT | NT | NT | NT | + | NT | NT | NT | NT | NT | NT | NT | NT |
| TIC868_11 | 36 | NT | NT | NT | + | NT | NT | NT | NT | + | NT | NT | NT | NT | NT | NT | NT | NT |
| TIC868_12 | 39 | NT | NT | NT | + | NT | NT | NT | NT | + | NT | NT | NT | NT | NT | NT | NT | NT |
| TIC869 | 50 | + | + | | | | | + | + | + | | | | | | + | | |
| TIC836 | 53 | + | | | | + | | + | + | + | | | | | | | | |

Example 6

Lepidopteran Activity of the Chimeric Insecticidal Proteins in Stably Transformed Soybean This Example illustrates the inhibitory activity exhibited by the chimeric insecticidal proteins against Lepidopteran pests when expressed in soybean plants and provided as a diet to the respective insect pest.

The coding sequences for selected chimeric insecticidal proteins were redesigned for plant expression, cloned into a binary plant transformation vector, and used to transform soybean plant cells using methods known in the art. Tissues are harvested from the transformants and used in insect bioassay against various Lepidopteran insects. The plant transformation vectors comprised a first transgene cassette for expression of the chimeric insecticidal protein as described in Example 4 and a second transgene cassette for the selection of transformed plant cells using spectinomycin selection. In some instances, such as in the case of TIC1100, TIC860 and TIC836, a chloroplast transit peptide coding sequence was operably linked to the chimeric insecticidal coding sequence. Assays were performed with plastid targeted and untargeted TIC1100, TIC860 and TIC836. Table 5 below shows the chimeric insecticidal and TIC867 variant chimeric insecticidal protein and associated coding sequences used for expression in stably transformed soybean.

Soybean plant cells were transformed using the binary transformation vectors described above by *Agrobacterium*-mediated transformation. The resulting transformed plant cells were induced to form whole soybean plants. Leaf tissue was harvested and used in bioassay as described in Example 5 or alternatively, lyophilized tissue was used in the insect diet for bioassay. Bioassay was performed against Fall armyworm (FAW, *Spodoptera frugiperda*), Southern armyworm (SAW, *Spodoptera eridania*), Soybean looper (SBL, *Chrysodeixis includens*), Soybean Pod Worm (SPW, *Helicoverpa zea*), Velvetbean caterpillar (VBC, *Anticarsia gemmatalis*), Tobacco budworm (TBW, *Heliothis virescens*), Black armyworm (BLAW, *Spodoptera cosmioides*), Lesser cornstalk borer (LSCB, *Elasmopalpus lignosellus*) and Old World bollworm (OBW, *Helicoverpa armigera*).

Table 5 shows the activity against selected species of *Lepidoptera* for each insecticidal protein in $R_0$ generation plants, wherein '+' indicates activity. As can be seen in Table 5, each of the chimeric insecticidal proteins expressed in stably transformed soybean demonstrated activity against multiple Lepidopteran species. Of particular note is that the TIC867 variant, TIC867_23 demonstrated activity against SPW.

TABLE 5

Bioassay activity of chimeric insecticidal proteins from stably transformed $R_0$ soybean leaf tissue.

| Insecticidal Protein | FAW | SAW | SBL | SPW | VBC | TBW | BLAW | LSCB | OBW |
|---|---|---|---|---|---|---|---|---|---|
| TIC1100 | + | + | + | | + | | + | + | + |
| TIC860 | + | + | + | | + | | | + | |
| TIC867 | + | + | + | | + | + | | + | |
| TIC867_20 | | + | + | | | | | | |
| TIC867_21 | | + | + | | | | | | |
| TIC867_22 | | + | + | | | | | | |
| TIC867_23 | + | + | + | + | | | | | |
| TIC867_24 | | + | + | | | | | | |
| TIC867_25 | | + | + | | | | | | |
| TIC868 | + | | + | | + | | + | + | |
| TIC869 | | | + | | + | + | | + | |
| TIC836 | + | + | + | | + | + | + | | + |

Selected transformed events were allowed to self-pollinate and the resulting seed was grown. Leaf tissue was harvested from the $R_1$ generation plants and used in a feeding bioassay. $R_1$ plants expressing TIC1100, TIC860, TIC867, TIC868, TIC869 and TIC836 were assayed for activity against SAW, SBL, SPW and VBC. Table 6 shows the activity observed in these tests. A '+' sign indicates activity observed to the specific insect pest. As demonstrated in Table 6, most of the expressed chimeric insecticidal proteins from $R_1$ generation plants demonstrated activity to one or more Lepidopteran species.

TABLE 6

Bioassay activity of chimeric insecticidal proteins from stably transformed $R_1$ soybean leaf tissue.

| Toxin | SAW | SBL | SPW | VBC |
|---|---|---|---|---|
| TIC1100 | + | + | | + |
| TIC860 | + | + | | + |
| TIC867 | + | | | |
| TIC868 | + | + | | + |
| TIC869 | + | + | | + |
| TIC836 | + | + | | + |

Table 7 demonstrates the results of field tests conducted in screen houses with stably transformed $R_1$ generation soybean plants expressing TIC1100, TIC860, and TIC836. Species used to infest plants in the screen houses include SAW, SBL and SPW. Resistance was defined as being less than or equal to fifteen percent defoliation in the soybean plants. The resistance observed in these cage trials is consistent with the resistance observed in the $R_1$ generation soybean leaf tissue assay presented in Table 6. A '+' sign indicates activity observed to the specific insect pest.

TABLE 7

Activity Profile of TIC1100, TIC860 and TIC836 Expressed in $R_1$ Generation Soybean Tested in Screen House Field Tests.

| Toxin | SAW | SBL | SPW |
|---|---|---|---|
| TIC1100 | + | + | |
| TIC860 | + | + | |
| TIC836 | + | + | |

Field tests in screen houses with stably transformed $R_1$ generation soybean plants expressing TIC867 and TIC869 were also conducted at two different locations in Argentina, Acevedo and Fontezuela. Species used to infest plants in the screen houses include South American bollworm (SABW, *Helicoverpa gelotopeon*), VBC, BLAW, and Sunflower looper (SFL, *Rachiplusia nu*). Resistance was defined as being less than or equal to fifteen percent defoliation in the soybean plants. Table 8 below shows the resistance observed. A '+' sign indicates activity observed to the specific insect pest. As demonstrated in Table 8, transgenic soybean plants expressing TIC867 demonstrated resistance to BLAW and VBC. Transgenic soybean plants expressing TIC869 demonstrated resistance to SABW, SFL, BLAW, and VBC.

TABLE 8

Activity Profile of TIC867 and TIC869 Expressed in $R_1$ Generation Soybean Tested in Screen House Field Tests.

| | Acevedo | | | Fontezuela | | |
|---|---|---|---|---|---|---|
| Toxin | SABW | SFL | VBC | SABW | BLAW | VBC |
| TIC867 | | | + | | + | + |
| TIC869 | | + | + | + | + | + |

Example 7

Lepidopteran Activity of the Chimeric Insecticidal Proteins in Stably Transformed Cotton This Example illustrates the inhibitory activity exhibited by the chimeric insecticidal proteins against Lepidopteran pests when expressed in cotton plants and provided as a diet to the respective insect pest.

The coding sequences for selected chimeric insecticidal proteins were redesigned for plant expression, cloned into a binary plant transformation vector, and used to transform cotton plant cells using methods known in the art. The resulting binary vectors were similar to those described in Example 4 and were used to express plastid targeted and untargeted TIC860 (coding sequence: SEQ ID NO: 6; protein sequence: SEQ ID NO: 7), TIC867 (coding sequence: SEQ ID NO: 9; protein sequence: SEQ ID NO: 10), TIC868 (coding sequence: SEQ ID NO: 27; protein sequence: SEQ ID NO: 28), and TIC867_23 (coding sequence: SEQ ID NO: 20; protein sequence: SEQ ID NO: 23).

Cotton plant cells were transformed by an *Agrobacterium*-mediated transformation method. Transformed cotton cells were induced to form whole plants. Cotton leaf tissue was used in bioassay as described in Example 5 against Cotton Boll Worm (CBW, *Helicoverpa zea*), FAW, TBW and SBL. Table 9 shows the activity observed against these Lepidopteran species for TIC860, TIC867, and TIC868 in stably transformed $R_0$ generation cotton, wherein '+' indicate activity. As can be seen in Table 9, TIC860, TIC867, and TIC868 demonstrated activity against two or more Lepidopteran pest species in stably transformed $R_0$ generation cotton.

TABLE 9

Bioassay activity of TIC860 TIC867 and TIC868 from stably transformed $R_0$ cotton leaf tissue.

| Toxin | CBW | FAW | TBW | SBL |
|---|---|---|---|---|
| TIC860 | | + | | + |
| TIC867 | + | + | + | NT |
| TIC868 | | + | | + |

Selected transformation events were used to produce $R_1$ seed. $R_1$ Plants expressing TIC860, TIC867, and TIC868 were assayed for resistance to CBW, FAW, TBW, and SBL. Leaf, square and boll tissues were used in assay. Table 10 shows the activity observed in these tests. A '+' sign indicates activity observed to the specific insect pest. As demonstrated in Table 10, TIC860 demonstrated activity against FAW in the leaf tissue. Further, the chimeric insecticidal protein TIC867 demonstrated activity against CBW and FAW in the leaf, square and boll tissues, as well as TBW and SBL in the leaf. The chimeric insecticidal protein TIC868 demonstrated activity against FAW in the leaf, square and boll tissues, as well as TBW and SBL in the leaf.

TABLE 10

Bioassay activity of chimeric insecticidal proteins from stably transformed $R_1$ cotton leaf tissue.

| | CBW | | | FAW | | | TBW | SBL |
|---|---|---|---|---|---|---|---|---|
| Toxin | Leaf | Square | Boll | Leaf | Square | Boll | Leaf | Leaf |
| TIC860 | | | | + | | | | |
| TIC867 | + | + | + | + | + | + | + | + |
| TIC868 | | | | + | + | + | + | + |

US 12,668,613 B2

33

Example 8

Cloning of Lepidopteran-Active Novel Chimeric Insecticidal Protein Coding Sequences Recombinant nucleic acid sequences were constructed from known Cry protein genes using to produce coding sequences encoding novel chimeric insecticidal proteins. The resulting coding sequences were cloned into a *Bacillus thuringiensis* (Bt) expression plasmid vector. After confirmation of the cloned sequence, the expression plasmid was transformed into Bt and expressed. Preparations of the expressed novel chimeric Cry proteins were assayed for activity against various Lepidopteran pests. Many coding sequences encoding chimeric insecticidal proteins were produced and tested in bioassay. Not all of the chimeric insecticidal proteins demonstrated activity. Only a few of the chimeric insecticidal proteins were selected based upon their activity to specific *Lepidoptera*, and are presented in Table 11 below.

TABLE 11

Novel chimeric pesticidal proteins and their corresponding bacterial coding sequence and protein sequence.

| Pesticidal Protein | Bacterial DNA SEQ ID NO: | Protein SEQ ID NO: |
|---|---|---|
| TIC713 | 54 | 55 |
| TIC843 | 56 | 57 |
| TIC862 | 58 | 59 |
| TIC1099 | 60 | 61 |
| TIC1103 | 78 | 79 |
| TIC1101 | 80 | 81 |
| TIC845 | 82 | 83 |
| TIC846 | 84 | 85 |
| TIC858 | 86 | 87 |
| TIC865 | 88 | 89 |
| TIC866 | 90 | 91 |
| TIC838 | 92 | 93 |
| TIC839 | 94 | 95 |
| TIC841 | 96 | 97 |
| TIC842 | 98 | 99 |
| TIC850 | 100 | 101 |
| TIC859 | 102 | 103 |
| TIC861 | 104 | 105 |

34

TABLE 11-continued

Novel chimeric pesticidal proteins and their corresponding bacterial coding sequence and protein sequence.

| Pesticidal Protein | Bacterial DNA SEQ ID NO: | Protein SEQ ID NO: |
|---|---|---|
| TIC848 | 106 | 107 |
| TIC849 | 108 | 109 |
| TIC847 | 110 | 111 |

Example 9

The Novel Chimeric Insecticidal Proteins Demonstrate Activity Against Lepidopteran Pests Coding sequences encoding chimeric insecticidal proteins were expressed in Bt. The expressed proteins were then assayed against a variety of *Lepidoptera* known to be pests of corn, sugarcane, soybean and cotton, as well as other crop plants. The insecticidal proteins were assayed for activity against Velvetbean caterpillar (VBC, *Anticarsia gemmatalis*), Sugarcane borer (SCB, *Diatraea saccharalis*), Lesser cornstalk borer (LSCB, *Elasmopalpus lignosellus*), Corn earworm (CEW, *Helicoverpa zea*), Tobacco budworm (TBW, *Heliothis virescens*), Soybean looper (SBL, *Chrysodeixis includens*), Black armyworm (BLAW, *Spodoptera cosmioides*), Southern armyworm (SAW, *Spodoptera eridania*), Fall armyworm (FAW, *Spodoptera frugiperda*), Beet armyworm (BAW, *Spodoptera exigua*), Old World bollworm (OBW, *Helicoverpa armigera*), Oriental leafworm (OLW, *Spodoptera litura*), Pink bollworm (PBW, *Pectinophora gossypiella*), Black cutworm (BCW, *Agrotis ipsilon*), Southwestern Corn Borer (SWCB, *Diatraea grandiosella*) and European corn borer (ECB, *Ostrinia nubilalis*). Corn earworm (CEW, *Helicoverpa zea*) is also referred to as Soybean pod worm (SPW) and Cotton bowl worm (CBW). Activity was determined through a combination of mortality and stunting scores as well as MIC50 scores. MIC50 refers to a molt inhibition concentration wherein both the dead larvae and L1 larvae (larvae that failed to mol to second instars) are factored into the score. Table 12 below shows the activity of each chimeric insecticidal protein. A '+' sign indicates activity observed to the specific insect pest.

TABLE 12

Bioassay activity against selected Lepidoptera.

| | | | | Insect | | | | | | | | | | | | |
|---|---|---|---|---|---|---|---|---|---|---|---|---|---|---|---|---|
| PRT SEQ ID NO: | VBC | SCB | LSCB | CEW SPW CBW | TBW | SBL | BLAW | SAW | FAW | BAW | OBW | OLW | PBW | BCW | SWCB | ECB |
| 55 | + | + | + | + | + | + | + | | + | + | + | + | + | | + | + |
| 57 | + | + | + | + | + | + | + | | | + | | + | + | | + | |
| 59 | + | + | + | + | + | + | | + | + | | | | | | + | |
| 61 | + | + | | + | | + | + | | + | + | + | + | + | | + | + |
| 79 | + | + | | + | + | + | + | | | + | + | + | + | + | + | + |
| 81 | + | + | | | | + | + | | | | | | | | | |
| 83 | + | + | | | | + | | + | | + | | | + | | + | |
| 85 | + | + | | | | + | | + | | | | + | | | + | |
| 87 | + | + | | | | + | | + | | + | | + | + | | + | |
| 89 | + | + | + | | + | + | + | + | + | | | | | | + | |
| 91 | + | + | | | | + | | | + | | | + | | | + | |
| 93 | + | + | + | | + | + | | + | + | + | | | | | + | |
| 95 | + | + | | | | + | + | + | | | | | | | + | |
| 97 | + | + | | | | + | + | | | | | | + | | + | |
| 99 | + | + | + | | + | + | + | + | + | + | + | + | | + | + | |
| 101 | + | | | | | + | + | + | + | + | | + | | + | + | |

TABLE 12-continued

Bioassay activity against selected Lepidoptera.

Insect

| PRT SEQ ID NO: | VBC | SCB | LSCB | CEW SPW CBW | TBW | SBL | BLAW | SAW | FAW | BAW | OBW | OLW | PBW | BCW | SWCB | ECB |
|---|---|---|---|---|---|---|---|---|---|---|---|---|---|---|---|---|
| 103 | + | + |  | + | + | + | + | + | + | + |  | + |  | + | + |  |
| 105 | + | + |  |  | + | + |  | + |  |  |  |  |  |  | + |  |
| 107 | + | + | + | + | + | + |  | + | + |  |  | + | + |  |  |  |
| 109 | + | + | + | + | + | + |  | + | + |  |  | + | + |  |  |  |
| 111 | + | + |  |  | + | + |  | + | + |  |  | + | + |  | + |  |

As can be seen in Table 12 above, all of the chimeric insecticidal proteins exhibited activity against multiple Lepidopteran species.

Example 10

Amino Acid Variants of TIC1099 Demonstrate Lepidopteran Activity

The coding sequence for TIC1099 (SEQ ID NO: 60) was modified by methods known in the art to alter specific amino acids from the original TIC1099 protein sequence (SEQ ID NO: 61). The resultant variants were assayed for activity against selected *Lepidoptera*. Table 13 below shows the TIC1099 variants and the corresponding DNA and protein SEQ ID NOs.

TABLE 13

TIC1099 variants

| TIC1099 Variant | DNA SEQ ID NO: | PRT SEQ ID NO: |
|---|---|---|
| TIC1099-T507E | 62 | 63 |
| TIC1099-R522K | 64 | 65 |
| TIC1099-K490S | 66 | 67 |
| TIC1099-T562R | 68 | 69 |
| TIC1099-S553R | 70 | 71 |
| TIC1099-G498D | 72 | 73 |
| TIC1099-K490A | 74 | 75 |
| TIC1099-E564A | 76 | 77 |

Each variant was assayed for mortality and stunting against Fall armyworm (FAW, *Spodoptera frugiperda*), Corn earworm (CEW, *Helicoverpa zea*), Black cutworm (BCW, *Agrotis ipsilon*), Soybean looper (SBL, *Chrysodeixis includens*) and Southwestern Corn Borer (SWCB, *Diatraea grandiosella*). Table 14 below shows the activity against each Lepidopteran pest. The activity is rated from '+' to '++++' based upon the percent mortality.

TABLE 14

Lepidoptera activity of TIC1099 variants.

| TIC1099 Variant | PRT SEQ ID NO: | FAW | CEW | BCW | SBL | SWCB |
|---|---|---|---|---|---|---|
| TIC1099 | 61 | ++++ | +++ | ++++ | ++++ | +++ |
| TIC1099-T507E | 63 | ++++ | ++++ | ++++ | ++++ | ++++ |
| TIC1099-R522K | 65 | ++++ | ++++ | ++++ | +++ | ++++ |
| TIC1099-K490S | 67 | ++++ | +++ | ++++ | ++ | + |
| TIC1099-T562R | 69 | ++++ | ++++ | ++++ | ++++ | ++++ |
| TIC1099-S553R | 71 | ++++ | ++++ | ++++ | ++++ | ++++ |
| TIC1099-G498D | 73 | ++++ | ++++ | ++++ | ++++ | ++++ |
| TIC1099-K490A | 75 | ++++ | ++++ | ++++ | +++ | +++ |
| TIC1099-E564A | 77 | +++ | ++ | +++ | + | + |

All of the TIC1099 variants demonstrated activity against the five tested Lepidopteran species. A few of the variants demonstrated lower activity when compared to the others for specific pests.

Example 11

The Chimeric Insecticidal Proteins Expressed in Stably Transformed Corn Demonstrate Activity Against Lepidopteran Pests Synthetic coding sequences were constructed for use in expression of the encoded protein in plants, cloned into a binary plant transformation vector, and used to transform corn plant cells. The plant transformation vectors comprised a first transgene cassette for expression of the chimeric insecticidal protein which comprised a constitutive promoter, operably linked 5' to a leader, operably linked 5' to an intron, operably linked 5' to the chimeric insecticidal protein coding sequence, which was in turn operably linked 5' to a 3' UTR and; a second transgene cassette for the selection of transformed plant cells using glyphosate selection. Table 15 below shows the chimeric insecticidal protein coding sequences used for expression in corn and the corresponding SEQ ID NOS.

TABLE 15

Insecticidal protein coding sequences and corresponding SEQ ID NOs.

| Insecticidal Protein | DNA SEQ ID NO: | PRT SEQ ID NO: |
|---|---|---|
| TIC713 | 112 | 55 |
| TIC713 | 113 | 55 |
| TIC843 | 114 | 57 |
| TIC862 | 115 | 59 |
| TIC1099 | 116 | 61 |
| TIC1103 | 117 | 79 |
| TIC845 | 118 | 83 |
| TIC846 | 119 | 85 |

TABLE 15-continued

| Insecticidal Protein | DNA SEQ ID NO: | PRT SEQ ID NO: |
|---|---|---|
| TIC858 | 120 | 87 |
| TIC866 | 121 | 91 |
| TIC838 | 122 | 93 |
| TIC841 | 123 | 97 |
| TIC842 | 124 | 99 |
| TIC850 | 125 | 101 |
| TIC859 | 126 | 103 |
| TIC861 | 127 | 105 |
| TIC848 | 128 | 107 |
| TIC849 | 129 | 109 |
| TIC847 | 130 | 111 |

*Insecticidal protein coding sequences and corresponding SEQ ID NOs.*

Corn variety LH244 was transformed with the binary transformation vectors described above using an *Agrobacterium*-mediated transformation method. The transformed cells were induced to form plants by methods known in the art. Bioassays using plant leaf disks were performed analogous to those described in U.S. Pat. No. 8,344,207. A non-transformed LH244 plant was used to obtain tissue to be used as a negative control. Multiple transformation events from each binary vector were assessed against Corn earworm (CEW, *Helicoverpa zea*), Fall armyworm (FAW, *Spodoptera frugiperda*), Black cutworm (BCW, *Agrotis ipsilon*) and Southwestern Corn Borer (SWCB, *Diatraea grandiosella*). The assay results are shown in Table 16 below wherein '+' indicate activity.

TABLE 16

Bioassay activity of chimeric insecticidal proteins from stably transformed corn leaf tissue.

| Insecticidal Protein | CEW | FAW | BCW | SWCB |
|---|---|---|---|---|
| TIC713 | + | + | | + |
| TIC843 | + | + | | + |
| TIC862 | + | + | | + |
| TIC1099 | + | + | + | + |
| TIC1103 | + | + | | + |
| TIC845 | + | + | | + |
| TIC846 | + | + | | + |
| TIC858 | + | + | | + |
| TIC866 | + | + | | + |
| TIC838 | | + | | + |
| TIC841 | + | + | | + |
| TIC842 | + | + | + | + |
| TIC850 | + | + | | + |
| TIC859 | + | + | | + |
| TIC861 | + | + | | + |
| TIC848 | + | + | | + |
| TIC849 | + | + | | + |
| TIC847 | | + | | + |

As can be seen in Table 16 above, all of the chimeric insecticidal proteins demonstrated activity against two or more Lepidopteran species.

Example 12

The Chimeric Insecticidal Proteins Expressed in Stably Transformed Soybean Demonstrate Activity Against Lepidopteran Pests The coding sequences for selected chimeric insecticidal proteins were redesigned for plant expression, cloned into a binary plant transformation vector, and used to transform soybean plant cells. The plant transformation vectors comprised a first transgene cassette for expression of the chimeric insecticidal protein which comprised a constitutive promoter, operably linked 5' to a leader, operably linked 5' to the chimeric insecticidal protein coding sequence, which was in turn operably linked 5' to a 3' UTR and; a second transgene cassette for the selection of transformed plant cells using spectinomycin selection. Table 17 below shows the chimeric insecticidal protein coding sequences used for expression in soybean and the corresponding SEQ ID NOs.

TABLE 17

Insecticidal protein coding sequences and corresponding SEQ ID NOs.

| Insecticidal Protein | DNA SEQ ID NO: | PRT SEQ ID NO: |
|---|---|---|
| TIC1103 | 117 | 79 |
| TIC866 | 121 | 91 |
| TIC842 | 124 | 99 |
| TIC849 | 129 | 109 |

Soybean plant cells were transformed using the binary transformation vectors described above by *Agrobacterium*-mediated transformation. The resulting transformed plant cells were induced to form whole soybean plants. Leaf tissue was harvested and used in bioassay as described in Example 11 or alternatively, lyophilized tissue was used in the insect diet for bioassay. Bioassay was performed against Fall armyworm (FAW, *Spodoptera frugiperda*), Southern armyworm (SAW, *Spodoptera eridania*), Soybean looper (SBL, *Chrysodeixis includens*), Soybean Pod Worm (SPW, *Helicoverpa zea*), Velvetbean caterpillar (VBC, *Anticarsia gemmatalis*), Soybean looper (SBL, *Chrysodeixis includens*), Tobacco budworm (TBW, *Heliothis virescens*), Black armyworm (BLAW, *Spodoptera cosmioides*), Southern armyworm (SAW, *Spodoptera eridania*), Lesser cornstalk borer (LSCB, *Elasmopalpus lignosellus*) and Old World bollworm (OBW, *Helicoverpa armigera*). Table 18 below shows the activity against selected species of *Lepidoptera* for each insecticidal protein in R0 generation plants.

TABLE 18

Bioassay activity of chimeric insecticidal proteins from stably transformed R0 soybean leaf tissue.

| Insecticidal Protein | FAW | SAW | SBL | SPW | VBC | TBW | BLAW | SAW | LSCB | OBW |
|---|---|---|---|---|---|---|---|---|---|---|
| TIC1103 | | + | + | + | + | + | | | + | + |
| TIC866 | + | | + | | + | | | | + | + |
| TIC842 | + | + | + | | + | + | + | + | + | + |
| TIC849 | | + | + | + | + | + | | | + | |

As can be seen in Table 18, each of the chimeric insecticidal proteins expressed in stably transformed soybean demonstrated activity against multiple Lepidopteran species.

Selected transformed events were allowed to self-pollinate and the resulting seed was grown. Leaf tissue was harvested from the R1 generation plants and used in a feeding bioassay. Table 19 shows the activity observed against selected Lepidopteran species from insecticidal proteins expressed in the R1 generation soybean leaf tissue.

TABLE 19

| Bioassay activity of chimeric insecticidal proteins from stably transformed $R_1$ soybean leaf tissue. | | | | |
|---|---|---|---|---|
| Toxin | SAW | SBL | SPW | VBC |
| TIC1103 | | + | + | + |
| TIC866 | + | + | | + |
| TIC842 | | + | + | |
| TIC849 | | + | + | |

As can be seen in Table 19 above, the expressed chimeric insecticidal proteins from R1 generation plants demonstrated activity to two or more Lepidopteran species.

Example 13

Lepidopteran Activity of the Chimeric Insecticidal Proteins in Stably Transformed Corn This Example illustrates the inhibitory activity exhibited by the TIC838 chimeric insecticidal protein against Lepidopteran pests when expressed in corn plants and provided as a diet to the respective corn insect pest.

Corn variety LH244 was transformed with the binary transformation vectors described in Example 4 using an *Agrobacterium*-mediated transformation method. The transformed cells were induced to form plants by methods known in the art. Bioassays using plant leaf disks were performed analogous to those described in U.S. Pat. No. 8,344,207. A non-transformed LH244 plant was used to obtain tissue to be used as a negative control. Multiple transformation events the binary vector were assessed against Corn earworm (CEW, *Helicoverpa zea*), Fall armyworm (FAW, *Spodoptera frugiperda*), and Southwestern Corn Borer (SWCB, *Diatraea grandiosella*).

Leaf disc bioassay was performed on $R_0$ generation transgenic plants. In addition, leaf damage ratings were assessed for whole transgenic $F_1$ plants in the greenhouse. $F_1$ transgenic events were also assessed for activity in the field against FAW and SWCB at three different sites. Assay against SWCB in the field was performed two times at the three different sites, while assay against FAW was performed once in each of the three sites. The assay results are shown in Table 4. A '+' sign indicates activity observed to the specific insect pest. As can be seen in Table 4, the TIC838 chimeric insecticidal protein demonstrated activity against the Lepidopteran pest species FAW and SWCB in $R_0$ generation transgenic plants in leaf disc bioassay and demonstrated activity against SWCB in whole plant feeding studies in the greenhouse and field.

TABLE 20

| Activity of TIC838 from $R_0$ and $F_1$ stably transformed corn plants. | | | | | | | |
|---|---|---|---|---|---|---|---|
| R0 Leaf Disk | | | Greenhouse trial | | | Field Trials | |
| CEW | FAW | SWCB | CEW | FAW | SWCB | FAW | SWCB |
| | + | + | | | + | | + |

Example 14

Assay of Activity of TIC838 in Stably Transformed Soybean Against Lepidopteran Insect Pests This Example illustrates assaying TIC838 for Lepidopteran-inhibitory activity in stably transformed soybean plants.

Binary plant transformation vectors comprising transgene cassettes designed to express both plastid targeted and untargeted TIC838 insecticidal protein are cloned using methods known in the art. Tissues are harvested from the transformants and used in insect bioassay against various Lepidopteran insects. The plant transformation vectors comprise a first transgene cassette for expression of the TIC838 chimeric insecticidal protein as described in Example 4 and a second transgene cassette for the selection of transformed plant cells using spectinomycin selection.

Soybean plant cells are transformed using the binary transformation vectors described above by *Agrobacterium*-mediated transformation. The resulting transformed plant cells are induced to form whole soybean plants. Leaf tissue is harvested and used in bioassay as described in Example 5 or alternatively, lyophilized tissue is used in the insect diet for bioassay. Bioassay is performed against Fall armyworm (FAW, *Spodoptera frugiperda*), Southern armyworm (SAW, *Spodoptera eridania*), Soybean looper (SBL, *Chrysodeixis includens*), Soybean Pod Worm (SPW, *Helicoverpa zea*), Velvetbean caterpillar (VBC, *Anticarsia gemmatalis*), Tobacco budworm (TBW, *Heliothis virescens*), Black armyworm (BLAW, *Spodoptera cosmioides*), Lesser cornstalk borer (LSCB, *Elasmopalpus lignosellus*) and Old World bollworm (OBW, *Helicoverpa armigera*); as well as other Lepidopteran insect pests. Measurements of activity such as mortality and stunting of the Lepidopteran insect pest are recorded and used to determine the effectiveness of TIC838 in controlling the insect pest when expressed in soybean tissues. Whole plant assays are also performed in the greenhouse and field to assess damage to various organs such as, but not limited to, the leaf, flower, pod, and seed.

Example 15

Assay of Activity of TIC838 in Stably Transformed Cotton Against Lepidopteran Insect Pests This Example illustrates assaying TIC838 for Lepidopteran-inhibitory activity in stably transformed cotton plants.

Binary plant transformation vectors comprising transgene cassettes designed to express both plastid targeted and untargeted TIC838 insecticidal protein are cloned using methods known in the art. Tissues are harvested from the transformants and used in insect bioassay against various Lepidopteran insects. The plant transformation vectors comprise a first transgene cassette for expression of the TIC838 chimeric insecticidal protein as described in Example 4 and a second transgene cassette for the selection of transformed plant cells using spectinomycin selection.

Cotton plant cells are transformed using the binary transformation vectors described above by *Agrobacterium*-mediated transformation. The resulting transformed plant cells are induced to form whole soybean plants. Leaf tissue is harvested and used in bioassay as described in Example 5 or alternatively, lyophilized tissue is used in the insect diet for bioassay. Bioassay is performed against Cotton bowlworm (CBW, *Helicoverpa zea*), Fall armyworm (FAW, *Spodoptera frugiperda*), Soybean looper (SBL, *Chrysodeixis includens*), and Tobacco budworm (TBW, *Heliothis virescens*); as well as other Lepidopteran insect pests. Measurements of activity such as mortality and stunting of the Lepidopteran insect pest are recorded and used to determine the effectiveness of TIC838 in controlling the insect pest when expressed in soybean tissues. Tissues such as $R_0$ leaf, $R_0$ squares, $R_0$ bolls, $R_1$ leaf, $R_1$ squares and $R_1$ bolls are used in bioassay to determine the activity of TIC838 against the Lepidopteran insect pest species. Measurements of activity such as mortality and stunting of the Lepidopteran insect pest are recorded and used to determine the effectiveness of TIC838 in controlling the insect pest when expressed in soybean tissues. Whole plant assays are also performed in the greenhouse and field to assess damage to various organs such as, but not limited to, leaves, squares, and bolls.

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

What is claimed is:

1. A chimeric insecticidal protein comprising the amino acid sequence as set forth in SEQ ID NO: 109 or comprising an amino acid sequence having at least 95% sequence identity to the amino acid sequence of SEQ ID NO:109.

2. The chimeric insecticidal protein of claim 1, wherein the chimeric insecticidal protein comprises the amino acid sequence as set forth in SEQ ID NO:109.

3. A polynucleotide encoding the chimeric insecticidal protein according to claim 1, wherein the polynucleotide is operably linked to a heterologous promoter.

4. A host cell comprising the polynucleotide set forth in claim 3, wherein the host cell is selected from the group consisting of a bacterial host cell and a plant host cell.

5. The host cell of claim 4, wherein the bacterial host cell is selected from the group consisting of *Agrobacterium, Rhizobium, Bacillus, Brevibacillus, Escherichia, Pseudomonas, Klebsiella,* and *Erwinia*; and wherein the *Bacillus* species is a *Bacillus cereus* or a *Bacillus thuringiensis*, said *Brevibacillus* is a *Brevibacillus laterosporus*, and said *Escherichia* is an *Escherichia coli*.

6. The host cell of claim 4, wherein the plant host cell is selected from the group of plants consisting of monocots and dicots.

7. An insect inhibitory composition comprising the chimeric insecticidal protein according to claim 1.

8. The insect inhibitory composition of claim 7, further comprising at least one insect inhibitory agent different from the chimeric insecticidal protein.

9. The insect inhibitory composition of claim 8, wherein the at least one insect inhibitory agent is selected from the group consisting of an insect inhibitory protein and an insect inhibitory dsRNA molecule.

10. The insect inhibitory composition of claim 8, wherein the at least one insect inhibitory agent exhibits activity against one or more pest species of the orders *Lepidoptera*, Coleoptera, Hemiptera, Homoptera, or Thysanoptera.

11. A seed comprising an insect inhibitory effective amount of the chimeric insecticidal protein of claim 1.

12. A method of controlling a Lepidopteran pest, the method comprising contacting the Lepidopteran pest with an inhibitory amount of the chimeric insecticidal protein of claim 1.

13. A recombinant nucleic acid molecule comprising a heterologous promoter operably linked to a polynucleotide segment encoding a chimeric insecticidal protein, wherein the chimeric insecticidal protein comprises an amino acid sequence having at least 95% identity to the amino acid sequence of SEQ ID NO: 109.

14. A transgenic plant cell, plant or plant part comprising the recombinant nucleic acid molecule of claim 13.

15. A method of controlling a Lepidopteran pest, comprising exposing the pest to the transgenic plant cell, plant or plant part of claim 14, wherein said plant cell, plant or plant part expresses a Lepidopteran inhibitory amount of the chimeric insecticidal protein.

16. A commodity product derived from the plant cell, plant, or plant part of claim 14, wherein the product comprises a detectable amount of the chimeric insecticidal protein.

17. The commodity product of claim 16, wherein the product is selected from the group consisting of plant biomass, oil, meal, animal feed, flour, flakes, bran, lint, hulls, and processed seed.

18. A method of producing a seed comprising the chimeric insecticidal protein of claim 1, the method comprising:
   a) planting at least one seed comprising the chimeric insecticidal protein of claim 1;
   b) growing plants from the seed; and
   c) harvesting seed from the plants, wherein the harvested seed comprises the chimeric insecticidal protein of claim 1.

19. A recombinant polynucleotide molecule encoding the chimeric insecticidal protein of claim 1, wherein said recombinant polynucleotide molecule comprises the nucleotide sequence of SEQ ID NO:129.

* * * * *